United States Patent
Berry et al.

(10) Patent No.: US 7,232,679 B2
(45) Date of Patent: Jun. 19, 2007

(54) ISOPRENOID PRODUCTION

(75) Inventors: Alan Berry, Arlesheim (CH); Werner Bretzel, Loerrach (DE); Markus Hümbelin, Basel (CH); Rual Lopez-Ulibarri, Sissein (CH); Anne Françoise Mayer, Basel (CH); Alexei A. Yeliseev, Lafayette, CA (US)

(73) Assignee: DSM IP Assets B.V., Heerlen (NL)

( * ) Notice: Subject to any disclaimer, the term of this patent is extended or adjusted under 35 U.S.C. 154(b) by 208 days.

(21) Appl. No.: 11/129,143

(22) Filed: May 13, 2005

(65) Prior Publication Data
US 2005/0266518 A1    Dec. 1, 2005

Related U.S. Application Data

(62) Division of application No. 10/166,225, filed on Jun. 5, 2002, now Pat. No. 6,989,257.

(60) Provisional application No. 60/296,299, filed on Jun. 6, 2001, now abandoned.

(51) Int. Cl.
C12N 9/88 (2006.01)
(52) U.S. Cl. ..................................................... 435/232
(58) Field of Classification Search ..................... None
See application file for complete search history.

(56) References Cited

U.S. PATENT DOCUMENTS 3,891,504 A    6/1975  Schocher et al.
5,015,580 A    5/1991  Christou et al.
5,328,845 A    7/1994  Finkelstein et al.
5,935,808 A    8/1999  Hirschberg et al.
5,985,623 A   11/1999  Pollock et al.
6,015,684 A    1/2000  Jacobson et al.
6,087,152 A    7/2000  Hohmann et al.
6,208,893 B1   3/2001  Hofmann

FOREIGN PATENT DOCUMENTS

| EP | 0 747 483 A2 | 12/1996 |
| EP | 0 872 554 A2 | 10/1998 |
| WO | WO 99/06586 | 2/1999 |
| WO | WO 00/01649 | 1/2000 |
| WO | WO 00/77234 | 12/2000 |
| WO | WO 01/01650 | 1/2001 |

OTHER PUBLICATIONS

Albrecht et al., "Novel hydroxycarotenoids with improved antioxidative properties produced by gene combination in *Escherichia coli*," Nature Biotechnol., 18, 843-846 (2000).
Altschul et al., "Basic Local Alignment Search Tool," J. Mol. Biol., 215:403-410 (1990).

(Continued)

*Primary Examiner*—Nashaat T. Nashed
(74) *Attorney, Agent, or Firm*—Bryan Cave LLP

(57) ABSTRACT

Isolated polynucleotides encoding polypeptides having the activity of enzymes in the mevalonate pathway are provided. These sequences are useful for recombinantly producing isoprenoid compounds, such as carotenoids, in particular zeaxanthin. Expression vectors, cultured cells, and methods of making isoprenoid compounds are also provided.

10 Claims, 45 Drawing Sheets

OTHER PUBLICATIONS

Arigoni et al., "Terpenoid biosynthesis from 1-deoxy-D-xylulose in higher plants by intramolecular skeletal rearrangement," Proc. Natl. Acad. Sci. 94, 10600-10605 (1997).

Ausabel, F.M., Brent R., Kingston, R.E., Moore, D.D., Seidman, J.G., Smith, J.A. and Struhl, K. (ed.), Current Protocols in Molecular Biology, Greene Publishing and Wiley Interscience, New York, pp. 2.4.1-2.4.5 (1987).

Bochar et al., "Sequence Comparisons Reveal Two Classes of 3-Hydroxy-3-methylglutaryl Coenzyme A Reductase," Mol. Genet. Metab., 66, 122-127 (1999).

Borowitzka, M.A., "Commercial production of microalgae: ponds, tanks, tubes, and fermenters," J. Biotechnol., 70, 313-321 (1999).

Boucher and Doolittle, "The role of lateral gene transfer in the evolution of isoprenoid biosynthesis pathways," Mol. Microbiol., 37 (4), 703-716 (2000).

Bradford, "A Rapid and Sensitive Method for the Quantitation of Microgram Quantities of Protein Utilizing the Principle of Protein-Dye Binding," Anal. Biochem., 72, 248-254 (1976).

Britton et al., "Stereochemistry of Cyclization in Carotenoid Biosynthesis; Use of 13C-Labelling to Elucidate the Stereochemical Behaviour of the C-1 Methyl Substituents during Zeaxanthin Biosynthesis in a Flavobacterium," J. Chem. Soc. Chem. Comm., 27-28 (1979).

Britton et al., "The carotenoids of Flavobacterium strain R1560," Arch. Microbiol., 113, 33-37 (1977).

Campos et al., "*Escherichia coli* engineered to synthesize isopentyl diphosphate and dimethylallyl diphosphate from mevalonate: a novel system for the genetic analysis of the 2-C-methyl-D-erythritol 4-phosphate pathway for isoprenoid biosynthesis," Biochem. J., 353, 59-67 (2001).

Chohan, S. and Copeland, L., "Acetoacetyl Coenzyme A Reductase and Polyhydroxybutyrate Synthesis in Rhizobium (Cicer) sp. Strain CC 1192," Appl. Environ. Microbiol., 64(8), 2859-2863 (1998).

Dairi et al., "Cloning of the gene encoding 3-hydroxy-3-methylglutaryl coenzyme A reductase from terpenoid antibiotic-producing Streptomyces strains," Mol. Gen. Genet., 262, 957-964 (2000).

De Ley et al., "The Quantitative Measurement of DNA Hybridization from Renaturation Rates," Eur. J. Biochem., 12, 133-142 (1970).

Dunstan et al., "Discrimination by *Paracoccus denitrificans* between (6-13C)Glucose and (1-13C)Glucose as Carbon Substrates for Growth: An Investigation Using Gas Chromatography/Mass Spectrometry," Biomedical and Environ. Mass Spectrometry, 19, 369-381 (1990).

Eisenreich et al., "The deoxyxylulose phosphate pathway of terpenoid biosynthesis in plants and microorganisms," Chemistry and Biology, 5, R221-R233 (1998).

Eisenreich, W. and Bacher, A., "Elucidation of Biosynthetic Pathways By Retrodictive/Predictive Comparison of Isotopomer Patterns Determined by NMR Spectroscopy," Genetic Engineering, Principles and Methods, J. Setlow, eds., Kluwer Academic/Plenum Publishers, New York, vol. 22, 121-153 (2000).

Feng, D. and Doolittle, R., "Progressive Sequence Alignment as a Prerequisite to Correct Phylogenetic Trees," J. Mol. Evol., 25, 351-360 (1987).

Goodwin, T.W., "Recent developments in the biosynthesis of carotenoids," Biochem. Soc. Symp., 35, 233-244 (1972).

Harker, M. and Bramley, P.M., "Expression of prokaryotic 1-deoxy-D-xylulose-5-phosphatases in *Escherichia coli* increases carotenoid and ubiquinon biosynthesis," FEBS Lett., 448, 115-119 (1999).

Harker et al., "*Paracoccus marcusii* sp. nov., an orange Gram-negative coccus," Int. J. Syst. Bacteriol., 48, 543-548 (1998).

Henikoff, S. and Henikoff, J., "Amino acid substitution matrices from protein blocks," Proc. Natl. Acad. Sci. USA, 89, 10915-10919 (1992).

Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate," Proc. Nat. Acad. Sci., 97(6), 2486-2490 (2000).

Higgins, D. and Sharp, P., "Fast and sensitive multiple sequence alignments on a microcomputer," Cabios Communications, 5(2),151-153 (1989).

Honda et al., "Regulation of Early Cholesterol Biosynthesis in Rat Liver: Effects of Sterols, Bile Acids, Lovastatin, and BM 15.766 on 3-Hydroxy-3-Methylglutaryl Coenzyme A Synthase and Acetoacetyl Coenzyme A Thiolase Activites," Hepatology, 27(1), 154-159 (1998).

Hugh, R. and Leifson, E., "The Taxonomic Significance of Fermentative Versus Oxidative Metabolism of Carbohydrates By Varios Gram Negative Bacteria," J. Bacteriol., 66(1), 24-26 (1953).

Janssen et al., "Evaluation of the DNA fingerprinting method AFLP as a new tool in bacterial taxonomy," Microbiology, 142, 1881-1893 (1996).

Kajiwara et al. "Expression of an exogenous isopentenyl diphosphate isomerase gene enhances isopernoid biosynthesis in *Escherichia coli*," Biochem. J., 324, 421-426 (1997).

Kaneda et al., "An unusual isopentyl diphosphate isomerase found in the mevalonate pathway gene cluster from Streptomyces sp. strain CL190," Proc. Nat. Acad. Sci., 98(3), 932-937 (2001).

Karlin, S. and Altschul, S., "Applications and statistics for multiple high-scoring segments in molecular sequences," Proc. Nat'l. Acad. Sci. USA, 90, 5873-5877 (1993).

Kim, S. W. and Keasling, J.D., "Metabolic Engineering of the Nonmevalonate Isopentyl Diphosphate Synthesis Pathway in *Escherichia coli* Enhances Lycopene Production," Biotechnol. Bioeng., 72(4), 408-415 (2001).

Koehler, T. and Thorne, C., "*Bacillus subtilis* (natto) Plasmid pLS20 Mediates Interspecies Plasmid Transfer," J. Bacteriol., 169(11), 5271-5278 (1987).

Kovach et al., "Four new derivatives of the broad-host-range cloning vector pBBR1MCS, carrying different antibiotic-resistance cassettes," Gene, 166, 175-176 (1995).

Kuzuguchi et al., "Human Geranylgeranyl Diphosphate Synthase," J. Biol. Chem., 274(9), 5888-5894 (1999).

Lagarde et al., "Increased Production of Zeaxanthin and Other Pigments by Application of Genetic Engineering Techniques to Synechocystis sp. strain PCC 6803," Appl. Env. Microbiol., 66(1), 64-72, (2000).

Lange et al., "Isoprenoid biosynthesis: The evolution of two ancient and distinct pathways across genomes," Proc. Nat. Acad. Sci., 97(24), 13172-13177 (2000).

Logan et al., "Aerobic endospore-forming bacteria from geothermal environments in northern Victoria Land, Anarctica, and Candlemas Island, South Sandwich archipelago, with the proposal of *Bacillus fumarioli* sp. nov.," Int J. Syst. Evol. Microbiol., 50, 1741-1753 (2000).

Lorenz, T.R. and Cysewski G.R., "Commercial protential for *Haematococcus microalgae* as a natural source of astaxanthin," Trends Biotechnol., 18(4), 160-167 (2000).

Madison, L.L. and Huisman, G.W., "Metabolic Engineering of Poly(3-Hydroxyalkanoates): From DNA to Plastic," Microbiol. Mol. Rev., 63(1), 21-53 (1999).

Matthews, P.D. and Wurtzek, E.R., "Metabolic engineering of carotenoid accumulation in *Escherichia coli* by modulation of the isoprenoid precursor pool with expression of deoxyxylulose phosphate synthase," Appl. Microbiol. Biotechnol.,53, 396-400 (2000).

McDermott et al., "Carotenoid Biosynthesis in a Flavobacterium sp.: Stereochemistry of Hydrogen Elimination in the Desaturation of Phyteone to Lycopene, Rubixanthin and Zeacanthin," Biochem. J., 134, 1115-1117 (1973).

Mesbah et al., "Precise Measurement of the G+C Content of Deoxyribonucleic Acid by High-Performance Liquid Chromatography," Int. J. Syst. Bacteriol., 39(2), 159-167 (1989).

Myers, E. and Miller W., "Optimal alignments in linear space," CABIOS, 4(1), 11-17 (1988).

Misawa, N. and Shimada H., "Metabolic engineering for the production of carotenoids in non-carotengenic bacteria and yeasts," J. Biotechnol., 59, 169-181 (1998).

Mohanty et al., "Stereochemistry of formation of the •-ring of lycopene: Biosynthesis of (1R, 1'R)-:.-[16, 16, 16, 16', 16', 16'-2H6] carotene from [16, 16, 16, 16', 16', 16'-2H6]lycopene in Flavobacterium R 1560," Helvetica Chimica Acta, 83, 2036-2053 (2000).

Needleman, S. and Wunsch, C., "A General Method Applicable to the Search for Similiarities in the Amino Acid Sequence of Two Proteins," J. Mol. Biol., 48,443-453 (1970).

Niemann et al., "Evaluation of the resolving power of three different DNA fingerprinting methods to discriminate among isolates of a natural *Rhizobium melilotl* population," J. Appl. Microbiol., 82(4), 477-484, (1997).

Nolan, C. (ed.), Molecular Cloning: A Laboratory Manual (Second Edition), p. A.12 (1989).

Olaizola, M., "Commercial produciton of astaxanthin from *Haematococcus pluvialis* using 25,000-liter outdoor photobioreactors," J. Appl. Phycol., 12, 499-506 (2000).

Pasamontes et al., "Isolation and characterization of the carotenoid biosynthesis genes of Flavobacterium sp. strain R1534," Gene, 185, 35-41 (1997).

Pearson, W. and Lipman, D., "Improved tools for biological sequence comparison," Proc. Nat'l, Acad. Sci. USA, 85, 2444-2448 (1988).

Popjäk, "Enzymes of Sterol Biosynthesis in Liver and Intermediated of Sterol Biosynthesis," Methods in Enzymology, vol. 15, Chapter 12, 393-454, Academic Press, New York, (1969).

Priefer et al., "Extension of the Host Range of *Escherichia coli* Vectors by Incorporation of RSF1010 Replication and Mobilization Functions," J. Bacteriol. 163(1), 324-330 (1985).

Sandmann et al., "The biotechnological potential and design of novel carotenoids by gene combination in *Escherichia coli*," Trends Biotechnol., 17, 233-237 (1999).

Schmidt-Dannert et al., "Molecular breeding of carotenoid biosynthetic pathways" Nature Biotechnol., 18, 750-753 (2000).

Seto et al., "Simultaneous Operation of the Mevalonate and Non-Mevalonate Pathways in the Biosynthesis of Isopentyl diphosphate in *Streptomyces aeriouvifer*," Tetrahedron Lett., 37(44), 7979-7982 (1996).

Shigekawa and Dower, "Electroporation of Eukaryotes and Prokaryotes: A General Approach to the Introduction of Macromolecules into Cells," BioTechniques, 6(8), 742-751 (1988).

Siller et. al., "Isolation and Characterization of a New Gram-Negative, Acetone-Degrading, Nitrate-Reducing Bactrium from Soil, *Paracoccus solventivorans* sp. nov.," Int. J. Syst. Bacteriol. 46(4), 1125-1130 (1996).

Slater et al., "Multiple •-Ketothiolases Mediate Poly(•-Hydroxyalkanote) Copolymer Synthesis in *Ralstonia eutropha*," J. Bacteriol., 180(8), 1979-1987 (1998).

Smit, A. and Mushegian, A., "Biosynthesis of Isoprenoids via Mevalonate in Archaea: The Lost Pathway," Genome Res., 10, 1468-1484 (2000).

Smith, T. and Waterman, M., "Comparison of Biosequences," Adv. Appl. Math., 2, 482-489 (1981).

Spurgeon et al., "Isopentenyl Pyrophosphate Isomerase and Prenyltransferase from Tomato Fruit Plastids," Arch. Biochem. Biophys., 230(2), 446-454 (1984).

Stackebrandt, E. and Goebel, B.M., "Taxonomic Note: A Place for DNA-DNA Reassociation and 16S rRNA Sequence Analysis in the Present Species Definition in Bacteriology," Int. J. Syst. Bacteriol., 44(4), 846-849 (1994).

Takagi et al., "A Gene Cluster for the Mevalonate Pathway from Streotomyces sp. strain CL190," J. Bacteriol., 182(15), 4153-4157 (2000).

Takahashi et al., "Purification, Characterization, and Cloning of a Eubacterial 3-Hydroxy-3-Methylglutaryt Coenzyme A Reductase, a Key Enzyme Involved in Biosynthesis of Terpenoids," J. Bacteriol., 181(4), 1256-1263 (1999).

Tijssen, "Overview of principles of hybridization and the strategy of nucleic acid probe assays," Laboratory Techniques in Biochemistry and Molecular Biology—Hybridization with Nucleic Probes, Chapter 2, Amsterdam: Elsevier Science Publishers B.V., 19-78 (1993).

Tsubokura et al., "*Paracoccus carotinifaciens* sp. nov., a new aerobic Gram-negative astaxanthin-producing bacterium," Int. J. Syst. Bacteriol., 49, 277-282 (1999).

Ueda et al., "Molecular Analysis of the Poly(3-Hydroxyalkanoate) Synthase Gene from a Methylotrophic Bacterium, *Paracoccus denitrificans*," J. Bacteriol., 178(3), 774-779 (1996).

Vandamme et al., "Polyphasic Taxonomy, a Consensus Approach to Bacterial Systematics," Microbiological Reviews, 60(2), 407-438 (1996).

Vauterin et al., "Reclassification of Xanthomonas," Int. J. Syst. Bacteriol., 45 (3), 472-489 (1995).

Verdoes, J.C. and Van Ooyen, A.J.J., "Isolation of the isopentyl diphosphate isomerase encoding gene of *Phaffia rhodoyma*; improved carotenoid produciton in *Escherichia coli*," Acta Bot. Gallica, 146 (1), 43-53 (1999).

Villarejo, M.R. and Zabin, I., "•-Galactosidase from Termination and Deletion Mutant Strains," J. Bacteriol., 120, 466-474 (1974).

Vos et al. "AFLP: a new technique for DNA fingerprinting," Nucleic Acids Research, 23(21), 4407-4414 (1995).

Wang et al., "Engineered Isoprenoid Pathway Enhances Astaxanthin Production in *Escherichia coli*," Biotechnol. Bioeng., 62(2), 235-241 (1999).

Wang et al., "Directed Evolution of Metabolically Engineered *Escherichia coli* for Carotenoid Production," Biotechnol. Prog., 16, 922-926 (2000).

Wayne et al., "Report of the Ad Hoc Committee on Reconciliation of Approached to Baterical Systematics," Int. J. Syst. Bacteriol., 37(4), 463-464 (1987).

Wilding et al., "Identification, Evolution, and Essentiality of the Mevalonate Pathway for Isopentyl Diphosphate Biosynthesis in Gram-Positive Cocci," J. Bacteriol., 182(15), 4319-4327 (2000).

Yabutani et al., "Analysis of •-ketothiolase and acetoacetyl-CoA reductase genes of a methylotrophic bacterium, *Paracoccus denitrificans*, and their expression in *Escherichia coli*," FEMS Microbiol. Lett., 133, 85-90 (1995).

Hembelin et al., "Genetics of Isoprenoid Biosynthesis in *Paracoccus zeaxanthinifaciens*," Gene, 297, 129-139 (2002).

Eisenreich et al., "Biosynthesis of Zeaxanthin via Mevalonate in Paracoccus Species Strain PTA-3335. A Product-Based Retrobiosynthetic Study," J. Org. Chem., 67, 871-875 (2002).

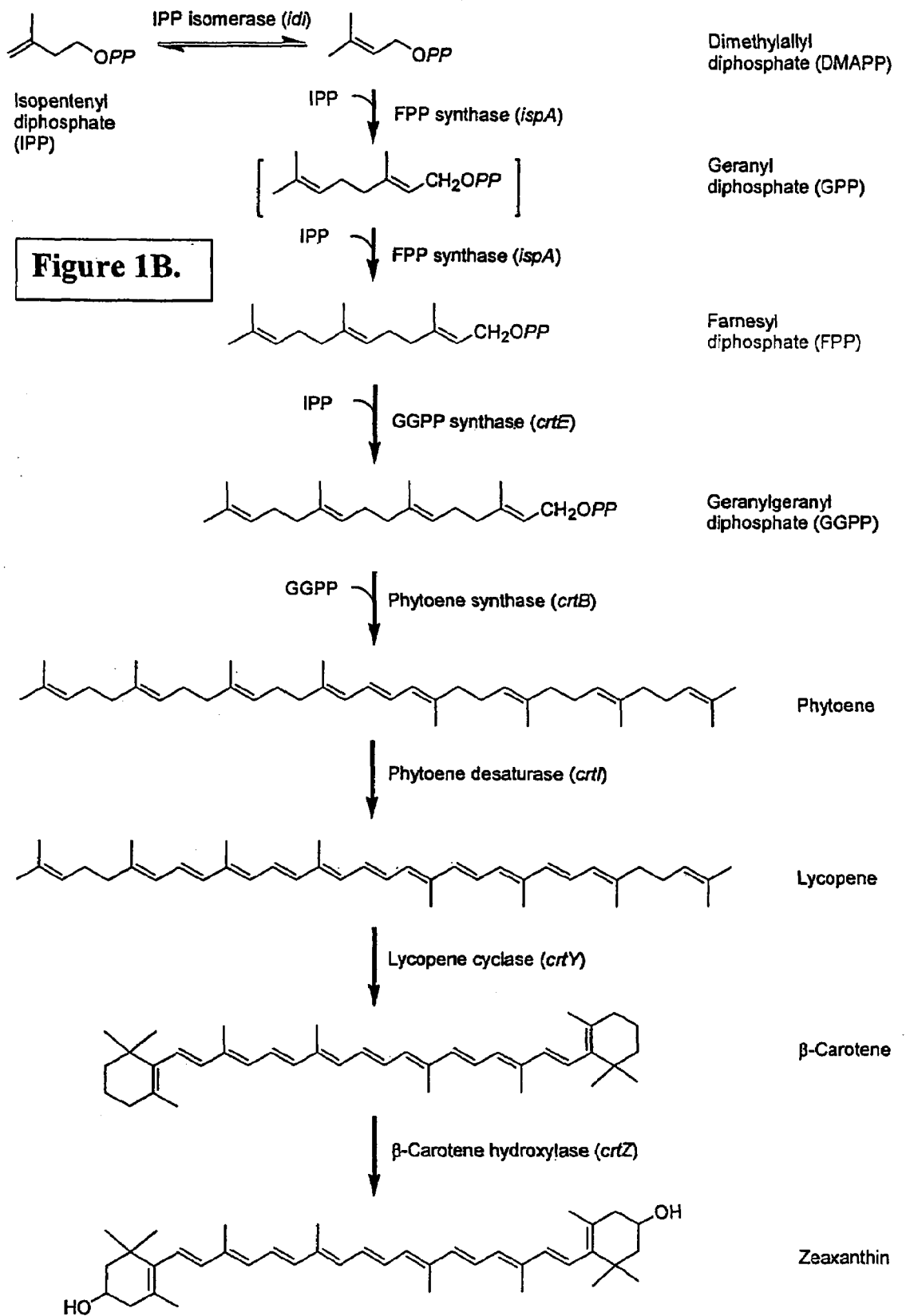

```
GCGGCAGGCTTAACACATGCAAGTCGAGCGAGGTCTTCGGACCTAGCGGCGGACGGGTGAGTAA
CGCGTGGGAACGTGCCCTTTGCTACGGAATAGTCCCGGGAAACTGGGTTTAATACCGTATGTGC
CCTACGGGGGAAAGATTTATCGGCAAAGGATCGGCCCGCGTTGGATTAGGTAGTTGGTGGGGTA
ATGGCCTACCAAGCCGACGATCCATAGCTGGTTTGAGAGGATGATCAGCCACACTGGGACTGAG
ACACGGCCCAGACTCCTACGGGAGGCAGCAGTGGGGAATCTTAGACAATGGGGGCAACCCTGAT
CTAGCCATGCCGCGTGAGTGATGAAGGCCCTAGGGTTGTAAAGCTCTTTCAGCTGGGAAGATAA
TGACGGTACCAGCAGAAGAAGCCCCGGCTAACTCCGTGCCAGCAGCCGCGGTAATACGGAGGGG
GCTAGCGTTGTTCGGAATTACTGGGCGTAAAGCGCACGTAGGCGGACTGGAAAGTTGGGGGTGA
AATCCCGGGGCTCAACCTCGGAACTGCCTCCAAAACTATCAGTCTGGAGTTCGAGAGAGGTGAG
TGGAATACCGAGTGTAGAGGTGAAATTCGTAGATATTCGGTGGAACACCAGTGGCGAAGGCGGC
TCACTGGCTCGATACTGACGCTGAGGTGCGAAAGCGTGGGGAGCAAACAGGATTAGATACCCTG
GTAGTCCACGCCGTAAACGATGAATGCCAGTCGTCGGGTTGCATGCAATTCGGTGACACACCTA
ACGGATTAAGCATTCCGCCTGGGGAGTACGGTCGCAAGATTAAAACTCAAAGGAATTGACGGGG
GCCCGCACAAGCGGTGGAGCATGTGGTTTAATTCGAAGCAACGCGCAGAACCTTACCAACCCTT
GACATCCCTGGACATCCCGAGAGATCGGGCTTTCACTTCGGTGACCAGGAGACAGGTGCTGCAT
GGCTGTCGTCAGCTCGTGTCGTGAGATGTTCGGTTAAGTCCGGCAACGAGCGCAACCCACGTCC
CTAGTTGCCAGCATTCAGTTGGGCACTCTATGGAAACTGCCGATGATAAGTCGGAGGAAGGTGT
GGATGACGTCAAGTCCTCATGGCCCTTACGGGTTGGGCTACACACGTGCTACAATGGTGGTGAC
AGTGGGTTAATCCCCAAAAGCCATCTCAGTTCGGATTGTCCTCTGCAACTCGAGGGCATGAAGT
TGGAATCGCTAGTAATCGCGGAACAGCATGCCGCGGTGAATACGTTCCCGGGCCTTGTACACAC
CGCCCGTCACACCATGGGAGTTGGTTCTACCCGACGACGCTGCGCTAACCCTTCGGGGAGGCAG
GCGGCCACGGTAGGATCAGCGACTGGGGTGAAGTCGTAACAAGGTAGCCGTAGGGGAACC
```

Figure 2.

```
   1 GGATCCGGCAGCTCGACACGCCGCAGAACCTGTACGAACGTCCCGCCAGCCGCTTCGTCG
  61 CGGAATTCGTCGGGCGCGGGACGGTGGTGCCCGTGCAGGCCCATGACGGCGCGGGCCGCG
 121 CCCGCATCCTGGGGGCCGAGGTGGCGGTGAACGCCGCCCGCAATCGCGCTTTGTCGATC
 181 ACGTCTGCCTGCGCCCCGAGAACCTTGCCATCTCCGAGACGGGCGACCTGCGCGCCAAGG
 241 TCGCGCGCGTCACCTATCTTGGCGGGAAATACCTGCTGGAAACCGTGCTGGATTGCGGCA
 301 CCCGGCTGGTGACCGAGACCCGCGCCCGCTTCGATACGGGCGCGCAGCTTGGCCTGACCA
 361 TCAACGCCCCTGGGCCTTTGCCGAGGATTGAATGGACAGCGTGAAGATCCTTTCGGGCA
 421 TGGGCGTGAAGGGCCCTGCCTGCATCAGGCTGGATGTCGGCGGGATGCGCCTGATCCTCG
 481 ATTGCGGGACCGGCCCGGACGAGGGCGCGGAGTTCGACCCCGCCTGGCTGGCGGACGCGG
 541 ATGCGGTGCTGATCACCCATGACCACGTGGACCATATCGGCGGCGCGCGTCACGCGGTCG
 601 CGGCGGGGCTGCCGATCCATGCGACGCGGCAGACGGCGGGGTTGCTGCCCGCGGGGGCGG
 661 ATCTGCGCCTGCTGCCCAACGCGGTGTCACGCGGATCGCCGGGGTCGATCTGACGACCG
 721 GTCGCAACGGGCATGCCGCGGGCGGCGTCTGGATGCATTTCGACATGGGCGAGGGGCTGT
 781 TCTATTCCGGCGACTGGTCCGAGGAATCCGACTGGTTCGCCTTCGATCCGCCCCCGCCTG
 841 CGGGGACGGCGATTCTCGACTGCTCCTATGGCGGTTTCGACGTGGCGCAATCGGATTGCA
 901 TCGCGGACCTGGACGACCTGCTCGAGGTGCTGCCGGGGCAGGTACTGCTGCCGGTGCCGC
 961 CATCCGGCCGCGCGGCCGAGCTGGCCCTGCGGCTGATCCGCCGCCACGGACCGGGCAGCG
1021 TGATGGTCGACGACGCCTGCCTGCCGGCCATCGCGCAACTGCCCGAGGCGCGCGGACTGG
1081 CCTACGCCACCGAGGCACGCTTTCTTGTCTGCGACACGCCGAACGCCGAAAGCCGGCGCG
1141 GCATGGCGGCATCTGCAAGCATGGCGCGATGCGGGCAGGCTGGGCGGGACGCGCATGTC
1201 GTCTTCACCGGGCACATGAACGTCCATGCGCGCGCATTCTGCGACCGCCCCGGCGGGCAT
1261 TTCCGCCGCTGGAACGTGCATCCGCCGCTGCGCGACCAGCGACGGATGCTGGAACGGCTG
1321 GCCGCGCGGCGCTTTGCCCCGGCCTTCTGCCCCGACCCCGAGATCTATCTGGCGCTGGAC
1381 ATGGGCGCGCAGGTCTTCATGCACCAGGAGGTGACGCCATGATCCCGCCCGCAGCTTCT
1441 GCCTGATCCGCCACGGCGAAACGACCGCCAATGCAGGGGCGATCATCGCGGGCGCAACCG
1501 ATGTGCCCTGACGCCAAGGGGCCGCGATCAGGCCCGCGCCCTGGCAGGGCGCGAATGGC
1561 CATCGGGCATCGCGCTGTTCGCCAGCCCGATGTCGCGTGCCCGCGATACCGCGCTGCTGG
1621 CCTTTCCGGGGCGCGACCACCAGCCCGAACCCGATCTGCGCGAACGCGACTGGGGCATCT
1681 TCGAGGGACGCCCCGTCGCCGATCTGCCCCCGCGCGAAATCACGCCGCAGGGGGCGAGG
1741 GCTGGGACGACGTGATGGCCCGCGTGGACCGCGCGATCCGGCGGATCTGCGCGACCTCGG
1801 GCGATGCGCTGCCGGTGCTGGTCTGCCATTCGGGCGTGATCCGTGCCGCGCGCGTGCTGT
1861 GGACCACCGGCGATGCGGGCGATCGTCCGCCCAACGCCACGCCGATCCTGTTCAGCCCGG
1921 ACGGCGACCGATTAAAGGAAGGAACGATATGACCGCCACCACCCCCTGCGTCGTCTTCGA
1981 ACGTGGACGGCACGCTTGCCGAATTCGACGCCGACCGCCTGGGCCATCTTGTCCACGGCA
2041 CGACCAAGCACTGGGACGCCTTCCACCACGCGATGGCCGACGCCCCGCCCATCCCCGAGG
2101 TCGCCCGCCTGATGCGCAAGCTGAAGGAGGGGGGCGAGACGGTCGTCATCTGCTCGGGGC
2161 GGCCCCGCGGCTGGCAGGATCAGACGATCGCATGGCTGCGCAAGCACGACCTGCCCTTCG
2221 ACGGGATCTATCTGCGCCCCGAGGATCAGGACGGCGCCAGCGACCCCGAGGTCAAGCGCC
2281 GCGCCCTAGCCGAGATGCGCGCCGACGGGCTGGCGCCCTGGCTGGTCGTGGACGACCGGC
2341 GGTCCGTCGTGGATGCCTGGCGGGCCGAGGGCTGGTCTGCCTGCAATGCGCGCCGGGGG
2401 ACTTCTAGGGCCGCGCGACGGGGGCGCGGACAGGCTGGGCGGGAAACCGCCCCGCCACCA
2461 TGTCCTGCACGCGTCGAACCGCCCGTCCGACGCCGGTTTCCGCACGGAAACGCGCGGCAA
2521 GTTGACATAACTTGCACGCGACGTCTCGATTCTGCCCGCGAAGAATGCGATGCATCCAGA
2581 TGATGCAGAACGAAGAAGCGGAAGCGCCCGTGAAAGACCAGATGATTTCCCATACCCCGG
                                               MvaA   M   I   S   H   T   P   V
2641 TGCCCACGCAATGGGTCGGCCCGATCCTGTTCCGCGGCCCCGTCGTCGAGGGCCCGATCA
         P   T   Q   W   V   G   P   I   L   F   R   G   P   V   V   E   G   P   I   S
2701 GCGCGCCGCTGGCCACCTACGAGACGCCGCTCTGGCCCTCGACCGCGCGGGGGGCAGGGG
             A   P   L   A   T   Y   E   T   P   L   W   P   S   T   A   R   G   A   G   V
2761 TTTCCCGGCATTCGGGCGGGATCCAGGTCTCGCTGGTCGACGAACGCATGAGCCGCTCGA
             S   R   H   S   G   G   I   Q   V   S   L   V   D   E   R   M   S   R   S   I
2821 TCGCGCTGCGGGCGCATGACGGGGCGGCGGCGACCGCCGCCTGGCAGTCGATCAAGGCCC
             A   L   R   A   H   D   G   A   A   A   T   A   A   W   Q   S   I   K   A   R
2881 GCCAGGAAGAGGTCGCGGCCGTGGTCGCCACCACCAGCCGCTTCGCCCGCCTTGTCGAGC
             Q   E   E   V   A   A   V   V   A   T   T   S   R   F   A   R   L   V   E   L
2941 TGAATCGCCAGATCGTGGGCAACCTGCTTTACATCCGCATCGAATGCGTGACGGGCGACG
             N   R   Q   I   V   G   N   L   L   Y   I   R   I   E   C   V   T   G   D   A
```

Figure 14A.

```
3001 CCTCGGGTCACAACATGGTCACCAAGGCCGCCGAGGCCGTGCAGGGCTGGATCCTGTCGG
       S  G  H  N  M  V  T  K  A  A  E  A  V  Q  G  W  I  L  S  E
3061 AATACCCGATGCTGGCCTATTCCACGATCTCGGGGAACCTGTGCACCGACAAGAAGGCGT
       Y  P  M  L  A  Y  S  T  I  S  G  N  L  C  T  D  K  K  A  S
3121 CGGCGGTCAACGGCATCCTGGGCCGCGGCAAATACGCCGTCGCCGAGGTCGAGATCCCGC
       A  V  N  G  I  L  G  R  G  K  Y  A  V  A  E  V  E  I  P  R
3181 GCAAGATCCTGACCCGCGTGCTGCGCACCAGCGCCGAGAAGATGGTCCGCCTGAACTACG
       K  I  L  T  R  V  L  R  T  S  A  E  K  M  V  R  L  N  Y  E
3241 AGAAGAACTATGTCGGGGGTACGCTGGCGGGTCGCTGCGCAGTGCGAACGCGCATTTCG
       K  N  Y  V  G  G  T  L  A  G  S  L  R  S  A  N  A  H  F  A
3301 CCAACATGCTGCTGGGCTTCTACCTGGCGACGGGGCAGGACGCGGCCAACATCATCGAGG
       N  M  L  L  G  F  Y  L  A  T  G  Q  D  A  A  N  I  I  E  A
3361 CCAGCCAGGGCTTCGTCCATTGCGAGGCCCGCGGCGAGGATCTGTATTTCTCGTGCACGC
       S  Q  G  F  V  H  C  E  A  R  G  E  D  L  Y  F  S  C  T  L
3421 TGCCCAACCTCATCATGGGCTCGGTCGGTGCCGGCAAGGGCATCCCCTCGATCGAGGAGA
       P  N  L  I  M  G  S  V  G  A  G  K  G  I  P  S  I  E  E  N
3481 ACCTGTCGCGGATGGGCTGCCGCCAGCCGGGCGAACCCGGCGACAACGCGCGCCGTCTTG
       L  S  R  M  G  C  R  Q  P  G  E  P  G  D  N  A  R  R  L  A
3541 CGGCGATCTGCGCGGGCGTCGTGCTGTGTGGTGAATTGTCGCTGCTTGCGGCCCAGACCA
       A  I  C  A  G  V  V  L  C  G  E  L  S  L  L  A  A  Q  T  N
3601 ACCCCGGAGAGTTGGTCCGCACCCACATGGAGATGGAGCGATGACCGACAGCAAGGATCA
       P  G  E  L  V  R  T  H  M  E  M  E  R  *
                                             Idi M  T  D  S  K  D  H
3661 CCATGTCGCGGGGCGCAAGCTGGACCATCTGCGTGCATTGGACGACGATGCGGATATCGA
       H  V  A  G  R  K  L  D  H  L  R  A  L  D  D  D  A  D  I  D
3721 CCGGGGCGACAGCGGCTTCGACCGCATCGCGCTGACCCATCGCGCCCTGCCCGAGGTGGA
       R  G  D  S  G  F  D  R  I  A  L  T  H  R  A  L  P  E  V  D
3781 TTTCGACGCCATCGACACGGCGACCAGCTTCCTGGGCCGTGAACTGTCCTTCCCGCTGCT
       F  D  A  I  D  T  A  T  S  F  L  G  R  E  L  S  F  P  L  L
3841 GATCTCGTCCATGACCGGCGGCACCGGCGAGGAGATCGAGCGCATCAACCGCAACCTGGC
       I  S  S  M  T  G  G  T  G  E  E  I  E  R  I  N  R  N  L  A
3901 CGCTGGTGCCGAGGAGGCCCGCGTCGCCATGGCGGTGGGCTCGCAGCGCGTGATGTTCAC
       A  G  A  E  E  A  R  V  A  M  A  V  G  S  Q  R  V  M  F  T
3961 CGACCCCTCGGCGCGGGCCAGCTTCGACCTGCGCGCCCATGCGCCCACCGTGCCGCTGCT
       D  P  S  A  R  A  S  F  D  L  R  A  H  A  P  T  V  P  L  L
4021 GGCCAATATCGGCGCGGTGCAGCTGAACATGGGGCTGGGGCTGAAGGAATGCCTGGCCGC
       A  N  I  G  A  V  Q  L  N  M  G  L  G  L  K  E  C  L  A  A
4081 GATCGAGGTGCTGCAGGCGGACGGCCTGTATCTGCACCTGAACCCCCTGCAAGAGGCCGT
       I  E  V  L  Q  A  D  G  L  Y  L  H  L  N  P  L  Q  E  A  V
4141 CCAGCCCGAGGGGGATCGCGACTTTGCCGATCTGGGCAGCAAGATCGCGGCCATCGCCCG
       Q  P  E  G  D  R  D  F  A  D  L  G  S  K  I  A  A  I  A  R
4201 CGACGTTCCCGTGCCCGTCCTGCTGAAGGAGGTGGGCTGCGGCCTGTCGGCGGCCGATAT
       D  V  P  V  P  V  L  L  K  E  V  G  C  G  L  S  A  A  D  I
4261 CGCCATCGGGCTGCGCGCCGGGATCCGGCATTTCGACGTGGCCGGTCGCGGCGGCACATC
       A  I  G  L  R  A  G  I  R  H  F  D  V  A  G  R  G  G  T  S
4321 CTGGAGCCGGATCGAGTATCGCCGCCGCCAGCGGGCCGATGACGACCTGGGCCTGGTCTT
       W  S  R  I  E  Y  R  R  R  Q  R  A  D  D  D  L  G  L  V  F
4381 CCAGGACTGGGGCCTGCAGACCGTGGACGCCCTGCGCGAGGCGCGGCCCGCGCTTGCGGC
       Q  D  W  G  L  Q  T  V  D  A  L  R  E  A  R  P  A  L  A  A
4441 CCATGATGGAACCAGCGTGCTGATCGCCAGCGGCGGCATCCGCAACGGTGTCGACATGGC
       H  D  G  T  S  V  L  I  A  S  G  G  I  R  N  G  V  D  M  A
4501 GAAATGCGTCATCCTGGGGGCCGACATGTGCGGGGTCGCCGCGCCCCTGCTGAAAGCGGC
       K  C  V  I  L  G  A  D  M  C  G  V  A  A  P  L  L  K  A  A
4561 CCAAAACTCGCGCGAGGCGGTTGTATCCGCCATCCGGAAACTGCATCTGGAGTTCCGGAC
       Q  N  S  R  E  A  V  V  S  A  I  R  K  L  H  L  E  F  R  T
4621 AGCCATGTTCCTCCTGGGTTGCGGCACGCTTGCCGACCTGAAGGACAATTCCTCGCTTAT
       A  M  F  L  L  G  C  G  T  L  A  D  L  K  D  N  S  S  L  I
```

Figure 14B.

```
4681 CCGTCAATGAAAGTGCCTAAGATGACCGTGACAGGAATCGAAGCGATCAGCTTCTACACC
      R  Q  *
     Hcs M  K  V  P  K  M  T  V  T  G  I  E  A  I  S  F  Y  T
4741 CCCCAGAACTACGTGGGACTGGATATCCTTGCCGCGCATCACGGGATCGACCCCGAGAAG
      P  Q  N  Y  V  G  L  D  I  L  A  A  H  H  G  I  D  P  E  K
4801 TTCTCGAAGGGGATCGGGCAGGAGAAAATCGCACTGCCCGGCCATGACGAGGATATCGTG
      F  S  K  G  I  G  Q  E  K  I  A  L  P  G  H  D  E  D  I  V
4861 ACCATGGCCGCCGAGGCCGCGCTGCCGATCATCGAACGCGCGGGCACGCAGGGCATCGAC
      T  M  A  A  E  A  A  L  P  I  I  E  R  A  G  T  Q  G  I  D
4921 ACGGTTCTGTTCGCCACCGAGAGCGGGATCGACCAGTCGAAGGCCGCCGCCATCTATCTG
      T  V  L  F  A  T  E  S  G  I  D  Q  S  K  A  A  A  I  Y  L
4981 CGCCGCCTGCTGGACCTGTCGCCCAACTGCCGTTGCGTCGAGCTGAAGCAGGCCTGCTAT
      R  R  L  L  D  L  S  P  N  C  R  V  E  L  K  Q  A  C  Y
5041 TCCGCGACGGCGGCGCTGCAGATGGCCTGCGCGCATGTCGCCCGCAAGCCCGACCGCAAG
      S  A  T  A  A  L  Q  M  A  C  A  H  V  A  R  K  P  D  R  K
5101 GTGCTGGTGATCGCGTCCGATGTCGCGCGCTATGACCGCGAAAGCTCGGGCGAGGCGACG
      V  L  V  I  A  S  D  V  A  R  Y  D  R  E  S  S  G  E  A  T
5161 CAGGGTGCGGGCGCCGTCGCCATCCTTGTCAGCGCCGATCCCAAGGTGGCCGAGATCGGC
      Q  G  A  G  A  V  A  I  L  V  S  A  D  P  K  V  A  E  I  G
5221 ACCGTCTCGGGGCTGTTCACCGAGGATATCATGGATTTCTGGCGGCCGAACCACCGCCGC
      T  V  S  G  L  F  T  E  D  I  M  D  F  W  R  P  N  H  R  R
5281 ACGCCCCTGTTCGACGGCAAGGCATCGACGCTGCGCTATCTGAACGCGCTGGTCGAGGCG
      T  P  L  F  D  G  K  A  S  T  L  R  Y  L  N  A  L  V  E  A
5341 TGGAACGACTATCGCGCGAATGGCGGCCACGAGTTCGCCGATTTCGCGCATTTCTGCTAT
      W  N  D  Y  R  A  N  G  G  H  E  F  A  D  F  A  H  F  C  Y
5401 CACGTGCCGTTCTCGCGGATGGGCGAGAAGGCGAACAGCCACCTGGCCAAGGCGAACAAG
      H  V  P  F  S  R  M  G  E  K  A  N  S  H  L  A  K  A  N  K
5461 ACGCCGGTGGACATGGGGCAGGTGCAGACGGGCCTGATCTACAACCGGCAGGTCGGGAAC
      T  P  V  D  M  G  Q  V  Q  T  G  L  I  Y  N  R  Q  V  G  N
5521 TGCTATACCGGGTCGATCTACCTGGCATTCGCCTCGCTGCTGGAGAACGCTCAGGAGGAC
      C  Y  T  G  S  I  Y  L  A  F  A  S  L  L  E  N  A  Q  E  D
5581 CTGACCGGCGCGCTGGTCGGTCTGTTCAGCTATGGCTCGGGTGCGACGGGCGAATTCTTC
      L  T  G  A  L  V  G  L  F  S  Y  G  S  G  A  T  G  E  F  F
5641 GATGCGCGGATCGCGCCCGGTTACCGCGACCACCTGTTCGCGGAACGCCATCGCGAATTG
      D  A  R  I  A  P  G  Y  R  D  H  L  F  A  E  R  H  R  E  L
5701 CTGCAGGATCGCACGCCCGTCACATATGACGAATACGTTGCCCTGTGGGACGAGATCGAC
      L  Q  D  R  T  P  V  T  Y  D  E  Y  V  A  L  W  D  E  I  D
5761 CTGACGCAGGGCGCGCCCGACAAGGCGCGCGGTCGTTTCAGGCTGGCAGGTATCGAGGAC
      L  T  Q  G  A  P  D  K  A  R  G  R  F  R  L  A  G  I  E  D
5821 GAGAAGCGCATCTATGTCGACCGGCAGGCCTGAAGCAGGCGCCCATGCCCCGGGCAAGCT
      E  K  R  I  Y  V  D  R  Q  A  *
           Mvk M  S  T  G  R  P  E  A  G  A  H  A  P  G  K  L
5881 GATCCTGTCCGGGGAACATTCCGTGCTCTATGGTGCGCCCGCGCTTGCCATGGCCATCGC
      I  L  S  G  E  H  S  V  L  Y  G  A  P  A  L  A  M  A  I  A
5941 CCGCTATACCGAGGTGTGGTTCACGCCGCTTGGCATTGGCGAGGGGATACGCACGACATT
      R  Y  T  E  V  W  F  T  P  L  G  I  G  E  G  I  R  T  T  F
6001 CGCCAATCTCTCGGGCGGGGCGACCTATTCGCTGAAGCTGCTGTCGGGGTTCAAGTCGCG
      A  N  L  S  G  G  A  T  Y  S  L  K  L  L  S  G  F  K  S  R
6061 GCTGGACCGCCGGTTCGAGCAGTTCCTGAACGGCGACCTAAAGGTGCACAAGGTCCTGAC
      L  D  R  R  F  E  Q  F  L  N  G  D  L  K  V  H  K  V  L  T
6121 CCATCCCGACGATCTGGCGGTCTATGCGCTGGCGTCGCTTCTGCACGACAAGCCGCCGGG
      H  P  D  D  L  A  V  Y  A  L  A  S  L  L  H  D  K  P  P  G
6181 GACCGCCGCGATGCCGGGCATCGGCGCGATGCACCACCTGCCGCGACCGGGTGAGCTGGG
      T  A  A  M  P  G  I  G  A  M  H  H  L  P  R  P  G  E  L  G
6241 CAGCCGGACGGAGCTGCCCATCGGCGCGGGCATGGGGTCGTCTGCGGCCATCGTCGCGGC
      S  R  T  E  L  P  I  G  A  G  M  G  S  S  A  A  I  V  A  A
```

Figure 14C.

```
6301 CACCACGGTCCTGTTCGAGACGCTGCTGGACCGGCCCAAGACGCCCGAACAGCGCTTCGA
      T  T  V  L  F  E  T  L  L  D  R  P  K  T  P  E  Q  R  F  D
6361 CCGCGTCCGCTTCTGCGAGCGGTTGAAGCACGGCAAGGCCGGTCCCATCGACGCGGCCAG
      R  V  R  F  C  E  R  L  K  H  G  K  A  G  P  I  D  A  A  S
6421 CGTCGTGCGCGGCGGGCTTGTCCGCGTGGGCGGGAACGGGCCGGGTTCGATCAGCAGCTT
      V  V  R  G  G  L  V  R  V  G  G  N  G  P  G  S  I  S  S  F
6481 CGATTTGCCCGAGGATCACGACCTTGTCGCGGGACGCGGCTGGTACTGGGTACTGCACGG
      D  L  P  E  D  H  D  L  V  A  G  R  G  W  Y  W  V  L  H  G
6541 GCGCCCCGTCAGCGGGACCGGCGAATGCGTCAGCGCGGTCGCGGCGGCGCATGGTCGCGA
      R  P  V  S  G  T  G  E  C  V  S  A  V  A  A  A  H  G  R  D
6601 TGCGGCGCTGTGGGACGCCTTCGCAGTCTGCACCCGCGCGTTGGAGGCCGCGCTGCTGTC
      A  A  L  W  D  A  F  A  V  C  T  R  A  L  E  A  A  L  L  S
6661 TGGGGGCAGCCCCGACGCCGCCATCACCGAGAACCAGCGCCTGCTGGAACGCATCGGCGT
      G  G  S  P  D  A  A  I  T  E  N  Q  R  L  L  E  R  I  G  V
6721 CGTGCCGGCAGCGACGCAGGCCCTCGTGGCCCAGATCGAGGAGGCGGGTGGCGCGGCCAA
      V  P  A  A  T  Q  A  L  V  A  Q  I  E  E  A  G  G  A  A  K
6781 GATCTGCGGCGCAGGTTCCGTGCGGGGCGATCACGGCGGGGCGGTCCTCGTGCGGATTGA
      I  C  G  A  G  S  V  R  G  D  H  G  G  A  V  L  V  R  I  D
6841 CGACGCGCAGGCGATGGCTTCGGTCATGGCGCGCCATCCCGACCTCGACTGGGCGCCCCT
      D  A  Q  A  M  A  S  V  M  A  R  H  P  D  L  D  W  A  P  L
6901 GCGCATGTCGCGCACGGGGGCGGCACCCGGCCCCGCGCCGCGTGCGCAACCGCTGCCGGG
      R  M  S  R  T  G  A  A  P  G  P  A  P  R  A  Q  P  L  P  G
6961 GCAGGGCTGATGGATCAGGTCATCCGCGCCAGCGCGCCGGGTTCGGTCATGATCACGGGC
      Q  G  *
           Pmk  M  D  Q  V  I  R  A  S  A  P  G  S  V  M  I  T  G
7021 GAACATGCCGTGGTCTATGGACACCGCGCCATCGTCGCCGGGATCGAGCAGCGCGCCCAT
      E  H  A  V  V  Y  G  H  R  A  I  V  A  G  I  E  Q  R  A  H
7081 GTGACGATCGTCCCGCGTGCCGACCGCATGTTTCGCATCACCTCGCAGATCGGGGCGCCG
      V  T  I  V  P  R  A  D  R  M  F  R  I  T  S  Q  I  G  A  P
7141 CAGCAGGGGTCGCTGGACGATCTGCCTGCGGGCGGGACCTATCGCTTCGTGCTGGCCGCC
      Q  Q  G  S  L  D  D  L  P  A  G  G  T  Y  R  F  V  L  A  A
7201 ATCGCGCGACACGCGCCGGACCTGCCTTGCGGGTTCGACATGGACATCACCTCGGGGATC
      I  A  R  H  A  P  D  L  P  C  G  F  D  M  D  I  T  S  G  I
7261 GATCCGAGGCTCGGGCTTGGATCCTCGGCGGCGGTGACGGTCGCCTGCCTCGGCGCGCTG
      D  P  R  L  G  L  G  S  S  A  A  V  T  V  A  C  L  G  A  L
7321 TCGCGGCTGGCGGGGCGGGGGACCGAGGGGCTGCATGACGACGCGCTGCGCATCGTCCGC
      S  R  L  A  G  R  G  T  E  G  L  H  D  D  A  L  R  I  V  R
7381 GCCATCCAGGGCAGGGGCAGCGGGGCCGATCTGGCGGCCAGCCTGCATGGCGGCTTCGTC
      A  I  Q  G  R  G  S  G  A  D  L  A  A  S  L  H  G  G  F  V
7441 GCCTATCGCGCGCCCGATGGCGGTGCCGCGCAGATCGAGGCGCTTCCGGTGCCGCCGGGG
      A  Y  R  A  P  D  G  G  A  A  Q  I  E  A  L  P  V  P  P  G
7501 CCGTTCGGCCTGCGCTATGCGGGCTACAAGACCCCGACAGCCGAGGTGCTGCGCCTTGTG
      P  F  G  L  R  Y  A  G  Y  K  T  P  T  A  E  V  L  R  L  V
7561 GCCGATCGGATGGCGGGCAACGAGGCCGCTTTCGACGCGCTCTACTCCCGGATGGGCGCA
      A  D  R  M  A  G  N  E  A  A  F  D  A  L  Y  S  R  M  G  A
7621 AGCGCAGATGCCGCGATCCGCGCGGCGCAAGGGCTGGACTGGGCTGCATTCCACGACGCG
      S  A  D  A  A  I  R  A  A  Q  G  L  D  W  A  A  F  H  D  A
7681 CTGAACGAATACCAGCGCCCTGATGGAGCAGCTGGGCGTGTCCGACGACACGCTGGACGCG
      L  N  E  Y  Q  R  L  M  E  Q  L  G  V  S  D  D  T  L  D  A
7741 ATCATCCGCGAGGCGCGCGACGCGGGCGCCGCAGTCGCCAAGATCTCCGGCTCGGGGCTG
      I  I  R  E  A  R  D  A  G  A  A  V  A  K  I  S  G  S  G  L
7801 GGGGATTGCGTGCTGGCACTGGGCGACCAGCCCAAGGGTTTCGTGCCCGCAAGCATTGCC
      G  D  C  V  L  A  L  G  D  Q  P  K  G  F  V  P  A  S  I  A
7861 GAGAAGGGACTTGTTTTCGATGACTGATGCCGTCCGCGACATGATCGCCCGTGCCATGGC
      E  K  G  L  V  F  D  D  *
                    Mvd  M  T  D  A  V  R  D  M  I  A  R  A  M  A
```

Figure 14D.

```
7921 GGGCGCGACCGACATCCGAGCAGCCGAGGCTTATGCGCCCAGCAACATCGCGCTGTCGAA
      G  A  T  D  I  R  A  A  E  A  Y  A  P  S  N  I  A  L  S  K
7981 ATACTGGGGCAAGCGCGACGCCGCGCGGAACCTTCCGCTGAACAGCTCCGTCTCGATCTC
      Y  W  G  K  R  D  A  A  R  N  L  P  L  N  S  S  V  S  I  S
8041 GTTGGCGAACTGGGGCTCTCATACGCGGGTCGAGGGGTCCGGCACGGGCCACGACGAGGT
      L  A  N  W  G  S  H  T  R  V  E  G  S  G  T  G  H  D  E  V
8101 GCATCACAACGGCACGCTGCTGGATCCGGGCGACGCCTTCGCGCGCCGCGCGTTGGCATT
      H  H  N  G  T  L  L  D  P  G  D  A  F  A  R  R  A  L  A  F
8161 CGCTGACCTGTTCCGGGGGGGGAGGCACCTGCCGCTGCGGATCACGACGCAGAACTCGAT
      A  D  L  F  R  G  G  R  H  L  P  L  R  I  T  T  Q  N  S  I
8221 CCCGACGGCGGCGGGGCTTGCCTCGTCGGCCTCGGGGTTCGCGGCGCTGACCCGTGCGCT
      P  T  A  A  G  L  A  S  S  A  S  G  F  A  A  L  T  R  A  L
8281 GGCGGGGGCGTTCGGGCTGGATCTGGACGACACGGATCTGAGCCGCATCGCCCGGATCGG
      A  G  A  F  G  L  D  L  D  D  T  D  L  S  R  I  A  R  I  G
8341 CAGTGGCAGCGCCGCCCGCTCGATCTGGCACGGCTTCGTCCGCTGGAACCGGGGCGAGGC
      S  G  S  A  A  R  S  I  W  H  G  F  V  R  W  N  R  G  E  A
8401 CGAGGATGGGCATGACAGCCACGGCGTCCGCTGGACCTGCGCTGGCCCGGCTTCCGCAT
      E  D  G  H  D  S  H  G  V  P  L  D  L  R  W  P  G  F  R  I
8461 CGCGATCGTGGCCGTGGACAAGGGGCCCAAGCCTTTCAGTTCGCGCGACGGCATGAACCA
      A  I  V  A  V  D  K  G  P  K  P  F  S  S  R  D  G  M  N  H
8521 CACGGTCGAGACCAGCCCGCTGTTCCCGCCCTGGCCTGCGCAGGCGGAAGCGGATTGCCG
      T  V  E  T  S  P  L  F  P  P  W  P  A  Q  E  A  D  C  R
8581 CGTCATCGAGGATGCGATCGCCGCCCGCGACATGGCCGCCCTGGGTCCGCGGGTCGAGGC
      V  I  E  D  A  I  A  A  R  D  M  A  A  L  G  P  R  V  E  A
8641 GAACGCCCTTGCGATGCACGCCACGATGATGGCCGCGCGCCCGCCGCTCTGCTACCTGAC
      N  A  L  A  M  H  A  T  M  M  A  A  R  P  P  L  C  Y  L  T
8701 GGGCGGCAGCTGGCAGGTGCTGGAACGCCTGTGGCAGGCCCGCGCGGACGGGCTTGCGGC
      G  G  S  W  Q  V  L  E  R  L  W  Q  A  R  A  D  G  L  A  A
8761 CTTTGCGACGATGGATGCCGGCCCGAACGTCAAGCTGATCTTCGAGGAAAGCAGCGCCGC
      F  A  T  M  D  A  G  P  N  V  K  L  I  F  E  E  S  S  A  A
8821 CGACGTGCTGTACCTGTTCCCCGACGCCAGCCTGATCGCGCCGTTCGAGGGGCGTTGAAC
      D  V  L  Y  L  F  P  D  A  S  L  I  A  P  F  E  G  R  *
8881 GCGTAAGACGACCACTGGGTAAGGTTCTGCCGCGCGTGGTCTCGACTGCCTGCAAAGAGG
8941 TGCTTGAGTTGCTGCGTGACTGCGGCGGCCGACTTCGTGGGACTTGCCCGCCACGCTGAC
9001 GCGCTGGAAACGCGCCCGCGGATTACGACCGCGTCATTGCCCTGAACCAATTTCCCGTCG
9061 GTCGAC
```

Figure 14E.

| | |
|---|---|
| *Paracoccus* sp. strain R114 | MISHTPV PTQWVGPILF |
| *Streptomyces* sp. strain CL190 | MTETHAIAGV PMRWVGPLRI |
| *Streptomyces griseolosporeus* | MTEAHATAGV PMRWVGPVRI |
| *Streptomyces* sp. strain KO-3899 | MTDTHAIAMV PMKWVGPLRI |

```
RGPVVEGPIS  APLATYETPL  WPSTARGAGV  SRHS.GGIQV  SLVDERMSRS
SGNVAETETQ  VPLATYESPL  WPSVGRGAKV  SRLTEKGIVA  TLVDERMTRS
SGNVATIETQ  VPLATYESPL  WPSVGRGAKV  SRLTEKGIVA  TLVDERMTRS
SGNVATTETH  VPLATYETPL  WPSVGRGAKV  SMLSERGIAA  TLVDERMTRS

IALRAHDGAA  ATAAWQSIKA  RQEEVAAVVA  TTSRFARLVE  LNRQIVGNLL
VIVEATDAQT  AYMAAQTIHA  RIDELREVVR  GCSRFAQLIN  IKHEINANLL
VLVEATDALT  ALSAARTIEA  RIDELRELVR  GCSRFAQLIG  IRHEITGNLL
VLVEATDAQT  AYTAARAIEA  RIEELRAVVR  TCSRFAELLQ  VRHEIAGNLL

YIRIECVTGD  ASGHNMVTKA  AEAVQGWILS  EYPMLAYSTI  SGNLCTDKKA
FIRFEFTTGD  ASGHNMATLA  SDVLLGHLLE  TIPGISYGSI  SGNYCTDKKA
FVRFEFSTGD  ASGHNMATLA  SDVLLQHLLE  TVPGISYGSI  SGNYCTDKKA
FVRFEFSTRR  PSGHNMATLA  SDALLAHLLQ  TIPGISYGSI  SGNYCTDKKA

SAVNGILGRG  KYAVAEVEIP  RKILTRVLRT  SAEKMVRLNY  EKNYVGGTLA
TAINGILGRG  KNVITELLVP  RDVVENNLHT  TAAKIVELNI  RKNLLGTLLA
TAINGILGRG  KNVVTELLVP  RDVVADVLNT  TAAKIAELNL  RKNLLGTLLA
TAINGILGRG  KNVVTELVVP  REVVERVLHT  TAAKIVELNI  RKNLLGTLLA

GSLRSANAHF  ANMLLGFYLA  TGQDAANIIE  ASQGFVHCEA  RGEDLYFSCT
GGIRSANAHF  ANMLLGFYLA  TGQDAANIVE  GSQGVVMAED  RDGDLYFACT
GGIRSANAHY  ANMLLAFYLA  TGQDAANIVE  GSQGVVTAED  RDGDLYLACT
GGIRSANAHY  ANMLLGFYLA  TGQDAANIVE  GSQGVTLAED  RDGDLYFSCN

LPNLIMGSVG  AGKGIPSIEE  NLSRMGCRQP  GEPGDNARRL  AAICAGVVLC
LPNLIVGTVG  NGKGLGFVET  NLARLGCRAD  REPGENARRL  AVIAAATVLC
LPNLIVGTVG  NGKGLGFVET  NLNRLGCRAD  REPGENARRL  AVIAAATVLC
LPNLIVGTVG  NGKGLEFVET  NLNRLGCRED  RAPGENARRL  AVIAAATVLC

GELSLLAAQT  NPGELVRTHM  EMER
GELSLLAAQT  NPGELMRAHV  QLERDNKTAK  VGA
GELSLLAAQT  NPGELMRAHV  QLERGHTTAK  AGV
GELSLLAAQT  NPGELMRAHV  ELERDNTTAE  VGV
```

Figure 16.

```
Paracoccus sp. strain R114                    ------------------MTDSKDHHVAGHSLDELR.ALDDDADIDRGDSG
Erwinia herbicola (Q01335)                    -------------------MKDERLVQRKNDELDIVLDPRRAVTQASAG
Borrelia burgdorferi (O51627)                 ----------------MMDTEFMGIEPNILENKKRHIEICLNKN..DVKGGCN
Synechocystis sp. PCC 6803 (P74287)           ---------------------MDSTPHRLSDLIRIVLEEDVVGKGISTG
Streptomyces sp. CL190 (Q9KWG2)               ---------------------------MTSAQRKDDHVRLAIEQH.NAHSGRNQ
Streptomyces griseolosporeus (Q9KWF6)         ---------------------------MSSAQRKDDHVRLATEQQ.RAHSGRNQ
Sulfolobus solfataricus (P95997)              ---------------------MPDIVNRKVEHVEIAAFENY.DGLSSST
Rickettsia prowazekii (Q9ZD90)                ---------------------MPKEQNLDIERSQEHIEINLKQNY.NSTLKSG
Deinococcus radiodurans (Q9RVE2)              ------------------------------------------------
Aeropyrum pernix (Q9YB30)                     -----------------------------------MIVSSKYES.RESTL
Halobacterium sp. NRC-1 (O54623)              MGESRYNSIVFPSLVQTRLMTAQDSTQTEDRKDDELQIVQERDVE.T.TGTG
Archaeoglobus fulgidus (O27997)               ------------------------------------------------
Pyrococcus abyssi (Q9UZS9)                    ----------------------MEEQTILRKFEHIKHCLTKNVE.AHVTNG
Pyrococcus horikoshii (O58893)                ---------------------MKEELTILRKFEHIEHCLKRNVE.AHVSNG
Methanobacterium thermoautotrophicum (O26154) -------------MISDRHLEHLILCASCDVE.YRKKTG
Methanococcus jannaschii (Q58272)             -----------------MVNNRNEIEVRKLEHIFLCSYCNVE.YEKTTL
Thermoplasma acidophilum (CAC11250)           ----------------------MIGKRHEEHIRI...AENEDVSSFHN
Leishmania major (Q9NDJ5)                     --------------MSSRDCTVDREAAVQKRKDHIDICLHQDVEPHKRRTS P.r.  E.DRIAETHRAEPEVDFDAIDTATSELGREESFELLISSTGGTGE...EIERINRNHHAGHEEARVAMAVGSQRVMFTDP
E.h.  .ERWRFTHCAEPELNFSDITLETTHLNRQHQAPLLISSWTGGVER...SRHINKHLHEAHQVLKHAMGVGSQRVAHE.S
B.b.  HLKFIKHKHNAHSDFNFSEHNIKEEIFGYNISMPVFISSMTGGSKEGND...FMKSHVRIHNYLKHPIGLGSFKLLFKYH
Syn.  H.ERLMIEHCAHBAVDLDAVHLGLTLWHKSHTYHWLISSMTGGTPE...AKQHNLFHHEVHQALGHAMHLGSQRAATHNH
Str.  H.DDVSFVHHAHAGIDRPDVSLATSHAHISWQVFIYHNAHTGGSEK...TGLINRDHATHARETGVPIASGSMNAYHKDH
S.g.  H.DDVSFVHHAHAGIDRPDVRLATTHAHITWRLHLYHNAHTGGSAK...TGAHNRDHAVHARETGAAIASGSMHHFFRDH
S.s.  HLNDVIHVHQGFHGISFSEHNTKTKHFRKEISAHIMVTGHTGG...RNELGRHNHIIHEVHEKFGHPMGVGSQRVAHHKA
R.p.  L.ESIKFIHNAEEHINYDSHHTTTTHLGKDMKAHILHSSMTGGTAR...ARDINYRIHQHAQKSGHAMHLGSMRILLTKH
D.r.  ~~~~~~~~~~MRLDTVHLGRREHKAHVLHGAHTGGAEK...AGVHNRNHHTAHRNLGLGMMLGSQRVMLHHH
A.p.  L.EYVRIVHNPTHRVNLGDVSLEIDHCGGRERAHLVITGHTGG...HPDVEWINREEHSVHEELGHAIGVGSQRAAHHDH
Hal.  H.DDVHHVHNAHPHLDYDAHHPSIDHLGHDHSAHIFHESHTGG...HHNTTEINRAHHRAHSETGHAMHLGSQRAGLHLD
A.f.  ----MMLIHKAHPHVDYWKHHTEIEHFGKKHSFPLLHASHTGG...HPETKEINARHGEHVEEAGHGMGVGSQRAAHHDE
P.a.  H.EDVHHHIHKSHPHIDKDEHHLSVKHHHRKFDYPIMHTGHTGGTRKGEIAWRINHTHHQHQELNIHPLHLGSQRAMHHKH
P.h.  H.EDVYFVHKSHPHIDKDEHDLTVEHHLGRKFDYPIMHTGHTGGTRREEIAGKINHTHMAHEELNHPFGVGSQRAMHHKH
M.t.  H.EDIEIVHRAIPHINKEKHHISLDHHLHREHSSHPVMHSAIHGG...HPASMKINREIHRAHEKLGHALGLGSQRAGVHHH
M.j.  L.EDIEHIHKGTCGINFNDHETEIELFHGKKHSAHIIVSGHTGG...HSKAKEINREIHRAHEKLGHALGLGSQRAAHVND
T.a.  HWDDISHMHEADPHVNYDEHHTSVDHLHKKHKFPMIHSSHTGG...AEIAKNINHNHHAVHAHERFGGMGVGSMRAAIVDR
L.m.  IWNKYTHPYKAEPHVDLQKHHTSCEHMGKRISFPFFHSSMTGGEAHGRV...INENHHHKHCEAEKIPFGLGSMRH..HINR P.r.  SAR..ASHDL.RAHAHTVPHLANIHAVGLNMG....LGLKECLAHIEVLQHDGHYLHHHHQHAVQHEGDRDFADLGSKI
E.h.  DAGLGLDKTL.HQLAHDVPHLANIGAHLTGR....KGIDYARRHVEMHEADAHIVHHNHHGHALHPGGDRDWRG...RL
B.b.  E..YIRDHTLKH.YAHNIPHFANVHAVGHI.....VEFGISKIAEMIKRLEVHAIIVHHNAGHBLMKVDGHRNFKGIRESI
Syn.  D..LAFTYQH.HSVAHDIHFANLGLVGLNYG....YGLEQAHRHVEMHEADAHIIHHNHEHGAVHFDGDRLWSGLWSKL
Str.  S..CADTHRVLHDENHNGFVIHANHIHAHHHH....TVDNAQRHAIDLHHEANHQIHHINTAQHTPMHHEGDRSFASWVPQI
S.g.  S..CADTHRVLHRTENHDGFVMAHVNHTA........SVDNARRHAVDLHHEANHQIHHNTAQHTPMHHEGDRSFGSWPAQI
S.s.  EAR..ESHTIVHKVAHTIPIIANHLGMPHLVKG....YGLKEFQDHIQMHEADAHIAVHHNBAQHVFQHEGEPEYQ..IYAL
R.p.  D..TIKTHTYH.HHVAHDIPHLANIHAVGLNYG....VTPKECQYLIDTHKHDHHILHHNVHELTQHEGNKNWENLLPKI
D.r.  D..AWESHNVH.HVAHBILHIGHLGAHGFMLG....YGAEQARRHVDEVMHDAHAIHHNHEHGEALGRGGHTRWQGVTYRL
A.p.  S..LARTHRAAHEAHENAFHIANLHAPHLSLG....YSVREVRMHVEMHDAHAIHHNHGQHAYGHEGPFYRGVV...
Hal.  DERVLESYTQVHDAAHEDAFIYGNLGHAHL.....REYDIEMVEQAVEMHDADAHVHHNFHEHATQHEGHVDGRNCV...
A.f.  S..LADSHTVVHEKAHENAFVYHNIHEMPHV.....IERGVEIVDRAVDVMHDAHVHHNYHGEAIQHEGDLNAEKGL...
P.a.  E..TWESYYH.HDVAHEDVFHVGNHLGAPGFGRNAKKRYSVDEVLYAIEKHEHHHHHMNHLGESIQHEGHTTFSGVL...
P.h.  E..TWESYYVHRDVAHHDIFHVGNHLGAPGFGKNAKKRYSVKEVLYAIEKHEHHHHMNHDGESIVQHEGHTTYAGVL...
M.t.  E..LEGTYTIAHEEAHSAMHIGNHIGSSHI......EYAER....AVEMHDADHAVHHNHEHLGESIDHEGHVDSSGAL...
M.j.  E..LIDTYSIVHDYTNN.LVIGNLGAVNFIVD...DWDEEIIDKHIEMHDADAHIAIHNHEHLQEIIQHEGDLNFKNLYKLK
T.a.  S..IEDTYSHINESHVP.LKIANIGAPHLVRQDKDAVSNRDIAYIYDLHKHLHFDAVHHNFHEMVQHEGDRNSKGVI...
L.m.  YASAVHTHNVH.KEFCHSVPMLANIGLVGHLNYG....FGPKEVNNLVNSVRHADGGCIHHNHTCHVCQHEGHTNFEGLIEKL
```

Figure 17A.

```
P.s.  AAIAR....DVPVELLKEVGCGLQAADIAIGLRASIRHFDVAGRIGTSWSRIEYRRRQRADDDL....GLVPQDWGLQI
E.h.  AAIETLVR.ELPVELVVKDVGAGISRTVAGQFIDAATVIDVAGACGISWAAVEGES...AATEQQRSVANVEADEGIPI
B.b.  AKLSDF....LSVELIVKETGFGISPKDVKEFFSLGASYVPLAGSCGINWILVEGMKSNNLN......IASCESDEGIPS
Syn.  EALVE....ALEVEVIVKEVGNGISGPVAKRIQECCUGAIEUAGACGTSWSEVEAHE...QTDRQAKEVAHNEADEGLEI
Str.  EKIA....AAVDIEVIVKEVGNGLSRQTILLEADLEQAAEVSGRGIDFARIENGERELGDYA.......FLHGEGQSE
S.g.  AKIT....AAVDVEVIVKEVGNGLSRQTLLAEPDLIERVAEVSGREGIDFARIENSERPLGDYA........FLHGEGQSE
S.s.  ERLRDISKEL.SVEILVKESGNGISMETAKLIYSYGIKNFDTSGQGGINWIAIEMIDEDIRRGN.WKAESAKNELDEGVPI
R.p.  KEVIN....YLSVEVIVKEVGYGLSKQVAKKEIKAEQKVLEIAGSGGTEWSQVEAYE...AKNSMQNRIASSEINEGITE
D.r.  KQVAR....ELDFEVEIKEVGHGLDAATLRAEADGPPAAYEVAGAEGISWARVEQLVAHG..QVHSPD....LCELGVPE
A.p.  GKIAEAAEAA.GVEVEVKETGNGLSREAVAQERALEURCFEVAGLGGINWIKIEVLEGRKAGSPLE..AGPLQDFEGNEE
Hal.  AAIERVSEAL.SVEILVKETGNGISGETAREETAAGVDALEVAGKGGTTWSGIEAYEAAAAANAPRQKQIGTLEREEGIEE
A.f.  EVLEEVCRSV.KVEDVEAKETGAGISREVAVMEKRAGVSAIDVGGKGGTTFSGVEVYE...VNDEVSKSVGIDEWDEGLPE
P.a.  EALAEITSTI.DYEVEAKETGAGVSKEVAVEEEAVEVDAIEISGLEGTSESAVEYYE...TKDGEKRNLALKEWDEGIKE
P.h.  EALAEIKSSI.NYEVEAKETGAGVSKEVAIEEESVGIDAIEISGLEGTSWSAVEYYE...AKDSEKRKIALKEWDEGIKE
M.t.  ESISAIVESV.DVEVMVKETGAGICSEDAIEEESCEVSAIDVAGACGISWAAVETYR...ADD...RYLGELEWDEGIPE
M.j.  EIISNYKKSYKNIEFEAKQVEEGFSKEDALIEKDIGEDAIENQGSEGTEWAKVEIYE...VKEEEIKRLAEKEANEGIPE
T.a.  ...DRIKDLSGSFNIEAKETGSGFERRTAERLEIDAEVKAIEVSGVSGTTFAAVEYYEARKENNLEKMRIGETEWNEGIES
L.m.  RQLL....PHIKVEVLVKGVGHGIDYESMVAIKASGVKYVEVSGCGGTSWAWIEGREQPY..KAEEENIGYLLRDEGVPE

P.r.  VDAEREARPALAAHDGTSVLIESGGIENEVMEKCVILGEDMCEVEAELEKAEQNS.REAEVSAIRKLHLEFRTAMELLE
E.h.  EEAEVDIAEAWP....QMPLEASGGIKNEVDAAEAELREGACMVEQAAAVEGSEGVS.TEKVEIDHFNVIIEQERVECECTE
B.b.  VFTELSIDDSLKAN.....IFESGGYETEMEIEEKGIEMLGEERLIEVEAVVEFAFYDSGEDAEFGLFSDYEHIEKMSMELSG
Syn.  EWSEQQVVQNTE....QILVFEASGGIESEIDEAEAEAEGEATLVGSEAEVEAEAKIN.AQREYDHYQARLREPQIEAEECCD
Str.  EACELDAQ......DISLPVLESGGVRHPLEVVREAEGERAVESSAGFERTLMDDGVDALITKLTTWLDQEAALQTMLE
S.g.  PACELDAQ......DVGFPLLESGGIENPLEVERAEAEGAGAVESSGVFERTLIDGGVSALVAQISTWLDQEAALQTMLE
S.s.  EAETIEVRYSIP....DAFLVGESGGIESELEAEAEAEMGEDIAGMELEVEKSEIE.GKESLEQFFRKIIFELKATEMLTE
R.p.  LDSEKMLQEISK....DITIEESGGLQSEIDEAERMGENIFGLAGKLEKAEDIA.ESLELEEIQVIIEQEKITMLCTE
D.r.  EQAERQ.ARKTLPG.AQ..LEAEGGIRSELEAARELSEGAEVVAREELEEPALDS.SEAAEAWLRNFIQEERVALEVGE
A.p.  EAAEMEAR..TAAPD...AYIEESGGVENELEAARAEAEGEDAAEGVELEAIRSLLSGGRQATLKLLKAIEYQEKTEVYMVE
Hal.  EASTIECV...AE....HDCVEASGGVRTGLEVKAEAEAGERAGGELAKEFEKPETDG.PDAEIERVGDLIAEERTAMEVTE
A.f.  EFEIVDCR...GI....LP.VEETGGLPSELVEEESUAIGEELGSAELEFERAEVES.AEKVREEIEYFRRGEKTAMELTE
P.a.  EISEAEVRW.AT....NLPIEESGGMEDEITMEERLEMGESMVEIELEVERPEAKGDVEGVIRIIKGYAEEIRNVMELVE
P.h.  EISEAEVRW.AT....NLPIEESGGMEDEITMEERLEMGEESMVEIELEVERPEAARGDVEGVVRIIRGYAEEIKNVMELVE
M.t.  EASETVEVVE.SV....SIPVEESGGIESEIDAAEAISEGEAEMVEIELEVEAEGHGYRE.EIKVIEGFNEAERTAMELAE
M.j.  EAEIFEVKSVY.....DGIVEGGGIRGELDEIAEYCEEIGCDCCSVELEIEKASLKGW.EEVVKVLESYIKEFKIAMELVE
T.a.  PAEVYYC...SD....LAPVEGEGGLENELELEKAEAEMGETAGEFERSLEKDE.DTDPEMLKNIELIQRBFRVALELTE
L.m.  DVCEERESAPLTVNGDLH..LEAEGGIRNEMEVELAELMMGEAEYATAEMEFEAAELES.SEAEVRAVIQRMQEERVSMETCE

P.r.  CGTLADEKDNSSLIRQ
E.h.  SRSLSDEKQADIRYVRDTP
B.b.  SKSLLEFRNNKYFLSSYLLDELGVFKQFYGT
Syn.  AANLTQEAQVPL.WDRQSGQRLTKP
Str.  ARTPADETRCDVLLHGELRDFCADRGIDTRRLAQRSSSIE.ALQTTGSTR
S.g.  ARTPADETRCDVLIHGPLRSFCTDRGIDIGRFARRSSADIRSEMTGSTR
S.s.  SKNVEAEKRSSIVILGKLKEWAEYRGINLSIYEKVRKRE
R.p.  SCTLKDEAKAEIMW
D.r.  YRDVREVRGG
A.p.  ETRVRGEWRAPIVVWGRLAEEAEARGIDPRWYTNTLRLEALVYKDVK
Hal.  SGSIDEEQQVEYVLHGKTREYVEQRTSSE
A.f.  CKNVEEEKGLKVFVSGRLKEWIDFRG
P.a.  ARNIKEERKVPLVITGFVREWLLQR.IDLNSYLRARFKM
P.h.  ARNIREERRVPLVITGFVREWLLQR.IDLNSYLRSRFKH
M.t.  AETLDDEKKSPVIITGHTGEWLNQRGFETKKYARRS
M.j.  AENIEEEKKTSYIVKGTLKEWISQRLK
T.a.  NKNVYEEKFTKKVIVDPLRSWLEAK
L.m.  ARNIEEERRMKVIELGHL
```

```
?QD?TPVTYD E?VALWD..E IDLTQGAPDK ARGR...?R? AG?EDE.K?I ?VDRQA
?NQ?TAL?VA D?EKV?FEEV NLDETNSAQF AGYENQD?A? VE?LDH.Q?R ?SKVEK    (AAG02453)
?DQ?TRL?VS K??DL?YEQV QLDDNGNANF DIYLTGK?A? TA?KEH.Q?I ?HTNDKN   (AAG02448)
?DN?TEL?IA E?FAM?A..E TLDTDID.QT LEDELK.YSI SA?NNT.V?S ?RN       (AAG02438)
?DS?TRIT?D E??TI?S..E TLPEHGECAE YTSDVP.?SI TK?END.I?Y ?KI       (AAG02443)
?NE?QEVS?E D?DSF?KRFD DLEFDHATEQ TDDDKSIYY? EN?QDD.I?Q ?HIPK     (AAG02427)
?NN?IEVS?D E??HF?KRFD QLELNHELEK SNADRDI?Y? KS?DNN.I?E ?HIAE     (AAG02433)
?NN?TEV??D A??TF?KRFD DVEFDEEQDA VHEDRHI?Y? SN?ENN.V?E ?HRPE     (AAG02422)
?DN?KAL??E E??KF?NRFD NLEFDTETEL EVEPKGN?Y? KE?SDN.I?Y ?DTVK     (Q9ZB67)
IAR?KSVDYA T?REL.HEYT LPSDGGDHAT PVQTTGP?R? AG?NDH.K?I ?EAR      (Q9KWG1)
VSR?RPIDYA G?REL.HEWA FPARRGAHST PQQTTGP?R? SG?SGH.K?L ?RAC      (Q9KWF5)
IKN?NNANFE E?KDF?QNKI IPGESRG... .......?Y? KELRNDGY?V ?GYRA    (O51626)
```

Figure 18B.

```
Paracoccus sp. strain R114    MTDAVRDMIA RAMAGATDIR AAERYAPS   A SKYWGKRD AARNL LNSS
Streptococcus pneumoniae      ---------- ------MDRE PVTVRSYA   AIIKYWGKKK  KEMV ATSS
Streptococcus pyrogenes       ---------- ------MDPN VITVTSYA   AIIKYWGKEN QAKMI STSS
Enterococcus faecalis         ---------- --------ML SGKARAHT   A IKYWGKAN  EY L MNSS
Enterococcus faecium          ---------- --------MF KGKARAYT   A IKYWGKKN  E  L MNNS
Staphylococcus haemolyticus   ---------- -------MKK SGKARAHT   A IKYWGKA   EA   PMNNS
Staphylococcus epidermis      ---------- -------MVK SGKARAHT   A IKYWGKAD  TY  IPMNNS
Staphylococcus aureus         ---------- -------MIK SGKARAHT   A IKYWGKKD  A   PMNNS
Streptomyces sp. CL190        MRSEHPTTTV LQSREQGSAA GATAVAHP   A IKYWGKRE  R   CTTS
Streptomyces griseolosporeus  ---------- ---------. .ATAVAQP   A IKYWGKK   H  VL RTDS
Borrelia burgdorferi          ---------- --------M  KI CKVHASL A IKYWGK D VF NI ATSS
```

Figure 19.

```
Paracoccus sp. strain R114      ------------------------MSTGRPEA GAH PK I  SGEHS L  A
Streptococcus pneumoniae        ------------------------MTKKV  V Q HS     IGEHAV   Y
Streptococcus pyrogenes         ------------------------MNENI  Y K HS     IGEHAV   Y
Enterococcus faecalis           ------------------------MNIKKQ  L  T K II MGEHAV
Enterococcus faecium            ------------------------MANY   Q ESS  III MGEHAV
Staphylococcus haemolyticus     ------------------------MVQR  Y ESN  K II IGEHAVTF E
Staphylococcus epidermis        ------------------------MTRQ  Y EST  III MGEHAVTF Q
Staphylococcus aureus           ------------------------MTRK  Y EST  III IGEHAVTF E
Streptomyces sp. CL190          MQKRQRELSA LTLPTSAEGV SESHRARSV  I R HA A II LGEHAV   A
Streptomyces griseolosporeus    ---------- MTLPTSVEEG SKAHRARAV  T R HA A II LGEHAV   T
Borrelia burgdorferi            ------------------------ML RIRKPA    F LGEHSA   F P L MAIARY TEVWFTPLGI GEGIRTTFAN LSGGATYSLK LLSGFKSRLD RRFEQFLNGD LKVHKVLTHP DDLAVYALAS
P SL LLEV E TCKVVSAE .... PWRLY EED....... ....T SMAV YASLEYLDI. .TEAC..VRC ..........
P  L LTDI E VCHIFPAD ...KPLVFD FYD....... ....T STAI YAALDYLQR. .LQEP..IAY ..........
P  F FQAT EITAVFTPAK TM...QIDCA YFTGL EDVP QE ANIKEVV QQTLHFLKED TFKGT.. TL ..........
P  F FYAT K TAFLEELD AMD.DQLVSS YYSGN AEAP HA KNIKKLF ...IHLKKQH DIQKN.. QL ..........
P  I  FTSG K KVLIESLE KGNY AIQSD VYDGP YDAP EH KS IG.. ....HFVENK KVEEP.. LI ..........
P  I  FNAG KIKVLIESLD EGNY SITSD VYDGM YDAP EH KSIIN.. ....RFVEKS GVKEP.. SV ..........
P  V FNAG KIKVLIEALE SGNY SIKSD VYDGM YDAP DH KS VN.. ....RFVELN NITEP.. AV ..........
P L  IPQL T TASVGWSS EASD AGGLS YTMTGTPSRA LVTQASDGLH RLTAEFMARM GVTNAPH DV ..........
P  M IPQL A TASAGWSG RSAE RGGPT FTMTGSASRA VTAQA DGLR RLTASVKAHT GVTDGQH DV ..........
 V GATVP.. .IYMDLIYSV SKNWK..... ....Y GKPS TR NS ISFI V........S NYSKVNPIEF ..........

LLHDKPPGTA AMPGIGAMHH LPRPGELGSR TEL SA G M  SSA IVA TT VLFETLLDR PKTPEQRFDR  RFC RLK  K
.......... .......... .......E D SA EK GM  SSA ISI AI  VF YYQA D PHDV I   NR E   MN
.......... .......... ......E V SQV QK GM  SSA VSI AI  VFSYCQE P SDDL I   NK E   TN
.......... .......... .........T ST PAE GM  SSA T  IV  SL  YFDY AYTYQ F     SLS K  CN
.......... .......... .........T E ST PAE GM  SSA V  VT  FY YLAF P SREI LEN  QLS K  CN
.......... .......... .........K  Q ANL PS G   SSA V  FI  SY YLGL P TDKE LENA DW    HGK
.......... .......... .........K  Q TNL PS G   SSA V  FV  SY FMDQ P DDKT IKEA NW    HGK
.......... .......... .........T  Q TNL PS G   SSA V  FV  SY FLGK S TKEE IEKA NW    HGK
.......... .......... .........ILD GA  PHG G   SSA GSR IA LALADLFGH E AEHTAYE    QT E M HCR
.......... .......... .........SLD GA PPG  G   SSA N  II LALAD LFGR E TEGEVFD   QE E NLT CR
.......... .......... .........D I SE  PIGV L  SSASLSLCFA EYITSHFEY KDCNKI ...  A NQI N FEK

AGP D ASVV RGGLVRVGGN GPGSISSFD  PE HDL  AGR GWYWVLHGRP  SGTGECVSA VAAAHGRDAA LWDAFAVCTR
 SGLD K CL SDQ IR IKN VGFTELEMD ..SA L I D  GVY H RE  IQV QNKGKD A....LPFLH AL  E TQQ  E
 SGLD K CL SDHAIK IRN IGFETIEIA ..NG LII D  GIH H TRE  NK AQFEET N....LPYLA KL AI TQALE
 SG  D AATS GAD LF TR  FPPTHFSMN  S.NA L WAD  IK Q RE  KDIAQLAQN NPTAIAETMK QL GSFTKE  K
 SG  D AATS SLQ IY TK  HPFDYFS NI ..BAFLI AD  IK Q RE  KD AHLFET QPHETGQMIQ KL YL TKQ K
 SG  DTK IV TNQ VWYQK  EVEILKT D ..DG MW ID  VK S IKQ  ED HQLCD. NDKNYMQVVK HI S VYS  S
 SG  DTQ IV SNK VW KQ  QAETLKS D ..NG YM  I D  VK S IKQ  ED HVLCE. SDE.YMKYIE HI T VHS  S
 SG  DTQ IV SGK VW QK  QAETLKT  T ..EG YM V ID  VK S IRQ  ED HKLCE. DPQ.YMSHVK HI K VLR  S
 S VD A  VG ASR LL QQ  RTE...R AI GC SLFI   S VPGS KE  EMLREGFTR SAGTQERFVG RATE TEA R
 S VD A  VG ATA LL RA  TAQ...A DI GC ALF  AD  S TA S KE  IELLRAGFRA GAGKEERFMH RAAH LVDD R
SSGM IRLID LNGTFYLEKK ENVLHSKKIK DSGFYFLIGA IKRDLT K I  VNLKKDLLS NAYLFV.FIE KL LAVSNSY

ALEAALLSGG SPDAAITENQ R LERIGVVP AATQALVAQI EEAGGA IC  A SVRGDHG GAVLVRIDDA QAMASVMARH
V  SQKYAEG  GLIFSQAHL H KEIG  SP EA F VETAL SY   G KMS  G LE   I A  VTNLTH QE LAER  EK A
R  NQKNKVA IGQLMTQAHS A KAIG SIS KA Q VEAAL RA   G KM   GG  LE  M A  DTKDM EK  SHK  KEE A
Q  LQDDKQK  GQLMTLAQE Q QQ  TV ND MLER VALSL EH   G K T  GG RG  M I  TDNKKT QT  AQT    NC A
Q   IENSPET  AQTMDESQS L LEK TISND FLNL IQTAK DT   GA K T  GG RG  M A  QTKTK QE  SQA E    A
E   HHSFDQ   ATIFNQCQD D RT TV HD KIEMFLRLGE EN SVAG K    GG RG  M LI  AKELQT KN  VAAV K  A
ES   QHDFHH  ADIFNACQE D RH T V HD KIEK L QIGK EH  IA  K  T  G  RG  M LL  DENLKT KT  VAAV K  A
DV  HHNFEA  ADIFNECHA D KA T V HD KIEQ MKIGK EN  IAG K T  G  RG  M LL  AKDLPT KN  VKAV K  A
Q ADGRPEE  GSQLTYYHE L HEARL T  GI ALVEAAL KA SG  K IT  G  LG   M   QA RP.EQ RE VTRQ HE  C
ASLAEGEPEA FGSCLTEYHG L RGAGL T   RI A VDAAL QADS  K IT  G  LG  VL   MSRP.ER EE VARQ HA  C
ASFQNKDVYS   ANEMNIAQC  L KR GL ND TL W ISEGI KL  ISG K S  GA KG  A F F  FESLIK NI VQKE INNM.L

PDLDWAP RMSRTGAAP GPAPRAQPLPGQG
VQ   ES                         (AAG02455)
VN   QM                         (AAG02450)
VA   QS EVKK                    (AAG02440)
AE   QG GVHTYV                  (AAG02445)
QH   EK GG                      (AAG02430)
AH   EH GG                      (AAG02435)
```

Figure 20A.

```
AHTIENLGG          (AAG02424)
VQLVVPLKGLDNHAQ    (Q9KWG5)
VRTAVQLR.RSTHER    (Q9KWF9)
KDSKIDLLKLKVIET    (O51631)
```

Figure 20B.

```
Paracoccus sp.strain R114    ---MDQVIRA SAPGSVMITG ERAWV.YGHR AIVAGIEQRA HVIIVP....
Streptococcus pneumoniae     ------MIAV KTCGKIFWAG EYAILEPGQL ALIKDIPIYM RAEIAFSDSY
Streptococcus pyrogenes      ----MSNYCV QTGKLWLTG EYAILIPGQK ALIHFIPLMM IAEISPAAHI
Enterococcus faecalis        ------MIEV TTEGKLFIAG EYAIVEPCHP AIIVAIQFV IVIVEETTD.
Enterococcus faecium         ------MIEV SAEGKIMIAG EYAIVETCHP AVIAAIQFV IVIVESARK.
Staphylococcus haemolyticus  ------MIQI KAEGKLMVAG EYAIVTEPGYK SVLIAVDRFI ASIEASNAV
Staphylococcus epidermis     ------MIQI KAEGKLMIAG EYAIVTEPGYK AAIIEASNKV
Staphylococcus aureus        ------MIQI KIEGKLMIAG EYAIVTEPGYK SVLIAILRFV AAIIEEATQY
Streptomyces sp. CL190       MTTGQRTIVR HAEGKIFVAG EYAIVDPGNP AILVAIERHI SVIIVSDADAD
Streptomyces griseolosporeus -MTGPRAVTR RAIGKLFVAG EYAIVEECNR AILVAIERYI IVIVSD....
Borrelia burgdorferi         ----MDLISF SVIGNILLMG ERTILEEKGL GLAIAINKRA FFSFKKSDS.

RADRMFRITG  ..QIGAIQQG .......SLD DLPA.GGTYR ...FILATIA RHA....... PD..LPCGID MDII...TSGI
R.......IYS ........... .......DMF DFAVDLRPNP DYSLIQETIA LMGDFLAVRG QN...ERPIS UKI...CGKM
Q.......LAS ........... .......DMF SHKAGMTPDA SYALIQATVK TFADIL...G QSIDQIEPIS III...TGKM
EIS....IQS  AQYSSLIIRW TRRNGELVL. II....R.EN PFHYILAAIA LTEKIAQEQN KE...ISFYH IKV...TSEI
VIS....IQS  AQYSGMEIRW TRRNGELVL. II....R.EN PFHYILAAIR LTEKIAQEKN IL...ISFYD IKV...TSEI
TST....IHS  KTLHYEIVTF NRNEDKIDIS IA....NAAS QLKYIVTAIE VFEQIARSCN VK...IKHIH IEI...DSNI
EIS....IHS  KTLHYEIIKF DRNEDRIEIS IV....QAAK QLKYIVTAIE VFEQIVRSCN MN...IKHIH ITI...DSNI
KIT....IHS  KALHHNIITF SRDEDSIVIS IP....HAAK QLNYIVTAIE IFEQIAKSCD IA...MKHIH ITI...DSNI
TIAA.DVVIS  SDLGPQAIGW RWHDGRLVVR IPDDGQQARS ALAHIVSAIE TVGRLLGERG QK...VPALT ISV...SSRI
.IAAPGVVVS  SDIGAGEIHH PWQDGRLT.. ...GG....T GTPEIVAIVE TVARLLAERG RS...VPPLG WSI...SIT
........... ........W RFFSKKKKID IFSLIENRSD ...FI....F KMFAILSQNC ..FFNIENIA YDVYIDTINF

....DPRLII  GSSAAVTIAC LGILSRLAGR GTEGLHDDAL RIVRA..... IQGRISGADL AASLHGGFVI IR........
.EREIKKFGI  GSSIGVVVLV IKAILALIMI S..VDQNLLI IITSAV.LLK RGDNISMGDL ACIVAEDLVL IQ........
.ERDIKKFGI  GSSISVTLLT LKAISAYMQI T..ITPELII IGAYT.LLK QGDNISMGDI ACIAIQTLVI IT........
DSSNIRIYGI  GSSIGVTIGT IKIINIIID G..IENEEII KISALI.HLA VQGNISICGDI AASIGIIIF FS........
DSSNIRIYGI  GSSIGVTVAT IKAINVEIAI N..ISQLEII IIIALI.NLA VQDNISICGIIF AASIGIIF FS........
DDASINIKYGI GSSIGVIUSV IKPINEIIDM Q..ISNLYII IIVIS.NMR LQSLSICGDI AVSVMISIIA IS........
ADNSIQIYGI  GSSIAVLISV IKINEIIGI E..ISNLYII IIVII.NMK LQSLSICGDI AVSVMIGIII IS........
DDSNIHIYGI  GSSIAVLISV IKVINEIIDM K..ISNLYII IIVII.NMK LQSLSICIDI AVSVMIIIIA IS........
HE.DIRIFGI  GSSIAVTVAT IAIAAHICGI E..ISTDERI RIAMLI.TAE LDPKISGGDL AASTWGIIP IQ........
HE.DIRIFGI  GSSIAVTVAT ISAVAAHCGI E..ITAEERI RTALI.SAR IDPRISGCDI AIGTWGIIP IR........
FFNDITIKGF  GSSAVIAIGI IGILFLIHNA TNVVEKGEIS KYCLEIYRYS QGGIIGSYDI ATSIFGIVIE FEGGFNPKCR

.....APIGG  AAQIEALPVP PGPFGIRY.. AIYKT...PT AEVLRLVADR MAGNEAIFDA LYSRMGASAD ..........
.....SIIRQ  KAAAWLEE.E NLATVIERDI .CFFI..SQV KPTLECDFIV GITKEVIVSS HMIQQIKQN. .....INQNI
.....SIIRE  QISNWLQT.M PLKKIIVKDI .GYHI..QVI QPALPCDFIV GITKIPIISR QMIQQITAS. .....ITPAI
.....TIIHD  WINQKVTT.E TLTDLIAMDI IELMI..FPI KVIKQLRLII GITISIPASTS DINIDRIIHQSK EEKQAAIEQI
.....TIIHP  WLQEQETQ.H SISELIALDI IGLSI..EPI IAIEDLRLII GITISIPASTS DINIDQIHISR EDKMVAIQLI
.....TIIHD  WIKQQMEE.H SVNEVIEKNI IGLHI..EPI QAIENMEVLI GITISIPASSP HIISEIKILK SDPSF.IGRI
.....TIIHD  WIKQQMEE.T SVNDVIEKNI IGLHI..EPI QAIENMEVLI GITISIPASSP HIISEIKILK SDPSF.IGDI
.....TIIHE  WIKHQIED.T TVEEVIIKNI IGLHI..EPI QAIENMEVLI GITISIPASSP HFISEIKRLK SDPSF.IGDI
.....APIRA  FILDLARR.V GVDRTIIKAPI IGHSV..RRI PAIKGLTLEV GITIEPASTA SAISDLHIRT WRGSASHQRI
.....APIRD  AILDLTRR.Q GVDEAIRAPI ICFSV..RLS P.IRNLCLEV GITIEIVSTT SILTDLHIRT WRGSPAIRRY
QLGAVEINDF  YLMQGLQAIK TTTSICIYNK HRNSILDFII KCNLEMKKIV ..LNASNIKS AIISSLRIAK ELGLAIGEAI

........... ........... ...IAIRAAQ GLDWAAFHDA LNEYQRIMEQ LGVSDDILDA .IIREARDAG AAVIKISISI
.....ISSS.  ....KETIVS LVEILEQGIKA EKVIEQVEVA SKLLEGIIST. ...DIYIPLI RQIKEASQDL QAVIKSCAGI
.....IRTS.  ....YQLTQS AMVIILQEIHK EELKKSLAGA SHLLKEIIHP. ...AIYHPKI VTIVAACQKQ DAVIKSCAGI
.....IMKI.  ....RLCIET MINGFNTIKI SVIQKQITKI IOLLAEIISSL TGVVIEIEAL KNIGILAIESY TIAIKSCAGI
.....IKNI.  ....TECIVNE MIKGFKENNV TLIQQMIRKN IGLLHDISAI TGVVIEIPAI NKIGNLAIGQY EGIAIKSCAGI
.....IDQI.  ....HTGIVEN LIVIFKTDNI KGVQKMIRQN IMIIQQMDNE ATVDIIIENL KMIGIIGIRY GAIAIKTSAGI
.....IDQS.  ....HAGIES LIGIFKTNNI KGVQKMIIII IRIIQSMDNE ASVEIIDKI KKIGIVGIKH GGIASKTSAGI
.....IEDS.  ....HRCIKS LIHIFKTNNI KGVQKMVIQI ITIIQRMDKE ATVDIIIEKI KYIGLIAIKY HIASKTSCAGI
.....VETT.  ....TDGIRS AVTILESIDD TSLLHEIIRA IQELARIIDDE VGLGIILITPKI TAICIAAIAV GIAIKPSCAGI
.....VGAT.  ....GEIVDA AVIAILEDIDT EGLLRQVIRA IHEMVRIIDDE VGLGIIIIPEL TAICIAIAGIR. AGIAIKPSCAGI
GVSAAIPSIF  DHLLGQI..D LIKAILGAICNE TFL..VYIPI IEAF.NISKI ISIVLINEGI KFESIKC--- ----------

IIDIVLAL.G DQPKGFVPAS IAEKGLVFDD ----------
GGDCCIIALSF DAQSSRN... TLKNRIIADLI IELI....IQ ERIIHDDKS                    (AAG02457)
GGDCCIIALAF N.QDARD... TLISKIQEAD IALI....IQ ERWIEND                       (AAG02452)
GGDCCIIVI.F RQ...KSGII PLMTAIIEKDI IITIPLHVIT Y..IQKECKE KHESKR            (AAG02442)
GGDCCIIVI.V DQ...KSGII PLMSAIIEKAE ITEIPLHVIS D..QRKENR                    (AAG02447)
GGDCCIIAI.I DNRIDKNRII ..YNEIASHI IKEIKFKII. H..IQ                         (AAG02432)
GGDCCIITI.I NKVIDKNIII ..YNEIQMND IKEIKFKIV. H..IQ                         (AAG02437)
```

Figure 21A.

```
GGDCGTI.I NKDVDKEKE.  ..YDEWTKHG KELKFNIM. H..GQ       (AAG02426)
GGDCGIAL.L DAEASRD.HT HVRQRWSTAG VLPLPLTPAL E..GI      (Q9KWG3)
GGDKGIAL.L DAEARYD.RS PLHRQWAAAG VLPLLVSPAT E..GVEE    (Q9KWF7)     Figure 21B.
---------- ---------- ---------- ----------           (051630)
```

```
NcoI
CCATGGCATCCGGTCGGATGCCGTCTATGTTGGCCCGAACAGGCAGCAGGAGGCCCCATGAGCGATATCCAGACCCTCTCGTTCGAGGAAGCCATGCGCGAGCTGGAGGCGACCGTCGGC
              XseB  M  S  D  I  Q  T  L  S  F  E  E  A  M  R  E  L  E  A  T  V  G

AAGCTGGAAACCGGCGAGGCGACGCTCGAGGACTCCATCGCGCTCTATGAACGCGGGGCGGCGCTGCGCGCCCATTGCGAAACCCGCCTGCGCGAGGCCGAGGAGCGGGTCGAGAAGATC
 K  L  E  T  G  E  A  T  L  E  D  S  I  A  L  Y  E  R  G  A  A  L  R  A  H  C  E  T  R  L  R  E  A  E  E  R  V  E  K  I

ACCCTGGCCGCGAACGGGCAGCCGTCCGGAACCGAGCCCGCCGAGGGCCTGTGATGCAGGCCCGCCTGGCCGAGATCCGGCCCCTGGTCGAGGCCGAGCTGAACGCCGCCATCGACGCGC
 T  L  A  A  N  G  Q  P  S  G  T  E  P  A  E  G  L  *
                                       IspA (M) M  Q  A  R  L  A  E  I  R  P  L  V  E  A  E  L  N  A  A  I  D  A  L

TGCCCGCGGGCGATCTGTCGGATGCGATGCGCTATGCCGTGCAGGGCGGCAAGCGGCTGCGCGCGTTGCCTGGTGATGCAGTCGGCGCGCCTGCACGGGCTGGAACGACGACGCAATCGC
 P  A  G  D  L  S  D  A  M  R  Y  A  V  Q  G  G  K  R  L  R  A  L  P  G  D  A  V  G  A  P  A  R  A  G  T  T  T  Q  S  L

TGCCCGTCGCCGCGCGGTCGAGGCGCTGCACGCCTACAGCTTGGTCCATGACGACCTGCCCGCGATGGATGACGACGACCTGCGGCGCGGTCAGCCCACCGTCCACGTCAAATGGACCG
  P  V  A  A  A  V  E  A  L  H  A  Y  S  L  V  H  D  D  L  P  A  M  D  D  D  D  L  R  R  G  Q  P  T  V  H  V  K  W  T  E

AGGCGACCGCGATCCTTGCGGGCGATGCGCTGCAGACGCTGGCCTTCCAGCTGCTGGCCGATCCGCGCGTGGGCGACGATGCGGCGCGGATGCGGCTGGTCGGTTCGCTGGCGCAGGCAT
  A  T  A  I  L  A  G  D  A  L  Q  T  L  A  F  Q  L  L  A  D  P  R  V  G  D  D  A  A  R  M  R  L  V  G  S  L  A  Q  A  S

CGGGGGCTGCGGGCATGGTCTGGGGCCAGGCGCTGGACATCGCGGCCGAGATCTCGGGCGTGCCGCTGGATCTGGACGCGATCATCCGCCTGCAGGGTGGCAAGACCGGCGCGCTGATCC
  G  A  A  G  M  V  W  G  Q  A  L  D  I  A  A  E  I  S  G  V  P  L  D  L  D  A  I  I  R  L  Q  G  G  K  T  G  A  L  I  R

GCTTTGCCGCGACCGCCGGGCCGCTGATGGCGGGGGCGGACCCTGCCGCGCTGGACGATTATGCGCAGGCCGTCGGGCTGGCCTTCCAGATCGCGGACGACATCCTGGACGTCGAGGCT
  F  A  A  T  A  G  P  L  M  A  G  A  D  P  A  A  L  D  D  Y  A  Q  A  V  G  L  A  F  Q  I  A  D  D  I  L  D  V  E  G  C

GCGAGGCCGCGACCGGCAAGCGCGTCGGCAAGGATGCGGATGCCAACAAGGCGACCTTCGTCTCGCTGCTGGGGCCTGAGGGGGCGCGGTCCGAGGCGCGTCGCCTGGCCGATGCGGGGC
 E  A  A  T  G  K  R  V  G  K  D  A  D  A  N  K  A  T  F  V  S  L  L  G  L  E  G  A  R  S  E  A  R  R  L  A  D  A  G  Q

AGGACGCGCTGGCGGGTTACGGCGATGCTGCGGGGAACCTTCGGGACCTGGCGCGCTTCGTGATCGAACGCGACAGCTGATCGCCGCCTTCCCGCCAAGGGGCAAGATGATGACCGACGG
 D  A  L  A  G  Y  G  D  A  A  G  N  L  R  D  L  A  R  F  V  I  R  R  D  S  *                        Dxs  M  M  T  D  G

ACCCGCAACCCGATCCTGGACCGCGTCCAGCAGCCATCCGACCTGGCATCGCTGGACGATGCGCAGCTGCGCCTGCTGGCGGACGAGCTGCGGGCCGAGACCATCGACATGTCAGCCG
 P  A  T  P  I  L  D  R  V  Q  Q  P  S  D  L  A  S  L  D  D  A  Q  L  R  L  L  A  D  E  L  R  A  E  T  I  D  I  V  S  R

CACGGGCGGTCACCTGGGCGCGGGGCTGGGCGTGGTCGAACTGACGGTCGCCCTGCACGCCGTCTTTCGGGCGCCGGCGCAAGATCGTCTGGGACGTGGGGCATCAATGCTATCCCCA
 T  G  G  H  L  G  A  G  L  G  V  V  E  L  T  V  A  L  H  A  V  F  R  A  P  R  D  K  I  V  W  D  V  G  H  Q  C  Y  P  H

CAAGATCCTGACGGGCAGGCGGGACCGGATGCGCACGCTGCGCATGGGCGGCGGGCTGTCGGGGTTCACCAAGCGGCAGGAAAGCGCGTTCGATCCGTTCGGTGCGGGGCACAGCTCGAC
 K  I  L  T  G  R  R  D  R  M  R  T  L  R  M  G  G  G  L  S  G  F  T  K  R  Q  E  S  A  F  D  P  F  G  A  G  H  S  S  T
                                                       BamHI
CTCGATCTCGGCGGCGCTGGGCTTCGCGATGGCCGTGAACTTGGCGGGGATCC
 S  I  S  A  A  L  G  F  A  M  A  R  E  L  G  G  D  P
```

Figure 30.

```
ATGGACCCCATCGTCATCACCGGCGCGATGCGCACCCCGATGGGGGCATTCCAGGGCGAT
 M  D  P  I  V  I  T  G  A  M  R  T  P  M  G  A  F  Q  G  D
CTTGCCGCGATGGATGCCCCGACCCTTGGCGCGGCCGCGATCCGCGCCGCGCTGAACGGC
 L  A  A  M  D  A  P  T  L  G  A  A  A  I  R  A  A  L  N  G
CTGTCGCCCGACATGGTGGACGAGGTGCTGATGGGCTGCGTCCTGCCCGCGGGCCAGGGT
 L  S  P  D  M  V  D  E  V  L  M  G  C  V  L  P  A  G  Q  G
CAGGCACCGGCACGTCAGGCGGCGCTTGACGCCGGACTGCCGCTGTCGGCGGGCGCGACC
 Q  A  P  A  R  Q  A  A  L  D  A  G  L  P  L  S  A  G  A  T
ACCATCAACAAGATGTGCGGATCGGGCATGAAGGCCGCGATGCTGGGCCATGACCTGATC
 T  I  N  K  M  C  G  S  G  M  K  A  A  M  L  G  H  D  L  I
GCCGCGGGATCGGCGGGCATCGTCGTCGCCGGCGGGATGGAGAGCATGTCGAACGCCCCC
 A  A  G  S  A  G  I  V  V  A  G  G  M  E  S  M  S  N  A  P
TACCTGCTGCCCAAGGCGCGGTCGGGGATGCGCATGGGCCATGACCGTGTGCTGGATCAC
 Y  L  L  P  K  A  R  S  G  M  R  M  G  H  D  R  V  L  D  H
ATGTTCCTCGACGGGTTGGAGGACGCCTATGACAAGGGCCGCCTGATGGGCACCTTCGCC
 M  F  L  D  G  L  E  D  A  Y  D  K  G  R  L  M  G  T  F  A
GAGGATTGCGCCGGCGATCACGGTTTCACCCGCGAGGCGCAGGACGACTATGCGCTGACC
 E  D  C  A  G  D  H  G  F  T  R  E  A  Q  D  D  Y  A  L  T
AGCCTGGCCCGCGCGCAGGACGCCATCGCCAGCGGTGCCTTCGCCGCCGAGATCGCGCCC
 S  L  A  R  A  Q  D  A  I  A  S  G  A  F  A  A  E  I  A  P
GTGACCGTCACGGCACGCAAGGTGCAGACCACCGTCGATACCGACGAGATGCCCGGCAAG
 V  T  V  T  A  R  K  V  Q  T  T  V  D  T  D  E  M  P  G  K
GCCCGCCCCGAGAAGATCCCCCATCTGAAGCCCGCCTTCCGTGACGGTGGCACGGTCACG
 A  R  P  E  K  I  P  H  L  K  P  A  F  R  D  G  T  V  T
GCGGCGAACAGCTCGTCGATCTCGGACGGGGCGGCGGCGCTGGTGATGATGCGCCAGTCG
 A  A  N  S  S  S  I  S  D  G  A  A  A  L  V  M  M  R  Q  S
CAGGCCGAGAAGCTGGGCCTGACGCCGATCGCGCGGATCATCGGTCATGCGACCCATGCC
 Q  A  E  K  L  G  L  T  P  I  A  R  I  I  G  H  A  T  H  A
GACCGTCCCGGCCTGTTCCCGACGGCCCCCATCGGCGCGATGCGCAAGCTGCTGGACCGC
 D  R  P  G  L  F  P  T  A  P  I  G  A  M  R  K  L  L  D  R
ACGGACACCCGCCTTGGCGATTACGACCTGTTCGAGGTGAACGAGGCATTCGCCGTCGTC
 T  D  T  R  L  G  D  Y  D  L  F  E  V  N  E  A  F  A  V  V
GCCATGATCGCGATGAAGGAGCTTGGCCTGCCACACGATGCCACGAACATCAACGGCGGG
 A  M  I  A  M  K  E  L  G  L  P  H  D  A  T  N  I  N  G  G
GCCTGCGCGCTTGGGCATCCCATCGGCGCGTCGGGGGCGCGGATCATGGTCACGCTGCTG
 A  C  A  L  G  H  P  I  G  A  S  G  A  R  I  M  V  T  L  L
AACGCGATGGCGGCGCGGGGCGCGACGCGCGGGGCCGCATCCGTCTGCATCGGCGGGGGC
 N  A  M  A  A  R  G  A  T  R  G  A  A  S  V  C  I  G  G
GAGGCGACGGCCATCGCGCTGGAACGGCTGAGCTAA
 E  A  T  A  I  A  L  E  R  L  S  *
```

Figure 31.

```
ATGACCAAAGCCGTAATCGTATCTGCCGCACGTACCCCCGTCGGCAGCTTCATGGGCGCA
 M  T  K  A  V  I  V  S  A  A  R  T  P  V  G  S  F  M  G  A
TTCGCCAATGTCCCCGCACATGATCTGGGCGCCGCCGTCCTGCGCGAGGTCGTGGCCCGC
 F  A  N  V  P  A  H  D  L  G  A  A  V  L  R  E  V  V  A  R
GCCGGTGTCGACCCCGCCGAGGTCAGCGAGACGATCCTGGGCCAGGTGCTGACCGCCGCG
 A  G  V  D  P  A  E  V  S  E  T  I  L  G  Q  V  L  T  A  A
CAGGGCCAGAACCCCGCGCGCCAGGCGCATATCAATGCGGGCCTGCCCAAGGAATCGGCG
 Q  G  Q  N  P  A  R  Q  A  H  I  N  A  G  L  P  K  E  S  A
GCGTGGCTCATCAACCAGGTCTGCGGCTCGGGGCTGCGCGCCGTCGCGCTGGCGGCGCAG
 A  W  L  I  N  Q  V  C  G  S  G  L  R  A  V  A  L  A  A  Q
CAGGTCATGCTGGGCGATGCGCAGATCGTTCTGGCGGGGGGCCAGGAGAGCATGTCGCTG
 Q  V  M  L  G  D  A  Q  I  V  L  A  G  G  Q  E  S  M  S  L
TCGACCCATGCCGCCTATCTGCGCGCGGGCCAGAAGATGGGCGACATGAAGATGATCGAC
 S  T  H  A  A  Y  L  R  A  G  Q  K  M  G  D  M  K  M  I  D
ACCATGATCCGCGACGGGCTGTGGGATGCCTTCAACGGCTATCACATGGGTCAGACCGCC
 T  M  I  R  D  G  L  W  D  A  F  N  G  Y  H  M  G  Q  T  A
GAGAACGTGGCCGACCAGTGGTCGATCAGCCGCGACCAGCAGGACGAATTCGCCCTGGCT
 E  N  V  A  D  Q  W  S  I  S  R  D  Q  Q  D  E  F  A  L  A
TCGCAGAACAAGGCCGAGGCCGCGCAGAATGCGGGCCGCTTCGATGACGAAATCGTCGCC
 S  Q  N  K  A  E  A  A  Q  N  A  G  R  F  D  D  E  I  V  A
TATACCGTCAAGGGCCGCAAGGGCGACACGGTCGTCGACAAGGACGAATACATCCGCCAC
 Y  T  V  K  G  R  K  G  D  T  V  V  D  K  D  E  Y  I  R  H
GGCGCCACGATCGAGGGCATGCAGAAGCTGCGCCCCGCCTTCACCAAGGAAGGCTCGGTC
 G  A  T  I  E  G  M  Q  K  L  R  P  A  F  T  K  E  G  S  V
ACGGCGGGCAACGCGTCGGGCCTGAACGACGGCGCGGCGGCCGTCATGGTCATGTCCGAG
 T  A  G  N  A  S  G  L  N  D  G  A  A  A  V  M  V  M  S  E
GACGAGGCCGCACGCCGCGGGCTGACGCCGCTGGCGCGCATCGCCTCCTATGCGACGGCG
 D  E  A  A  R  R  G  L  T  P  L  A  R  I  A  S  Y  A  T  A
GGCCTCGACCCGGCGATCATGGGCACCGGGCCGATCCCCTCCAGCCGCAAGGCGCTGGAA
 G  L  D  P  A  I  M  G  T  G  P  I  P  S  S  R  K  A  L  E
AAGGCGGGCTGGTCGGTCGGCGACCTGGACCTGGTCGAGGCGAACGAGGCCTTTGCCGCG
 K  A  G  W  S  V  G  D  L  D  L  V  E  A  N  E  A  F  A  A
CAGGCCTGCGCCGTGAACAAGGACATGGGCTGGGATCCGTCCATCGTGAACGTCAACGGC
 Q  A  C  A  V  N  K  D  M  G  W  D  P  S  I  V  N  V  N  G
GGCGCGATCGCCATCGGCCACCCGATCGGCGCCTCGGGGGCGCGGATCCTGAACACCCTG
 G  A  I  A  I  G  H  P  I  G  A  S  G  A  R  I  L  N  T  L
CTGTTCGAGATGCAGCGCCGCGACGCCAAGAAGGGCCTTGCGACGCTGTGCATCGGCGGC
 L  F  E  M  Q  R  R  D  A  K  K  G  L  A  T  L  C  I  G  G
GGCATGGGCGTCGCCATGTGCCTCGAACGCTGAACGACCGGCGTGTGCGCAATTTAATTG
 G  M  G  V  A  M  C  L  E  R  *
CGCACACGCCCCCTGCAAAGTAGCAATGTTTTACGATAACGAATGAAGGGGGGAATCATG
                                                           M
```

Figure 33A.

```
TCCAAGGTAGCACTGGTCACCGGCGGATCGCGCGGCATCGGCGCCGAGATCTGCAAGGCG
 S   K   V   A   L   V   T   G   G   S   R   G   I   G   A   E   I   C   K   A
CTTCAGGCCGCAGGCTATACCGTCGCCGCGAACTATGCCGGCAATGACGACGCGGCCAAG
 L   Q   A   A   G   Y   T   V   A   A   N   Y   A   G   N   D   D   A   A   K
GCCTTCACCGAGGAAACCGGCATCAAGACCTACAAGTGGTCGGTCGCCGATTACGATGCC
 A   F   T   E   E   T   G   I   K   T   Y   K   W   S   V   A   D   Y   D   A
TGCAAGGCCGGCATCGCCCAGGTCGAAGAGGATCTGGGCCCGATCGCCGTGCTGATCAAC
 C   K   A   G   I   A   Q   V   E   E   D   L   G   P   I   A   V   L   I   N
AATGCCGGGATCACCCGCGACGCGCCCTTCCACAAGATGACGCCCGAGAAGTGGAAGGAG
 N   A   G   I   T   R   D   A   P   F   H   K   M   T   P   E   K   W   K   E
GTCATCGACACCAACCTGACCGGCACCTTCAACATGACCCATCCGGTCTGGCCGGGCATG
 V   I   D   T   N   L   T   G   T   F   N   M   T   H   P   V   W   P   G   M
CGCGAACGCAAGTTCGGACGCGTCATCAACATCAGCTCGATCAACGGGCAGAAGGGCCAG
 R   E   R   K   F   G   R   V   I   N   I   S   S   I   N   G   Q   K   G   Q
TTCGGGCAGGCGAACTATGCCGCGGCCAAGGCGGGCGACCTGGGCTTCACCAAGTCGCTG
 F   G   Q   A   N   Y   A   A   A   K   A   G   D   L   G   F   T   K   S   L
GCGCAGGAAGGCGCGCGCAACAACATCACCGTCAACGCGATCTGCCCCGGCTATATCGCG
 A   Q   E   G   A   R   N   N   I   T   V   N   A   I   C   P   G   Y   I   A
ACGGACATGGTGATGGCCGTTCCCGAACAGGTCCGCGAGGGGATCATCGCGCAGATCCCC
 T   D   M   V   M   A   V   P   E   Q   V   R   E   G   I   I   A   Q   I   P
GTCGGCCGCTTGGGCGAGCCGTCCGAGATCGCGCGCTGCGTGGTGTTCCTGGCCTCCGAC
 V   G   R   L   G   E   P   S   E   I   A   R   C   V   V   F   L   A   S   D
GATGCGGGCTTCGTCACAGGCTCGACCATCACGGCGAATGGCGGCCAGTACTACATCTGA
 D   A   G   F   V   T   G   S   T   I   T   A   N   G   G   Q   Y   Y   I   *
```

Figure 33B.

| Plasmid: | Polylinker: |
|---|---|
| pOCV-1 | GTGCAGCCTCAGGTCGACATATGCGGCCGCATCCGGATCCCTCCTCCTCCAG<br>CACGTCGGAGTCCAGCTGTATACGCCGGCGTAGGCCTAGGGAGGAGGAGGTC<br>  BsgI   BseMII    NdeI             BamHI (BseRI)GsuI |
| pOCV-2 | GTGCAGGAGGAGGTCGACATATGCGGCCGCATCCGGATCCCTGAGGCTCCAG<br>CACGTCCTCCTCCAGCTGTATACGCCGGCGTAGGCCTAGGGACTCCGAGGTC<br>  BsgI   BseRI    NdeI             BamHIBseMII  GsuI |
| pOCV-3 | CTGGAGCCTCAGGTCGACATATGCGGCCGCATCCGGATCCCTCCTCCTGCAC<br>GACCTCGGAGTCCAGCTGTATACGCCGGCGTAGGCCTAGGGAGGAGGACGTG<br>  GsuI   BseMII   NdeI             BamHI BseRI  BsgI |
| pOCV-4 | CTGGAGGAGGAGGTCGACATATGCGGCCGCATCCGGATCCCTGAGGCTGCAC<br>GACCTCCTCCTCCAGCTGTATACGCCGGCGTAGGCCTAGGGACTCCGACGTG<br>  GsuI (BseRI)    NdeI           BamHI BseMII BsgI |

Figure 35.

SEQUENCE LISTING

<160> NUMBER OF SEQ ID NOS: 197

<210> SEQ ID NO 1
<211> LENGTH: 20
<212> TYPE: DNA
<213> ORGANISM: Artificial
<220> FEATURE:
<223> OTHER INFORMATION: synthetic construct

<400> SEQUENCE: 1
agagtttgat cctggctcag                                            20

<210> SEQ ID NO 2
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (12)..(12)
<223> OTHER INFORMATION: n is c or t

<400> SEQUENCE: 2
ctggctcagg angaacgctg                                            20

<210> SEQ ID NO 3
<211> LENGTH: 20
<212> TYPE: DNA
<213> ORGANISM: Artificial
<220> FEATURE:
<223> OTHER INFORMATION: synthetic construct

<400> SEQUENCE: 3
aaggaggtga tccagccgca                                            20

<210> SEQ ID NO 4
<211> LENGTH: 20
<212> TYPE: DNA
<213> ORGANISM: Artificial
<220> FEATURE:
<223> OTHER INFORMATION: synthetic construct

<400> SEQUENCE: 4
ctcctacggg aggcagcagt                                            20

<210> SEQ ID NO 5
<211> LENGTH: 18
<212> TYPE: DNA
<213> ORGANISM: Artificial
<220> FEATURE:
<223> OTHER INFORMATION: synthetic construct

<400> SEQUENCE: 5
cagcagccgc ggtaatac                                              18

<210> SEQ ID NO 6
<211> LENGTH: 19
<212> TYPE: DNA
<213> ORGANISM: Artificial
<220> FEATURE:
<223> OTHER INFORMATION: synthetic construct

<400> SEQUENCE: 6
aactcaaagg aattgacgg                                             19

<210> SEQ ID NO 7
<211> LENGTH: 20
<212> TYPE: DNA
<213> ORGANISM: Artificial
<220> FEATURE:
<223> OTHER INFORMATION: synthetic construct

<400> SEQUENCE: 7
agtcccgcaa cgagcgcaac                                           20

<210> SEQ ID NO 8
<211> LENGTH: 20
<212> TYPE: DNA
<213> ORGANISM: Artificial
<220> FEATURE:
<223> OTHER INFORMATION: synthetic construct

<400> SEQUENCE: 8
gctacacacg tgctacaatg                                           20

<210> SEQ ID NO 9
<211> LENGTH: 20
<212> TYPE: DNA
<213> ORGANISM: Artificial
<220> FEATURE:
<223> OTHER INFORMATION: synthetic construct

<400> SEQUENCE: 9
actgctgcct cccgtaggag                                           20

<210> SEQ ID NO 10
<211> LENGTH: 18
<212> TYPE: DNA
<213> ORGANISM: Artificial
<220> FEATURE:
<223> OTHER INFORMATION: synthetic construct

<400> SEQUENCE: 10
gtattaccgc ggctgctg                                             18

<210> SEQ ID NO 11
<211> LENGTH: 20
<212> TYPE: DNA
<213> ORGANISM: Artificial
<220> FEATURE:
<223> OTHER INFORMATION: synthetic construct

<400> SEQUENCE: 11
gttgcgctcg ttgcgggact                                           20

<210> SEQ ID NO 12
<211> LENGTH: 1404
<212> TYPE: DNA
<213> ORGANISM: Paracoccus sp. R-1512

<400> SEQUENCE: 12
gcggcaggct taacacatgc aagtcgagcg aggtcttcgg acctagcggc ggacgggtga      60
gtaacgcgtg ggaacgtgcc ctttgctacg aatagtccc gggaaactgg gtttaatacc     120
gtatgtgccc tacgggggaa agatttatcg gcaaaggatc ggcccgcgtt ggattaggta    180
gttggtgggg taatggccta ccaagccgac gatccatagc tggtttgaga ggatgatcag    240
ccacactggg actgagacac ggcccagact cctacgggag gcagcagtgg ggaatcttag    300

```
acaatggggg caaccctgat ctagccatgc cgcgtgagtg atgaaggccc tagggttgta    360
aagctctttc agctgggaag ataatgacgg taccagcaga agaagcccg gctaactccg     420 tgccagcagc cgcggtaata cggagggggc tagcgttgtt cggaattact gggcgtaaag    480
cgcacgtagg cggactggaa agttgggggt gaaatcccgg ggctcaacct cggaactgcc    540
tccaaaacta tcagtctgga gttcgagaga ggtgagtgga ataccgagtg tagaggtgaa    600
attcgtagat attcggtgga acaccagtgg cgaaggcggc tcactggctc gatactgacg    660
ctgaggtgcg aaagcgtggg gagcaaacag gattagatac cctggtagtc cacgccgtaa    720
acgatgaatg ccagtcgtcg ggttgcatgc aattcggtga cacacctaac ggattaagca    780
ttccgcctgg ggagtacggt cgcaagatta aaactcaaag gaattgacgg gggcccgcac    840
aagcggtgga gcatgtggtt taattcgaag caacgcgcag aaccttacca acccttgaca    900
tccctggaca tcccgagaga tcgggctttc acttcggtga ccaggagaca ggtgctgcat    960
ggctgtcgtc agctcgtgtc gtgagatgtt cggttaagtc cggcaacgag cgcaacccac   1020
gtccctagtt gccagcattc agttgggcac tctatggaaa ctgccgatga taagtcggag   1080
gaaggtgtgg atgacgtcaa gtcctcatgg cccttacggg ttgggctaca cacgtgctac   1140
aatggtggtg acagtgggtt aatccccaaa agccatctca gttcggattg tcctctgcaa   1200
ctcgagggca tgaagttgga atcgctagta atcgcggaac agcatgccgc ggtgaatacg   1260
ttcccgggcc ttgtacacac cgcccgtcac accatgggag ttggttctac ccgacgacgc   1320
tgcgctaacc cttcggggag gcaggcggcc acggtaggat cagcgactgg ggtgaagtcg   1380
taacaaggta gccgtagggg aacc                                          1404

<210> SEQ ID NO 13
<211> LENGTH: 20
<212> TYPE: DNA
<213> ORGANISM: Artificial
<220> FEATURE:
<223> OTHER INFORMATION: synthetic construct

<400> SEQUENCE: 13
tcgtagactg cgtacaggcc                                                 20

<210> SEQ ID NO 14
<211> LENGTH: 14
<212> TYPE: DNA
<213> ORGANISM: Artificial
<220> FEATURE:
<223> OTHER INFORMATION: synthetic construct

<400> SEQUENCE: 14
catctgacgc atgt                                                       14

<210> SEQ ID NO 15
<211> LENGTH: 16
<212> TYPE: DNA
<213> ORGANISM: Artificial
<220> FEATURE:
<223> OTHER INFORMATION: synthetic construct

<400> SEQUENCE: 15
gacgatgagt cctgac                                                     16

<210> SEQ ID NO 16
<211> LENGTH: 14
<212> TYPE: DNA
<213> ORGANISM: Artificial
```

```
<220> FEATURE:
<223> OTHER INFORMATION: synthetic construct

<400> SEQUENCE: 16
tactcaggac tggc                                                        14

<210> SEQ ID NO 17
<211> LENGTH: 17
<212> TYPE: DNA
<213> ORGANISM: Artificial
<220> FEATURE:
<223> OTHER INFORMATION: synthetic construct

<400> SEQUENCE: 17
gactgcgtac aggccca                                                     17

<210> SEQ ID NO 18
<211> LENGTH: 18
<212> TYPE: DNA
<213> ORGANISM: Artificial
<220> FEATURE:
<223> OTHER INFORMATION: synthetic construct

<400> SEQUENCE: 18
cgatgagtcc tgaccgaa                                                    18

<210> SEQ ID NO 19
<211> LENGTH: 18
<212> TYPE: DNA
<213> ORGANISM: Artificial
<220> FEATURE:
<223> OTHER INFORMATION: synthetic construct

<400> SEQUENCE: 19
cgatgagtcc tgaccgac                                                    18

<210> SEQ ID NO 20
<211> LENGTH: 17
<212> TYPE: DNA
<213> ORGANISM: Artificial
<220> FEATURE:
<223> OTHER INFORMATION: synthetic construct

<400> SEQUENCE: 20
gactgcgtac aggcccc                                                     17

<210> SEQ ID NO 21
<211> LENGTH: 17
<212> TYPE: DNA
<213> ORGANISM: Artificial
<220> FEATURE:
<223> OTHER INFORMATION: synthetic construct

<400> SEQUENCE: 21
gactgcgtac aggcccg                                                     17

<210> SEQ ID NO 22
<211> LENGTH: 18
<212> TYPE: DNA
<213> ORGANISM: Artificial
<220> FEATURE:
<223> OTHER INFORMATION: synthetic construct

<400> SEQUENCE: 22
cgatgagtcc tgaccgag                                                    18
```

```
<210> SEQ ID NO 23
<211> LENGTH: 8
<212> TYPE: PRT
<213> ORGANISM: Paracoccus sp. R1534
<220> FEATURE:
<221> NAME/KEY: MISC_FEATURE
<222> LOCATION: (2)..(2)
<223> OTHER INFORMATION: Xaa is Leu or Ile

<400> SEQUENCE: 23

Ala Xaa Ile Lys Tyr Trp Gly Lys
1               5

<210> SEQ ID NO 24
<211> LENGTH: 27
<212> TYPE: DNA
<213> ORGANISM: Paracoccus sp. R1534

<400> SEQUENCE: 24
ccsctgatca artaytgggg baaratc                                       27

<210> SEQ ID NO 25
<211> LENGTH: 20
<212> TYPE: DNA
<213> ORGANISM: Paracoccus sp. R1534

<400> SEQUENCE: 25
gcsctgatca artaytgggg                                               20

<210> SEQ ID NO 26
<211> LENGTH: 20
<212> TYPE: DNA
<213> ORGANISM: Paracoccus sp. R1534

<400> SEQUENCE: 26
gcsatcatca artaytgggg                                               20

<210> SEQ ID NO 27
<211> LENGTH: 17
<212> TYPE: DNA
<213> ORGANISM: Paracoccus sp. R1534

<400> SEQUENCE: 27
atcaartayt ggggtaa                                                  17

<210> SEQ ID NO 28
<211> LENGTH: 17
<212> TYPE: DNA
<213> ORGANISM: Paracoccus sp. R1534

<400> SEQUENCE: 28
atcaartayt gggggcaa                                                 17

<210> SEQ ID NO 29
<211> LENGTH: 17
<212> TYPE: DNA
<213> ORGANISM: Paracoccus sp. R1534

<400> SEQUENCE: 29
atcaartayt gggggaa                                                  17

<210> SEQ ID NO 30
<211> LENGTH: 17
<212> TYPE: DNA
```

-continued

```
<213> ORGANISM: Paracoccus sp. R1534

<400> SEQUENCE: 30
atcaartayt ggggaaa                                                    17

<210> SEQ ID NO 31
<211> LENGTH: 8
<212> TYPE: PRT
<213> ORGANISM: Paracoccus sp. R1534
<220> FEATURE:
<221> NAME/KEY: MISC_FEATURE
<222> LOCATION: (7)..(7)
<223> OTHER INFORMATION: Xaa is Asn or Gln

<400> SEQUENCE: 31

Thr Met Asp Ala Gly Pro Xaa Val
1               5

<210> SEQ ID NO 32
<211> LENGTH: 24
<212> TYPE: DNA
<213> ORGANISM: Paracoccus sp. R1534
<220> FEATURE:
<221> NAME/KEY: misc_feature
<222> LOCATION: (19)..(19)
<223> OTHER INFORMATION: n is a or c
<220> FEATURE:
<221> NAME/KEY: misc_feature
<222> LOCATION: (21)..(21)
<223> OTHER INFORMATION: n is y or r

<400> SEQUENCE: 32
acsatggayg csggbccsna ngts                                            24

<210> SEQ ID NO 33
<211> LENGTH: 24
<212> TYPE: DNA
<213> ORGANISM: Paracoccus sp. R1534
<220> FEATURE:
<221> NAME/KEY: misc_feature
<222> LOCATION: (19)..(19)
<223> OTHER INFORMATION: n is t or g
<220> FEATURE:
<221> NAME/KEY: misc_feature
<222> LOCATION: (21)..(21)
<223> OTHER INFORMATION: n is r or y

<400> SEQUENCE: 33
tgstacctrc gsccvggsnt ncas                                            24

<210> SEQ ID NO 34
<211> LENGTH: 17
<212> TYPE: DNA
<213> ORGANISM: Paracoccus sp. R1534

<400> SEQUENCE: 34
tggtacctac gsccvgg                                                    17

<210> SEQ ID NO 35
<211> LENGTH: 17
<212> TYPE: DNA
<213> ORGANISM: Paracoccus sp. R1534

<400> SEQUENCE: 35
tggtacctgc gsccvgg                                                    17

<210> SEQ ID NO 36
```

```
-continued

<210> SEQ ID NO 36
<211> LENGTH: 17
<212> TYPE: DNA
<213> ORGANISM: Paracoccus sp. R1534

<400> SEQUENCE: 36
tgctacctac gsccvgg                                                    17

<210> SEQ ID NO 37
<211> LENGTH: 17
<212> TYPE: DNA
<213> ORGANISM: Paracoccus sp. R1534

<400> SEQUENCE: 37
tgctacctgc gsccvgg                                                    17

<210> SEQ ID NO 38
<211> LENGTH: 20
<212> TYPE: DNA
<213> ORGANISM: Paracoccus sp. R1534

<400> SEQUENCE: 38
tacctacgsc cvggsttrca                                                 20

<210> SEQ ID NO 39
<211> LENGTH: 20
<212> TYPE: DNA
<213> ORGANISM: Paracoccus sp. R1534

<400> SEQUENCE: 39
tacctgcgsc cvggsttrca                                                 20

<210> SEQ ID NO 40
<211> LENGTH: 20
<212> TYPE: DNA
<213> ORGANISM: Paracoccus sp. R1534

<400> SEQUENCE: 40
tacctacgsc cvggsgtyca                                                 20

<210> SEQ ID NO 41
<211> LENGTH: 20
<212> TYPE: DNA
<213> ORGANISM: Paracoccus sp. R1534

<400> SEQUENCE: 41
tacctgcgsc cvggsgtyca                                                 20

<210> SEQ ID NO 42
<211> LENGTH: 9066
<212> TYPE: DNA
<213> ORGANISM: Paracoccus sp. R114
<220> FEATURE:
<221> NAME/KEY: CDS
<222> LOCATION: (2622)..(3644)
<223> OTHER INFORMATION: mvaA gene

<400> SEQUENCE: 42
ggatccggca gctcgacacg ccgcagaacc tgtacgaacg tcccgccagc cgcttcgtcg      60
cggaattcgt cgggcgcggg acgtggtgc cgtgcaggc ccatgacggc gcgggccgcg      120
cccgcatcct gggggccgag gtggcggtga acgccgcccc gcaatcgcgc tttgtcgatc     180
acgtctgcct gcgccccgag aaccttgcca tctccgagac gggcgacctg cgcgccaagg     240
tcgcgcgcgt cacctatctt ggcgggaaat acctgctgga aaccgtgctg gattgcggca     300
```

-continued

| | |
|---|---|
| cccggctggt gaccgagacc cgcgcccgct tcgatacggg cgcgcagctt ggcctgacca | 360 |
| tcaacgcccc ctgggccttt gccgaggatt gaatggacag cgtgaagatc ctttcgggca | 420 |
| tgggcgtgaa gggccctgcc tgcatcaggc tggatgtcgg cgggatgcgc ctgatcctcg | 480 |
| attgcgggac cggcccggac gagggcgcgg agttcgaccc cgcctggctg gcggacgcgg | 540 |
| atgcggtgct gatcacccat gaccacgtgg accatatcgg cggcgcgcgt cacgcggtcg | 600 |
| cggcggggct gccgatccat gcgacgcggc agacggcggg gttgctgccc gcggggcgg | 660 |
| atctgcgcct gctgcccgaa cgcggtgtca cgcggatcgc cggggtcgat ctgacgaccg | 720 |
| gtcgcaacgg gcatgccgcg ggcggcgtct ggatgcattt cgacatgggc gagggctgt | 780 |
| tctattccgg cgactggtcc gaggaatccg actggttcgc cttcgatccg cccccgcctg | 840 |
| cggggacggc gattctcgac tgctcctatg gcggtttcga cgtggcgcaa tcggattgca | 900 |
| tcgcggacct ggacgacctg ctcgaggtgc tgccggggca ggtactgctg ccggtgccgc | 960 |
| catccggccg cgcggccgag ctggccctgc ggctgatccg ccgccacgga ccgggcagcg | 1020 |
| tgatggtcga cgacgcctgc ctgccggcca tcgcgcaact gcccgaggcg cgcggactgg | 1080 |
| cctacgccac cgaggcacgc tttcttgtct gcgacacgcc gaacgccgaa agccggcgcg | 1140 |
| gcatggcgga atctgcaagc atggcgcgat gcgggcaggc tggggcggga cgcgcatgtc | 1200 |
| gtcttcaccg ggcacatgaa cgtccatgcg cgcgcattct gcgaccgccc cggcgggcat | 1260 |
| ttccgccgct ggaacgtgca tccgccgctg cgcgaccagc gacggatgct ggaacggctg | 1320 |
| gccgcgcggc gctttgcccc ggccttctgc cccgaccccg agatctatct ggcgctggac | 1380 |
| atgggcgcgc aggtcttcat gcaccaggag gtgacgccat gatccccgcc cgcagcttct | 1440 |
| gcctgatccg ccacggcgaa acgaccgcca atgcagggc gatcatcgcg ggcgcaaccg | 1500 |
| atgtgcccct gacgccaagg ggccgcgatc aggcccgcgc cctggcaggg cgcgaatggc | 1560 |
| catcgggcat cgcgctgttc gccagcccga tgtcgcgtgc ccgcgatacc gcgctgctgg | 1620 |
| cctttccggg gcgcgaccac cagcccgaac ccgatctgcg cgaacgcgac tggggcatct | 1680 |
| tcgagggacg ccccgtcgcc gatctgcccc cgcgcgaaat cacgccgcag ggggcgagg | 1740 |
| gctgggacga cgtgatggcc cgcgtggacc gcgcgatccg gcggatctgc gcgacctcgg | 1800 |
| gcgatgcgct gccggtgctg gtctgccatt cgggcgtgat ccgtgccgcg cgcgtgctgt | 1860 |
| ggaccaccgg cgatgcgggc gatcgtccgc ccaacgccac gccgatcctg ttcagcccgg | 1920 |
| acggcgaccg attaaaggaa ggaacgatat gaccgccacc accccctgcg tcgtcttcga | 1980 |
| acgtggacgg cacgcttgcc gaattcgacg ccgaccgcct gggccatctt gtccacggca | 2040 |
| cgaccaagca ctgggacgcc ttccaccacg cgatggccga cgccccgccc atccccgagg | 2100 |
| tcgcccgcct gatgcgcaag ctgaaggagg ggggcgagac ggtcgtcatc tgctcggggc | 2160 |
| ggcccccgcg gctggcaggat cagacgatcg catggctgcg caagcacgac ctgcccttcg | 2220 |
| acgggatcta tctgcgcccc gaggatcagg acggcgccag cgaccccgag gtcaagcgcc | 2280 |
| gcgccctagc cgagatgcgc gccgacgggc tggcgccctg gctggtcgtg acgaccggc | 2340 |
| ggtccgtcgt ggatgcctgg cgggccgagg ggctggtctg cctgcaatgc gcgccggggg | 2400 |
| acttctaggg ccgcgcgacg ggggcgcgga caggctgggc gggaaaccgc ccgccacca | 2460 |
| tgtcctgcac gcgtcgaacc gcccgtccga cgccggtttc cgcacggaaa cgcgcggcaa | 2520 |
| gttgacataa cttgcacgcg acgtctcgat tctgcccgcg aagaatgcga tgcatccaga | 2580 |
| tgatgcagaa cgaagaagcg gaagcgcccg tgaaagacca g atg att tcc cat acc | 2636 |
|                                                                                         Met Ile Ser His Thr | |

-continued

```
                    1                     5
ccg gtg ccc acg caa tgg gtc ggc ccg atc ctg ttc cgc ggc ccc gtc    2684
Pro Val Pro Thr Gln Trp Val Gly Pro Ile Leu Phe Arg Gly Pro Val
            10                  15                  20 gtc gag ggc ccg atc agc gcg ccg ctg gcc acc tac gag acg ccg ctc    2732
Val Glu Gly Pro Ile Ser Ala Pro Leu Ala Thr Tyr Glu Thr Pro Leu
        25                  30                  35 tgg ccc tcg acc gcg cgg ggg gca ggg gtt tcc cgg cat tcg ggc ggg    2780
Trp Pro Ser Thr Ala Arg Gly Ala Gly Val Ser Arg His Ser Gly Gly
    40                  45                  50 atc cag gtc tcg ctg gtc gac gaa cgc atg agc cgc tcg atc gcg ctg    2828
Ile Gln Val Ser Leu Val Asp Glu Arg Met Ser Arg Ser Ile Ala Leu
55                  60                  65 cgg gcg cat gac ggg gcg gcg gcg acc gcc gcc tgg cag tcg atc aag    2876
Arg Ala His Asp Gly Ala Ala Ala Thr Ala Ala Trp Gln Ser Ile Lys
70                  75                  80                  85 gcc cgc cag gaa gag gtc gcg gcc gtg gtc gcc acc acc agc cgc ttc    2924
Ala Arg Gln Glu Glu Val Ala Ala Val Val Ala Thr Thr Ser Arg Phe
            90                  95                  100 gcc cgc ctt gtc gag ctg aat cgc cag atc gtg ggc aac ctg ctt tac    2972
Ala Arg Leu Val Glu Leu Asn Arg Gln Ile Val Gly Asn Leu Leu Tyr
            105                 110                 115 atc cgc atc gaa tgc gtg acg ggc gac gcc tcg ggt cac aac atg gtc    3020
Ile Arg Ile Glu Cys Val Thr Gly Asp Ala Ser Gly His Asn Met Val
            120                 125                 130 acc aag gcc gcc gag gcc gtg cag ggc tgg atc ctg tcg gaa tac ccg    3068
Thr Lys Ala Ala Glu Ala Val Gln Gly Trp Ile Leu Ser Glu Tyr Pro
    135                 140                 145 atg ctg gcc tat tcc acg atc tcg ggg aac ctg tgc acc gac aag aag    3116
Met Leu Ala Tyr Ser Thr Ile Ser Gly Asn Leu Cys Thr Asp Lys Lys
150                 155                 160                 165 gcg tcg gcg gtc aac ggc atc ctg ggc cgc ggc aaa tac gcc gtc gcc    3164
Ala Ser Ala Val Asn Gly Ile Leu Gly Arg Gly Lys Tyr Ala Val Ala
            170                 175                 180 gag gtc gag atc ccg cgc aag atc ctg acc cgc gtg ctg cgc acc agc    3212
Glu Val Glu Ile Pro Arg Lys Ile Leu Thr Arg Val Leu Arg Thr Ser
            185                 190                 195 gcc gag aag atg gtc cgc ctg aac tac gag aag aac tat gtc ggg ggt    3260
Ala Glu Lys Met Val Arg Leu Asn Tyr Glu Lys Asn Tyr Val Gly Gly
            200                 205                 210 acg ctg gcg ggg tcg ctg cgc agt gcg aac gcg cat ttc gcc aac atg    3308
Thr Leu Ala Gly Ser Leu Arg Ser Ala Asn Ala His Phe Ala Asn Met
    215                 220                 225 ctg ctg ggc ttc tac ctg gcg acg ggg cag gac gcg gcc aac atc atc    3356
Leu Leu Gly Phe Tyr Leu Ala Thr Gly Gln Asp Ala Ala Asn Ile Ile
230                 235                 240                 245 gag gcc agc cag ggc ttc gtc cat tgc gag gcc cgc ggc gag gat ctg    3404
Glu Ala Ser Gln Gly Phe Val His Cys Glu Ala Arg Gly Glu Asp Leu
            250                 255                 260 tat ttc tcg tgc acg ctg ccc aac ctc atc atg ggc tcg gtc ggt gcc    3452
Tyr Phe Ser Cys Thr Leu Pro Asn Leu Ile Met Gly Ser Val Gly Ala
            265                 270                 275 ggc aag ggc atc ccc tcg atc gag gag aac ctg tcg cgg atg ggc tgc    3500
Gly Lys Gly Ile Pro Ser Ile Glu Glu Asn Leu Ser Arg Met Gly Cys
    280                 285                 290 cgc cag ccg ggc gaa ccc ggc gac aac gcg cgc cgt ctt gcg gcg atc    3548
Arg Gln Pro Gly Glu Pro Gly Asp Asn Ala Arg Arg Leu Ala Ala Ile
    295                 300                 305 tgc gcg ggc gtc gtg ctg tgt ggt gaa ttg tcg ctg ctt gcg gcc cag    3596
```

```
Cys Ala Gly Val Val Leu Cys Gly Glu Leu Ser Leu Leu Ala Ala Gln
310                 315                 320                 325 acc aac ccc gga gag ttg gtc cgc acc cac atg gag atg gag cga tga        3644
Thr Asn Pro Gly Glu Leu Val Arg Thr His Met Glu Met Glu Arg
                330                 335                 340 ccgacagcaa ggatcaccat gtcgcgggcc gcaagctgga ccatctgcgt gcattggacg      3704
acgatgcgga tatcgaccgg ggcgacagcg gcttcgaccg catcgcgctg acccatcgcg      3764
ccctgcccga ggtggatttc gacgccatcg acacggcgac cagcttcctg ggccgtgaac      3824
tgtccttccc gctgctgatc tcgtccatga ccggcggcac cggcgaggag atcgagcgca      3884
tcaaccgcaa cctggccgct ggtgccgagg aggcccgcgt cgccatggcg gtgggctcgc      3944
agcgcgtgat gttcaccgac ccctcggcgc gggccagctt cgacctgcgc gcccatgcgc      4004
ccaccgtgcc gctgctggcc aatatcggcg cggtgcagct gaacatgggg ctggggctga      4064
aggaatgcct ggccgcgatc gaggtgctgc aggcggacgg cctgtatctg cacctgaacc      4124
ccctgcaaga ggccgtccag cccgaggggg atcgcgactt tgccgatctg gcagcaaga      4184 tcgcggccat cgcccgcgac gttcccgtgc ccgtcctgct gaaggaggtg ggctgcggcc      4244
tgtcggcggc cgatatcgcc atcgggctgc gcgccggat ccggcatttc gacgtggccg       4304
gtcgcggcgg cacatcctgg agccggatcg agtatcgccg ccgccagcgg gccgatgacg      4364
acctgggcct ggtcttccag gactgggccc tgcagaccgt ggacgccctg cgcgaggcgc      4424
ggcccgcgct tgcggcccat gatgaaacca gcgtgctgat cgccagcggc ggcatccgca      4484
acggtgtcga catggcgaaa tcgtcatcc tggggccga catgtgcggg gtcgccgcgc        4544
ccctgctgaa agcggcccaa aactcgcgcg aggcggttgt atccgccatc cggaaactgc      4604
atctggagtt ccggacagcc atgttcctcc tgggttgcgg cacgcttgcc gacctgaagg      4664
acaattcctc gcttatccgt caatgaaagt gcctaagatg accgtgacag gaatcgaagc      4724
gatcagcttt tacacccccc agaactacgt gggactggat atccttgccg cgcatcacgg      4784
gatcgacccc gagaagttct cgaagggat cgggcaggag aaaatcgcac tgcccggcca      4844
tgacgaggat atcgtgacca tggccgccga ggccgcgctg ccgatcatcg aacgcgcggg      4904
cacgcagggc atcgacacgg ttctgttcgc caccgagagc gggatcgacc agtcgaaggc      4964
cgccgccatc tatctgcgcc gcctgctgga cctgtcgccc aactgccgtt gcgtcgagct      5024
gaagcaggcc tgctattccg cgacggcggc gctgcagatg gcctgcgcgc atgtcgcccg      5084
caagcccgac cgcaaggtgc tggtgatcgc gtccgatgtc gcgcgctatg accgcgaaag      5144
ctcgggcgag gcgacgcagg gtgcgggcgc cgtcgccatc cttgtcagcg ccgatcccaa      5204 ggtgccgga tcggcaccg tctcggggct gttcaccgag gatatcatgg atttctggcg       5264
gccgaaccac cgccgcacgc ccctgttcga cggcaaggca tcgacgctgc gctatctgaa      5324
cgcgctggtc gaggcgtgga acgactatcg cgcgaatggc ggccacgagt tcgccgattt     5384
cgcgcatttc tgctatcacg tgccgttctc gcggatgggc gagaaggcga acagccacct      5444
ggccaaggcg aacaagacgc cggtggacat ggggcaggtg cagacgggcc tgatctacaa      5504
ccggcaggtc gggaactgct ataccgggtc gatctacctg gcattcgcct cgctgctgga      5564
gaacgctcag gaggacctga ccggcgcgct ggtcggtctg ttcagctatg gctcgggtgc      5624
gacgggcgaa ttcttcgatg cgcggatcgc gcccggttac cgcgaccacc tgttcgcgga      5684
acgccatcgc gaattgctgc aggatcgcac gcccgtcaca tatgacgaat acgttgccct      5744
gtgggacgag atcgacctga cgcagggcgc gcccgacaag gcgcgcggtc gtttcaggct      5804
```

```
ggcaggtatc gaggacgaga agcgcatcta tgtcgaccgg caggcctgaa gcaggcgccc    5864
atgccccggg caagctgatc ctgtccgggg aacattccgt gctctatggt gcgcccgcgc    5924
ttgccatggc catcgcccgc tataccgagg tgtggttcac gccgcttggc attggcgagg    5984
ggatacgcac gacattcgcc aatctctcgg gcggggcgac ctattcgctg aagctgctgt    6044
cggggttcaa gtcgcggctg gaccgccggt tcgagcagtt cctgaacggg gacctaaagg    6104
tgcacaaggt cctgacccat cccgacgatc tggcggtcta tgcgctggcg tcgcttctgc    6164
acgacaagcc gccggggacc gccgcgatgc cgggcatcgg cgcgatgcac cacctgccgc    6224
gaccgggtga gctgggcagc cggacggagc tgcccatcgg cgcgggcatg gggtcgtctg    6284
cggccatcgt cgcggccacc acggtcctgt cgagacgct gctggaccgg cccaagacgc     6344
ccgaacagcg cttcgaccgc gtccgcttct gcgagcggtt gaagcacggc aaggccggtc    6404
ccatcgacgc ggccagcgtc gtgcgcggcg ggcttgtccg cgtgggcggg aacgggccgg    6464
gttcgatcag cagcttcgat ttgcccgagg atcacgacct tgtcgcggga cgcggctggt    6524
actgggtact gcacgggcgc cccgtcagcg ggaccggcga atgcgtcagc gcggtcgcgg    6584
cggcgcatgt tcgcgatgcg gcgctgtggg acgccttcgc agtctgcacc cgcgcgttgg    6644
aggccgcgct gctgtctggg ggcagccccg acgccgccat caccgagaac cagcgcctgc    6704
tggaacgcat cggcgtcgtg ccggcagcga cgcaggccct cgtggcccag atcgaggagg    6764
cgggtggcgc ggccaagatc tgcggcgcag gttccgtgcg gggcgatcac ggcggggcgg    6824
tcctcgtgcg gattgacgac gcgcaggcga tggcttcggt catggcgcgc catcccgacc    6884
tcgactgggc gcccctgcgc atgtcgcgca cggggcggc acccggcccc gcgccgcgtg     6944
cgcaaccgct gccggggcag ggctgatgga tcaggtcatc cgcgccagcg cgccgggttc    7004
ggtcatgatc acgggcgaac atgccgtggt ctatggacac cgcgccatcg tcgccgggat    7064
cgagcagcgc gcccatgtga cgatcgtccc gcgtgccgac cgcatgtttc gcatcacctc    7124
gcagatcggg gcgccgcagc aggggtcgct ggacgatctg cctgcgggcg ggacctatcg    7184
cttcgtgctg gccgccatcg cgcgacacgc gccggacctg ccttgcgggt tcgacatgga    7244
catcacctcg gggatcgatc cgaggctcgg gcttggatcc tcggcggcgg tgacggtcgc    7304
ctgcctcggc gcgctgtcgc ggctggcggg gcggggacc gagggctgc atgacgacgc      7364
gctgcgcatc gtccgcgcca tccagggcag gggcagcggg gccgatctgg cggccagcct    7424
gcatggcggc ttcgtcgcct atcgcgcgcc cgatggcggt gccgcgcaga tcgaggcgct    7484
tccggtgccg ccggggccgt tcggcctgcg ctatgcgggc tacaagaccc cgacagccga    7544
ggtgctgcgc cttgtggccg atcggatggc gggcaacgag gccgctttcg acgcgctcta    7604
ctcccggatg ggcgcaagcg cagatgccgc gatccgcgcg gcgcaagggc tggactgggc    7664
tgcattccac gacgcgctga acgaatacca gcgcctgatg gagcagctgg gcgtgtccga    7724
cgacacgctg gacgcgatca tccgcgaggc gcgcgacgcg ggcgccgcag tcgccaagat    7784
ctccggctcg ggctggggg attgcgtgct ggcactgggc gaccagccca agggtttcgt     7844
gcccgcaagc attgccgaga agggacttgt tttcgatgac tgatgccgtc cgcgacatga    7904
tcgcccgtgc catggcgggc gcgaccgaca tccgagcagc cgaggcttat gcgcccagca    7964
acatcgcgct gtcgaaatac tggggcaagc gcgacgccgc gcggaacctt ccgctgaaca    8024
gctccgtctc gatctcgttg gcgaactggg gctctcatac gcgggtcgag ggtccggca    8084
cggggccacga cgaggtgcat cacaacggca cgctgctgga tccgggcgac gccttcgcgc    8144
gccgcgcgtt ggcattcgct gacctgttcc gggggggag gcacctgccg ctgcggatca    8204
```

-continued

```
cgacgcagaa ctcgatcccg acggcggcgg ggcttgcctc gtcggcctcg gggttcgcgg    8264
cgctgacccg tgcgctggcg ggggcgttcg ggctggatct ggacgacacg gatctgagcc    8324
gcatcgcccg gatcggcagt ggcagcgccc cccgctcgat ctggcacggc ttcgtccgct    8384
ggaaccgggg cgaggccgag gatgggcatg acagccacgg cgtcccgctg gacctgcgct    8444
ggcccggctt ccgcatcgcg atcgtggccg tggacaaggg gcccaagcct ttcagttcgc    8504
gcgacggcat gaaccacacg gtcgagacca gcccgctgtt cccgccctgg cctgcgcagg    8564
cggaagcgga ttgccgcgtc atcgaggatg cgatcgccgc ccgcgacatg gccgccctgg    8624
gtccgcgggt cgaggcgaac gcccttgcga tgcacgccac gatgatggcc gcgcgcccgc    8684
cgctctgcta cctgacgggc ggcagctggc aggtgctgga acgcctgtgg caggcccgcg    8744
cggacgggct tgcggccttt gcgacgatgg atgccggccc gaacgtcaag ctgatcttcg    8804
aggaaagcag cgccgccgac gtgctgtacc tgttccccga cgccagcctg atcgcgccgt    8864
tcgaggggcg ttgaacgcgt aagacgacca ctgggtaagg ttctgccgcg cgtggtctcg    8924
actgcctgca aagaggtgct tgagttgctg cgtgactgcg gcggccgact tcgtgggact    8984
tgcccgccac gctgacgcgc tggaaacgcg cccgcggatt acgaccgcgt cattgccctg    9044
aaccaatttc ccgtcggtcg ac                                             9066
```

<210> SEQ ID NO 43
<211> LENGTH: 340
<212> TYPE: PRT
<213> ORGANISM: Paracoccus sp. R114

<400> SEQUENCE: 43

```
Met Ile Ser His Thr Pro Val Pro Thr Gln Trp Val Gly Pro Ile Leu
1               5                   10                  15

Phe Arg Gly Pro Val Val Glu Gly Pro Ile Ser Ala Pro Leu Ala Thr
            20                  25                  30

Tyr Glu Thr Pro Leu Trp Pro Ser Thr Ala Arg Gly Ala Gly Val Ser
        35                  40                  45

Arg His Ser Gly Gly Ile Gln Val Ser Leu Val Asp Glu Arg Met Ser
    50                  55                  60

Arg Ser Ile Ala Leu Arg Ala His Asp Gly Ala Ala Thr Ala Ala
65                  70                  75                  80

Trp Gln Ser Ile Lys Ala Arg Gln Glu Val Ala Ala Val Val Ala
                85                  90                  95

Thr Thr Ser Arg Phe Ala Arg Leu Val Glu Leu Asn Arg Gln Ile Val
            100                 105                 110

Gly Asn Leu Leu Tyr Ile Arg Ile Glu Cys Val Thr Gly Asp Ala Ser
        115                 120                 125

Gly His Asn Met Val Thr Lys Ala Ala Glu Ala Val Gln Gly Trp Ile
    130                 135                 140

Leu Ser Glu Tyr Pro Met Leu Ala Tyr Ser Thr Ile Ser Gly Asn Leu
145                 150                 155                 160

Cys Thr Asp Lys Lys Ala Ser Ala Val Asn Gly Ile Leu Gly Arg Gly
                165                 170                 175

Lys Tyr Ala Val Ala Glu Val Glu Ile Pro Arg Lys Ile Leu Thr Arg
            180                 185                 190

Val Leu Arg Thr Ser Ala Glu Lys Met Val Arg Leu Asn Tyr Glu Lys
        195                 200                 205

Asn Tyr Val Gly Gly Thr Leu Ala Gly Ser Leu Arg Ser Ala Asn Ala
```

```
                    210                     215                     220
His Phe Ala Asn Met Leu Leu Gly Phe Tyr Leu Ala Thr Gly Gln Asp
225                     230                     235                     240

Ala Ala Asn Ile Ile Glu Ala Ser Gln Gly Phe Val His Cys Glu Ala
                245                     250                     255

Arg Gly Glu Asp Leu Tyr Phe Ser Cys Thr Leu Pro Asn Leu Ile Met
                260                     265                     270

Gly Ser Val Gly Ala Gly Lys Gly Ile Pro Ser Ile Glu Glu Asn Leu
        275                     280                     285

Ser Arg Met Gly Cys Arg Gln Pro Gly Glu Pro Gly Asp Asn Ala Arg
        290                     295                     300

Arg Leu Ala Ala Ile Cys Ala Gly Val Val Leu Cys Gly Glu Leu Ser
305                     310                     315                     320

Leu Leu Ala Ala Gln Thr Asn Pro Gly Glu Leu Val Arg Thr His Met
                325                     330                     335

Glu Met Glu Arg
            340

<210> SEQ ID NO 44
<211> LENGTH: 9066
<212> TYPE: DNA
<213> ORGANISM: Paracoccus sp. R114
<220> FEATURE:
<221> NAME/KEY: CDS
<222> LOCATION: (3641)..(4690)
<223> OTHER INFORMATION: idi

<400> SEQUENCE: 44
```

| | | | | |
|---|---|---|---|---|
| ggatccggca gctcgacacg ccgcagaacc tgtacgaacg tcccgccagc cgcttcgtcg | 60 |
| cggaattcgt cgggcgcggg acggtggtgc ccgtgcaggc ccatgacggc gcgggccgcg | 120 |
| cccgcatcct gggggccgag gtggcggtga acgccgcccc gcaatcgcgc tttgtcgatc | 180 |
| acgtctgcct gcgccccgag aaccttgcca tctccgagac gggcgacctg cgcgccaagg | 240 |
| tcgcgcgcgt cacctatctt ggcgggaaat acctgctgga aaccgtgctg gattgcggca | 300 |
| cccggctggt gaccgagacc cgcgcccgct tcgatacggg cgcgcagctt ggcctgacca | 360 |
| tcaacgcccc ctgggccttt gccgaggatt gaatggacag cgtgaagatc ctttcgggca | 420 |
| tgggcgtgaa gggccctgcc tgcatcaggc tggatgtcgg cgggatgcgc ctgatcctcg | 480 |
| attgcgggac cggcccggac gagggcgcgg agttcgaccc cgcctggctg gcggacgcgg | 540 |
| atgcggtgct gatcacccat gaccacgtgg accatatcgg cggcgcgcgt cacgcggtcg | 600 |
| cggcggggct gccgatccat gcgacgcggc agacggcggg gttgctgccc gcggggggcgg | 660 |
| atctgcgcct gctgcccgaa gcggtgtca gcggatcgc cggggtcgat ctgacgaccg | 720 |
| gtcgcaacgg gcatgccgcg ggcggcgtct ggatgcattt cgacatgggc gaggggctgt | 780 |
| tctattccgg cgactggtcc gaggaatccg actggttcgc cttcgatccg cccccgcctg | 840 |
| cggggacggc gattctcgac tgctcctatg gcggtttcga cgtggcgcaa tcggattgca | 900 |
| tcgcggacct ggacgacctg ctcgaggtgc tgccggggca ggtactgctg ccggtgccgc | 960 |
| catccggccg gcggccgag ctggccctgc ggctgatccg ccgccacgga ccgggcagcg | 1020 |
| tgatggtcga cgacgcctgc ctgccggcca tcgcgcaact gcccgaggcg cgcggactgg | 1080 |
| cctacgccac cgaggcacgc tttcttgtct gcgacacgcc gaacgccgaa agccggcgcg | 1140 |
| gcatggcggc atctgcaagc atggcgcgat gcgggcaggc tggggcggga cgcgcatgtc | 1200 |
| gtcttcaccg ggcacatgaa cgtccatgcg cgcgcattct gcgaccgccc cggcgggcat | 1260 |

-continued

```
ttccgccgct ggaacgtgca tccgccgctg cgcgaccagc gacggatgct ggaacggctg   1320
gccgcgcggc gctttgcccc ggccttctgc cccgaccccg agatctatct ggcgctggac   1380
atgggcgcgc aggtcttcat gcaccaggag gtgacgccat gatccccgcc cgcagcttct   1440
gcctgatccg ccacggcgaa acgaccgcca atgcagggc gatcatcgcg gcgcaaccg    1500 atgtgcccct gacgccaagg ggccgcgatc aggcccgcgc cctggcaggg cgcgaatggc   1560
catcgggcat cgcgctgttc gccagcccga tgtcgcgtgc ccgcgatacc gcgctgctgg   1620
cctttccggg gcgcgaccac cagcccgaac ccgatctgcg cgaacgcgac tggggcatct   1680
tcgagggacg ccccgtcgcc gatctgcccc cgcgcgaaat cacgccgcag ggggcgagg    1740 gctgggacga cgtgatggcc cgcgtggacc gcgcgatccg gcggatctgc gcgacctcgg   1800
gcgatgcgct gccggtgctg gtctgccatt cgggcgtgat ccgtgccgcg cgcgtgctgt   1860
ggaccaccgg cgatgcggc gatcgtccgc ccaacgccac gccgatcctg ttcagcccgg    1920
acggcgaccg attaaaggaa ggaacgatat gaccgccacc acccctgcg tcgtcttcga    1980 acgtggacgg cacgcttgcc gaattcgacg ccgaccgcct gggccatctt gtccacggca   2040
cgaccaagca ctgggacgcc ttccaccacg cgatggccga cgccccgccc atccccgagg   2100
tcgcccgcct gatgcgcaag ctgaaggagg ggcgagac ggtcgtcatc tgctcggggc     2160
ggccccgcgg ctggcaggat cagacgatcg catggctgcg caagcacgac ctgcccttcg   2220
acgggatcta tctgcgcccc gaggatcagg acggcgccag cgaccccgag gtcaagcgcc   2280
gcgccctagc cgagatgcgc gccgacgggc tggcgcccctg gctggtcgtg gacgaccggc  2340
ggtccgtcgt ggatgcctgg cgggccgagg ggctggtctg cctgcaatgc gcgccggggg   2400
acttctaggg ccgcgcgacg ggggcgcgga caggctgggc gggaaaccgc cccgccacca   2460
tgtcctgcac gcgtcgaacc gcccgtccga cgccggtttc cgcacggaaa cgcgcggcaa   2520
gttgacataa cttgcacgcg acgtctcgat tctgcccgcg aagaatgcga tgcatccaga   2580
tgatgcagaa cgaagaagcg gaagcgcccg tgaaagacca gatgatttcc catacccgg    2640 tgcccacgca atgggtcggc ccgatcctgt tccgcggccc cgtcgtcgag ggcccgatca   2700
gcgcgccgct ggccacctac gagacgccgc tctggccctc gaccgcgcgg ggggcagggg   2760
tttcccggca ttcgggcggg atccaggtct cgctggtcga cgaacgcatg agccgctcga   2820
tcgcgctgcg ggcgcatgac ggggcggcgg cgaccgccgc ctggcagtcg atcaaggccc   2880
gccaggaaga ggtcgcggcc gtggtcgcca ccaccagccg cttcgcccgc cttgtcgagc   2940
tgaatcgcca gatcgtgggc aacctgcttt acatccgcat cgaatgcgtg acgggcgacg   3000
cctcgggtca caacatggtc accaaggccg ccgaggccgt gcagggctgg atcctgtcgg   3060 aataccccgat gctggcctat tccacgatct cggggaacct gtgcaccgac aagaaggcgt   3120
cggcggtcaa cggcatcctg gccgcgggca aatacgccgt cgccgaggtc gagatcccgc   3180
gcaagatcct gacccgcgtg ctgcgcacca gcgccgagaa gatggtccgc ctgaactacg   3240
agaagaacta tgtcgggggt acgctggcgg ggtcgctgcg cagtgcgaac gcgcatttcg   3300
ccaacatgct gctgggcttc tacctggcga cggggcagga cgcggccaac atcatcgagg   3360
ccagccaggg cttcgtccat tgcgaggccc gcggcgagga tctgtatttc tcgtgcacgc   3420
tgcccaacct catcatgggc tcggtcggtg ccggcaaggg catcccctcg atcgaggaga   3480
acctgtcgcg gatgggctgc cgccagccgg gcgaacccgg cgacaacgcg cgccgtcttg   3540
cggcgatctg cgcgggcgtc gtgctgtgtg gtgaattgtc gctgcttgcg gcccagacca   3600
```

```
acccggaga gttggtccgc acccacatgg agatggagcg atg acc gac agc aag      3655
                                            Met Thr Asp Ser Lys
                                            1               5 gat cac cat gtc gcg ggg cgc aag ctg gac cat ctg cgt gca ttg gac      3703
Asp His His Val Ala Gly Arg Lys Leu Asp His Leu Arg Ala Leu Asp
            10                  15                  20 gac gat gcg gat atc gac cgg ggc gac agc ggc ttc gac cgc atc gcg      3751
Asp Asp Ala Asp Ile Asp Arg Gly Asp Ser Gly Phe Asp Arg Ile Ala
            25                  30                  35 ctg acc cat cgc gcc ctg ccc gag gtg gat ttc gac gcc atc gac acg      3799
Leu Thr His Arg Ala Leu Pro Glu Val Asp Phe Asp Ala Ile Asp Thr
            40                  45                  50 gcg acc agc ttc ctg ggc cgt gaa ctg tcc ttc ccg ctg ctg atc tcg      3847
Ala Thr Ser Phe Leu Gly Arg Glu Leu Ser Phe Pro Leu Leu Ile Ser
55              60                  65 tcc atg acc ggc ggc acc ggc gag gag atc gag cgc atc aac cgc aac      3895
Ser Met Thr Gly Gly Thr Gly Glu Glu Ile Glu Arg Ile Asn Arg Asn
70              75                  80                  85 ctg gcc gct ggt gcc gag gag gcc cgc gtc gcc atg gcg gtg ggc tcg      3943
Leu Ala Ala Gly Ala Glu Glu Ala Arg Val Ala Met Ala Val Gly Ser
                90                  95                  100 cag cgc gtg atg ttc acc gac ccc tcg gcg cgg gcc agc ttc gac ctg      3991
Gln Arg Val Met Phe Thr Asp Pro Ser Ala Arg Ala Ser Phe Asp Leu
                105                 110                 115 cgc gcc cat gcg ccc acc gtg ccg ctg ctg gcc aat atc ggc gcg gtg      4039
Arg Ala His Ala Pro Thr Val Pro Leu Leu Ala Asn Ile Gly Ala Val
                120                 125                 130 cag ctg aac atg ggg ctg ggg ctg aag gaa tgc ctg gcc gcg atc gag      4087
Gln Leu Asn Met Gly Leu Gly Leu Lys Glu Cys Leu Ala Ala Ile Glu
135                 140                 145 gtg ctg cag gcg gac ggc ctg tat ctg cac ctg aac ccc ctg caa gag      4135
Val Leu Gln Ala Asp Gly Leu Tyr Leu His Leu Asn Pro Leu Gln Glu
150                 155                 160                 165 gcc gtc cag ccc gag ggg gat cgc gac ttt gcc gat ctg ggc agc aag      4183
Ala Val Gln Pro Glu Gly Asp Arg Asp Phe Ala Asp Leu Gly Ser Lys
                170                 175                 180 atc gcg gcc atc gcc cgc gac gtt ccc gtg ccc gtc ctg ctg aag gag      4231
Ile Ala Ala Ile Ala Arg Asp Val Pro Val Pro Val Leu Leu Lys Glu
                185                 190                 195 gtg ggc tgc ggc ctg tcg gcg gcc gat atc gcc atc ggg ctg cgc gcc      4279
Val Gly Cys Gly Leu Ser Ala Ala Asp Ile Ala Ile Gly Leu Arg Ala
                200                 205                 210 ggg atc cgg cat ttc gac gtg gcc ggt cgc ggc ggc aca tcc tgg agc      4327
Gly Ile Arg His Phe Asp Val Ala Gly Arg Gly Gly Thr Ser Trp Ser
215                 220                 225 cgg atc gag tat cgc cgc cgc cag cgg gcc gat gac gac ctg ggc ctg      4375
Arg Ile Glu Tyr Arg Arg Arg Gln Arg Ala Asp Asp Asp Leu Gly Leu
230                 235                 240                 245 gtc ttc cag gac tgg ggc ctg cag acc gtg gac gcc ctg cgc gag gcg      4423
Val Phe Gln Asp Trp Gly Leu Gln Thr Val Asp Ala Leu Arg Glu Ala
                250                 255                 260 cgg ccc gcg ctt gcg gcc cat gat gga acc agc gtg ctg atc gcc agc      4471
Arg Pro Ala Leu Ala Ala His Asp Gly Thr Ser Val Leu Ile Ala Ser
                265                 270                 275 ggc ggc atc cgc aac ggt gtc gac atg gcg aaa tgc gtc atc ctg ggg      4519
Gly Gly Ile Arg Asn Gly Val Asp Met Ala Lys Cys Val Ile Leu Gly
                280                 285                 290 gcc gac atg tgc ggg gtc gcc gcg ccc ctg ctg aaa gcg gcc caa aac      4567
Ala Asp Met Cys Gly Val Ala Ala Pro Leu Leu Lys Ala Ala Gln Asn
295                 300                 305
```

```
tcg cgc gag gcg gtt gta tcc gcc atc cgg aaa ctg cat ctg gag ttc       4615
Ser Arg Glu Ala Val Val Ser Ala Ile Arg Lys Leu His Leu Glu Phe
310                 315                 320                 325 cgg aca gcc atg ttc ctc ctg ggt tgc ggc acg ctt gcc gac ctg aag       4663
Arg Thr Ala Met Phe Leu Leu Gly Cys Gly Thr Leu Ala Asp Leu Lys
                330                 335                 340 gac aat tcc tcg ctt atc cgt caa tga aagtgcctaa gatgaccgtg             4710
Asp Asn Ser Ser Leu Ile Arg Gln
                345
```

| | |
|---|---|
| acaggaatcg aagcgatcag cttctacacc ccccagaact acgtgggact ggatatcctt | 4770 |
| gccgcgcatc acgggatcga ccccgagaag ttctcgaagg ggatcgggca ggagaaaatc | 4830 |
| gcactgcccg gccatgacga ggatatcgtg accatggccg ccgaggccgc gctgccgatc | 4890 |
| atcgaacgcg cgggcacgca gggcatcgac acggttctgt tcgccaccga gagcgggatc | 4950 |
| gaccagtcga aggccgccgc catctatctg cgccgcctgc tggacctgtc gcccaactgc | 5010 |
| cgttgcgtcg agctgaagca ggcctgctat tccgcgacgg cggcgctgca gatggcctgc | 5070 |
| gcgcatgtcg cccgcaagcc cgaccgcaag gtgctggtga tcgcgtccga tgtcgcgcgc | 5130 |
| tatgaccgcg aaagctcggg cgaggcgacg cagggtgcgg gcgccgtcgc catccttgtc | 5190 |
| agcgccgatc ccaaggtggc cgagatcggc accgtctcgg ggctgttcac cgaggatatc | 5250 |
| atggatttct ggcggccgaa ccaccgccgc acgcccctgt tcgacggcaa ggcatcgacg | 5310 |
| ctgcgctatc tgaacgcgct ggtcgaggcg tggaacgact atcgcgcgaa tggcggccac | 5370 |
| gagttcgccg atttcgcgca tttctgctat cacgtgccgt tctcgcggat gggcgagaag | 5430 |
| gcgaacagcc acctggccaa ggcgaacaag acgccggtgg acatggggca ggtgcagacg | 5490 |
| ggcctgatct acaaccggca ggtcgggaac tgctataccg ggtcgatcta cctggcattc | 5550 |
| gcctcgctgc tggagaacgc tcaggaggac ctgaccggcg cgctggtcgg tctgttcagc | 5610 |
| tatggctcgg gtgcgacggg cgaattcttc gatgcgcgga tcgcgcccgg ttaccgcgac | 5670 |
| cacctgttcg cggaacgcca tcgcgaattg ctgcaggatc gcacgcccgt cacatatgac | 5730 |
| gaatacgttg ccctgtggga cgagatcgac ctgacgcagg gcgcgcccga caaggcgcgc | 5790 |
| ggtcgtttca ggctggcagg tatcgaggac gagaagcgca tctatgtcga ccggcaggcc | 5850 |
| tgaagcaggc gcccatgccc cgggcaagct gatcctgtcc ggggaacatt ccgtgctcta | 5910 |
| tggtgcgccc gcgcttgcca tggccatcgc ccgctatacc gaggtgtggt tcacgccgct | 5970 |
| tggcattggc gagggatac gcacgacatt cgccaatctc tcgggcgggg cgacctattc | 6030 |
| gctgaagctg ctgtcggggt tcaagtcgcg gctggaccgc cggttcgagc agttcctgaa | 6090 |
| cggcgaccta aaggtgcaca aggtcctgac ccatcccgac gatctggcgg tctatgcgct | 6150 |
| ggcgtcgctt ctgcacgaca agccgccggg gaccgccgcg atgccgggca tcggcgcgat | 6210 |
| gcaccacctg ccgcgaccgg gtgagctggg cagccggacg gagctgccca tcggcgcggg | 6270 |
| catgggggtcg tctgcggcca tcgtcgcggc caccacggtc ctgttcgaga cgctgctgga | 6330 |
| ccggcccaag acgcccgaac agcgcttcga ccgcgtccgc ttctgcgagc ggttgaagca | 6390 |
| cggcaaggcc ggtcccatcg acgcggccag cgtcgtgcgc ggcgggcttg tccgcgtggg | 6450 |
| cgggaacggg ccgggttcga tcagcagctt cgatttgccc gaggatcacg accttgtcgc | 6510 |
| gggacgcggc tggtactggg tactgcacgg gcgccccgtc agcgggaccg gcgaatgcgt | 6570 |
| cagcgcggtc gcggcggcgc atggtcgcga tgcggcgctg tgggacgcct tcgcagtctg | 6630 |
| cacccgcgcg ttggaggccg cgctgctgtc tgggggcagc cccgacgccg ccatcaccga | 6690 |

-continued

```
gaaccagcgc ctgctggaac gcatcggcgt cgtgccggca gcgacgcagg ccctcgtggc      6750
ccagatcgag gaggcgggtg gcgcggccaa gatctgcggc gcaggttccg tgcggggcga      6810
tcacggcggg gcggtcctcg tgcggattga cgacgcgcag gcgatggctt cggtcatggc      6870
gcgccatccc gacctcgact gggcgcccct gcgcatgtcg cgcacggggg cggcacccgg      6930
ccccgcgccg cgtgcgcaac cgctgccggg gcagggctga tggatcaggt catccgcgcc      6990
agcgcgccgg gttcggtcat gatcacgggc gaacatgccg tggtctatgg acaccgcgcc      7050
atcgtcgccg ggatcgagca gcgcgcccat gtgacgatcg tcccgcgtgc cgaccgcatg      7110
tttcgcatca cctcgcagat cggggcgccg cagcagggt cgctggacga tctgcctgcg      7170
ggcgggacct atcgcttcgt gctggccgcc atcgcgcgac acgcgccgga cctgccttgc      7230
gggttcgaca tggacatcac ctcggggatc gatccgaggc tcgggcttgg atcctcggcg      7290
gcggtgacgg tcgcctgcct cggcgcgctg tcgcggctgg cggggcgggg gaccgagggg      7350
ctgcatgacg acgcgctgcg catcgtccgc gccatccagg gcaggggcag cggggccgat      7410
ctggcggcca gcctgcatgg cggcttcgtc gcctatcgcg cgcccgatgg cggtgccgcg      7470
cagatcgagg cgcttccggt gccgccgggg ccgttcggcc tgcgctatgc gggctacaag      7530
accccgacag ccgaggtgct gcgccttgtg gccgatcgga tggcgggcaa cgaggccgct      7590
ttcgacgcgc tctactcccg gatgggcgca agcgcagatg ccgcgatccg cgcggcgcaa      7650
gggctggact gggctgcatt ccacgacgcg ctgaacgaat accagcgcct gatggagcag      7710
ctgggcgtgt ccgacgacac gctggacgcg atcatccgcg aggcgcgcga cgcgggcgcc      7770
gcagtcgcca agatctccgg ctcggggctg ggggattgcg tgctggcact gggcgaccag      7830 cccaaggggtt tcgtgcccgc aagcattgcc gagaagggac ttgttttcga tgactgatgc      7890
cgtccgcgac atgatcgccc gtgccatggc gggcgcgacc gacatccgag cagccgaggc      7950
ttatgcgccc agcaacatcg cgctgtcgaa atactgggc aagcgcgacg ccgcgcggaa      8010
ccttccgctg aacagctccg tctcgatctc gttggcgaac tggggctctc atacgcgggt      8070 cgagggtcc ggcacgggcc acgacgaggt gcatcacaac ggcacgctgc tggatccggg      8130
cgacgccttc gcgcgccgcg cgttggcatt cgctgacctg ttccgggggg ggaggcacct      8190
gccgctgcgg atcacgacgc agaactcgat cccgacggcg gcggggcttg cctcgtcggc      8250
ctcggggttc gcggcgctga cccgtgcgct ggcggggggcg ttcgggctgg atctggacga      8310
cacggatctg agccgcatcg cccggatcgg cagtggcagc gccgcccgct cgatctggca      8370
cggcttcgtc cgctggaacc ggggcgaggc cgaggatggg catgacagcc acggcgtccc      8430
gctggacctg cgctggcccg gcttccgcat cgcgatcgtg gccgtggaca aggggcccaa      8490
gcctttcagt tcgcgcgacg gcatgaacca cacggtcgag accagcccgc tgttcccgcc      8550
ctggcctgcg caggcggaag cggattgccg cgtcatcgag gatgcgatcg ccgcccgcga      8610
catggccgcc ctgggtccgc gggtcgaggc gaacgcccct tgcgatgcacg ccacgatgat      8670 ggccgcgcgc ccgccgctct gctacctgac gggcggcagc tggcaggtgc tggaacgcct      8730
gtggcaggcc cgcgcggacg ggcttgcggc ctttgcgacg atggatgccg gcccgaacgt      8790
caagctgatc ttcgaggaaa gcagcgccgc cgacgtgctg tacctgttcc ccgacgccag      8850
cctgatcgcg ccgttcgagg ggcgttgaac gcgtaagacg accactgggt aaggttctgc      8910
cgcgcgtggt ctcgactgcc tgcaaagagg tgcttgagtt gctgcgtgac tgcggcggcc      8970
gacttcgtgg gacttgcccg ccacgctgac gcgctggaaa cgcgcccgcg gattacgacc      9030
gcgtcattgc cctgaaccaa tttcccgtcg gtcgac                               9066
```

<210> SEQ ID NO 45
<211> LENGTH: 349
<212> TYPE: PRT
<213> ORGANISM: Paracoccus sp. R114

<400> SEQUENCE: 45

Met Thr Asp Ser Lys Asp His His Val Ala Gly Arg Lys Leu Asp His
1               5                   10                  15

Leu Arg Ala Leu Asp Asp Ala Asp Ile Asp Arg Gly Asp Ser Gly
            20                  25                  30

Phe Asp Arg Ile Ala Leu Thr His Arg Ala Leu Pro Glu Val Asp Phe
        35                  40                  45

Asp Ala Ile Asp Thr Ala Thr Ser Phe Leu Gly Arg Glu Leu Ser Phe
    50                  55                  60

Pro Leu Leu Ile Ser Ser Met Thr Gly Gly Thr Gly Glu Glu Ile Glu
65                  70                  75                  80

Arg Ile Asn Arg Asn Leu Ala Ala Gly Ala Glu Ala Arg Val Ala
                85                  90                  95

Met Ala Val Gly Ser Gln Arg Val Met Phe Thr Asp Pro Ser Ala Arg
            100                 105                 110

Ala Ser Phe Asp Leu Arg Ala His Ala Pro Thr Val Pro Leu Leu Ala
        115                 120                 125

Asn Ile Gly Ala Val Gln Leu Asn Met Gly Leu Gly Leu Lys Glu Cys
    130                 135                 140

Leu Ala Ala Ile Glu Val Leu Gln Ala Asp Gly Leu Tyr Leu His Leu
145                 150                 155                 160

Asn Pro Leu Gln Glu Ala Val Gln Pro Glu Gly Asp Arg Asp Phe Ala
                165                 170                 175

Asp Leu Gly Ser Lys Ile Ala Ala Ile Ala Arg Asp Val Pro Val Pro
            180                 185                 190

Val Leu Leu Lys Glu Val Gly Cys Gly Leu Ser Ala Ala Asp Ile Ala
        195                 200                 205

Ile Gly Leu Arg Ala Gly Ile Arg His Phe Asp Val Ala Gly Arg Gly
    210                 215                 220

Gly Thr Ser Trp Ser Arg Ile Glu Tyr Arg Arg Arg Gln Arg Ala Asp
225                 230                 235                 240

Asp Asp Leu Gly Leu Val Phe Gln Asp Trp Gly Leu Gln Thr Val Asp
                245                 250                 255

Ala Leu Arg Glu Ala Arg Pro Ala Leu Ala Ala His Asp Gly Thr Ser
            260                 265                 270

Val Leu Ile Ala Ser Gly Gly Ile Arg Asn Gly Val Asp Met Ala Lys
        275                 280                 285

Cys Val Ile Leu Gly Ala Asp Met Cys Gly Val Ala Ala Pro Leu Leu
    290                 295                 300

Lys Ala Ala Gln Asn Ser Arg Glu Ala Val Val Ser Ala Ile Arg Lys
305                 310                 315                 320

Leu His Leu Glu Phe Arg Thr Ala Met Phe Leu Leu Gly Cys Gly Thr
                325                 330                 335

Leu Ala Asp Leu Lys Asp Asn Ser Ser Leu Ile Arg Gln
            340                 345

<210> SEQ ID NO 46
<211> LENGTH: 9066
<212> TYPE: DNA

<213> ORGANISM: Paracoccus sp. R114
<220> FEATURE:
<221> NAME/KEY: CDS
<222> LOCATION: (4687)..(5853)
<223> OTHER INFORMATION: hcs

<400> SEQUENCE: 46

```
ggatccggca gctcgacacg ccgcagaacc tgtacgaacg tcccgccagc cgcttcgtcg      60
cggaattcgt cgggcgcggg acggtggtgc ccgtgcaggc ccatgacggc gcgggccgcg     120
cccgcatcct gggggccgag gtggcggtga acgccgcccc gcaatcgcgc tttgtcgatc     180
acgtctgcct gcgccccgag aaccttgcca tctccgagac gggcgacctg cgcgccaagg     240
tcgcgcgcgt cacctatctt ggcgggaaat acctgctgga aaccgtgctg gattgcggca     300
cccgctggt gaccgagacc cgcgcccgct tcgatacggg cgcgcagctt ggcctgacca     360
tcaacgcccc ctgggccttt gccgaggatt gaatggacag cgtgaagatc ctttcgggca     420
tgggcgtgaa gggccctgcc tgcatcaggc tggatgtcgg cgggatgcgc ctgatcctcg     480
attgcgggac cggcccggac gagggcgcgg agttcgaccc cgcctggctg cggacgcgg      540
atgcggtgct gatcacccat gaccacgtgg accatatcgg cggcgcgcgt cacgcggtcg     600
cggcggggct gccgatccat gcgacgcggc agacggcggg gttgctgccc gcggggcgg      660
atctgcgcct gctgcccgaa cgcggtgtca cgcggatcgc cggggtcgat ctgacgaccg     720
gtcgcaacgg gcatgccgcg ggcggcgtct ggatgcattt cgacatgggc gagggctgt      780
tctattccgg cgactggtcc gaggaatccg actggttcgc cttcgatccg cccccgcctg     840
cggggacggc gattctcgac tgctcctatg gcggtttcga cgtggcgcaa tcggattgca     900
tcgcggacct ggacgacctg ctcgaggtgc tgccggggca ggtactgctg ccggtgccgc     960
catccggccg cgcggccgag ctggccctgc ggctgatccg ccgccacgga ccgggcagcg    1020
tgatggtcga cgacgcctgc ctgccggcca tcgcgcaact gcccgaggcg cgcggactgg    1080
cctacgccac cgaggcacgc tttcttgtct gcgacacgcc gaacgccgaa agccggcgcg    1140
gcatggcggc atctgcaagc atggcgcgat gcgggcaggc tggggcggga cgcgcatgtc    1200
gtcttcaccg ggcacatgaa cgtccatgcg cgcgcattct gcgaccgccc cggcgggcat    1260
ttccgccgct ggaacgtgca tccgccgctg cgcgaccagc gacggatgct ggaacggctg    1320
gccgcgcggc gctttgcccc ggccttctgc cccgaccccg agatctatct ggcgctggac    1380
atgggcgcgc aggtcttcat gcaccaggag gtgacgccat gatccccgcc cgcagcttct    1440
gcctgatccg ccacggcgaa acgaccgcca atgcaggggc gatcatcgcg ggcgcaaccg    1500
atgtgcccct gacgccaagg ggccgcgatc aggcccgcgc cctggcaggg cgcgaatggc    1560
catcgggcat cgcgctgttc gccagcccga tgtcgcgtgc ccgcgatacc gcgctgctgg    1620
cctttccggg gcgcgaccac cagcccgaac ccgatctgcg cgaacgcgac tgggcatct     1680
tcgagggacg ccccgtcgcc gatctgcccc cgcgcgaaat cacgccgcag ggggcgaggg    1740
gctgggacga cgtgatggcc cgcgtggacc gcgcgatccg gcggatctgc gcgacctcgg    1800
gcgatgcgct gccggtgctg gtctgccatt cgggcgtgat ccgtgccgcg cgcgtgctgt    1860
ggaccaccgg cgatgcgggc gatcgtccgc ccaacgccac gccgatcctg ttcagcccgg    1920
acggcgaccg attaaaggaa ggaacgatat gaccgccacc accccctgcg tcgtcttcga    1980
acgtggacgg cacgcttgcc gaattcgacg ccgaccgcct gggccatctt gtccacggca    2040
cgaccaagca ctgggacgcc ttccaccacg cgatggccga cgccccgccc atccccgagg    2100
tcgcccgcct gatgcgcaag ctgaaggagg ggggcgagac ggtcgtcatc tgctcggggc    2160
```

```
ggccccgcgg ctggcaggat cagacgatcg catggctgcg caagcacgac ctgcccttcg    2220
acgggatcta tctgcgcccc gaggatcagg acggcgccag cgaccccgag gtcaagcgcc    2280
gcgccctagc cgagatgcgc gccgacgggc tggcgccctg gctggtcgtg gacgaccggc    2340
ggtccgtcgt ggatgcctgg cgggccgagg ggctggtctg cctgcaatgc gcgccggggg    2400
acttctaggg ccgcgcgacg ggggcgcgga caggctgggc gggaaaccgc cccgccacca    2460
tgtcctgcac gcgtcgaacc gcccgtccga cgccggtttc cgcacggaaa cgcgcggcaa    2520
gttgacataa cttgcacgcg acgtctcgat tctgcccgcg aagaatgcga tgcatccaga    2580
tgatgcagaa cgaagaagcg gaagcgcccg tgaaagacca gatgatttcc catacccgg     2640 tgcccacgca atgggtcggc ccgatcctgt tccgcggccc cgtcgtcgag ggcccgatca    2700
gcgcgccgct ggccacctac gagacgccgc tctggccctc gaccgcgcgg ggggcagggg    2760
tttcccggca ttcgggcggg atccaggtct cgctggtcga cgaacgcatg agccgctcga    2820
tcgcgctgcg ggcgcatgac ggggcggcgg cgaccgccgc ctggcagtcg atcaaggccc    2880
gccaggaaga ggtcgcggcc gtggtcgcca ccaccagccg cttcgcccgc cttgtcgagc    2940
tgaatcgcca gatcgtgggc aacctgcttt acatccgcat cgaatgcgtg acgggcgacg    3000
cctcgggtca caacatggtc accaaggccg ccgaggccgt gcagggctgg atcctgtcgg    3060
aatacccgat gctggcctat tccacgatct cggggaacct gtgcaccgac aagaaggcgt    3120
cggcggtcaa cggcatcctg ggccgcggca atacgccgt cgccgaggtc gagatcccgc    3180
gcaagatcct gacccgcgtg ctgcgcacca gcgccgagaa gatggtccgc ctgaactacg    3240
agaagaacta tgtcgggggt acgctggcgg ggtcgctgcg cagtgcgaac gcgcatttcg    3300
ccaacatgct gctgggcttc tacctggcga cggggcagga cgcggccaac atcatcgagg    3360
ccagccaggg cttcgtccat tgcgaggccc gcggcgagga tctgtatttc tcgtgcacgc    3420
tgcccaacct catcatgggc tcggtcggtg ccggcaaggg catcccctcg atcgaggaga    3480
acctgtcgcg gatgggctgc cgccagccgg gcgaacccgg cgacaacgcg cgccgtcttg    3540
cggcgatctg cgcgggcgtc gtgctgtgtg gtgaattgtc gctgcttgcg gcccagacca    3600
accccggaga gttggtccgc acccacatgg agatggagcg atgaccgaca gcaaggatca    3660
ccatgtcgcg gggcgcaagc tggaccatct gcgtgcattg gacgacgatg cggatatcga    3720
ccggggcgac agcggcttcg accgcatcgc gctgacccat cgcgccctgc cgaggtggaa    3780
tttcgacgcc atcgacacgg cgaccagctt cctgggccgt gaactgtcct tcccgctgct    3840
gatctcgtcc atgaccggcg gcaccggcga ggagatcgag cgcatcaacc gcaacctggc    3900
cgctggtgcc gaggaggccc gcgtcgccat ggcggtgggc tcgcagcgcg tgatgttcac    3960
cgacccctcg gcgcgggcca gcttcgacct gcgcgcccat gcgccaccg tgccgctgct    4020 ggccaatatc ggcgcggtgc agctgaacat ggggctgggg ctgaaggaat gcctggccgc    4080
gatcgaggtg ctgcaggcgg acggcctgta tctgcacctg aaccccctgc aagaggccgt    4140
ccagcccgag ggggatcgcg actttgccga tctgggcagc aagatcgcgg ccatcgcccg    4200
cgacgttccc gtgcccgtcc tgctgaagga ggtgggctgc ggcctgtcgg cggccgatat    4260
cgccatcggg ctgcgcgccg ggatccggca tttcgacgtg gccggtcgcg gcggcacatc    4320
ctggagccgg atcgagtatc gccgccgcca gcgggccgat gacgacctgg gcctggtctt    4380
ccaggactgg ggcctgcaga ccgtggacgc cctgcgcgag gcgcggcccg cgcttgcggc    4440
ccatgatgga accagcgtgc tgatcgccag cggcggcatc cgcaacggtg tcgacatggc    4500
```

-continued

```
gaaatgcgtc atcctggggg ccgacatgtg cggggtcgcc gcgcccctgc tgaaagcggc    4560
ccaaaactcg cgcgaggcgg ttgtatccgc catccgaaa ctgcatctgg agttccggac     4620
agccatgttc ctcctgggtt gcggcacgct tgccgacctg aaggacaatt cctcgcttat    4680 ccgtca atg aaa gtg cct aag atg acc gtg aca gga atc gaa gcg atc       4728
       Met Lys Val Pro Lys Met Thr Val Thr Gly Ile Glu Ala Ile
        1               5                   10 agc ttc tac acc ccc cag aac tac gtg gga ctg gat atc ctt gcc gcg      4776
Ser Phe Tyr Thr Pro Gln Asn Tyr Val Gly Leu Asp Ile Leu Ala Ala
15                  20                  25                  30 cat cac ggg atc gac ccc gag aag ttc tcg aag ggg atc ggg cag gag      4824
His His Gly Ile Asp Pro Glu Lys Phe Ser Lys Gly Ile Gly Gln Glu
                35                  40                  45 aaa atc gca ctg ccc ggc cat gac gag gat atc gtg acc atg gcc gcc      4872
Lys Ile Ala Leu Pro Gly His Asp Glu Asp Ile Val Thr Met Ala Ala
                    50                  55                  60 gag gcc gcg ctg ccg atc atc gaa cgc gcg ggc acg cag ggc atc gac      4920
Glu Ala Ala Leu Pro Ile Ile Glu Arg Ala Gly Thr Gln Gly Ile Asp
                65                  70                  75 acg gtt ctg ttc gcc acc gag agc ggg atc gac cag tcg aag gcc gcc      4968
Thr Val Leu Phe Ala Thr Glu Ser Gly Ile Asp Gln Ser Lys Ala Ala
            80                  85                  90 gcc atc tat ctg cgc cgc ctg ctg gac ctg tcg ccc aac tgc cgt tgc      5016
Ala Ile Tyr Leu Arg Arg Leu Leu Asp Leu Ser Pro Asn Cys Arg Cys
95                  100                 105                 110 gtc gag ctg aag cag gcc tgc tat tcc gcg acg gcg gcg ctg cag atg      5064
Val Glu Leu Lys Gln Ala Cys Tyr Ser Ala Thr Ala Ala Leu Gln Met
                    115                 120                 125 gcc tgc gcg cat gtc gcc cgc aag ccc gac cgc aag gtg ctg gtg atc      5112
Ala Cys Ala His Val Ala Arg Lys Pro Asp Arg Lys Val Leu Val Ile
                130                 135                 140 gcg tcc gat gtc gcg cgc tat gac cgc gaa agc tcg ggc gag gcg acg      5160
Ala Ser Asp Val Ala Arg Tyr Asp Arg Glu Ser Ser Gly Glu Ala Thr
            145                 150                 155 cag ggt gcg ggc gcc gtc gcc atc ctt gtc agc gcc gat ccc aag gtg      5208
Gln Gly Ala Gly Ala Val Ala Ile Leu Val Ser Ala Asp Pro Lys Val
            160                 165                 170 gcc gag atc ggc acc gtc tcg ggg ctg ttc acc gag gat atc atg gat      5256
Ala Glu Ile Gly Thr Val Ser Gly Leu Phe Thr Glu Asp Ile Met Asp
175                 180                 185                 190 ttc tgg cgg ccg aac cac cgc gcg acg ccc ctg ttc gac ggc aag gca      5304
Phe Trp Arg Pro Asn His Arg Arg Thr Pro Leu Phe Asp Gly Lys Ala
                195                 200                 205 tcg acg ctg cgc tat ctg aac gcg ctg gtc gag gcg tgg aac gac tat      5352
Ser Thr Leu Arg Tyr Leu Asn Ala Leu Val Glu Ala Trp Asn Asp Tyr
            210                 215                 220 cgc gcg aat ggc ggc cac gag ttc gcc gat ttc gcg cat ttc tgc tat      5400
Arg Ala Asn Gly Gly His Glu Phe Ala Asp Phe Ala His Phe Cys Tyr
            225                 230                 235 cac gtg ccg ttc tcg cgg atg ggc gag aag gcg aac agc cac ctg gcc      5448
His Val Pro Phe Ser Arg Met Gly Glu Lys Ala Asn Ser His Leu Ala
        240                 245                 250 aag gcg aac aag acg ccg gtg gac atg ggg cag gtg cag acg ggc ctg      5496
Lys Ala Asn Lys Thr Pro Val Asp Met Gly Gln Val Gln Thr Gly Leu
255                 260                 265                 270 atc tac aac cgg cag gtc ggg aac tgc tat acc ggg tcg atc tac ctg      5544
Ile Tyr Asn Arg Gln Val Gly Asn Cys Tyr Thr Gly Ser Ile Tyr Leu
                275                 280                 285 gca ttc gcc tcg ctg ctg gag aac gct cag gag gac ctg acc ggc gcg      5592
Ala Phe Ala Ser Leu Leu Glu Asn Ala Gln Glu Asp Leu Thr Gly Ala
```

```
                Ala Phe Ala Ser Leu Leu Glu Asn Ala Gln Glu Asp Leu Thr Gly Ala
                            290                 295                 300 ctg gtc ggt ctg ttc agc tat ggc tcg ggt gcg acg ggc gaa ttc ttc          5640
Leu Val Gly Leu Phe Ser Tyr Gly Ser Gly Ala Thr Gly Glu Phe Phe
            305                 310                 315 gat gcg cgg atc gcg ccc ggt tac cgc gac cac ctg ttc gcg gaa cgc          5688
Asp Ala Arg Ile Ala Pro Gly Tyr Arg Asp His Leu Phe Ala Glu Arg
        320                 325                 330 cat cgc gaa ttg ctg cag gat cgc acg ccc gtc aca tat gac gaa tac          5736
His Arg Glu Leu Leu Gln Asp Arg Thr Pro Val Thr Tyr Asp Glu Tyr
335                 340                 345                 350 gtt gcc ctg tgg gac gag atc gac ctg acg cag ggc gcg ccc gac aag          5784
Val Ala Leu Trp Asp Glu Ile Asp Leu Thr Gln Gly Ala Pro Asp Lys
                355                 360                 365 gcg cgc ggt cgt ttc agg ctg gca ggt atc gag gac gag aag cgc atc          5832
Ala Arg Gly Arg Phe Arg Leu Ala Gly Ile Glu Asp Glu Lys Arg Ile
            370                 375                 380 tat gtc gac cgg cag gcc tga agcaggcgcc catgccccgg gcaagctgat             5883
Tyr Val Asp Arg Gln Ala
            385 cctgtccggg gaacattccg tgctctatgg tgcgcccgcg cttgccatgg ccatcgcccg        5943
ctataccgag gtgtggttca cgccgcttgg cattggcgag gggatacgca cgacattcgc        6003
caatctctcg ggcggggcga cctattcgct gaagctgctg tcgggttca agtcgcggct         6063
ggaccgccgg ttcgagcagt tcctgaacgg cgacctaaag gtgcacaagg tcctgaccca        6123
tcccgacgat ctggcggtct atgcgctggc gtcgcttctg cacgacaagc cgccggggac        6183
cgccgcgatg ccgggcatcg gcgcgatgca ccacctgccg cgaccgggtg agctgggcag        6243
ccggacggag ctgcccatcg gcgcgggcat ggggtcgtct gcggccatcg tcgcggccac        6303
cacggtcctg ttcgagacgc tgctggaccg gcccaagacg cccgaacagc gcttcgaccg        6363
cgtccgcttc tgcgagcggt tgaagcacgg caaggccggt cccatcgacg cggccagcgt        6423
cgtgcgcggc gggcttgtcc gcgtgggcgg gaacgggccg ggttcgatca gcagcttcga        6483
tttgcccgag gatcacgacc ttgtcgcggg acgcggctgg tactgggtac tgcacgggcg        6543
ccccgtcagc gggaccggcg aatgcgtcag cgcggtcgcg gcggcgcatg gtcgcgatgc        6603
ggcgctgtgg gacgccttcg cagtctgcac ccgcgcgttg gaggccgcgc tgctgtctgg        6663
gggcagcccc gacgccgcca tcaccgagaa ccagcgcctg ctggaacgca tcggcgtcgt        6723
gccggcagcg acgcaggccc tcgtggccca gatcgaggag gcgggtggcg cggccaagat        6783
ctgcggcgca ggttccgtgc ggggcgatca cggcggggcg gtcctcgtgc ggattgacga        6843
cgcgcaggcg atggcttcgg tcatggcgcg ccatcccgac ctcgactggg cgccctgcg         6903
catgtcgcgc acggggcgg caccggccc cgcgccgcgt gcgcaaccgc tgccggggca         6963
gggctgatgg atcaggtcat ccgcgccagc gcgccgggtt cggtcatgat acgggcgaa         7023
catgccgtgg tctatggaca ccgcgccatc gtcgccggga tcgagcagcg cgcccatgtg        7083
acgatcgtcc cgcgtgccga ccgcatgttt cgcatcacct cgcagatcgg ggcgccgcag        7143
cagggtcgc tggacgatct gcctgcgggc gggacctatc gcttcgtgct ggccgccatc         7203
gcgcgacacg cgccggacct gccttgcggg ttcgacatgg acatcacctc ggggatcgat        7263
ccgaggctcg ggcttggatc ctcggcggcg gtgacggtcg cctgcctcgg cgcgctgtcg        7323
cggctggcgg ggcgggggac cgaggggctg catgacgacg cgctgcgcat cgtccgcgcc        7383
atccagggca ggggcagcgg ggccgatctg cggccagcc tgcatggcgg cttcgtcgcc         7443
```

```
tatcgcgcgc ccgatggcgg tgccgcgcag atcgaggcgc ttccggtgcc gccggggccg      7503
ttcggcctgc gctatgcggg ctacaagacc ccgacagccg aggtgctgcg ccttgtggcc      7563
gatcggatgg cgggcaacga ggccgctttc gacgcgctct actcccggat gggcgcaagc      7623
gcagatgccg cgatccgcgc ggcgcaaggg ctggactggg ctgcattcca cgacgcgctg      7683
aacgaatacc agcgcctgat ggagcagctg ggcgtgtccg acgacacgct ggacgcgatc      7743
atccgcgagg cgcgcgacgc gggcgccgca gtcgccaaga tctccggctc ggggctgggg      7803
gattgcgtgc tggcactggg cgaccagccc aagggtttcg tgcccgcaag cattgccgag      7863
aagggacttg ttttcgatga ctgatgccgt ccgcgacatg atcgcccgtg ccatggcggg      7923
cgcgaccgac atccgagcag ccgaggctta tgcgcccagc aacatcgcgc tgtcgaaata      7983
ctggggcaag cgcgacgccg cgcggaacct tccgctgaac agctccgtct cgatctcgtt      8043
ggcgaactgg ggctctcata cgcgggtcga ggggtccggc acgggccacg acgaggtgca      8103
tcacaacggc acgctgctgg atccgggcga cgccttcgcg cgccgcgcgt tggcattcgc      8163
tgacctgttc cggggggga ggcacctgcc gctgcggatc acgacgcaga actcgatccc      8223
gacggcggcg gggcttgcct cgtcggcctc ggggttcgcg gcgctgaccc gtgcgctggc      8283
gggggcgttc gggctggatc tggacgacac ggatctgagc cgcatcgccc ggatcggcag      8343
tggcagcgcc gcccgctcga tctggcacgg cttcgtccgc tggaaccggg gcgaggccga      8403
ggatgggcat gacagccacg gcgtcccgct ggacctgcgc tggcccggct ccgcatcgc      8463 gatcgtggcc gtggacaagg ggcccaagcc tttcagttcg cgcgacggca tgaaccacac      8523
ggtcgagacc agcccgctgt tcccgccctg gcctgcgcag gcggaagcgg attgccgcgt      8583
catcgaggat gcgatcgccg cccgcgacat ggccgccctg ggtccgcggg tcgaggcgaa      8643
cgcccttgcg atgcacgcca cgatgatggc cgcgcgcccg ccgctctgct acctgacggg      8703
cggcagctgg caggtgctgg aacgcctgtg gcaggcccgc gcggacgggc ttgcggcctt      8763
tgcgacgatg gatgccggcc cgaacgtcaa gctgatcttc gaggaaagca gcgccgccga      8823
cgtgctgtac ctgttccccg acgccagcct gatcgcgccg ttcgaggggc gttgaacgcg      8883
taagacgacc actgggtaag gttctgccgc gcgtggtctc gactgcctgc aaagaggtgc      8943
ttgagttgct gcgtgactgc ggcggccgac ttcgtgggac ttgcccgcca cgctgacgcg      9003
ctggaaacgc gcccgcggat tacgaccgcg tcattgccct gaaccaattt cccgtcggtc      9063
gac                                                                   9066
```

<210> SEQ ID NO 47
<211> LENGTH: 388
<212> TYPE: PRT
<213> ORGANISM: Paracoccus sp. R114

<400> SEQUENCE: 47

```
Met Lys Val Pro Lys Met Thr Val Thr Gly Ile Glu Ala Ile Ser Phe
1               5                   10                  15

Tyr Thr Pro Gln Asn Tyr Val Gly Leu Asp Ile Leu Ala Ala His His
            20                  25                  30

Gly Ile Asp Pro Glu Lys Phe Ser Lys Gly Ile Gly Gln Glu Lys Ile
        35                  40                  45

Ala Leu Pro Gly His Asp Glu Asp Ile Val Thr Met Ala Ala Glu Ala
    50                  55                  60

Ala Leu Pro Ile Ile Glu Arg Ala Gly Thr Gln Gly Ile Asp Thr Val
65                  70                  75                  80
```

```
Leu Phe Ala Thr Glu Ser Gly Ile Asp Gln Ser Lys Ala Ala Ile
                85                  90                  95

Tyr Leu Arg Arg Leu Leu Asp Leu Ser Pro Asn Cys Arg Cys Val Glu
            100                 105                 110

Leu Lys Gln Ala Cys Tyr Ser Ala Thr Ala Ala Leu Gln Met Ala Cys
            115                 120                 125

Ala His Val Ala Arg Lys Pro Asp Arg Lys Val Leu Val Ile Ala Ser
        130                 135                 140

Asp Val Ala Arg Tyr Asp Arg Glu Ser Ser Gly Glu Ala Thr Gln Gly
145                 150                 155                 160

Ala Gly Ala Val Ala Ile Leu Val Ser Ala Asp Pro Lys Val Ala Glu
                165                 170                 175

Ile Gly Thr Val Ser Gly Leu Phe Thr Glu Asp Ile Met Asp Phe Trp
            180                 185                 190

Arg Pro Asn His Arg Arg Thr Pro Leu Phe Asp Gly Lys Ala Ser Thr
        195                 200                 205

Leu Arg Tyr Leu Asn Ala Leu Val Glu Ala Trp Asn Asp Tyr Arg Ala
    210                 215                 220

Asn Gly Gly His Glu Phe Ala Asp Phe Ala His Phe Cys Tyr His Val
225                 230                 235                 240

Pro Phe Ser Arg Met Gly Glu Lys Ala Asn Ser His Leu Ala Lys Ala
                245                 250                 255

Asn Lys Thr Pro Val Asp Met Gly Gln Val Gln Thr Gly Leu Ile Tyr
            260                 265                 270

Asn Arg Gln Val Gly Asn Cys Tyr Thr Gly Ser Ile Tyr Leu Ala Phe
        275                 280                 285

Ala Ser Leu Leu Glu Asn Ala Gln Glu Asp Leu Thr Gly Ala Leu Val
290                 295                 300

Gly Leu Phe Ser Tyr Gly Ser Gly Ala Thr Gly Glu Phe Phe Asp Ala
305                 310                 315                 320

Arg Ile Ala Pro Gly Tyr Arg Asp His Leu Phe Ala Glu Arg His Arg
                325                 330                 335

Glu Leu Leu Gln Asp Arg Thr Pro Val Thr Tyr Asp Glu Tyr Val Ala
            340                 345                 350

Leu Trp Asp Glu Ile Asp Leu Thr Gln Gly Ala Pro Asp Lys Ala Arg
        355                 360                 365

Gly Arg Phe Arg Leu Ala Gly Ile Glu Asp Glu Lys Arg Ile Tyr Val
    370                 375                 380

Asp Arg Gln Ala
385

<210> SEQ ID NO 48
<211> LENGTH: 9066
<212> TYPE: DNA
<213> ORGANISM: Paracoccus sp. R114
<220> FEATURE:
<221> NAME/KEY: CDS
<222> LOCATION: (5834)..(6970)
<223> OTHER INFORMATION: mvk

<400> SEQUENCE: 48
ggatccggca gctcgacacg ccgcagaacc tgtacgaacg tcccgccagc cgcttcgtcg      60
cggaattcgt cgggcgcggg acggtggtgc ccgtgcaggc ccatgacggc gcgggccgcg     120
cccgcatcct gggggccgag gtggcggtga acgccgcccc gcaatcgcgc tttgtcgatc     180
acgtctgcct gcgccccgag aaccttgcca tctccgagac gggcgacctg cgcgccaagg     240
```

```
                                           -continued tcgcgcgcgt cacctatctt ggcgggaaat acctgctgga aaccgtgctg gattgcggca    300
cccggctggt gaccgagacc cgcgcccgct tcgatacggg cgcgcagctt ggcctgacca    360
tcaacgcccc ctgggccttt gccgaggatt gaatggacag cgtgaagatc ctttcgggca    420
tgggcgtgaa gggccctgcc tgcatcaggc tggatgtcgg cgggatgcgc ctgatcctcg    480
attgcgggac cggcccggac gagggcgcgg agttcgaccc cgcctggctg gcggacgcgg    540
atgcggtgct gatcacccat gaccacgtgg accatatcgg cggcgcgcgt cacgcggtcg    600
cggcggggct gccgatccat gcgacgcggc agacggcggg gttgctgccc gcgggggcgg    660
atctgcgcct gctgcccgaa cgcggtgtca cgcggatcgc cggggtcgat ctgacgaccg    720
gtcgcaacgg gcatgccgcg ggcggcgtct ggatgcattt cgacatgggc gaggggctgt    780
tctattccgg cgactggtcc gaggaatccg actggttcgc cttcgatccg cccccgcctg    840
cggggacggc gattctcgac tgctcctatg gcggtttcga cgtggcgcaa tcggattgca    900
tcgcggacct ggacgacctg ctcgaggtgc tgccggggca ggtactgctg ccggtgccgc    960 catccgccg cgcggccgag ctggccctgc ggctgatccg ccgccacgga ccgggcagcg   1020
tgatggtcga cgacgcctgc ctgccggcca tcgcgcaact gcccgaggcg cgcggactgg   1080
cctacgccac cgaggcacgc tttcttgtct gcgacacgcc gaacgccgaa agccggcgcg   1140
gcatggcggc atctgcaagc atggcgcgat gcgggcaggc tggggcggga cgcgcatgtc   1200
gtcttcaccg gcacatgaa cgtccatgcg cgcgcattct gcgaccgccc cggcgggcat   1260
ttccgccgct ggaacgtgca tccgccgctg cgcgaccagc gacggatgct ggaacggctg   1320
gccgcgcggc gctttgcccc ggccttctgc cccgacccg agatctatct ggcgctggac   1380
atgggcgcgc aggtcttcat gcaccaggag gtgacgccat gatccccgcc cgcagcttct   1440
gcctgatccg ccacggcgaa acgaccgcca atgcaggggc gatcatcgcg ggcgcaaccg   1500
atgtgcccct gacgccaagg ggccgcgatc aggcccgcgc cctggcaggg cgcgaatggc   1560
catcgggcat cgcgctgttc gccagcccga tgtcgcgtgc ccgcgatacc gcgctgctgg   1620
cctttccggg gcgcgaccac cagcccgaac ccgatctgcg cgaacgcgac tgggcatct    1680 tcgagggacg ccccgtcgcc gatctgcccc cgcgcgaaat cacgccgcag gggggcgagg   1740
gctgggacga cgtgatggcc cgcgtggacc gcgcgatccg gcggatctgc gcgacctcgg   1800
gcgatgcgct gccggtgctg gtctgccatt cgggcgtgat ccgtgccgcg cgcgtgctgt   1860
ggaccaccgg cgatgcgggc gatcgtccgc ccaacgccac gccgatcctg ttcagcccgg   1920
acggcgaccg attaaaggaa ggaacgatat gaccgccacc accccctgcg tcgtcttcga   1980
acgtggacgg cacgcttgcc gaattcgacg ccgaccgcct gggccatctt gtccacggca   2040
cgaccaagca ctggacgcc ttccaccacg cgatggccga cgccccgccc atccccgagg   2100
tcgcccgcct gatgcgcaag ctgaaggagg gggcgagac ggtcgtcatc tgctcggggc   2160
ggccccgcgg ctggcaggat cagacgatcg catggctgcg caagcacgac ctgcccttcg   2220
acgggatcta tctgcgcccc gaggatcagg acggcgccag cgaccccgag gtcaagcgcc   2280
gcgccctagc cgagatgcgc gccgacgggc tggcgccctg gctggtcgtg gacgaccggc   2340
ggtccgtcgt ggatgcctgg cgggccgagg gctggtctg cctgcaatgc gcgccggggg   2400
acttctaggg ccgcgcgacg ggggcgcgga caggctgggc gggaaaccgc cccgccacca   2460
tgtcctgcac gcgtcgaacc gcccgtccga cgccggtttc cgcacggaaa cgcgcggcaa   2520
gttgacataa cttgcacgcg acgtctcgat tctgcccgcg aagaatgcga tgcatccaga   2580
```

```
tgatgcagaa cgaagaagcg gaagcgcccg tgaaagacca gatgatttcc catacccogg    2640 tgcccacgca atgggtcggc ccgatcctgt tccgcggccc cgtcgtcgag ggcccgatca    2700
gcgcgccgct ggccacctac gagacgccgc tctggccctc gaccgcgcgg ggggcagggg    2760 tttccoggca ttcgggcggg atccaggtct cgctggtcga cgaacgcatg agccgctcga    2820
tcgcgctgcg ggcgcatgac ggggcggcgg cgaccgccgc ctggcagtcg atcaaggccc    2880
gccaggaaga ggtcgcggcc gtggtcgcca ccaccagccc cttcgcccgc cttgtcgagc    2940
tgaatcgcca gatcgtgggc aacctgcttt acatccgcat cgaatgcgtg acgggcgacg    3000
cctcgggtca caacatggtc accaaggccg ccgaggccgt gcaggctgg atcctgtcgg     3060 aatacccgat gctggcctat tccacgatct cggggaacct gtgcaccgac aagaaggcgt    3120
cggcggtcaa cggcatcctg ggccgcggca aatacgccgt cgccgaggtc gagatcccgc    3180
gcaagatcct gacccgcgtg ctgcgcacca gcgccgagaa gatggtccgc ctgaactacg    3240
agaagaacta tgtcggggt acgctggcgg ggtcgctgcg cagtgcgaac gcgcatttcg     3300
ccaacatgct gctgggcttc tacctggcga cggggcagga cgcggccaac atcatcgagg    3360
ccagccaggg cttcgtccat tgcgaggccc gcggcgagga tctgtatttc tcgtgcacgc    3420
tgcccaacct catcatgggc tcggtcggtg ccggcaaggg catcccctcg atcgaggaga    3480
acctgtcgcg gatgggctgc cgccagccgg gcgaacccgg cgacaacgcg cgccgtcttg    3540
cggcgatctg cgcgggcgtc gtgctgtgtg gtgaattgtc gctgcttgcg gcccagacca    3600 acccoggaga gttggtccgc acccacatgg agatggagcg atgaccgaca gcaaggatca    3660
ccatgtcgcg gggcgcaagc tggaccatct gcgtgcattg gacgacgatg cggatatcga    3720
ccggggcgac agcggcttcg accgcatcgc gctgacccat cgcgccctgc ccgaggtgga    3780
tttcgacgcc atcgacacgg cgaccagctt cctgggccgt gaactgtcct cccgctgct    3840 gatctcgtcc atgaccggcg gcaccggcga ggagatcgag cgcatcaacc gcaacctggc    3900
cgctggtgcc gaggaggccc gcgtcgccat ggcggtgggc tcgcagcgcg tgatgttcac    3960
cgacccctcg gcgcgggcca gcttcgacct gcgcgcccat gcgcccaccg tgccgctgct    4020
ggccaatatc ggcgcggtgc agctgaacat ggggctgggg ctgaaggaat gcctggccgc    4080
gatcgaggtg ctgcaggcgg acggcctgta tctgcacctg aaccccctgc aagaggccgt    4140
ccagcccgag ggggatcgcg actttgccga tctgggcagc aagatcgcgg ccatcgcccg    4200
cgacgttccc gtgcccgtcc tgctgaagga ggtgggctgc ggcctgtcgg cggccgatat    4260
cgccatcggg ctgcgcgccg ggatccggca tttcgacgtg gccggtcgcg gcggcacatc    4320
ctggagccgg atcgagtatc gccgccgcca gcgggccgat gacgacctgg gcctggtctt    4380
ccaggactgg ggcctgcaga ccgtggacgc cctgcgcgag gcgcggcccg cgcttgcggc    4440
ccatgatgga accagcgtgc tgatcgccag cggcggcatc cgcaacggtg tcgacatggc    4500
gaaatgcgtc atcctggggg ccgacatgtg cggggtcgcc gcgcccctgc tgaaagcggc    4560
ccaaaactcg cgcgaggcgg ttgtatccgc catccggaaa ctgcatctgg agttccggac    4620
agccatgttc ctcctggggtt gcggcacgct tgccgacctg aaggacaatt cctcgcttat    4680
ccgtcaatga aagtgcctaa gatgaccgtg acaggaatcg aagcgatcag cttctacacc    4740
ccccagaact acgtgggact ggatatcctt gccgcgcatc acgggatcga ccccgagaag    4800
ttctcgaagg ggatcgggca ggagaaaatc gcactgcccg gccatgacga ggatatcgtg    4860
accatggccg ccgaggccgc gctgccgatc atcgaacgcg cgggcacgca gggcatcgac    4920
acggttctgt tcgccaccga gagcgggatc gaccagtcga aggccgccgc catctatctg    4980
```

-continued

```
cgccgcctgc tggacctgtc gcccaactgc cgttgcgtcg agctgaagca ggcctgctat    5040
tccgcgacgg cggcgctgca gatggcctgc gcgcatgtcg cccgcaagcc cgaccgcaag    5100
gtgctggtga tcgcgtccga tgtcgcgcgc tatgaccgcg aaagctcggg cgaggcgacg    5160
cagggtgcgg gcgccgtcgc catccttgtc agcgccgatc ccaaggtggc cgagatcggc    5220
accgtctcgg ggctgttcac cgaggatatc atggatttct gcggccgaa  ccaccgccgc    5280 acgcccctgt tcgacggcaa ggcatcgacg ctgcgctatc tgaacgcgct ggtcgaggcg    5340
tggaacgact atcgcgcgaa tggcggccac gagttcgccg atttcgcgca tttctgctat    5400
cacgtgccgt tctcgcggat gggcgagaag gcgaacagcc acctggccaa ggcgaacaag    5460
acgccggtgg acatggggca ggtgcagacg ggcctgatct acaaccggca ggtcgggaac    5520
tgctataccg ggtcgatcta cctggcattc gcctcgctgc tggagaacgc tcaggaggac    5580
ctgaccggcg cgctggtcgg tctgttcagc tatggctcgg gtgcgacggg cgaattcttc    5640
gatgcgcgga tcgcgcccgg ttaccgcgac cacctgttcg cggaacgcca tcgcgaattg    5700
ctgcaggatc gcacgcccgt cacatatgac gaatacgttg ccctgtggga cgagatcgac    5760
ctgacgcagg gcgcgcccga caaggcgcgc ggtcgtttca ggctggcagg tatcgaggac    5820
```

| | | |
|---|---|---|
| gagaagcgca tct atg tcg acc ggc agg cct gaa gca ggc gcc cat gcc<br>               Met Ser Thr Gly Arg Pro Glu Ala Gly Ala His Ala<br>                1                   5                   10 | | 5869 |

```
ccg ggc aag ctg atc ctg tcc ggg gaa cat tcc gtg ctc tat ggt gcg    5917
Pro Gly Lys Leu Ile Leu Ser Gly Glu His Ser Val Leu Tyr Gly Ala
         15                  20                  25 ccc gcg ctt gcc atg gcc atc gcc cgc tat acc gag gtg tgg ttc acg    5965
Pro Ala Leu Ala Met Ala Ile Ala Arg Tyr Thr Glu Val Trp Phe Thr
 30                  35                  40 ccg ctt ggc att ggc gag ggg ata cgc acg aca ttc gcc aat ctc tcg    6013
Pro Leu Gly Ile Gly Glu Gly Ile Arg Thr Thr Phe Ala Asn Leu Ser
 45                  50                  55                  60 ggc ggg gcg acc tat tcg ctg aag ctg ctg tcg ggg ttc aag tcg cgg    6061
Gly Gly Ala Thr Tyr Ser Leu Lys Leu Leu Ser Gly Phe Lys Ser Arg
                 65                  70                  75 ctg gac cgc cgg ttc gag cag ttc ctg aac ggc gac cta aag gtg cac    6109
Leu Asp Arg Arg Phe Glu Gln Phe Leu Asn Gly Asp Leu Lys Val His
             80                  85                  90 aag gtc ctg acc cat ccc gac gat ctg gcg gtc tat gcg ctg gcg tcg    6157
Lys Val Leu Thr His Pro Asp Asp Leu Ala Val Tyr Ala Leu Ala Ser
         95                  100                 105 ctt ctg cac gac aag ccg ccg ggg acc gcc gcg atg ccg ggc atc ggc    6205
Leu Leu His Asp Lys Pro Pro Gly Thr Ala Ala Met Pro Gly Ile Gly
 110                 115                 120 gcg atg cac cac ctg ccg cga ccg ggt gag ctg ggc agc cgg acg gag    6253
Ala Met His His Leu Pro Arg Pro Gly Glu Leu Gly Ser Arg Thr Glu
125                 130                 135                 140 ctg ccc atc ggc gcg ggc atg ggg tcg tct gcg gcc atc gtc gcg gcc    6301
Leu Pro Ile Gly Ala Gly Met Gly Ser Ser Ala Ala Ile Val Ala Ala
                 145                 150                 155 acc acg gtc ctg ttc gag acg ctg ctg gac cgg ccc aag acg ccc gaa    6349
Thr Thr Val Leu Phe Glu Thr Leu Leu Asp Arg Pro Lys Thr Pro Glu
             160                 165                 170 cag cgc ttc gac cgc gtc cgc ttc tgc gag cgg ttg aag cac ggc aag    6397
Gln Arg Phe Asp Arg Val Arg Phe Cys Glu Arg Leu Lys His Gly Lys
         175                 180                 185 gcc ggt ccc atc gac gcg gcc agc gtc gtg cgc ggc ggg ctt gtc cgc    6445
Ala Gly Pro Ile Asp Ala Ala Ser Val Val Arg Gly Gly Leu Val Arg
```

```
                                               -continued
           190                 195                 200
gtg ggc ggg aac ggg ccg ggt tcg atc agc agc ttc gat ttg ccc gag      6493
Val Gly Gly Asn Gly Pro Gly Ser Ile Ser Ser Phe Asp Leu Pro Glu
205                 210                 215                 220 gat cac gac ctt gtc gcg gga cgc ggc tgg tac tgg gta ctg cac ggg      6541
Asp His Asp Leu Val Ala Gly Arg Gly Trp Tyr Trp Val Leu His Gly
                225                 230                 235 cgc ccc gtc agc ggg acc ggc gaa tgc gtc agc gcg gtc gcg gcg gcg      6589
Arg Pro Val Ser Gly Thr Gly Glu Cys Val Ser Ala Val Ala Ala Ala
            240                 245                 250 cat ggt cgc gat gcg gcg ctg tgg gac gcc ttc gca gtc tgc acc cgc      6637
His Gly Arg Asp Ala Ala Leu Trp Asp Ala Phe Ala Val Cys Thr Arg
        255                 260                 265 gcg ttg gag gcc gcg ctg ctg tct ggg ggc agc ccc gac gcc gcc atc      6685
Ala Leu Glu Ala Ala Leu Leu Ser Gly Gly Ser Pro Asp Ala Ala Ile
    270                 275                 280 acc gag aac cag cgc ctg ctg gaa cgc atc ggc gtc gtg ccg gca gcg      6733
Thr Glu Asn Gln Arg Leu Leu Glu Arg Ile Gly Val Val Pro Ala Ala
285                 290                 295                 300 acg cag gcc ctc gtg gcc cag atc gag gag gcg ggt ggc gcg gcc aag      6781
Thr Gln Ala Leu Val Ala Gln Ile Glu Glu Ala Gly Gly Ala Ala Lys
                305                 310                 315 atc tgc ggc gca ggt tcc gtg cgg ggc gat cac ggc ggg gcg gtc ctc      6829
Ile Cys Gly Ala Gly Ser Val Arg Gly Asp His Gly Gly Ala Val Leu
            320                 325                 330 gtg cgg att gac gac gcg cag gcg atg gct tcg gtc atg gcg cgc cat      6877
Val Arg Ile Asp Asp Ala Gln Ala Met Ala Ser Val Met Ala Arg His
        335                 340                 345 ccc gac ctc gac tgg gcg ccc ctg cgc atg tcg cgc acg ggg gcg gca      6925
Pro Asp Leu Asp Trp Ala Pro Leu Arg Met Ser Arg Thr Gly Ala Ala
    350                 355                 360 ccc ggc ccc gcg ccg cgt gcg caa ccg ctg ccg ggg cag ggc tga          6970
Pro Gly Pro Ala Pro Arg Ala Gln Pro Leu Pro Gly Gln Gly
365                 370                 375 tggatcaggt catccgcgcc agcgcgccgg gttcggtcat gatcacgggc gaacatgccg    7030
tggtctatgg acaccgcgcc atcgtcgccg ggatcgagca gcgcgcccat gtgacgatcg    7090
tcccgcgtgc cgaccgcatg tttcgcatca cctcgcagat cggggcgccg cagcaggggt    7150
cgctggacga tctgcctgcg ggcgggacct atcgcttcgt gctggccgcc atcgcgcgac    7210
acgcgccgga cctgccttgc gggttcgaca tggacatcac ctcggggatc gatccgaggc    7270
tcgggcttgg atcctcggcg gcggtgacgg tcgcctgcct cggcgcgctg tcgcggctgg    7330
cggggcgggg gaccgagggg ctgcatgacg acgcgctgcg catcgtccgc gccatccagg    7390
gcaggggcag cggggccgat ctgcggccaa gcctgcatgg cggcttcgtc gcctatcgcg    7450
cgcccgatgg cggtgccgcg cagatcgagg cgcttccggt gccgccgggg ccgttcggcc    7510
tgcgctatgc gggctacaag accccgacag ccgaggtgct gcgccttgtg gccgatcgga    7570
tggcgggcaa cgaggccgct ttcgacgcgc tctactcccg gatgggcgca agcgcagatg    7630
ccgcgatccg cgcggcgcaa gggctggact gggctgcatt ccacgacgcg ctgaacgaat    7690
accagcgcct gatggagcag ctgggcgtgt ccgacgacac gctggacgcg atcatccgcg    7750
aggcgcgcga cgcgggcgcc gcagtcgcca agatctccgg ctcggggctg ggggattgcg    7810
tgctggcact gggcgaccag cccaaggggt tcgtgcccgc aagcattgcc gagaagggac    7870
ttgttttcga tgactgatgc cgtccgcgac atgatcgccc gtgccatggc gggcgcgacc    7930
gacatccgag cagccgaggc ttatgcgccc agcaacatcg cgctgtcgaa atactgggc     7990
```

-continued

```
aagcgcgacg ccgcgcggaa ccttccgctg aacagctccg tctcgatctc gttggcgaac      8050
tggggctctc atacgcgggt cgaggggtcc ggcacgggcc acgacgaggt gcatcacaac      8110
ggcacgctgc tggatccggg cgacgccttc gcgcgccgcg cgttggcatt cgctgacctg      8170
ttccgggggg ggaggcacct gccgctgcgg atcacgacgc agaactcgat cccgacggcg      8230
gcggggcttg cctcgtcggc ctcggggttc gcggcgctga cccgtgcgct ggcggggcg       8290 ttcgggctgg atctggacga cacggatctg agccgcatcg cccggatcgg cagtggcagc     8350
gccgcccgct cgatctggca cggcttcgtc cgctggaacc ggggcgaggc cgaggatggg      8410
catgacagcc acggcgtccc gctggacctg cgctggcccg gcttccgcat cgcgatcgtg      8470
gccgtggaca aggggcccaa gcctttcagt tcgcgcgacg gcatgaacca cacggtcgag      8530
accagcccgc tgttcccgcc ctggcctgcg caggcggaag cggattgccg cgtcatcgag      8590
gatgcgatcg ccgcccgcga catggccgcc ctgggtccgc gggtcgaggc gaacgccctt      8650
gcgatgcacg ccacgatgat ggccgcgcgc ccgccgctct gctacctgac gggcggcagc      8710
tggcaggtgc tggaacgcct gtggcaggcc cgcgcggacg ggcttgcggc ctttgcgacg      8770
atggatgccg gcccgaacgt caagctgatc ttcgaggaaa gcagcgccgc cgacgtgctg      8830
tacctgttcc ccgacgccag cctgatcgcg ccgttcgagg ggcgttgaac gcgtaagacg      8890
accactgggt aaggttctgc cgcgcgtggt ctcgactgcc tgcaaagagg tgcttgagtt      8950
gctgcgtgac tgcggcggcc gacttcgtgg gacttgcccg ccacgctgac gcgctggaaa     9010
cgcgcccgcg gattacagacc gcgtcattgc cctgaaccaa tttcccgtcg gtcgac        9066
```

<210> SEQ ID NO 49
<211> LENGTH: 378
<212> TYPE: PRT
<213> ORGANISM: Paracoccus sp. R114

<400> SEQUENCE: 49

```
Met Ser Thr Gly Arg Pro Glu Ala Gly Ala His Ala Pro Gly Lys Leu
1               5                   10                  15

Ile Leu Ser Gly Glu His Ser Val Leu Tyr Gly Ala Pro Ala Leu Ala
            20                  25                  30

Met Ala Ile Ala Arg Tyr Thr Glu Val Trp Phe Thr Pro Leu Gly Ile
        35                  40                  45

Gly Glu Gly Ile Arg Thr Thr Phe Ala Asn Leu Ser Gly Gly Ala Thr
    50                  55                  60

Tyr Ser Leu Lys Leu Leu Ser Gly Phe Lys Ser Arg Leu Asp Arg Arg
65                  70                  75                  80

Phe Glu Gln Phe Leu Asn Gly Asp Leu Lys Val His Lys Val Leu Thr
                85                  90                  95

His Pro Asp Asp Leu Ala Val Tyr Ala Leu Ala Ser Leu Leu His Asp
            100                 105                 110

Lys Pro Pro Gly Thr Ala Ala Met Pro Gly Ile Gly Ala Met His His
        115                 120                 125

Leu Pro Arg Pro Gly Glu Leu Gly Ser Arg Thr Glu Leu Pro Ile Gly
    130                 135                 140

Ala Gly Met Gly Ser Ser Ala Ala Ile Val Ala Thr Thr Val Leu
145                 150                 155                 160

Phe Glu Thr Leu Leu Asp Arg Pro Lys Thr Pro Glu Gln Arg Phe Asp
                165                 170                 175

Arg Val Arg Phe Cys Glu Arg Leu Lys His Gly Lys Ala Gly Pro Ile
```

```
                    180                 185                 190
Asp Ala Ala Ser Val Val Arg Gly Gly Leu Val Arg Val Gly Gly Asn
                195                 200                 205
Gly Pro Gly Ser Ile Ser Ser Phe Asp Leu Pro Glu Asp His Asp Leu
            210                 215                 220
Val Ala Gly Arg Gly Trp Tyr Trp Val Leu His Gly Arg Pro Val Ser
225                 230                 235                 240
Gly Thr Gly Glu Cys Val Ser Ala Val Ala Ala His Gly Arg Asp
                245                 250                 255
Ala Ala Leu Trp Asp Ala Phe Ala Val Cys Thr Arg Ala Leu Glu Ala
            260                 265                 270
Ala Leu Leu Ser Gly Gly Ser Pro Asp Ala Ala Ile Thr Glu Asn Gln
        275                 280                 285
Arg Leu Leu Glu Arg Ile Gly Val Val Pro Ala Ala Thr Gln Ala Leu
        290                 295                 300
Val Ala Gln Ile Glu Glu Ala Gly Gly Ala Ala Lys Ile Cys Gly Ala
305                 310                 315                 320
Gly Ser Val Arg Gly Asp His Gly Gly Ala Val Leu Val Arg Ile Asp
                325                 330                 335
Asp Ala Gln Ala Met Ala Ser Val Met Ala Arg His Pro Asp Leu Asp
            340                 345                 350
Trp Ala Pro Leu Arg Met Ser Arg Thr Gly Ala Ala Pro Gly Pro Ala
        355                 360                 365
Pro Arg Ala Gln Pro Leu Pro Gly Gln Gly
    370                 375

<210> SEQ ID NO 50
<211> LENGTH: 9066
<212> TYPE: DNA
<213> ORGANISM: Paracoccus sp. R114
<220> FEATURE:
<221> NAME/KEY: CDS
<222> LOCATION: (6970)..(7887)
<223> OTHER INFORMATION: pmk

<400> SEQUENCE: 50
ggatccggca gctcgacacg ccgcagaacc tgtacgaacg tcccgccagc cgcttcgtcg      60
cggaattcgt cgggcgcggg acggtggtgc ccgtgcaggc ccatgacggc gcgggccgcg     120
cccgcatcct gggggccgag gtggcggtga acgccgcccc gcaatcgcgc tttgtcgatc     180
acgtctgcct gcgccccgag aaccttgcca tctccgagac gggcgacctg cgcgccaagg     240
tcgcgcgcgt cacctatctt ggcgggaaat acctgctgga aaccgtgctg gattgcggca     300
cccggctggt gaccgagacc cgcgcccgct tcgatacggg cgcgcagctt ggcctgacca     360
tcaacgcccc ctgggccttt gccgaggatt gaatggacag cgtgaagatc ctttcgggca     420
tgggcgtgaa gggccctgcc tgcatcaggc tggatgtcgg cgggatgcgc ctgatcctcg     480
attgcgggac cggccggac gagggcgcgg agttcgaccc cgcctggctg cggacgcgg       540
atgcggtgct gatcacccat gaccacgtgg accatatcgg cggcgcgcgt cacgcggtcg     600
cggcggggct gccgatccat gcgacgcggc agacggcggg gttgctgccc gcggggggcgg   660
atctgcgcct gctgcccgaa cgcggtgtca cgcggatcgc cggggtcgat ctgacgaccg     720
gtcgcaacgg gcatgccgcg ggcggcgtct ggatgcattt cgacatgggc gagggggctgt   780
tctattccgg cgactggtcc gaggaatccg actggttcgc cttcgatccg ccccgcctg     840
cggggacggc gattctcgac tgctcctatg gcggtttcga cgtggcgcaa tcggattgca    900
```

-continued

```
tcgcggacct ggacgacctg ctcgaggtgc tgccggggca ggtactgctg ccggtgccgc      960
catccggccg cgcggccgag ctggccctgc ggctgatccg ccgccacgga ccgggcagcg     1020
tgatggtcga cgacgcctgc ctgccggcca tcgcgcaact gcccgaggcg cgcggactgg     1080
cctacgccac cgaggcacgc tttcttgtct gcgacacgcc gaacgccgaa agccggcgcg     1140
gcatggcggc atctgcaagc atggcgcgat gcgggcaggc tggggcggga cgcgcatgtc     1200
gtcttcaccg ggcacatgaa cgtccatgcg cgcgcattct gcgaccgccc cggcgggcat     1260
ttccgccgct ggaacgtgca tccgccgctg cgcgaccagc gacggatgct ggaacggctg     1320
gccgcgcggc gctttgcccc ggccttctgc cccgaccccg agatctatct ggcgctggac     1380
atgggcgcgc aggtcttcat gcaccaggag gtgacgccat gatccccgcc cgcagcttct     1440
gcctgatccg ccacggcgaa acgaccgcca atgcagggc gatcatcgcg ggcgcaaccg     1500
atgtgcccct gacgccaagg ggccgcgatc aggcccgcgc cctggcaggg cgcgaatggc     1560
catcgggcat cgcgctgttc gccagcccga tgtcgcgtgc ccgcgatacc gcgctgctgg     1620
cctttccggg gcgcgaccac cagcccgaac ccgatctgcg cgaacgcgac tgggcatct      1680
tcgagggacg ccccgtcgcc gatctgcccc cgcgcgaaat cacgccgcag gggggcgagg     1740
gctgggacga cgtgatggcc cgcgtggacc gcgcgatccg gcggatctgc gcgacctcgg     1800
gcgatgcgct gccggtgctg gtctgccatt cgggcgtgat ccgtgccgcg cgcgtgctgt     1860
ggaccaccgg cgatgcgggc gatcgtccgc ccaacgccac gccgatcctg ttcagcccgg     1920
acggcgaccg attaaaggaa ggaacgatat gaccgccacc accccctgcg tcgtcttcga     1980
acgtggacgg cacgcttgcc gaattcgacg ccgaccgcct gggccatctt gtccacggca     2040
cgaccaagca ctgggacgcc ttccaccacg cgatggccga cgccccgccc atccccgagg     2100
tcgcccgcct gatgcgcaag ctgaaggagg ggggcgagac ggtcgtcatc tgctcggggc     2160
ggccccgcgg ctggcaggat cagacgatcg catggctgcg caagcacgac ctgccccttcg    2220
acgggatcta tctgcgcccc gaggatcagg acggcgccag cgaccccgag gtcaagcgcc     2280
gcgccctagc cgagatgcgc gccgacgggc tggcgccctg gctggtcgtg gacgaccggc     2340
ggtccgtcgt ggatgcctgg cgggccgagg ggctggtctg cctgcaatgc gcgccggggg     2400
acttctaggg ccgcgcgacg ggggcgcgga caggctgggc gggaaaccgc cccgccacca     2460
tgtcctgcac gcgtcgaacc gcccgtccga cgccggtttc gcacggaaa cgcgcggcaa      2520
gttgacataa cttgcacgcg acgtctcgat tctgcccgcg aagaatgcga tgcatccaga     2580
tgatgcagaa cgaagaagcg gaagcgcccg tgaaagacca gatgatttcc catacccgg     2640
tgcccacgca atgggtcggc ccgatcctgt tccgcggccc cgtcgtcgag ggcccgatca     2700
gcgcgccgct ggccacctac gagacgccgc tctggccctc gaccgcgcgg ggggcagggg     2760
tttcccggca ttcgggcggg atccaggtct cgctggtcga cgaacgcatg agccgctcga     2820
tcgcgctgcg ggcgcatgac ggggcggcgg cgaccgccgc ctggcagtcg atcaaggccc     2880
gccaggaaga ggtcgcggcc gtggtcgcca ccaccagccg cttcgcccgc cttgtcgagc     2940
tgaatcgcca gatcgtgggc aacctgcttt acatccgcat cgaatgcgtg acgggcgacg     3000
cctcgggtca caacatggtc accaaggccg ccgaggccgt gcagggctgg atcctgtcgg     3060
aatacccgat gctggcctat tccacgatct cggggaacct gtgcaccgac aagaaggcgt     3120
cggcggtcaa cggcatcctg ggccgcggca aatacgccgt cgccgaggtc gagatcccgc     3180
gcaagatcct gacccgcgtg ctgcgcacca gcgccgagaa gatggtccgc ctgaactacg     3240
```

-continued

```
agaagaacta tgtcgggggt acgctggcgg ggtcgctgcg cagtgcgaac gcgcatttcg    3300
ccaacatgct gctgggcttc tacctggcga cggggcagga cgcggccaac atcatcgagg    3360
ccagccaggg cttcgtccat tgcgaggccc gcggcgagga tctgtatttc tcgtgcacgc    3420
tgcccaacct catcatgggc tcggtcggtg ccggcaaggg catccctcg atcgaggaga     3480
acctgtcgcg gatgggctgc cgccagccgg gcgaacccgg cgacaacgcg cgccgtcttg    3540
cggcgatctg cgcgggcgtc gtgctgtgtg gtgaattgtc gctgcttgcg gcccagacca    3600
accccggaga gttggtccgc acccacatgg agatggagcg atgaccgaca gcaaggatca    3660
ccatgtcgcg gggcgcaagc tggaccatct gcgtgcattg gacgacgatg cggatatcga    3720
ccggggcgac agcggcttcg accgcatcgc gctgacccat cgcgccctgc ccgaggtgga    3780
tttcgacgcc atcgacacgg cgaccagctt cctgggccgt gaactgtcct tcccgctgct    3840
gatctcgtcc atgaccggcg gcaccggcga ggagatcgag cgcatcaacc gcaacctggc    3900
cgctggtgcc gaggaggccc gcgtcgccat ggcggtgggc tcgcagcgcg tgatgttcac    3960
cgaccccctcg gcgcgggcca gcttcgacct gcgcgcccat gcgcccaccg tgccgctgct   4020
ggccaatatc ggcgcggtgc agctgaacat ggggctgggg ctgaaggaat gcctggccgc    4080
gatcgaggtg ctgcaggcgg acggcctgta tctgcacctg aaccccctgc aagaggccgt    4140
ccagcccgag ggggatcgcg actttgccga tctgggcagc aagatcgcgg ccatcgcccg    4200
cgacgttccc gtgcccgtcc tgctgaagga ggtgggctgc ggcctgtcgg cggccgatat    4260
cgccatcggg ctgcgcgccg ggatccggca tttcgacgtg gccggtcgcg gcggcacatc    4320
ctggagccgg atcgagtatc gccgccgcca gcgggccgat gacgacctgg gcctggtctt    4380
ccaggactgg ggcctgcaga ccgtggacgc cctgcgcgag gcgcggcccg cgcttgcggc    4440
ccatgatgga accagcgtgc tgatcgccag cggcggcatc cgcaacggtg tcgacatggc    4500
gaaatgcgtc atcctggggg ccgacatgtg cggggtcgcc gcgcccctgc tgaaagcggc    4560
ccaaaactcg cgcgaggcgg ttgtatccgc catccggaaa ctgcatctgg agttccggac    4620
agccatgttc ctcctggggtt gcggcacgct tgccgacctg aaggacaatt cctcgcttat    4680
ccgtcaatga aagtgcctaa gatgaccgtg acaggaatcg aagcgatcag cttctacacc    4740
ccccagaact acgtgggact ggatatcctt gccgcgcatc acgggatcga ccccgagaag    4800
ttctcgaagg ggatcgggca ggagaaaatc gcactgcccg gccatgacga ggatatcgtg    4860
accatggccg ccgaggccgc gctgccgatc atcgaacgcg cgggcacgca gggcatcgac    4920
acggttctgt tcgccaccga gagcgggatc gaccagtcga aggccgccgc catctatctg    4980
cgccgcctgc tggacctgtc gcccaactgc cgttgcgtcg agctgaagca ggcctgctat    5040
tccgcgacgg cggcgctgca gatggcctgc gcgcatgtcg cccgcaagcc cgaccgcaag    5100
gtgctggtga tcgcgtccga tgtcgcgcgc tatgaccgcg aaagctcggg cgaggcgacg    5160
cagggtgcgg cgccgtcgc catccttgtc agcgccgatc ccaaggtggc cgagatcggc    5220
accgtctcgg ggctgttcac cgaggatatc atggatttct ggcggccgaa ccaccgccgc    5280
acgcccctgt tcgacggcaa ggcatcgacg ctgcgctatc tgaacgcgct ggtcgaggcg    5340
tggaacgact atcgcgcgaa tggcggccac gagttcgccg atttcgcgca tttctgctat    5400
cacgtgccgt tctcgcggat gggcgagaag gcgaacagcc acctggccaa ggcgaacaag    5460
acgccggtgg acatggggca ggtgcagacg ggcctgatct acaaccggca ggtcgggaac    5520
tgctatacag gtcgatcta cctggcattc gcctcgctgc tggagaacgc tcaggaggac    5580
ctgaccggcg cgctggtcgg tctgttcagc tatggctcgg gtgcgacggg cgaattcttc    5640
```

```
                                                       -continued gatgcgcgga tcgcgcccgg ttaccgcgac cacctgttcg cggaacgcca tcgcgaattg     5700
ctgcaggatc gcacgcccgt cacatatgac gaatacgttg ccctgtggga cgagatcgac     5760
ctgacgcagg gcgcgcccga caaggcgcgc ggtcgtttca ggctggcagg tatcgaggac     5820
gagaagcgca tctatgtcga ccggcaggcc tgaagcaggc gcccatgccc cgggcaagct     5880
gatcctgtcc ggggaacatt ccgtgctcta tggtgcgccc gcgcttgcca tggccatcgc     5940
ccgctatacc gaggtgtggt tcacgccgct tggcattggc gagggatac gcacgacatt      6000 cgccaatctc tcgggcgggg cgacctattc gctgaagctg ctgtcgggt tcaagtcgcg       6060 gctggaccgc cggttcgagc agttcctgaa cggcgaccta aaggtgcaca aggtcctgac      6120
ccatcccgac gatctggcgg tctatgcgct ggcgtcgctt ctgcacgaca gccgccggg      6180 gaccgccgcg atgccgggca tcggcgcgat gcaccacctg ccgcgaccgg gtgagctggg     6240
cagccggacg gagctgccca tcggcgcggg catggggtcg tctgcggcca tcgtcgcggc    6300
caccacggtc ctgttcgaga cgctgctgga ccggcccaag acgcccgaac agcgcttcga    6360
ccgcgtccgc ttctgcgagc ggttgaagca cggcaaggcc ggtcccatcg acgcggccag    6420
cgtcgtgcgc ggcgggcttg tccgcgtggg cgggaacggg ccgggttcga tcagcagctt   6480
cgatttgccc gaggatcacg accttgtcgc gggacgcggc tggtactggg tactgcacgg   6540
gcgccccgtc agcgggaccg gcgaatgcgt cagcgcggtc gcggcggcgc atggtcgcga   6600
tgcggcgctg tgggacgcct tcgcagtctg caccccgcgcg ttggaggccg cgctgctgtc  6660
tgggggcagc cccgacgccg ccatcaccga gaaccagcgc ctgctggaac gcatcggcgt  6720
cgtgccggca gcgacgcagg ccctcgtggc ccagatcgag gaggcgggtg gcgcggccaa   6780
gatctgcggc gcaggttccg tgcggggcga tcacggcggg gcggtcctcg tgcggattga   6840
cgacgcgcag gcgatggctt cggtcatggc gcgccatccc gacctcgact gggcgcccct   6900
gcgcatgtcg cgcacggggg cggcacccgg ccccgcgccg cgtgcgcaac cgctgccggg   6960 gcagggctg  atg gat cag gtc atc cgc gcc agc gcg ccg ggt tcg gtc atg  7011
           Met Asp Gln Val Ile Arg Ala Ser Ala Pro Gly Ser Val Met
           1               5                   10 atc acg ggc gaa cat gcc gtg gtc tat gga cac cgc gcc atc gtc gcc         7059
Ile Thr Gly Glu His Ala Val Val Tyr Gly His Arg Ala Ile Val Ala
 15              20                  25                  30 ggg atc gag cag cgc gcc cat gtg acg atc gtc ccg cgt gcc gac cgc        7107
Gly Ile Glu Gln Arg Ala His Val Thr Ile Val Pro Arg Ala Asp Arg
             35                  40                  45 atg ttt cgc atc acc tcg cag atc ggg gcg ccg cag cag ggg tcg ctg        7155
Met Phe Arg Ile Thr Ser Gln Ile Gly Ala Pro Gln Gln Gly Ser Leu
                 50                  55                  60 gac gat ctg cct gcg ggc ggg acc tat cgc ttc gtg ctg gcc gcc atc        7203
Asp Asp Leu Pro Ala Gly Gly Thr Tyr Arg Phe Val Leu Ala Ala Ile
             65                  70                  75 gcg cga cac gcg ccg gac ctg cct tgc ggg ttc gac atg gac atc acc       7251
Ala Arg His Ala Pro Asp Leu Pro Cys Gly Phe Asp Met Asp Ile Thr
 80                  85                  90 tcg ggg atc gat ccg agg ctc ggg ctt gga tcc tcg gcg gcg gtg acg       7299
Ser Gly Ile Asp Pro Arg Leu Gly Leu Gly Ser Ser Ala Ala Val Thr
 95                 100                 105                 110 gtc gcc tgc ctc ggc gcg ctg tcg cgg ctg gcg ggg cgg ggg acc gag       7347
Val Ala Cys Leu Gly Ala Leu Ser Arg Leu Ala Gly Arg Gly Thr Glu
             115                 120                 125 ggg ctg cat gac gac gcg ctg cgc atc gtc cgc gcc atc cag ggc agg       7395
Gly Leu His Asp Asp Ala Leu Arg Ile Val Arg Ala Ile Gln Gly Arg
```

```
                130              135              140
ggc agc ggg gcc gat ctg gcg gcc agc ctg cat ggc ggc ttc gtc gcc      7443
Gly Ser Gly Ala Asp Leu Ala Ala Ser Leu His Gly Gly Phe Val Ala
        145                 150                 155 tat cgc gcg ccc gat ggc ggt gcc gcg cag atc gag gcg ctt ccg gtg      7491
Tyr Arg Ala Pro Asp Gly Gly Ala Ala Gln Ile Glu Ala Leu Pro Val
    160                 165                 170 ccg ccg ggg ccg ttc ggc ctg cgc tat gcg ggc tac aag acc ccg aca      7539
Pro Pro Gly Pro Phe Gly Leu Arg Tyr Ala Gly Tyr Lys Thr Pro Thr
175                 180                 185                 190 gcc gag gtg ctg cgc ctt gtg gcc gat cgg atg gcg ggc aac gag gcc      7587
Ala Glu Val Leu Arg Leu Val Ala Asp Arg Met Ala Gly Asn Glu Ala
                195                 200                 205 gct ttc gac gcg ctc tac tcc cgg atg ggc gca agc gca gat gcc gcg      7635
Ala Phe Asp Ala Leu Tyr Ser Arg Met Gly Ala Ser Ala Asp Ala Ala
            210                 215                 220 atc cgc gcg gcg caa ggg ctg gac tgg gct gca ttc cac gac gcg ctg      7683
Ile Arg Ala Ala Gln Gly Leu Asp Trp Ala Ala Phe His Asp Ala Leu
        225                 230                 235 aac gaa tac cag cgc ctg atg gag cag ctg ggc gtg tcc gac gac acg      7731
Asn Glu Tyr Gln Arg Leu Met Glu Gln Leu Gly Val Ser Asp Asp Thr
    240                 245                 250 ctg gac gcg atc atc cgc gag gcg cgc gac gcg ggc gcc gca gtc gcc      7779
Leu Asp Ala Ile Ile Arg Glu Ala Arg Asp Ala Gly Ala Ala Val Ala
255                 260                 265                 270 aag atc tcc ggc tcg ggg ctg ggg gat tgc gtg ctg gca ctg ggc gac      7827
Lys Ile Ser Gly Ser Gly Leu Gly Asp Cys Val Leu Ala Leu Gly Asp
                275                 280                 285 cag ccc aag ggt ttc gtg ccc gca agc att gcc gag aag gga ctt gtt      7875
Gln Pro Lys Gly Phe Val Pro Ala Ser Ile Ala Glu Lys Gly Leu Val
            290                 295                 300 ttc gat gac tga tgccgtccgc gacatgatcg cccgtgccat ggcgggcgcg          7927
Phe Asp Asp
        305 accgacatcc gagcagccga ggcttatgcg cccagcaaca tcgcgctgtc gaaatactgg    7987 ggcaagcgcg acgccgcgcg gaaccttccg ctgaacagct ccgtctcgat ctcgttggcg    8047 aactggggct ctcatacgcg ggtcgagggg tccggcacgg gccacgacga ggtgcatcac    8107 aacggcacgc tgctggatcc gggcgacgcc ttcgcgcgcc gcgcgttggc attcgctgac    8167 ctgttccggg gggggaggca cctgccgctg cggatcacga cgcagaactc gatcccgacg    8227 gcggcggggc ttgcctcgtc ggcctcgggg ttcgcgcgcg tgacccgtgc gctggcgggg    8287 gcgttcgggc tggatctgga cgacacggat ctgagccgca tcgcccggat cggcagtggc    8347 agcgccgccc gctcgatctg gcacggcttc gtccgctgga accggggcga ggccgaggat    8407 gggcatgaca gccacggcgt cccgctggac ctgcgctggc ccggcttccg catcgcgatc    8467 gtggccgtgg acaaggggcc caagcctttc agttcgcgcg acggcatgaa ccacacggtc    8527 gagaccagcc cgctgttccc gccctggcct gcgcaggcgg aagcggattg ccgcgtcatc    8587 gaggatgcga tcgccgcccg cgacatggcc gccctgggtc gcgggtcga ggcgaacgcc     8647 cttgcgatgc acgccacgat gatggccgcg cgcccgccgc tctgctacct gacgggcggc    8707 agctggcagg tgctggaacg cctgtggcag gcccgcgcgg acgggcttgc ggcctttgcg    8767 acgatggatg ccggcccgaa cgtcaagctg atcttcgagg aaagcagcgc cgccgacgtg    8827 ctgtacctgt tccccgacgc cagcctgatc gcgccgttcg agggggcgttg aacgcgtaag   8887 acgaccactg ggtaaggttc tgccgcgcgt ggtctcgact gcctgcaaag aggtgcttga    8947
```

-continued gttgctgcgt gactgcggcg gccgacttcg tgggacttgc ccgccacgct gacgcgctgg    9007
aaacgcgccc gcggattacg accgcgtcat tgccctgaac caatttcccg tcggtcgac     9066

<210> SEQ ID NO 51
<211> LENGTH: 305
<212> TYPE: PRT
<213> ORGANISM: Paracoccus sp. R114

<400> SEQUENCE: 51

```
Met Asp Gln Val Ile Arg Ala Ser Ala Pro Gly Ser Val Met Ile Thr
1               5                   10                  15

Gly Glu His Ala Val Val Tyr Gly His Arg Ala Ile Val Ala Gly Ile
            20                  25                  30

Glu Gln Arg Ala His Val Thr Ile Val Pro Arg Ala Asp Arg Met Phe
        35                  40                  45

Arg Ile Thr Ser Gln Ile Gly Ala Pro Gln Gln Gly Ser Leu Asp Asp
    50                  55                  60

Leu Pro Ala Gly Gly Thr Tyr Arg Phe Val Leu Ala Ala Ile Ala Arg
65                  70                  75                  80

His Ala Pro Asp Leu Pro Cys Gly Phe Asp Met Asp Ile Thr Ser Gly
                85                  90                  95

Ile Asp Pro Arg Leu Gly Leu Gly Ser Ser Ala Ala Val Thr Val Ala
            100                 105                 110

Cys Leu Gly Ala Leu Ser Arg Leu Ala Gly Arg Gly Thr Glu Gly Leu
        115                 120                 125

His Asp Asp Ala Leu Arg Ile Val Arg Ala Ile Gln Gly Arg Gly Ser
    130                 135                 140

Gly Ala Asp Leu Ala Ala Ser Leu His Gly Gly Phe Val Ala Tyr Arg
145                 150                 155                 160

Ala Pro Asp Gly Gly Ala Ala Gln Ile Glu Ala Leu Pro Val Pro Pro
                165                 170                 175

Gly Pro Phe Gly Leu Arg Tyr Ala Gly Tyr Lys Thr Pro Thr Ala Glu
            180                 185                 190

Val Leu Arg Leu Val Ala Asp Arg Met Ala Gly Asn Glu Ala Ala Phe
        195                 200                 205

Asp Ala Leu Tyr Ser Arg Met Gly Ala Ser Ala Asp Ala Ala Ile Arg
    210                 215                 220

Ala Ala Gln Gly Leu Asp Trp Ala Ala Phe His Asp Ala Leu Asn Glu
225                 230                 235                 240

Tyr Gln Arg Leu Met Glu Gln Leu Gly Val Ser Asp Asp Thr Leu Asp
                245                 250                 255

Ala Ile Ile Arg Glu Ala Arg Asp Ala Gly Ala Ala Val Ala Lys Ile
            260                 265                 270

Ser Gly Ser Gly Leu Gly Asp Cys Val Leu Ala Leu Gly Asp Gln Pro
        275                 280                 285

Lys Gly Phe Val Pro Ala Ser Ile Ala Glu Lys Gly Leu Val Phe Asp
    290                 295                 300

Asp
305
```

<210> SEQ ID NO 52
<211> LENGTH: 9066
<212> TYPE: DNA
<213> ORGANISM: Paracoccus sp. R114
<220> FEATURE:

-continued

```
<221> NAME/KEY: CDS
<222> LOCATION: (7880)..(8878)
<223> OTHER INFORMATION: mvd

<400> SEQUENCE: 52
```

| | | | | | |
|---|---|---|---|---|---|
| ggatccggca | gctcgacacg | ccgcagaacc | tgtacgaacg | tcccgccagc | cgcttcgtcg | 60 |
| cggaattcgt | cgggcgcggg | acggtggtgc | ccgtgcaggc | ccatgacggc | gcggccgcg | 120 |
| cccgcatcct | gggggccgag | gtggcggtga | acgccgcccc | gcaatcgcgc | tttgtcgatc | 180 |
| acgtctgcct | gcgccccgag | aaccttgcca | tctccgagac | gggcgacctg | cgcgccaagg | 240 |
| tcgcgcgcgt | cacctatctt | ggcgggaaat | acctgctgga | aaccgtgctg | gattgcggca | 300 |
| cccggctggt | gaccgagacc | cgcgcccgct | tcgatacggg | cgcgcagctt | ggcctgacca | 360 |
| tcaacgcccc | ctgggccttt | gccgaggatt | gaatggacag | cgtgaagatc | ctttcgggca | 420 |
| tgggcgtgaa | gggccctgcc | tgcatcaggc | tggatgtcgg | cgggatgcgc | ctgatcctcg | 480 |
| attgcgggac | cggcccggac | gagggcgcgg | agttcgaccc | cgcctggctg | gcggacgcgg | 540 |
| atgcggtgct | gatcacccat | gaccacgtgg | accatatcgg | cggcgcgcgt | cacgcggtcg | 600 |
| cggcggggct | gccgatccat | gcgacgcggc | agacggcggg | gttgctgccc | gcgggggcgg | 660 |
| atctgcgcct | gctgcccgaa | cgcggtgtca | cgcggatcgc | cggggtcgat | ctgacgaccg | 720 |
| gtcgcaacgg | gcatgccgcg | ggcggcgtct | ggatgcattt | cgacatgggc | gaggggctgt | 780 |
| tctattccgg | cgactggtcc | gaggaatccg | actggttcgc | cttcgatccg | ccccgcctg | 840 |
| cggggacggc | gattctcgac | tgctcctatg | gcggtttcga | cgtggcgcaa | tcggattgca | 900 |
| tcgcggacct | ggacgacctg | ctcgaggtgc | tgccggggca | ggtactgctg | ccggtgccgc | 960 |
| catccgccg | cgcggccgag | ctggccctgc | ggctgatccg | ccgccacgga | ccgggcagcg | 1020 |
| tgatggtcga | cgacgcctgc | ctgccggcca | tcgcgcaact | gcccgaggcg | cgcggactgg | 1080 |
| cctacgccac | cgaggcacgc | tttcttgtct | gcgacacgcc | gaacgccgaa | agccggcgcg | 1140 |
| gcatggcggc | atctgcaagc | atggcgcgat | gcgggcaggc | tggggcggga | cgcgcatgtc | 1200 |
| gtcttcaccg | ggcacatgaa | cgtccatgcg | cgcgcattct | gcgaccgccc | cggcgggcat | 1260 |
| ttccgccgct | ggaacgtgca | tccgccgctg | cgcgaccagc | gacggatgct | ggaacggctg | 1320 |
| gccgcgcggc | gctttgcccc | ggccttctgc | cccgaccccg | agatctatct | ggcgctggac | 1380 |
| atgggcgcgc | aggtcttcat | gcaccaggag | gtgacgccat | gatccccgcc | cgcagcttct | 1440 |
| gcctgatccg | ccacggcgaa | acgaccgcca | atgcaggggc | gatcatcgcg | ggcgcaaccg | 1500 |
| atgtgcccct | gacgccaagg | ggccgcgatc | aggcccgcgc | cctggcaggg | cgcgaatggc | 1560 |
| catcgggcat | cgcgctgttc | gccagcccga | tgtcgcgtgc | ccgcgatacc | gcgctgctgg | 1620 |
| cctttccggg | gcgcgaccac | cagcccgaac | ccgatctgcg | cgaacgcgac | tggggcatct | 1680 |
| tcgaggacg | ccccgtcgcc | gatctgcccc | cgcgcgaaat | cacgccgcag | ggggcgagg | 1740 |
| gctgggacga | cgtgatggcc | cgcgtggacc | gcgcgatccg | gcggatctgc | gcgacctcgg | 1800 |
| gcgatgcgct | gccggtgctg | gtctgccatt | cgggcgtgat | ccgtgccgcg | cgcgtgctgt | 1860 |
| ggaccaccgg | cgatgcgggc | gatcgtccgc | ccaacgccac | gccgatcctg | ttcagcccgg | 1920 |
| acggcgaccg | attaaaggaa | ggaacgatat | gaccgccacc | accccctgcg | tcgtcttcga | 1980 |
| acgtggacga | cacgcttgcc | gaattcgacg | ccgaccgcct | gggccatctt | gtccacggca | 2040 |
| cgaccaagca | ctgggacgcc | ttccaccacg | cgatggccga | cgccccgccc | atccccgagg | 2100 |
| tcgcccgcct | gatgcgcaag | ctgaaggagg | gggcgagac | ggtcgtcatc | tgctcggggc | 2160 |
| ggccccgcgg | ctggcaggat | cagacgatcg | catggctgcg | caagcacgac | ctgcccttcg | 2220 |

-continued

```
acgggatcta tctgcgcccc gaggatcagg acggcgccag cgaccccgag gtcaagcgcc    2280
gcgccctagc cgagatgcgc gccgacgggc tggcgccctg gctggtcgtg gacgaccggc    2340
ggtccgtcgt ggatgcctgg cgggccgagg ggctggtctg cctgcaatgc gcgccggggg    2400
acttctaggg ccgcgcgacg ggggcgcgga caggctgggc gggaaaccgc cccgccacca    2460
tgtcctgcac gcgtcgaacc gcccgtccga cgccggtttc cgcacggaaa cgcgcggcaa    2520
gttgacataa cttgcacgcg acgtctcgat tctgcccgcg aagaatgcga tgcatccaga    2580
tgatgcagaa cgaagaagcg gaagcgcccg tgaaagacca gatgatttcc catacccagg    2640
tgcccacgca atgggtcggc ccgatcctgt tccgcggccc cgtcgtcgag ggcccgatca    2700
gcgcgccgct ggccacctac gagacgccgc tctggccctc gaccgcgcgg ggggcagggg    2760
tttcccggca ttcgggcggg atccaggtct cgctggtcga cgaacgcatg agccgctcga    2820
tcgcgctgcg ggcgcatgac ggggcggcgg cgaccgccgc ctggcagtcg atcaaggccc    2880
gccaggaaga ggtcgcggcc gtggtcgcca ccaccagccg cttcgcccgc cttgtcgagc    2940
tgaatcgcca gatcgtgggc aacctgcttt acatccgcat cgaatgcgtg acgggcgacg    3000
cctcgggtca caacatggtc accaaggccg ccgaggccgt gcagggctgg atcctgtcgg    3060
aatacccgat gctggcctat tccacgatct cggggaacct gtgcaccgac aagaaggcgt    3120
cggcggtcaa cggcatcctg ggccgcggca aatacgccgc cgccgaggtc gagatcccgc    3180
gcaagatcct gacccgcgtg ctgcgcacca gcgccgagaa gatggtccgc ctgaactacg    3240
agaagaacta tgtcggtggt acgctggcgg ggtcgctgcg cagtgcgaac gcgcatttcg    3300
ccaacatgct gctgggcttc tacctggcga cggggcagga cgcggccaac atcatcgagg    3360
ccagccaggg cttcgtccat tgcgaggccc gcggcgagga tctgtatttc tcgtgcacgc    3420
tgcccaacct catcatgggc tcggtcggtg ccggcaaggg catcccctcg atcgaggaga    3480
acctgtcgcg gatgggctgc cgccagccgg gcgaacccgg cgacaacgcg cgccgtcttg    3540
cggcgatctg cgcgggcgtc gtgctgtgtg gtgaattgtc gctgcttgcg gcccagacca    3600
accccggaga gttggtccgc acccacatgg agatggagcg atgaccgaca gcaaggatca    3660
ccatgtcgcg gggcgcaagc tggaccatct gcgtgcattg gacgacgatg cggatatcga    3720
ccggggcgac agcggcttcg accgcatcgc gctgacccat cgcgcccgc cgaggtgga    3780 tttcgacgcc atcgacacgg cgaccagctt cctgggccgt gaactgtcct tcccgctgct    3840
gatctcgtcc atgaccggcg gcaccggcga ggagatcgag cgcatcaacc gcaacctggc    3900
cgctggtgcc gaggaggccc gcgtcgccat ggcggtgggc tcgcagcgcg tgatgttcac    3960 cgaccccctcg gcgcgggcca gcttcgacct gcgcgcccat gcgcccaccg tgccgctgct    4020
ggccaatatc ggcgcggtgc agctgaacat ggggctgggg ctgaaggaat gcctggccgc    4080
gatcgaggtg ctgcaggcgg acggcctgta tctgcacctg aaccccctgc aagaggccgt    4140
ccagcccgag ggggatcgcg actttgccga tctgggcagc aagatcgcgg ccatcgcccg    4200
cgacgttccc gtgcccgtcc tgctgaagga ggtgggctgc ggcctgtcgg cggccgatat    4260
cgccatcggg ctgcgcgccg ggatccggca tttcgacgtg gccggtcgcg gcggcacatc    4320
ctggagccgg atcgagtatc gccgccgcca gcgggccgat gacgacctgg gcctggtctt    4380
ccaggactgg ggcctgcaga ccgtggacgc cctgcgcgag gcgcggcccg cgcttgcggc    4440
ccatgatgga accagcgtgc tgatcgccag cggcggcatc cgcaacggtg tcgacatggc    4500
gaaatgcgtc atcctggggg ccgacatgtg cggggtcgcc gcgcccctgc tgaaagcggc    4560
```

```
ccaaaactcg cgcgaggcgg ttgtatccgc catccggaaa ctgcatctgg agttccggac     4620
agccatgttc ctcctgggtt gcggcacgct tgccgacctg aaggacaatt cctcgcttat     4680
ccgtcaatga aagtgcctaa gatgaccgtg acaggaatcg aagcgatcag cttctacacc     4740
ccccagaact acgtgggact ggatatcctt gccgcgcatc acgggatcga ccccgagaag     4800
ttctcgaagg ggatcgggca ggagaaaatc gcactgcccg gccatgacga ggatatcgtg     4860
accatggccg ccgaggccgc gctgccgatc atcgaacgcg cgggcacgca gggcatcgac     4920
acggttctgt tcgccaccga gagcgggatc gaccagtcga aggccgccgc catctatctg     4980
cgccgcctgc tggacctgtc gcccaactgc cgttgcgtcg agctgaagca ggcctgctat     5040
tccgcgacgg cggcgctgca gatggcctgc gcgcatgtcg cccgcaagcc cgaccgcaag     5100
gtgctggtga tcgcgtccga tgtcgcgcgc tatgaccgcg aaagctcggg cgaggcgacg     5160
cagggtgcgg gcgccgtcgc catccttgtc agcgccgatc ccaaggtggc cgagatcggc     5220
accgtctcgg ggctgttcac cgaggatatc atggatttct gcggccgaa ccaccgccgc     5280 acgcccctgt tcgacggcaa ggcatcgacg ctgcgctatc tgaacgcgct ggtcgaggcg     5340
tggaacgact atcgcgcgaa tggcggccac gagttcgccg atttcgcgca tttctgctat     5400
cacgtgccgt tctcgcggat gggcgagaag gcgaacagcc acctggccaa ggcgaacaag     5460
acgccggtgg acatgggca ggtgcagacg ggcctgatct acaaccggca ggtcgggaac     5520
tgctataccg ggtcgatcta cctggcattc gcctcgctgc tggagaacgc tcaggaggac     5580
ctgaccggcg cgctggtcgg tctgttcagc tatggctcgg gtgcgacggg cgaattcttc     5640
gatgcgcgga tcgcgcccgg ttaccgcgac cacctgttcg cggaacgcca tcgcgaattg     5700
ctgcaggatc gcacgcccgt cacatatgac gaatacgttg ccctgtggga cgagatcgac     5760
ctgacgcagg gcgcgcccga caaggcgcgc ggtcgtttca ggctggcagg tatcgaggac     5820
gagaagcgca tctatgtcga ccggcaggcc tgaagcaggc gcccatgccc cgggcaagct     5880
gatcctgtcc ggggaacatt ccgtgctcta tggtgcgccc gcgcttgcca tggccatcgc     5940
ccgctatacc gaggtgtggt tcacgccgct tggcattggc gagggatac gcacgacatt     6000 cgccaatctc tcgggcgggg cgacctattc gctgaagctg ctgtcgggt tcaagtcgcg     6060 gctggaccgc cggttcgagc agttcctgaa cggcgaccta aggtgcaca aggtcctgac     6120 ccatcccgac gatctggcgg tctatgcgct ggcgtcgctt ctgcacgaca agccgccggg     6180
gaccgccgcg atgccgggca tcggcgcgat gcaccacctg ccgcgaccgg gtgagctggg     6240
cagccggacg gagctgccca tcggcgcggg catgggtcg tctgcggcca tcgtcgcggc     6300
caccacggtc ctgttcgaga cgctgctgga ccggcccaag acgcccgaac agcgcttcga     6360
ccgcgtccgc ttctgcgagc ggttgaagca cggcaaggcc ggtccatcg acgcggccag     6420 cgtcgtgcgc ggcgggcttg tccgcgtggg cgggaacggg ccgggttcga tcagcagctt     6480
cgatttgccc gaggatcacg accttgtcgc gggacgcggc tggtactggg tactgcacgg     6540 gcgcccgtc agcgggaccg gcgaatgcgt cagcgcggtc gcggcggcgc atggtcgcga     6600
tgcggcgctc tgggacgcct tcgcagtctg cacccgcgcg ttggaggccg cgctgctgtc     6660
tgggggcagc cccgacgccg ccatcaccga gaaccagcgc ctgctggaac gcatcggcgt     6720
cgtgccggca gcgacgcagg ccctcgtggc ccagatcgag gaggcgggtg gcgcggccaa     6780
gatctgcggc gcaggttccg tgcggggcga tcacggcggg gcggtcctcg tgcggattga     6840
cgacgcgcag gcgatggctt cggtcatggc gcgccatccc gacctcgact gggcgccccct     6900 gcgcatgtcg cgcacgggg cggcacccgg ccccgcgccg cgtgcgcaac cgctgccggg     6960
```

-continued

```
gcagggctga tggatcaggt catccgcgcc agcgcgccgg gttcggtcat gatcacgggc    7020
gaacatgccg tggtctatgg acaccgcgcc atcgtcgccg ggatcgagca gcgcgcccat    7080
gtgacgatcg tcccgcgtgc cgaccgcatg tttcgcatca cctcgcagat cggggcgccg    7140 cagcagggt cgctggacga tctgcctgcg ggcgggacct atcgcttcgt gctggccgcc     7200
atcgcgcgac acgcgccgga cctgccttgc gggttcgaca tggacatcac ctcgggatc    7260 gatccgaggc tcgggcttgg atcctcggcg gcggtgacgg tcgcctgcct cggcgcgctg    7320
tcgcggctgg cggggcgggg gaccgagggg ctgcatgacg acgcgctgcg catcgtccgc    7380
gccatccagg gcaggggcag cggggccgat ctggcggcca gcctgcatgg cggcttcgtc    7440
gcctatcgcg cgcccgatgg cggtgccgcg cagatcgagg cgcttccggt gccgccgggg    7500
ccgttcggcc tgcgctatgc gggctacaag accccgacag ccgaggtgct gcgccttgtg    7560
gccgatcgga tggcgggcaa cgaggccgct ttcgacgcgc tctactcccg gatgggcgca    7620
agcgcagatg ccgcgatccg cgcggcgcaa gggctggact gggctgcatt ccacgacgcg    7680
ctgaacgaat accagcgcct gatggagcag ctgggcgtgt ccgacgacac gctgacgcg     7740 atcatccgcg aggcgcgcga cgcgggcgcc gcagtcgcca agatctccgg ctcggggctg    7800
ggggattgcg tgctggcact gggcgaccag cccaagggtt tcgtgcccgc aagcattgcc    7860
```

| | | | | | | | | | | |
|---|---|---|---|---|---|---|---|---|---|---|
| gagaagggac ttgtttcg | atg | act | gat | gcc | gtc | cgc | gac | atg | atc | gcc | cgt | 7912 |
| | Met | Thr | Asp | Ala | Val | Arg | Asp | Met | Ile | Ala | Arg |
| | 1 | | | 5 | | | | | 10 | | |

| gcc | atg | gcg | ggc | gcg | acc | gac | atc | cga | gca | gcc | gag | gct | tat | gcg | ccc | 7960 |
|---|---|---|---|---|---|---|---|---|---|---|---|---|---|---|---|---|
| Ala | Met | Ala | Gly | Ala | Thr | Asp | Ile | Arg | Ala | Ala | Glu | Ala | Tyr | Ala | Pro |
| | | 15 | | | | | 20 | | | | | 25 | | | |

| agc | aac | atc | gcg | ctg | tcg | aaa | tac | tgg | ggc | aag | cgc | gac | gcc | gcg | cgg | 8008 |
|---|---|---|---|---|---|---|---|---|---|---|---|---|---|---|---|---|
| Ser | Asn | Ile | Ala | Leu | Ser | Lys | Tyr | Trp | Gly | Lys | Arg | Asp | Ala | Ala | Arg |
| | 30 | | | | | 35 | | | | | 40 | | | | |

| aac | ctt | ccg | ctg | aac | agc | tcc | gtc | tcg | atc | tcg | ttg | gcg | aac | tgg | ggc | 8056 |
|---|---|---|---|---|---|---|---|---|---|---|---|---|---|---|---|---|
| Asn | Leu | Pro | Leu | Asn | Ser | Ser | Val | Ser | Ile | Ser | Leu | Ala | Asn | Trp | Gly |
| 45 | | | | | 50 | | | | | 55 | | | | | |

| tct | cat | acg | cgg | gtc | gag | ggg | tcc | ggc | acg | ggc | cac | gac | gag | gtg | cat | 8104 |
|---|---|---|---|---|---|---|---|---|---|---|---|---|---|---|---|---|
| Ser | His | Thr | Arg | Val | Glu | Gly | Ser | Gly | Thr | Gly | His | Asp | Glu | Val | His |
| 60 | | | | 65 | | | | | 70 | | | | | 75 | |

| cac | aac | ggc | acg | ctg | ctg | gat | ccg | ggc | gac | gcc | ttc | gcg | cgc | cgc | gcg | 8152 |
|---|---|---|---|---|---|---|---|---|---|---|---|---|---|---|---|---|
| His | Asn | Gly | Thr | Leu | Leu | Asp | Pro | Gly | Asp | Ala | Phe | Ala | Arg | Arg | Ala |
| | | | | | 80 | | | | | 85 | | | | | 90 |

| ttg | gca | ttc | gct | gac | ctg | ttc | cgg | ggg | ggg | agg | cac | ctg | ccg | ctg | cgg | 8200 |
|---|---|---|---|---|---|---|---|---|---|---|---|---|---|---|---|---|
| Leu | Ala | Phe | Ala | Asp | Leu | Phe | Arg | Gly | Gly | Arg | His | Leu | Pro | Leu | Arg |
| | | | | 95 | | | | | 100 | | | | | 105 | |

| atc | acg | acg | cag | aac | tcg | atc | ccg | acg | gcg | gcg | ggg | ctt | gcc | tcg | tcg | 8248 |
|---|---|---|---|---|---|---|---|---|---|---|---|---|---|---|---|---|
| Ile | Thr | Thr | Gln | Asn | Ser | Ile | Pro | Thr | Ala | Ala | Gly | Leu | Ala | Ser | Ser |
| | | | 110 | | | | | 115 | | | | | 120 | | |

| gcc | tcg | ggg | ttc | gcg | gcg | ctg | acc | cgt | gcg | ctg | gcg | ggg | gcg | ttc | ggg | 8296 |
|---|---|---|---|---|---|---|---|---|---|---|---|---|---|---|---|---|
| Ala | Ser | Gly | Phe | Ala | Ala | Leu | Thr | Arg | Ala | Leu | Ala | Gly | Ala | Phe | Gly |
| | 125 | | | | | 130 | | | | | 135 | | | | |

| ctg | gat | ctg | gac | gac | acg | gat | ctg | agc | cgc | atc | gcc | cgg | atc | ggc | agt | 8344 |
|---|---|---|---|---|---|---|---|---|---|---|---|---|---|---|---|---|
| Leu | Asp | Leu | Asp | Asp | Thr | Asp | Leu | Ser | Arg | Ile | Ala | Arg | Ile | Gly | Ser |
| 140 | | | | | 145 | | | | | 150 | | | | | 155 |

| ggc | agc | gcc | gcc | cgc | tcg | atc | tgg | cac | ggc | ttc | gtc | cgc | tgg | aac | cgg | 8392 |
|---|---|---|---|---|---|---|---|---|---|---|---|---|---|---|---|---|
| Gly | Ser | Ala | Ala | Arg | Ser | Ile | Trp | His | Gly | Phe | Val | Arg | Trp | Asn | Arg |
| | | | | 160 | | | | | 165 | | | | | 170 | |

| ggc | gag | gcc | gag | gat | ggg | cat | gac | agc | cac | ggc | gtc | ccg | ctg | gac | ctg | 8440 |
|---|---|---|---|---|---|---|---|---|---|---|---|---|---|---|---|---|
| Gly | Glu | Ala | Glu | Asp | Gly | His | Asp | Ser | His | Gly | Val | Pro | Leu | Asp | Leu |
| | | | 175 | | | | | 180 | | | | | 185 | | |

-continued

| | | | | | | | | | | | | | | | | |
|---|---|---|---|---|---|---|---|---|---|---|---|---|---|---|---|---|
|cgc|tgg|ccc|ggc|ttc|cgc|atc|gcg|atc|gtg|gcc|gtg|gac|aag|ggg|ccc|8488|
|Arg|Trp|Pro|Gly|Phe|Arg|Ile|Ala|Ile|Val|Ala|Val|Asp|Lys|Gly|Pro| |
| | |190| | | |195| | | |200| | | | | | |
|aag|cct|ttc|agt|tcg|cgc|gac|ggc|atg|aac|cac|acg|gtc|gag|acc|agc|8536|
|Lys|Pro|Phe|Ser|Ser|Arg|Asp|Gly|Met|Asn|His|Thr|Val|Glu|Thr|Ser| |
|205| | | | |210| | | | |215| | | | | | |
|ccg|ctg|ttc|ccg|ccc|tgg|cct|gcg|cag|gcg|gaa|gcg|gat|tgc|cgc|gtc|8584|
|Pro|Leu|Phe|Pro|Pro|Trp|Pro|Ala|Gln|Ala|Glu|Ala|Asp|Cys|Arg|Val| |
|220| | | | |225| | | | |230| | | | |235| |
|atc|gag|gat|gcg|atc|gcc|gcc|cgc|gac|atg|gcc|gcc|ctg|ggt|ccg|cgg|8632|
|Ile|Glu|Asp|Ala|Ile|Ala|Ala|Arg|Asp|Met|Ala|Ala|Leu|Gly|Pro|Arg| |
| | | | |240| | | | |245| | | | |250| | |
|gtc|gag|gcg|aac|gcc|ctt|gcg|atg|cac|gcc|acg|atg|atg|gcc|gcg|cgc|8680|
|Val|Glu|Ala|Asn|Ala|Leu|Ala|Met|His|Ala|Thr|Met|Met|Ala|Ala|Arg| |
| | | | |255| | | | |260| | | | |265| | |
|ccg|ccg|ctc|tgc|tac|ctg|acg|ggc|ggc|agc|tgg|cag|gtg|ctg|gaa|cgc|8728|
|Pro|Pro|Leu|Cys|Tyr|Leu|Thr|Gly|Gly|Ser|Trp|Gln|Val|Leu|Glu|Arg| |
| | |270| | | | |275| | | | |280| | | | |
|ctg|tgg|cag|gcc|cgc|gcg|gac|ggg|ctt|gcg|gcc|ttt|gcg|acg|atg|gat|8776|
|Leu|Trp|Gln|Ala|Arg|Ala|Asp|Gly|Leu|Ala|Ala|Phe|Ala|Thr|Met|Asp| |
| |285| | | | |290| | | | |295| | | | | |
|gcc|ggc|ccg|aac|gtc|aag|ctg|atc|ttc|gag|gaa|agc|agc|gcc|gcc|gac|8824|
|Ala|Gly|Pro|Asn|Val|Lys|Leu|Ile|Phe|Glu|Glu|Ser|Ser|Ala|Ala|Asp| |
|300| | | | |305| | | | |310| | | | |315| |
|gtg|ctg|tac|ctg|ttc|ccc|gac|gcc|agc|ctg|atc|gcg|ccg|ttc|gag|ggg|8872|
|Val|Leu|Tyr|Leu|Phe|Pro|Asp|Ala|Ser|Leu|Ile|Ala|Pro|Phe|Glu|Gly| |
| | | | |320| | | | |325| | | | |330| | |
|cgt|tga|acgcgtaaga|cgaccactgg|gtaaggttct|gccgcgcgtg|gtctcgactg| | | | | | | | | |8928|
|Arg| | | | | | | | | | | | | | | | | cctgcaaaga ggtgcttgag ttgctgcgtg actgcggcgg ccgacttcgt gggacttgcc   8988 cgccacgctg acgcgctgga aacgcgcccg cggattacga ccgcgtcatt gccctgaacc   9048 aatttcccgt cggtcgac                                                 9066

<210> SEQ ID NO 53
<211> LENGTH: 332
<212> TYPE: PRT
<213> ORGANISM: Paracoccus sp. R114

<400> SEQUENCE: 53

Met Thr Asp Ala Val Arg Asp Met Ile Ala Arg Ala Met Ala Gly Ala
1               5                   10                  15

Thr Asp Ile Arg Ala Ala Glu Ala Tyr Ala Pro Ser Asn Ile Ala Leu
            20                  25                  30

Ser Lys Tyr Trp Gly Lys Arg Asp Ala Ala Arg Asn Leu Pro Leu Asn
        35                  40                  45

Ser Ser Val Ser Ile Ser Leu Ala Asn Trp Gly Ser His Thr Arg Val
    50                  55                  60

Glu Gly Ser Gly Thr Gly His Asp Glu Val His His Asn Gly Thr Leu
65                  70                  75                  80

Leu Asp Pro Gly Asp Ala Phe Ala Arg Arg Ala Leu Ala Phe Ala Asp
                85                  90                  95

Leu Phe Arg Gly Gly Arg His Leu Pro Leu Arg Ile Thr Thr Gln Asn
            100                 105                 110

Ser Ile Pro Thr Ala Ala Gly Leu Ala Ser Ser Ala Ser Gly Phe Ala
        115                 120                 125

Ala Leu Thr Arg Ala Leu Ala Gly Ala Phe Gly Leu Asp Leu Asp Asp
    130                 135                 140

```
Thr Asp Leu Ser Arg Ile Ala Arg Ile Gly Ser Gly Ser Ala Ala Arg
145                 150                 155                 160

Ser Ile Trp His Gly Phe Val Arg Trp Asn Arg Gly Glu Ala Glu Asp
                165                 170                 175

Gly His Asp Ser His Gly Val Pro Leu Asp Leu Arg Trp Pro Gly Phe
            180                 185                 190

Arg Ile Ala Ile Val Ala Val Asp Lys Gly Pro Lys Pro Phe Ser Ser
        195                 200                 205

Arg Asp Gly Met Asn His Thr Val Glu Thr Ser Pro Leu Phe Pro Pro
    210                 215                 220

Trp Pro Ala Gln Ala Glu Ala Asp Cys Arg Val Ile Glu Asp Ala Ile
225                 230                 235                 240

Ala Ala Arg Asp Met Ala Ala Leu Gly Pro Arg Val Glu Ala Asn Ala
                245                 250                 255

Leu Ala Met His Ala Thr Met Met Ala Ala Arg Pro Pro Leu Cys Tyr
            260                 265                 270

Leu Thr Gly Gly Ser Trp Gln Val Leu Glu Arg Leu Trp Gln Ala Arg
        275                 280                 285

Ala Asp Gly Leu Ala Ala Phe Ala Thr Met Asp Ala Gly Pro Asn Val
    290                 295                 300

Lys Leu Ile Phe Glu Glu Ser Ala Ala Asp Val Leu Tyr Leu Phe
305                 310                 315                 320

Pro Asp Ala Ser Leu Ile Ala Pro Phe Glu Gly Arg
                325                 330
```

<210> SEQ ID NO 54
<211> LENGTH: 353
<212> TYPE: PRT
<213> ORGANISM: Streptomyces sp. strain CL190

<400> SEQUENCE: 54

```
Met Thr Glu Thr His Ala Ile Ala Gly Val Pro Met Arg Trp Val Gly
1               5                   10                  15

Pro Leu Arg Ile Ser Gly Asn Val Ala Glu Thr Glu Thr Gln Val Pro
                20                  25                  30

Leu Ala Thr Tyr Glu Ser Pro Leu Trp Pro Ser Val Gly Arg Gly Ala
            35                  40                  45

Lys Val Ser Arg Leu Thr Glu Lys Gly Ile Val Ala Thr Leu Val Asp
        50                  55                  60

Glu Arg Met Thr Arg Ser Val Ile Val Glu Ala Thr Asp Ala Gln Thr
65                  70                  75                  80

Ala Tyr Met Ala Ala Gln Thr Ile His Ala Arg Ile Asp Glu Leu Arg
                85                  90                  95

Glu Val Val Arg Gly Cys Ser Arg Phe Ala Gln Leu Ile Asn Ile Lys
            100                 105                 110

His Glu Ile Asn Ala Asn Leu Leu Phe Ile Arg Phe Glu Phe Thr Thr
        115                 120                 125

Gly Asp Ala Ser Gly His Asn Met Ala Thr Leu Ala Ser Asp Val Leu
    130                 135                 140

Leu Gly His Leu Leu Glu Thr Ile Pro Gly Ile Ser Tyr Gly Ser Ile
145                 150                 155                 160

Ser Gly Asn Tyr Cys Thr Asp Lys Lys Ala Thr Ala Ile Asn Gly Ile
                165                 170                 175

Leu Gly Arg Gly Lys Asn Val Ile Thr Glu Leu Leu Val Pro Arg Asp
```

```
                180                 185                 190
Val Val Glu Asn Asn Leu His Thr Thr Ala Ala Lys Ile Val Glu Leu
            195                 200                 205
Asn Ile Arg Lys Asn Leu Leu Gly Thr Leu Leu Ala Gly Gly Ile Arg
210                 215                 220
Ser Ala Asn Ala His Phe Ala Asn Met Leu Leu Gly Phe Tyr Leu Ala
225                 230                 235                 240
Thr Gly Gln Asp Ala Ala Asn Ile Val Glu Gly Ser Gln Gly Val Val
            245                 250                 255
Met Ala Glu Asp Arg Asp Gly Asp Leu Tyr Phe Ala Cys Thr Leu Pro
            260                 265                 270
Asn Leu Ile Val Gly Thr Val Gly Asn Gly Lys Gly Leu Gly Phe Val
            275                 280                 285
Glu Thr Asn Leu Ala Arg Leu Gly Cys Arg Ala Asp Arg Glu Pro Gly
            290                 295                 300
Glu Asn Ala Arg Arg Leu Ala Val Ile Ala Ala Thr Val Leu Cys
305                 310                 315                 320
Gly Glu Leu Ser Leu Leu Ala Ala Gln Thr Asn Pro Gly Glu Leu Met
            325                 330                 335
Arg Ala His Val Gln Leu Glu Arg Asp Asn Lys Thr Ala Lys Val Gly
            340                 345                 350
Ala

<210> SEQ ID NO 55
<211> LENGTH: 353
<212> TYPE: PRT
<213> ORGANISM: Streptomyces griseolosporeus

<400> SEQUENCE: 55

Met Thr Glu Ala His Ala Thr Ala Gly Val Pro Met Arg Trp Val Gly
1               5                   10                  15
Pro Val Arg Ile Ser Gly Asn Val Ala Thr Ile Glu Thr Gln Val Pro
            20                  25                  30
Leu Ala Thr Tyr Glu Ser Pro Leu Trp Pro Ser Val Gly Arg Gly Ala
        35                  40                  45
Lys Val Ser Arg Leu Thr Glu Lys Gly Ile Val Ala Thr Leu Val Asp
    50                  55                  60
Glu Arg Met Thr Arg Ser Val Leu Val Glu Ala Thr Asp Ala Leu Thr
65                  70                  75                  80
Ala Leu Ser Ala Ala Arg Thr Ile Glu Ala Ile Asp Glu Leu Arg
            85                  90                  95
Glu Leu Val Arg Gly Cys Ser Arg Phe Ala Gln Leu Ile Gly Ile Arg
            100                 105                 110
His Glu Ile Thr Gly Asn Leu Leu Phe Val Arg Phe Glu Phe Ser Thr
            115                 120                 125
Gly Asp Ala Ser Gly His Asn Met Ala Thr Leu Ala Ser Asp Val Leu
        130                 135                 140
Leu Gln His Leu Leu Glu Thr Val Pro Gly Ile Ser Tyr Gly Ser Ile
145                 150                 155                 160
Ser Gly Asn Tyr Cys Thr Asp Lys Lys Ala Thr Ala Ile Asn Gly Ile
            165                 170                 175
Leu Gly Arg Gly Lys Asn Val Val Thr Glu Leu Leu Val Pro Arg Asp
            180                 185                 190
Val Val Ala Asp Val Leu Asn Thr Thr Ala Ala Lys Ile Ala Glu Leu
```

```
                195                 200                 205
Asn Leu Arg Lys Asn Leu Leu Gly Thr Leu Leu Ala Gly Gly Ile Arg
    210                 215                 220

Ser Ala Asn Ala His Tyr Ala Asn Met Leu Leu Ala Phe Tyr Leu Ala
225                 230                 235                 240

Thr Gly Gln Asp Ala Ala Asn Ile Val Glu Gly Ser Gln Gly Val Val
                245                 250                 255

Thr Ala Glu Asp Arg Asp Gly Asp Leu Tyr Leu Ala Cys Thr Leu Pro
                260                 265                 270

Asn Leu Ile Val Gly Thr Val Gly Asn Gly Lys Gly Leu Gly Phe Val
            275                 280                 285

Glu Thr Asn Leu Asn Arg Leu Gly Cys Arg Ala Asp Arg Glu Pro Gly
    290                 295                 300

Glu Asn Ala Arg Arg Leu Ala Val Ile Ala Ala Thr Val Leu Cys
305                 310                 315                 320

Gly Glu Leu Ser Leu Leu Ala Ala Gln Thr Asn Pro Gly Glu Leu Met
                325                 330                 335

Arg Ala His Val Gln Leu Glu Arg Gly His Thr Thr Ala Lys Ala Gly
                340                 345                 350

Val
```

<210> SEQ ID NO 56
<211> LENGTH: 353
<212> TYPE: PRT
<213> ORGANISM: Streptomyces sp. strain KO-3899

<400> SEQUENCE: 56

```
Met Thr Asp Thr His Ala Ile Ala Met Val Pro Met Lys Trp Val Gly
1               5                   10                  15

Pro Leu Arg Ile Ser Gly Asn Val Ala Thr Thr Glu Thr His Val Pro
            20                  25                  30

Leu Ala Thr Tyr Glu Thr Pro Leu Trp Pro Ser Val Gly Arg Gly Ala
        35                  40                  45

Lys Val Ser Met Leu Ser Glu Arg Gly Ile Ala Ala Thr Leu Val Asp
    50                  55                  60

Glu Arg Met Thr Arg Ser Val Leu Val Glu Ala Thr Asp Ala Gln Thr
65                  70                  75                  80

Ala Tyr Thr Ala Ala Arg Ala Ile Glu Ala Arg Ile Glu Glu Leu Arg
                85                  90                  95

Ala Val Val Arg Thr Cys Ser Arg Phe Ala Glu Leu Leu Gln Val Arg
            100                 105                 110

His Glu Ile Ala Gly Asn Leu Leu Phe Val Arg Phe Glu Phe Ser Thr
        115                 120                 125

Arg Arg Pro Ser Gly His Asn Met Ala Thr Leu Ala Ser Asp Ala Leu
    130                 135                 140

Leu Ala His Leu Leu Gln Thr Ile Pro Gly Ile Ser Tyr Gly Ser Ile
145                 150                 155                 160

Ser Gly Asn Tyr Cys Thr Asp Lys Lys Ala Thr Ala Ile Asn Gly Ile
                165                 170                 175

Leu Gly Arg Gly Lys Asn Val Val Thr Glu Leu Val Val Pro Arg Glu
            180                 185                 190

Val Val Glu Arg Val Leu His Thr Thr Ala Ala Lys Ile Val Glu Leu
        195                 200                 205

Asn Ile Arg Lys Asn Leu Leu Gly Thr Leu Leu Ala Gly Gly Ile Arg
```

-continued

```
            210                 215                 220
Ser Ala Asn Ala His Tyr Ala Asn Met Leu Leu Gly Phe Tyr Leu Ala
225                 230                 235                 240

Thr Gly Gln Asp Ala Ala Asn Ile Val Glu Gly Ser Gln Gly Val Thr
                245                 250                 255

Leu Ala Glu Asp Arg Asp Gly Asp Leu Tyr Phe Ser Cys Asn Leu Pro
                260                 265                 270

Asn Leu Ile Val Gly Thr Val Gly Asn Gly Lys Gly Leu Glu Phe Val
                275                 280                 285

Glu Thr Asn Leu Asn Arg Leu Gly Cys Arg Glu Asp Arg Ala Pro Gly
                290                 295                 300

Glu Asn Ala Arg Arg Leu Ala Val Ile Ala Ala Thr Val Leu Cys
305                 310                 315                 320

Gly Glu Leu Ser Leu Leu Ala Ala Gln Thr Asn Pro Gly Glu Leu Met
                325                 330                 335

Arg Ala His Val Glu Leu Glu Arg Asp Asn Thr Thr Ala Glu Val Gly
                340                 345                 350

Val
```

<210> SEQ ID NO 57
<211> LENGTH: 347
<212> TYPE: PRT
<213> ORGANISM: Erwinia herbicola

<400> SEQUENCE: 57

```
Met Lys Asp Glu Arg Leu Val Gln Arg Lys Asn Asp His Leu Asp Ile
1               5                   10                  15

Val Leu Asp Pro Arg Arg Ala Val Thr Gln Ala Ser Ala Gly Phe Glu
                20                  25                  30

Arg Trp Arg Phe Thr His Cys Ala Leu Pro Glu Leu Asn Phe Ser Asp
            35                  40                  45

Ile Thr Leu Glu Thr Thr Phe Leu Asn Arg Gln Leu Gln Ala Pro Leu
50                  55                  60

Leu Ile Ser Ser Met Thr Gly Gly Val Glu Arg Ser Arg His Ile Asn
65                  70                  75                  80

Arg His Leu Ala Glu Ala Ala Gln Val Leu Lys Ile Ala Met Gly Val
                85                  90                  95

Gly Ser Gln Arg Val Ala Ile Glu Ser Asp Ala Gly Leu Gly Leu Asp
                100                 105                 110

Lys Thr Leu Arg Gln Leu Ala Pro Asp Val Pro Leu Leu Ala Asn Leu
            115                 120                 125

Gly Ala Ala Gln Leu Thr Gly Arg Lys Gly Ile Asp Tyr Ala Arg Arg
            130                 135                 140

Ala Val Glu Met Ile Glu Ala Asp Ala Leu Ile Val His Leu Asn Pro
145                 150                 155                 160

Leu Gln Glu Ala Leu Gln Pro Gly Gly Asp Arg Asp Trp Arg Gly Arg
                165                 170                 175

Leu Ala Ala Ile Glu Thr Leu Val Arg Glu Leu Pro Val Pro Leu Val
                180                 185                 190

Val Lys Glu Val Gly Ala Gly Ile Ser Arg Thr Val Ala Gly Gln Leu
            195                 200                 205

Ile Asp Ala Gly Val Thr Val Ile Asp Val Ala Gly Ala Gly Gly Thr
            210                 215                 220

Ser Trp Ala Ala Val Glu Gly Glu Arg Ala Ala Thr Glu Gln Gln Arg
```

```
                225                 230                 235                 240
Ser Val Asn Val Phe Ala Asp Trp Gly Ile Pro Thr Ala Glu Ala
                    245                 250                 255

Leu Val Asp Ile Ala Glu Ala Trp Pro Gln Met Pro Leu Ile Ala Ser
                    260                 265                 270

Gly Gly Ile Lys Asn Gly Val Asp Ala Ala Lys Ala Leu Arg Leu Gly
                    275                 280                 285

Ala Cys Met Val Gly Gln Ala Ala Val Leu Gly Ser Ala Gly Val
        290                 295                 300

Ser Thr Glu Lys Val Ile Asp His Phe Asn Val Ile Glu Gln Leu
305                 310                 315                 320

Arg Val Ala Cys Phe Cys Thr Gly Ser Arg Ser Leu Ser Asp Leu Lys
                    325                 330                 335

Gln Ala Asp Ile Arg Tyr Val Arg Asp Thr Pro
                    340                 345

<210> SEQ ID NO 58
<211> LENGTH: 360
<212> TYPE: PRT
<213> ORGANISM: Borrelia burgdorferi

<400> SEQUENCE: 58

Met Met Asp Thr Glu Phe Met Gly Ile Glu Pro Asn Ile Leu Glu Asn
1               5                   10                  15

Lys Lys Arg His Ile Glu Ile Cys Leu Asn Lys Asn Asp Val Lys Gly
                20                  25                  30

Gly Cys Asn Phe Leu Lys Phe Ile Lys Leu Lys His Asn Ala Leu Ser
            35                  40                  45

Asp Phe Asn Phe Ser Glu Ile Asn Ile Lys Glu Glu Ile Phe Gly Tyr
        50                  55                  60

Asn Ile Ser Met Pro Val Phe Ile Ser Ser Met Thr Gly Gly Ser Lys
65                  70                  75                  80

Glu Gly Asn Asp Phe Asn Lys Ser Leu Val Arg Ile Ala Asn Tyr Leu
                85                  90                  95

Lys Ile Pro Ile Gly Leu Gly Ser Phe Lys Leu Leu Phe Lys Tyr Pro
                100                 105                 110

Glu Tyr Ile Arg Asp Phe Thr Leu Lys Arg Tyr Ala His Asn Ile Pro
            115                 120                 125

Leu Phe Ala Asn Val Gly Ala Val Gln Ile Val Glu Phe Gly Ile Ser
        130                 135                 140

Lys Ile Ala Glu Met Ile Lys Arg Leu Glu Val Asp Ala Ile Ile Val
145                 150                 155                 160

His Leu Asn Ala Gly Gln Glu Leu Met Lys Val Asp Gly Asp Arg Asn
                165                 170                 175

Phe Lys Gly Ile Arg Glu Ser Ile Ala Lys Leu Ser Asp Phe Leu Ser
            180                 185                 190

Val Pro Leu Ile Val Lys Glu Thr Gly Phe Gly Ile Ser Pro Lys Asp
        195                 200                 205

Val Lys Glu Leu Phe Ser Leu Gly Ala Ser Tyr Val Asp Leu Ala Gly
    210                 215                 220

Ser Gly Gly Thr Asn Trp Ile Leu Val Glu Gly Met Lys Ser Asn Asn
225                 230                 235                 240

Leu Asn Ile Ala Ser Cys Phe Ser Asp Trp Gly Ile Pro Ser Val Phe
                245                 250                 255
```

```
Thr Leu Leu Ser Ile Asp Asp Ser Leu Lys Ala Asn Ile Phe Ala Ser
            260                 265                 270

Gly Gly Tyr Glu Thr Gly Met Asp Ile Ala Lys Gly Ile Ala Leu Gly
        275                 280                 285

Ala Arg Leu Ile Gly Val Ala Val Val Leu Arg Ala Phe Tyr Asp
    290                 295                 300

Ser Gly Glu Asp Ala Val Phe Gly Leu Phe Ser Asp Tyr Glu His Ile
305                 310                 315                 320

Leu Lys Met Ser Met Phe Leu Ser Gly Ser Lys Ser Leu Leu Glu Phe
                325                 330                 335

Arg Asn Asn Lys Tyr Phe Leu Ser Ser Tyr Leu Leu Asp Glu Leu Gly
            340                 345                 350

Val Phe Lys Gln Phe Tyr Gly Thr
            355                 360

<210> SEQ ID NO 59
<211> LENGTH: 349
<212> TYPE: PRT
<213> ORGANISM: Synechocystis sp. PCC 6803

<400> SEQUENCE: 59

Met Asp Ser Thr Pro His Arg Lys Ser Asp His Ile Arg Ile Val Leu
1               5                   10                  15

Glu Glu Asp Val Val Gly Lys Gly Ile Ser Thr Gly Phe Glu Arg Leu
            20                  25                  30

Met Leu Glu His Cys Ala Leu Pro Ala Val Asp Leu Asp Ala Val Asp
        35                  40                  45

Leu Gly Leu Thr Leu Trp Gly Lys Ser Leu Thr Tyr Pro Trp Leu Ile
    50                  55                  60

Ser Ser Met Thr Gly Gly Thr Pro Glu Ala Lys Gln Ile Asn Leu Phe
65                  70                  75                  80

Leu Ala Glu Val Ala Gln Ala Leu Gly Ile Ala Met Gly Leu Gly Ser
                85                  90                  95

Gln Arg Ala Ala Ile Glu Asn Pro Asp Leu Ala Phe Thr Tyr Gln Val
            100                 105                 110

Arg Ser Val Ala Pro Asp Ile Leu Leu Phe Ala Asn Leu Gly Leu Val
        115                 120                 125

Gln Leu Asn Tyr Gly Tyr Gly Leu Glu Gln Ala Gln Arg Ala Val Asp
    130                 135                 140

Met Ile Glu Ala Asp Ala Leu Ile Leu His Leu Asn Pro Leu Gln Glu
145                 150                 155                 160

Ala Val Gln Pro Asp Gly Asp Arg Leu Trp Ser Gly Leu Trp Ser Lys
                165                 170                 175

Leu Glu Ala Leu Val Glu Ala Leu Glu Val Pro Val Ile Val Lys Glu
            180                 185                 190

Val Gly Asn Gly Ile Ser Gly Pro Val Ala Lys Arg Leu Gln Glu Cys
        195                 200                 205

Gly Val Gly Ala Ile Asp Val Ala Gly Ala Gly Thr Ser Trp Ser
    210                 215                 220

Glu Val Glu Ala His Arg Gln Thr Asp Arg Gln Ala Lys Glu Val Ala
225                 230                 235                 240

His Asn Phe Ala Asp Trp Gly Leu Pro Thr Ala Trp Ser Leu Gln Gln
                245                 250                 255

Val Val Gln Asn Thr Glu Gln Ile Leu Val Phe Ala Ser Gly Gly Ile
            260                 265                 270
```

```
Arg Ser Gly Ile Asp Gly Ala Lys Ala Ile Ala Leu Gly Ala Thr Leu
        275                 280                 285

Val Gly Ser Ala Ala Pro Val Leu Ala Glu Ala Lys Ile Asn Ala Gln
    290                 295                 300

Arg Val Tyr Asp His Tyr Gln Ala Arg Leu Arg Glu Leu Gln Ile Ala
305                 310                 315                 320

Ala Phe Cys Cys Asp Ala Ala Asn Leu Thr Gln Leu Ala Gln Val Pro
                325                 330                 335

Leu Trp Asp Arg Gln Ser Gly Gln Arg Leu Thr Lys Pro
            340                 345
```

<210> SEQ ID NO 60
<211> LENGTH: 361
<212> TYPE: PRT
<213> ORGANISM: Streptomyces sp. CL190

<400> SEQUENCE: 60

```
Met Thr Ser Ala Gln Arg Lys Asp Asp His Val Arg Leu Ala Ile Glu
1               5                   10                  15

Gln His Asn Ala His Ser Gly Arg Asn Gln Asp Val Ser Phe Val
            20                  25                  30

His His Ala Leu Ala Gly Ile Asp Arg Pro Asp Val Ser Leu Ala Thr
            35                  40                  45

Ser Phe Ala Gly Ile Ser Trp Gln Val Pro Ile Tyr Ile Asn Ala Met
    50                  55                  60

Thr Gly Gly Ser Glu Lys Thr Gly Leu Ile Asn Arg Asp Leu Ala Thr
65                  70                  75                  80

Ala Ala Arg Glu Thr Gly Val Pro Ile Ala Ser Gly Ser Met Asn Ala
            85                  90                  95

Tyr Ile Lys Asp Pro Cys Ala Asp Thr Phe Arg Val Leu Arg Asp Glu
            100                 105                 110

Asn Pro Asn Gly Phe Val Ile Ala Asn Ile Asn Ala Thr Thr Thr Val
            115                 120                 125

Asp Asn Ala Gln Arg Ala Ile Asp Leu Ile Glu Ala Asn Ala Leu Gln
130                 135                 140

Ile His Ile Asn Thr Ala Gln Glu Thr Pro Met Pro Glu Gly Asp Arg
145                 150                 155                 160

Ser Phe Ala Ser Trp Val Pro Gln Ile Glu Lys Ile Ala Ala Val
            165                 170                 175

Asp Ile Pro Val Ile Val Lys Glu Val Gly Asn Gly Leu Ser Arg Gln
            180                 185                 190

Thr Ile Leu Leu Leu Ala Asp Leu Gly Val Gln Ala Ala Asp Val Ser
            195                 200                 205

Gly Arg Gly Gly Thr Asp Phe Ala Arg Ile Glu Asn Gly Arg Arg Glu
    210                 215                 220

Leu Gly Asp Tyr Ala Phe Leu His Gly Trp Gly Gln Ser Thr Ala Ala
225                 230                 235                 240

Cys Leu Leu Asp Ala Gln Asp Ile Ser Leu Pro Val Leu Ala Ser Gly
                245                 250                 255

Gly Val Arg His Pro Leu Asp Val Arg Ala Leu Ala Leu Gly Ala
            260                 265                 270

Arg Ala Val Gly Ser Ser Ala Gly Phe Leu Arg Thr Leu Met Asp Asp
            275                 280                 285

Gly Val Asp Ala Leu Ile Thr Lys Leu Thr Thr Trp Leu Asp Gln Leu
```

```
                    290             295             300
Ala Ala Leu Gln Thr Met Leu Gly Ala Arg Thr Pro Ala Asp Leu Thr
305                 310             315                 320

Arg Cys Asp Val Leu Leu His Gly Glu Leu Arg Asp Phe Cys Ala Asp
                325             330             335

Arg Gly Ile Asp Thr Arg Arg Leu Ala Gln Arg Ser Ser Ile Glu
            340             345             350

Ala Leu Gln Thr Thr Gly Ser Thr Arg
        355             360

<210> SEQ ID NO 61
<211> LENGTH: 364
<212> TYPE: PRT
<213> ORGANISM: Streptomyces griseolosporeus

<400> SEQUENCE: 61

Met Ser Ser Ala Gln Arg Lys Asp Asp His Val Arg Leu Ala Thr Glu
1               5                   10                  15

Gln Gln Arg Ala His Ser Gly Arg Asn Gln Phe Asp Asp Val Ser Phe
                20                  25                  30

Val His His Ala Leu Ala Gly Ile Asp Arg Pro Asp Val Arg Leu Ala
            35                  40                  45

Thr Thr Phe Ala Gly Ile Thr Trp Arg Leu Pro Leu Tyr Ile Asn Ala
50                  55                  60

Met Thr Gly Gly Ser Ala Lys Thr Gly Ala Ile Asn Arg Asp Leu Ala
65                  70                  75                  80

Val Ala Ala Arg Glu Thr Gly Ala Ala Ile Ala Ser Gly Ser Met His
                85                  90                  95

Ala Phe Phe Arg Asp Pro Ser Cys Ala Asp Thr Phe Arg Val Leu Arg
            100                 105                 110

Thr Glu Asn Pro Asp Gly Phe Val Met Ala Asn Val Asn Ala Thr Ala
        115                 120                 125

Ser Val Asp Asn Ala Arg Arg Ala Val Asp Leu Ile Glu Ala Asn Ala
130                 135                 140

Leu Gln Ile His Leu Asn Thr Ala Gln Glu Thr Pro Met Pro Glu Gly
145                 150                 155                 160

Asp Arg Ser Phe Gly Ser Trp Pro Ala Gln Ile Ala Lys Ile Thr Ala
                165                 170                 175

Ala Val Asp Val Pro Val Ile Val Lys Glu Val Gly Asn Gly Leu Ser
            180                 185                 190

Arg Gln Thr Leu Leu Ala Leu Pro Asp Leu Gly Val Arg Val Ala Asp
        195                 200                 205

Val Ser Gly Arg Gly Gly Thr Asp Phe Ala Arg Ile Glu Asn Ser Arg
210                 215                 220

Arg Pro Leu Gly Asp Tyr Ala Phe Leu His Gly Trp Gly Gln Ser Thr
225                 230                 235                 240

Pro Ala Cys Leu Leu Asp Ala Gln Asp Val Gly Phe Pro Leu Leu Ala
                245                 250                 255

Ser Gly Gly Ile Arg Asn Pro Leu Asp Val Ala Arg Ala Leu Ala Leu
            260                 265                 270

Gly Ala Gly Ala Val Gly Ser Ser Gly Val Phe Leu Arg Thr Leu Ile
        275                 280                 285

Asp Gly Gly Val Ser Ala Leu Val Ala Gln Ile Ser Thr Trp Leu Asp
    290                 295                 300
```

-continued

Gln Leu Ala Ala Leu Gln Thr Met Leu Gly Ala Arg Thr Pro Ala Asp
305                 310                 315                 320

Leu Thr Arg Cys Asp Val Leu Ile His Gly Pro Leu Arg Ser Phe Cys
            325                 330                 335

Thr Asp Arg Gly Ile Asp Ile Gly Arg Phe Ala Arg Arg Ser Ser Ser
            340                 345                 350

Ala Asp Ile Arg Ser Glu Met Thr Gly Ser Thr Arg
        355                 360

<210> SEQ ID NO 62
<211> LENGTH: 368
<212> TYPE: PRT
<213> ORGANISM: Sulfolobus solfataricus

<400> SEQUENCE: 62

Met Pro Asp Ile Val Asn Arg Lys Val Glu His Val Glu Ile Ala Ala
1               5                   10                  15

Phe Glu Asn Val Asp Gly Leu Ser Ser Thr Phe Leu Asn Asp Val
                20                  25                  30

Ile Leu Val His Gln Gly Phe Pro Gly Ile Ser Phe Ser Glu Ile Asn
        35                  40                  45

Thr Lys Thr Lys Phe Phe Arg Lys Glu Ile Ser Ala Pro Ile Met Val
    50                  55                  60

Thr Gly Met Thr Gly Gly Arg Asn Glu Leu Gly Arg Ile Asn Arg Ile
65                  70                  75                  80

Ile Ala Glu Val Ala Glu Lys Phe Gly Ile Pro Met Gly Val Gly Ser
                85                  90                  95

Gln Arg Val Ala Ile Glu Lys Ala Glu Ala Arg Glu Ser Phe Thr Ile
            100                 105                 110

Val Arg Lys Val Ala Pro Thr Ile Pro Ile Ile Ala Asn Leu Gly Met
        115                 120                 125

Pro Gln Leu Val Lys Gly Tyr Gly Leu Lys Glu Phe Gln Asp Ala Ile
    130                 135                 140

Gln Met Ile Glu Ala Asp Ala Ile Ala Val His Leu Asn Pro Ala Gln
145                 150                 155                 160

Glu Val Phe Gln Pro Glu Gly Glu Pro Glu Tyr Gln Ile Tyr Ala Leu
                165                 170                 175

Glu Arg Leu Arg Asp Ile Ser Lys Glu Leu Ser Val Pro Ile Ile Val
            180                 185                 190

Lys Glu Ser Gly Asn Gly Ile Ser Met Glu Thr Ala Lys Leu Leu Tyr
        195                 200                 205

Ser Tyr Gly Ile Lys Asn Phe Asp Thr Ser Gly Gln Gly Gly Thr Asn
    210                 215                 220

Trp Ile Ala Ile Glu Met Ile Arg Asp Ile Arg Arg Gly Asn Trp Lys
225                 230                 235                 240

Ala Glu Ser Ala Lys Asn Phe Leu Asp Trp Gly Val Pro Thr Ala Ala
                245                 250                 255

Ser Ile Ile Glu Val Arg Tyr Ser Ile Pro Asp Ala Phe Leu Val Gly
            260                 265                 270

Ser Gly Gly Ile Arg Ser Gly Leu Asp Ala Ala Lys Ala Ile Ala Leu
        275                 280                 285

Gly Ala Asp Ile Ala Gly Met Ala Leu Pro Val Leu Lys Ser Ala Ile
    290                 295                 300

Glu Gly Lys Glu Ser Leu Glu Gln Phe Phe Arg Lys Ile Ile Phe Glu
305                 310                 315                 320

```
Leu Lys Ala Thr Met Met Leu Thr Gly Ser Lys Asn Val Glu Ala Leu
                325                 330                 335
Lys Arg Ser Ser Ile Val Ile Leu Gly Lys Leu Lys Glu Trp Ala Glu
                340                 345                 350
Tyr Arg Gly Ile Asn Leu Ser Ile Tyr Glu Lys Val Arg Lys Arg Glu
                355                 360                 365

<210> SEQ ID NO 63
<211> LENGTH: 342
<212> TYPE: PRT
<213> ORGANISM: Rickettsia prowazekii

<400> SEQUENCE: 63

Met Pro Lys Glu Gln Asn Leu Asp Ile Glu Arg Lys Gln Glu His Ile
 1               5                  10                  15
Glu Ile Asn Leu Lys Gln Asn Val Asn Ser Thr Leu Lys Ser Gly Leu
                20                  25                  30
Glu Ser Ile Lys Phe Ile His Asn Ala Leu Pro Glu Ile Asn Tyr Asp
            35                  40                  45
Ser Ile Asp Thr Thr Thr Thr Phe Leu Gly Lys Asp Met Lys Ala Pro
    50                  55                  60
Ile Leu Ile Ser Ser Met Thr Gly Gly Thr Ala Arg Ala Arg Asp Ile
65                  70                  75                  80
Asn Tyr Arg Leu Ala Gln Ala Ala Gln Lys Ser Gly Ile Ala Met Gly
                85                  90                  95
Leu Gly Ser Met Arg Ile Leu Leu Thr Lys Pro Asp Thr Ile Lys Thr
                100                 105                 110
Phe Thr Val Arg His Val Ala Pro Asp Ile Pro Leu Leu Ala Asn Ile
                115                 120                 125
Gly Ala Val Gln Leu Asn Tyr Gly Val Thr Pro Lys Glu Cys Gln Tyr
        130                 135                 140
Leu Ile Asp Thr Ile Lys Ala Asp Ala Leu Ile Leu His Leu Asn Val
145                 150                 155                 160
Leu His Glu Leu Thr Gln Pro Glu Gly Asn Lys Asn Trp Glu Asn Leu
                165                 170                 175
Leu Pro Lys Ile Lys Glu Val Ile Asn Tyr Leu Ser Val Pro Val Ile
                180                 185                 190
Val Lys Glu Val Gly Tyr Gly Leu Ser Lys Gln Val Ala Lys Lys Leu
                195                 200                 205
Ile Lys Ala Gly Val Lys Val Leu Asp Ile Ala Gly Ser Gly Gly Thr
        210                 215                 220
Ser Trp Ser Gln Val Glu Ala Tyr Arg Ala Lys Asn Ser Met Gln Asn
225                 230                 235                 240
Arg Ile Ala Ser Ser Phe Ile Asn Trp Gly Ile Thr Thr Leu Asp Ser
                245                 250                 255
Leu Lys Met Leu Gln Glu Ile Ser Lys Asp Ile Thr Ile Ala Ser
                260                 265                 270
Gly Gly Leu Gln Ser Gly Ile Asp Gly Ala Lys Ala Ile Arg Met Gly
        275                 280                 285
Ala Asn Ile Phe Gly Leu Ala Gly Lys Leu Leu Lys Ala Ala Asp Ile
    290                 295                 300
Ala Glu Ser Leu Val Leu Glu Glu Ile Gln Val Ile Glu Gln Leu
305                 310                 315                 320
Lys Ile Thr Met Leu Cys Thr Gly Ser Cys Thr Leu Lys Asp Leu Ala
```

```
                    325                 330                 335
Lys Ala Glu Ile Met Trp
            340

<210> SEQ ID NO 64
<211> LENGTH: 286
<212> TYPE: PRT
<213> ORGANISM: Deinococcus radiodurans

<400> SEQUENCE: 64

Met Arg Leu Asp Thr Val Phe Leu Gly Arg Arg Leu Lys Ala Pro Val
1               5                   10                  15

Leu Ile Gly Ala Met Thr Gly Gly Ala Glu Lys Ala Gly Val Ile Asn
            20                  25                  30

Arg Asn Leu Ala Thr Ala Ala Arg Asn Leu Gly Leu Gly Met Met Leu
        35                  40                  45

Gly Ser Gln Arg Val Met Leu Glu His Pro Asp Ala Trp Glu Ser Phe
    50                  55                  60

Asn Val Arg Glu Val Ala Pro Glu Ile Leu Leu Ile Gly Asn Leu Gly
65                  70                  75                  80

Ala Ala Gln Phe Met Leu Gly Tyr Gly Ala Glu Gln Ala Arg Arg Ala
                85                  90                  95

Val Asp Glu Val Met Ala Asp Ala Leu Ala Ile His Leu Asn Pro Leu
            100                 105                 110

Gln Glu Ala Leu Gln Arg Gly Gly Asp Thr Arg Trp Gln Gly Val Thr
        115                 120                 125

Tyr Arg Leu Lys Gln Val Ala Arg Glu Leu Asp Phe Pro Val Ile Ile
    130                 135                 140

Lys Glu Val Gly His Gly Leu Asp Ala Ala Thr Leu Arg Ala Leu Ala
145                 150                 155                 160

Asp Gly Pro Phe Ala Ala Tyr Asp Val Ala Gly Ala Gly Gly Thr Ser
                165                 170                 175

Trp Ala Arg Val Glu Gln Leu Val Ala His Gly Gln Val His Ser Pro
            180                 185                 190

Asp Leu Cys Glu Leu Gly Val Pro Thr Ala Gln Ala Leu Arg Gln Ala
        195                 200                 205

Arg Lys Thr Leu Pro Gly Ala Gln Leu Ile Ala Ser Gly Gly Ile Arg
    210                 215                 220

Ser Gly Leu Asp Ala Ala Arg Ala Leu Ser Leu Gly Ala Glu Val Val
225                 230                 235                 240

Ala Val Ala Arg Pro Leu Leu Glu Pro Ala Leu Asp Ser Ser Glu Ala
                245                 250                 255

Ala Glu Ala Trp Leu Arg Asn Phe Ile Gln Glu Leu Arg Val Ala Leu
            260                 265                 270

Phe Val Gly Gly Tyr Arg Asp Val Arg Glu Val Arg Gly Gly
        275                 280                 285

<210> SEQ ID NO 65
<211> LENGTH: 361
<212> TYPE: PRT
<213> ORGANISM: Aeropyrum pernix

<400> SEQUENCE: 65

Met Ile Val Ser Ser Lys Val Glu Ser Arg Glu Ser Thr Leu Leu Glu
1               5                   10                  15

Tyr Val Arg Ile Val His Asn Pro Thr Pro Glu Val Asn Leu Gly Asp
```

```
                    20                  25                  30
Val Ser Leu Glu Ile Asp Phe Cys Gly Gly Arg Leu Arg Ala Pro Leu
            35                  40                  45
Val Ile Thr Gly Met Thr Gly Gly His Pro Asp Val Glu Trp Ile Asn
    50                  55                  60
Arg Glu Leu Ala Ser Val Ala Glu Glu Leu Gly Ile Ala Ile Gly Val
65                  70                  75                  80
Gly Ser Gln Arg Ala Ala Ile Glu Asp Pro Ser Leu Ala Arg Thr Phe
                85                  90                  95
Arg Ala Ala Arg Glu Ala Pro Asn Ala Phe Leu Ile Ala Asn Leu
            100                 105                 110
Gly Ala Pro Gln Leu Ser Leu Gly Tyr Ser Val Arg Glu Val Arg Met
            115                 120                 125
Ala Val Glu Met Ile Asp Ala Asp Ala Ile Ala Ile His Leu Asn Pro
            130                 135                 140
Gly Gln Glu Ala Tyr Gln Pro Glu Gly Asp Pro Phe Tyr Arg Gly Val
145                 150                 155                 160
Val Gly Lys Ile Ala Glu Ala Ala Glu Ala Gly Val Pro Val Ile
                165                 170                 175
Val Lys Glu Thr Gly Asn Gly Leu Ser Arg Glu Ala Val Ala Gln Leu
            180                 185                 190
Arg Ala Leu Gly Val Arg Cys Phe Asp Val Ala Gly Leu Gly Gly Thr
            195                 200                 205
Asn Trp Ile Lys Ile Glu Val Leu Arg Gly Arg Lys Ala Gly Ser Pro
            210                 215                 220
Leu Glu Ala Gly Pro Leu Gln Asp Phe Trp Gly Asn Pro Thr Ala Ala
225                 230                 235                 240
Ala Leu Met Glu Ala Arg Thr Ala Ala Pro Asp Ala Tyr Ile Ile Ala
                245                 250                 255
Ser Gly Gly Val Arg Asn Gly Leu Asp Ala Ala Arg Ala Ile Ala Leu
            260                 265                 270
Gly Ala Asp Ala Ala Gly Val Ala Leu Pro Ala Ile Arg Ser Leu Leu
            275                 280                 285
Ser Gly Gly Arg Gln Ala Thr Leu Lys Leu Lys Ala Ile Glu Tyr
            290                 295                 300
Gln Leu Lys Thr Ala Val Tyr Met Val Gly Glu Thr Arg Val Arg Gly
305                 310                 315                 320
Leu Trp Arg Ala Pro Ile Val Val Trp Gly Arg Leu Ala Glu Glu Ala
                325                 330                 335
Glu Ala Arg Gly Ile Asp Pro Arg Trp Tyr Thr Asn Thr Leu Arg Leu
            340                 345                 350
Glu Ala Leu Val Tyr Lys Asp Val Lys
            355                 360

<210> SEQ ID NO 66
<211> LENGTH: 379
<212> TYPE: PRT
<213> ORGANISM: Halobacterium sp. NRC-1

<400> SEQUENCE: 66

Met Gly Glu Ser Arg Tyr Asn Ser Ile Val Phe Pro Ser Leu Val Gln
1               5                   10                  15

Thr Arg Leu Met Thr Ala Gln Asp Ser Thr Gln Thr Glu Asp Arg Lys
            20                  25                  30
```

```
Asp Asp His Leu Gln Ile Val Gln Glu Arg Asp Val Glu Thr Thr Gly
            35                  40                  45

Thr Gly Phe Asp Asp Val His Leu Val His Asn Ala Leu Pro Glu Leu
 50                  55                  60

Asp Tyr Asp Ala Ile Asp Pro Ser Ile Asp Phe Leu Gly His Asp Leu
 65                  70                  75                  80

Ser Ala Pro Ile Phe Ile Glu Ser Met Thr Gly Gly His His Asn Thr
                 85                  90                  95

Thr Glu Ile Asn Arg Ala Leu Ala Arg Ala Ala Ser Glu Thr Gly Ile
            100                 105                 110

Ala Met Gly Leu Gly Ser Gln Arg Ala Gly Leu Glu Leu Asp Asp Glu
            115                 120                 125

Arg Val Leu Glu Ser Tyr Thr Val Arg Asp Ala Ala Pro Asp Ala
            130                 135                 140

Phe Ile Tyr Gly Asn Leu Gly Ala Ala Gln Leu Arg Glu Tyr Asp Ile
145                 150                 155                 160

Glu Met Val Glu Gln Ala Val Glu Met Ile Asp Ala Asp Ala Leu Ala
                165                 170                 175

Val His Leu Asn Phe Leu Gln Glu Ala Thr Gln Pro Glu Gly Asp Val
            180                 185                 190

Asp Gly Arg Asn Cys Val Ala Ala Ile Glu Arg Val Ser Glu Ala Leu
            195                 200                 205

Ser Val Pro Ile Ile Val Lys Glu Thr Gly Asn Gly Ile Ser Gly Glu
            210                 215                 220

Thr Ala Arg Glu Leu Thr Ala Ala Gly Val Asp Ala Leu Asp Val Ala
225                 230                 235                 240

Gly Lys Gly Gly Thr Thr Trp Ser Gly Ile Glu Ala Tyr Arg Ala Ala
                245                 250                 255

Ala Ala Asn Ala Pro Arg Gln Lys Gln Ile Gly Thr Leu Phe Arg Glu
            260                 265                 270

Trp Gly Ile Pro Thr Ala Ala Ser Thr Ile Glu Cys Val Ala Glu His
            275                 280                 285

Asp Cys Val Ile Ala Ser Gly Gly Val Arg Thr Gly Leu Asp Val Ala
            290                 295                 300

Lys Ala Ile Ala Leu Gly Ala Arg Ala Gly Gly Leu Ala Lys Pro Phe
305                 310                 315                 320

Leu Lys Pro Ala Thr Asp Gly Pro Asp Ala Val Ile Glu Arg Val Gly
                325                 330                 335

Asp Leu Ile Ala Glu Leu Arg Thr Ala Met Phe Val Thr Gly Ser Gly
            340                 345                 350

Ser Ile Asp Glu Leu Gln Gln Val Glu Tyr Val Leu His Gly Lys Thr
            355                 360                 365

Arg Glu Tyr Val Glu Gln Arg Thr Ser Ser Glu
    370                 375

<210> SEQ ID NO 67
<211> LENGTH: 317
<212> TYPE: PRT
<213> ORGANISM: Archaeoglobus fulgidus

<400> SEQUENCE: 67

Met Met Leu Ile His Lys Ala Leu Pro Glu Val Asp Tyr Trp Lys Ile
1                5                  10                  15

Asp Thr Glu Ile Glu Phe Phe Gly Lys Lys Leu Ser Phe Pro Leu Leu
            20                  25                  30
```

-continued

Ile Ala Ser Met Thr Gly Gly His Pro Glu Thr Lys Glu Ile Asn Ala
             35                  40                  45

Arg Leu Gly Glu Ala Val Glu Ala Gly Ile Gly Met Gly Val Gly
 50                  55                  60

Ser Gln Arg Ala Ala Ile Glu Asp Glu Ser Leu Ala Asp Ser Phe Thr
 65                  70                  75                  80

Val Val Arg Glu Lys Ala Pro Asn Ala Phe Val Tyr Ala Asn Ile Gly
                 85                  90                  95

Met Pro Gln Val Ile Glu Arg Gly Val Glu Ile Val Asp Arg Ala Val
                100                 105                 110

Glu Met Ile Asp Ala Asp Ala Val Ala Ile His Leu Asn Tyr Leu Gln
            115                 120                 125

Glu Ala Ile Gln Pro Glu Gly Asp Leu Asn Ala Glu Lys Gly Leu Glu
        130                 135                 140

Val Leu Glu Glu Val Cys Arg Ser Val Lys Val Pro Val Ile Ala Lys
145                 150                 155                 160

Glu Thr Gly Ala Gly Ile Ser Arg Glu Val Ala Val Met Leu Lys Arg
                165                 170                 175

Ala Gly Val Ser Ala Ile Asp Val Gly Gly Lys Gly Gly Thr Thr Phe
                180                 185                 190

Ser Gly Val Glu Val Tyr Arg Val Asn Asp Glu Val Ser Lys Ser Val
                195                 200                 205

Gly Ile Asp Phe Trp Asp Trp Gly Leu Pro Thr Ala Phe Ser Ile Val
        210                 215                 220

Asp Cys Arg Gly Ile Leu Pro Val Ile Ala Thr Gly Gly Leu Arg Ser
225                 230                 235                 240

Gly Leu Asp Val Ala Lys Ser Ile Ala Ile Gly Ala Glu Leu Gly Ser
                245                 250                 255

Ala Ala Leu Pro Phe Leu Arg Ala Ala Val Glu Ser Ala Glu Lys Val
                260                 265                 270

Arg Glu Glu Ile Glu Tyr Phe Arg Arg Gly Leu Lys Thr Ala Met Phe
            275                 280                 285

Leu Thr Gly Cys Lys Asn Val Glu Glu Leu Lys Gly Leu Lys Val Phe
290                 295                 300

Val Ser Gly Arg Leu Lys Glu Trp Ile Asp Phe Arg Gly
305                 310                 315

<210> SEQ ID NO 68
<211> LENGTH: 370
<212> TYPE: PRT
<213> ORGANISM: Pyrococcus abyssi

<400> SEQUENCE: 68

Met Glu Glu Gln Thr Ile Leu Arg Lys Phe Glu His Ile Lys His Cys
1               5                   10                  15

Leu Thr Lys Asn Val Glu Ala His Val Thr Asn Gly Phe Glu Asp Val
            20                  25                  30

His Leu Ile His Lys Ser Leu Pro Glu Ile Asp Lys Asp Glu Ile Asp
        35                  40                  45

Leu Ser Val Lys Phe Leu Gly Arg Lys Phe Asp Tyr Pro Ile Met Ile
    50                  55                  60

Thr Gly Met Thr Gly Gly Thr Arg Lys Gly Glu Ile Ala Trp Arg Ile
65                  70                  75                  80

Asn Arg Thr Leu Ala Gln Ala Ala Gln Glu Leu Asn Ile Pro Leu Gly

```
                85                  90                  95
Leu Gly Ser Gln Arg Ala Met Ile Glu Lys Pro Glu Thr Trp Glu Ser
            100                 105                 110
Tyr Tyr Val Arg Asp Val Ala Pro Asp Val Phe Leu Val Gly Asn Leu
            115                 120                 125
Gly Ala Pro Gln Phe Gly Arg Asn Ala Lys Lys Arg Tyr Ser Val Asp
        130                 135                 140
Glu Val Leu Tyr Ala Ile Glu Lys Ile Glu Ala Asp Ala Ile Ala Ile
145                 150                 155                 160
His Met Asn Pro Leu Gln Glu Ser Ile Gln Pro Glu Gly Asp Thr Thr
                165                 170                 175
Phe Ser Gly Val Leu Glu Ala Leu Ala Glu Ile Thr Ser Thr Ile Asp
            180                 185                 190
Tyr Pro Val Ile Ala Lys Glu Thr Gly Ala Gly Val Ser Lys Glu Val
            195                 200                 205
Ala Val Glu Leu Glu Ala Gly Val Asp Ala Ile Asp Ile Ser Gly
        210                 215                 220
Leu Gly Gly Thr Ser Trp Ser Ala Val Glu Tyr Tyr Arg Thr Lys Asp
225                 230                 235                 240
Gly Glu Lys Arg Asn Leu Ala Leu Lys Phe Trp Asp Trp Gly Ile Lys
                245                 250                 255
Thr Ala Ile Ser Leu Ala Glu Val Arg Trp Ala Thr Asn Leu Pro Ile
            260                 265                 270
Ile Ala Ser Gly Gly Met Arg Asp Gly Ile Thr Met Ala Lys Ala Leu
            275                 280                 285
Ala Met Gly Ala Ser Met Val Gly Ile Ala Leu Pro Val Leu Arg Pro
290                 295                 300
Ala Ala Lys Gly Asp Val Glu Gly Val Ile Arg Ile Lys Gly Tyr
305                 310                 315                 320
Ala Glu Glu Ile Arg Asn Val Met Phe Leu Val Gly Ala Arg Asn Ile
                325                 330                 335
Lys Glu Leu Arg Lys Val Pro Leu Val Ile Thr Gly Phe Val Arg Glu
            340                 345                 350
Trp Leu Leu Gln Arg Ile Asp Leu Asn Ser Tyr Leu Arg Ala Arg Phe
            355                 360                 365
Lys Met
    370

<210> SEQ ID NO 69
<211> LENGTH: 371
<212> TYPE: PRT
<213> ORGANISM: Pyrococcus horikoshii

<400> SEQUENCE: 69

Met Lys Glu Glu Leu Thr Ile Leu Arg Lys Phe Glu His Ile Glu His
1               5                   10                  15
Cys Leu Lys Arg Asn Val Glu Ala His Val Ser Asn Gly Phe Glu Asp
            20                  25                  30
Val Tyr Phe Val His Lys Ser Leu Pro Glu Ile Asp Lys Asp Glu Ile
        35                  40                  45
Asp Leu Thr Val Glu Phe Leu Gly Arg Lys Phe Asp Tyr Pro Ile Met
    50                  55                  60
Ile Thr Gly Met Thr Gly Gly Thr Arg Arg Glu Glu Ile Ala Gly Lys
65                  70                  75                  80
```

```
Ile Asn Arg Thr Leu Ala Met Ala Ala Glu Glu Leu Asn Ile Pro Phe
                85                  90                  95

Gly Val Gly Ser Gln Arg Ala Met Ile Glu Lys Pro Glu Thr Trp Glu
            100                 105                 110

Ser Tyr Tyr Val Arg Asp Val Ala Pro Asp Ile Phe Leu Ile Gly Asn
            115                 120                 125

Leu Gly Ala Pro Gln Phe Gly Lys Asn Ala Lys Lys Arg Tyr Ser Val
130                 135                 140

Lys Glu Val Leu Tyr Ala Ile Glu Lys Ile Glu Ala Asp Ala Ile Ala
145                 150                 155                 160

Ile His Met Asn Pro Leu Gln Glu Ser Val Gln Pro Glu Gly Asp Thr
                165                 170                 175

Thr Tyr Ala Gly Val Leu Glu Ala Leu Ala Glu Ile Lys Ser Ser Ile
            180                 185                 190

Asn Tyr Pro Val Ile Ala Lys Glu Thr Gly Ala Gly Val Ser Lys Glu
            195                 200                 205

Val Ala Ile Glu Leu Glu Ser Val Gly Ile Asp Ala Ile Asp Ile Ser
        210                 215                 220

Gly Leu Gly Gly Thr Ser Trp Ser Ala Val Glu Tyr Tyr Arg Ala Lys
225                 230                 235                 240

Asp Ser Glu Lys Arg Lys Ile Ala Leu Lys Phe Trp Asp Trp Gly Ile
                245                 250                 255

Lys Thr Ala Ile Ser Leu Ala Glu Val Arg Trp Ala Thr Asn Leu Pro
            260                 265                 270

Ile Ile Ala Ser Gly Gly Met Arg Asp Gly Val Met Met Ala Lys Ala
            275                 280                 285

Leu Ala Met Gly Ala Ser Leu Val Gly Ile Ala Leu Pro Val Leu Arg
290                 295                 300

Pro Ala Ala Arg Gly Asp Val Glu Gly Val Val Arg Ile Ile Arg Gly
305                 310                 315                 320

Tyr Ala Glu Glu Ile Lys Asn Val Met Phe Leu Val Gly Ala Arg Asn
                325                 330                 335

Ile Arg Glu Leu Arg Arg Val Pro Leu Val Ile Thr Gly Phe Val Arg
            340                 345                 350

Glu Trp Leu Leu Gln Arg Ile Asp Leu Asn Ser Tyr Leu Arg Ser Arg
            355                 360                 365

Phe Lys His
    370

<210> SEQ ID NO 70
<211> LENGTH: 349
<212> TYPE: PRT
<213> ORGANISM: Methanobacterium thermoautotrophicum

<400> SEQUENCE: 70

Met Ile Ser Asp Arg Lys Leu Glu His Leu Ile Leu Cys Ala Ser Cys
1               5                   10                  15

Asp Val Glu Tyr Arg Lys Lys Thr Gly Phe Glu Asp Ile Glu Ile Val
            20                  25                  30

His Arg Ala Ile Pro Glu Ile Asn Lys Glu Lys Ile Asp Ile Ser Leu
        35                  40                  45

Asp Phe Leu Gly Arg Glu Leu Ser Ser Pro Val Met Ile Ser Ala Ile
    50                  55                  60

Thr Gly Gly His Pro Ala Ser Met Lys Ile Asn Arg Glu Leu Ala Arg
65                  70                  75                  80
```

```
Ala Ala Glu Lys Leu Gly Ile Ala Leu Gly Leu Gly Ser Gln Arg Ala
            85                  90                  95

Gly Val Glu His Pro Glu Leu Glu Gly Thr Tyr Thr Ile Ala Arg Glu
        100                 105                 110

Glu Ala Pro Ser Ala Met Leu Ile Gly Asn Ile Gly Ser Ser His Ile
    115                 120                 125

Glu Tyr Ala Glu Arg Ala Val Glu Met Ile Asp Ala Asp Ala Leu Ala
130                 135                 140

Val His Leu Asn Pro Leu Gln Glu Ser Ile Gln Pro Gly Gly Asp Val
145                 150                 155                 160

Asp Ser Ser Gly Ala Leu Glu Ser Ile Ser Ala Ile Val Glu Ser Val
                165                 170                 175

Asp Val Pro Val Met Val Lys Glu Thr Gly Ala Gly Ile Cys Ser Glu
                180                 185                 190

Asp Ala Ile Glu Leu Glu Ser Cys Gly Val Ser Ala Ile Asp Val Ala
            195                 200                 205

Gly Ala Gly Gly Thr Ser Trp Ala Ala Val Glu Thr Tyr Arg Ala Asp
    210                 215                 220

Asp Arg Tyr Leu Gly Glu Leu Phe Trp Asp Trp Gly Ile Pro Thr Ala
225                 230                 235                 240

Ala Ser Thr Val Glu Val Val Glu Ser Val Ser Ile Pro Val Ile Ala
                245                 250                 255

Ser Gly Gly Ile Arg Ser Gly Ile Asp Ala Ala Lys Ala Ile Ser Leu
            260                 265                 270

Gly Ala Glu Met Val Gly Ile Ala Leu Pro Val Leu Glu Ala Ala Gly
    275                 280                 285

His Gly Tyr Arg Glu Val Ile Lys Val Ile Glu Gly Phe Asn Glu Ala
        290                 295                 300

Leu Arg Thr Ala Met Tyr Leu Ala Gly Ala Glu Thr Leu Asp Asp Leu
305                 310                 315                 320

Lys Lys Ser Pro Val Ile Ile Thr Gly His Thr Gly Glu Trp Leu Asn
                325                 330                 335

Gln Arg Gly Phe Glu Thr Lys Lys Tyr Ala Arg Arg Ser
            340                 345

<210> SEQ ID NO 71
<211> LENGTH: 359
<212> TYPE: PRT
<213> ORGANISM: Methanococcus jannaschii

<400> SEQUENCE: 71

Met Val Asn Asn Arg Asn Glu Ile Glu Val Arg Lys Leu Glu His Ile
1               5                   10                  15

Phe Leu Cys Ser Tyr Cys Asn Val Glu Tyr Glu Lys Thr Thr Leu Leu
            20                  25                  30

Glu Asp Ile Glu Leu Ile His Lys Gly Thr Cys Gly Ile Asn Phe Asn
        35                  40                  45

Asp Ile Glu Thr Glu Ile Glu Leu Phe Gly Lys Lys Leu Ser Ala Pro
    50                  55                  60

Ile Ile Val Ser Gly Met Thr Gly Gly His Ser Lys Ala Lys Glu Ile
65                  70                  75                  80

Asn Lys Asn Ile Ala Lys Ala Val Glu Glu Leu Gly Leu Gly Met Gly
                85                  90                  95

Val Gly Ser Gln Arg Ala Ala Ile Val Asn Asp Glu Leu Ile Asp Thr
```

```
            100                 105                 110
Tyr Ser Ile Val Arg Asp Tyr Thr Asn Asn Leu Val Ile Gly Asn Leu
            115                 120                 125

Gly Ala Val Asn Phe Ile Val Asp Asp Trp Asp Glu Ile Ile Asp
    130                 135                 140

Lys Ala Ile Glu Met Ile Asp Ala Asp Ala Ile Ala Ile His Phe Asn
145                 150                 155                 160

Pro Leu Gln Glu Ile Ile Gln Pro Glu Gly Asp Leu Asn Phe Lys Asn
                165                 170                 175

Leu Tyr Lys Leu Lys Glu Ile Ile Ser Asn Tyr Lys Lys Ser Tyr Lys
            180                 185                 190

Asn Ile Pro Phe Ile Ala Lys Gln Val Gly Glu Gly Phe Ser Lys Glu
            195                 200                 205

Asp Ala Leu Ile Leu Lys Asp Ile Gly Phe Asp Ala Ile Asp Val Gln
    210                 215                 220

Gly Ser Gly Gly Thr Ser Trp Ala Lys Val Glu Ile Tyr Arg Val Lys
225                 230                 235                 240

Glu Glu Glu Ile Lys Arg Leu Ala Glu Lys Phe Ala Asn Trp Gly Ile
                245                 250                 255

Pro Thr Ala Ala Ser Ile Phe Glu Val Lys Ser Val Tyr Asp Gly Ile
            260                 265                 270

Val Ile Gly Ser Gly Gly Ile Arg Gly Gly Leu Asp Ile Ala Lys Cys
            275                 280                 285

Ile Ala Ile Gly Cys Asp Cys Cys Ser Val Ala Leu Pro Ile Leu Lys
        290                 295                 300

Ala Ser Leu Lys Gly Trp Glu Glu Val Lys Val Leu Glu Ser Tyr
305                 310                 315                 320

Ile Lys Glu Leu Lys Ile Ala Met Phe Leu Val Gly Ala Glu Asn Ile
            325                 330                 335

Glu Glu Leu Lys Lys Thr Ser Tyr Ile Val Lys Gly Thr Leu Lys Glu
            340                 345                 350

Trp Ile Ser Gln Arg Leu Lys
        355

<210> SEQ ID NO 72
<211> LENGTH: 348
<212> TYPE: PRT
<213> ORGANISM: Thermoplasma acidophilum

<400> SEQUENCE: 72

Met Ile Gly Lys Arg Lys Glu Glu His Ile Arg Ile Ala Glu Asn Glu
1               5                   10                  15

Asp Val Ser Ser Phe His Asn Phe Trp Asp Asp Ile Ser Leu Met His
            20                  25                  30

Glu Ala Asp Pro Glu Val Asn Tyr Asp Glu Ile Asp Thr Ser Val Asp
        35                  40                  45

Phe Leu Gly Lys Lys Leu Lys Phe Pro Met Ile Ile Ser Ser Met Thr
    50                  55                  60

Gly Gly Ala Glu Ile Ala Lys Asn Ile Asn Arg Asn Leu Ala Val Ala
65                  70                  75                  80

Ala Glu Arg Phe Gly Ile Gly Met Gly Val Gly Ser Met Arg Ala Ala
                85                  90                  95

Ile Val Asp Arg Ser Ile Glu Asp Thr Tyr Ser Val Ile Asn Glu Ser
            100                 105                 110
```

```
His Val Pro Leu Lys Ile Ala Asn Ile Gly Ala Pro Gln Leu Val Arg
        115                 120                 125

Gln Asp Lys Asp Ala Val Ser Asn Arg Asp Ile Ala Tyr Ile Tyr Asp
130                 135                 140

Leu Ile Lys Ala Asp Phe Leu Ala Val His Phe Asn Phe Leu Gln Glu
145                 150                 155                 160

Met Val Gln Pro Glu Gly Asp Arg Asn Ser Lys Gly Val Ile Asp Arg
                165                 170                 175

Ile Lys Asp Leu Ser Gly Ser Phe Asn Ile Ile Ala Lys Glu Thr Gly
                180                 185                 190

Ser Gly Phe Ser Arg Arg Thr Ala Glu Arg Leu Ile Asp Ala Gly Val
            195                 200                 205

Lys Ala Ile Glu Val Ser Gly Val Ser Gly Thr Thr Phe Ala Ala Val
        210                 215                 220

Glu Tyr Tyr Arg Ala Arg Lys Glu Asn Asn Leu Glu Lys Met Arg Ile
225                 230                 235                 240

Gly Glu Thr Phe Trp Asn Trp Gly Ile Pro Ser Pro Ala Ser Val Tyr
                245                 250                 255

Tyr Cys Ser Asp Leu Ala Pro Val Ile Gly Ser Gly Leu Arg Asn
                260                 265                 270

Gly Leu Asp Leu Ala Lys Ala Ile Ala Met Gly Ala Thr Ala Gly Gly
            275                 280                 285

Phe Ala Arg Ser Leu Leu Lys Asp Ala Asp Thr Asp Pro Glu Met Leu
        290                 295                 300

Met Lys Asn Ile Glu Leu Ile Gln Arg Glu Phe Arg Val Ala Leu Phe
305                 310                 315                 320

Leu Thr Gly Asn Lys Asn Val Tyr Glu Leu Lys Phe Thr Lys Lys Val
                325                 330                 335

Ile Val Asp Pro Leu Arg Ser Trp Leu Glu Ala Lys
                340                 345

<210> SEQ ID NO 73
<211> LENGTH: 357
<212> TYPE: PRT
<213> ORGANISM: Leishmania major

<400> SEQUENCE: 73

Met Ser Ser Arg Asp Cys Thr Val Asp Arg Glu Ala Ala Val Gln Lys
1               5                   10                  15

Arg Lys Lys Asp His Ile Asp Ile Cys Leu His Gln Asp Val Glu Pro
                20                  25                  30

His Lys Arg Arg Thr Ser Ile Trp Asn Lys Tyr Thr Leu Pro Tyr Lys
            35                  40                  45

Ala Leu Pro Glu Val Asp Leu Gln Lys Ile Asp Thr Ser Cys Glu Phe
50                  55                  60

Met Gly Lys Arg Ile Ser Phe Pro Phe Ile Ser Ser Met Thr Gly
65                  70                  75                  80

Gly Glu Ala His Gly Arg Val Ile Asn Glu Asn Leu Ala Lys Ala Cys
                85                  90                  95

Glu Ala Glu Lys Ile Pro Phe Gly Leu Gly Ser Met Arg Ile Ile Asn
            100                 105                 110

Arg Tyr Ala Ser Ala Val His Thr Phe Asn Val Lys Glu Phe Cys Pro
        115                 120                 125

Ser Val Pro Met Leu Ala Asn Ile Gly Leu Val Gln Leu Asn Tyr Gly
    130                 135                 140
```

```
Phe Gly Pro Lys Glu Val Asn Asn Leu Val Asn Ser Val Arg Ala Asp
145                 150                 155                 160

Gly Leu Cys Ile His Leu Asn His Thr Gln Glu Val Cys Gln Pro Glu
            165                 170                 175

Gly Asp Thr Asn Phe Glu Gly Leu Ile Glu Lys Leu Arg Gln Leu Leu
            180                 185                 190

Pro His Ile Lys Val Pro Val Leu Val Lys Gly Val His Gly Ile
        195                 200                 205

Asp Tyr Glu Ser Met Val Ala Ile Lys Ala Ser Gly Val Lys Tyr Val
    210                 215                 220

Asp Val Ser Gly Cys Gly Gly Thr Ser Trp Ala Trp Ile Glu Gly Arg
225                 230                 235                 240

Arg Gln Pro Tyr Lys Ala Glu Glu Asn Ile Gly Tyr Leu Leu Arg
                245                 250                 255

Asp Ile Gly Val Pro Thr Asp Val Cys Leu Arg Glu Ser Ala Pro Leu
            260                 265                 270

Thr Val Asn Gly Asp Leu His Leu Ile Ala Gly Gly Ile Arg Asn
    275                 280                 285

Gly Met Asp Val Ala Lys Ala Leu Met Met Gly Ala Glu Tyr Ala Thr
    290                 295                 300

Ala Ala Met Pro Phe Leu Ala Ala Leu Glu Ser Ser Glu Ala Val
305                 310                 315                 320

Arg Ala Val Ile Gln Arg Met Arg Gln Glu Leu Arg Val Ser Met Phe
                325                 330                 335

Thr Cys Gly Ala Arg Asn Ile Glu Glu Leu Arg Arg Met Lys Val Ile
            340                 345                 350

Glu Leu Gly His Leu
        355

<210> SEQ ID NO 74
<211> LENGTH: 398
<212> TYPE: PRT
<213> ORGANISM: Streptococcus pneumoniae

<400> SEQUENCE: 74

Met Asn Asp Lys Thr Glu Val Asn Met Thr Ile Gly Ile Asp Lys Ile
1               5                   10                  15

Gly Phe Ala Thr Ser Gln Tyr Val Leu Lys Leu Gln Asp Leu Ala Glu
            20                  25                  30

Ala Arg Gly Ile Asp Pro Glu Lys Leu Ser Lys Gly Leu Leu Leu Lys
        35                  40                  45

Glu Leu Ser Ile Ala Pro Leu Thr Glu Asp Ile Val Thr Leu Ala Ala
    50                  55                  60

Ser Ala Ser Asp Ser Ile Leu Thr Glu Gln Glu Arg Gln Glu Val Asp
65                  70                  75                  80

Met Val Ile Val Ala Thr Glu Ser Gly Ile Asp Gln Ser Lys Ala Ala
                85                  90                  95

Ala Val Phe Val His Gly Leu Leu Gly Ile Gln Pro Phe Ala Arg Ser
            100                 105                 110

Phe Glu Ile Lys Glu Ala Cys Tyr Gly Ala Thr Ala Ala Leu His Tyr
        115                 120                 125

Ala Lys Leu His Val Glu Asn Ser Pro Glu Ser Lys Val Leu Val Ile
    130                 135                 140

Ala Ser Asp Ile Ala Lys Tyr Gly Ile Glu Thr Pro Gly Glu Pro Thr
```

```
                145                 150                 155                 160
Gln Gly Ala Gly Ser Val Ala Met Leu Ile Thr Gln Asn Pro Arg Met
                    165                 170                 175
Met Ala Phe Asn Asn Asp Asn Val Ala Gln Thr Arg Asp Ile Met Asp
                180                 185                 190
Phe Trp Arg Pro Asn Tyr Ser Thr Pro Tyr Val Asn Gly Val Tyr
            195                 200                 205
Ser Thr Gln Gln Tyr Leu Asp Ser Leu Lys Thr Thr Trp Leu Glu Tyr
        210                 215                 220
Gln Lys Arg Tyr Gln Leu Thr Leu Asp Asp Phe Ala Val Cys Phe
225                 230                 235                 240
His Leu Pro Tyr Pro Lys Leu Ala Leu Lys Gly Leu Lys Lys Ile Met
                245                 250                 255
Asp Lys Asn Leu Pro Gln Glu Lys Lys Asp Leu Leu Gln Lys His Phe
                260                 265                 270
Asp Gln Ser Ile Leu Tyr Ser Gln Lys Val Gly Asn Ile Tyr Thr Gly
            275                 280                 285
Ser Leu Phe Leu Gly Leu Leu Ser Leu Leu Glu Asn Thr Asp Ser Leu
        290                 295                 300
Lys Ala Gly Asp Lys Ile Ala Leu Tyr Ser Tyr Gly Ser Gly Ala Val
305                 310                 315                 320
Ala Glu Phe Phe Ser Gly Glu Leu Val Glu Gly Tyr Glu Ala Tyr Leu
                325                 330                 335
Asp Lys Asp Arg Leu Asn Lys Leu Asn Gln Arg Thr Ala Leu Ser Val
                340                 345                 350
Ala Asp Tyr Glu Lys Val Phe Phe Glu Glu Val Asn Leu Asp Glu Thr
            355                 360                 365
Asn Ser Ala Gln Phe Ala Gly Tyr Glu Asn Gln Asp Phe Ala Leu Val
        370                 375                 380
Glu Ile Leu Asp His Gln Arg Arg Tyr Ser Lys Val Glu Lys
385                 390                 395

<210> SEQ ID NO 75
<211> LENGTH: 391
<212> TYPE: PRT
<213> ORGANISM: Streptococcus pyrogenes

<400> SEQUENCE: 75

Met Thr Ile Gly Ile Asp Lys Ile Gly Phe Ala Thr Ser Gln Tyr Val
1               5                   10                  15
Leu Lys Leu Glu Asp Leu Ala Leu Ala Arg Gln Val Asp Pro Ala Lys
                20                  25                  30
Phe Ser Gln Gly Leu Leu Ile Glu Ser Phe Ser Val Ala Pro Ile Thr
            35                  40                  45
Glu Asp Ile Ile Thr Leu Ala Ala Ser Ala Ala Asp Gln Ile Leu Thr
        50                  55                  60
Asp Glu Asp Arg Ala Lys Ile Asp Met Val Ile Leu Ala Thr Glu Ser
65                  70                  75                  80
Ser Thr Asp Gln Ser Lys Ala Ser Ala Ile Tyr Val His His Leu Val
                85                  90                  95
Gly Ile Gln Pro Phe Ala Arg Ser Phe Glu Val Lys Gln Ala Cys Tyr
            100                 105                 110
Ser Ala Thr Ala Ala Leu Asp Tyr Ala Lys Leu His Val Ala Ser Lys
        115                 120                 125
```

```
Pro Asp Ser Arg Val Leu Val Ile Ala Ser Asp Ile Ala Arg Tyr Gly
    130                 135                 140

Val Gly Ser Pro Gly Glu Ser Thr Gln Gly Ser Gly Ser Ile Ala Leu
145                 150                 155                 160

Leu Val Thr Ala Asp Pro Arg Ile Leu Ala Leu Asn Glu Asp Asn Val
                165                 170                 175

Ala Gln Thr Arg Asp Ile Met Asp Phe Trp Arg Pro Asn Tyr Ser Phe
            180                 185                 190

Thr Pro Tyr Val Asp Gly Ile Tyr Ser Thr Lys Gln Tyr Leu Asn Cys
        195                 200                 205

Leu Glu Thr Thr Trp Gln Ala Tyr Gln Lys Arg Glu Asn Leu Gln Leu
    210                 215                 220

Ser Asp Phe Ala Ala Val Cys Phe His Ile Pro Phe Pro Lys Leu Ala
225                 230                 235                 240

Leu Lys Gly Leu Asn Asn Ile Met Asp Asn Thr Val Pro Pro Glu His
                245                 250                 255

Arg Glu Lys Leu Ile Glu Ala Phe Gln Ala Ser Ile Thr Tyr Ser Lys
            260                 265                 270

Gln Ile Gly Asn Ile Tyr Thr Gly Ser Leu Tyr Leu Gly Leu Leu Ser
        275                 280                 285

Leu Leu Glu Asn Ser Lys Val Leu Gln Ser Gly Asp Lys Ile Gly Phe
    290                 295                 300

Phe Ser Tyr Gly Ser Gly Ala Val Ser Glu Phe Tyr Ser Gly Gln Leu
305                 310                 315                 320

Val Ala Gly Tyr Asp Lys Met Leu Met Thr Asn Arg Gln Ala Leu Leu
                325                 330                 335

Asp Gln Arg Thr Arg Leu Ser Val Ser Lys Tyr Glu Asp Leu Phe Tyr
            340                 345                 350

Glu Gln Val Gln Leu Asp Asp Asn Gly Asn Ala Asn Phe Asp Ile Tyr
        355                 360                 365

Leu Thr Gly Lys Phe Ala Leu Thr Ala Ile Lys Glu His Gln Arg Ile
    370                 375                 380

Tyr His Thr Asn Asp Lys Asn
385                 390

<210> SEQ ID NO 76
<211> LENGTH: 383
<212> TYPE: PRT
<213> ORGANISM: Enterococcus faecalis

<400> SEQUENCE: 76

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110
```

```
Gly Ala Thr Ala Gly Leu Gln Leu Ala Lys Asn His Val Ala Leu His
            115                 120                 125

Pro Asp Lys Lys Val Leu Val Ala Ala Asp Ile Ala Lys Tyr Gly
130                 135                 140

Leu Asn Ser Gly Gly Glu Pro Thr Gln Gly Ala Gly Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380

<210> SEQ ID NO 77
<211> LENGTH: 384
<212> TYPE: PRT
<213> ORGANISM: Enterococcus faecium

<400> SEQUENCE: 77

Met Lys Ile Gly Ile Asp Arg Leu Ser Phe Phe Ile Pro Asn Leu Tyr
1               5                   10                  15

Leu Asp Met Thr Glu Leu Ala Glu Ser Arg Gly Asp Asp Pro Ala Lys
            20                  25                  30

Tyr His Ile Gly Ile Gly Gln Asp Gln Met Ala Val Asn Arg Ala Asn
        35                  40                  45

Glu Asp Ile Ile Thr Leu Gly Ala Asn Ala Ala Ser Lys Ile Val Thr
    50                  55                  60

Glu Lys Asp Arg Glu Leu Ile Asp Met Val Ile Val Gly Thr Glu Ser
65                  70                  75                  80

Gly Ile Asp His Ser Lys Ala Ser Ala Val Ile His His Leu Leu
                85                  90                  95

Lys Ile Gln Ser Phe Ala Arg Ser Phe Glu Val Lys Glu Ala Cys Tyr
```

```
                100                 105                 110
Gly Gly Thr Ala Ala Leu His Met Ala Lys Glu Tyr Val Lys Asn His
            115                 120                 125

Pro Glu Arg Lys Val Leu Val Ile Ala Ser Asp Ile Ala Arg Tyr Gly
        130                 135                 140

Leu Ala Ser Gly Gly Glu Val Thr Gln Gly Val Gly Ala Val Ala Met
145                 150                 155                 160

Met Ile Thr Gln Asn Pro Arg Ile Leu Ser Ile Glu Asp Asp Ser Val
                165                 170                 175

Phe Leu Thr Glu Asp Ile Tyr Asp Phe Trp Arg Pro Asp Tyr Ser Glu
            180                 185                 190

Phe Pro Val Val Asp Gly Pro Leu Ser Asn Ser Thr Tyr Ile Glu Ser
        195                 200                 205

Phe Gln Lys Val Trp Asn Arg His Lys Glu Leu Ser Gly Arg Gly Leu
    210                 215                 220

Glu Asp Tyr Gln Ala Ile Ala Phe His Ile Pro Tyr Thr Lys Met Gly
225                 230                 235                 240

Lys Lys Ala Leu Gln Ser Val Leu Asp Gln Thr Asp Glu Asp Asn Gln
                245                 250                 255

Glu Arg Leu Met Ala Arg Tyr Glu Glu Ser Ile Arg Tyr Ser Arg Arg
            260                 265                 270

Ile Gly Asn Leu Tyr Thr Gly Ser Leu Tyr Leu Gly Leu Thr Ser Leu
        275                 280                 285

Leu Glu Asn Ser Lys Ser Leu Gln Pro Gly Asp Arg Ile Gly Leu Phe
    290                 295                 300

Ser Tyr Gly Ser Gly Ala Val Ser Glu Phe Phe Thr Gly Tyr Leu Glu
305                 310                 315                 320

Glu Asn Tyr Gln Glu Tyr Leu Phe Ala Gln Ser His Gln Glu Met Leu
                325                 330                 335

Asp Ser Arg Thr Arg Ile Thr Val Asp Glu Tyr Glu Thr Ile Phe Ser
            340                 345                 350

Glu Thr Leu Pro Glu His Gly Glu Cys Ala Glu Tyr Thr Ser Asp Val
        355                 360                 365

Pro Phe Ser Ile Thr Lys Ile Glu Asn Asp Ile Arg Tyr Tyr Lys Ile
    370                 375                 380

<210> SEQ ID NO 78
<211> LENGTH: 388
<212> TYPE: PRT
<213> ORGANISM: Staphylococcus haemolyticus

<400> SEQUENCE: 78

Met Ser Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Gln Met Ala Val Ser Pro Val Ser
        35                  40                  45

Gln Asp Ile Val Ser Met Gly Ala Asn Ala Ala Lys Asp Ile Ile Thr
    50                  55                  60

Asp Asp Asp Lys Lys His Ile Gly Met Val Ile Ala Thr Glu Ser
65                  70                  75                  80

Ala Ile Asp Asn Ala Lys Ala Ala Val Gln Ile His Asn Leu Leu
            85                  90                  95
```

```
Gly Val Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Ile Glu Lys Arg
        115                 120                 125

Pro Asn Glu Lys Val Leu Val Ile Ala Ser Asp Thr Ala Arg Tyr Gly
    130                 135                 140

Ile Gln Ser Gly Gly Glu Pro Thr Gln Gly Ala Gly Val Ala Met
145                 150                 155                 160

Leu Ile Ser Asn Asn Pro Ser Ile Leu Glu Leu Asn Asp Asp Ala Val
                165                 170                 175

Ala Tyr Thr Glu Asp Val Tyr Asp Phe Trp Arg Pro Thr Gly His Lys
        180                 185                 190

Tyr Pro Leu Val Ala Gly Ala Leu Ser Lys Asp Ala Tyr Ile Lys Ser
        195                 200                 205

Phe Gln Glu Ser Trp Asn Glu Tyr Ala Arg Arg Glu Asp Lys Thr Leu
    210                 215                 220

Ser Asp Phe Glu Ser Leu Cys Phe His Val Pro Phe Thr Lys Met Gly
225                 230                 235                 240

Lys Lys Ala Leu Asp Ser Ile Ile Asn Asp Ala Asp Glu Thr Thr Gln
                245                 250                 255

Glu Arg Leu Thr Ser Gly Tyr Glu Asp Ala Val Tyr Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Asn Arg Ser Leu Lys Gly Gly Gln Thr Ile Gly Leu Phe Ser
    290                 295                 300

Tyr Gly Ser Gly Ser Val Gly Glu Phe Phe Ser Ala Thr Leu Val Glu
305                 310                 315                 320

Gly Tyr Glu Lys Gln Leu Asp Ile Glu Gly His Lys Ala Leu Leu Asn
                325                 330                 335

Glu Arg Gln Glu Val Ser Val Glu Asp Tyr Glu Ser Phe Phe Lys Arg
            340                 345                 350

Phe Asp Asp Leu Glu Phe Asp His Ala Thr Glu Gln Thr Asp Asp Asp
        355                 360                 365

Lys Ser Ile Tyr Tyr Leu Glu Asn Ile Gln Asp Asp Ile Arg Gln Tyr
370                 375                 380

His Ile Pro Lys
385

<210> SEQ ID NO 79
<211> LENGTH: 388
<212> TYPE: PRT
<213> ORGANISM: Staphylococcus epidermis

<400> SEQUENCE: 79

Met Asn Ile Gly Ile Asp Lys Ile Ser Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Glu Met Thr Val Ser Pro Val Asn
        35                  40                  45

Gln Asp Ile Val Ser Met Gly Ala Asn Ala Ala Lys Asp Ile Ile Thr
    50                  55                  60

Glu Glu Asp Lys Lys Asn Ile Gly Met Val Ile Val Ala Thr Glu Ser
65                  70                  75                  80
```

```
Ala Ile Asp Asn Ala Lys Ala Ala Val Gln Ile His His Leu Leu
            85                  90                  95

Gly Ile Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Leu Ala Gln Arg
            115                 120                 125

Pro Asn Glu Lys Val Leu Val Ile Ala Ser Asp Thr Ala Arg Tyr Gly
            130                 135                 140

Ile His Ser Gly Gly Glu Pro Thr Gln Gly Ala Gly Ala Val Ala Met
145                 150                 155                 160

Met Ile Ser His Asp Pro Ser Ile Leu Lys Leu Asn Asp Asp Ala Val
                165                 170                 175

Ala Tyr Thr Glu Asp Val Tyr Asp Phe Trp Arg Pro Thr Gly His Gln
            180                 185                 190

Tyr Pro Leu Val Ala Gly Ala Leu Ser Lys Asp Ala Tyr Ile Lys Ser
            195                 200                 205

Phe Gln Glu Ser Trp Asn Glu Tyr Ala Arg Arg His Asn Lys Thr Leu
            210                 215                 220

Ala Asp Phe Ala Ser Leu Cys Phe His Val Pro Phe Thr Lys Met Gly
225                 230                 235                 240

Gln Lys Ala Leu Asp Ser Ile Ile Asn His Ala Asp Glu Thr Thr Gln
                245                 250                 255

Asp Arg Leu Asn Ser Ser Tyr Gln Asp Ala Val Asp Tyr Asn Arg Tyr
            260                 265                 270

Val Gly Asn Ile Tyr Thr Gly Ser Leu Tyr Leu Ser Leu Ile Ser Leu
            275                 280                 285

Leu Glu Thr Arg Asp Leu Lys Gly Gly Gln Thr Ile Gly Leu Phe Ser
    290                 295                 300

Tyr Gly Ser Gly Ser Val Gly Glu Phe Phe Ser Gly Thr Leu Val Asp
305                 310                 315                 320

Gly Phe Lys Glu Gln Leu Asp Val Glu Arg His Lys Ser Leu Leu Asn
            325                 330                 335

Asn Arg Ile Glu Val Ser Val Asp Glu Tyr Glu His Phe Phe Lys Arg
            340                 345                 350

Phe Asp Gln Leu Glu Leu Asn His Glu Leu Glu Lys Ser Asn Ala Asp
            355                 360                 365

Arg Asp Ile Phe Tyr Leu Lys Ser Ile Asp Asn Asn Ile Arg Glu Tyr
    370                 375                 380

His Ile Ala Glu
385

<210> SEQ ID NO 80
<211> LENGTH: 388
<212> TYPE: PRT
<213> ORGANISM: Staphylococcus aureus

<400> SEQUENCE: 80

Met Thr Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Glu Met Ala Val Ser Pro Val Asn
            35                  40                  45

Gln Asp Ile Val Ser Met Gly Ala Asn Ala Ala Lys Asp Ile Ile Thr
```

```
                    50                  55                  60
Asp Glu Asp Lys Lys Ile Gly Met Val Ile Val Ala Thr Glu Ser
 65                  70                  75                  80

Ala Val Asp Ala Ala Lys Ala Ala Val Gln Ile His Asn Leu Leu
                     85                  90                  95

Gly Ile Gln Pro Phe Ala Arg Cys Phe Glu Met Lys Glu Ala Cys Tyr
                100                 105                 110

Ala Ala Thr Pro Ala Ile Gln Leu Ala Lys Asp Tyr Leu Ala Thr Arg
                115                 120                 125

Pro Asn Glu Lys Val Leu Val Ile Ala Thr Asp Thr Ala Arg Tyr Gly
                130                 135                 140

Leu Asn Ser Gly Gly Glu Pro Thr Gln Gly Ala Gly Ala Val Ala Met
145                 150                 155                 160

Val Ile Ala His Asn Pro Ser Ile Leu Ala Leu Asn Glu Asp Ala Val
                165                 170                 175

Ala Tyr Thr Glu Asp Val Tyr Asp Phe Trp Arg Pro Thr Gly His Lys
                180                 185                 190

Tyr Pro Leu Val Asp Gly Ala Leu Ser Lys Asp Ala Tyr Ile Arg Ser
                195                 200                 205

Phe Gln Gln Ser Trp Asn Glu Tyr Ala Lys Arg Gln Gly Lys Ser Leu
                210                 215                 220

Ala Asp Phe Ala Ser Leu Cys Phe His Val Pro Phe Thr Lys Met Gly
225                 230                 235                 240

Lys Lys Ala Leu Glu Ser Ile Ile Asp Asn Ala Asp Glu Thr Thr Gln
                245                 250                 255

Glu Arg Leu Arg Ser Gly Tyr Glu Asp Ala Val Asp Tyr Asn Arg Tyr
                260                 265                 270

Val Gly Asn Ile Tyr Thr Gly Ser Leu Tyr Leu Ser Leu Ile Ser Leu
                275                 280                 285

Leu Glu Asn Arg Asp Leu Gln Ala Gly Glu Thr Ile Gly Leu Phe Ser
                290                 295                 300

Tyr Gly Ser Gly Ser Val Val Glu Phe Tyr Ser Ala Thr Leu Val Val
305                 310                 315                 320

Gly Tyr Lys Asp His Leu Asp Gln Ala Ala His Lys Ala Leu Leu Asn
                325                 330                 335

Asn Arg Thr Glu Val Ser Val Asp Ala Tyr Glu Thr Phe Phe Lys Arg
                340                 345                 350

Phe Asp Asp Val Glu Phe Asp Glu Gln Asp Ala Val His Glu Asp
                355                 360                 365

Arg His Ile Phe Tyr Leu Ser Asn Ile Glu Asn Asn Val Arg Glu Tyr
                370                 375                 380

His Arg Pro Glu
385

<210> SEQ ID NO 81
<211> LENGTH: 389
<212> TYPE: PRT
<213> ORGANISM: Staphylococcus carnosus

<400> SEQUENCE: 81

Met Thr Ile Gly Ile Asp Gln Leu Asn Phe Tyr Ile Pro Asn Phe Tyr
 1               5                  10                  15

Val Asp Met Ala Glu Leu Ala Glu Ala Arg Gly Val Asp Pro Asn Lys
                20                  25                  30
```

-continued

Phe Leu Ile Gly Ile Gly Gln Ser Gln Met Ala Val Ser Pro Val Ser
            35                  40                  45

Gln Asp Ile Val Ser Met Gly Ala Asn Ala Ala Gln Pro Ile Leu Ser
 50                  55                  60

Glu Gln Asp Lys Lys Asp Ile Thr Met Val Ile Val Ala Thr Glu Ser
65                  70                  75                  80

Ala Ile Asp Ser Ala Lys Ala Ser Ala Val Gln Ile His His Leu Leu
                85                  90                  95

Gly Ile Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Leu Val Pro Arg
            115                 120                 125

Pro Lys Glu Lys Val Leu Val Ile Ala Ser Asp Thr Ala Arg Tyr Gly
        130                 135                 140

Leu Asn Ser Gly Gly Glu Pro Thr Gln Gly Ala Gly Ala Val Ala Met
145                 150                 155                 160

Val Ile Ser His Asn Pro Ser Ile Leu Glu Leu His Asp Asp Ser Val
                165                 170                 175

Ala Tyr Thr Glu Asp Val Tyr Asp Phe Trp Arg Pro Ser Gly Glu Ile
            180                 185                 190

Tyr Pro Leu Val Ala Gly Lys Leu Ser Lys Asp Ala Tyr Ile Lys Ser
            195                 200                 205

Phe Gln Glu Ser Trp Asn Glu Tyr Ala Lys Arg His His Lys Ser Leu
        210                 215                 220

Ser Asp Phe Ala Ala Leu Cys Phe His Val Pro Phe Thr Lys Met Gly
225                 230                 235                 240

Gln Lys Ala Leu Asp Ser Ile Leu Thr Asp Ser Ala Ser Glu Asp Thr
                245                 250                 255

Gln Ala Arg Leu Asn Glu Gly Tyr Lys Ser Ala Thr Asp Tyr Asn Arg
            260                 265                 270

Tyr Val Gly Asn Val Tyr Thr Gly Ser Leu Tyr Leu Ser Leu Ile Ser
            275                 280                 285

Leu Leu Glu Asn His Lys Leu Asn Gly Gly Asp Asn Ile Gly Leu Phe
        290                 295                 300

Ser Tyr Gly Ser Gly Ser Val Gly Glu Phe Phe Ser Ala Thr Leu Val
305                 310                 315                 320

Asp Asn Tyr Gln Asp His Leu Asp Val Lys Ala His Lys Ala Met Leu
                325                 330                 335

Asp Asn Arg Lys Ala Leu Ser Val Glu Glu Tyr Glu Lys Phe Phe Asn
            340                 345                 350

Arg Phe Asp Asn Leu Glu Phe Asp Thr Glu Thr Glu Leu Glu Val Glu
            355                 360                 365

Pro Lys Gly Asn Phe Tyr Leu Lys Glu Ile Ser Asp Asn Ile Arg Tyr
        370                 375                 380

Tyr Asp Thr Val Lys
385

<210> SEQ ID NO 82
<211> LENGTH: 389
<212> TYPE: PRT
<213> ORGANISM: Streptomyces sp. CL190

<400> SEQUENCE: 82

Met Ser Ile Ser Ile Gly Ile His Asp Leu Ser Phe Ala Thr Thr Glu
1               5                   10                  15

```
Phe Val Leu Pro His Thr Ala Leu Ala Glu Tyr Asn Gly Thr Glu Ile
         20                  25                  30
Gly Lys Tyr His Val Gly Ile Gly Gln Gln Ser Met Ser Val Pro Ala
         35                  40                  45
Ala Asp Glu Asp Ile Val Thr Met Ala Ala Thr Ala Ala Arg Pro Ile
         50                  55                  60
Ile Glu Arg Asn Gly Lys Ser Arg Ile Arg Thr Val Val Phe Ala Thr
 65                  70                  75                  80
Glu Ser Ser Ile Asp Gln Ala Lys Ala Gly Gly Val Tyr Val His Ser
                 85                  90                  95
Leu Leu Gly Leu Glu Ser Ala Cys Arg Val Val Glu Leu Lys Gln Ala
             100                 105                 110
Cys Tyr Gly Ala Thr Ala Ala Leu Gln Phe Ala Ile Gly Leu Val Arg
             115                 120                 125
Arg Asp Pro Ala Gln Gln Val Leu Val Ile Ala Ser Asp Val Ser Lys
         130                 135                 140
Tyr Glu Leu Asp Ser Pro Gly Glu Ala Thr Gln Gly Ala Ala Ala Val
145                 150                 155                 160
Ala Met Leu Val Gly Ala Asp Pro Ala Leu Leu Arg Ile Glu Glu Pro
                 165                 170                 175
Ser Gly Leu Phe Thr Ala Asp Val Met Asp Phe Trp Arg Pro Asn Tyr
             180                 185                 190
Leu Thr Thr Ala Leu Val Asp Gly Gln Glu Ser Ile Asn Ala Tyr Leu
             195                 200                 205
Gln Ala Val Glu Gly Ala Trp Lys Asp Tyr Ala Glu Gln Asp Gly Arg
         210                 215                 220
Ser Leu Glu Glu Phe Ala Ala Phe Val Tyr His Gln Pro Phe Thr Lys
225                 230                 235                 240
Met Ala Tyr Lys Ala His Arg His Leu Leu Asn Phe Asn Gly Tyr Asp
                 245                 250                 255
Thr Asp Lys Asp Ala Ile Glu Gly Ala Leu Gly Gln Thr Thr Ala Tyr
             260                 265                 270
Asn Asn Val Ile Gly Asn Ser Tyr Thr Ala Ser Val Tyr Leu Gly Leu
             275                 280                 285
Ala Ala Leu Leu Asp Gln Ala Asp Asp Leu Thr Gly Arg Ser Ile Gly
         290                 295                 300
Phe Leu Ser Tyr Gly Ser Gly Ser Val Ala Glu Phe Phe Ser Gly Thr
305                 310                 315                 320
Val Val Ala Gly Tyr Arg Glu Arg Leu Arg Thr Glu Ala Asn Gln Glu
                 325                 330                 335
Ala Ile Ala Arg Arg Lys Ser Val Asp Tyr Ala Thr Tyr Arg Glu Leu
             340                 345                 350
His Glu Tyr Thr Leu Pro Ser Asp Gly Asp His Ala Thr Pro Val
             355                 360                 365
Gln Thr Thr Gly Pro Phe Arg Leu Ala Gly Ile Asn Asp His Lys Arg
         370                 375                 380
Ile Tyr Glu Ala Arg
385

<210> SEQ ID NO 83
<211> LENGTH: 389
<212> TYPE: PRT
<213> ORGANISM: Streptomyces griseolosporeus
```

<400> SEQUENCE: 83

```
Met Pro Leu Ala Ile Gly Ile His Asp Leu Ser Phe Ala Thr Gly Glu
 1               5                  10                  15

Phe Val Leu Pro His Thr Ala Leu Ala Ala His Asn Gly Thr Glu Ile
             20                  25                  30

Gly Lys Tyr His Ala Gly Ile Gly Gln Glu Ser Met Ser Val Pro Ala
         35                  40                  45

Ala Asp Glu Asp Ile Val Thr Leu Ala Ala Thr Ala Ala Ala Pro Ile
     50                  55                  60

Val Ala Arg His Gly Ser Asp Arg Ile Arg Thr Val Val Leu Ala Thr
 65                  70                  75                  80

Glu Ser Ser Ile Asp Gln Ala Lys Ser Ala Gly Val Tyr Val His Ser
                 85                  90                  95

Leu Leu Gly Leu Pro Ser Ala Thr Arg Val Val Glu Leu Lys Gln Ala
             100                 105                 110

Cys Tyr Gly Ala Thr Ala Gly Leu Gln Phe Ala Ile Gly Leu Val Gln
         115                 120                 125

Arg Asp Pro Ala Gln Gln Val Leu Val Ile Ala Ser Asp Val Ser Lys
130                 135                 140

Tyr Asp Leu Asp Ser Pro Gly Glu Ala Thr Gln Gly Ala Ala Ala Val
145                 150                 155                 160

Ala Met Leu Val Gly Ala Asp Pro Gly Leu Val Arg Ile Glu Asp Pro
                165                 170                 175

Ser Gly Leu Phe Thr Val Asp Val Met Asp Phe Trp Arg Pro Asn Tyr
            180                 185                 190

Arg Thr Thr Ala Leu Val Asp Gly Gln Glu Ser Ile Gly Ala Tyr Leu
        195                 200                 205

Gln Ala Val Glu Gly Ala Trp Lys Asp Tyr Ser Glu Arg Gly Gly His
    210                 215                 220

Ser Leu Glu Gln Phe Ala Ala Phe Cys Tyr His Gln Pro Phe Thr Lys
225                 230                 235                 240

Met Ala His Lys Ala His Arg His Leu Leu Asn Tyr Cys Ser His Asp
                245                 250                 255

Ile His His Asp Asp Val Thr Arg Ala Val Gly Arg Thr Thr Ala Tyr
            260                 265                 270

Asn Arg Val Ile Gly Asn Ser Tyr Thr Ala Ser Val Tyr Leu Gly Leu
        275                 280                 285

Ala Ala Leu Leu Asp Gln Ala Asp Asp Leu Thr Gly Glu Arg Ile Gly
    290                 295                 300

Phe Leu Ser Tyr Gly Ser Gly Ser Val Ala Glu Phe Phe Gly Gly Ile
305                 310                 315                 320

Val Val Ala Gly Tyr Arg Asp Arg Leu Arg Thr Ala Ala Asn Ile Glu
                325                 330                 335

Ala Val Ser Arg Arg Pro Ile Asp Tyr Ala Gly Tyr Arg Glu Leu
            340                 345                 350

His Glu Trp Ala Phe Pro Ala Arg Arg Gly Ala His Ser Thr Pro Gln
        355                 360                 365

Gln Thr Thr Gly Pro Phe Arg Leu Ser Gly Ile Ser Gly His Lys Arg
    370                 375                 380

Leu Tyr Arg Ala Cys
385
```

<210> SEQ ID NO 84

```
<211> LENGTH: 407
<212> TYPE: PRT
<213> ORGANISM: Borrelia burgdorferi

<400> SEQUENCE: 84
```

| | | | | | | | | | | | | | | |
|---|---|---|---|---|---|---|---|---|---|---|---|---|---|---|
| Met | Arg | Ile | Gly | Ile | Ser | Asp | Ile | Arg | Ile | Phe | Leu | Pro | Leu | Asn | Tyr |
| 1 | | | | 5 | | | | | 10 | | | | | 15 | |
| Leu | Asp | Phe | Ser | Val | Leu | Leu | Glu | Asn | Pro | Leu | Tyr | Phe | Ser | Asn | Glu |
| | | | 20 | | | | | 25 | | | | | 30 | | |
| Val | Phe | Phe | Lys | Lys | Ile | Asn | Arg | Ala | Ile | Asp | Ala | Thr | Leu | Gln | Lys |
| | | 35 | | | | | 40 | | | | | 45 | | | |
| Gly | Phe | Arg | Phe | Thr | Ser | Pro | Asn | Glu | Asp | Ser | Val | Thr | Met | Ala | Ser |
| | 50 | | | | | 55 | | | | | 60 | | | | |
| Ser | Ala | Val | Lys | Leu | Ile | Phe | Asp | Asn | Asn | Leu | Asp | Leu | Ser | Lys |
| 65 | | | | 70 | | | | | 75 | | | | | 80 |
| Ile | Arg | Ile | Leu | Leu | Gly | Gly | Thr | Glu | Thr | Gly | Val | Asp | His | Ser | Lys |
| | | | | 85 | | | | | 90 | | | | | 95 | |
| Ala | Ile | Ser | Ser | Tyr | Val | Phe | Gly | Ala | Leu | Lys | Gln | Ser | Gly | Ile | Cys |
| | | | 100 | | | | | 105 | | | | | 110 | | |
| Leu | Gly | Asn | Asn | Phe | Leu | Thr | Phe | Gln | Val | Gln | His | Ala | Cys | Ala | Gly |
| | | 115 | | | | | 120 | | | | | 125 | | | |
| Ala | Ala | Met | Ser | Leu | His | Thr | Val | Ala | Ser | Val | Leu | Ser | His | Ser | Asn |
| | 130 | | | | | 135 | | | | | 140 | | | | |
| Asn | Ser | Glu | Tyr | Gly | Ile | Val | Phe | Ser | Ser | Asp | Ile | Ala | His | Tyr | Ser |
| 145 | | | | | 150 | | | | | 155 | | | | | 160 |
| Asn | Leu | Thr | Thr | Ala | Glu | Ile | Thr | Gln | Gly | Ala | Gly | Ala | Thr | Ala | Ile |
| | | | | 165 | | | | | 170 | | | | | 175 | |
| Leu | Ile | Glu | Lys | Asn | Pro | Lys | Ile | Leu | Ser | Ile | Asn | Leu | Ser | Glu | Phe |
| | | | 180 | | | | | 185 | | | | | 190 | | |
| Gly | Val | Tyr | Thr | Asp | Asp | Val | Asp | Asp | Phe | Phe | Arg | Pro | Phe | Gly | Ser |
| | | 195 | | | | | 200 | | | | | 205 | | | |
| Val | Glu | Ala | Lys | Val | Arg | Gly | Gln | Tyr | Ser | Val | Glu | Cys | Tyr | Asn | Asn |
| | 210 | | | | | 215 | | | | | 220 | | | | |
| Ala | Asn | Glu | Asn | Ala | Leu | Arg | Asp | Phe | Ala | Phe | Lys | Lys | Gln | Leu | Ser |
| 225 | | | | | 230 | | | | | 235 | | | | | 240 |
| Met | Lys | Asp | Leu | Phe | Ser | Asn | Tyr | Arg | Phe | Val | Leu | His | Val | Pro | Phe |
| | | | | 245 | | | | | 250 | | | | | 255 | |
| Ala | Lys | Met | Pro | Ile | Asp | Ser | Met | His | Tyr | Ile | Leu | Lys | Lys | Tyr | Tyr |
| | | | 260 | | | | | 265 | | | | | 270 | | |
| Ser | Asp | Asp | Glu | Ser | Val | Arg | Asn | Ala | Tyr | Leu | Glu | Ser | Ile | Asp | Phe |
| | | 275 | | | | | 280 | | | | | 285 | | | |
| Tyr | Asp | Gly | Val | Glu | Ala | Ala | Met | Glu | Val | Gly | Asn | Leu | Tyr | Thr | Gly |
| | 290 | | | | | 295 | | | | | 300 | | | | |
| Ser | Ile | Phe | Leu | Ser | Leu | Ala | Phe | Tyr | Leu | Lys | Arg | Val | Phe | Ser | Lys |
| 305 | | | | | 310 | | | | | 315 | | | | | 320 |
| Lys | Asp | Ile | Thr | Gly | Glu | Lys | Ile | Leu | Phe | Cys | Ser | Tyr | Gly | Ser | Gly |
| | | | | 325 | | | | | 330 | | | | | 335 | |
| Asn | Ile | Met | Ile | Ile | Tyr | Glu | Leu | Thr | Ile | Glu | Lys | Ser | Ala | Phe | Asp |
| | | | 340 | | | | | 345 | | | | | 350 | | |
| Val | Ile | Lys | Leu | Trp | Asp | Leu | Glu | Gly | Leu | Ile | Lys | Asn | Arg | Asn | Asn |
| | | 355 | | | | | 360 | | | | | 365 | | | |
| Ala | Asn | Phe | Glu | Glu | Tyr | Lys | Asp | Phe | Phe | Gln | Asn | Lys | Ile | Ile | Pro |
| | 370 | | | | | 375 | | | | | 380 | | | | |
| Gly | Glu | Ser | Arg | Gly | Phe | Tyr | Leu | Lys | Glu | Leu | Arg | Asn | Asp | Gly | Tyr |

```
385             390             395             400
Arg Val Tyr Gly Tyr Arg Ala
                405

<210> SEQ ID NO 85
<211> LENGTH: 317
<212> TYPE: PRT
<213> ORGANISM: Streptococcus pneumoniae

<400> SEQUENCE: 85

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
            35                  40                  45

Ser Pro Leu Pro Ala Asn Val Thr Ala Asp Glu Phe Tyr Ile Asn Gly
        50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315

<210> SEQ ID NO 86
<211> LENGTH: 314
<212> TYPE: PRT
<213> ORGANISM: Streptococcus pyrogenes
```

```
<400> SEQUENCE: 86

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr Ser Asp Gln Phe Tyr Ile Asn Gly
    50                  55                  60

Val Leu Gln Asn Asp Glu Glu His Thr Lys Ile Ser Thr Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asp Thr Gln Leu Asp Gln
            115                 120                 125

Lys Ala Leu Ala Gln Lys Ala Lys Phe Ala Ser Gly Ser Ser Ser Arg
130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Glu Trp Val Glu Gln Ser Ala Ile
            195                 200                 205

Asp Tyr Gln His Met Leu Thr Tyr Leu Lys Thr Asn Asn Phe Glu Lys
        210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
        275                 280                 285

Asp Leu Ala Gln Leu Ala Glu Arg Leu Gly Lys Asn Tyr Arg Ile Ile
    290                 295                 300

Val Ser Lys Thr Lys Asp Leu Pro Asp Val
305                 310

<210> SEQ ID NO 87
<211> LENGTH: 331
<212> TYPE: PRT
<213> ORGANISM: Enterococcus faecalis

<400> SEQUENCE: 87

Met Leu Ser Gly Lys Ala Arg Ala His Thr Asn Ile Ala Leu Ile Lys
1               5                   10                  15

Tyr Trp Gly Lys Ala Asn Glu Glu Tyr Ile Leu Pro Met Asn Ser Ser
            20                  25                  30

Leu Ser Leu Thr Leu Asp Ala Phe Tyr Thr Glu Thr Thr Val Thr Phe
        35                  40                  45
```

```
Asp Ala His Tyr Ser Glu Asp Val Phe Ile Leu Asn Gly Ile Leu Gln
         50                  55                  60

Asn Glu Lys Gln Thr Lys Val Lys Glu Phe Leu Asn Leu Val Arg
 65                  70                  75                  80

Gln Gln Ala Asp Cys Thr Trp Phe Ala Lys Val Glu Ser Gln Asn Phe
                 85                  90                  95

Val Pro Thr Ala Ala Gly Leu Ala Ser Ser Ala Ser Gly Leu Ala Ala
                100                 105                 110

Leu Ala Gly Ala Cys Asn Val Ala Leu Gly Leu Asn Leu Ser Ala Lys
            115                 120                 125

Asp Leu Ser Arg Leu Ala Arg Arg Gly Ser Gly Ser Ala Cys Arg Ser
        130                 135                 140

Ile Phe Gly Gly Phe Ala Gln Trp Asn Lys Gly His Ser Asp Glu Thr
145                 150                 155                 160

Ser Phe Ala Glu Asn Ile Pro Ala Asn Asn Trp Glu Asn Glu Leu Ala
                165                 170                 175

Met Leu Phe Ile Leu Ile Asn Asp Gly Glu Lys Asp Val Ser Ser Arg
            180                 185                 190

Asp Gly Met Lys Arg Thr Val Glu Thr Ser Ser Phe Tyr Gln Gly Trp
        195                 200                 205

Leu Asp Asn Val Glu Lys Asp Leu Ser Gln Val His Glu Ala Ile Lys
210                 215                 220

Thr Lys Asp Phe Pro Arg Leu Gly Glu Ile Ile Glu Ala Asn Gly Leu
225                 230                 235                 240

Arg Met His Gly Thr Thr Leu Gly Ala Val Pro Pro Phe Thr Tyr Trp
                245                 250                 255

Ser Pro Gly Ser Leu Gln Ala Met Ala Leu Val Arg Gln Ala Arg Ala
            260                 265                 270

Lys Gly Ile Pro Cys Tyr Phe Thr Met Asp Ala Gly Pro Asn Val Lys
        275                 280                 285

Val Leu Val Glu Lys Lys Asn Leu Glu Ala Leu Lys Thr Phe Leu Ser
290                 295                 300

Glu His Phe Ser Lys Glu Gln Leu Val Pro Ala Phe Ala Gly Pro Gly
305                 310                 315                 320

Ile Glu Leu Phe Glu Thr Lys Gly Met Asp Lys
                325                 330

<210> SEQ ID NO 88
<211> LENGTH: 325
<212> TYPE: PRT
<213> ORGANISM: Enterococcus faecium

<400> SEQUENCE: 88

Met Phe Lys Gly Lys Ala Arg Ala Tyr Thr Asn Ile Ala Leu Ile Lys
 1               5                  10                  15

Tyr Trp Gly Lys Lys Asn Glu Glu Leu Ile Leu Pro Met Asn Asn Ser
                 20                  25                  30

Leu Ser Leu Thr Leu Asp Ala Phe Tyr Thr Glu Thr Glu Val Ile Phe
             35                  40                  45

Ser Asp Ser Tyr Met Val Asp Glu Phe Tyr Leu Asp Gly Thr Leu Gln
         50                  55                  60

Asp Glu Lys Ala Thr Lys Lys Val Ser Gln Phe Leu Asp Leu Phe Arg
 65                  70                  75                  80

Lys Glu Ala Gly Leu Ser Leu Lys Ala Ser Val Ile Ser Gln Asn Phe
                 85                  90                  95
```

```
Val Pro Thr Ala Ala Gly Leu Ala Ser Ser Ala Ser Gly Leu Ala Ala
            100                 105                 110

Leu Ala Gly Ala Cys Asn Thr Ala Leu Lys Leu Gly Leu Asp Asp Leu
            115                 120                 125

Ser Leu Ser Arg Phe Ala Arg Arg Gly Ser Gly Ser Ala Cys Arg Ser
            130                 135                 140

Ile Phe Gly Gly Phe Val Glu Trp Glu Lys Gly His Asp Asp Leu Ser
145                 150                 155                 160

Ser Tyr Ala Lys Pro Val Pro Ser Asp Ser Phe Glu Asp Asp Leu Ala
                    165                 170                 175

Met Val Phe Val Leu Ile Asn Asp Gln Lys Lys Glu Val Ser Ser Arg
            180                 185                 190

Asn Gly Met Arg Arg Thr Val Glu Thr Ser Asn Phe Tyr Gln Gly Trp
            195                 200                 205

Leu Asp Ser Val Glu Gly Asp Leu Tyr Gln Leu Lys Gln Ala Ile Lys
            210                 215                 220

Thr Lys Asp Phe Gln Leu Leu Gly Glu Thr Met Glu Arg Asn Gly Leu
225                 230                 235                 240

Lys Met His Gly Thr Thr Leu Ala Ala Gln Pro Pro Phe Thr Tyr Trp
                    245                 250                 255

Ser Pro Asn Ser Leu Lys Ala Met Asp Ala Val Arg Gln Leu Arg Lys
            260                 265                 270

Gln Gly Ile Pro Cys Tyr Phe Thr Met Asp Ala Gly Pro Asn Val Lys
            275                 280                 285

Val Leu Val Glu Asn Ser His Leu Ser Glu Val Gln Glu Thr Phe Thr
            290                 295                 300

Lys Leu Phe Ser Lys Glu Gln Val Ile Thr Ala His Ala Gly Pro Gly
305                 310                 315                 320

Ile Ala Ile Ile Glu
                325

<210> SEQ ID NO 89
<211> LENGTH: 327
<212> TYPE: PRT
<213> ORGANISM: Staphylococcus haemolyticus

<400> SEQUENCE: 89

Met Lys Lys Ser Gly Lys Ala Arg Ala His Thr Asn Ile Ala Leu Ile
1               5                   10                  15

Lys Tyr Trp Gly Lys Ala Asp Glu Ala Leu Ile Ile Pro Met Asn Asn
            20                  25                  30

Ser Leu Ser Val Thr Leu Asp Arg Phe Tyr Thr Glu Thr Arg Val Thr
            35                  40                  45

Phe Asp Glu Thr Leu Thr Glu Asp Gln Leu Ile Leu Asn Gly Glu Ala
        50                  55                  60

Val Asn Ala Lys Glu Ser Ala Lys Ile Gln Arg Tyr Met Glu Met Ile
65                  70                  75                  80

Arg Lys Glu Ala Gly Ile Ser His Glu Ala Leu Ile Glu Ser Glu Asn
                85                  90                  95

Phe Val Pro Thr Ala Ala Gly Leu Ala Ser Ser Ala Ser Ala Tyr Ala
            100                 105                 110

Ala Leu Ala Gly Ala Cys Asn Glu Ala Leu Gln Leu Gly Leu Ser Asp
            115                 120                 125

Lys Asp Leu Ser Arg Leu Ala Arg Arg Gly Ser Gly Ser Ala Ser Arg
```

```
            130                 135                 140
Ser Ile Tyr Gly Gly Phe Ala Glu Trp Glu Lys Gly Asn Asp Asp Glu
145                 150                 155                 160

Thr Ser Phe Ala His Arg Val Glu Ala Asp Gly Trp Glu Asn Glu Leu
                165                 170                 175

Ala Met Val Phe Val Ile Asn Asn Lys Ser Lys Val Ser Ser
            180                 185                 190

Arg Ser Gly Met Ser Leu Thr Arg Asp Thr Ser Arg Phe Tyr Gln Tyr
                195                 200                 205

Trp Leu Asp Asn Val Glu Pro Asp Leu Lys Glu Thr Lys Glu Ala Ile
210                 215                 220

Ala Gln Lys Asp Phe Lys Arg Met Gly Glu Val Ile Glu Ala Asn Gly
225                 230                 235                 240

Leu Arg Met His Ala Thr Asn Leu Gly Ala Gln Pro Pro Phe Thr Tyr
                245                 250                 255

Leu Val Pro Glu Ser Tyr Asp Ala Met Arg Ile Val His Glu Cys Arg
                260                 265                 270

Glu Ala Gly Leu Pro Cys Tyr Phe Thr Met Asp Ala Gly Pro Asn Val
                275                 280                 285

Lys Val Leu Ile Glu Lys Lys Asn Gln Gln Ala Ile Val Asp Lys Phe
                290                 295                 300

Leu Gln Glu Phe Asp Gln Ser Gln Ile Ile Thr Ser Asp Ile Thr Gln
305                 310                 315                 320

Ser Gly Val Glu Ile Ile Lys
                325

<210> SEQ ID NO 90
<211> LENGTH: 327
<212> TYPE: PRT
<213> ORGANISM: Staphylococcus epidermis

<400> SEQUENCE: 90

Met Val Lys Ser Gly Lys Ala Arg Ala His Thr Asn Ile Ala Leu Ile
1               5                   10                  15

Lys Tyr Trp Gly Lys Ala Asp Glu Thr Tyr Ile Ile Pro Met Asn Asn
                20                  25                  30

Ser Leu Ser Val Thr Leu Asp Arg Phe Tyr Thr Glu Thr Lys Val Thr
            35                  40                  45

Phe Asp Pro Asp Phe Thr Glu Asp Cys Leu Ile Leu Asn Gly Asn Glu
        50                  55                  60

Val Asn Ala Lys Glu Lys Glu Lys Ile Gln Asn Tyr Met Asn Ile Val
65                  70                  75                  80

Arg Asp Leu Ala Gly Asn Arg Leu His Ala Arg Ile Glu Ser Glu Asn
                85                  90                  95

Tyr Val Pro Thr Ala Ala Gly Leu Ala Ser Ser Ala Ser Ala Tyr Ala
                100                 105                 110

Ala Leu Ala Ala Ala Cys Asn Glu Ala Leu Ser Leu Asn Leu Ser Asp
            115                 120                 125

Thr Asp Leu Ser Arg Leu Ala Arg Arg Gly Ser Gly Ser Ala Ser Arg
        130                 135                 140

Ser Ile Phe Gly Gly Phe Ala Glu Trp Glu Lys Gly His Asp Asp Leu
145                 150                 155                 160

Thr Ser Tyr Ala His Gly Ile Asn Ser Asn Gly Trp Glu Lys Asp Leu
                165                 170                 175
```

```
Ser Met Ile Phe Val Ile Asn Asn Gln Ser Lys Lys Val Ser Ser
            180                 185                 190

Arg Ser Gly Met Ser Leu Thr Arg Asp Thr Ser Arg Phe Tyr Gln Tyr
        195                 200                 205

Trp Leu Asp His Val Asp Glu Asp Leu Asn Glu Ala Lys Glu Ala Val
    210                 215                 220

Lys Asn Gln Asp Phe Gln Arg Leu Gly Glu Val Ile Glu Ala Asn Gly
225                 230                 235                 240

Leu Arg Met His Ala Thr Asn Leu Gly Ala Gln Pro Pro Phe Thr Tyr
                245                 250                 255

Leu Val Gln Glu Ser Tyr Asp Ala Met Ala Ile Val Glu Gln Cys Arg
            260                 265                 270

Lys Ala Asn Leu Pro Cys Tyr Phe Thr Met Asp Ala Gly Pro Asn Val
        275                 280                 285

Lys Val Leu Val Glu Lys Lys Asn Lys Gln Ala Val Met Glu Gln Phe
290                 295                 300

Leu Lys Val Phe Asp Glu Ser Lys Ile Ile Ala Ser Asp Ile Ile Ser
305                 310                 315                 320

Ser Gly Val Glu Ile Ile Lys
                325

<210> SEQ ID NO 91
<211> LENGTH: 327
<212> TYPE: PRT
<213> ORGANISM: Staphylococcus aureus

<400> SEQUENCE: 91

Met Ile Lys Ser Gly Lys Ala Arg Ala His Thr Asn Ile Ala Leu Ile
1               5                   10                  15

Lys Tyr Trp Gly Lys Lys Asp Glu Ala Leu Ile Ile Pro Met Asn Asn
            20                  25                  30

Ser Ile Ser Val Thr Leu Glu Lys Phe Tyr Thr Glu Thr Lys Val Thr
        35                  40                  45

Phe Asn Asp Gln Leu Thr Gln Asp Gln Phe Trp Leu Asn Gly Glu Lys
    50                  55                  60

Val Ser Gly Lys Glu Leu Glu Lys Ile Ser Lys Tyr Met Asp Ile Val
65                  70                  75                  80

Arg Asn Arg Ala Gly Ile Asp Trp Tyr Ala Glu Ile Glu Ser Asp Asn
                85                  90                  95

Phe Val Pro Thr Ala Ala Gly Leu Ala Ser Ser Ala Ser Ala Tyr Ala
            100                 105                 110

Ala Leu Ala Ala Ala Cys Asn Gln Ala Leu Asp Leu Gln Leu Ser Asp
        115                 120                 125

Lys Asp Leu Ser Arg Leu Ala Arg Ile Gly Ser Gly Ser Ala Ser Arg
    130                 135                 140

Ser Ile Tyr Gly Gly Phe Ala Glu Trp Glu Lys Gly Tyr Asn Asp Glu
145                 150                 155                 160

Thr Ser Tyr Ala Val Pro Leu Glu Ser Asn His Phe Glu Asp Asp Leu
                165                 170                 175

Ala Met Ile Phe Val Ile Asn Gln His Ser Lys Lys Val Pro Ser
            180                 185                 190

Arg Tyr Gly Met Ser Leu Thr Arg Asn Thr Ser Arg Phe Tyr Gln Tyr
        195                 200                 205

Trp Leu Asp His Ile Asp Glu Asp Leu Ala Glu Ala Lys Ala Ala Ile
    210                 215                 220
```

-continued

Gln Asp Lys Asp Phe Lys Arg Leu Gly Glu Val Ile Glu Glu Asn Gly
225                 230                 235                 240

Leu Arg Met His Ala Thr Asn Leu Gly Ser Thr Pro Pro Phe Thr Tyr
            245                 250                 255

Leu Val Gln Glu Ser Tyr Asp Val Met Ala Leu Val His Glu Cys Arg
            260                 265                 270

Glu Ala Gly Tyr Pro Cys Tyr Phe Thr Met Asp Ala Gly Pro Asn Val
            275                 280                 285

Lys Ile Leu Val Glu Lys Lys Asn Lys Gln Gln Ile Ile Asp Lys Leu
        290                 295                 300

Leu Thr Gln Phe Asp Asn Asn Gln Ile Ile Asp Ser Asp Ile Ile Ala
305                 310                 315                 320

Thr Gly Ile Glu Ile Ile Glu
                325

<210> SEQ ID NO 92
<211> LENGTH: 350
<212> TYPE: PRT
<213> ORGANISM: Streptomyces sp. CL190

<400> SEQUENCE: 92

Met Arg Ser Glu His Pro Thr Thr Thr Val Leu Gln Ser Arg Glu Gln
1               5                   10                  15

Gly Ser Ala Ala Gly Ala Thr Ala Val Ala His Pro Asn Ile Ala Leu
            20                  25                  30

Ile Lys Tyr Trp Gly Lys Arg Asp Glu Arg Leu Ile Leu Pro Cys Thr
        35                  40                  45

Thr Ser Leu Ser Met Thr Leu Asp Val Phe Pro Thr Thr Thr Glu Val
    50                  55                  60

Arg Leu Asp Pro Ala Ala Glu His Asp Thr Ala Ala Leu Asn Gly Glu
65                  70                  75                  80

Val Ala Thr Gly Glu Thr Leu Arg Arg Ile Ser Ala Phe Leu Ser Leu
                85                  90                  95

Val Arg Glu Val Ala Gly Ser Asp Gln Arg Ala Val Val Asp Thr Arg
            100                 105                 110

Asn Thr Val Pro Thr Gly Ala Gly Leu Ala Ser Ser Ala Ser Gly Phe
        115                 120                 125

Ala Ala Leu Ala Val Ala Ala Ala Ala Tyr Gly Leu Glu Leu Asp
    130                 135                 140

Asp Arg Gly Leu Ser Arg Leu Ala Arg Arg Gly Ser Gly Ser Ala Ser
145                 150                 155                 160

Arg Ser Ile Phe Gly Gly Phe Ala Val Trp His Ala Gly Pro Asp Gly
                165                 170                 175

Thr Ala Thr Glu Ala Asp Leu Gly Ser Tyr Ala Glu Pro Val Pro Ala
            180                 185                 190

Ala Asp Leu Asp Pro Ala Leu Val Ile Ala Val Val Asn Ala Gly Pro
        195                 200                 205

Lys Pro Val Ser Ser Arg Glu Ala Met Arg Arg Thr Val Asp Thr Ser
    210                 215                 220

Pro Leu Tyr Arg Pro Trp Ala Asp Ser Ser Lys Asp Asp Leu Asp Glu
225                 230                 235                 240

Met Arg Ser Ala Leu Leu Arg Gly Asp Leu Glu Ala Val Gly Glu Ile
                245                 250                 255

Ala Glu Arg Asn Ala Leu Gly Met His Ala Thr Met Leu Ala Ala Arg

```
                   260                 265                 270
Pro Ala Val Arg Tyr Leu Ser Pro Ala Thr Val Thr Val Leu Asp Ser
                275                 280                 285
Val Leu Gln Leu Arg Lys Asp Gly Val Leu Ala Tyr Ala Thr Met Asp
    290                 295                 300
Ala Gly Pro Asn Val Lys Val Leu Cys Arg Arg Ala Asp Ala Glu Arg
305                 310                 315                 320
Val Ala Asp Val Val Arg Ala Ala Ser Gly Gln Val Leu Val
                325                 330                 335
Ala Gly Pro Gly Asp Gly Ala Arg Leu Leu Ser Glu Gly Ala
                340                 345                 350

<210> SEQ ID NO 93
<211> LENGTH: 331
<212> TYPE: PRT
<213> ORGANISM: Streptomyces griseolosporeus

<400> SEQUENCE: 93

Ala Thr Ala Val Ala Gln Pro Asn Ile Ala Leu Ile Lys Tyr Trp Gly
1               5                   10                  15
Lys Lys Asp Glu His Leu Val Leu Pro Arg Thr Asp Ser Leu Ser Met
                20                  25                  30
Thr Leu Asp Ile Phe Pro Thr Thr Arg Val Gln Leu Ala Pro Gly
            35                  40                  45
Ala Gly Gln Asp Thr Val Ala Phe Asn Gly Glu Pro Ala Thr Gly Glu
        50                  55                  60
Ala Glu Arg Arg Ile Thr Ala Phe Leu Arg Leu Val Arg Glu Arg Ser
65                  70                  75                  80
Gly Arg Thr Glu Arg Ala Arg Val Glu Thr Glu Asn Thr Val Pro Thr
                85                  90                  95
Gly Ala Gly Leu Ala Ser Ser Ala Ser Gly Phe Ala Ala Leu Ala Val
            100                 105                 110
Ala Ala Ala Ala Ala Tyr Gly Leu Gly Leu Asp Ala Arg Gly Leu Ser
        115                 120                 125
Arg Leu Ala Arg Arg Gly Ser Gly Ser Ala Ser Arg Ser Ile Phe Asp
130                 135                 140
Gly Phe Ala Val Trp His Ala Gly His Ala Gly Gly Thr Pro Glu Glu
145                 150                 155                 160
Ala Asp Leu Gly Ser Tyr Ala Glu Pro Val Pro Ala Val Asp Leu Glu
                165                 170                 175
Pro Ala Leu Val Val Ala Val Val Ser Ala Ala Pro Lys Ala Val Ser
            180                 185                 190
Ser Arg Glu Ala Met Arg Arg Thr Val Asp Thr Ser Pro Leu Tyr Glu
        195                 200                 205
Pro Trp Ala Val Ser Ser Arg Ala Asp Leu Ala Asp Ile Gly Ala Ala
    210                 215                 220
Leu Ala Arg Gly Asn Leu Pro Ala Val Gly Glu Ile Ala Glu Arg Asn
225                 230                 235                 240
Ala Leu Gly Met His Ala Thr Met Leu Ala Ala Arg Pro Ala Val Arg
                245                 250                 255
Tyr Leu Ser Pro Ala Ser Leu Ala Val Leu Asp Gly Val Leu Gln Leu
            260                 265                 270
Arg Arg Asp Gly Val Pro Ala Tyr Ala Thr Met Asp Ala Gly Pro Asn
        275                 280                 285
```

```
Val Lys Val Leu Cys Pro Arg Ser Asp Ala Glu Arg Val Ala Glu Ala
    290             295                 300

Leu Arg Ala Ala Ala Pro Val Gly Ala Val His Ile Ala Gly Pro Gly
305             310                 315                 320

Arg Gly Ala Arg Leu Val Ala Glu Glu Cys Arg
            325                 330

<210> SEQ ID NO 94
<211> LENGTH: 312
<212> TYPE: PRT
<213> ORGANISM: Borrelia burgdorferi

<400> SEQUENCE: 94

Met Lys Ile Lys Cys Lys Val His Ala Ser Leu Ala Leu Ile Lys Tyr
1               5                   10                  15

Trp Gly Lys Lys Asp Val Phe Leu Asn Ile Pro Ala Thr Ser Ser Leu
                20                  25                  30

Ala Val Ser Val Asp Lys Phe Tyr Ser Ile Ser Glu Leu Glu Leu Ser
            35                  40                  45

Asn Arg Asp Glu Ile Ile Leu Asn Ser Lys Pro Val Ile Leu Lys Asn
50                  55                  60

Arg Glu Lys Val Phe Phe Asp Tyr Ala Arg Lys Ile Leu Asn Glu Pro
65                  70                  75                  80

Asn Val Arg Phe Lys Ile Lys Ser Lys Asn Phe Pro Thr Ala Ala
                85                  90                  95

Gly Leu Ala Ser Ser Ser Gly Phe Ala Ser Ile Ala Ala Cys Ile
            100                 105                 110

Leu Lys Tyr Phe Asn Lys Tyr Ser Cys Asn Ser Ala Ser Asn Leu Ala
        115                 120                 125

Arg Val Gly Ser Ala Ser Ala Ala Arg Ala Ile Tyr Gly Gly Phe Thr
130                 135                 140

Ile Leu Lys Glu Gly Ser Lys Glu Ser Phe Gln Leu Arg Asp Gln Ser
145                 150                 155                 160

Tyr Phe Asn Asp Leu Arg Ile Ile Phe Ala Ile Asp Ser Asn Glu
                165                 170                 175

Lys Glu Leu Ser Ser Arg Ala Ala Met Asn Ile Cys Lys Arg His Lys
            180                 185                 190

Phe Tyr Tyr Asp Ala Trp Ile Ala Ser Ser Lys Lys Ile Phe Lys Asp
        195                 200                 205

Ala Leu Tyr Phe Phe Leu Lys Lys Asp Phe Ile His Phe Gly Ala Thr
210                 215                 220

Ile Val Lys Ser Tyr Gln Asn Met Phe Ala Leu Met Phe Ala Ser Ser
225                 230                 235                 240

Ile Phe Tyr Phe Lys Asn Ser Thr Ile Asp Leu Ile Arg Tyr Ala Ala
                245                 250                 255

Asp Leu Arg Asn Glu Gly Ile Phe Val Phe Glu Thr Met Asp Ala Gly
            260                 265                 270

Pro Gln Val Lys Phe Leu Cys Leu Glu Glu Asn Leu Asn Thr Ile Leu
        275                 280                 285

Lys Gly Leu Lys Gln Asn Phe Thr Gly Ile Asp Phe Ile Val Ser Lys
290                 295                 300

Val Gly Cys Asp Leu Glu Trp Ile
305                 310

<210> SEQ ID NO 95
```

```
<211> LENGTH: 292
<212> TYPE: PRT
<213> ORGANISM: Streptococcus pneumoniae

<400> SEQUENCE: 95

Met Thr Lys Lys Val Gly Val Gly Gln Ala His Ser Lys Ile Ile Leu
1               5                   10                  15

Ile Gly Glu His Ala Val Val Tyr Gly Tyr Pro Ala Ile Ser Leu Pro
            20                  25                  30

Leu Leu Glu Val Glu Val Thr Cys Lys Val Val Ser Ala Glu Ser Pro
        35                  40                  45

Trp Arg Leu Tyr Glu Glu Asp Thr Leu Ser Met Ala Val Tyr Ala Ser
    50                  55                  60

Leu Glu Tyr Leu Asp Ile Thr Glu Ala Cys Val Arg Cys Glu Ile Asp
65                  70                  75                  80

Ser Ala Ile Pro Glu Lys Arg Gly Met Gly Ser Ser Ala Ala Ile Ser
                85                  90                  95

Ile Ala Ala Ile Arg Ala Val Phe Asp Tyr Tyr Gln Ala Asp Leu Pro
            100                 105                 110

His Asp Val Leu Glu Ile Leu Val Asn Arg Ala Glu Met Ile Ala His
        115                 120                 125

Met Asn Pro Ser Gly Leu Asp Ala Lys Thr Cys Leu Ser Asp Gln Pro
130                 135                 140

Ile Arg Phe Ile Lys Asn Val Gly Phe Thr Glu Leu Glu Met Asp Leu
145                 150                 155                 160

Ser Ala Tyr Leu Val Ile Ala Asp Thr Gly Val Tyr Gly His Thr Arg
                165                 170                 175

Glu Ala Ile Gln Val Val Gln Asn Lys Gly Lys Asp Ala Leu Pro Phe
            180                 185                 190

Leu His Ala Leu Gly Glu Leu Thr Gln Gln Ala Glu Val Ala Ile Ser
        195                 200                 205

Gln Lys Tyr Ala Glu Gly Leu Gly Leu Ile Phe Ser Gln Ala His Leu
    210                 215                 220

His Leu Lys Glu Ile Gly Val Ser Ser Pro Glu Ala Asp Phe Leu Val
225                 230                 235                 240

Glu Thr Ala Leu Ser Tyr Gly Ala Leu Gly Ala Lys Met Ser Gly Gly
                245                 250                 255

Gly Leu Gly Gly Cys Ile Ile Ala Leu Val Thr Asn Leu Thr His Ala
            260                 265                 270

Gln Glu Leu Ala Glu Arg Leu Glu Glu Lys Gly Ala Val Gln Thr Trp
        275                 280                 285

Ile Glu Ser Leu
    290

<210> SEQ ID NO 96
<211> LENGTH: 292
<212> TYPE: PRT
<213> ORGANISM: Streptococcus pyrogenes

<400> SEQUENCE: 96

Met Asn Glu Asn Ile Gly Tyr Gly Lys Ala His Ser Lys Ile Ile Leu
1               5                   10                  15

Ile Gly Glu His Ala Val Val Tyr Gly Tyr Pro Ala Ile Ala Leu Pro
            20                  25                  30

Leu Thr Asp Ile Glu Val Val Cys His Ile Phe Pro Ala Asp Lys Pro
        35                  40                  45
```

```
Leu Val Phe Asp Phe Tyr Asp Thr Leu Ser Thr Ala Ile Tyr Ala Ala
    50                  55                  60

Leu Asp Tyr Leu Gln Arg Leu Gln Glu Pro Ile Ala Tyr Glu Ile Val
65                  70                  75                  80

Ser Gln Val Pro Gln Lys Arg Gly Met Gly Ser Ser Ala Ala Val Ser
                85                  90                  95

Ile Ala Ala Ile Arg Ala Val Phe Ser Tyr Cys Gln Glu Pro Leu Ser
                100                 105                 110

Asp Asp Leu Leu Glu Ile Leu Val Asn Lys Ala Glu Ile Ile Ala His
                115                 120                 125

Thr Asn Pro Ser Gly Leu Asp Ala Lys Thr Cys Leu Ser Asp His Ala
    130                 135                 140

Ile Lys Phe Ile Arg Asn Ile Gly Phe Glu Thr Ile Glu Ile Ala Leu
145                 150                 155                 160

Asn Gly Tyr Leu Ile Ile Ala Asp Thr Gly Ile His Gly His Thr Arg
                165                 170                 175

Glu Ala Val Asn Lys Val Ala Gln Phe Glu Glu Thr Asn Leu Pro Tyr
                180                 185                 190

Leu Ala Lys Leu Gly Ala Leu Thr Gln Ala Leu Glu Arg Ala Ile Asn
            195                 200                 205

Gln Lys Asn Lys Val Ala Ile Gly Gln Leu Met Thr Gln Ala His Ser
    210                 215                 220

Ala Leu Lys Ala Ile Gly Val Ser Ile Ser Lys Ala Asp Gln Leu Val
225                 230                 235                 240

Glu Ala Ala Leu Arg Ala Gly Ala Leu Gly Ala Lys Met Thr Gly Gly
                245                 250                 255

Gly Leu Gly Gly Cys Met Ile Ala Leu Ala Asp Thr Lys Asp Met Ala
                260                 265                 270

Glu Lys Ile Ser His Lys Leu Lys Glu Glu Gly Ala Val Asn Thr Trp
                275                 280                 285

Ile Gln Met Leu
    290

<210> SEQ ID NO 97
<211> LENGTH: 314
<212> TYPE: PRT
<213> ORGANISM: Enterococcus faecalis

<400> SEQUENCE: 97

Met Asn Ile Lys Lys Gln Gly Leu Gly Gln Ala Thr Gly Lys Ile Ile
1               5                   10                  15

Leu Met Gly Glu His Ala Val Val Tyr Gly Glu Pro Ala Ile Ala Phe
                20                  25                  30

Pro Phe Gln Ala Thr Glu Ile Thr Ala Val Phe Thr Pro Ala Lys Thr
            35                  40                  45

Met Gln Ile Asp Cys Ala Tyr Phe Thr Gly Leu Leu Glu Asp Val Pro
    50                  55                  60

Gln Glu Leu Ala Asn Ile Lys Glu Val Val Gln Thr Leu His Phe
65                  70                  75                  80

Leu Lys Glu Asp Thr Phe Lys Gly Thr Leu Thr Leu Ser Thr Ile
                85                  90                  95

Pro Ala Glu Arg Gly Met Gly Ser Ser Ala Ala Thr Ala Val Ala Ile
                100                 105                 110

Val Arg Ser Leu Phe Asp Tyr Phe Asp Tyr Ala Tyr Thr Tyr Gln Glu
```

```
                115                 120                 125
Leu Phe Glu Leu Val Ser Leu Ser Glu Lys Ile Ala His Gly Asn Pro
    130                 135                 140

Ser Gly Ile Asp Ala Ala Thr Ser Gly Ala Asp Pro Leu Phe Phe
145                 150                 155                 160

Thr Arg Gly Phe Pro Pro Thr His Phe Ser Met Asn Leu Ser Asn Ala
                165                 170                 175

Tyr Leu Val Val Ala Asp Thr Gly Ile Lys Gly Gln Thr Arg Glu Ala
            180                 185                 190

Val Lys Asp Ile Ala Gln Leu Ala Gln Asn Asn Pro Thr Ala Ile Ala
        195                 200                 205

Glu Thr Met Lys Gln Leu Gly Ser Phe Thr Lys Glu Ala Lys Gln Ala
    210                 215                 220

Ile Leu Gln Asp Asp Lys Gln Lys Leu Gly Gln Leu Met Thr Leu Ala
225                 230                 235                 240

Gln Glu Gln Leu Gln Gln Leu Thr Val Ser Asn Asp Met Leu Asp Arg
                245                 250                 255

Leu Val Ala Leu Ser Leu Glu His Gly Ala Leu Gly Ala Lys Leu Thr
            260                 265                 270

Gly Gly Gly Arg Gly Gly Cys Met Ile Ala Leu Thr Asp Asn Lys Lys
        275                 280                 285

Thr Ala Gln Thr Ile Ala Gln Thr Leu Glu Glu Asn Gly Ala Val Ala
    290                 295                 300

Thr Trp Ile Gln Ser Leu Glu Val Lys Lys
305                 310

<210> SEQ ID NO 98
<211> LENGTH: 314
<212> TYPE: PRT
<213> ORGANISM: Enterococcus faecium

<400> SEQUENCE: 98

Met Ala Asn Tyr Gly Gln Gly Glu Ser Ser Gly Lys Ile Ile Leu Met
1               5                   10                  15

Gly Glu His Ala Val Val Tyr Gly Glu Pro Ala Ile Ala Phe Pro Phe
            20                  25                  30

Tyr Ala Thr Lys Val Thr Ala Phe Leu Glu Leu Asp Ala Met Asp
        35                  40                  45

Asp Gln Leu Val Ser Ser Tyr Tyr Ser Gly Asn Leu Ala Glu Ala Pro
    50                  55                  60

His Ala Leu Lys Asn Ile Lys Lys Leu Phe Ile His Leu Lys Lys Gln
65                  70                  75                  80

His Asp Ile Gln Lys Asn Leu Gln Leu Thr Ile Glu Ser Thr Ile Pro
                85                  90                  95

Ala Glu Arg Gly Met Gly Ser Ser Ala Ala Val Ala Thr Ala Val Thr
            100                 105                 110

Arg Ala Phe Tyr Asp Tyr Leu Ala Phe Pro Leu Ser Arg Glu Ile Leu
        115                 120                 125

Leu Glu Asn Val Gln Leu Ser Glu Lys Ile Ala His Gly Asn Pro Ser
    130                 135                 140

Gly Ile Asp Ala Ala Ala Thr Ser Ser Leu Gln Pro Ile Tyr Phe Thr
145                 150                 155                 160

Lys Gly His Pro Phe Asp Tyr Phe Ser Leu Asn Ile Asp Ala Phe Leu
                165                 170                 175
```

-continued

```
Ile Val Ala Asp Thr Gly Ile Lys Gly Gln Thr Arg Glu Ala Val Lys
                180                 185                 190

Asp Val Ala His Leu Phe Glu Thr Gln Pro His Glu Thr Gly Gln Met
            195                 200                 205

Ile Gln Lys Leu Gly Tyr Leu Thr Lys Gln Ala Lys Gln Ala Ile Ile
        210                 215                 220

Glu Asn Ser Pro Glu Thr Leu Ala Gln Thr Met Asp Glu Ser Gln Ser
225                 230                 235                 240

Leu Leu Glu Lys Leu Thr Ile Ser Asn Asp Phe Leu Asn Leu Leu Ile
                245                 250                 255

Gln Thr Ala Lys Asp Thr Gly Ala Leu Gly Ala Lys Leu Thr Gly Gly
            260                 265                 270

Gly Arg Gly Gly Cys Met Ile Ala Leu Ala Gln Thr Lys Thr Lys Ala
        275                 280                 285

Gln Glu Ile Ser Gln Ala Leu Glu Asp Ala Gly Ala Ala Glu Thr Trp
    290                 295                 300

Ile Gln Gly Leu Gly Val His Thr Tyr Val
305                 310
```

<210> SEQ ID NO 99
<211> LENGTH: 307
<212> TYPE: PRT
<213> ORGANISM: Staphylococcus haemolyticus

<400> SEQUENCE: 99

```
Met Val Gln Arg Gly Tyr Gly Glu Ser Asn Gly Lys Ile Ile Leu Ile
1               5                   10                  15

Gly Glu His Ala Val Thr Phe Gly Glu Pro Ala Ile Ala Ile Pro Phe
                20                  25                  30

Thr Ser Gly Lys Val Lys Val Leu Ile Glu Ser Leu Glu Lys Gly Asn
            35                  40                  45

Tyr Ser Ala Ile Gln Ser Asp Val Tyr Asp Gly Pro Leu Tyr Asp Ala
        50                  55                  60

Pro Glu His Leu Lys Ser Leu Ile Gly His Phe Val Glu Asn Lys Lys
65                  70                  75                  80

Val Glu Glu Pro Leu Leu Ile Lys Ile Gln Ala Asn Leu Pro Pro Ser
                85                  90                  95

Arg Gly Leu Gly Ser Ser Ala Ala Val Ala Val Ala Phe Ile Arg Ala
            100                 105                 110

Ser Tyr Asp Tyr Leu Gly Leu Pro Leu Thr Asp Lys Glu Leu Leu Glu
        115                 120                 125

Asn Ala Asp Trp Ala Glu Arg Ile Ala His Gly Lys Pro Ser Gly Ile
    130                 135                 140

Asp Thr Lys Thr Ile Val Thr Asn Gln Pro Val Trp Tyr Gln Lys Gly
145                 150                 155                 160

Glu Val Glu Ile Leu Lys Thr Leu Asp Leu Asp Gly Tyr Met Val Val
                165                 170                 175

Ile Asp Thr Gly Val Lys Gly Ser Thr Lys Gln Ala Val Glu Asp Val
            180                 185                 190

His Gln Leu Cys Asp Asn Asp Lys Asn Tyr Met Gln Val Val Lys His
        195                 200                 205

Ile Gly Ser Leu Val Tyr Ser Ala Ser Glu Ala Ile Glu His His Ser
    210                 215                 220

Phe Asp Gln Leu Ala Thr Ile Phe Asn Gln Cys Gln Asp Asp Leu Arg
225                 230                 235                 240
```

-continued

```
Thr Leu Thr Val Ser His Asp Lys Ile Glu Met Phe Leu Arg Leu Gly
                245                 250                 255
Glu Glu Asn Gly Ser Val Ala Gly Lys Leu Thr Gly Gly Arg Gly
            260                 265                 270
Gly Ser Met Leu Ile Leu Ala Lys Glu Leu Gln Thr Ala Lys Asn Ile
            275                 280                 285
Val Ala Val Glu Lys Ala Gly Ala Gln His Thr Trp Ile Glu Lys
        290                 295                 300
Leu Gly Gly
305

<210> SEQ ID NO 100
<211> LENGTH: 306
<212> TYPE: PRT
<213> ORGANISM: Staphylococcus epidermis

<400> SEQUENCE: 100

Met Thr Arg Gln Gly Tyr Gly Glu Ser Thr Gly Lys Ile Ile Leu Met
1               5                   10                  15
Gly Glu His Ala Val Thr Phe Gly Gln Pro Ala Ile Ala Ile Pro Phe
            20                  25                  30
Asn Ala Gly Lys Ile Lys Val Leu Ile Glu Ser Leu Asp Glu Gly Asn
        35                  40                  45
Tyr Ser Ser Ile Thr Ser Asp Val Tyr Asp Gly Met Leu Tyr Asp Ala
    50                  55                  60
Pro Glu His Leu Lys Ser Ile Ile Asn Arg Phe Val Glu Lys Ser Gly
65                  70                  75                  80
Val Lys Glu Pro Leu Ser Val Lys Ile Gln Thr Asn Leu Pro Pro Ser
                85                  90                  95
Arg Gly Leu Gly Ser Ser Ala Ala Val Ala Val Ala Phe Val Arg Ala
            100                 105                 110
Ser Tyr Asp Phe Met Asp Gln Pro Leu Asp Asp Lys Thr Leu Ile Lys
            115                 120                 125
Glu Ala Asn Trp Ala Glu Gln Ile Ala His Gly Lys Pro Ser Gly Ile
        130                 135                 140
Asp Thr Gln Thr Ile Val Ser Asn Lys Pro Val Trp Phe Lys Gln Gly
145                 150                 155                 160
Gln Ala Glu Thr Leu Lys Ser Leu Lys Leu Asn Gly Tyr Met Val Val
                165                 170                 175
Ile Asp Thr Gly Val Lys Gly Ser Thr Lys Gln Ala Val Glu Asp Val
            180                 185                 190
His Val Leu Cys Glu Ser Asp Glu Tyr Met Lys Tyr Ile Glu His Ile
        195                 200                 205
Gly Thr Leu Val His Ser Ala Ser Glu Ser Ile Glu Gln His Asp Phe
    210                 215                 220
His His Leu Ala Asp Ile Phe Asn Ala Cys Gln Glu Asp Leu Arg His
225                 230                 235                 240
Leu Thr Val Ser His Asp Lys Ile Glu Lys Leu Leu Gln Ile Gly Lys
                245                 250                 255
Glu His Gly Ala Ile Ala Gly Lys Leu Thr Gly Gly Arg Gly Gly
            260                 265                 270
Ser Met Leu Leu Leu Ala Glu Asn Leu Lys Thr Ala Lys Thr Ile Val
            275                 280                 285
Ala Ala Val Glu Lys Ala Gly Ala Ala His Thr Trp Ile Glu His Leu
```

-continued

```
            290                 295                 300
Gly Gly
305

<210> SEQ ID NO 101
<211> LENGTH: 306
<212> TYPE: PRT
<213> ORGANISM: Staphylococcus aureus

<400> SEQUENCE: 101

Met Thr Arg Lys Gly Tyr Gly Glu Ser Thr Gly Lys Ile Ile Leu Ile
1               5                   10                  15

Gly Glu His Ala Val Thr Phe Gly Glu Pro Ala Ile Ala Val Pro Phe
            20                  25                  30

Asn Ala Gly Lys Ile Lys Val Leu Ile Glu Ala Leu Glu Ser Gly Asn
        35                  40                  45

Tyr Ser Ser Ile Lys Ser Asp Val Tyr Asp Gly Met Leu Tyr Asp Ala
    50                  55                  60

Pro Asp His Leu Lys Ser Leu Val Asn Arg Phe Val Glu Leu Asn Asn
65                  70                  75                  80

Ile Thr Glu Pro Leu Ala Val Thr Ile Gln Thr Asn Leu Pro Pro Ser
                85                  90                  95

Arg Gly Leu Gly Ser Ser Ala Ala Val Ala Val Ala Phe Val Arg Ala
            100                 105                 110

Ser Tyr Asp Phe Leu Gly Lys Ser Leu Thr Lys Glu Glu Leu Ile Glu
        115                 120                 125

Lys Ala Asn Trp Ala Glu Gln Ile Ala His Gly Lys Pro Ser Gly Ile
    130                 135                 140

Asp Thr Gln Thr Ile Val Ser Gly Lys Pro Val Trp Phe Gln Lys Gly
145                 150                 155                 160

Gln Ala Glu Thr Leu Lys Thr Leu Ser Leu Asp Gly Tyr Met Val Val
                165                 170                 175

Ile Asp Thr Gly Val Lys Gly Ser Thr Arg Gln Ala Val Glu Asp Val
            180                 185                 190

His Lys Leu Cys Glu Asp Pro Gln Tyr Met Ser His Val Lys His Ile
        195                 200                 205

Gly Lys Leu Val Leu Arg Ala Ser Asp Val Ile Glu His His Asn Phe
    210                 215                 220

Glu Ala Leu Ala Asp Ile Phe Asn Glu Cys His Ala Asp Leu Lys Ala
225                 230                 235                 240

Leu Thr Val Ser His Asp Lys Ile Glu Gln Leu Met Lys Ile Gly Lys
                245                 250                 255

Glu Asn Gly Ala Ile Ala Gly Lys Leu Thr Gly Ala Gly Arg Gly Gly
            260                 265                 270

Ser Met Leu Leu Leu Ala Lys Asp Leu Pro Thr Ala Lys Asn Ile Val
        275                 280                 285

Lys Ala Val Glu Lys Ala Gly Ala Ala His Thr Trp Ile Glu Asn Leu
    290                 295                 300

Gly Gly
305

<210> SEQ ID NO 102
<211> LENGTH: 345
<212> TYPE: PRT
<213> ORGANISM: Streptomyces sp. CL190
```

<400> SEQUENCE: 102

```
Met Gln Lys Arg Gln Arg Glu Leu Ser Ala Leu Thr Leu Pro Thr Ser
1               5                   10                  15

Ala Glu Gly Val Ser Glu Ser His Arg Ala Arg Ser Val Gly Ile Gly
            20                  25                  30

Arg Ala His Ala Lys Ala Ile Leu Leu Gly Glu His Ala Val Val Tyr
        35                  40                  45

Gly Ala Pro Ala Leu Ala Leu Pro Ile Pro Gln Leu Thr Val Thr Ala
    50                  55                  60

Ser Val Gly Trp Ser Ser Glu Ala Ser Asp Ser Ala Gly Gly Leu Ser
65                  70                  75                  80

Tyr Thr Met Thr Gly Thr Pro Ser Arg Ala Leu Val Thr Gln Ala Ser
                85                  90                  95

Asp Gly Leu His Arg Leu Thr Ala Glu Phe Met Ala Arg Met Gly Val
            100                 105                 110

Thr Asn Ala Pro His Leu Asp Val Ile Leu Asp Gly Ala Ile Pro His
        115                 120                 125

Gly Arg Gly Leu Gly Ser Ser Ala Ala Gly Ser Arg Ala Ile Ala Leu
    130                 135                 140

Ala Leu Ala Asp Leu Phe Gly His Glu Leu Ala Glu His Thr Ala Tyr
145                 150                 155                 160

Glu Leu Val Gln Thr Ala Glu Asn Met Ala His Gly Arg Ala Ser Gly
                165                 170                 175

Val Asp Ala Met Thr Val Gly Ala Ser Arg Pro Leu Leu Phe Gln Gln
            180                 185                 190

Gly Arg Thr Glu Arg Leu Ala Ile Gly Cys Asp Ser Leu Phe Ile Val
        195                 200                 205

Ala Asp Ser Gly Val Pro Gly Ser Thr Lys Glu Ala Val Glu Met Leu
    210                 215                 220

Arg Glu Gly Phe Thr Arg Ser Ala Gly Thr Gln Glu Arg Phe Val Gly
225                 230                 235                 240

Arg Ala Thr Glu Leu Thr Glu Ala Ala Arg Gln Ala Leu Ala Asp Gly
                245                 250                 255

Arg Pro Glu Glu Leu Gly Ser Gln Leu Thr Tyr Tyr His Glu Leu Leu
            260                 265                 270

His Glu Ala Arg Leu Ser Thr Asp Gly Ile Asp Ala Leu Val Glu Ala
        275                 280                 285

Ala Leu Lys Ala Gly Ser Leu Gly Ala Lys Ile Thr Gly Gly Gly Leu
    290                 295                 300

Gly Gly Cys Met Ile Ala Gln Ala Arg Pro Glu Gln Ala Arg Glu Val
305                 310                 315                 320

Thr Arg Gln Leu His Glu Ala Gly Ala Val Gln Thr Trp Val Val Pro
                325                 330                 335

Leu Lys Gly Leu Asp Asn His Ala Gln
            340                 345
```

<210> SEQ ID NO 103
<211> LENGTH: 334
<212> TYPE: PRT
<213> ORGANISM: Streptomyces griseolosporeus

<400> SEQUENCE: 103

```
Met Thr Leu Pro Thr Ser Val Glu Glu Gly Ser Lys Ala His Arg Ala
1               5                   10                  15
```

```
Arg Ala Val Gly Thr Gly Arg Ala His Ala Lys Ala Ile Leu Leu Gly
             20                  25                  30

Glu His Ala Val Val Tyr Gly Thr Pro Ala Leu Ala Met Pro Ile Pro
         35                  40                  45

Gln Leu Ala Val Thr Ala Ser Ala Gly Trp Ser Gly Arg Ser Ala Glu
 50                  55                  60

Ser Arg Gly Gly Pro Thr Phe Thr Met Thr Gly Ser Ala Ser Arg Ala
 65                  70                  75                  80

Val Thr Ala Gln Ala Leu Asp Gly Leu Arg Arg Leu Thr Ala Ser Val
                 85                  90                  95

Lys Ala His Thr Gly Val Thr Asp Gly Gln His Leu Asp Val Ser Leu
            100                 105                 110

Asp Gly Ala Ile Pro Pro Gly Arg Gly Leu Gly Ser Ser Ala Ala Asn
            115                 120                 125

Ala Arg Ala Ile Ile Leu Ala Leu Ala Asp Leu Phe Gly Arg Glu Leu
130                 135                 140

Thr Glu Gly Glu Val Phe Asp Leu Val Gln Glu Ala Glu Asn Leu Thr
145                 150                 155                 160

His Gly Arg Ala Ser Gly Val Asp Ala Val Thr Val Gly Ala Thr Ala
                165                 170                 175

Pro Leu Leu Phe Arg Ala Gly Thr Ala Gln Ala Leu Asp Ile Gly Cys
            180                 185                 190

Asp Ala Leu Phe Val Val Ala Asp Ser Gly Thr Ala Gly Ser Thr Lys
            195                 200                 205

Glu Ala Ile Glu Leu Leu Arg Ala Gly Phe Arg Ala Gly Ala Gly Lys
210                 215                 220

Glu Glu Arg Phe Met His Arg Ala Ala His Leu Val Asp Asp Ala Arg
225                 230                 235                 240

Ala Ser Leu Ala Glu Gly Glu Pro Glu Ala Phe Gly Ser Cys Leu Thr
                245                 250                 255

Glu Tyr His Gly Leu Leu Arg Gly Ala Gly Leu Ser Thr Asp Arg Ile
            260                 265                 270

Asp Ala Leu Val Asp Ala Ala Leu Gln Ala Asp Ser Leu Gly Ala Lys
            275                 280                 285

Ile Thr Gly Gly Gly Leu Gly Gly Cys Val Leu Ala Met Ser Arg Pro
290                 295                 300

Glu Arg Ala Glu Val Ala Arg Gln Leu His Ala Ala Gly Ala Val
305                 310                 315                 320

Arg Thr Trp Ala Val Gln Leu Arg Arg Ser Thr His Glu Arg
                325                 330

<210> SEQ ID NO 104
<211> LENGTH: 296
<212> TYPE: PRT
<213> ORGANISM: Borrelia burgdorferi

<400> SEQUENCE: 104

Met Leu Arg Ile Arg Lys Pro Ala Lys Ile Leu Phe Leu Gly Glu His
  1               5                  10                  15

Ser Ala Val Tyr Gly Phe Pro Val Ile Gly Ala Thr Val Pro Ile Tyr
             20                  25                  30

Met Asp Leu Ile Tyr Ser Val Ser Lys Asn Trp Lys Tyr Leu Gly Lys
         35                  40                  45

Pro Ser Thr Arg Leu Asn Ser Leu Ile Ser Phe Ile Val Ser Asn Tyr
 50                  55                  60
```

```
Ser Lys Val Asn Pro Ile Glu Phe Asp Ile Ile Ser Glu Ile Pro Ile
 65                  70                  75                  80

Gly Val Gly Leu Gly Ser Ser Ala Ser Leu Ser Leu Cys Phe Ala Glu
                 85                  90                  95

Tyr Ile Thr Ser His Phe Glu Tyr Lys Asp Cys Asn Lys Ile Leu Leu
            100                 105                 110

Ala Asn Gln Ile Glu Asn Ile Phe His Gly Lys Ser Ser Gly Met Asp
        115                 120                 125

Ile Arg Leu Ile Asp Leu Asn Gly Thr Phe Tyr Leu Glu Lys Lys Glu
130                 135                 140

Asn Val Leu His Ser Lys Lys Ile Lys Asp Ser Gly Phe Tyr Phe Leu
145                 150                 155                 160

Ile Gly Ala Ile Lys Arg Asp Leu Thr Thr Lys Glu Ile Val Val Asn
                165                 170                 175

Leu Lys Lys Asp Leu Leu Ser Asn Ala Tyr Leu Phe Val Phe Ile Glu
            180                 185                 190

Lys Leu Gly Leu Ala Val Ser Asn Ser Tyr Ala Ser Phe Gln Asn Lys
        195                 200                 205

Asp Val Tyr Ser Leu Ala Asn Glu Met Asn Ile Ala Gln Cys Cys Leu
210                 215                 220

Lys Arg Leu Gly Leu Ser Asn Asp Thr Leu Asp Trp Leu Ile Ser Glu
225                 230                 235                 240

Gly Ile Lys Leu Gly Ala Leu Ser Gly Lys Leu Ser Gly Ala Gly Lys
                245                 250                 255

Gly Gly Ala Phe Ile Phe Leu Phe Glu Ser Leu Ile Lys Ala Asn Ile
            260                 265                 270

Val Gln Lys Glu Leu Asn Asn Met Leu Asp Ser Lys Ile Asp Leu Leu
        275                 280                 285

Leu Lys Leu Lys Val Ile Glu Thr
290                 295

<210> SEQ ID NO 105
<211> LENGTH: 336
<212> TYPE: PRT
<213> ORGANISM: Streptococcus pneumoniae

<400> SEQUENCE: 105

Met Ile Ala Val Lys Thr Cys Gly Lys Leu Tyr Trp Ala Gly Glu Tyr
  1               5                  10                  15

Ala Ile Leu Glu Pro Gly Gln Leu Ala Leu Ile Lys Asp Ile Pro Ile
                 20                  25                  30

Tyr Met Arg Ala Glu Ile Ala Phe Ser Asp Ser Tyr Arg Ile Tyr Ser
             35                  40                  45

Asp Met Phe Asp Phe Ala Val Asp Leu Arg Pro Asn Pro Asp Tyr Ser
         50                  55                  60

Leu Ile Gln Glu Thr Ile Ala Leu Met Gly Asp Phe Leu Ala Val Arg
 65                  70                  75                  80

Gly Gln Asn Leu Arg Pro Phe Ser Leu Lys Ile Cys Gly Lys Met Glu
                 85                  90                  95

Arg Glu Gly Lys Lys Phe Gly Leu Gly Ser Ser Gly Ser Val Val Val
            100                 105                 110

Leu Val Val Lys Ala Leu Leu Ala Leu Tyr Asn Leu Ser Val Asp Gln
        115                 120                 125

Asn Leu Leu Phe Lys Leu Thr Ser Ala Val Leu Leu Lys Arg Gly Asp
```

```
                130                 135                 140
Asn Gly Ser Met Gly Asp Leu Ala Cys Ile Val Ala Glu Asp Leu Val
145                 150                 155                 160

Leu Tyr Gln Ser Phe Asp Arg Gln Lys Ala Ala Trp Leu Glu Glu
                165                 170                 175

Glu Asn Leu Ala Thr Val Leu Glu Arg Asp Trp Gly Phe Phe Ile Ser
                180                 185                 190

Gln Val Lys Pro Thr Leu Glu Cys Asp Phe Leu Val Gly Trp Thr Lys
                195                 200                 205

Glu Val Ala Val Ser Ser His Met Val Gln Gln Ile Lys Gln Asn Ile
210                 215                 220

Asn Gln Asn Phe Leu Ser Ser Ser Lys Glu Thr Val Val Ser Leu Val
225                 230                 235                 240

Glu Ala Leu Glu Gln Gly Lys Ala Glu Lys Val Ile Glu Gln Val Glu
                245                 250                 255

Val Ala Ser Lys Leu Leu Glu Gly Leu Ser Thr Asp Ile Tyr Thr Pro
                260                 265                 270

Leu Leu Arg Gln Leu Lys Glu Ala Ser Gln Asp Leu Gln Ala Val Ala
                275                 280                 285

Lys Ser Ser Gly Ala Gly Gly Asp Cys Gly Ile Ala Leu Ser Phe
                290                 295                 300

Asp Ala Gln Ser Ser Arg Asn Thr Leu Lys Asn Arg Trp Ala Asp Leu
305                 310                 315                 320

Gly Ile Glu Leu Leu Tyr Gln Glu Arg Ile Gly His Asp Asp Lys Ser
                325                 330                 335

<210> SEQ ID NO 106
<211> LENGTH: 335
<212> TYPE: PRT
<213> ORGANISM: Streptococcus pyrogenes

<400> SEQUENCE: 106

Met Ser Asn Tyr Cys Val Gln Thr Gly Gly Lys Leu Tyr Leu Thr Gly
1               5                   10                  15

Glu Tyr Ala Ile Leu Ile Pro Gly Gln Lys Ala Leu Ile His Phe Ile
                20                  25                  30

Pro Leu Met Met Thr Ala Glu Ile Ser Pro Ala Ala His Ile Gln Leu
                35                  40                  45

Ala Ser Asp Met Phe Ser His Lys Ala Gly Met Thr Pro Asp Ala Ser
50                  55                  60

Tyr Ala Leu Ile Gln Ala Thr Val Lys Thr Phe Ala Asp Tyr Leu Gly
65                  70                  75                  80

Gln Ser Ile Asp Gln Leu Glu Pro Phe Ser Leu Ile Ile Thr Gly Lys
                85                  90                  95

Met Glu Arg Asp Gly Lys Lys Phe Gly Ile Gly Ser Ser Gly Ser Val
                100                 105                 110

Thr Leu Leu Thr Leu Lys Ala Leu Ser Ala Tyr Tyr Gln Ile Thr Leu
                115                 120                 125

Thr Pro Glu Leu Leu Phe Lys Leu Ala Ala Tyr Thr Leu Leu Lys Gln
                130                 135                 140

Gly Asp Asn Gly Ser Met Gly Asp Ile Ala Cys Ile Ala Tyr Gln Thr
145                 150                 155                 160

Leu Val Ala Tyr Thr Ser Phe Asp Arg Glu Gln Val Ser Asn Trp Leu
                165                 170                 175
```

-continued

```
Gln Thr Met Pro Leu Lys Lys Leu Leu Val Lys Asp Trp Gly Tyr His
            180                 185                 190
Ile Gln Val Ile Gln Pro Ala Leu Pro Cys Asp Phe Leu Val Gly Trp
        195                 200                 205
Thr Lys Ile Pro Ala Ile Ser Arg Gln Met Ile Gln Val Thr Ala
    210                 215                 220
Ser Ile Thr Pro Ala Phe Leu Arg Thr Ser Tyr Gln Leu Thr Gln Ser
225                 230                 235                 240
Ala Met Val Ala Leu Gln Glu Gly His Lys Glu Leu Lys Lys Ser
                245                 250                 255
Leu Ala Gly Ala Ser His Leu Leu Lys Glu Leu His Pro Ala Ile Tyr
            260                 265                 270
His Pro Lys Leu Val Thr Leu Val Ala Ala Cys Gln Lys Gln Asp Ala
        275                 280                 285
Val Ala Lys Ser Ser Gly Ala Gly Gly Asp Cys Gly Ile Ala Leu
    290                 295                 300
Ala Phe Asn Gln Asp Ala Arg Asp Thr Leu Ile Ser Lys Trp Gln Glu
305                 310                 315                 320
Ala Asp Ile Ala Leu Leu Tyr Gln Glu Arg Trp Gly Glu Asn Asp
                325                 330                 335

<210> SEQ ID NO 107
<211> LENGTH: 368
<212> TYPE: PRT
<213> ORGANISM: Enterococcus faecalis

<400> SEQUENCE: 107

Met Ile Glu Val Thr Thr Pro Gly Lys Leu Phe Ile Ala Gly Glu Tyr
1               5                   10                  15
Ala Val Val Glu Pro Gly His Pro Ala Ile Ile Val Ala Val Asp Gln
            20                  25                  30
Phe Val Thr Val Thr Val Glu Glu Thr Thr Asp Glu Gly Ser Ile Gln
        35                  40                  45
Ser Ala Gln Tyr Ser Ser Leu Pro Ile Arg Trp Thr Arg Arg Asn Gly
    50                  55                  60
Glu Leu Val Leu Asp Ile Arg Glu Asn Pro Phe His Tyr Val Leu Ala
65                  70                  75                  80
Ala Ile His Leu Thr Glu Lys Tyr Ala Gln Glu Gln Asn Lys Glu Leu
                85                  90                  95
Ser Phe Tyr His Leu Lys Val Thr Ser Glu Leu Asp Ser Ser Asn Gly
            100                 105                 110
Arg Lys Tyr Gly Leu Gly Ser Ser Gly Ala Val Thr Val Gly Thr Val
        115                 120                 125
Lys Ala Leu Asn Ile Phe Tyr Asp Leu Gly Leu Glu Asn Glu Glu Ile
    130                 135                 140
Phe Lys Leu Ser Ala Leu Ala His Leu Ala Val Gln Gly Asn Gly Ser
145                 150                 155                 160
Cys Gly Asp Ile Ala Ala Ser Cys Tyr Gly Gly Trp Ile Ala Phe Ser
                165                 170                 175
Thr Phe Asp His Asp Trp Val Asn Gln Lys Val Thr Thr Glu Thr Leu
            180                 185                 190
Thr Asp Leu Leu Ala Met Asp Trp Pro Glu Leu Met Ile Phe Pro Leu
        195                 200                 205
Lys Val Pro Lys Gln Leu Arg Leu Leu Ile Gly Trp Thr Gly Ser Pro
    210                 215                 220
```

```
Ala Ser Thr Ser Asp Leu Val Asp Arg Val His Gln Ser Lys Glu Glu
225                 230                 235                 240

Lys Gln Ala Ala Tyr Glu Gln Phe Leu Met Lys Ser Arg Leu Cys Val
            245                 250                 255

Glu Thr Met Ile Asn Gly Phe Asn Thr Gly Lys Ile Ser Val Ile Gln
            260                 265                 270

Lys Gln Ile Thr Lys Asn Arg Gln Leu Leu Ala Glu Leu Ser Ser Leu
        275                 280                 285

Thr Gly Val Val Ile Glu Thr Glu Ala Leu Lys Asn Leu Cys Asp Leu
    290                 295                 300

Ala Glu Ser Tyr Thr Gly Ala Ala Lys Ser Ser Gly Ala Gly Gly Gly
305                 310                 315                 320

Asp Cys Gly Ile Val Ile Phe Arg Gln Lys Ser Gly Ile Leu Pro Leu
            325                 330                 335

Met Thr Ala Trp Glu Lys Asp Gly Ile Thr Pro Leu Pro Leu His Val
            340                 345                 350

Tyr Thr Tyr Gly Gln Lys Glu Cys Lys Glu Lys His Glu Ser Lys Arg
        355                 360                 365

<210> SEQ ID NO 108
<211> LENGTH: 361
<212> TYPE: PRT
<213> ORGANISM: Enterococcus faecium

<400> SEQUENCE: 108

Met Ile Glu Val Ser Ala Pro Gly Lys Leu Tyr Ile Ala Gly Glu Tyr
1               5                   10                  15

Ala Val Val Glu Thr Gly His Pro Ala Val Ile Ala Ala Val Asp Gln
            20                  25                  30

Phe Val Thr Val Thr Val Glu Ser Ala Arg Lys Val Gly Ser Ile Gln
        35                  40                  45

Ser Ala Gln Tyr Ser Gly Met Pro Val Arg Trp Thr Arg Arg Asn Gly
    50                  55                  60

Glu Leu Val Leu Asp Ile Arg Glu Asn Pro Phe His Tyr Ile Leu Ala
65                  70                  75                  80

Ala Ile Arg Leu Thr Glu Lys Tyr Ala Gln Glu Lys Asn Ile Leu Leu
                85                  90                  95

Ser Phe Tyr Asp Leu Lys Val Thr Ser Glu Leu Asp Ser Ser Asn Gly
            100                 105                 110

Arg Lys Tyr Gly Leu Gly Ser Ser Gly Ala Val Thr Val Ala Thr Val
        115                 120                 125

Lys Ala Leu Asn Val Phe Tyr Ala Leu Asn Leu Ser Gln Leu Glu Ile
    130                 135                 140

Phe Lys Ile Ala Ala Leu Ala Asn Leu Ala Val Gln Asp Asn Gly Ser
145                 150                 155                 160

Cys Gly Asp Ile Ala Ala Ser Cys Tyr Gly Gly Trp Ile Ala Phe Ser
                165                 170                 175

Thr Phe Asp His Pro Trp Leu Gln Glu Gln Thr Gln His Ser Ile
            180                 185                 190

Ser Glu Leu Leu Ala Leu Asp Trp Pro Gly Leu Ser Ile Glu Pro Leu
        195                 200                 205

Ile Ala Pro Glu Asp Leu Arg Leu Leu Ile Gly Trp Thr Gly Ser Pro
    210                 215                 220

Ala Ser Thr Ser Asp Leu Val Asp Gln Val His Arg Ser Arg Glu Asp
```

```
                    225                 230                 235                 240
Lys Met Val Ala Tyr Gln Leu Phe Leu Lys Asn Ser Thr Glu Cys Val
                245                 250                 255

Asn Glu Met Ile Lys Gly Phe Lys Glu Asn Asn Val Thr Leu Ile Gln
            260                 265                 270

Gln Met Ile Arg Lys Asn Arg Gln Leu Leu His Asp Leu Ser Ala Ile
            275                 280                 285

Thr Gly Val Val Ile Glu Thr Pro Ala Leu Asn Lys Leu Cys Asn Leu
        290                 295                 300

Ala Glu Gln Tyr Glu Gly Ala Ala Lys Ser Gly Ala Gly Gly
305                 310                 315                 320

Asp Cys Gly Ile Val Ile Val Asp Gln Lys Ser Gly Ile Leu Pro Leu
                325                 330                 335

Met Ser Ala Trp Glu Lys Ala Glu Ile Thr Pro Leu Pro Leu His Val
            340                 345                 350

Tyr Ser Asp Gln Arg Lys Glu Asn Arg
        355                 360

<210> SEQ ID NO 109
<211> LENGTH: 358
<212> TYPE: PRT
<213> ORGANISM: Staphylococcus haemolyticus

<400> SEQUENCE: 109

Met Ile Gln Val Lys Ala Pro Gly Lys Leu Tyr Val Ala Gly Glu Tyr
1               5                   10                  15

Ala Val Thr Glu Pro Gly Tyr Lys Ser Val Leu Ile Ala Val Asp Arg
            20                  25                  30

Phe Val Thr Ala Ser Ile Glu Ala Ser Asn Ala Val Thr Ser Thr Ile
        35                  40                  45

His Ser Lys Thr Leu His Tyr Glu Pro Val Thr Phe Asn Arg Asn Glu
    50                  55                  60

Asp Lys Ile Asp Ile Ser Asp Ala Asn Ala Ala Ser Gln Leu Lys Tyr
65                  70                  75                  80

Val Val Thr Ala Ile Glu Val Phe Glu Gln Tyr Ala Arg Ser Cys Asn
                85                  90                  95

Val Lys Leu Lys His Phe His Leu Glu Ile Asp Ser Asn Leu Asp Asp
            100                 105                 110

Ala Ser Gly Asn Lys Tyr Gly Leu Gly Ser Ser Ala Ala Val Leu Val
        115                 120                 125

Ser Val Val Lys Ala Leu Asn Glu Phe Tyr Asp Met Gln Leu Ser Asn
    130                 135                 140

Leu Tyr Ile Tyr Lys Leu Ala Val Ile Ser Asn Met Arg Leu Gln Ser
145                 150                 155                 160

Leu Ser Ser Cys Gly Asp Ile Ala Val Ser Val Tyr Ser Gly Trp Leu
                165                 170                 175

Ala Tyr Ser Thr Phe Asp His Asp Trp Val Lys Gln Gln Met Glu Glu
            180                 185                 190

Thr Ser Val Asn Glu Val Leu Glu Lys Asn Trp Pro Gly Leu His Ile
        195                 200                 205

Glu Pro Leu Gln Ala Pro Glu Asn Met Glu Val Leu Ile Gly Trp Thr
    210                 215                 220

Gly Ser Pro Ala Ser Ser Pro His Leu Val Ser Glu Val Lys Arg Leu
225                 230                 235                 240
```

```
Lys Ser Asp Pro Ser Phe Tyr Gly Arg Phe Leu Asp Gln Ser His Thr
            245                 250                 255

Cys Val Glu Asn Leu Ile Tyr Ala Phe Lys Thr Asp Asn Ile Lys Gly
        260                 265                 270

Val Gln Lys Met Ile Arg Gln Asn Arg Met Ile Ile Gln Gln Met Asp
    275                 280                 285

Asn Glu Ala Thr Val Asp Ile Glu Thr Glu Asn Leu Lys Met Leu Cys
290                 295                 300

Asp Ile Gly Glu Arg Tyr Gly Ala Ala Lys Thr Ser Gly Ala Gly
305                 310                 315                 320

Gly Gly Asp Cys Gly Ile Ala Ile Ile Asp Asn Arg Ile Asp Lys Asn
            325                 330                 335

Arg Ile Tyr Asn Glu Trp Ala Ser His Gly Ile Lys Pro Leu Lys Phe
        340                 345                 350

Lys Ile Tyr His Gly Gln
        355
```

<210> SEQ ID NO 110
<211> LENGTH: 358
<212> TYPE: PRT
<213> ORGANISM: Staphylococcus epidermis

<400> SEQUENCE: 110

```
Met Ile Gln Val Lys Ala Pro Gly Lys Leu Tyr Ile Ala Gly Glu Tyr
1               5                   10                  15

Ala Val Thr Glu Pro Gly Tyr Lys Ser Ile Leu Ile Ala Val Asn Arg
            20                  25                  30

Phe Val Thr Ala Thr Ile Glu Ala Ser Asn Lys Val Glu Gly Ser Ile
        35                  40                  45

His Ser Lys Thr Leu His Tyr Glu Pro Val Lys Phe Asp Arg Asn Glu
    50                  55                  60

Asp Arg Ile Glu Ile Ser Asp Val Gln Ala Ala Lys Gln Leu Lys Tyr
65                  70                  75                  80

Val Val Thr Ala Ile Glu Val Phe Glu Gln Tyr Val Arg Ser Cys Asn
            85                  90                  95

Met Asn Leu Lys His Phe His Leu Thr Ile Asp Ser Asn Leu Ala Asp
        100                 105                 110

Asn Ser Gly Gln Lys Tyr Gly Leu Gly Ser Ser Ala Ala Val Leu Val
    115                 120                 125

Ser Val Val Lys Ala Leu Asn Glu Phe Tyr Gly Leu Glu Leu Ser Asn
130                 135                 140

Leu Tyr Ile Tyr Lys Leu Ala Val Ile Ala Asn Met Lys Leu Gln Ser
145                 150                 155                 160

Leu Ser Ser Cys Gly Asp Ile Ala Val Ser Val Tyr Ser Gly Trp Leu
            165                 170                 175

Ala Tyr Ser Thr Phe Asp His Asp Trp Val Lys Gln Met Glu Glu
        180                 185                 190

Thr Ser Val Asn Asp Val Leu Glu Lys Asn Trp Pro Gly Leu His Ile
    195                 200                 205

Glu Pro Leu Gln Ala Pro Glu Asn Met Glu Val Leu Ile Gly Trp Thr
210                 215                 220

Gly Ser Pro Ala Ser Ser Pro His Leu Val Ser Glu Val Lys Arg Leu
225                 230                 235                 240

Lys Ser Asp Pro Ser Phe Tyr Gly Asp Phe Leu Asp Gln Ser His Ala
            245                 250                 255
```

```
Cys Val Glu Ser Leu Ile Gln Ala Phe Lys Thr Asn Asn Ile Lys Gly
            260                 265                 270

Val Gln Lys Met Ile Arg Ile Asn Arg Arg Ile Ile Gln Ser Met Asp
            275                 280                 285

Asn Glu Ala Ser Val Glu Ile Glu Thr Asp Lys Leu Lys Lys Leu Cys
            290                 295                 300

Asp Val Gly Glu Lys His Gly Gly Ala Ser Lys Thr Ser Gly Ala Gly
305                 310                 315                 320

Gly Gly Asp Cys Gly Ile Thr Ile Ile Asn Lys Val Ile Asp Lys Asn
                325                 330                 335

Ile Ile Tyr Asn Glu Trp Gln Met Asn Asp Ile Lys Pro Leu Lys Phe
            340                 345                 350

Lys Ile Tyr His Gly Gln
            355

<210> SEQ ID NO 111
<211> LENGTH: 358
<212> TYPE: PRT
<213> ORGANISM: Staphylococcus aureus

<400> SEQUENCE: 111

Met Ile Gln Val Lys Ala Pro Gly Lys Leu Tyr Ile Ala Gly Glu Tyr
1               5                   10                  15

Ala Val Thr Glu Pro Gly Tyr Lys Ser Val Leu Ile Ala Leu Asp Arg
            20                  25                  30

Phe Val Thr Ala Thr Ile Glu Ala Thr Gln Tyr Lys Gly Thr Ile
            35                  40                  45

His Ser Lys Ala Leu His His Asn Pro Val Thr Phe Ser Arg Asp Glu
        50                  55                  60

Asp Ser Ile Val Ile Ser Asp Pro His Ala Ala Lys Gln Leu Asn Tyr
65                  70                  75                  80

Val Val Thr Ala Ile Glu Ile Phe Glu Gln Tyr Ala Lys Ser Cys Asp
                85                  90                  95

Ile Ala Met Lys His Phe His Leu Thr Ile Asp Ser Asn Leu Asp Asp
            100                 105                 110

Ser Asn Gly His Lys Tyr Gly Leu Gly Ser Ser Ala Ala Val Leu Val
            115                 120                 125

Ser Val Ile Lys Val Leu Asn Glu Phe Tyr Asp Met Lys Leu Ser Asn
130                 135                 140

Leu Tyr Ile Tyr Lys Leu Ala Val Ile Ala Asn Met Lys Leu Gln Ser
145                 150                 155                 160

Leu Ser Ser Cys Gly Asp Ile Ala Val Ser Val Tyr Ser Gly Trp Leu
                165                 170                 175

Ala Tyr Ser Thr Phe Asp His Glu Trp Val Lys His Gln Ile Glu Asp
            180                 185                 190

Thr Thr Val Glu Glu Val Leu Ile Lys Asn Trp Pro Gly Leu His Ile
            195                 200                 205

Glu Pro Leu Gln Ala Pro Glu Asn Met Glu Val Leu Ile Gly Trp Thr
    210                 215                 220

Gly Ser Pro Ala Ser Ser Pro His Phe Val Ser Glu Val Lys Arg Leu
225                 230                 235                 240

Lys Ser Asp Pro Ser Phe Tyr Gly Asp Phe Leu Glu Asp Ser His Arg
                245                 250                 255

Cys Val Glu Lys Leu Ile His Ala Phe Lys Thr Asn Asn Ile Lys Gly
```

```
                  260                 265                 270
Val Gln Lys Met Val Arg Gln Asn Arg Thr Ile Ile Gln Arg Met Asp
        275                 280                 285

Lys Glu Ala Thr Val Asp Ile Glu Thr Glu Lys Leu Lys Tyr Leu Cys
        290                 295                 300

Asp Ile Ala Glu Lys Tyr His Gly Ala Ser Lys Thr Ser Gly Ala Gly
305                 310                 315                 320

Gly Gly Asp Cys Gly Ile Thr Ile Ile Asn Lys Asp Val Asp Lys Glu
                325                 330                 335

Lys Ile Tyr Asp Glu Trp Thr Lys His Gly Ile Lys Pro Leu Lys Phe
        340                 345                 350

Asn Ile Tyr His Gly Gln
        355

<210> SEQ ID NO 112
<211> LENGTH: 374
<212> TYPE: PRT
<213> ORGANISM: Streptomyces sp. CL190

<400> SEQUENCE: 112

Met Thr Thr Gly Gln Arg Thr Ile Val Arg His Ala Pro Gly Lys Leu
1               5                   10                  15

Phe Val Ala Gly Glu Tyr Ala Val Val Asp Pro Gly Asn Pro Ala Ile
                20                  25                  30

Leu Val Ala Val Asp Arg His Ile Ser Val Thr Val Ser Asp Ala Asp
            35                  40                  45

Ala Asp Thr Gly Ala Ala Asp Val Val Ile Ser Ser Asp Leu Gly Pro
        50                  55                  60

Gln Ala Val Gly Trp Arg Trp His Asp Gly Arg Leu Val Val Arg Asp
65                  70                  75                  80

Pro Asp Asp Gly Gln Gln Ala Arg Ser Ala Leu Ala His Val Val Ser
                85                  90                  95

Ala Ile Glu Thr Val Gly Arg Leu Leu Gly Glu Arg Gly Gln Lys Val
            100                 105                 110

Pro Ala Leu Thr Leu Ser Val Ser Ser Arg Leu His Glu Asp Gly Arg
        115                 120                 125

Lys Phe Gly Leu Gly Ser Ser Gly Ala Val Thr Val Ala Thr Val Ala
    130                 135                 140

Ala Val Ala Ala Phe Cys Gly Leu Glu Leu Ser Thr Asp Glu Arg Phe
145                 150                 155                 160

Arg Leu Ala Met Leu Ala Thr Ala Glu Leu Asp Pro Lys Gly Ser Gly
                165                 170                 175

Gly Asp Leu Ala Ala Ser Thr Trp Gly Gly Trp Ile Ala Tyr Gln Ala
            180                 185                 190

Pro Asp Arg Ala Phe Val Leu Asp Leu Ala Arg Arg Val Gly Val Asp
        195                 200                 205

Arg Thr Leu Lys Ala Pro Trp Pro Gly His Ser Val Arg Arg Leu Pro
    210                 215                 220

Ala Pro Lys Gly Leu Thr Leu Glu Val Gly Trp Thr Gly Glu Pro Ala
225                 230                 235                 240

Ser Thr Ala Ser Leu Val Ser Asp Leu His Arg Thr Trp Arg Gly
                245                 250                 255

Ser Ala Ser His Gln Arg Phe Val Glu Thr Thr Asp Cys Val Arg
            260                 265                 270
```

```
Ser Ala Val Thr Ala Leu Glu Ser Gly Asp Asp Thr Ser Leu Leu His
        275                 280                 285

Glu Ile Arg Arg Ala Arg Gln Glu Leu Ala Arg Leu Asp Asp Glu Val
        290                 295                 300

Gly Leu Gly Ile Phe Thr Pro Lys Leu Thr Ala Leu Cys Asp Ala Ala
305                 310                 315                 320

Glu Ala Val Gly Gly Ala Ala Lys Pro Ser Gly Ala Gly Gly Asp
                325                 330                 335

Cys Gly Ile Ala Leu Leu Asp Ala Glu Ala Ser Arg Asp Ile Thr His
                340                 345                 350

Val Arg Gln Arg Trp Glu Thr Ala Gly Val Leu Pro Leu Pro Leu Thr
        355                 360                 365

Pro Ala Leu Glu Gly Ile
        370

<210> SEQ ID NO 113
<211> LENGTH: 360
<212> TYPE: PRT
<213> ORGANISM: Streptomyces griseolosporeus

<400> SEQUENCE: 113

Met Thr Gly Pro Arg Ala Val Thr Arg Arg Ala Pro Gly Lys Leu Phe
1               5                   10                  15

Val Ala Gly Glu Tyr Ala Val Val Glu Pro Gly Asn Arg Ala Ile Leu
                20                  25                  30

Val Ala Val Asp Arg Tyr Val Thr Val Ser Asp Gly Ala Ala
        35                  40                  45

Pro Gly Val Val Ser Ser Asp Ile Gly Ala Gly Pro Val His His
        50                  55                  60

Pro Trp Gln Asp Gly Arg Leu Thr Gly Thr Gly Thr Pro His Val
65                  70                  75                  80

Val Ala Ala Val Glu Thr Val Ala Arg Leu Ala Glu Arg Gly Arg
                85                  90                  95

Ser Val Pro Pro Leu Gly Trp Ser Ile Ser Ser Thr Leu His Glu Asp
                100                 105                 110

Gly Arg Lys Phe Gly Leu Gly Ser Ser Gly Ala Val Thr Val Ala Thr
        115                 120                 125

Val Ser Ala Val Ala Ala His Cys Gly Leu Glu Leu Thr Ala Glu Glu
130                 135                 140

Arg Phe Arg Thr Ala Leu Ile Ala Ser Ala Arg Ile Asp Pro Arg Gly
145                 150                 155                 160

Ser Gly Gly Asp Ile Ala Thr Ser Thr Trp Gly Gly Trp Ile Ala Tyr
                165                 170                 175

Arg Ala Pro Asp Arg Asp Ala Val Leu Asp Leu Thr Arg Arg Gln Gly
                180                 185                 190

Val Asp Glu Ala Leu Arg Ala Pro Trp Pro Gly Phe Ser Val Arg Leu
        195                 200                 205

Ser Pro Pro Arg Asn Leu Cys Leu Glu Val Gly Trp Thr Gly Asn Pro
        210                 215                 220

Val Ser Thr Thr Ser Leu Leu Thr Asp Leu His Arg Arg Thr Trp Arg
225                 230                 235                 240

Gly Ser Pro Ala Tyr Arg Arg Tyr Val Gly Ala Thr Gly Glu Leu Val
                245                 250                 255

Asp Ala Ala Val Ile Ala Leu Glu Asp Gly Asp Thr Glu Gly Leu Leu
                260                 265                 270
```

```
Arg Gln Val Arg Arg Ala Arg His Glu Met Val Arg Leu Asp Asp Glu
        275                 280                 285
Val Gly Leu Gly Ile Phe Thr Pro Glu Leu Thr Ala Leu Cys Ala Ile
    290                 295                 300
Ala Glu Arg Ala Gly Ala Ala Lys Pro Ser Gly Ala Gly Gly Gly Asp
305                 310                 315                 320
Cys Gly Ile Ala Leu Leu Asp Ala Glu Ala Arg Tyr Asp Arg Ser Pro
                325                 330                 335
Leu His Arg Gln Trp Ala Ala Ala Gly Val Leu Pro Leu Leu Val Ser
                340                 345                 350
Pro Ala Thr Glu Gly Val Glu Glu
                355                 360

<210> SEQ ID NO 114
<211> LENGTH: 317
<212> TYPE: PRT
<213> ORGANISM: Borrelia burgdorferi

<400> SEQUENCE: 114

Met Asp Leu Ile Ser Phe Ser Val Pro Gly Asn Leu Leu Met Gly
1               5                   10                  15
Glu Tyr Thr Ile Leu Glu Glu Lys Gly Leu Gly Leu Ala Ile Ala Ile
                20                  25                  30
Asn Lys Arg Ala Phe Phe Ser Phe Lys Lys Ser Asp Ser Trp Arg Phe
            35                  40                  45
Phe Ser Lys Lys Lys Ile Asp Asp Phe Ser Leu Ile Glu Asn Arg
        50                  55                  60
Ser Asp Phe Val Phe Lys Met Phe Ala Tyr Leu Ser Gln Asn Cys Phe
65                  70                  75                  80
Phe Asn Leu Glu Asn Phe Ala Tyr Asp Val Tyr Ile Asp Thr Ser Asn
                85                  90                  95
Phe Phe Phe Asn Asp Gly Thr Lys Lys Gly Phe Gly Ser Ser Ala Val
                100                 105                 110
Val Ala Ile Gly Ile Val Cys Gly Leu Phe Leu Ile His Asn Ala Thr
            115                 120                 125
Asn Val Val Glu Lys Gly Glu Ile Phe Lys Tyr Cys Leu Glu Ala Tyr
        130                 135                 140
Arg Tyr Ser Gln Gly Gly Ile Gly Ser Gly Tyr Asp Ile Ala Thr Ser
145                 150                 155                 160
Ile Phe Gly Gly Val Ile Glu Phe Glu Gly Phe Asn Pro Lys Cys
                165                 170                 175
Arg Gln Leu Gly Ala Val Glu Phe Asn Asp Phe Tyr Leu Met Gln Gly
                180                 185                 190
Leu Gln Ala Ile Lys Thr Thr Thr Ser Ile Cys Glu Tyr Asn Lys His
            195                 200                 205
Arg Asn Ser Ile Leu Asp Phe Ile Lys Cys Asn Leu Glu Met Lys
        210                 215                 220
Lys Leu Val Leu Asn Ala Ser Asn Ser Lys Ser Ala Leu Ile Ser Ser
225                 230                 235                 240
Leu Arg Arg Ala Lys Glu Leu Gly Leu Ala Ile Gly Glu Ala Ile Gly
                245                 250                 255
Val Ser Ala Ala Leu Pro Ser Ser Phe Asp His Leu Leu Gly Gln Cys
                260                 265                 270
Asp Leu Ile Lys Ala Leu Gly Ala Gly Asn Glu Thr Phe Leu Val Tyr
```

```
            275                 280                 285
Arg Pro Asn Ile Glu Ala Phe Asn Leu Ser Lys Ile Ile Ser Ile Val
    290                 295                 300

Leu Glu Asn Glu Gly Ile Lys Phe Glu Ser Asp Lys Cys
305                 310                 315
```

<210> SEQ ID NO 115
<211> LENGTH: 30
<212> TYPE: DNA
<213> ORGANISM: Artificial
<220> FEATURE:
<223> OTHER INFORMATION: synthetic construct

<400> SEQUENCE: 115
gggcaagctt gtccacggca cgaccaagca                     30

<210> SEQ ID NO 116
<211> LENGTH: 30
<212> TYPE: DNA
<213> ORGANISM: Artificial
<220> FEATURE:
<223> OTHER INFORMATION: synthetic construct

<400> SEQUENCE: 116
cgtaatccgc ggccgcgttt ccagcgcgtc                     30

<210> SEQ ID NO 117
<211> LENGTH: 28
<212> TYPE: DNA
<213> ORGANISM: Artificial
<220> FEATURE:
<223> OTHER INFORMATION: synthetic construct

<400> SEQUENCE: 117
aattaaagga gggtttcata tgaattcg                       28

<210> SEQ ID NO 118
<211> LENGTH: 28
<212> TYPE: DNA
<213> ORGANISM: Artificial
<220> FEATURE:
<223> OTHER INFORMATION: synthetic construct

<400> SEQUENCE: 118
gatccgaatt catatgaaac cctcctttt                      28

<210> SEQ ID NO 119
<211> LENGTH: 30
<212> TYPE: DNA
<213> ORGANISM: Artificial
<220> FEATURE:
<223> OTHER INFORMATION: synthetic construct

<400> SEQUENCE: 119
aaggcctcat atgatttccc ataccccggt                     30

<210> SEQ ID NO 120
<211> LENGTH: 28
<212> TYPE: DNA
<213> ORGANISM: Artificial
<220> FEATURE:
<223> OTHER INFORMATION: synthetic construct

<400> SEQUENCE: 120
cgggatcctc atcgctccat ctccatgt                       28

<210> SEQ ID NO 121
<211> LENGTH: 30
<212> TYPE: DNA
<213> ORGANISM: Artificial
<220> FEATURE:
<223> OTHER INFORMATION: synthetic construct

<400> SEQUENCE: 121
aaggcctcat atgaccgaca gcaaggatca                                    30

<210> SEQ ID NO 122
<211> LENGTH: 28
<212> TYPE: DNA
<213> ORGANISM: Artificial
<220> FEATURE:
<223> OTHER INFORMATION: synthetic construct

<400> SEQUENCE: 122
cgggatcctc attgacggat aagcgagg                                      28

<210> SEQ ID NO 123
<211> LENGTH: 29
<212> TYPE: DNA
<213> ORGANISM: Artificial
<220> FEATURE:
<223> OTHER INFORMATION: synthetic construct

<400> SEQUENCE: 123
aaggcctcat atgaaagtgc ctaagatga                                     29

<210> SEQ ID NO 124
<211> LENGTH: 28
<212> TYPE: DNA
<213> ORGANISM: Artificial
<220> FEATURE:
<223> OTHER INFORMATION: synthetic construct

<400> SEQUENCE: 124
cgggatcctc aggcctgccg gtcgacat                                      28

<210> SEQ ID NO 125
<211> LENGTH: 34
<212> TYPE: DNA
<213> ORGANISM: Artificial
<220> FEATURE:
<223> OTHER INFORMATION: synthetic construct

<400> SEQUENCE: 125
aaggcctcat atgagcaccg gcaggcctga agca                               34

<210> SEQ ID NO 126
<211> LENGTH: 31
<212> TYPE: DNA
<213> ORGANISM: Artificial
<220> FEATURE:
<223> OTHER INFORMATION: synthetic construct

<400> SEQUENCE: 126
cgggatcctc atccctgccc cggcagcggt t                                  31

<210> SEQ ID NO 127
<211> LENGTH: 30
<212> TYPE: DNA
<213> ORGANISM: Artificial
<220> FEATURE:

```
<223> OTHER INFORMATION: synthetic construct

<400> SEQUENCE: 127
aaggcctcat atggatcagg tcatccgcgc                                    30

<210> SEQ ID NO 128
<211> LENGTH: 28
<212> TYPE: DNA
<213> ORGANISM: Artificial
<220> FEATURE:
<223> OTHER INFORMATION: synthetic construct

<400> SEQUENCE: 128
cgggatcctc agtcatcgaa aacaagtc                                      28

<210> SEQ ID NO 129
<211> LENGTH: 30
<212> TYPE: DNA
<213> ORGANISM: Artificial
<220> FEATURE:
<223> OTHER INFORMATION: synthetic construct

<400> SEQUENCE: 129
aaggcctcat atgactgatg ccgtccgcga                                    30

<210> SEQ ID NO 130
<211> LENGTH: 28
<212> TYPE: DNA
<213> ORGANISM: Artificial
<220> FEATURE:
<223> OTHER INFORMATION: synthetic construct

<400> SEQUENCE: 130
cgggatcctc aacgccctc gaacggcg                                       28

<210> SEQ ID NO 131
<211> LENGTH: 31
<212> TYPE: DNA
<213> ORGANISM: Artificial
<220> FEATURE:
<223> OTHER INFORMATION: synthetic construct

<400> SEQUENCE: 131
ccggcattcg ggcggcatcc aggtctcgct g                                  31

<210> SEQ ID NO 132
<211> LENGTH: 31
<212> TYPE: DNA
<213> ORGANISM: Artificial
<220> FEATURE:
<223> OTHER INFORMATION: synthetic construct

<400> SEQUENCE: 132
cagcgagacc tggatgccgc ccgaatgccg g                                  31

<210> SEQ ID NO 133
<211> LENGTH: 31
<212> TYPE: DNA
<213> ORGANISM: Artificial
<220> FEATURE:
<223> OTHER INFORMATION: synthetic construct

<400> SEQUENCE: 133
cgtgcagggc tggattctgt cggaataccc g                                  31
```

<210> SEQ ID NO 134
<211> LENGTH: 31
<212> TYPE: DNA
<213> ORGANISM: Artificial
<220> FEATURE:
<223> OTHER INFORMATION: synthetic construct

<400> SEQUENCE: 134
cgggtattcc gacagaatcc agccctgcac g                       31

<210> SEQ ID NO 135
<211> LENGTH: 31
<212> TYPE: DNA
<213> ORGANISM: Artificial
<220> FEATURE:
<223> OTHER INFORMATION: synthetic construct

<400> SEQUENCE: 135
gggctgcgcg ccggcatccg gcatttcgac g                       31

<210> SEQ ID NO 136
<211> LENGTH: 31
<212> TYPE: DNA
<213> ORGANISM: Artificial
<220> FEATURE:
<223> OTHER INFORMATION: synthetic construct

<400> SEQUENCE: 136
cgtcgaaatg ccggatgccg gcgcgcagcc c                       31

<210> SEQ ID NO 137
<211> LENGTH: 31
<212> TYPE: DNA
<213> ORGANISM: Artificial
<220> FEATURE:
<223> OTHER INFORMATION: synthetic construct

<400> SEQUENCE: 137
gggtgcgacg ggcgagttct tcgatgcgcg g                       31

<210> SEQ ID NO 138
<211> LENGTH: 31
<212> TYPE: DNA
<213> ORGANISM: Artificial
<220> FEATURE:
<223> OTHER INFORMATION: synthetic construct

<400> SEQUENCE: 138
ccgcgcatcg aagaactcgc ccgtcgcacc c                       31

<210> SEQ ID NO 139
<211> LENGTH: 31
<212> TYPE: DNA
<213> ORGANISM: Artificial
<220> FEATURE:
<223> OTHER INFORMATION: synthetic construct

<400> SEQUENCE: 139
cacgcccgtc acatacgacg aatacgttgc c                       31

<210> SEQ ID NO 140
<211> LENGTH: 31
<212> TYPE: DNA
<213> ORGANISM: Artificial
<220> FEATURE:
<223> OTHER INFORMATION: synthetic construct

```
<400> SEQUENCE: 140
ggcaacgtat tcgtcgtatg tgacgggcgt g                              31

<210> SEQ ID NO 141
<211> LENGTH: 31
<212> TYPE: DNA
<213> ORGANISM: Artificial
<220> FEATURE:
<223> OTHER INFORMATION: synthetic construct

<400> SEQUENCE: 141
gaggctcggg cttggctcct cggcggcggt g                              31

<210> SEQ ID NO 142
<211> LENGTH: 31
<212> TYPE: DNA
<213> ORGANISM: Artificial
<220> FEATURE:
<223> OTHER INFORMATION: synthetic construct

<400> SEQUENCE: 142
caccgccgcc gaggagccaa gcccgagcct c                              31

<210> SEQ ID NO 143
<211> LENGTH: 31
<212> TYPE: DNA
<213> ORGANISM: Artificial
<220> FEATURE:
<223> OTHER INFORMATION: synthetic construct

<400> SEQUENCE: 143
cggcacgctg ctggacccgg gcgacgcctt c                              31

<210> SEQ ID NO 144
<211> LENGTH: 31
<212> TYPE: DNA
<213> ORGANISM: Artificial
<220> FEATURE:
<223> OTHER INFORMATION: synthetic construct

<400> SEQUENCE: 144
gaaggcgtcg cccgggtcca gcagcgtgcc g                              31

<210> SEQ ID NO 145
<211> LENGTH: 36
<212> TYPE: DNA
<213> ORGANISM: Artificial
<220> FEATURE:
<223> OTHER INFORMATION: synthetic construct

<400> SEQUENCE: 145
tcagaattcg gtaccatatg aagcttggat ccgggg                         36

<210> SEQ ID NO 146
<211> LENGTH: 29
<212> TYPE: DNA
<213> ORGANISM: Artificial
<220> FEATURE:
<223> OTHER INFORMATION: synthetic construct

<400> SEQUENCE: 146
ggatccaagc ttcatatggt accgaattc                                 29

<210> SEQ ID NO 147
<211> LENGTH: 26
```

```
<212> TYPE: DNA
<213> ORGANISM: Artificial
<220> FEATURE:
<223> OTHER INFORMATION: synthetic construct

<400> SEQUENCE: 147
ggaattcgct gctgaacgcg atggcg                                      26

<210> SEQ ID NO 148
<211> LENGTH: 32
<212> TYPE: DNA
<213> ORGANISM: Artificial
<220> FEATURE:
<223> OTHER INFORMATION: synthetic construct

<400> SEQUENCE: 148
ggggtaccat atgtgccttc gttgcgtcag tc                               32

<210> SEQ ID NO 149
<211> LENGTH: 50
<212> TYPE: DNA
<213> ORGANISM: Artificial
<220> FEATURE:
<223> OTHER INFORMATION: synthetic construct

<400> SEQUENCE: 149
gatccggcgt gtgcgcaatt taattgcgca cacgccccct gcgtttaaac             50

<210> SEQ ID NO 150
<211> LENGTH: 50
<212> TYPE: DNA
<213> ORGANISM: Artificial
<220> FEATURE:
<223> OTHER INFORMATION: synthetic construct

<400> SEQUENCE: 150
gatcgtttaa acgcaggggg cgtgtgcgca attaaattgc gcacacgccg             50

<210> SEQ ID NO 151
<211> LENGTH: 30
<212> TYPE: DNA
<213> ORGANISM: Artificial
<220> FEATURE:
<223> OTHER INFORMATION: synthetic construct

<400> SEQUENCE: 151
aaggcctcat atgacgccca agcagcaatt                                  30

<210> SEQ ID NO 152
<211> LENGTH: 26
<212> TYPE: DNA
<213> ORGANISM: Artificial
<220> FEATURE:
<223> OTHER INFORMATION: synthetic construct

<400> SEQUENCE: 152
cgggatccta ggcgctgcgg cggatg                                      26

<210> SEQ ID NO 153
<211> LENGTH: 30
<212> TYPE: DNA
<213> ORGANISM: Artificial
<220> FEATURE:
<223> OTHER INFORMATION: synthetic construct

<400> SEQUENCE: 153
```

-continued

```
ccggatcctc atgcctgccg gtcgacatag                                    30

<210> SEQ ID NO 154
<211> LENGTH: 30
<212> TYPE: DNA
<213> ORGANISM: Artificial
<220> FEATURE:
<223> OTHER INFORMATION: synthetic construct

<400> SEQUENCE: 154
gaaggcacat atgaatcagg tcatccgcgc                                    30

<210> SEQ ID NO 155
<211> LENGTH: 30
<212> TYPE: DNA
<213> ORGANISM: Artificial
<220> FEATURE:
<223> OTHER INFORMATION: synthetic construct

<400> SEQUENCE: 155
gccggatcct cattcatcga aaacaagtcc                                    30

<210> SEQ ID NO 156
<211> LENGTH: 30
<212> TYPE: DNA
<213> ORGANISM: Artificial
<220> FEATURE:
<223> OTHER INFORMATION: synthetic construct

<400> SEQUENCE: 156
acgccggatc ctcatcgccc ctcgaacggc                                    30

<210> SEQ ID NO 157
<211> LENGTH: 1612
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (59)..(292)
<223> OTHER INFORMATION: XseB
<220> FEATURE:
<221> NAME/KEY: CDS
<222> LOCATION: (1185)..(1610)
<223> OTHER INFORMATION: IspA
<220> FEATURE:
<221> NAME/KEY: CDS
<222> LOCATION: (295)..(1158)
<223> OTHER INFORMATION: Dxs

<400> SEQUENCE: 157
ccatggcatc cgggtcggat gccgtctatg ttggcccgaa caggcagcag gaggcccc       58 atg agc gat atc cag acc ctc tcg ttc gag gaa gcc atg cgc gag ctg      106
Met Ser Asp Ile Gln Thr Leu Ser Phe Glu Glu Ala Met Arg Glu Leu
1               5                   10                  15 gag gcg acc gtc ggc aag ctg gaa acc ggc gag gcg acg ctc gag gac      154
Glu Ala Thr Val Gly Lys Leu Glu Thr Gly Glu Ala Thr Leu Glu Asp
                20                  25                  30 tcc atc gcg ctc tat gaa cgc ggg gcg gcg ctg cgc gcc cat tgc gaa      202
Ser Ile Ala Leu Tyr Glu Arg Gly Ala Ala Leu Arg Ala His Cys Glu
            35                  40                  45 acc cgc ctg cgc gag gcc gag gag cgg gtc gag aag atc acc ctg gcc      250
Thr Arg Leu Arg Glu Ala Glu Glu Arg Val Glu Lys Ile Thr Leu Ala
        50                  55                  60 gcg aac ggg cag ccg tcc gga acc gag ccc gcc gag ggc ctg tg atg       297
```

| | | |
|---|---|---|
| Ala Asn Gly Gln Pro Ser Gly Thr Glu Pro Ala Glu Gly Leu     Met<br>65                     70                     75 | | |
| cag gcc cgc ctg gcc gag atc cgg ccc ctg gtc gag gcc gag ctg aac<br>Gln Ala Arg Leu Ala Glu Ile Arg Pro Leu Val Glu Ala Glu Leu Asn<br>80                     85                     90                     95 | 345 | |
| gcc gcc atc gac gcg ctg ccc gcg ggc gat ctg tcg gat gcg atg cgc<br>Ala Ala Ile Asp Ala Leu Pro Ala Gly Asp Leu Ser Asp Ala Met Arg<br>                    100                    105                    110 | 393 | |
| tat gcc gtg cag ggc ggc aag cgg ctg cgc gcg ttc ctg gtg atg gag<br>Tyr Ala Val Gln Gly Gly Lys Arg Leu Arg Ala Phe Leu Val Met Glu<br>                    115                    120                    125 | 441 | |
| tcg gcg cgc ctg cac ggg ctg gac gac gac gca tcg ctg ccc gtc gcc<br>Ser Ala Arg Leu His Gly Leu Asp Asp Asp Ala Ser Leu Pro Val Ala<br>                    130                    135                    140 | 489 | |
| gcc gcg gtc gag gcg ctg cac gcc tac agc ttg gtc cat gac gac ctg<br>Ala Ala Val Glu Ala Leu His Ala Tyr Ser Leu Val His Asp Asp Leu<br>                    145                    150                    155 | 537 | |
| ccc gcg atg gat gac gac gac ctg cgg cgc ggt cag ccc acc gtc cac<br>Pro Ala Met Asp Asp Asp Asp Leu Arg Arg Gly Gln Pro Thr Val His<br>160                    165                    170                    175 | 585 | |
| gtc aaa tgg acc gag gcg acc gcg atc ctt gcg ggc gat gcg ctg cag<br>Val Lys Trp Thr Glu Ala Thr Ala Ile Leu Ala Gly Asp Ala Leu Gln<br>                    180                    185                    190 | 633 | |
| acg ctg gcc ttc cag ctg ctg gcc gat ccg cgc gtg ggc gac gat gcg<br>Thr Leu Ala Phe Gln Leu Leu Ala Asp Pro Arg Val Gly Asp Asp Ala<br>                    195                    200                    205 | 681 | |
| gcg cgg atg cgg ctg gtc ggt tcg ctg gcg cag gca tcg ggg gct gcg<br>Ala Arg Met Arg Leu Val Gly Ser Leu Ala Gln Ala Ser Gly Ala Ala<br>                    210                    215                    220 | 729 | |
| ggc atg gtc tgg ggc cag gcg ctg gac atc gcg gcc gag acc tcg ggc<br>Gly Met Val Trp Gly Gln Ala Leu Asp Ile Ala Ala Glu Thr Ser Gly<br>                    225                    230                    235 | 777 | |
| gtg ccg ctg gat ctg gac gcg atc atc cgc ctg cag ggt ggc aag acc<br>Val Pro Leu Asp Leu Asp Ala Ile Ile Arg Leu Gln Gly Gly Lys Thr<br>240                    245                    250                    255 | 825 | |
| ggc gcg ctg atc cgc ttt gcc gcg acc gcc ggg ccg ctg atg gcg ggg<br>Gly Ala Leu Ile Arg Phe Ala Ala Thr Ala Gly Pro Leu Met Ala Gly<br>                    260                    265                    270 | 873 | |
| gcg gac cct gcc gcg ctg gac gat tat gcg cag gcc gtc ggg ctg gcc<br>Ala Asp Pro Ala Ala Leu Asp Asp Tyr Ala Gln Ala Val Gly Leu Ala<br>                    275                    280                    285 | 921 | |
| ttc cag atc gcg gac gac atc ctg gac gtc gag ggc tgc gag gcc gcg<br>Phe Gln Ile Ala Asp Asp Ile Leu Asp Val Glu Gly Cys Glu Ala Ala<br>                    290                    295                    300 | 969 | |
| acc ggc aag cgc gtc ggc aag gat gcg gat gcc aac aag gcg acc ttc<br>Thr Gly Lys Arg Val Gly Lys Asp Ala Asp Ala Asn Lys Ala Thr Phe<br>                    305                    310                    315 | 1017 | |
| gtc tcg ctg ctg ggc ctc gag ggg gcg cgg tcc gag gcg cgt cgc ctg<br>Val Ser Leu Leu Gly Leu Glu Gly Ala Arg Ser Glu Ala Arg Arg Leu<br>320                    325                    330                    335 | 1065 | |
| gcc gat gcg ggg cag gac gcg ctg gcg ggt tac ggc gat gct gcg ggg<br>Ala Asp Ala Gly Gln Asp Ala Leu Ala Gly Tyr Gly Asp Ala Ala Gly<br>                    340                    345                    350 | 1113 | |
| aac ctt cgg gac ctg gcg cgc ttc gtg atc gaa cgc gac agc tga<br>Asn Leu Arg Asp Leu Ala Arg Phe Val Ile Glu Arg Asp Ser<br>                    355                    360                    365 | 1158 | |
| tcgccgcctt cccgccaagg ggcaag atg atg acc gac gga ccc gca acc ccg<br>                                    Met Met Thr Asp Gly Pro Ala Thr Pro<br>                                                          370 | 1211 | |

-continued

```
atc ctg gac cgc gtc cag cag cca tcc gac ctg gca tcg ctg gac gat    1259
Ile Leu Asp Arg Val Gln Gln Pro Ser Asp Leu Ala Ser Leu Asp Asp
375                 380                 385                 390 gcg cag ctg cgc ctg ctg gcg gac gag ctg cgg gcc gag acc atc gac    1307
Ala Gln Leu Arg Leu Leu Ala Asp Glu Leu Arg Ala Glu Thr Ile Asp
                395                 400                 405 atc gtc agc cgc acg ggc ggt cac ctg ggc gcg ggg ctg ggc gtg gtc    1355
Ile Val Ser Arg Thr Gly Gly His Leu Gly Ala Gly Leu Gly Val Val
            410                 415                 420 gaa ctg acg gtc gcc ctg cac gcc gtc ttt cgg gcg ccg cgc gac aag    1403
Glu Leu Thr Val Ala Leu His Ala Val Phe Arg Ala Pro Arg Asp Lys
        425                 430                 435 atc gtc tgg gac gtg ggg cat caa tgc tat ccc cac aag atc ctg acg    1451
Ile Val Trp Asp Val Gly His Gln Cys Tyr Pro His Lys Ile Leu Thr
    440                 445                 450 ggc agg cgg gac cgg atg cgc acg ctg cgc atg ggc ggc ggg ctg tcg    1499
Gly Arg Arg Asp Arg Met Arg Thr Leu Arg Met Gly Gly Gly Leu Ser
455                 460                 465                 470 ggg ttc acc aag cgg cag gaa agc gcg ttc gat ccg ttc ggt gcg ggg    1547
Gly Phe Thr Lys Arg Gln Glu Ser Ala Phe Asp Pro Phe Gly Ala Gly
                475                 480                 485 cac agc tcg acc tcg atc tcg gcg gcg ctg ggc ttc gcg atg gcg cgt    1595
His Ser Ser Thr Ser Ile Ser Ala Ala Leu Gly Phe Ala Met Ala Arg
            490                 495                 500 gaa ctt ggc ggg gat cc                                             1612
Glu Leu Gly Gly Asp
        505
```

<210> SEQ ID NO 158
<211> LENGTH: 78
<212> TYPE: PRT
<213> ORGANISM: Artificial
<220> FEATURE:
<223> OTHER INFORMATION: synthetic construct

<400> SEQUENCE: 158

```
Met Ser Asp Ile Gln Thr Leu Ser Phe Glu Glu Ala Met Arg Glu Leu
1               5                   10                  15

Glu Ala Thr Val Gly Lys Leu Glu Thr Gly Glu Ala Thr Leu Glu Asp
            20                  25                  30

Ser Ile Ala Leu Tyr Glu Arg Gly Ala Ala Leu Arg Ala His Cys Glu
        35                  40                  45

Thr Arg Leu Arg Glu Ala Glu Glu Arg Val Glu Lys Ile Thr Leu Ala
    50                  55                  60

Ala Asn Gly Gln Pro Ser Gly Thr Glu Pro Ala Glu Gly Leu
65                  70                  75
```

<210> SEQ ID NO 159
<211> LENGTH: 287
<212> TYPE: PRT
<213> ORGANISM: Artificial
<220> FEATURE:
<223> OTHER INFORMATION: synthetic construct

<400> SEQUENCE: 159

```
Met Gln Ala Arg Leu Ala Glu Ile Arg Pro Leu Val Glu Ala Glu Leu
1               5                   10                  15

Asn Ala Ala Ile Asp Ala Leu Pro Ala Gly Asp Leu Ser Asp Ala Met
            20                  25                  30

Arg Tyr Ala Val Gln Gly Gly Lys Arg Leu Arg Ala Phe Leu Val Met
        35                  40                  45
```

```
Glu Ser Ala Arg Leu His Gly Leu Asp Asp Ala Ser Leu Pro Val
 50                  55                  60

Ala Ala Ala Val Glu Ala Leu His Ala Tyr Ser Leu Val His Asp Asp
 65                  70                  75                  80

Leu Pro Ala Met Asp Asp Asp Leu Arg Arg Gly Gln Pro Thr Val
             85                  90                  95

His Val Lys Trp Thr Glu Ala Thr Ala Ile Leu Ala Gly Asp Ala Leu
            100                 105                 110

Gln Thr Leu Ala Phe Gln Leu Leu Ala Asp Pro Arg Val Gly Asp Asp
            115                 120                 125

Ala Ala Arg Met Arg Leu Val Gly Ser Leu Ala Gln Ala Ser Gly Ala
130                 135                 140

Ala Gly Met Val Trp Gly Gln Ala Leu Asp Ile Ala Ala Glu Thr Ser
145                 150                 155                 160

Gly Val Pro Leu Asp Leu Asp Ala Ile Ile Arg Leu Gln Gly Gly Lys
                165                 170                 175

Thr Gly Ala Leu Ile Arg Phe Ala Ala Thr Ala Gly Pro Leu Met Ala
            180                 185                 190

Gly Ala Asp Pro Ala Ala Leu Asp Asp Tyr Ala Gln Ala Val Gly Leu
            195                 200                 205

Ala Phe Gln Ile Ala Asp Asp Ile Leu Asp Val Glu Gly Cys Glu Ala
            210                 215                 220

Ala Thr Gly Lys Arg Val Gly Lys Asp Ala Asp Ala Asn Lys Ala Thr
225                 230                 235                 240

Phe Val Ser Leu Leu Gly Leu Glu Gly Ala Arg Ser Glu Ala Arg Arg
                245                 250                 255

Leu Ala Asp Ala Gly Gln Asp Ala Leu Ala Gly Tyr Gly Asp Ala Ala
            260                 265                 270

Gly Asn Leu Arg Asp Leu Ala Arg Phe Val Ile Glu Arg Asp Ser
            275                 280                 285

<210> SEQ ID NO 160
<211> LENGTH: 142
<212> TYPE: PRT
<213> ORGANISM: Artificial
<220> FEATURE:
<223> OTHER INFORMATION: synthetic construct

<400> SEQUENCE: 160

Met Met Thr Asp Gly Pro Ala Thr Pro Ile Leu Asp Arg Val Gln Gln
 1               5                  10                  15

Pro Ser Asp Leu Ala Ser Leu Asp Asp Ala Gln Leu Arg Leu Leu Ala
                20                  25                  30

Asp Glu Leu Arg Ala Glu Thr Ile Asp Ile Val Ser Arg Thr Gly Gly
             35                  40                  45

His Leu Gly Ala Gly Leu Gly Val Val Glu Leu Thr Val Ala Leu His
         50                  55                  60

Ala Val Phe Arg Ala Pro Arg Asp Lys Ile Val Trp Asp Val Gly His
 65                  70                  75                  80

Gln Cys Tyr Pro His Lys Ile Leu Thr Gly Arg Arg Asp Arg Met Arg
             85                  90                  95

Thr Leu Arg Met Gly Gly Gly Leu Ser Gly Phe Thr Lys Arg Gln Glu
            100                 105                 110

Ser Ala Phe Asp Pro Phe Gly Ala Gly His Ser Ser Thr Ser Ile Ser
            115                 120                 125
```

Ala Ala Leu Gly Phe Ala Met Ala Arg Glu Leu Gly Gly Asp
            130                 135                 140

<210> SEQ ID NO 161
<211> LENGTH: 6
<212> TYPE: PRT
<213> ORGANISM: Bradyrhizobium japonicum

<400> SEQUENCE: 161

Val His Asp Asp Leu Pro
1               5

<210> SEQ ID NO 162
<211> LENGTH: 6
<212> TYPE: PRT
<213> ORGANISM: Rhizobium sp. strain NGR234

<400> SEQUENCE: 162

Val His Asp Asp Leu Pro
1               5

<210> SEQ ID NO 163
<211> LENGTH: 6
<212> TYPE: PRT
<213> ORGANISM: Bacillus stearothermophilus

<400> SEQUENCE: 163

Ile His Asp Asp Leu Pro
1               5

<210> SEQ ID NO 164
<211> LENGTH: 6
<212> TYPE: PRT
<213> ORGANISM: Bacillus subtilis

<400> SEQUENCE: 164

Ile His Asp Asp Leu Pro
1               5

<210> SEQ ID NO 165
<211> LENGTH: 6
<212> TYPE: PRT
<213> ORGANISM: Escherichia coli

<400> SEQUENCE: 165

Ile His Asp Asp Leu Pro
1               5

<210> SEQ ID NO 166
<211> LENGTH: 6
<212> TYPE: PRT
<213> ORGANISM: Haemophilus influenzae

<400> SEQUENCE: 166

Ile His Asp Asp Leu Pro
1               5

<210> SEQ ID NO 167
<211> LENGTH: 16
<212> TYPE: DNA
<213> ORGANISM: Artificial
<220> FEATURE:
<223> OTHER INFORMATION: synthetic construct

<400> SEQUENCE: 167
tccaygayga yctgcc                                                    16

<210> SEQ ID NO 168
<211> LENGTH: 5
<212> TYPE: PRT
<213> ORGANISM: Bradyrhizobium japonicum

<400> SEQUENCE: 168

Asp Asp Ile Leu Asp
1               5

<210> SEQ ID NO 169
<211> LENGTH: 5
<212> TYPE: PRT
<213> ORGANISM: Rhizobium sp. strain NGR234

<400> SEQUENCE: 169

Asp Asp Ile Leu Asp
1               5

<210> SEQ ID NO 170
<211> LENGTH: 5
<212> TYPE: PRT
<213> ORGANISM: Bacillus stearothermophilus

<400> SEQUENCE: 170

Asp Asp Ile Leu Asp
1               5

<210> SEQ ID NO 171
<211> LENGTH: 5
<212> TYPE: PRT
<213> ORGANISM: Bacillus subtilis

<400> SEQUENCE: 171

Asp Asp Ile Leu Asp
1               5

<210> SEQ ID NO 172
<211> LENGTH: 5
<212> TYPE: PRT
<213> ORGANISM: Escherichia coli

<400> SEQUENCE: 172

Asp Asp Ile Leu Asp
1               5

<210> SEQ ID NO 173
<211> LENGTH: 5
<212> TYPE: PRT
<213> ORGANISM: Haemophilus influenzae

<400> SEQUENCE: 173

Asp Asp Ile Leu Asp
1               5

<210> SEQ ID NO 174
<211> LENGTH: 15
<212> TYPE: DNA
<213> ORGANISM: Artificial
<220> FEATURE:
<223> OTHER INFORMATION: synthetic construct

<400> SEQUENCE: 174

```
gaygayatcc tggay                                                         15
```

<210> SEQ ID NO 175
<211> LENGTH: 1176
<212> TYPE: DNA
<213> ORGANISM: Paracoccus sp. R1534
<220> FEATURE:
<221> NAME/KEY: CDS
<222> LOCATION: (1)..(1173)
<223> OTHER INFORMATION: acety-CoA acetyltransferase

<400> SEQUENCE: 175

```
atg gac ccc atc gtc atc acc ggc gcg atg cgc acc ccg atg ggg gca        48
Met Asp Pro Ile Val Ile Thr Gly Ala Met Arg Thr Pro Met Gly Ala
 1               5                  10                  15 ttc cag ggc gat ctt gcc gcg atg gat gcc ccg acc ctt ggc gcg gcc        96
Phe Gln Gly Asp Leu Ala Ala Met Asp Ala Pro Thr Leu Gly Ala Ala
             20                  25                  30 gcg atc cgc gcc gcg ctg aac ggc ctg tcg ccc gac atg gtg gac gag       144
Ala Ile Arg Ala Ala Leu Asn Gly Leu Ser Pro Asp Met Val Asp Glu
         35                  40                  45 gtg ctg atg ggc tgc gtc ctg ccc gcg ggc cag ggt cag gca ccg gca       192
Val Leu Met Gly Cys Val Leu Pro Ala Gly Gln Gly Gln Ala Pro Ala
     50                  55                  60 cgt cag gcg gcg ctt gac gcc gga ctg ccg ctg tcg gcg ggc gcg acc       240
Arg Gln Ala Ala Leu Asp Ala Gly Leu Pro Leu Ser Ala Gly Ala Thr
 65                  70                  75                  80 acc atc aac aag atg tgc gga tcg ggc atg aag gcc gcg atg ctg ggc       288
Thr Ile Asn Lys Met Cys Gly Ser Gly Met Lys Ala Ala Met Leu Gly
                 85                  90                  95 cat gac ctg atc gcc gcg gga tcg gcc ggc atc gtc gtc gcc ggc ggg       336
His Asp Leu Ile Ala Ala Gly Ser Ala Gly Ile Val Val Ala Gly Gly
            100                 105                 110 atg gag agc atg tcg aac gcc ccc tac ctg ctg ccc aag gcg cgg tcg       384
Met Glu Ser Met Ser Asn Ala Pro Tyr Leu Leu Pro Lys Ala Arg Ser
        115                 120                 125 ggg atg cgc atg ggc cat gac cgt gtg ctg gat cac atg ttc ctc gac       432
Gly Met Arg Met Gly His Asp Arg Val Leu Asp His Met Phe Leu Asp
    130                 135                 140 ggg ttg gag gac gcc tat gac aag ggc cgc ctg atg ggc acc ttc gcc       480
Gly Leu Glu Asp Ala Tyr Asp Lys Gly Arg Leu Met Gly Thr Phe Ala
145                 150                 155                 160 gag gat tgc gcc ggc gat cac ggt ttc acc cgc gag gcg cag gac gac       528
Glu Asp Cys Ala Gly Asp His Gly Phe Thr Arg Glu Ala Gln Asp Asp
                165                 170                 175 tat gcg ctg acc agc ctg gcc cgc gcg cag gac gcc atc gcc agc ggt       576
Tyr Ala Leu Thr Ser Leu Ala Arg Ala Gln Asp Ala Ile Ala Ser Gly
            180                 185                 190 gcc ttc gcc gcc gag atc gcg ccc gtg acc gtc acg gca cgc aag gtg       624
Ala Phe Ala Ala Glu Ile Ala Pro Val Thr Val Thr Ala Arg Lys Val
        195                 200                 205 cag acc acc gtc gat acc gac gag atg ccc ggc aag gcc cgc ccc gag       672
Gln Thr Thr Val Asp Thr Asp Glu Met Pro Gly Lys Ala Arg Pro Glu
    210                 215                 220 aag atc ccc cat ctg aag ccc gcc ttc cgt gac ggt ggc acg gtc acg       720
Lys Ile Pro His Leu Lys Pro Ala Phe Arg Asp Gly Gly Thr Val Thr
225                 230                 235                 240 gcg gcg aac agc tcg tcg atc tcg gac ggg gcg gcg gcg ctg gtg atg       768
Ala Ala Asn Ser Ser Ser Ile Ser Asp Gly Ala Ala Ala Leu Val Met
                245                 250                 255 atg cgc cag tcg cag gcc gag aag ctg ggc ctg acg ccg atc gcg cgg       816
```

-continued

```
Met Arg Gln Ser Gln Ala Glu Lys Leu Gly Leu Thr Pro Ile Ala Arg
              260                 265                 270 atc atc ggt cat gcg acc cat gcc gac cgt ccc ggc ctg ttc ccg acg    864
Ile Ile Gly His Ala Thr His Ala Asp Arg Pro Gly Leu Phe Pro Thr
            275                 280                 285 gcc ccc atc ggc gcg atg cgc aag ctg ctg gac cgc acg gac acc cgc    912
Ala Pro Ile Gly Ala Met Arg Lys Leu Leu Asp Arg Thr Asp Thr Arg
        290                 295                 300 ctt ggc gat tac gac ctg ttc gag gtg aac gag gca ttc gcc gtc gtc    960
Leu Gly Asp Tyr Asp Leu Phe Glu Val Asn Glu Ala Phe Ala Val Val
305                 310                 315                 320 gcc atg atc gcg atg aag gag ctt ggc ctg cca cac gat gcc acg aac   1008
Ala Met Ile Ala Met Lys Glu Leu Gly Leu Pro His Asp Ala Thr Asn
                325                 330                 335 atc aac ggc ggg gcc tgc gcg ctt ggg cat ccc atc ggc gcg tcg ggg   1056
Ile Asn Gly Gly Ala Cys Ala Leu Gly His Pro Ile Gly Ala Ser Gly
            340                 345                 350 gcg cgg atc atg gtc acg ctg ctg aac gcg atg gcg gcg cgg ggc gcg   1104
Ala Arg Ile Met Val Thr Leu Leu Asn Ala Met Ala Ala Arg Gly Ala
        355                 360                 365 acg cgc ggg gcc gca tcc gtc tgc atc ggc ggg ggc gag gcg acg gcc   1152
Thr Arg Gly Ala Ala Ser Val Cys Ile Gly Gly Gly Glu Ala Thr Ala
370                 375                 380 atc gcg ctg gaa cgg ctg agc taa                                   1176
Ile Ala Leu Glu Arg Leu Ser
385                 390
```

<210> SEQ ID NO 176
<211> LENGTH: 391
<212> TYPE: PRT
<213> ORGANISM: Paracoccus sp. R1534

<400> SEQUENCE: 176

```
Met Asp Pro Ile Val Ile Thr Gly Ala Met Arg Thr Pro Met Gly Ala
1               5                   10                  15

Phe Gln Gly Asp Leu Ala Ala Met Asp Ala Pro Thr Leu Gly Ala Ala
                20                  25                  30

Ala Ile Arg Ala Ala Leu Asn Gly Leu Ser Pro Asp Met Val Asp Glu
            35                  40                  45

Val Leu Met Gly Cys Val Leu Pro Ala Gly Gln Gly Gln Ala Pro Ala
        50                  55                  60

Arg Gln Ala Ala Leu Asp Ala Gly Leu Pro Leu Ser Ala Gly Ala Thr
65                  70                  75                  80

Thr Ile Asn Lys Met Cys Gly Ser Gly Met Lys Ala Ala Met Leu Gly
                85                  90                  95

His Asp Leu Ile Ala Ala Gly Ser Ala Gly Ile Val Val Ala Gly Gly
            100                 105                 110

Met Glu Ser Met Ser Asn Ala Pro Tyr Leu Leu Pro Lys Ala Arg Ser
        115                 120                 125

Gly Met Arg Met Gly His Asp Arg Val Leu Asp His Met Phe Leu Asp
    130                 135                 140

Gly Leu Glu Asp Ala Tyr Asp Lys Gly Arg Leu Met Gly Thr Phe Ala
145                 150                 155                 160

Glu Asp Cys Ala Gly Asp His Gly Phe Thr Arg Glu Ala Gln Asp Asp
                165                 170                 175

Tyr Ala Leu Thr Ser Leu Ala Arg Ala Gln Asp Ala Ile Ala Ser Gly
            180                 185                 190
```

-continued

```
Ala Phe Ala Ala Glu Ile Ala Pro Val Thr Val Thr Ala Arg Lys Val
        195                 200                 205

Gln Thr Thr Val Asp Thr Asp Glu Met Pro Gly Lys Ala Arg Pro Glu
    210                 215                 220

Lys Ile Pro His Leu Lys Pro Ala Phe Arg Asp Gly Gly Thr Val Thr
225                 230                 235                 240

Ala Ala Asn Ser Ser Ile Ser Asp Gly Ala Ala Leu Val Met
                245                 250                 255

Met Arg Gln Ser Gln Ala Glu Lys Leu Gly Leu Thr Pro Ile Ala Arg
                260                 265                 270

Ile Ile Gly His Ala Thr His Ala Asp Arg Pro Gly Leu Phe Pro Thr
                275                 280                 285

Ala Pro Ile Gly Ala Met Arg Lys Leu Leu Asp Arg Thr Asp Thr Arg
    290                 295                 300

Leu Gly Asp Tyr Asp Leu Phe Glu Val Asn Glu Ala Phe Ala Val Val
305                 310                 315                 320

Ala Met Ile Ala Met Lys Glu Leu Gly Leu Pro His Asp Ala Thr Asn
                325                 330                 335

Ile Asn Gly Gly Ala Cys Ala Leu Gly His Pro Ile Gly Ala Ser Gly
                340                 345                 350

Ala Arg Ile Met Val Thr Leu Leu Asn Ala Met Ala Ala Arg Gly Ala
                355                 360                 365

Thr Arg Gly Ala Ala Ser Val Cys Ile Gly Gly Glu Ala Thr Ala
    370                 375                 380

Ile Ala Leu Glu Arg Leu Ser
385                 390

<210> SEQ ID NO 177
<211> LENGTH: 1980
<212> TYPE: DNA
<213> ORGANISM: Paracoccus sp. R114
<220> FEATURE:
<221> NAME/KEY: CDS
<222> LOCATION: (1)..(1170)
<223> OTHER INFORMATION: phaA
<220> FEATURE:
<221> NAME/KEY: misc_feature
<222> LOCATION: (1179)..(1194)
<223> OTHER INFORMATION: inverted repeat between genes constituting a
      putative transcriptional stop
<220> FEATURE:
<221> NAME/KEY: misc_feature
<222> LOCATION: (1196)..(1210)
<223> OTHER INFORMATION: inverted repeat between genes constituting a
      putative transcriptional stop
<220> FEATURE:
<221> NAME/KEY: CDS
<222> LOCATION: (1258)..(1980)
<223> OTHER INFORMATION: phaB

<400> SEQUENCE: 177 atg acc aaa gcc gta atc gta tct gcc gca cgt acc ccc gtc ggc agc      48
Met Thr Lys Ala Val Ile Val Ser Ala Ala Arg Thr Pro Val Gly Ser
1               5                   10                  15 ttc atg ggc gca ttc gcc aat gtc ccc gca cat gat ctg ggc gcc gcc      96
Phe Met Gly Ala Phe Ala Asn Val Pro Ala His Asp Leu Gly Ala Ala
                20                  25                  30 gtc ctg cgc gag gtc gtg gcc cgc gcc ggt gtc gac ccc gcc gag gtc     144
Val Leu Arg Glu Val Val Ala Arg Ala Gly Val Asp Pro Ala Glu Val
            35                  40                  45 agc gag acg atc ctg ggc cag gtg ctg acc gcc gcg cag ggc cag aac     192
Ser Glu Thr Ile Leu Gly Gln Val Leu Thr Ala Ala Gln Gly Gln Asn
        50                  55                  60
```

```
                50                      55                      60
ccc gcg cgc cag gcg cat atc aat gcg ggc ctg ccc aag gaa tcg gcg       240
Pro Ala Arg Gln Ala His Ile Asn Ala Gly Leu Pro Lys Glu Ser Ala
65                  70                  75                  80 gcg tgg ctc atc aac cag gtc tgc ggc tcg ggg ctg cgc gcc gtc gcg       288
Ala Trp Leu Ile Asn Gln Val Cys Gly Ser Gly Leu Arg Ala Val Ala
                85                  90                  95 ctg gcg gcg cag cag gtc atg ctg ggc gat gcg cag atc gtt ctg gcg       336
Leu Ala Ala Gln Gln Val Met Leu Gly Asp Ala Gln Ile Val Leu Ala
            100                 105                 110 ggg ggc cag gag agc atg tcg ctg tcg acc cat gcc gcc tat ctg cgc       384
Gly Gly Gln Glu Ser Met Ser Leu Ser Thr His Ala Ala Tyr Leu Arg
        115                 120                 125 gcg ggc cag aag atg ggc gac atg aag atg atc gac acc atg atc cgc       432
Ala Gly Gln Lys Met Gly Asp Met Lys Met Ile Asp Thr Met Ile Arg
    130                 135                 140 gac ggg ctg tgg gat gcc ttc aac ggc tat cac atg ggt cag acc gcc       480
Asp Gly Leu Trp Asp Ala Phe Asn Gly Tyr His Met Gly Gln Thr Ala
145                 150                 155                 160 gag aac gtg gcc gac cag tgg tcg atc agc cgc gac cag cag gac gaa       528
Glu Asn Val Ala Asp Gln Trp Ser Ile Ser Arg Asp Gln Gln Asp Glu
                165                 170                 175 ttc gcc ctg gct tcg cag aac aag gcc gag gcc gcg cag aat gcg ggc       576
Phe Ala Leu Ala Ser Gln Asn Lys Ala Glu Ala Ala Gln Asn Ala Gly
            180                 185                 190 cgc ttc gat gac gaa atc gtc gcc tat acc gtc aag ggc cgc aag ggc       624
Arg Phe Asp Asp Glu Ile Val Ala Tyr Thr Val Lys Gly Arg Lys Gly
        195                 200                 205 gac acg gtc gtc gac aag gac gaa tac atc cgc cac ggc gcc acg atc       672
Asp Thr Val Val Asp Lys Asp Glu Tyr Ile Arg His Gly Ala Thr Ile
    210                 215                 220 gag ggc atg cag aag ctg cgc ccc gcc ttc acc aag gaa ggc tcg gtc       720
Glu Gly Met Gln Lys Leu Arg Pro Ala Phe Thr Lys Glu Gly Ser Val
225                 230                 235                 240 acg gcg ggc aac gcg tcg ggc ctg aac gac ggc gcg gcg gcc gtc atg       768
Thr Ala Gly Asn Ala Ser Gly Leu Asn Asp Gly Ala Ala Ala Val Met
                245                 250                 255 gtc atg tcc gag gac gag gcc gca cgc cgc ggg ctg acg ccg ctg gcg       816
Val Met Ser Glu Asp Glu Ala Ala Arg Arg Gly Leu Thr Pro Leu Ala
            260                 265                 270 cgc atc gcc tcc tat gcg acg gcg ggc ctc gac ccg gcg atc atg ggc       864
Arg Ile Ala Ser Tyr Ala Thr Ala Gly Leu Asp Pro Ala Ile Met Gly
        275                 280                 285 acc ggg ccg atc ccc tcc agc cgc aag gcg ctg gaa aag gcg ggc tgg       912
Thr Gly Pro Ile Pro Ser Ser Arg Lys Ala Leu Glu Lys Ala Gly Trp
    290                 295                 300 tcg gtc ggc gac ctg gac ctg gtc gag gcg aac gag gcc ttt gcc gcg       960
Ser Val Gly Asp Leu Asp Leu Val Glu Ala Asn Glu Ala Phe Ala Ala
305                 310                 315                 320 cag gcc tgc gcc gtg aac aag gac atg ggc tgg gat ccg tcc atc gtg      1008
Gln Ala Cys Ala Val Asn Lys Asp Met Gly Trp Asp Pro Ser Ile Val
                325                 330                 335 aac gtc aac ggc ggc gcg atc gcc atc ggc cac ccg atc ggc gcc tcg      1056
Asn Val Asn Gly Gly Ala Ile Ala Ile Gly His Pro Ile Gly Ala Ser
            340                 345                 350 ggg gcg cgg atc ctg aac acc ctg ctg ttc gag atg cag cgc cgc gac      1104
Gly Ala Arg Ile Leu Asn Thr Leu Leu Phe Glu Met Gln Arg Arg Asp
        355                 360                 365 gcc aag aag ggc ctt gcg acg ctg tgc atc ggc ggc ggc atg ggc gtc      1152
```

-continued

```
                Ala Lys Lys Gly Leu Ala Thr Leu Cys Ile Gly Gly Met Gly Val
                            370                 375                 380 gcc atg tgc ctc gaa cgc tgaacgaccg gcgtgtgcgc aatttaattg              1200
Ala Met Cys Leu Glu Arg
385                 390 cgcacacgcc ccctgcaaag tagcaatgtt ttacgataac gaatgaaggg gggaatc        1257 atg tcc aag gta gca ctg gtc acc ggc gga tcg cgc ggc atc ggc gcc      1305
Met Ser Lys Val Ala Leu Val Thr Gly Gly Ser Arg Gly Ile Gly Ala
                    395                 400                 405 gag atc tgc aag gcg ctt cag gcc gca ggc tat acc gtc gcc gcg aac      1353
Glu Ile Cys Lys Ala Leu Gln Ala Ala Gly Tyr Thr Val Ala Ala Asn
                410                 415                 420 tat gcc ggc aat gac gac gcg gcc aag gcc ttc acc gag gaa acc ggc      1401
Tyr Ala Gly Asn Asp Asp Ala Ala Lys Ala Phe Thr Glu Glu Thr Gly
            425                 430                 435 atc aag acc tac aag tgg tcg gtc gcc gat tac gat gcc tgc aag gcc      1449
Ile Lys Thr Tyr Lys Trp Ser Val Ala Asp Tyr Asp Ala Cys Lys Ala
        440                 445                 450 ggc atc gcc cag gtc gaa gag gat ctg ggc ccg atc gcc gtg ctg atc      1497
Gly Ile Ala Gln Val Glu Glu Asp Leu Gly Pro Ile Ala Val Leu Ile
455                 460                 465                 470 aac aat gcc ggg atc acc cgc gac gcg ccc ttc cac aag atg acg ccc      1545
Asn Asn Ala Gly Ile Thr Arg Asp Ala Pro Phe His Lys Met Thr Pro
                    475                 480                 485 gag aag tgg aag gag gtc atc gac acc aac ctg acc ggc acc ttc aac      1593
Glu Lys Trp Lys Glu Val Ile Asp Thr Asn Leu Thr Gly Thr Phe Asn
                490                 495                 500 atg acc cat ccg gtc tgg ccg ggc atg cgc gaa cgc aag ttc gga cgc      1641
Met Thr His Pro Val Trp Pro Gly Met Arg Glu Arg Lys Phe Gly Arg
            505                 510                 515 gtc atc aac atc agc tcg atc aac ggg cag aag ggc cag ttc ggg cag      1689
Val Ile Asn Ile Ser Ser Ile Asn Gly Gln Lys Gly Gln Phe Gly Gln
        520                 525                 530 gcg aac tat gcc gcg gcc aag gcg ggc gac ctg ggc ttc acc aag tcg      1737
Ala Asn Tyr Ala Ala Ala Lys Ala Gly Asp Leu Gly Phe Thr Lys Ser
535                 540                 545                 550 ctg gcg cag gaa ggc gcg cgc aac aac atc acc gtc aac gcg atc tgc      1785
Leu Ala Gln Glu Gly Ala Arg Asn Asn Ile Thr Val Asn Ala Ile Cys
                    555                 560                 565 ccc ggc tat atc gcg acg gac atg gtg atg gcc gtt ccc gaa cag gtc      1833
Pro Gly Tyr Ile Ala Thr Asp Met Val Met Ala Val Pro Glu Gln Val
                570                 575                 580 cgc gag ggg atc atc gcg cag atc ccc gtc ggc cgc ttg ggc gag ccg      1881
Arg Glu Gly Ile Ile Ala Gln Ile Pro Val Gly Arg Leu Gly Glu Pro
            585                 590                 595 tcc gag atc gcg cgc tgc gtg gtg ttc ctg gcc tcc gac gat gcg ggc      1929
Ser Glu Ile Ala Arg Cys Val Val Phe Leu Ala Ser Asp Asp Ala Gly
        600                 605                 610 ttc gtc aca ggc tcg acc atc acg gcg aat ggc ggc cag tac tac atc      1977
Phe Val Thr Gly Ser Thr Ile Thr Ala Asn Gly Gly Gln Tyr Tyr Ile
615                 620                 625                 630 tga                                                                   1980
```

<210> SEQ ID NO 178
<211> LENGTH: 390
<212> TYPE: PRT
<213> ORGANISM: Paracoccus sp. R114

<400> SEQUENCE: 178

```
Met Thr Lys Ala Val Ile Val Ser Ala Ala Arg Thr Pro Val Gly Ser
1               5                   10                  15

Phe Met Gly Ala Phe Ala Asn Val Pro Ala His Asp Leu Gly Ala Ala
            20                  25                  30

Val Leu Arg Glu Val Val Ala Arg Ala Gly Val Asp Pro Ala Glu Val
        35                  40                  45

Ser Glu Thr Ile Leu Gly Gln Val Leu Thr Ala Ala Gln Gly Gln Asn
50                  55                  60

Pro Ala Arg Gln Ala His Ile Asn Ala Gly Leu Pro Lys Glu Ser Ala
65                  70                  75                  80

Ala Trp Leu Ile Asn Gln Val Cys Gly Ser Gly Leu Arg Ala Val Ala
                85                  90                  95

Leu Ala Ala Gln Gln Val Met Leu Gly Asp Ala Gln Ile Val Leu Ala
                100                 105                 110

Gly Gly Gln Glu Ser Met Ser Leu Ser Thr His Ala Ala Tyr Leu Arg
            115                 120                 125

Ala Gly Gln Lys Met Gly Asp Met Lys Met Ile Asp Thr Met Ile Arg
130                 135                 140

Asp Gly Leu Trp Asp Ala Phe Asn Gly Tyr His Met Gly Gln Thr Ala
145                 150                 155                 160

Glu Asn Val Ala Asp Gln Trp Ser Ile Ser Arg Asp Gln Gln Asp Glu
                165                 170                 175

Phe Ala Leu Ala Ser Gln Asn Lys Ala Glu Ala Ala Gln Asn Ala Gly
                180                 185                 190

Arg Phe Asp Asp Glu Ile Val Ala Tyr Thr Val Lys Gly Arg Lys Gly
            195                 200                 205

Asp Thr Val Val Asp Lys Asp Glu Tyr Ile Arg His Gly Ala Thr Ile
210                 215                 220

Glu Gly Met Gln Lys Leu Arg Pro Ala Phe Thr Lys Glu Gly Ser Val
225                 230                 235                 240

Thr Ala Gly Asn Ala Ser Gly Leu Asn Asp Gly Ala Ala Ala Val Met
                245                 250                 255

Val Met Ser Glu Asp Glu Ala Ala Arg Arg Gly Leu Thr Pro Leu Ala
                260                 265                 270

Arg Ile Ala Ser Tyr Ala Thr Ala Gly Leu Asp Pro Ala Ile Met Gly
            275                 280                 285

Thr Gly Pro Ile Pro Ser Ser Arg Lys Ala Leu Glu Lys Ala Gly Trp
290                 295                 300

Ser Val Gly Asp Leu Asp Leu Val Glu Ala Asn Glu Ala Phe Ala Ala
305                 310                 315                 320

Gln Ala Cys Ala Val Asn Lys Asp Met Gly Trp Asp Pro Ser Ile Val
                325                 330                 335

Asn Val Asn Gly Gly Ala Ile Ala Ile Gly His Pro Ile Gly Ala Ser
            340                 345                 350

Gly Ala Arg Ile Leu Asn Thr Leu Leu Phe Glu Met Gln Arg Arg Asp
            355                 360                 365

Ala Lys Lys Gly Leu Ala Thr Leu Cys Ile Gly Gly Gly Met Gly Val
            370                 375                 380

Ala Met Cys Leu Glu Arg
385                 390

<210> SEQ ID NO 179
<211> LENGTH: 240
<212> TYPE: PRT
```

<213> ORGANISM: Paracoccus sp. R114

<400> SEQUENCE: 179

| | | | | | | | | | | | | | | |
|---|---|---|---|---|---|---|---|---|---|---|---|---|---|---|
| Met | Ser | Lys | Val | Ala | Leu | Val | Thr | Gly | Gly | Ser | Arg | Gly | Ile | Gly | Ala |
| 1 | | | | 5 | | | | | 10 | | | | | 15 | |
| Glu | Ile | Cys | Lys | Ala | Leu | Gln | Ala | Ala | Gly | Tyr | Thr | Val | Ala | Ala | Asn |
| | | | 20 | | | | | 25 | | | | | 30 | | |
| Tyr | Ala | Gly | Asn | Asp | Asp | Ala | Ala | Lys | Ala | Phe | Thr | Glu | Glu | Thr | Gly |
| | | 35 | | | | 40 | | | | | 45 | | | | |
| Ile | Lys | Thr | Tyr | Lys | Trp | Ser | Val | Ala | Asp | Tyr | Asp | Ala | Cys | Lys | Ala |
| | 50 | | | | | 55 | | | | | 60 | | | | |
| Gly | Ile | Ala | Gln | Val | Glu | Glu | Asp | Leu | Gly | Pro | Ile | Ala | Val | Leu | Ile |
| 65 | | | | | 70 | | | | | 75 | | | | | 80 |
| Asn | Asn | Ala | Gly | Ile | Thr | Arg | Asp | Ala | Pro | Phe | His | Lys | Met | Thr | Pro |
| | | | | 85 | | | | | 90 | | | | | 95 | |
| Glu | Lys | Trp | Lys | Glu | Val | Ile | Asp | Thr | Asn | Leu | Thr | Gly | Thr | Phe | Asn |
| | | | 100 | | | | | 105 | | | | | 110 | | |
| Met | Thr | His | Pro | Val | Trp | Pro | Gly | Met | Arg | Glu | Arg | Lys | Phe | Gly | Arg |
| | | | 115 | | | | | 120 | | | | | 125 | | |
| Val | Ile | Asn | Ile | Ser | Ser | Ile | Asn | Gly | Gln | Lys | Gly | Gln | Phe | Gly | Gln |
| | 130 | | | | | 135 | | | | | 140 | | | | |
| Ala | Asn | Tyr | Ala | Ala | Ala | Lys | Ala | Gly | Asp | Leu | Gly | Phe | Thr | Lys | Ser |
| 145 | | | | | 150 | | | | | 155 | | | | | 160 |
| Leu | Ala | Gln | Glu | Gly | Ala | Arg | Asn | Asn | Ile | Thr | Val | Asn | Ala | Ile | Cys |
| | | | | 165 | | | | | 170 | | | | | 175 | |
| Pro | Gly | Tyr | Ile | Ala | Thr | Asp | Met | Val | Met | Ala | Val | Pro | Glu | Gln | Val |
| | | | 180 | | | | | 185 | | | | | 190 | | |
| Arg | Glu | Gly | Ile | Ile | Ala | Gln | Ile | Pro | Val | Gly | Arg | Leu | Gly | Glu | Pro |
| | | 195 | | | | | 200 | | | | | 205 | | | |
| Ser | Glu | Ile | Ala | Arg | Cys | Val | Val | Phe | Leu | Ala | Ser | Asp | Asp | Ala | Gly |
| | 210 | | | | | 215 | | | | | 220 | | | | |
| Phe | Val | Thr | Gly | Ser | Thr | Ile | Thr | Ala | Asn | Gly | Gly | Gln | Tyr | Tyr | Ile |
| 225 | | | | | 230 | | | | | 235 | | | | | 240 |

<210> SEQ ID NO 180
<211> LENGTH: 729
<212> TYPE: DNA
<213> ORGANISM: Paracoccus carotinifaciens E-396
<220> FEATURE:
<221> NAME/KEY: CDS
<222> LOCATION: (1)..(726)
<223> OTHER INFORMATION: Beta-carotene Beta-4 oxygenase

<400> SEQUENCE: 180

| | | | | | | | | | | | | | | | | |
|---|---|---|---|---|---|---|---|---|---|---|---|---|---|---|---|---|
| atg | agc | gca | cat | gcc | ctg | ccc | aag | gca | gat | ctg | acc | gcc | acc | agt | ttg | 48 |
| Met | Ser | Ala | His | Ala | Leu | Pro | Lys | Ala | Asp | Leu | Thr | Ala | Thr | Ser | Leu | |
| 1 | | | | 5 | | | | | 10 | | | | | 15 | | |
| atc | gtc | tcg | ggc | ggc | atc | atc | gcc | gcg | tgg | ctg | gcc | ctg | cat | gtg | cat | 96 |
| Ile | Val | Ser | Gly | Gly | Ile | Ile | Ala | Ala | Trp | Leu | Ala | Leu | His | Val | His | |
| | | | 20 | | | | | 25 | | | | | 30 | | | |
| gcg | ctg | tgg | ttt | ctg | gac | gcg | gcg | gcg | cat | ccc | atc | ctg | gcg | gtc | gcg | 144 |
| Ala | Leu | Trp | Phe | Leu | Asp | Ala | Ala | Ala | His | Pro | Ile | Leu | Ala | Val | Ala | |
| | | 35 | | | | | 40 | | | | | 45 | | | | |
| aat | ttc | ctg | ggg | ctg | acc | tgg | ctg | tcg | gtc | ggt | ctg | ttc | atc | atc | gcg | 192 |
| Asn | Phe | Leu | Gly | Leu | Thr | Trp | Leu | Ser | Val | Gly | Leu | Phe | Ile | Ile | Ala | |
| | 50 | | | | | 55 | | | | | 60 | | | | | |
| cat | gac | gcg | atg | cat | ggg | tcg | gtc | gtg | ccg | ggg | cgc | ccg | cgc | gcc | aat | 240 |
| His | Asp | Ala | Met | His | Gly | Ser | Val | Val | Pro | Gly | Arg | Pro | Arg | Ala | Asn | |

```
                                                                     288
gcg gcg atg ggc cag ctt gtc ctg tgg ctg tat gcc gga ttt tcc tgg
Ala Ala Met Gly Gln Leu Val Leu Trp Leu Tyr Ala Gly Phe Ser Trp
             85                  90                  95

336
cgc aag atg atc gtc aag cac atg gcc cat cat cgc cat gcc gga acc
Arg Lys Met Ile Val Lys His Met Ala His His Arg His Ala Gly Thr
            100                 105                 110

384
gac gac gac cca gat ttc gac cat ggc ggc ccg gtc cgc tgg tac gcc
Asp Asp Asp Pro Asp Phe Asp His Gly Gly Pro Val Arg Trp Tyr Ala
        115                 120                 125

432
cgc ttc atc ggc acc tat ttc ggc tgg cgc gag ggg ctg ctg ctg ccc
Arg Phe Ile Gly Thr Tyr Phe Gly Trp Arg Glu Gly Leu Leu Leu Pro
    130                 135                 140

480
gtc atc gtg acg gtc tat gcg ctg atg ttg ggg gat cgc tgg atg tac
Val Ile Val Thr Val Tyr Ala Leu Met Leu Gly Asp Arg Trp Met Tyr
145                 150                 155                 160

528
gtg gtc ttc tgg ccg ttg ccg tcg atc ctg gcg tcg atc cag ctg ttc
Val Val Phe Trp Pro Leu Pro Ser Ile Leu Ala Ser Ile Gln Leu Phe
                165                 170                 175

576
gtg ttc ggc atc tgg ctg ccg cac cgc ccc ggc cac gac gcg ttc ccg
Val Phe Gly Ile Trp Leu Pro His Arg Pro Gly His Asp Ala Phe Pro
            180                 185                 190

624
gac cgc cac aat gcg cgg tcg tcg cgg atc agc gac ccc gtg tcg ctg
Asp Arg His Asn Ala Arg Ser Ser Arg Ile Ser Asp Pro Val Ser Leu
        195                 200                 205

672
ctg acc tgc ttt cac ttt ggc ggt tat cat cac gaa cac cac ctg cac
Leu Thr Cys Phe His Phe Gly Gly Tyr His His Glu His His Leu His
    210                 215                 220

720
ccg acg gtg cct tgg tgg cgc ctg ccc agc acc cgc acc aag ggg gac
Pro Thr Val Pro Trp Trp Arg Leu Pro Ser Thr Arg Thr Lys Gly Asp
225                 230                 235                 240

729
acc gca tga
Thr Ala

<210> SEQ ID NO 181
<211> LENGTH: 242
<212> TYPE: PRT
<213> ORGANISM: Paracoccus carotinifaciens E-396

<400> SEQUENCE: 181

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Val Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140
```

```
Val Ile Val Thr Val Tyr Ala Leu Met Leu Gly Asp Arg Trp Met Tyr
145                 150                 155                 160

Val Val Phe Trp Pro Leu Pro Ser Ile Leu Ala Ser Ile Gln Leu Phe
            165                 170                 175

Val Phe Gly Ile Trp Leu Pro His Arg Pro Gly His Asp Ala Phe Pro
            180                 185                 190

Asp Arg His Asn Ala Arg Ser Ser Arg Ile Ser Asp Pro Val Ser Leu
            195                 200                 205

Leu Thr Cys Phe His Phe Gly Gly Tyr His His Glu His His Leu His
            210                 215                 220

Pro Thr Val Pro Trp Trp Arg Leu Pro Ser Thr Arg Thr Lys Gly Asp
225                 230                 235                 240

Thr Ala
```

<210> SEQ ID NO 182
<211> LENGTH: 510
<212> TYPE: DNA
<213> ORGANISM: Paracoccus sp. R1534
<220> FEATURE:
<221> NAME/KEY: CDS
<222> LOCATION: (1)..(507)
<223> OTHER INFORMATION: Beta-Carotene hydroxylase

<400> SEQUENCE: 182

```
atg agc act tgg gcc gca atc ctg acc gtc atc ctg acc gtc gcc gcg      48
Met Ser Thr Trp Ala Ala Ile Leu Thr Val Ile Leu Thr Val Ala Ala
1               5                   10                  15 atg gag ctg acg gcc tac tcc gtc cat cgg tgg atc atg cat ggc ccc      96
Met Glu Leu Thr Ala Tyr Ser Val His Arg Trp Ile Met His Gly Pro
                20                  25                  30 ctg ggc tgg ggc tgg cat aaa tcg cac cac gac gag gat cac gac cac     144
Leu Gly Trp Gly Trp His Lys Ser His His Asp Glu Asp His Asp His
            35                  40                  45 gcg ctc gag aag aac gac ctc tat ggc gtc atc ttc gcg gta atc tcg     192
Ala Leu Glu Lys Asn Asp Leu Tyr Gly Val Ile Phe Ala Val Ile Ser
        50                  55                  60 atc gtg ctg ttc gcg atc ggc gcg atg ggg tcg gat ctg gcc tgg tgg     240
Ile Val Leu Phe Ala Ile Gly Ala Met Gly Ser Asp Leu Ala Trp Trp
65                  70                  75                  80 ctg gcg gtg ggg gtc acc tgc tac ggg ctg atc tac tat ttc ctg cat     288
Leu Ala Val Gly Val Thr Cys Tyr Gly Leu Ile Tyr Tyr Phe Leu His
                85                  90                  95 gac ggc ttg gtg cat ggg cgc tgg ccg ttc cgc tat gtc ccc aag cgc     336
Asp Gly Leu Val His Gly Arg Trp Pro Phe Arg Tyr Val Pro Lys Arg
            100                 105                 110 ggc tat ctt cgt cgc gtc tac cag gca cac agg atg cat cac gcg gtc     384
Gly Tyr Leu Arg Arg Val Tyr Gln Ala His Arg Met His His Ala Val
        115                 120                 125 cat ggc cgc gag aac tgc gtc agc ttc ggt ttc atc tgg gcg ccc tcg     432
His Gly Arg Glu Asn Cys Val Ser Phe Gly Phe Ile Trp Ala Pro Ser
    130                 135                 140 gtc gac agc ctc aag gca gag ctg aaa cgc tcg ggc gcg ctg ctg aag     480
Val Asp Ser Leu Lys Ala Glu Leu Lys Arg Ser Gly Ala Leu Leu Lys
145                 150                 155                 160 gac cgc gaa ggg gcg gat cgc aat aca tga                             510
Asp Arg Glu Gly Ala Asp Arg Asn Thr
                165
```

<210> SEQ ID NO 183

```
<211> LENGTH: 169
<212> TYPE: PRT
<213> ORGANISM: Paracoccus sp. R1534

<400> SEQUENCE: 183

Met Ser Thr Trp Ala Ala Ile Leu Thr Val Ile Leu Thr Val Ala Ala
1               5                   10                  15

Met Glu Leu Thr Ala Tyr Ser Val His Arg Trp Ile Met His Gly Pro
            20                  25                  30

Leu Gly Trp Gly Trp His Lys Ser His His Asp Glu Asp His Asp His
        35                  40                  45

Ala Leu Glu Lys Asn Asp Leu Tyr Gly Val Ile Phe Ala Val Ile Ser
    50                  55                  60

Ile Val Leu Phe Ala Ile Gly Ala Met Gly Ser Asp Leu Ala Trp Trp
65                  70                  75                  80

Leu Ala Val Gly Val Thr Cys Tyr Gly Leu Ile Tyr Tyr Phe Leu His
                85                  90                  95

Asp Gly Leu Val His Gly Arg Trp Pro Phe Arg Tyr Val Pro Lys Arg
            100                 105                 110

Gly Tyr Leu Arg Arg Val Tyr Gln Ala His Arg Met His His Ala Val
        115                 120                 125

His Gly Arg Glu Asn Cys Val Ser Phe Gly Phe Ile Trp Ala Pro Ser
130                 135                 140

Val Asp Ser Leu Lys Ala Glu Leu Lys Arg Ser Gly Ala Leu Leu Lys
145                 150                 155                 160

Asp Arg Glu Gly Ala Asp Arg Asn Thr
                165

<210> SEQ ID NO 184
<211> LENGTH: 888
<212> TYPE: DNA
<213> ORGANISM: Paracoccus sp. R1534
<220> FEATURE:
<221> NAME/KEY: CDS
<222> LOCATION: (1)..(885)
<223> OTHER INFORMATION: farnesyltransferase or geranylgeranyl
      diphosphate synthase

<400> SEQUENCE: 184 atg acg ccc aag cag caa ttc ccc cta cgc gat ctg gtc gag atc agg    48
Met Thr Pro Lys Gln Gln Phe Pro Leu Arg Asp Leu Val Glu Ile Arg
1               5                   10                  15 ctg gcg cag atc tcg ggc cag ttc ggc gtg gtc tcg gcc ccg ctc ggc    96
Leu Ala Gln Ile Ser Gly Gln Phe Gly Val Val Ser Ala Pro Leu Gly
            20                  25                  30 gcg gcc atg agc gat gcc gcc ctg tcc ccc ggc aaa cgc ttt cgc gcc   144
Ala Ala Met Ser Asp Ala Ala Leu Ser Pro Gly Lys Arg Phe Arg Ala
        35                  40                  45 gtg ctg atg ctg atg gtc gcc gaa agc tcg ggc ggg gtc tgc gat gcg   192
Val Leu Met Leu Met Val Ala Glu Ser Ser Gly Gly Val Cys Asp Ala
    50                  55                  60 atg gtc gat gcc gcc tgc gcg gtc gag atg gtc cat gcc gca tcg ctg   240
Met Val Asp Ala Ala Cys Ala Val Glu Met Val His Ala Ala Ser Leu
65                  70                  75                  80 atc ttc gac gac atg ccc tgc atg gac gat gcc agg acc cgt cgc ggt   288
Ile Phe Asp Asp Met Pro Cys Met Asp Asp Ala Arg Thr Arg Arg Gly
                85                  90                  95 cag ccc gcc acc cat gtc gcc cat ggc gag ggg cgc gcg gtg ctt gcg   336
Gln Pro Ala Thr His Val Ala His Gly Glu Gly Arg Ala Val Leu Ala
            100                 105                 110
```

```
ggc atc gcc ctg atc acc gag gcc atg cgg att ttg ggc gag gcg cgc      384
Gly Ile Ala Leu Ile Thr Glu Ala Met Arg Ile Leu Gly Glu Ala Arg
        115                 120                 125 ggc gcg acg ccg gat cag cgc gca agg ctg gtc gca tcc atg tcg cgc      432
Gly Ala Thr Pro Asp Gln Arg Ala Arg Leu Val Ala Ser Met Ser Arg
130                 135                 140 gcg atg gga ccg gtg ggg ctg tgc gca ggg cag gat ctg gac ctg cac      480
Ala Met Gly Pro Val Gly Leu Cys Ala Gly Gln Asp Leu Asp Leu His
145                 150                 155                 160 gcc ccc aag gac gcc gcc ggg atc gaa cgt gaa cag gac ctc aag acc      528
Ala Pro Lys Asp Ala Ala Gly Ile Glu Arg Glu Gln Asp Leu Lys Thr
                165                 170                 175 ggc gtg ctg ttc gtc gcg ggc ctc gag atg ctg tcc att att aag ggt      576
Gly Val Leu Phe Val Ala Gly Leu Glu Met Leu Ser Ile Ile Lys Gly
            180                 185                 190 ctg gac aag gcc gag acc gag cag ctc atg gcc ttc ggg cgt cag ctt      624
Leu Asp Lys Ala Glu Thr Glu Gln Leu Met Ala Phe Gly Arg Gln Leu
        195                 200                 205 ggt cgg gtc ttc cag tcc tat gac gac ctg ctg gac gtg atc ggc gac      672
Gly Arg Val Phe Gln Ser Tyr Asp Asp Leu Leu Asp Val Ile Gly Asp
    210                 215                 220 aag gcc agc acc ggc aag gat acg ggg cgc gac acc gcc gcc ccc ggc      720
Lys Ala Ser Thr Gly Lys Asp Thr Gly Arg Asp Thr Ala Ala Pro Gly
225                 230                 235                 240 cca aag cgc ggc ctg atg gcg gtc gga cag atg ggc gac gtg gcg cag      768
Pro Lys Arg Gly Leu Met Ala Val Gly Gln Met Gly Asp Val Ala Gln
                245                 250                 255 cat tac cgc gcc agc cgc gcg caa ctg gac gag ctg atg cgc acc cgg      816
His Tyr Arg Ala Ser Arg Ala Gln Leu Asp Glu Leu Met Arg Thr Arg
            260                 265                 270 ctg ttc cgc ggg ggg cag atc gcg gac ctg ctg gcc cgc gtg ctg ccg      864
Leu Phe Arg Gly Gly Gln Ile Ala Asp Leu Leu Ala Arg Val Leu Pro
        275                 280                 285 cat gac atc cgc cgc agc gcc tag                                      888
His Asp Ile Arg Arg Ser Ala
    290                 295

<210> SEQ ID NO 185
<211> LENGTH: 295
<212> TYPE: PRT
<213> ORGANISM: Paracoccus sp. R1534

<400> SEQUENCE: 185

Met Thr Pro Lys Gln Gln Phe Pro Leu Arg Asp Leu Val Glu Ile Arg
1               5                   10                  15

Leu Ala Gln Ile Ser Gly Gln Phe Gly Val Val Ser Ala Pro Leu Gly
            20                  25                  30

Ala Ala Met Ser Asp Ala Ala Leu Ser Pro Gly Lys Arg Phe Arg Ala
        35                  40                  45

Val Leu Met Leu Met Val Ala Glu Ser Ser Gly Gly Val Cys Asp Ala
    50                  55                  60

Met Val Asp Ala Ala Cys Ala Val Glu Met Val His Ala Ala Ser Leu
65                  70                  75                  80

Ile Phe Asp Asp Met Pro Cys Met Asp Asp Ala Arg Thr Arg Arg Gly
                85                  90                  95

Gln Pro Ala Thr His Val Ala His Gly Glu Gly Arg Ala Val Leu Ala
            100                 105                 110

Gly Ile Ala Leu Ile Thr Glu Ala Met Arg Ile Leu Gly Glu Ala Arg
```

```
            115                 120                 125
Gly Ala Thr Pro Asp Gln Arg Ala Arg Leu Val Ala Ser Met Ser Arg
    130                 135                 140

Ala Met Gly Pro Val Gly Leu Cys Ala Gly Gln Asp Leu Asp Leu His
145                 150                 155                 160

Ala Pro Lys Asp Ala Ala Gly Ile Glu Arg Glu Gln Asp Leu Lys Thr
                165                 170                 175

Gly Val Leu Phe Val Ala Gly Leu Glu Met Leu Ser Ile Ile Lys Gly
            180                 185                 190

Leu Asp Lys Ala Glu Thr Glu Gln Leu Met Ala Phe Gly Arg Gln Leu
        195                 200                 205

Gly Arg Val Phe Gln Ser Tyr Asp Asp Leu Leu Asp Val Ile Gly Asp
    210                 215                 220

Lys Ala Ser Thr Gly Lys Asp Thr Gly Arg Asp Thr Ala Ala Pro Gly
225                 230                 235                 240

Pro Lys Arg Gly Leu Met Ala Val Gly Gln Met Gly Asp Val Ala Gln
                245                 250                 255

His Tyr Arg Ala Ser Arg Ala Gln Leu Asp Glu Leu Met Arg Thr Arg
            260                 265                 270

Leu Phe Arg Gly Gly Gln Ile Ala Asp Leu Leu Ala Arg Val Leu Pro
        275                 280                 285

His Asp Ile Arg Arg Ser Ala
    290                 295

<210> SEQ ID NO 186
<211> LENGTH: 30
<212> TYPE: DNA
<213> ORGANISM: Artificial
<220> FEATURE:
<223> OTHER INFORMATION: synthetic construct

<400> SEQUENCE: 186
aaggcctcat atgagcgcac atgccctgcc                                          30

<210> SEQ ID NO 187
<211> LENGTH: 28
<212> TYPE: DNA
<213> ORGANISM: Artificial
<220> FEATURE:
<223> OTHER INFORMATION: synthetic construct

<400> SEQUENCE: 187
cgggatcctc atgcggtgtc ccccttgg                                            28

<210> SEQ ID NO 188
<211> LENGTH: 30
<212> TYPE: DNA
<213> ORGANISM: Artificial
<220> FEATURE:
<223> OTHER INFORMATION: synthetic construct

<400> SEQUENCE: 188
aaggcctcat atgagcactt gggccgcaat                                          30

<210> SEQ ID NO 189
<211> LENGTH: 30
<212> TYPE: DNA
<213> ORGANISM: Artificial
<220> FEATURE:
<223> OTHER INFORMATION: synthetic construct
```

```
<400> SEQUENCE: 189
aggatcctca tgtattgcga tccgcccctt                                30

<210> SEQ ID NO 190
<211> LENGTH: 52
<212> TYPE: DNA
<213> ORGANISM: Artificial
<220> FEATURE:
<223> OTHER INFORMATION: synthetic construct

<400> SEQUENCE: 190
gtgcagcctc aggtcgacat atgcggccgc atccggatcc ctcctcctcc ag       52

<210> SEQ ID NO 191
<211> LENGTH: 52
<212> TYPE: DNA
<213> ORGANISM: Artificial
<220> FEATURE:
<223> OTHER INFORMATION: synthetic construct

<400> SEQUENCE: 191
cacgtcggag tccagctgta tacgccggcg taggcctagg gaggaggagg tc       52

<210> SEQ ID NO 192
<211> LENGTH: 52
<212> TYPE: DNA
<213> ORGANISM: Artificial
<220> FEATURE:
<223> OTHER INFORMATION: synthetic construct

<400> SEQUENCE: 192
gtgcaggagg aggtcgacat atgcggccgc atccggatcc ctgaggctcc ag       52

<210> SEQ ID NO 193
<211> LENGTH: 52
<212> TYPE: DNA
<213> ORGANISM: Artificial
<220> FEATURE:
<223> OTHER INFORMATION: synthetic construct

<400> SEQUENCE: 193
cacgtcctcc tccagctgta tacgccggcg taggcctagg gactccgagg tc       52

<210> SEQ ID NO 194
<211> LENGTH: 52
<212> TYPE: DNA
<213> ORGANISM: Artificial
<220> FEATURE:
<223> OTHER INFORMATION: synthetic construct

<400> SEQUENCE: 194
ctggagcctc aggtcgacat atgcggccgc atccggatcc ctcctcctgc ac       52

<210> SEQ ID NO 195
<211> LENGTH: 52
<212> TYPE: DNA
<213> ORGANISM: Artificial
<220> FEATURE:
<223> OTHER INFORMATION: synthetic construct

<400> SEQUENCE: 195
gacctcggag tccagctgta tacgccggcg taggcctagg gaggaggacg tg       52

<210> SEQ ID NO 196
<211> LENGTH: 52
```

-continued

```
<212> TYPE: DNA
<213> ORGANISM: Artificial
<220> FEATURE:
<223> OTHER INFORMATION: synthetic construct

<400> SEQUENCE: 196
ctggaggagg aggtcgacat atgcggccgc atccggatcc ctgaggctgc ac        52

<210> SEQ ID NO 197
<211> LENGTH: 52
<212> TYPE: DNA
<213> ORGANISM: Artificial
<220> FEATURE:
<223> OTHER INFORMATION: synthetic construct

<400> SEQUENCE: 197
gacctcctcc tccagctgta tacgccggcg taggcctagg gactccgacg tg        52
```

ISOPRENOID PRODUCTION

This application is a divisional of U.S. patent application Ser. No. 10/166,225, filed Jun. 5, 2002 now U.S. Pat. No. 6,989,257, which claims priority under 35 U.S.C. § 119(e) of U.S. Provisional Application Ser. No. 60/296,299, filed Jun. 6, 2001, now abandoned.

FIELD OF THE INVENTION

The present invention relates to novel polynucleotides and polypeptide sequences useful in the isoprenoid biosynthetic pathway. More particularly, the present invention provides recombinantly produced cells that exhibit improved production of zeaxanthin. Methods of making and using such cell lines are also provided.

BACKGROUND OF THE INVENTION

Carotenoids are commercially important C-40 isoprenoid compounds used as nutritional supplements, pharmaceuticals and food colorants for humans and as pigments for animal feed. Currently industrially important carotenoids are produced mainly by chemical synthesis (β-carotene, canthaxanthin and astaxanthin) or extraction from natural sources (lutein from marigold, capsanthin from paprika). Production of carotenoids, however, using microorganisms has been achieved in some cases. For example, β-carotene is produced by fermentation with the fungus *Blakeslea trispora* (Finkelstein et al., U.S. Pat. No. 5,328,845) or by pond culture using the halotolerant alga *Dunaliella salina* (Borowitzka, J. Biotechnol. 70, 313-321, 1999). Lycopene production has also been reported in *B. trispora* (Bernasconi et al., International Patent Application Publication No. WO 00/77234). Astaxanthin is produced by fermentation using yeast (*Phaffia rhodozyma*, (recently renamed *Xanthophyllomyces dendorous*)). (Jacobson et al., U.S. Pat. No. 6,015,684) or in photobioreactors or open ponds using the alga *Haematococcus pluvialis* (Lorenz and Cysewski, Trends Biotechnol. 18, 160-167, 1999; Olaizola, J. Appl. Phycol. 12, 499-506, 2000). Such microbial production systems, however, do not produce carotenoids in amounts sufficient for economical industrial scale production.

In the mid-1960's, scientists at Hoffmann-La Roche isolated several marine bacteria that produced the yellow carotenoid zeaxanthin, which has application in poultry pigmentation and the prevention of age-related macular degeneration in humans. One bacterium, which showed promising levels of zeaxanthin production, was given the strain designation R-1512, and it was deposited at the American Type Culture Collection (ATCC, Manassas, Va., USA) as strain ATCC 21588 (Schocher and Wiss, U.S. Pat. No. 3,891,504). Using the accepted taxonomic standards of that time (classification performed by the Eidg. Technische Hochschule (Zurich) and the National Collection of Industrial Bacteria, Torry Research Station (Aberdeen, Scotland)), the zeaxanthin-producing organism was classified as a member of the genus *Flavobacterium*, but no species designation was assigned.

An extensive mutagenesis and screening program was subsequently conducted to isolate mutants of R-1512 with higher zeaxanthin productivities. With respect to the presently described work, two such mutants are significant. These mutants, listed in order of their zeaxanthin productivities, are R1534 and R114. A variety of other mutants have been used over the years for biochemical studies of carotenoid biosynthesis (Goodwin, Biochem. Soc. Symp. 35, 233-244, 1972; McDermott et al., Biochem. J. 134, 1115-1117, 1973; Britton et al., Arch. Microbiol. 113, 33-37, 1977; Mohanty et al., Helvetica Chimica Acta 83, 2036-2053, 2000).

The early attempts to develop a commercially viable fermentation process for the production of zeaxanthin using classically derived mutants of strain R-1512 were not successful. However, with the advent of molecular biology, the possibility arose that higher zeaxanthin-producing strains could be developed. The first step in this direction was taken with the cloning and sequencing of the carotenoid gene cluster from strain R1534 (Hohmann et al., U.S. Pat. No. 6,087,152 ("Hohmann '152"), which is hereby incorporated by reference as if recited in full herein). Hohmann '152 discloses that the carotenoid genes were functionally expressed in *Escherichia coli* and *Bacillus subtilis* resulting in zeaxanthin production in these hosts. Hohmann '152 also disclosed that by modifying the carotenoid gene cluster or by adding a gene from an astaxanthin producing bacterium, it was possible to produce carotenoids other than zeaxanthin (See also Pasamontes et al., EP Application No. 872,554 ("Pasamontes '554")). Moreover, Pasamontes '554 disclosed that carotenoid production was increased in strain R1534 by introducing cloned carotenoid gene clusters on a multi-copy plasmid.

Despite the enormous structural diversity in isoprenoid compounds, all are biosynthesized from a common C-5 precursor, isopentenyl pyrophosphate (IPP). Up until the early 1990's it was generally accepted that IPP was synthesized in all organisms via the mevalonate pathway (FIG. 1A), even though some experimental results were not consistent with this biogenic scheme (Eisenreich et al., Chemistry and Biology 5, R221-R233, 1998). The discrepancies have since been reconciled by the discovery of an alternate pathway of IPP biosynthesis, the deoxyxylulose (DXP) pathway (Note: The alternate pathway of IPP biosynthesis has been referred to by various names in the scientific literature (DXP pathway, DOXP pathway, MEP pathway, GAP/pyruvate pathway and the non-mevalonate pathway). We use the name DXP pathway here only for the sake of simplicity). The first five reactions of the DXP pathway have been identified (FIG. 1A) (Herz et al., Proc. Nat. Acad. Sci. 97, 2486-2490, 2000), but the subsequent steps leading to formation of IPP have not yet been elucidated.

McDermott et al. (Biochem. J. 134, 1115-1117, 1973) and Britton et al. (J. Chem. Soc. Chem. Comm. p. 27, 1979) showed that crude extracts of zeaxanthin producing mutant strains derived from the original Roche isolates incorporated labeled mevalonate into zeaxanthin. While there was no reason to question this evidence for IPP biosynthesis via the mevalonate pathway, the work was done prior to the discovery of the DXP pathway, and it has been reported that some bacteria (*Streptomyces* species) possess both pathways for IPP synthesis and that expression of these pathways is temporally regulated (Seto et al., Tetrahedron Lett. 37, 7979-7982, 1996; Dairi et al., Mol. Gen. Genet. 262, 957-964, 2000.). In addition, at present, only a small number of eubacteria have been shown to possess the mevalonate pathway for IPP synthesis. The genes encoding the enzymes of the mevalonate pathway have been cloned and sequenced from some of these bacteria. (Wilding et al., J. Bacteriol. 182, 4319-4327, 2000 and Takagi et al., J. Bacteriol.; 182, 4153-4157, 2000).

Several examples exist where the application of metabolic engineering has succeeded in altering or improving carotenoid production in microorganisms (Lagarde et al., Appl. Env. Microbiol. 66, 64-72, 2000.; Wang et al., Biotechnol.

Bioeng. 62, 235-241, 1999; Wang et al., Biotechnol. Prog. 16, 922-926, 2000 (and references therein); Sandmann et al., Trends Biotechnol. 17, 233-237, 2000; Misawa and Shimada, J. Biotechnol. 59, 169-181, 1998; Matthews and Wurtzel, Appl. Microbiol. Biotechnol. 53, 396-400, 2000; Albrecht et al., Nature Biotechnol. 18, 843-846, 2000; Schmidt-Dannert et al., Nature Biotechnol. 18, 750-753 2000). For example, *E. coli*, a non-carotenogenic bacterium, can be engineered to produce carotenoids by introducing the cloned carotenoid (crt) genes from the bacteria *Agrobacterium aurantiacum, Erwinia herbicola* or *Erwinia uredovora* (Misawa and Shimada, J. Biotechnol. 59, 169-181, 1998). Harker and Bramley (FEBS Lett. 448, 115-119, 1999) and Matthews and Wurtzel (Appl. Microbiol. Biotechnol. 53, 396-400, 2000) disclosed that carotenoid production in such engineered *E. coli* strains could be increased by over-expressing the gene coding for 1-deoxy-D-xylulose 5-phosphate synthase (DXPS), the first enzyme in the DXP pathway (*E. coli* possesses only the DXP pathway for isoprenoid biosynthesis and does not use the mevalonate pathway (Lange et al., Proc. Nat. Acad. Sci. 97, 13172-13177, 2000)). Harker and Bramley (FEBS. Lett., 448, 115-119, 1999) also disclosed an increase in the isoprenoid compound ubiquinone-8, in the cells overproducing DXPS. These results supported the hypothesis that limited availability of IPP, resulting from insufficient in vivo activity of DXPS, was limiting the production of carotenoids and other isoprenoid compounds in the engineered strains. Using a similar *E. coli* system, Kim and Keasling (Biotechnol. Bioeng., 72, 408-415, 2001) disclosed that the combined over-expression of the genes encoding DXPS and the second enzyme of the DXP pathway, DXP reductoisomerase (see FIG. 1A) gave higher carotenoid production than over-expression of just the gene encoding DXPS.

All of these studies were done in *E. coli* engineered to produce carotenoids. Accordingly, one disadvantage to these studies was that the amount of carotenoids produced by these recombinant *E. coli* strains were very low compared to the amounts produced by even non-recombinant microorganisms used for industrial production of carotenoids. Furthermore, improved carotenoid production in bacteria by genetic engineering of the IPP biosynthetic pathway has only been shown in organisms that utilize the DXP pathway for IPP formation. No similar studies have been reported for bacteria that produce IPP via the mevalonate pathway.

Metabolic engineering of the mevalonate pathway to improve production of isoprenoid compounds has been reported in yeast. For example, Millis et al. (International Patent Publication No. WO 00/01649) disclosed that production of isoprenoid compounds is increased in *Saccharomyces cerevisiae* when the gene coding for 3-hydroxy-3-methylglutaryl coenzyme A reductase (HMG-CoA reductase, refer to FIG. 1A) is over-expressed. However, it has not been shown that this strategy improves isoprenoid production in bacteria, and in particular, it has not been shown that carotenoid production in bacteria can be improved by amplifying expression of mevalonate pathway genes. While it has been shown that some mevalonate pathway genes from eukaryotes (Campos et al., Biochem. J., 353, 59-67, 2001) and from the bacterium *Streptomyces* sp. strain CL190 (Takagi et al., J. Bacteriol., 182, 4153-4157, 2000) can be expressed in *E. coli*, no increase in isoprenoid production was reported in the strains.

In addition to the reactions that form IPP (via the DXP or mevalonate pathways) and the reactions that convert farnesyl pyrophosphate (FPP) to various other isoprenoids (e.g., carotenoids, quinones) (FIG. 1B), two other reactions are known to be involved in isoprenoid biosynthesis. IPP isomerase interconverts IPP and its isomer, dimethylallyl pyrophosphate (DMAPP) (FIG. 1B). Two forms of IPP isomerase exist, the type 1 enzyme is well known in eukaryotes and some bacteria, and the newly identified type 2 enzyme that is FMN- and NADP(H)-dependent (Kaneda et al., Proc. Nat. Acad. Sci. 98, 932-937, 2001).

Several reports disclose that in *E. coli* engineered to produce carotenoids, amplification of native or heterologous type 1 IPP isomerase (idi) genes stimulates carotenoid production (Kajiwara et al., Biochem. J., 324, 421-426, 1997; Verdoes and van Ooyen, Acta Bot. Gallica, 146, 43-53, 1999; Wang et al., Biotechnol. Bioeng. 62, 235-241, 1999). In one report (Wang et al., Biotechnol. Bioeng. 62, 235-241, 1999), it was further disclosed that over-expression of the ispA gene, encoding FPP synthase increased carotenoid production in an engineered carotenogenic strain of *E. coli* when combined with over-expression of the idi and crtE (GGPP synthase) genes. As is the case for the pathway of IPP biosynthesis, however, it has not been shown that over-expression of genes coding for IPP isomerase or FPP synthase improves carotenoid production in a naturally carotenogenic microorganism. Also, the levels of carotenoids produced in the *E. coli* strains described above are very low, and it has not been shown that these strategies work in an industrial microorganism where carotenoid production was already high.

SUMMARY OF THE INVENTION

In sum, there is no prior evidence that increased expression of gene(s) coding for enzymes of the mevalonate pathway can improve production of carotenoids in naturally carotenogenic bacteria or in naturally non-carotenogenic bacteria engineered to be carotenogenic.

The present invention provides an isolated polypeptide having an amino acid sequence selected from (a) an amino acid sequence shown as residues 1 to 340 of SEQ ID NO:43, (b) an amino acid sequence shown as residues 1 to 349 of SEQ ID NO:45, (c) an amino acid sequence shown as residues 1 to 388 of SEQ ID NO:47, (d) an amino acid sequence shown as residues 1 to 378 of SEQ ID NO:49, (e) an amino acid sequence shown as residues 1 to 305 of SEQ ID NO:51, (f) an amino acid sequence shown as residues 1 to 332 of SEQ ID NO:53, (g) at least 30 contiguous amino acid residues of a polypeptide selected from the group consisting of SEQ ID NOs:43, 45, 47, 49, 51, and 53, (h) an amino acid sequence of a fragment of a polypeptide selected from the group consisting of SEQ ID NOs: 43, 45, 47, 49, 51, and 53, the fragment having the activity of hydroxymethylglutaryl-CoA reductase (HMG-CoA reductase), isopentenyl diphosphate isomerase, hydroxymethylglutaryl-CoA synthase (HMG-CoA synthase), mevalonate kinase, phosphomevalonate kinase, or diphosphomevalonate decarboxylase, (i) an amino acid sequence of a polypeptide encoded by a polynucleotide that hybridizes under stringent conditions to a hybridization probe comprising at least 30 consecutive nucleotides of SEQ ID NO:42 or a complement of SEQ ID NO:42, wherein the polypeptide has the activity of HMG-CoA reductase, isopentenyl diphosphate isomerase, HMG-CoA synthase, mevalonate kinase, phosphomevalonate kinase, or diphosphomevalonate decarboxylase; and (j) a conservatively modified variant of SEQ ID NO:43, 45, 47, 49, 51 or 53.

The present invention also provides an isolated polypeptide having an amino acid sequence selected from the group of: (a) an amino acid sequence shown as residues 1 to 287 of SEQ ID NO:159; (b) at least 30 contiguous amino acid residues of SEQ ID NO:159; (c) an amino acid sequence of a fragment of SEQ ID NO:159, the fragment having the activity of farnesyl-diphosphate synthase (FPP synthase); (d) an amino acid sequence of a polypeptide encoded by a polynucleotide that hybridizes under stringent conditions to a hybridization probe having at least 30 consecutive nucleotides spanning residues 295-1158 of SEQ ID NO:157 or a complement thereof, wherein the hybrid has the activity of FPP synthase; and (e) a conservatively modified variant of SEQ ID NO: 159.

The present invention also provides an isolated polypeptide having an amino acid sequence selected from the group of: (a) an amino acid sequence shown as residues 1 to 142 of SEQ ID NO:160; (b) at least 30 contiguous amino acid residues of SEQ ID NO:160; (c) an amino acid sequence of a fragment of SEQ ID NO: 160, the fragment having the activity of 1-deoxyxylulose-5-phosphate synthase (DXPS); (d) an amino acid sequence of a polypeptide encoded by a polynucleotide that hybridizes under stringent conditions to a hybridization probe having at least 30 consecutive nucleotides spanning residues 1185-1610 of SEQ ID NO:157 or a complement thereof, wherein the polypeptide has the activity of DXPS; and (e) a conservatively modified variant of SEQ ID NO:160.

The present invention also provides an isolated polypeptide having an amino acid sequence selected from the group of: (a) an amino acid sequence shown as residues 1 to 390 of SEQ ID NO:178; (b) at least 30 contiguous amino acid residues of SEQ ID NO:178; (c) an amino acid sequence of a fragment of SEQ ID NO: 178, the fragment having the activity of acetyl-CoA acetyltransferase; (d) an amino acid sequence of a polypeptide encoded by a polynucleotide that hybridizes under stringent conditions to a hybridization probe having at least 30 consecutive nucleotides spanning residues 1-1170 of SEQ ID NO:177 or a complement thereof, wherein the polypeptide has the activity of acetyl-CoA acetyltransferase; and (e) a conservatively modified variant of SEQ ID NO:178.

The present invention also provides an isolated polypeptide having an amino acid sequence selected from the group of: (a) an amino acid sequence shown as residues 1 to 240 of SEQ ID NO:179; (b) at least 30 contiguous amino acid residues of SEQ ID NO:179; (c) an amino acid sequence of a fragment of SEQ ID NO:179, the fragment having the activity of acetoacetyl-CoA reductase; (d) an amino acid sequence of a polypeptide encoded by a polynucleotide that hybridizes under stringent conditions to a hybridization probe having at least 30 consecutive nucleotides spanning residues 1258-1980 of SEQ ID NO:177 or a complement thereof, wherein the polypeptide has the activity of acetoacetyl-CoA reductase; and (e) a conservatively modified variant of SEQ ID NO:179.

The present invention also provides an isolated polynucleotide sequence selected from the following group: the nucleotide sequence of SEQ ID NO:42, variants of SEQ ID NO:42 containing one or more substitutions according to the *Paracoccus* sp. strain R1534 codon usage table (Table 14), fragments of SEQ ID NO:42 that encode a polypeptide having an activity selected from the group consisting of hydroxymethylglutaryl-CoA reductase (HMG-CoA reductase), isopentenyl diphosphate isomerase, hydroxymethylglutaryl-CoA synthase (HMG-CoA synthase), mevalonate kinase, phosphomevalonate kinase, and diphosphomevalonate decarboxylase, and polynucleotide sequences that hybridize under stringent conditions to a hybridization probe, the nucleotide sequence of which consists of at least 30 contiguous nucleotides of SEQ ID NO:42, or the complement of SEQ ID NO:42, which hybrid encodes a polypeptide having an activity selected from the group: HMG-CoA reductase, isopentenyl diphosphate isomerase, HMG-CoA synthase, mevalonate kinase, phosphomevalonate kinase, and diphosphomevalonate decarboxylase.

The present invention also provides an isolated polynucleotide sequence selected from the following group: the nucleotide sequence of SEQ ID NO:157, variants of SEQ ID NO:157 containing one or more substitutions according to the *Paracoccus* sp. strain R1534 codon usage table (Table 14), fragments of SEQ ID NO:157 that encode a polypeptide having farnesyl diphosphate (FPP) synthase activity, 1-deoxy-D-xylulose 5-phosphate synthase activity or a polypeptide having the activity of XseB, and polynucleotide sequences that hybridize under stringent conditions to a hybridization probe the nucleotide sequence of which consists of at least 30 contiguous nucleotides of SEQ ID NO:157, or the complement of SEQ ID NO:157, which hybrid encodes a polypeptide having FPP synthase activity, 1-deoxy-D-xylulose 5-phosphate synthase activity or the activity of XseB.

An isolated polynucleotide sequence is also provided that has a nucleotide sequence selected from the following group: SEQ ID NO:177, variants of SEQ ID NO:177 containing one or more substitutions according to the *Paracoccus* sp. strain R1534 codon usage table (Table 14), fragments of SEQ ID NO: 177 that encode a polypeptide having an activity selected from the group consisting of acetyl-CoA acetyltransferase and acetoacetyl-CoA reductase, and polynucleotide sequences that hybridize under stringent conditions to a hybridization probe the nucleotide sequence of which consists of at least 30 contiguous nucleotides of SEQ ID NO:177, or the complement of SEQ ID NO:177, which hybrid encodes a polypeptide having an activity selected from the group: acetyl-CoA acetyltransferase and acetoacetyl-CoA reductase.

An isolated polynucleotide sequence is also provided that has a nucleotide sequence selected from the following group: nucleotides spanning positions 59-292 of SEQ ID NO:157, variants of the nucleotide sequence spanning positions of SEQ ID NO:157 containing one or more substitutions according to the *Paracoccus* sp. strain R1534 codon usage table (Table 14), fragments of the nucleotide sequence spanning positions 59-292 of SEQ ID NO:157 that encode a polypeptide having a function of XseB, and polynucleotide sequences that hybridize under stringent conditions to a hybridization probe the nucleotide sequence of which consists of at least 30 contiguous nucleotides spanning positions 59-292 of SEQ ID NO:157, or the complement of such a sequence, wherein the hybrid encodes a polypeptide having a function of XseB.

Preferably, the isolated polynucleotide consists of nucleotides 59 to 292 of SEQ ID NO:157.

An isolated polynucleotide sequence is also provided that has a nucleotide sequence selected from the following group: nucleotides spanning positions 295-1158 of SEQ ID NO:157, variants of the nucleotide sequence spanning positions 295-1158 of SEQ ID NO:157 containing one or more substitutions according to the *Paracoccus* sp. strain R1534 codon usage table (Table 14), fragments of the nucleotide sequence spanning positions 295-1158 of SEQ ID NO:157 that encode a FPP synthase activity, and polynucleotide sequences that hybridize under stringent conditions to a hybridization probe the nucleotide sequence of which consists of at least 30 contiguous nucleotides spanning positions 295-1158 of SEQ ID NO:157, or the complement of such a sequence, wherein the hybrid encodes a polypeptide having FPP synthase activity.

Preferably, the isolated nucleotide sequence consists of nucleotides 295-1158 of SEQ ID NO:157.

Another isolated polynucleotide sequence is provided, which is selected from the following group: a nucleotide sequence spanning positions 1185-1610 of SEQ ID NO:157, variants of the nucleotide sequence spanning positions 1185-1610 of SEQ ID NO:157 containing one or more substitutions according to the *Paracoccus* sp. strain RI 534 codon usage table (Table 14), fragments of the nucleotide sequence spanning positions 1185-1610 of SEQ ID NO:157 that encode a polypeptide having 1-deoxyxylulose-5-phosphate synthase activity, and polynucleotide sequences that hybridize under stringent conditions to a hybridization probe the nucleotide sequence of which consists of at least 30 contiguous nucleotides spanning positions 1185-1610 of SEQ ID NO:157, or the complement of such a sequence, wherein the hybrid encodes a polypeptide having 1-deoxyxylulose-5-phosphate synthase activity.

Another isolated polynucleotide sequence is provided, which has a nucleotide sequence selected from the group: SEQ ID NO:42, SEQ ID NO:157, SEQ ID NO:177, and combinations thereof.

The invention also provides an expression vector containing any of the polynucleotide sequences set forth above. Particularly preferred expression vectors include, for example, pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof.

The invention further provides a cultured cell containing any of the polynucleotide sequences or combinations of such polynucleotide sequences set forth above, or a progeny of the cell, wherein the cell expresses a polypeptide encoded by the polynucleotide sequence.

The invention also provides novel *Paracoccus* strains including strains R-1506, R-1512, R1534, and R114.

A method of producing a carotenoid is also provided. The method includes culturing the cell according to the present invention under conditions permitting expression of a polypeptide encoded by a polynucleotide sequence according to the present invention, and isolating the carotenoid from the cell or the medium of the cell.

A method of making a carotenoid-producing cell is also provided. This method includes introducing into a cell a polynucleotide sequence encoding an enzyme in the mevalonate pathway, which enzyme is expressed in the cell; and selecting a cell containing the polynucleotide sequence that produces a carotenoid at a level that is about 1.1-1,000 times the level of the carotenoid produced by the cell before introduction of the polynucleotide sequence.

The present invention also provides a method for engineering a bacterium to produce an isoprenoid compound, which method includes (a) culturing a parent bacterium in a medium under conditions permitting expression of an isoprenoid compound, and selecting a mutant bacterium from the culture medium that produces about 1.1-1,000 times more of an isoprenoid compound than the parent bacterium, (b) introducing into the mutant bacterium an expression vector containing a polynucleotide sequence represented by SEQ ID NO:42 operably linked to an expression control sequence, and (c) selecting a bacterium that contains the expression vector and produces at least about 1.1 times of an isoprenoid compound than the mutant in step (a).

Another embodiment of the invention is a microorganism of the genus *Paracoccus*, which microorganism has the following characteristics: (a) a sequence similiarity to SEQ ID NO:12 of >97% using a similarity matrix obtained from a homology calculation using GeneCompar v. 2.0 software with a gap penalty of 0%; (b) a homology to strain R-1512, R1534, R114 or R-1506 of >70% using DNA:DNA hybridization at 81.5° C.; (c) a G+C content of its genomic DNA that varies less than 1% from the G+C content of the genomic DNA of R114, R-1512, R1534, and R-1506; and (d) an average DNA fingerprint that clusters at about 58% similarity to strains R-1512, R1534, R114 and R-1506 using the AFLP procedure of Example 2, with the proviso that the microorganism is not *Paracoccus* sp. (MBIC3966).

A further embodiment of the invention is a microorganism of the genus *Paracoccus*, which microorganism has the following characteristics: (a) 18:1w7c having at least about 75% of the total fatty acids of the cell membranes; (b) an inability to use adonitol, i-erythritol, gentiobiose, β-methylglucoside, D-sorbitol, xylitol and quinic acid as a carbon source for growth; and (c) an ability to use L-asparagine and L-aspartic acid as a carbon source for growth, with the proviso that the microorganism is not *Paracoccus* sp. (MBIC3966).

Another embodiment of the invention is a microorganism of the genus *Paracoccus*, which microorganism has the following characteristics: (a) an ability to grow at 40° C.; (b) an ability to grow in a medium having 8% NaCl; (c) an ability to grow in a medium having a pH of 9.1; and (d) a yellow-orange colony pigmentation, with the proviso that the microorganism is not *Paracoccus* sp. (MBIC3966).

DEFINITIONS

The terms "polypeptide," "polypeptide sequence," "amino acid," and "amino acid sequence" are used interchangeably herein, and mean an oligopeptide, peptide, polypeptide, or protein sequence, or a fragment of any of these, as well as naturally occurring or synthetic molecules. In this context, "fragments," "immnunogenic fragments," or "antigenic fragments" refer to fragments of any of the polypeptides defined herein which are at least about 30 amino acids in length and which retain some biological activity or immunological activity of the polypeptide in question. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, an "isolated" polynucleotide (e.g., an RNA, DNA or a mixed polymer) is one which is substantially separated from other cellular components which naturally accompany a native sequence or polypeptide, e.g., ribosomes, polymerases, many other genome sequences and proteins. The term embraces a polynucleotide that has been removed from its naturally occurring environment, and includes recombinant or cloned DNA isolates and chemically synthesized analogs or analogs biologically synthesized by heterologous systems.

With respect to polypeptides, the term "isolated" means a protein or a polypeptide that has been separated from components that accompany it in its natural state. A monomeric protein is isolated when at least about 60 to 75% of a sample exhibits a single polypeptide sequence. An isolated protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, using HPLC or other means well known in the art may provide higher resolution for purification.

As used herein, the term "biologically active," refers to a protein having structural, regulatory, or biochemical functions of a naturally occurring molecule. Likewise, "immunologically active" refers to the capability of the natural, recombinant, or synthetic polypeptide, or of any oligopeptide thereof, to induce a specific immune response in appropriate animals or cells and to bind with specific antibodies.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

An "expression control sequence" is defined as an array of nucleic acid control sequences that direct transcription of an operably linked nucleic acid. An example of such an expression control sequence is a "promoter." Promoters include necessary nucleic acid sequences near the start site of transcription. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter or array of transcription factor binding sites) and a second nucleic acid sequence, wherein the expression control sequence directs transcription of the nucleic acid corresponding to the second sequence.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived.

In the case where the inserted polynucleotide sequence is transcribed and translated to produce a functional polypeptide, one of skill will recognize that because of codon degeneracy a number of polynucleotide sequences will encode the same polypeptide. These variants are specifically within the scope of the present invention. In addition, the present invention specifically includes those sequences that are substantially identical (determined as described below) to each other and that encode polypeptides that are either mutants of wild type polypeptides or retain the function of the polypeptide (e.g., resulting from conservative substitutions of amino acids in the polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988), e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90-95%, nucleotide or amino acid residue identity when aligned for maximum correspondence over a comparison window as measured using one of the following sequence comparison algorithms or by manual alignment and visual inspection. This definition also refers to a sequence of which the complement of that sequence hybridizes to the test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l, Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acid codons encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, or substitutions to a peptide, polypeptide, or protein sequence which alters a single amino acid or a small percentage of amino acids (i.e. less than 20%, such as 15%, 10%, 5%, 4%, 3%, 2% or 1%) in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
Alanine (A), Serine (S), Threonine (T);
Aspartic acid (D), Glutamic acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target sequence, typically in a complex mixture of nucleic acid sequences, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of Principles of Hybridization and the Strategy of Nucleic Acid Assays" (1993). Generally, highly stringent conditions are selected to be about 5-10° C. lower than the thermal melting point ($T_m$) for the specific sequence at a defined ionic strength and pH. Low stringency conditions are generally selected to be about 15-30° C. below the $T_m$. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA containing nucleic acids of the invention can be identified in standard Southern blots under stringent conditions using the nucleic acid sequences disclosed here. For the purposes of this disclosure, suitable stringent conditions for such hybridizations are those which include hybridization in a buffer of 40% formamide, 1M NaCl, 1% sodium dodecyl sulfate (SDS) at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

As used herein, the phrase "expression vector" is a replicatable vehicle that carries, and is capable of mediating the expression of, a DNA sequence encoding the polynucleotide sequences set forth herein.

In the present context, the term "replicatable" means that the vector is able to replicate in a given type of host cell into which it has been introduced. Immediately upstream of the polynucleotide sequence(s) of interest, there may be provided a sequence coding for a signal peptide, the presence of which ensures secretion of the encoded polypeptide expressed by host cells harboring the vector. The signal sequence may be the one naturally associated with the selected polynucleotide sequence or of another origin.

The vector may be any vector that may conveniently be subjected to recombinant DNA procedures, and the choice of vector will often depend on the host cell into which it is to be introduced. Thus, the vector may be an autonomously replicating vector, i.e. a vector that exists as an extrachromosomal entity, the replication of which is independent of chromosomal replication; examples of such a vector are a plasmid, phage, cosmid or mini-chromosome. Alternatively, the vector may be one which, when introduced in a host cell, is integrated in the host cell genome and is replicated together with the chromosome(s) into which it has been integrated. Examples of suitable vectors are shown in the examples. The expression vector of the invention may carry any of the DNA sequences of the invention as defined below and be used for the expression of any of the polypeptides of the invention defined below.

BRIEF DESCRIPTION OF THE DRAWINGS

FIG. 1B shows the pathway for zeaxanthin biosynthesis from IPP in *Paracoccus* sp.

FIG. 2 shows the nucleotide sequence of the gene coding for 16S rDNA in *Paracoccus* sp. strain R-1512 (ATCC 21588) (SEQ ID NO:12).

glucose, respectively. Bold bars indicate contiguous $^{13}C$ atoms from [U-$^{13}C_6$] glucose.

Figure 10:
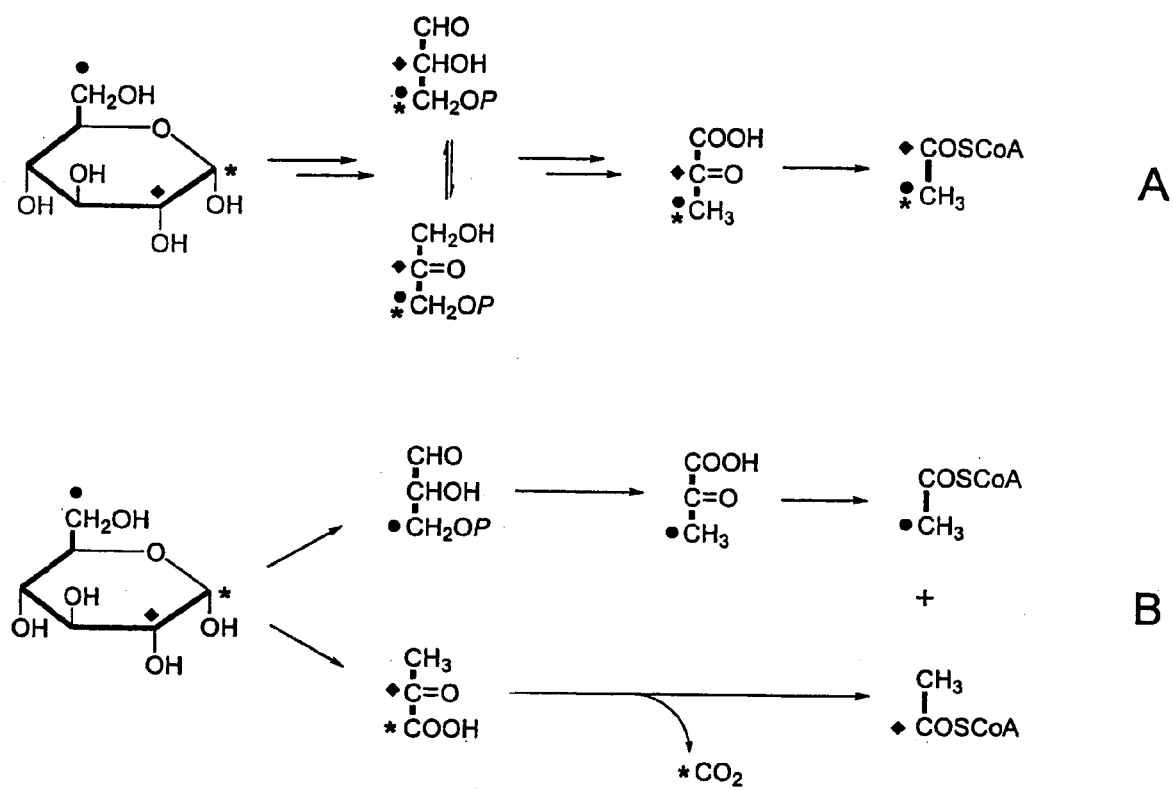

FIG. 10 shows the predicted labeling patterns for pyruvate and acetyl-CoA derived from glucose metabolism via (A) glycolysis or (B) the Entner-Doudoroff pathway. Symbols *, ♦ and ● indicate carbon atoms enriched from [1-$^{13}C_1$] glucose, [2-$^{13}C_1$] glucose and [6-$^{13}C_1$] glucose, respectively. Bold bars indicate contiguous $^{13}C$ atoms from [U-$^{13}C_6$] glucose.

Figure 11:
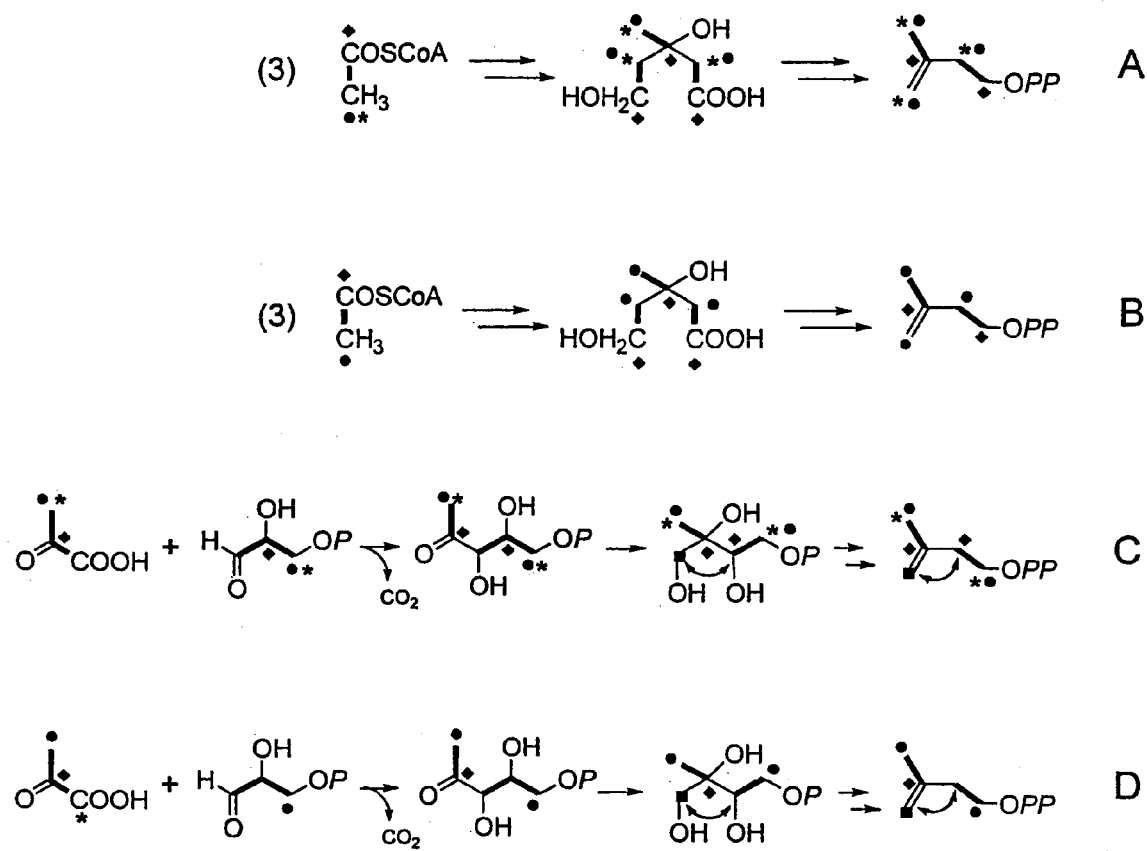

FIG. 11 shows the predicted labeling patterns for IPP produced via the mevalonate or DXP pathways. Schemes A and B show the expected labeling patterns for IPP produced from acetyl-CoA through the mevalonate pathway. Schemes A and B further assume glucose metabolism via glycolysis and the Entner-Doudoroff pathway, respectively. Schemes C and D assume IPP production via the DXP pathway and further assume glucose metabolism via glycolysis (C) or the Entner-Doudoroff pathway (D). Symbols are as described in the legend to FIG. 10.

Figure 12:
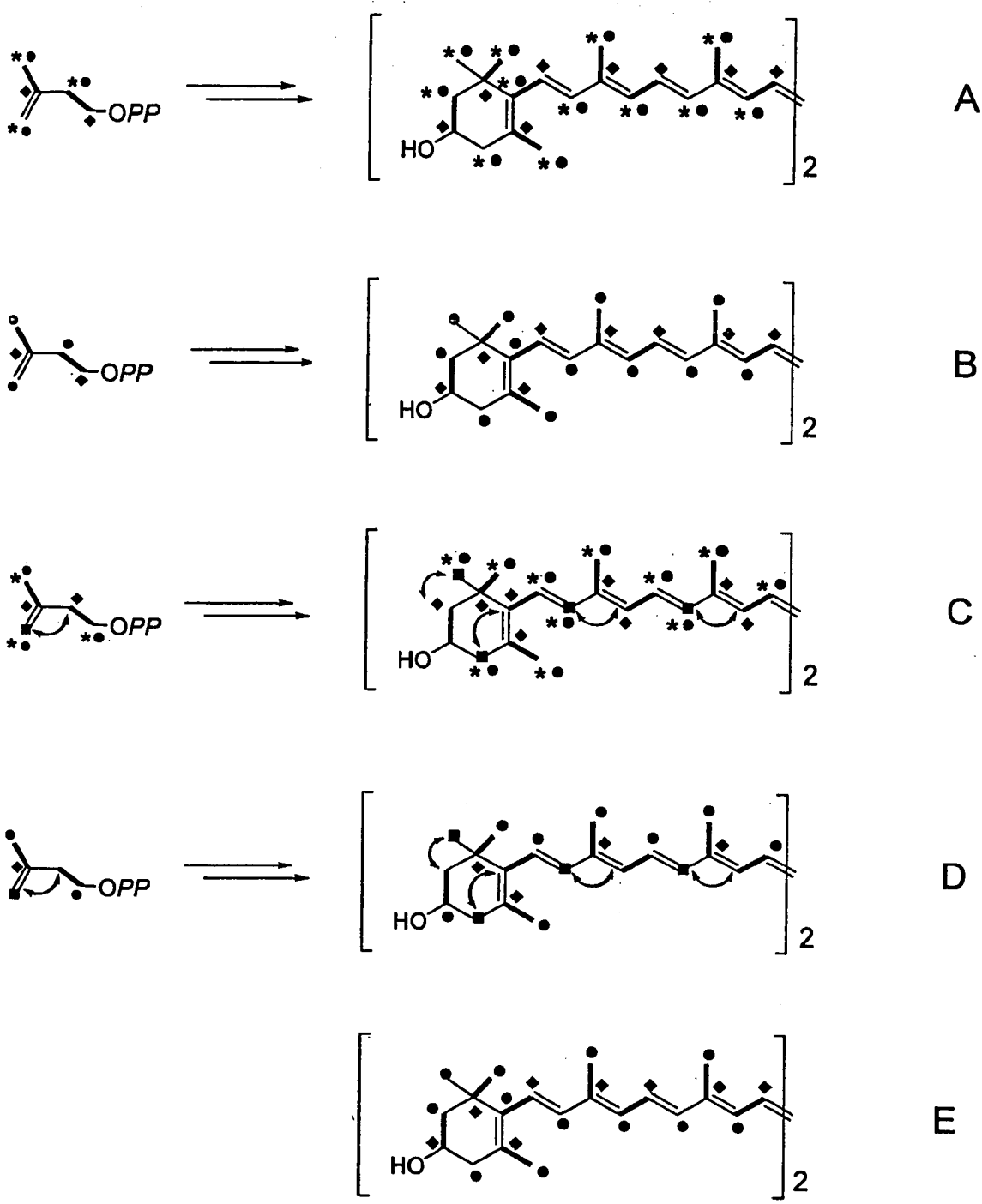

FIG. 12 shows the expected labeling patterns for zeaxanthin produced from IPP. Schemes A-D correspond to Schemes A-D in FIG. 11. Scheme E shows the actual observed labeling patterns of zeaxanthin purified from batch fermentations using *Paracoccus* sp. strain R114 grown in the presence of the glucoses labeled in different positions. Symbols are as described in the legend to FIG. 10.

Figure 13:
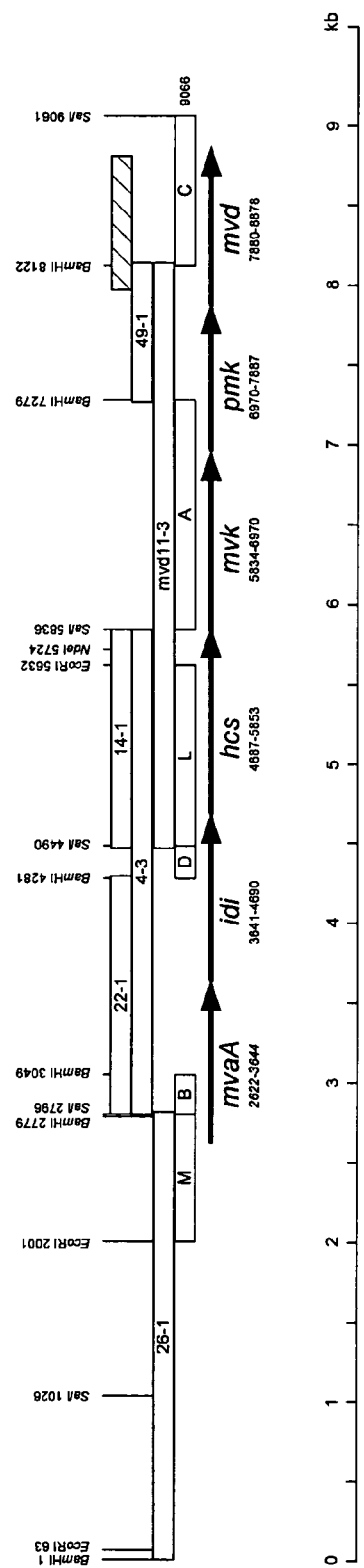

FIG. 13 is a restriction enzyme map of the mevalonate operon (SEQ ID NO:42) from *Paracoccus* sp., strain R114. The cloned restriction fragments and PCR fragments are represented as boxes. The hatched box represents the original PCR fragment obtained with degenerate primers. Arrows indicate the mevalonate pathway and idi genes, and the position of the first nucleotide of the start codon and the last nucleotide of the stop codon is given below each gene designation. Sites for the restriction endonucleases EcoRI, BamHI, SalI and NdeI are shown.

FIGS. 14A-14E show the DNA sequence of the mevalonate operon (SEQ ID NOs:42, 44, 46, 48, 50, and 52) from *Paracoccus* sp. strain R114 and amino acid sequences (SEQ ID NOs:43, 45, 47, 49, 51, and 53) of the encoded proteins.

Figure 15:
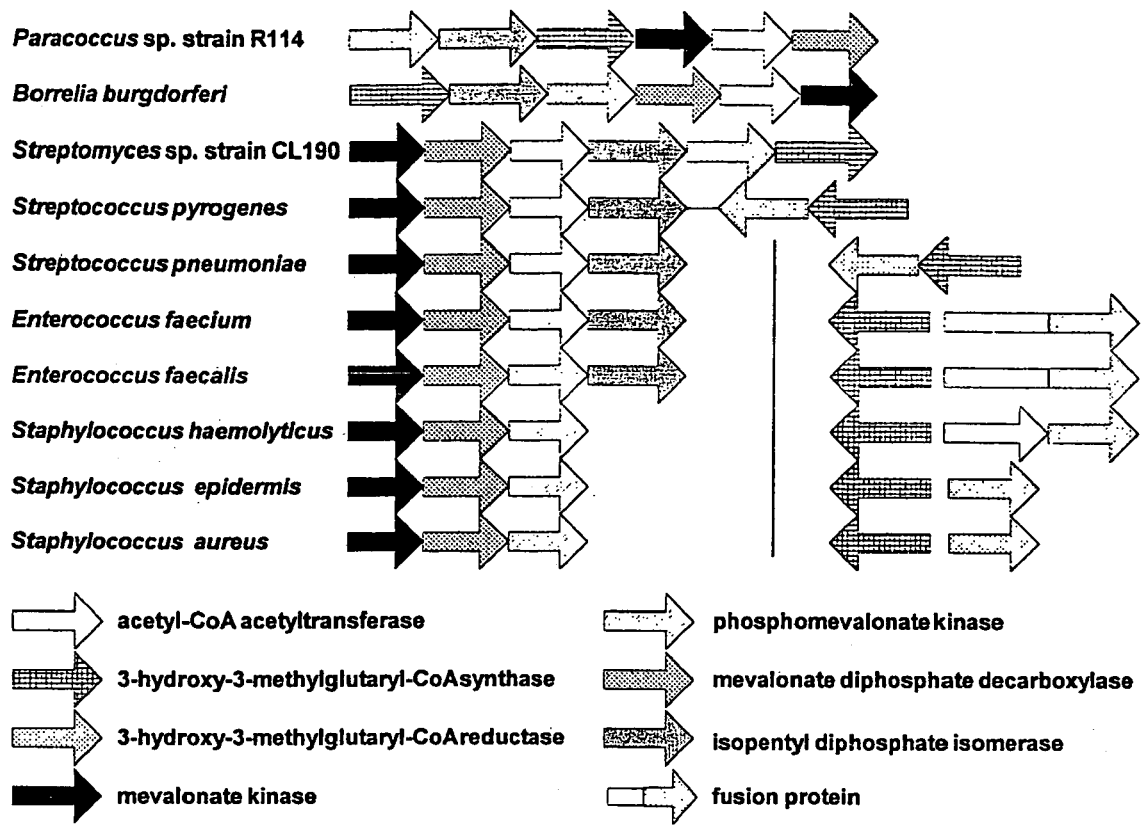

FIG. 15 shows the arrangement of genes in known bacterial mevalonate pathway gene clusters, as well as in strain R114. Genes are represented by patterned arrows as indicated in the Figure. The drawing is not to scale. The vertical bar in the lower six species indicates that the genes on the left and the right are not linked.

FIG. 16 shows an amino acid alignment of bacterial class I HMG-CoA reductases of *Paracoccus* sp. strain R114 (SEQ ID NO:43), *Streptomyces* sp. Strain CL190 (SEQ ID NO:54), *S. griseolosporeus* (SEQ ID NO:55), and *Streptomyces* sp. strain KO-3899 (SEQ ID NO:56). White symbols on black background indicate regions of 100% identity across all depicted species. EMBL/GenBank/DDBJ database accession numbers are q9z9n4 for *Streptomyces* sp. strain CL190, q9znh1 for *S. griseolosporeus* and q9znh0 for *Streptomyces* sp. strain KO-3899.

FIGS. 17A-17B show an amino acid alignment of isopentenyl diphosphate isomerase from *Paracoccus* sp. strain R114 (SEQ ID NO:45) with close homologs (SEQ ID NOs:57-73). Amino acid residues, which are identical in all depicted enzymes, are shown as white symbols on black background. Residues identical in at least fifteen sequences are shown as white on dark gray and identical amino acids in ten to fourteen proteins are indicated in black with a light gray background. The order of the sequences does not reflect the degree of homology. EMBL/GenBank/DDBJ database accession numbers are given after the organism's name in parentheses.

Figure 18A:
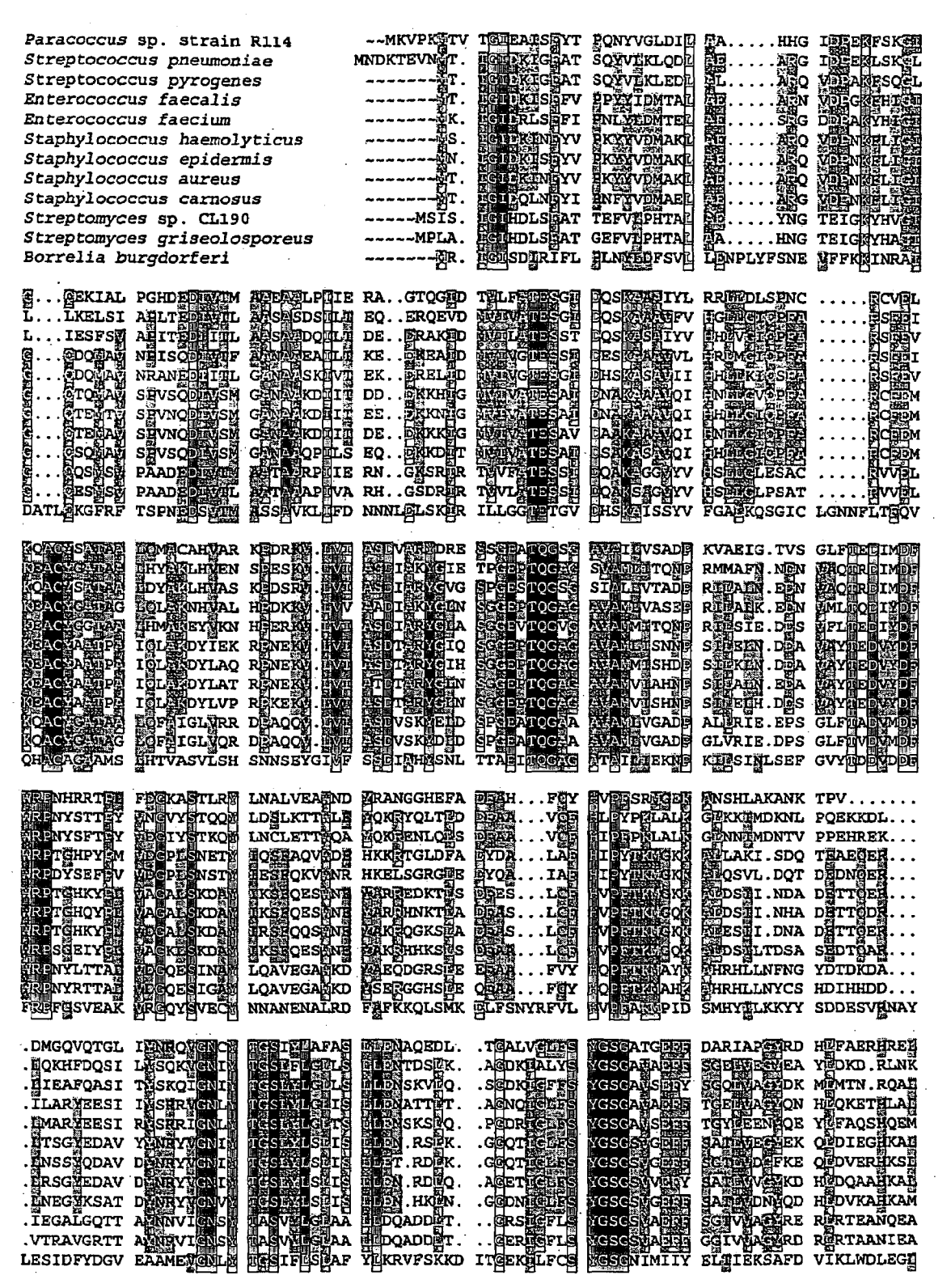

FIGS. 18A-18B show an amino acid alignment of bacterial HMG-CoA synthases (SEQ ID NOs:47 and 74-84). Amino acid residues, which are identical in all depicted enzymes, are shown as white symbols on black background. Residues identical in at least eight sequences are shown as white on dark gray and identical amino acids in six or seven proteins are indicated in black with a light gray background. EMBL/GenBank/DDBJ database accession numbers are given after each sequence in parentheses. The first 43 amino acids of the sequence from *Streptomyces griseolosporeus* are missing in the database version.

FIG. 19 shows an amino acid alignment of bacterial mevalonate diphosphate decarboxylases. (SEQ ID NOs:53 and 85-94). Amino acid residues, which are identical in all depicted enzymes, are shown as white symbols on black background. Residues identical in at least eight sequences are shown as white on dark gray and identical amino acids in six or seven proteins are indicated in black with a light gray background. EMBL/GenBank/DDBJ database accession numbers are given after each sequence in parentheses.

FIGS. 20A-20B show an amino acid alignment of bacterial mevalonate kinases (SEQ ID NOs:49 and 95-104). Amino acid residues, which are identical in all depicted enzymes, are shown as white symbols on black background. Residues identical in at least eight sequences are shown as white on dark gray and identical amino acids in six or seven proteins are indicated in black with a light gray background. EMBL/GenBank/DDBJ database accession numbers are given after each sequence in parentheses.

FIGS. 21A-21B show an amino acid alignment of bacterial phosphomevalonate kinases (SEQ ID NOs:51 and 105-114). Amino acid residues, which are identical in all depicted enzymes, are shown as white symbols on black background. Residues identical in at least eight sequences are shown as white on dark gray and identical amino acids in six or seven proteins are indicated in black with a light gray background. EMBL/GenBank/DDBJ database accession numbers are given after each sequence in parentheses.

Figure 22:
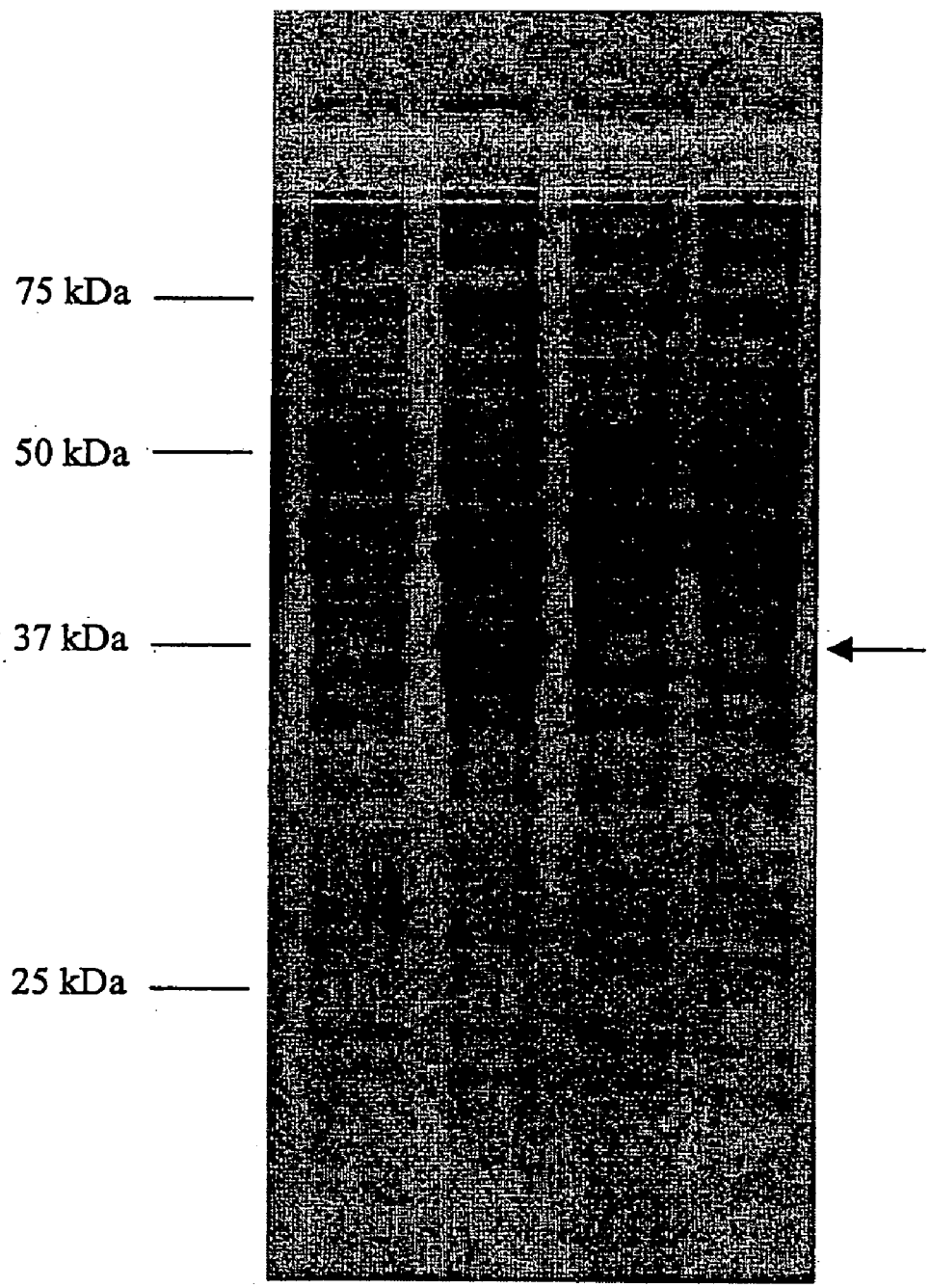

FIG. 22 shows overproduction of the *Paracoccus* sp. strain R114 mvaA gene product, HMG-CoA reductase, in *E. coli* M15. Lane 1, M15/pDS-mvaA (uninduced); Lane 2, M15/pDS-mvaA (induced); Lane 3, M15/pDS-His-mvaA (uninduced); Lane 4, M15/pDS-His-mvaA (induced). Arrow indicates overproduced HMG-CoA reductase in M15/pDS-mvaA.

Figure 23:
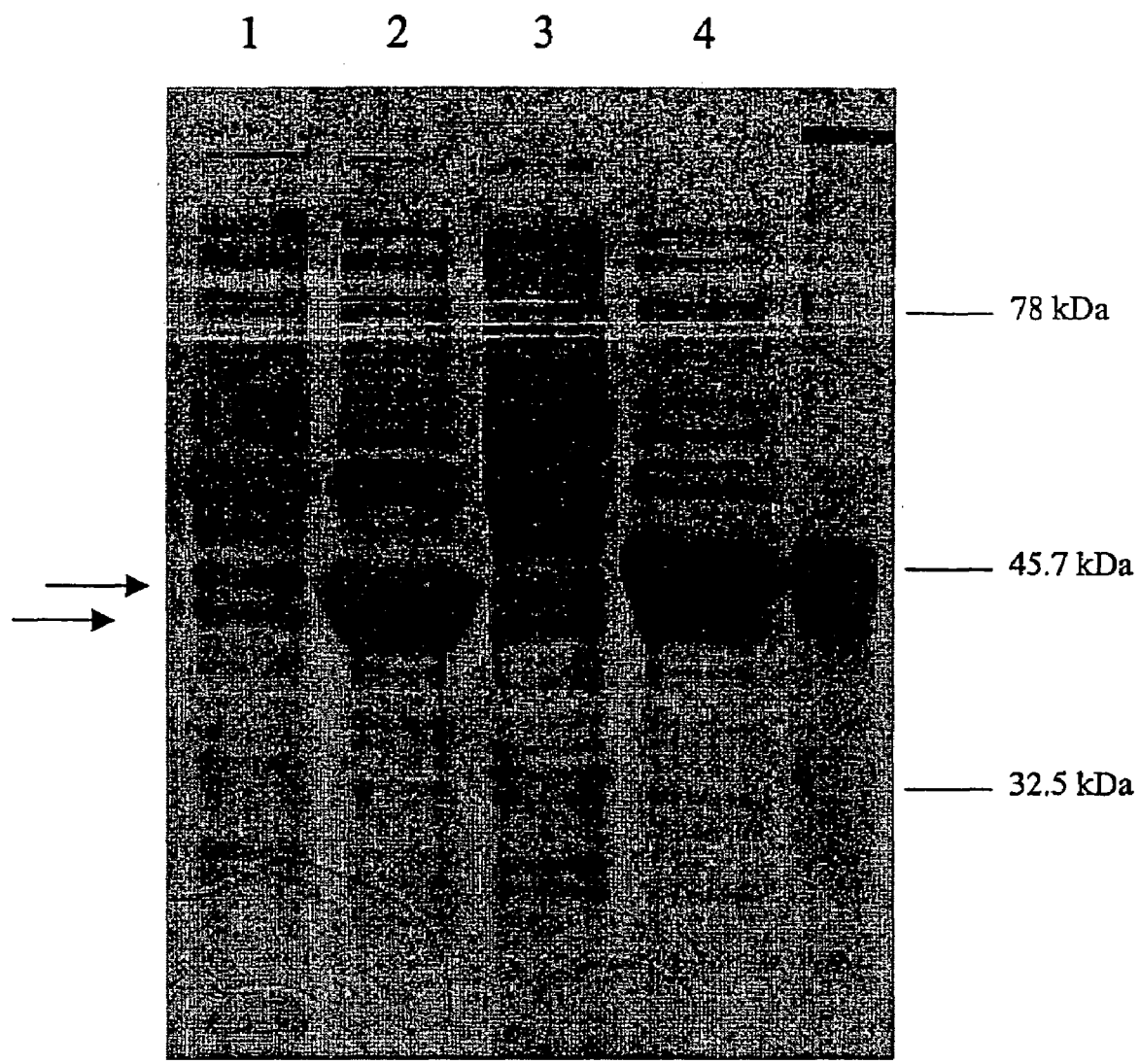

FIG. 23 shows overproduction of the *Paracoccus* sp. strain R114 idi gene product, IPP isomerase, in *E. coli* M15. Lane 1, M15/pDS-idi (uninduced); Lane 2, M15/pDS-idi (induced); Lane 3, M15/pDS-His-idi (uninduced); Lane 4, M15/pDS-His-idi (induced). Arrows indicates overproduced IPP isomerase in M15/pDS-idi and M15/pDS-His-idi.

Figure 24:
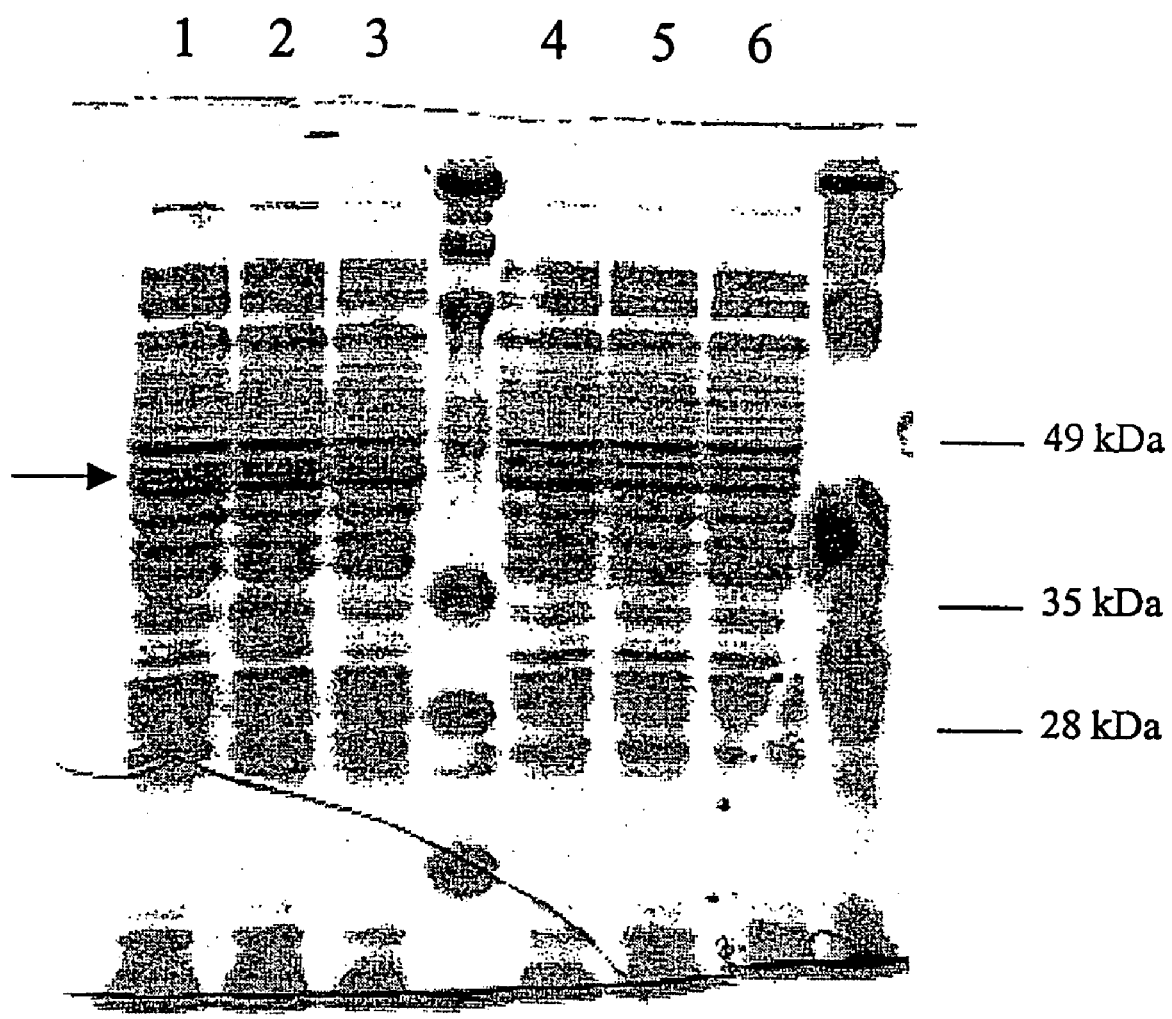

FIG. 24 shows overproduction of the *Paracoccus* sp. strain R114 hcs gene product, HMG-CoA synthase, in *E. coli* M15. Lanes 1-3, M15/pDS-His-hcs (induced); lanes 4-6, M15/pDS-His-hcs (uninduced). Arrow indicates overproduced HMG-CoA synthase.

Figure 25:
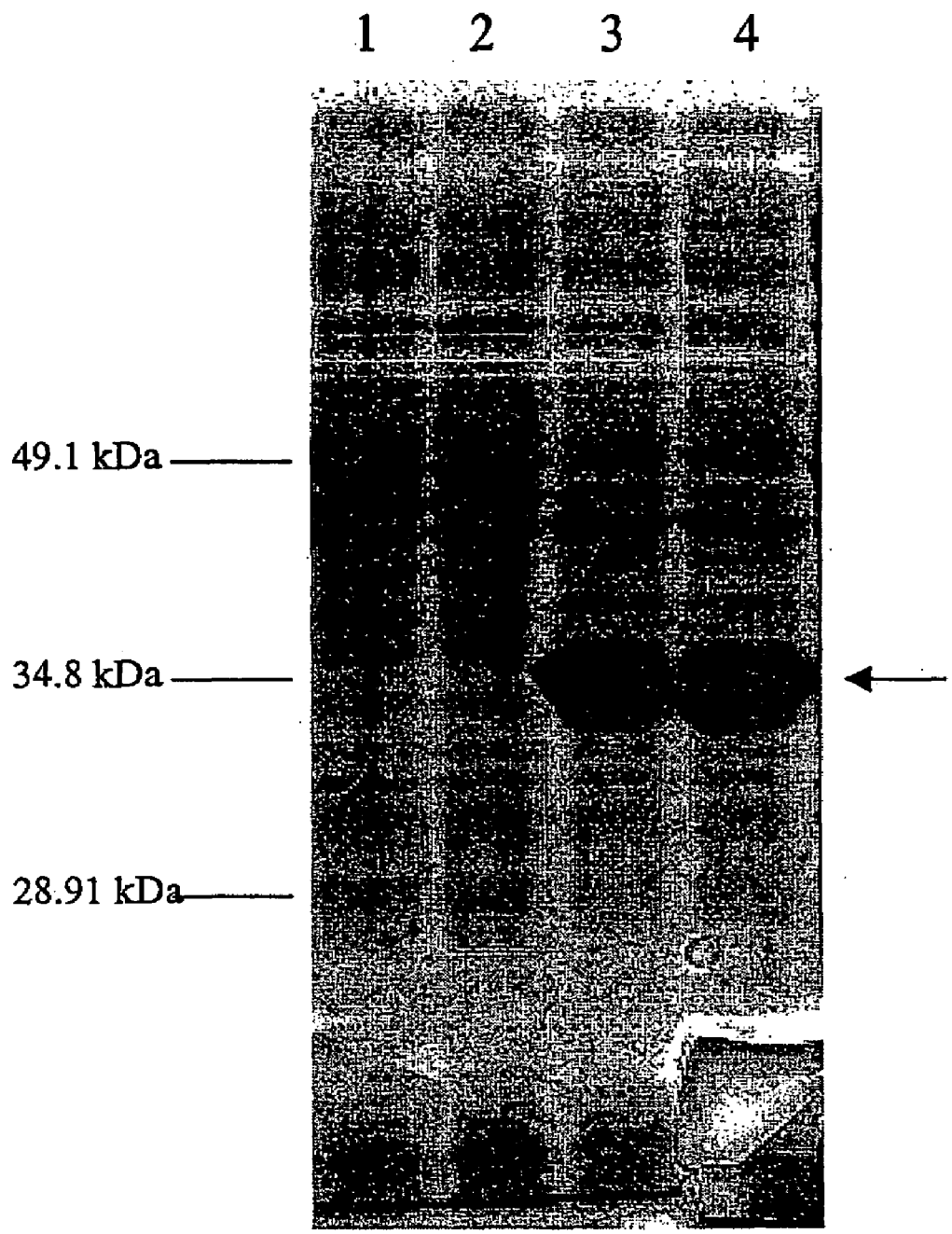

FIG. 25 shows overproduction of the *Paracoccus* sp. strain R114 pmk gene product, phosphomevalonate kinase, in *E. coli* M15. Lanes 1 and 2, M15/pDS-His-pmk (uninduced); lanes 3 and 4, M15/pDS-His-pmk (induced). Arrow indicates overproduced phosphomevalonate kinase.

Figure 26:
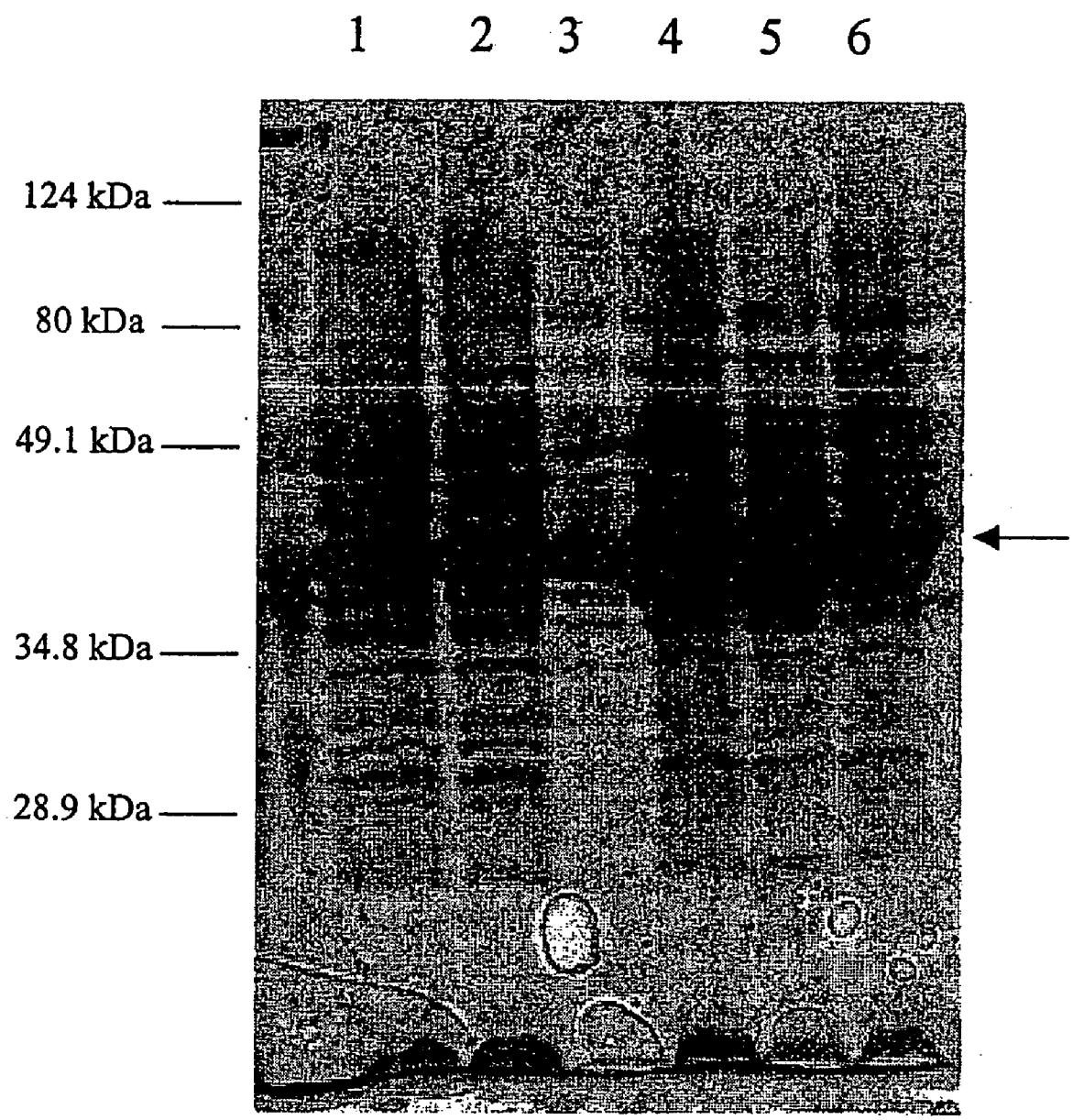

FIG. 26 shows overproduction of the *Paracoccus* sp. strain R114 mvk gene product, mevalonate kinase, in *E. coli* M15. Lanes 2-5, M15/pDS-His-mvk (induced for 30, 60, 120 and 240 min., respectively); lanes 1 and 6, uninduced controls (sampled at 30 min. and 240 min., respectively). Arrow indicates overproduced mevalonate kinase.

Figure 27:
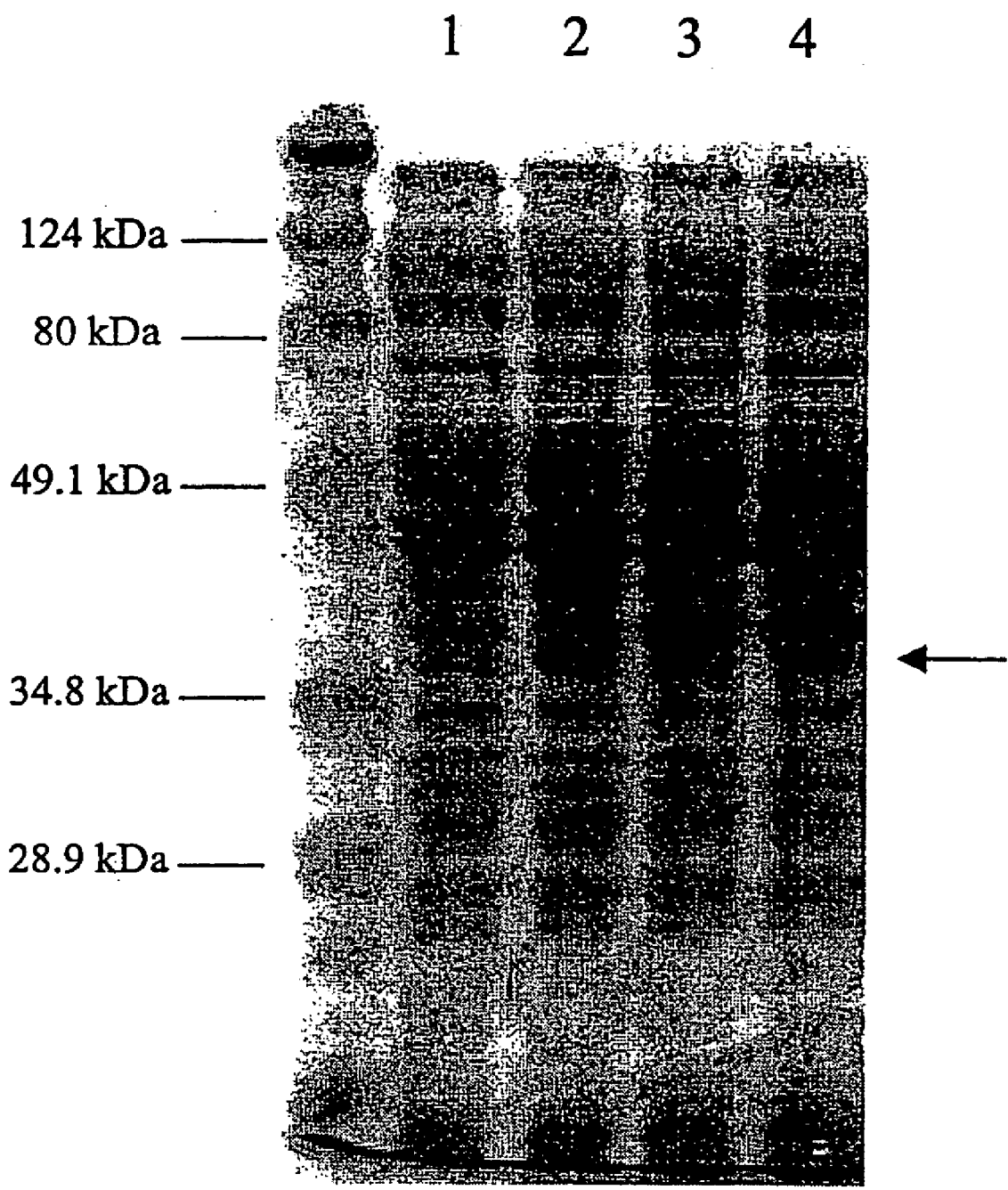

FIG. 27 shows overproduction of the *Paracoccus* sp. strain R114 mvd gene product, mevalonate diphosphate decarboxylase, in *E. coli* M15. Lanes 1 and 2, M15/pDS-His-mvd (uninduced); lanes 3 and 4, M15/pDS-His-mvd (induced). Arrow indicates overproduced mevalonate diphosphate decarboxylase.

Figure 28:
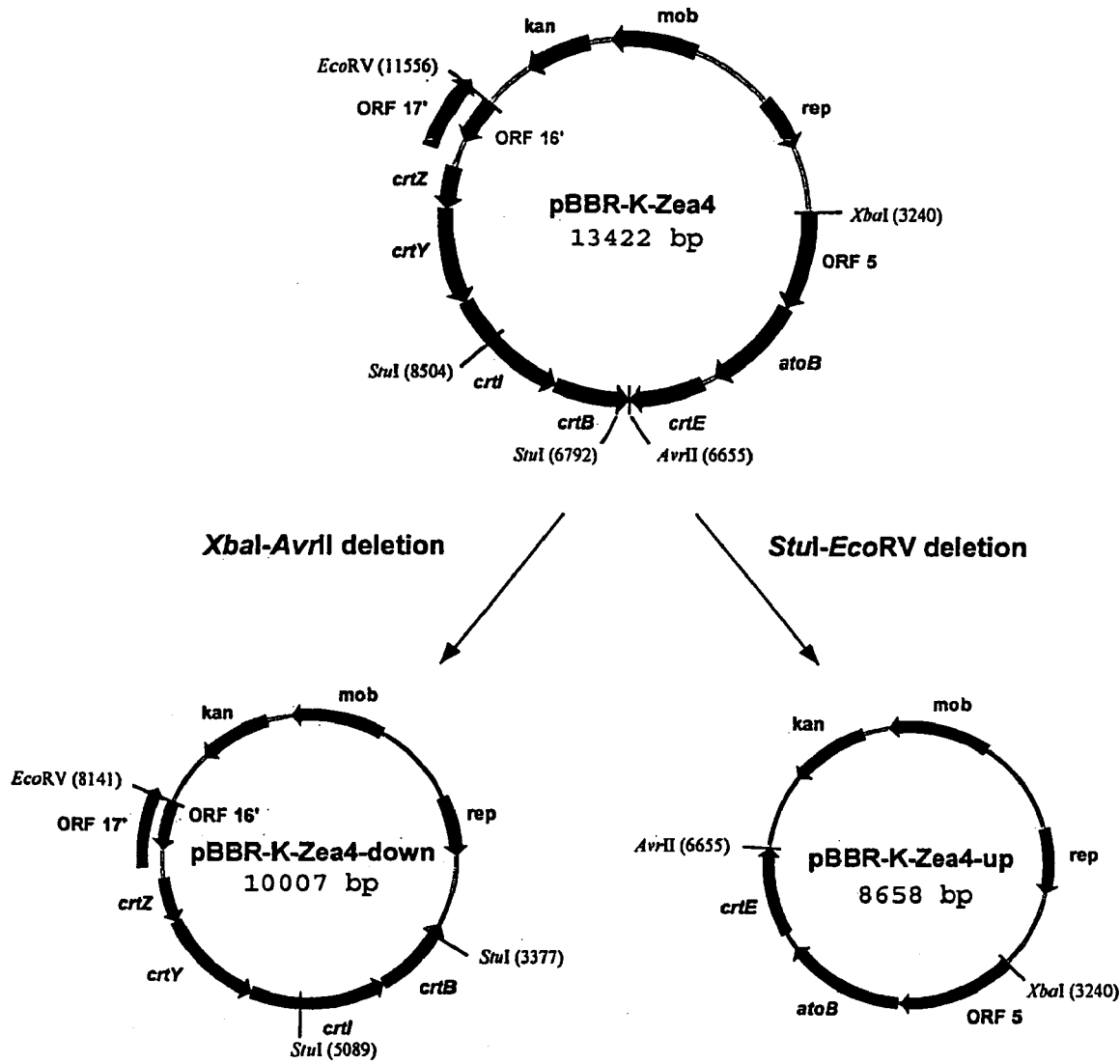

FIG. 28 shows plasmid maps of pBBR-K-Zea4, pBBR-K-Zea4-down, and pBBR-K-Zea4-up.

Figure 29:
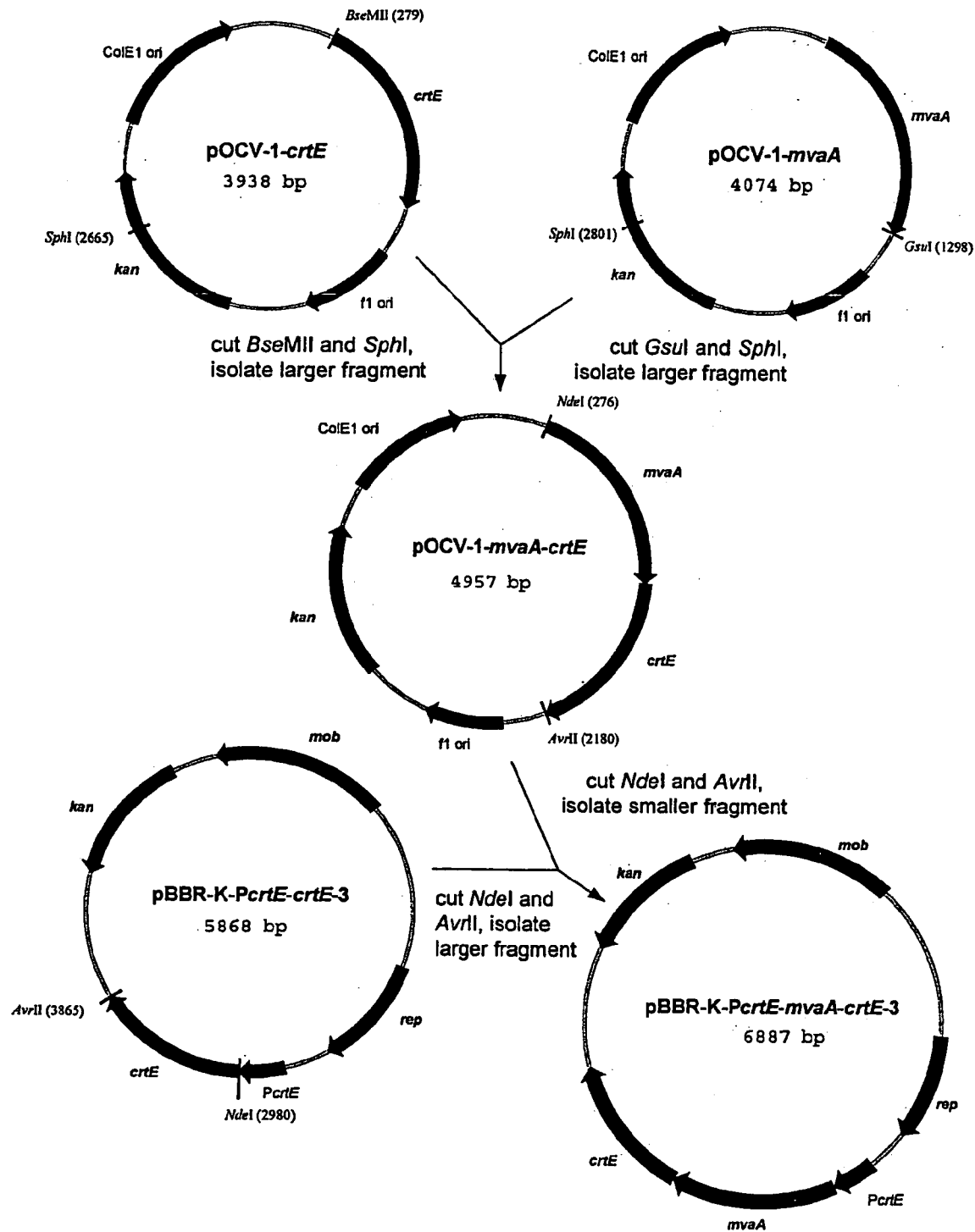

FIG. 29 depicts the construction of plasmid pBBR-K-PcrtE-mvaA-crtE-3.

FIG. 30 shows DNA and amino acid sequences of the ispA locus from *Paracoccus* sp. strain R114. The sequence of the cloned NcoI-BamHI fragment is shown (SEQ ID NO:157). The NcoI and BamHI sites and the amino acid sequences of XseB (SEQ ID NO:158), IspA (SEQ ID NO:159), and the N-terminus of Dxs (SEQ ID NO:160) are indicated. The start codon of ispA may be GTG or ATG resulting in two or one methionine residues, respectively, at the amino-terminus of the native IspA.

FIG. 31 shows the DNA sequence (SEQ ID NO:175) and deduced amino acid sequence (SEQ ID NO:176) of the atoB gene from *Paracoccus* sp. strain R1534.

Figure 32:
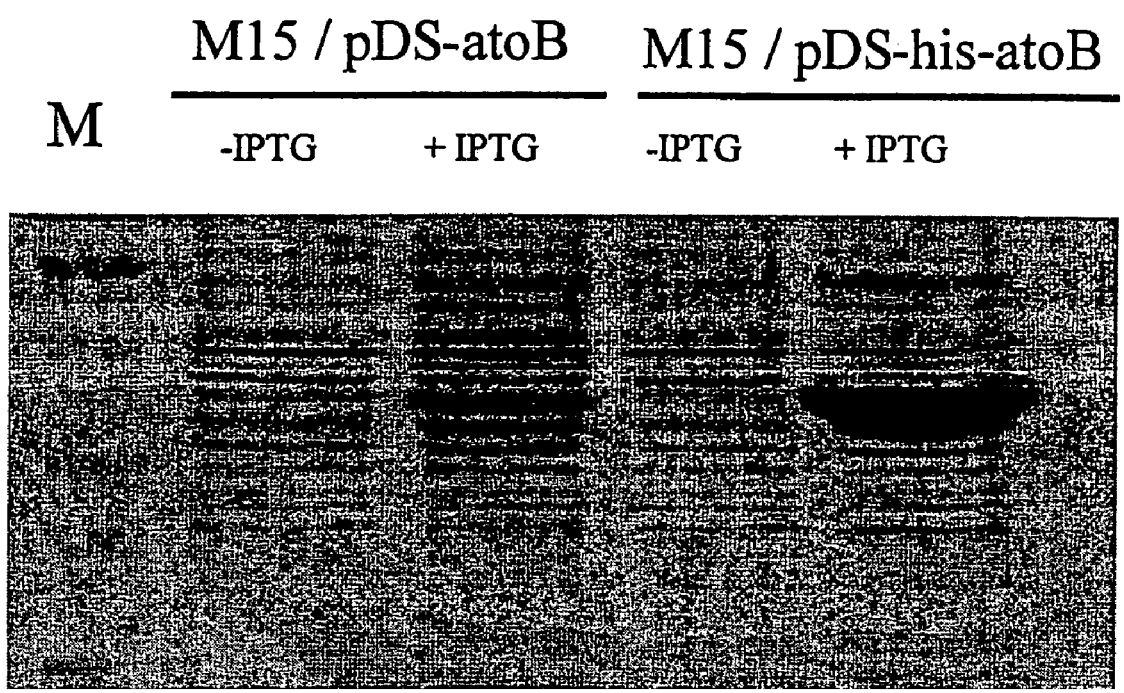

FIG. 32 shows overproduction of the *Paracoccus* sp. strain R1534 atoB gene product, acetyl-CoA acetyltransferase, in *E. coli* M15. Overproduction of the atoB gene product is shown in the induced (+IPTG) lanes compared to the uninduced (−IPTG) lanes. Both the native (M15/pDS-atoB) and His-tagged (M15/pDS/his-atoB) forms were overproduced.

FIGS. 33A-33B show the DNA sequence (SEQ ID NO:177) of the phaAB gene cluster from *Paracoccus* sp. strain R114 and the deduced amino acid sequences of the acetyl-CoA acetyltransferase (PhaA) (SEQ ID NO:178) and acetoacetyl-CoA reductase (PhaB) (SEQ ID NO:179) proteins. An inverted repeat between the genes, constituting a putative transcriptional stop, is underlined.

Figure 34:
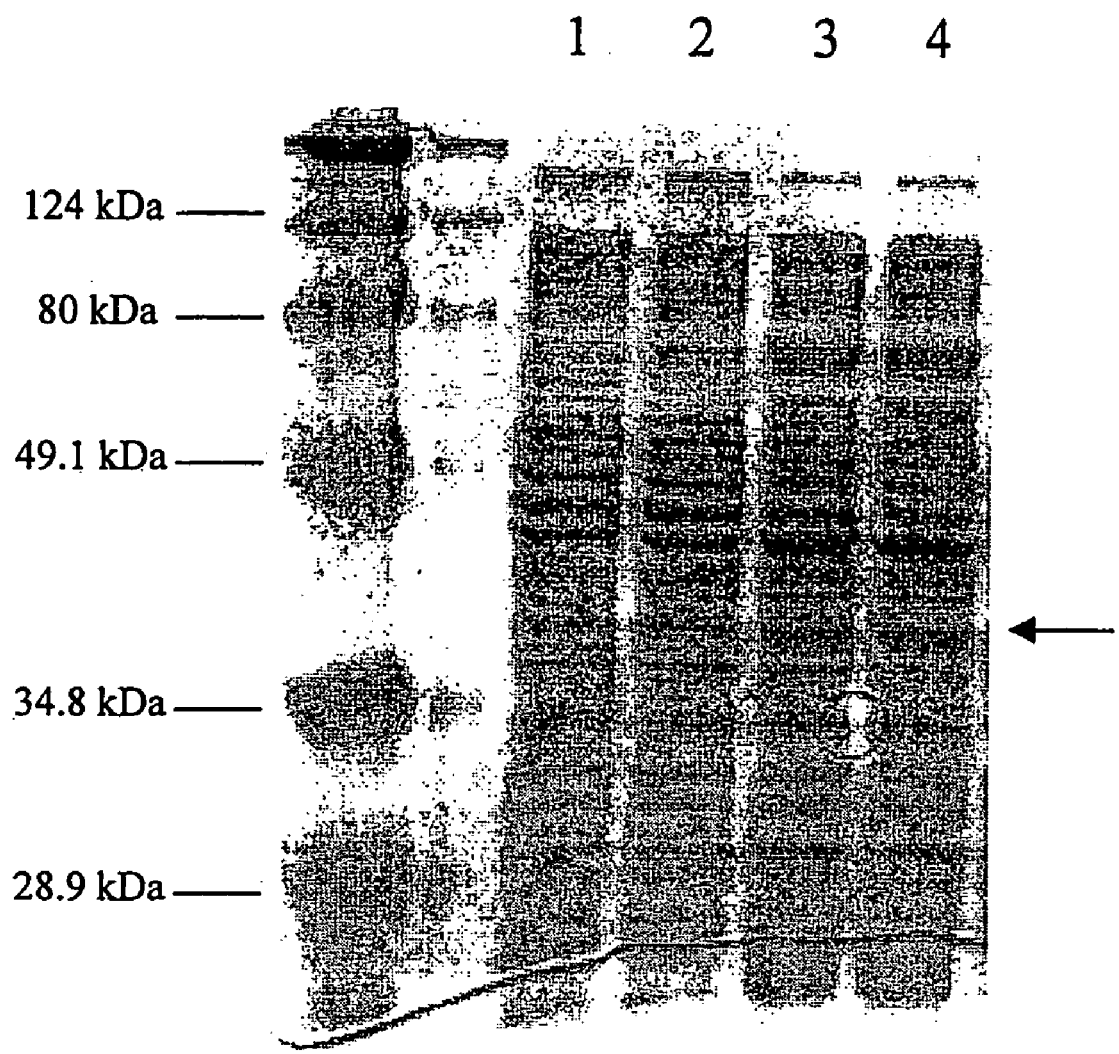

FIG. 34 shows overproduction of the *Paracoccus* sp. strain R114 phaA gene product, acetyl-CoA acetyltransferase, in *E. coli* M15. Lanes 1 and 2, M15/pDS-His-phaA (uninduced); lanes 3 and 4, M15/pDS-His-phaA (induced). Arrow indicates overproduced acetyl-CoA acetyltransferase.

FIG. 35 shows the polylinker regions of plasmids pOCV-1 through -4. Both strands of all four polylinker regions are shown (upper strand: 5'→3', lower strand: 3'→5') (SEQ ID NOs:190-197). The recognition sequences of the restriction endonucleases BsgI (GTGCAG (16/14)), BseMII (CTCAG (10/8)), NdeI (CA/TATG), BamHI (G/GATCC), BseRI (GAGGAG (10/8)) and GsuI (CTGGAG (16/14)) are indicated. The cleavage sites of the first two enzymes are within the NdeI site, between T and G in the upper strand and between A and T in the lower strand. The cleavage sites of the last two enzymes are before the BamHI site, between T and C in the upper strand and between G and T in the lower strand. The BseRI site in pOCV-1 and pOCV-4 is not unique and cannot be used for operon construction.

DETAILED DESCRIPTION OF THE INVENTION

One embodiment of the present invention is an isolated polypeptide that includes an amino acid sequence selected from the following group: (a) an amino acid sequence shown as residues 1 to 340 of SEQ ID NO:43; (b) an amino acid sequence shown as residues 1 to 349 of SEQ ID NO:45; (c) an amino acid sequence shown as residues 1 to 388 of SEQ ID NO:47; (d) an amino acid sequence shown as residues 1 to 378 of SEQ ID NO:49; (e) an amino acid sequence shown as residues 1 to 305 of SEQ ID NO:51; (f) an amino acid sequence shown as residues 1 to 332 of SEQ ID NO:53; (g) at least 30 contiguous amino acid residues of a polypeptide selected from the group consisting of SEQ ID NOs: 43, 45, 47, 49, 51, and 53; (h) an amino acid sequence of a fragment of a polypeptide selected from the group consisting of SEQ ID NOs: 43, 45, 47, 49, 51, and 53, the fragment having the activity of hydroxymethylglutaryl-CoA reductase (HMG-CoA reductase), isopentenyl diphosphate isomerase, hydroxymethylglutaryl-CoA synthase (HMG-CoA synthase), mevalonate kinase, phosphomevalonate kinase, or diphosphomevalonate decarboxylase; (i) an amino acid sequence of a polypeptide encoded by a polynucleotide that hybridizes under stringent conditions to a hybridization probe comprising at least 30 consecutive nucleotides of SEQ ID NO:42 or a complement of SEQ ID NO:42, wherein the polypeptide has the activity of HMG-CoA reductase, isopentenyl diphosphate isomerase, HMG-CoA synthase, isopentenyl diphosphate isomerase, mevalonate kinase, phosphomevalonate kinase, or diphosphomevalonate decarboxylase; and (j) a conservatively modified variant of SEQ ID NOs:43, 45, 47, 49, 51 or 53.

As noted above, the present invention includes SEQ ID Nos: 43, 45, 47, 49, 51, and 53, which are polypeptide sequences that correspond to the following enzymes of the mevalonate pathway: hydroxymethyl glutaryl CoA (HMG-CoA) reductase, isopentenyl diphosphate (IPP) isomerase, HMG-CoA synthase, mevalonate kinase, phosphomevalonate kinase, and diphosphomevalonate decarboxylase, respectively. The present invention also includes at least 30 contiguous amino acids of each identified sequence or a sufficient number of contiguous amino acids to define a biologically active molecule.

The present invention also includes fragments of a polypeptide selected from SEQ ID NOs: 43, 45, 47, 49, 51, and 53. The fragment should be at least about 30 amino acids in length but must have the activity of the identified polypeptide, e.g., in the case of SEQ ID NO:43, a fragment thereof that falls within the scope of the present invention has the activity of HMG-CoA reductase. As used herein, a measure of activity of the respective fragments is set forth in Example 1. A fragment having an activity above background in the assays set forth in Example 1 is considered to be biologically active and within the scope of the present invention.

The present invention also includes an amino acid sequence of a polypeptide encoded by a polynucleotide that hybridizes under stringent conditions, as defined above, to a hybridization probe that contains at least 30 contiguous nucleotides of SEQ ID NO:42 (i.e., the mevalonate operon) or a complement of SEQ ID NO:42. The polynucleotide must encode at least one of the enzymes in the mevalonate pathway. For purposes of the present invention, a "hybridization probe" is a polynucleotide sequence containing from about 10-9066 nucleotides of SEQ ID NO:42.

In this embodiment, the isolated polypeptide may have the amino acid sequence of SEQ ID NO:43, SEQ ID NO:45, SEQ ID NO:47, SEQ ID NO:49, SEQ ID NO:51 or SEQ ID NO:53. Alternatively, the isolated polypeptide may contain about 30 contiguous amino acids selected from an area of the respective amino acids sequences that have the least identity when compared to an enzyme with the same function from different species. (See e.g., FIGS. 16-21). Thus, for example, a polypeptide of the present invention may include amino acids 68-97 of SEQ ID NO:43, 1-30 of SEQ ID NO:45, 269-298 of SEQ ID NO:47, 109-138 of SEQ ID NO:49, 198-227 of SEQ. ID NO:51 or 81-110 of SEQ ID NO:53.

Another embodiment of the invention is an isolated polypeptide having an amino acid sequence selected from: (a) an amino acid sequence shown as residues 1 to 287 of SEQ ID NO:159; (b) at least 30 contiguous amino acid residues of SEQ ID NO:159; (c) an amino acid sequence of a fragment of SEQ ID NO:159, the fragment having the activity of farnesyl-diphosphate synthase (FPP synthase); (d) an amino acid sequence of a polypeptide encoded by a polynucleotide that hybridizes under stringent conditions to a hybridization probe containing at least 30 consecutive nucleotides of the ispA gene (i.e., nucleotides 295-1158 of SEQ ID NO:157) or a complement thereof, wherein the polypeptide has the activity of FPP synthase; and (e) conservatively modified variants of SEQ ID NO:159.

Thus, in this embodiment the amino acid may be encoded by the entire open reading frame that encodes FPP synthase, i.e, residues 1-287 of SEQ ID NO:159, at least 30 contiguous residues thereof, or a fragment of SEQ ID NO:159 that has FPP synthase activity as measured by the assay set forth in Example 1. Furthermore, this embodiment of the invention also includes amino acid sequence(s) encoded by polynucleotide(s) that hybridize under stringent conditions, as defined above, to a hybridization probe that includes at least 30 consecutive nucleotides of the ispA gene (i.e., nucleotides 295-1158 of SEQ ID NO:157) or a complement thereof, wherein the polypeptide has FPP synthase activity as defined above.

In a preferred embodiment, the polypeptide has the amino acid sequence of SEQ ID NO:159.

Another embodiment of the invention is an isolated polypeptide having an amino acid sequence selected from the following group: (a) an amino acid sequence shown as residues 1 to 142 of SEQ ID NO:160; (b) at least 30 contiguous amino acid residues of SEQ ID NO:160; (c) an amino acid sequence of a fragment of SEQ ID NO:160, the fragment having the activity of 1-deoxyxylulose-5-phosphate synthase (DXPS); (d) an amino acid sequence of a polypeptide encoded by a polynucleotide that hybridizes under stringent conditions to a hybridization probe containing at least 30 consecutive nucleotides spanning positions 1185-1610 of SEQ ID NO:157 or a complement thereof, wherein the polypeptide has the activity of DXPS; and (e) conservatively modified variants of SEQ ID NO:160.

Thus, in this embodiment the amino acid may be encoded by the entire open reading frame that encodes DXPS, i.e, residues 1-142 of SEQ ID NO:160, at least 30 contiguous residues thereof, or a fragment of SEQ ID NO:160 that has DXPS activity as measured by as measured by the assay set forth in Example 1. Furthermore, this embodiment of the invention also includes amino acid sequence(s) encoded by polynucleotide(s) that hybridize under stringent conditions, as defined above, to a hybridization probe that includes at least 30 consecutive nucleotides of the DXPS gene (i.e., nucleotides 1185-1610 of SEQ ID NO:157) or a complement thereof, wherein the polypeptide has DXPS activity as defined above.

In a preferred embodiment, the polypeptide has the amino acid sequence of SEQ ID NO:160.

Another embodiment of the invention is an isolated polypeptide having an amino acid sequence selected from: (a) an amino acid sequence shown as residues 1 to 390 of SEQ ID NO:178; (b) at least 30 contiguous amino acid residues of SEQ ID NO:178; (c) an amino acid sequence of a fragment of SEQ ID NO:178, the fragment having the activity of acetyl-CoA acetyltransferase; (d) an amino acid sequence of a polypeptide encoded by a polynucleotide that hybridizes under stringent conditions to a hybridization probe containing at least 30 consecutive nucleotides of the phaA gene (i.e., nucleotides 1-1179 of SEQ ID NO:177) or a complement thereof, wherein the polypeptide has the activity of acetyl-CoA acetyltransferase, and (e) conservatively modified variants of SEQ ID NO:178.

Thus, in this embodiment the amino acid may be encoded by the entire open reading frame that encodes acetyl-CoA acetyltransferase, i.e, residues 1-143 of SEQ ID NO:178, at least 30 contiguous residues thereof, or a fragment of SEQ ID NO:178 that has acetyl-CoA acetyltransferase activity as measured by the assay set forth in Example 1. Furthermore, this embodiment of the invention also includes amino acid sequence(s) encoded by polynucleotide(s) that hybridize under stringent conditions, as defined above, to a hybridization probe that includes at least 30 consecutive nucleotides of the phaA gene (i.e., nucleotides 1-1170 of SEQ ID NO:177), or a complement thereof, wherein the polypeptide has the acetyl-CoA acetyltransferase activity as defined above.

In a preferred embodiment, the polypeptide has the amino acid sequence of SEQ ID NO:178.

Another embodiment of the invention is an isolated polypeptide having an amino acid sequence selected from: (a) an amino acid sequence shown as residues 1 to 240 of SEQ ID NO:179; (b) at least 30 contiguous amino acid residues of SEQ ID NO:179; (c) an amino acid sequence of a fragment of a polypeptide of SEQ ID NO:179, the fragment having the activity of acetoacetyl-CoA reductase; (d) an amino acid sequence of a polypeptide encoded by a polynucleotide that hybridizes under stringent conditions to a hybridization probe containing at least 30 consecutive nucleotides of the phaB gene (i.e., nucleotides 1258-1980 of SEQ ID NO:177) or a complement thereof, wherein the polypeptide has the activity of acetoacetyl-CoA reductase; and (e) conservatively modified variants of SEQ ID NO:179.

Thus, in this embodiment the amino acid may be encoded by the entire open reading frame that encodes acetoacetyl-CoA reductase, i.e, residues 1-240 of SEQ ID NO:179, at least 30 contiguous residues thereof, or a fragment of SEQ ID NO:179 that has acetoacetyl-CoA reductase activity as measured by the assay set forth in Example 1. Furthermore, this embodiment of the invention also includes amino acid sequence(s) encoded by polynucleotide(s) that hybridize under stringent conditions, as defined above, to a hybridization probe that includes at least 30 consecutive nucleotides of the phaB gene (i.e., nucleotides 1258-1980 of SEQ ID NO:177) or a complement thereof, wherein the polypeptide has acetoacetyl-CoA reductase activity as defined above.

In a preferred embodiment, the polypeptide has the amino acid sequence of SEQ ID NO:179.

Another embodiment of the invention is an isolated polynucleotide sequence having the nucleotide sequence of the mevalonate operon (SEQ ID NO:42), variants of SEQ ID NO:42 containing one or more substitutions according to the *Paracoccus* sp. strain 1534 codon usage table (see Table 14) or fragments of SEQ ID NO:42. The variants and fragments of SEQ ID NO:42 must encode a polypeptide having an activity selected from: hydroxymethylglutaryl-CoA reductase (HMG-CoA reductase), isopentenyl diphosphate isomerase activity, hydroxymethylglutaryl-CoA synthase (HMG-CoA synthase), mevalonate kinase, phosphomevalonate kinase, and diphosphomevalonate decarboxylase. This embodiment also includes polynucleotide sequences that hybridize under stringent conditions, as defined above, to a hybridization probe, the nucleotide sequence of which consists of from about 10 to about 9066 nucleotides of SEQ ID NO:42, preferably at least 30 contiguous nucleotides of SEQ ID NO:42, or a complement of such sequences, which hybrid encodes a polypeptide having an activity selected from: HMG-CoA reductase, isopentenyl diphosphate isomerase, HMG-CoA synthase, mevalonate kinase, phosphomevalonate kinase, and diphosphomevalonate decarboxylase.

This embodiment also includes isolated polynucleotide sequences spanning the following residues of SEQ ID NO:42: 2622 to 3644, 3641 to 4690, 4687 to 5853, 5834 to 6970, 6970 to 7887, 7880 to 8878. Fragments of these sequences are also within the scope of the invention, so long as they encode a polypeptide having HMG-CoA reductase activity, isopentenyl diphosphate isomerase activity, HMG-CoA synthase activity, mevalonate kinase activity, phosphomevalonate kinase activity, and diphosphomevalonate decarboxylase activity, respectively.

This embodiment also includes polynucleotide sequences that hybridize under stringent conditions, as defined above, to a hybridization probe selected from a nucleotide sequence which consists of at least 30 contiguous nucleotides of the following residues of SEQ ID NO:42: 2622 to 3644, 3641 to 4690, 4687 to 5853, 5834 to 6970, 6970 to 7887, 7880 to 8878 or a complement thereof, wherein the hybrid encodes a polypeptide having HMG-CoA reductase activity, isopentenyl diphosphate isomerase activity, HMG-CoA synthase activity, mevalonate kinase activity, phosphomevalonate kinase activity, or diphosphomevalonate decarboxylase activity, respectively.

Preferably, the isolated polynucleotide consists of nucleotides 2622 to 3644, 3641 to 4690, 4687 to 5853, 5834 to 6970, 6970 to 7887 or 7880 to 8878 of SEQ ID NO:42.

Another embodiment of the invention is an isolated polynucleotide sequence having the nucleotide sequence of SEQ ID NO:157, variants of SEQ ID NO:157 containing one or more substitutions according to the *Paracoccus* sp. strain 1534 codon usage table (see Table 14) or fragments of SEQ ID NO:157 that encode a polypeptide having farnesyl diphosphate (FPP) synthase activity, 1-deoxy-D-xylulose 5-phosphate synthase activity or the activity of XseB. This embodiment also includes polynucleotide sequences that hybridize under stringent conditions, as defined above, to a hybridization probe the nucleotide sequence of which consists of at least 30 contiguous nucleotides of SEQ ID NO:157, or the complement of SEQ ID NO:157, wherein the hybrid encodes a polypeptide having FPP synthase activity, 1-deoxy-D-xylulose 5-phosphate synthase activity or the activity of XseB.

Preferably, the isolated polynucleotide consists of nucleotides 59-292, 295-1158 or 1185-1610 of SEQ ID NO:157.

Another embodiment of the invention is an isolated polynucleotide sequence having the nucleotide sequence of SEQ ID NO:177, variants of SEQ ID NO:177 containing one or more substitutions according to the *Paracoccus* sp. strain 1534 codon usage table (see Table 14) or fragments of SEQ ID NO:177 that encode a polypeptide having an activity selected from acetyl-CoA acetyltransferase and acetoacetyl-CoA reductase. This embodiment also includes polynucleotide sequences that hybridize under stringent conditions, as defined above, to a hybridization probe the nucleotide sequence of which consists of at least 30 contiguous nucleotides of SEQ ID NO:177, or a complement thereof, which hybrid encodes a polypeptide having an activity selected from the group consisting of acetyl-CoA acetyltransferase and acetoacetyl-CoA reductase.

In this embodiment the isolated polynucleotide sequence may include nucleotides 1 to 1170 of SEQ ID NO:177, variants of SEQ ID NO:177 containing one or more substitutions according to the *Paracoccus* sp. strain 1534 codon usage table (see Table 14) or fragments of SEQ ID NO:177 that encode a polypeptide having acetyl-CoA acetyltransferase activity. This embodiment also includes polynucleotide sequences that hybridize under stringent conditions to a hybridization probe the nucleotide sequence of which consists of at least 30 contiguous nucleotides of nucleotides 1 to 1170 of SEQ ID NO:177, or a complement thereof, wherein the hybrid encodes a polypeptide having acetyl-CoA acetyltransferase activity.

Preferably, the isolated polynucleotide sequence consists of nucleotides 1-1170 of SEQ ID NO:177.

In this embodiment, the isolated polynucleotide sequence may alternatively be nucleotides 1258-1980 of SEQ ID NO:177, variants of SEQ ID NO:177 containing one or more substitutions according to the *Paracoccus* sp. strain 1534 codon usage table (see Table 14) or fragments of SEQ ID NO:177 that encode a polypeptide having acetoacetyl-CoA reductase activity. This embodiment also includes polynucleotide sequences that hybridize under stringent conditions to a hybridization probe the nucleotide sequence of which consists of at least 30 contiguous nucleotides of nucleotides 1258-1980 of SEQ ID NO:177, or a complement thereof, wherein the hybrid encodes a polypeptide having acetoacetyl-CoA reductase activity.

Preferably, the isolated polynucleotide consists of nucleotides 1258-1980 of SEQ ID NO:177.

Another embodiment of the invention is an isolated polynucleotide sequence having the nucleotide sequence spanning positions 1185-1610 of SEQ ID NO:157, variants of the nucleotide sequence spanning positions 1185-1610 of SEQ ID NO:157 containing one or more substitutions according to the *Paracoccus* sp. strain 1534 codon usage table (see Table 14) or fragments of the nucleotide sequence spanning positions 1185-1610 of SEQ ID NO:157 that encode a polypeptide having 1-deoxyxylulose-5-phosphate synthase activity. This embodiment also includes polynucleotide sequences that hybridize under stringent conditions, as defined above, to a hybridization probe the nucleotide sequence of which consists of at least 30 contiguous nucleotides spanning positions 1185-1610 of SEQ ID NO:157, or a complement thereof, wherein the hybrid encodes a polypeptide having 1-deoxyxylulose-5-phosphate synthase activity.

Preferably, the isolated polynucleotide consists of nucleotides 1185 to 1610 of SEQ ID NO:157.

In another embodiment of the invention, the isolated polynucleotide sequence has a nucleotide sequence selected from SEQ ID NO:42, SEQ. ID NO:157, SEQ ID NO:177, and combinations thereof. As used herein, the phrase "and combinations thereof" when used in reference to nucleotide sequences means that any combination of the recited sequences may be combined to form the isolated polynucleotide sequence. Moreover, in the present invention, multiple copies of the same sequence, i.e., concatamers may be used. Likewise, and as set forth in more detail below, multiple copies of plasmids containing the same polynucleotide sequence may be transferred into suitable host cells.

The present invention also includes expression vectors as defined above. The expression vectors include one or more copies of each of the polynucleotide sequences set forth above. The expression vectors of the present invention may contain any of the polynucleotide sequences defined herein, such as for example SEQ ID NO:42, or the following residues of SEQ ID NO:42: 2622 to 3644, 3641 to 4690, 4687 to 5853, 5834 to 6970, 6970 to 7887, 7880 to 8878, as well as residues 59-292, 295-1158 or 1185-1610 of SEQ ID NO:157 and residues 1-1170 or 1258-1980 of SEQ ID NO:177. The expression vectors may contain combinations of the polynucleotide sequences identified herein, such as for example, SEQ ID NO:42, SEQ ID NO:157, and SEQ ID NO:177.

The polynucleotide sequences in the expression vectors may optionally be operably linked to an expression control sequence as defined above and exemplified in the Examples.

The present invention also includes for example, the following expression vectors: pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof. These expression vectors are defined in more detail in the examples below. Moreover, the present invention also includes any expression vector that contains one of the sequences defined herein, which expression vector is used to express an isoprenoid compound, such as a carotenoid, preferably zeaxanthin, in a suitable host cell.

The present invention also includes cultured cells containing one or more of the polynucleotide sequences and/or one or more of the expression vectors disclosed herein. As used herein, a "cultured cell" includes any cell capable of growing under defined conditions and expressing one or more of polypeptides encoded by a polynucleotide of the present invention. Preferably, the cultured cell is a yeast, fungus, bacterium, or alga. More preferably, the cultured cell is a *Paracoccus, Flavobacterium, Agrobacterium, Alcaligenes, Erwinia, E. coli* or *B. subtilis*. Even more preferably, the cell is a *Paracoccus*, such as for example, R-1506, R-1512, R1534 or R114. The present invention also includes the progeny of any of the cells identified herein that express a polypeptide disclosed herein. In the present invention, a cell is a progeny of another cell if its AFLP DNA fingerprint is indistinguishable using the conditions set forth in Example 2 from the fingerprint of the putative parental cell.

Thus, the cultured cells according to the present invention may contain, for example, SEQ ID NO:42, or the following residues of SEQ ID NO:42: 2622 to 3644, 3641 to 4690, 4687 to 5853, 5834 to 6970, 6970 to 7887, 7880 to 8878, as well as residues 59-292, 295-1158 or 1185-1610 of SEQ ID NO:157 and residues 1-1170 or 1258-1980 of SEQ ID NO:177. These sequences may be transferred to the cells alone or as part of an expression vector. These sequences also may optionally be operatively linked to expression control sequence(s). The cultured cells may also contain combinations of the polynucleotide sequences identified herein, such as for example, SEQ ID NO:42, SEQ ID NO:157, and SEQ ID NO:177.

The cultured cells according to the present invention may further contain polynucleotides that encode one or more enzymes in the carotenoid biosynthetic pathway. (See e.g., FIG. 1b). For example, the cultured cells according to the present invention may contain one or more copies of SEQ ID NOs:180, 182, and 184 alone or in combination with any of the polynucleotide sequences identified herein. Thus, the polynucleotide sequences disclosed herein may be transferred into a cultured cell alone or in combination with another polynucleotide sequence that would provide enhanced production of the target isoprenoid compound, such as, for example, carotenoids like zeaxanthin or astaxanthin. In this regard, the present invention includes the use of any polynucleotide encoding, for example, a polypeptide involved in carotenoid biosynthesis, such as GGPP synthase, β-carotene-β4-oxygenase (ketolase), and/or β-carotene hydroxylase. In addition, combinations of polynucleotides encoding polypeptides involved in carotenoid biosynthesis may be used in combination with one or more of the polynucleotides identified herein on the same or different expression vectors. Such constructs may be transferred to a cultured cell according to the present invention to provide a cell that expresses an isoprenoid of interest.

For example, a cultured cell according to the present invention may contain one or more of the following expression vectors: pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof.

Another embodiment of the invention is a method of producing a carotenoid. In this method, a cultured cell as defined above is cultured under conditions permitting expression of a polypeptide encoded by the polynucleotide sequence as defined above. Culture conditions that permit expression of a polypeptide are provided in the Examples below, but may be modified, if required, to suit the particular intended use. The carotenoid is then isolated from the cell or, if secreted, from the medium of the cell.

In the present invention, a "carotenoid" includes the following compounds: phytoene, lycopene, β-carotene, zeaxanthin, canthaxanthin, astaxanthin, adonixanthin, cryptoxanthin, echinenone, adonirubin, and combinations thereof. Preferably, the carotenoid is zeaxanthin.

Another embodiment of the invention is a method of making a carotenoid-producing cell. This method includes (a) introducing into a cell a polynucleotide sequence encoding an enzyme in the mevalonate pathway, which enzyme is expressed in the cell; and (b) selecting a cell containing the polynucleotide sequence of step (a) that produces a carotenoid at a level that is about 1.1-1,000 times the level of the carotenoid produced by the cell before introduction of the polynucleotide sequence.

Figure 1A:
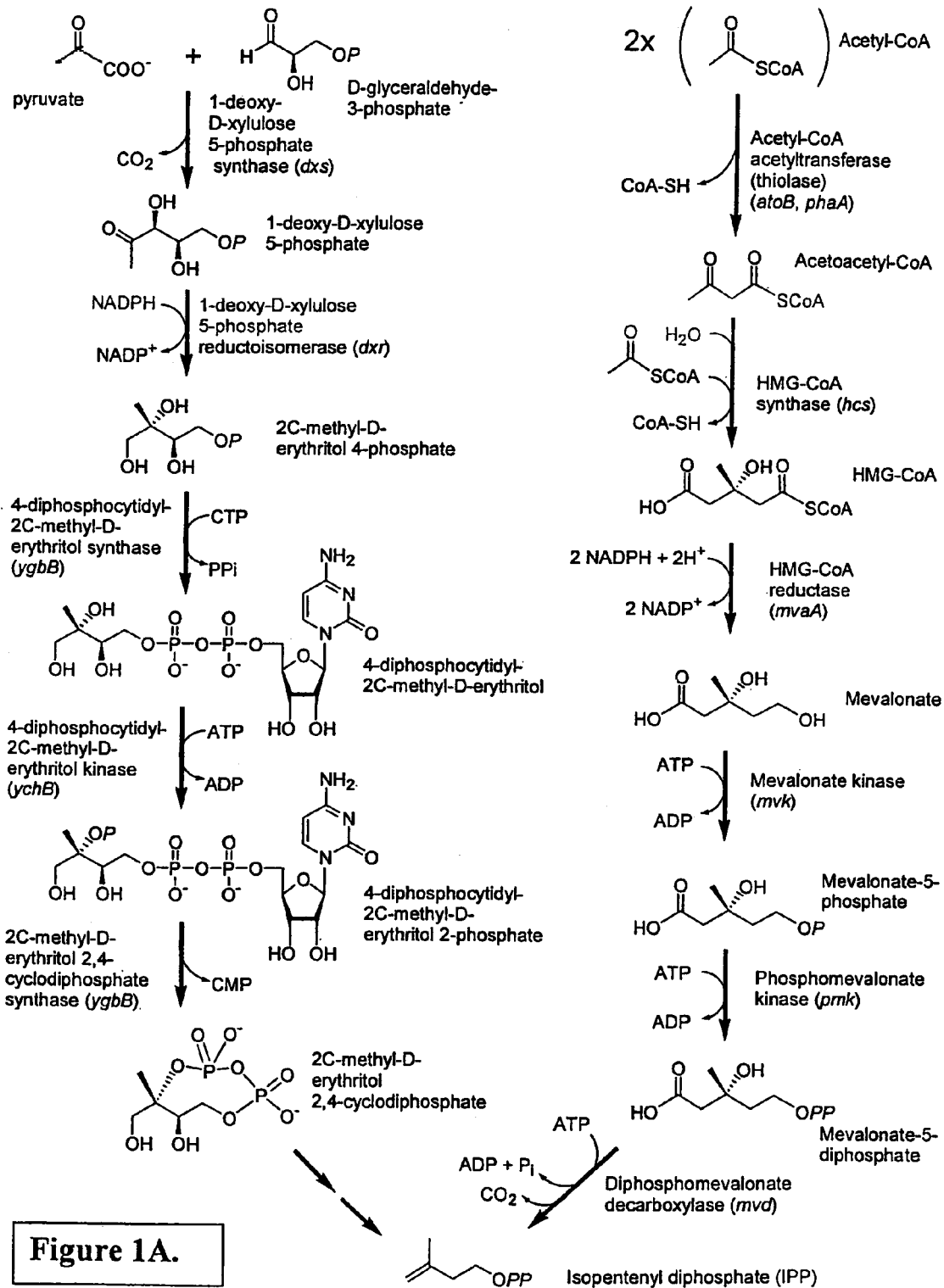
FIG. 1A shows the DXP and mevalonate pathways for IPP biosynthesis.

As used herein, the phrase "an enzyme in the mevalonate pathway" means the enzymes shown in FIG. 1A and encoded by the atoB or phaA, hcs, mvaA, mvk, pmk, and mvd genes. For purposes of the present invention, an enzyme is "expressed in the cell" if it is detected using any one of the activity assays set forth in Example 1. Assays for detecting the production of a carotenoid are well known in the art. Examples 1, 11, and 12 provide typical assay procedures for identifying the presence of zeaxanthin, lycopene, and astaxanthin, respectively. In a similar manner, assays for the other carotenoids may be used to detect the presence in the cell or medium of e.g. phytoene, canthaxanthin, adonixanthin, cryptoxanthin, echinenone, and adonirubin.

Thus, this method may be used to make the following exemplary carotenoids: phytoene, lycopene, β-carotene, zeaxanthin, canthaxanthin, astaxanthin, adonixanthin, cryptoxanthin, echinenone, adonirubin, and combinations thereof. In this method, zeaxanthin is the preferred carotenoid.

This method includes producing cells capable of producing a carotenoid at a level that is about 1.1-1,000 times, preferably about 1.5-500 times, such as about 100 times or at least 10 times, the level of the carotenoid produced by the cell before introduction of the polynucleotide sequence.

In this method, the cell produces from about 1 mg/L to about 10 g/L of a carotenoid. It is preferred that the cell produces from about 100 mg/L to about 9 g/L, such as, for example, from about 500 mg/L to about 8 g/L, or from about 1 g/L to about 5 g/L, of a carotenoid.

In this method, the cell may be selected from a yeast, fungus, bacterium, and alga. Preferably, the cell is a bacterium selected from *Paracoccus, Flavobacterium, Agrobacterium, Alcaligenes, Erwinia, E. coli*, and *B. subtilis*. More preferably, the bacterium is a *Paracoccus*.

In this method, the cell may be a mutant cell. As used herein, a "mutant cell" is any cell that contains a non-native polynucleotide sequence or a polynucleotide sequence that has been altered from its native form (e.g., by rearrangement or deletion or substitution of from 1-100, preferably 20-50, more preferably less than 10 nucleotides). Such a non-native sequence may be obtained by random mutagenesis, chemical mutagenesis, UV-irradiation, and the like. Preferably, the mutation results in the increased expression of one or more genes in the mevalonate pathway that results in an increase in the production of a carotenoid, such as zeaxanthin. Methods for generating, screening for, and identifying such mutant cells are well known in the art and are exemplified in the Examples below. Examples of such mutants are R114 or R1534. Preferably, the mutant cell is R114.

In this method, the polynucleotide sequence is SEQ ID NO:42, or the following residues of SEQ ID NO:42: 2622 to 3644, 3641 to 4690, 4687 to 5853, 5834 to 6970, 6970 to 7887, 7880 to 8878, as well as residues 59-292, 295-1158 or 1185-1610 of SEQ ID NO:157 and residues 1-1170 or 1258-1980 of SEQ ID NO:177. These sequences may be used in this method alone or as part of an expression vector. These sequences also may optionally be operatively linked to expression control sequence(s). In this method, combinations of the polynucleotide sequences identified herein may be used, such as for example, SEQ ID NO:42, SEQ ID NO:157, and SEQ ID NO:177.

Examples of expression vector that may be selected for use in this method include pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof.

In this method, the polynucleotide sequence is introduced into the cell using any conventional means. Examples of suitable methods for introducing a polynucleotide sequence into a cell include transformation, transduction, transfection, lipofection, electroporation (see e.g., Shigekawa and Dower, 1988, Biotechniques 6: 742-751), conjugation (see e.g., Koehler and Thorne, 1987, Journal of Bacteriology 169: 5771-5278), and biolistics.

The use of conjugation to transfer a polynucleotide sequence, such as in the form of an expression vector, into recipient bacteria is generally effective, and is a well-known procedure. (See for example, Pollock et al., U.S. Pat. No. 5,985,623). Depending on the strain of bacteria, it may be more common to use transformation of competent cells with purified DNA.

Known electroporation techniques (both in vitro and in vivo) function by applying a brief high voltage pulse to electrodes positioned around the treatment region. (See for example, Hofmann, U.S. Pat. No. 6,208,893). The electric field generated between the electrodes causes the cell membranes to temporarily become porous, whereupon molecules of the implant agent enter the cells. In known electroporation applications, this electric field comprises a single square wave pulse on the order of 1000 V/cm of about 100 μs duration. Such a pulse may be generated, for example, in known applications of the Electro Square Porator T820, made by the BTX Division of Genetronics, Inc.

Biolistics is a system for delivering polynucleotides into a target cell using microprojectile bombardment techniques. An illustrative embodiment of a method for delivering polynucleotides into target cells by acceleration is a Biolistics Particle Delivery System, which can be used to propel particles coated with DNA or cells through a screen, such as a stainless steel or Nytex screen, onto a filter surface covered with cultured target cells. The screen disperses the particles so that they are not delivered to the target cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, other target cells may be arranged on solid culture medium. The cells to be bombarded are positioned at an appropriate distance below the microprojectile stopping plate. If desired, one or more screens are also positioned between the acceleration device and the cells to be bombarded. Through the use of these well-known techniques one may obtain up to 1000 or more foci of cells transiently expressing a marker gene. The number of cells in a focus which express the exogenous gene product 48 hours postbombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the polynucleotide/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

Accordingly, it is contemplated that one may wish to adjust various of the bombardment parameters in small-scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well known to those of skill in the art. Choursiston et al., U.S. Pat. No. 5,015,580 (specifically incorporated herein by reference) describes the transformation of soybeans using such a technique.

Another embodiment of the invention is a method for engineering a bacterium to produce an isoprenoid compound. Such a bacterium is made by (a) culturing a parent bacterium in a medium under conditions permitting expression of an isoprenoid, and selecting a mutant bacterium from the culture medium that produces about 1.1-1,000 times more of an isoprenoid than the parent bacteria; (b) introducing into the mutant bacterium an expression vector containing a polynucleotide sequence represented by SEQ ID NO:42 operably linked to an expression control sequence; and (c) selecting a bacterium that contains the expression vector and produces at least about 1.1 times more of an isoprenoid than the mutant in step (a).

In this embodiment, an isoprenoid compound means a compound structurally based on isopentenyl diphosphate (IPP) units of the formula:

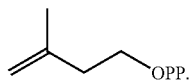

Such compounds include the hemiterpenes, monoterpenes, sesquiterpenes, diterpenes, triterpenes (e.g. phytosterols, phytoestrogens, phytoecdysones, estrogens, phytoestrogens), tetraterpenes (carotenoids), and polyterpenes. Preferably, the isoprenoid is a carotenoid, such as for example, one of the carotenoids identified above, in particular zeaxanthin.

The bacterium may be any bacterium that is capable of producing an isoprenoid compound using the processes disclosed herein. Preferably, the bacterium is a *Paracoccus, Flavobacterium, Agrobacterium, Alcaligenes, Erwinia, E. coli*, or *B. subtilis*. Even more preferably, the bacterium is a *Paracoccus*. Preferably, the parent bacterium is R-1506 or R-1512, and the mutant bacterium is R1534 or R114, preferably R114.

The bacterium is cultured in a media and under conditions that are optimized for the expression of the isoprenoid. The selection of media and culture conditions are well within the skill of the art. The assays set forth in Examples 1, 11, and 12 provide exemplary methods for measuring the presence of certain carotenoids in a culture media. By optimizing the culture conditions and measuring for the production of the target isoprenoid, the culturing and selection of a mutant that meets the specific production parameters recited herein may be met. In this way, a mutant bacterium producing from about 1.1-1,000 times more of an isoprenoid than the parent bacterium may be selected. Preferably, the mutant bacterium produces from about 1.5-500 times more of an isoprenoid than the parent bacterium, such as for example, at least about 100 times or at least about 10 times more of an isoprenoid than the parent bacterium. That bacterium is then cultured and used in subsequent steps.

After selecting the mutant bacterium that produces the desired level of an isoprenoid, an expression vector is introduced into the bacterium using any of the methods set forth above or described in the examples. Any of the expression vectors defined herein may be introduced into the mutant cell. Preferably, the expression vector contains SEQ ID NO:42.

Once the expression vector is introduced into the mutant bacteria, a stable transformant is selected that produces at least about 1.1 times, such as about 5 to about 20 times, more of an isoprenoid than the untransformed mutant. The selected transformant is then cultured under conditions suitable for isoprenoid production, and then the isoprenoid is isolated from the cell or the culture medium.

A further step in this method is introducing a mutation into the mutant bacterium that results in the increased production of an isoprenoid compound by the bacterium. The mutation may be selected from at least one of the following: inactivating the polyhydroxyalkanoate (PHA) pathway, increasing expression of acetyl-CoA acetyltransferase, increasing expression of farnesyl diphosphate (FPP) synthase, increasing expression of an enzyme in a carotenoid biosynthetic pathway, and increasing the expression of an enzyme for converting isopentenyl diphosphate (IPP) to dimethylallyl diphosphate (DMAPP).

The inactivating of the PHA pathway may be achieved by selecting for a mutant bacterium that does not express a polypeptide encoded by phaB (nucleotide positions 1258-1980 of SEQ ID NO:177) or by disrupting expression of the wild type phaB gene by homologous recombination using SEQ ID NO:177 or fragments thereof.

In this method, increasing expression of acetyl-CoA acetyltransferase may be achieved by introducing into the mutant bacterium a vector containing a polynucleotide sequence represented by SEQ ID NO:175 or nucleotide positions 1-1170 of SEQ ID NO:177 operably linked to an expression control sequence. In this method, increasing expression of FPP synthase may be achieved by introducing into the mutant bacterium a vector containing a polynucleotide sequence represented by nucleotides 295-1158 of SEQ ID NO:157 operably linked to an expression control sequence. In this method, increasing expression of a carotenoid gene may be achieved by introducing into the mutant bacterium a vector comprising a polynucleotide sequence that encodes one or more enzymes in the carotenoid biosynthetic pathway, such as for example a polynucleotide sequence selected from the group consisting of SEQ ID NOs:180, 182, and 184 operably linked to an expression control sequence.

In this method, it is preferred that the isoprenoid compound is isopentenyl diphosphate (IPP). It is also preferred that the isoprenoid compound is a carotenoid, such as for example, phytoene, lycopene, β-carotene, zeaxanthin, canthaxanthin, astaxanthin, adonixanthin, cryptoxanthin, echinenone, adonirubin, and combinations thereof.

Another embodiment of the invention is a microorganism of the genus *Paracoccus*, which microorganism has the following characteristics: (a) a sequence similiarity to SEQ ID NO:12 of >97% using a similarity matrix obtained from a homology calculation using GeneCompar v. 2.0 software with a gap penalty of 0%; (b) a homology to R-1512, R1534, R114 or R-1506 of >70% using DNA:DNA hybridization at 81.5° C.; (c) a G+C content of its genomic DNA that varies less than 1% from the G+C content of the genomic DNA of R114, R-1512, R1534, and R-1506; and (d) an average DNA fingerprint that clusters at about 58% similarity to strains R-1512, R1534, R114 and R-1506 using the AFLP procedure of Example 2, with the proviso that the microorganism is not *Paracoccus* sp. (MBIC3966).

Methods for determining each of these characteristics are fully set forth in Example 2, and it is contemplated when these methods are used that microorganisms meeting the above criteria will be readily identifiable. It is preferred that a microorganism of the present invention have each characteristic set forth above (i.e., a-d). However, any combination of the characteristics a-d, which provides sufficient information to taxonomically validly describe a microorganism belonging to the same species as R114, R-1512, R1534, and R-1506, with the exception of *Paracoccus* sp. (MBIC3966) is also within the scope of the invention.

Another embodiment of the invention is a microorganism of the genus *Paracoccus*, which microorganism has the following characteristics: (a) 18:1w7c comprising at least about 75% of the total fatty acids of the cell membranes; (b) an inability to use adonitol, i-erythritol, gentiobiose, β-methylglucoside, D-sorbitol, xylitol and quinic acid as carbon sources for growth; and (c) an ability to use L-asparagine and L-aspartic acid as carbon sources for growth, with the proviso that the microorganism is not *Paracoccus* sp. (MBIC3966).

Methods for determining each of these characteristics are also fully set forth in Example 2, and it is contemplated when these methods are used that microorganisms meeting the above criteria will be readily identifiable. It is preferred that a microorganism of the present invention have each characteristic set forth above (i.e., a-c). However, any combination of the characteristics a-c, which provides sufficient information to taxonomically validly describe a microorganism belonging to the same species as R114, R-1512, R1534, and R-1506, with the exception of *Paracoccus* sp. (MBIC3966) is also within the scope of the invention.

Another embodiment of the invention is a microorganism of the genus *Paracoccus*, which microorganism has the following characteristics: (a) an ability to grow at 40° C.; (b) an ability to grow in a medium having 8% NaCl; (c) an ability to grow in a medium having a pH of 9.1; and (d) a yellow-orange colony pigmentation, with the proviso that the microorganism is not *Paracoccus* sp. (MBIC3966).

Methods for determining each of these characteristics are also fully set forth in Example 2, and it is contemplated when these methods are used that microorganisms meeting the above criteria will be readily identifiable. It is preferred that a microorganism of the present invention have each characteristic set forth above (i.e., a-d). However, any combination of the characteristics a-d, which provides sufficient information to taxonomically validly describe a microorganism belonging to the same species as R114, R-1512, R1534, and R-1506, with the exception of *Paracoccus* sp. (MBIC3966) is also within the scope of the invention.

A microorganism of the present invention may also be identified using any combination of the 11 characteristics set forth above, which provide sufficient information to taxonomically validly describe a microorganism belonging to the same species as R114, R-1512, R1534, and R-1506, with the exception of *Paracoccus* sp. (MBIC3966).

The following examples are provided to further illustrate certain aspects of the present invention. These examples are illustrative only and are not intended to limit the scope of the invention in any way.

EXAMPLES

Example 1

Analytical and Biochemical Methods

Analysis of Carotenoids

Sample preparation. A solvent mixture of 1:1 dimethylsulfoxide (DMSO) and tetrahydrofuran (THF) was first prepared. This solvent mixture was stabilized by the addition of butylated hydroxytoluene (BHT, 0.5 g/l solvent mixture). Four milliliters of the stabilized DMSO/THF mixture was added to 0.4 ml of bacterial culture in a disposable 15-ml polypropylene centrifuge tube (gives a final dilution factor of 1/11). The tubes were capped and mixed using a Vortex mixer for 10 seconds each. The samples were then put on a Brinkmann Vibramix shaker for 20 minutes. The tubes were centrifuged at room temperature for 4 minutes at 4000 rpm and aliquots of the clear yellow/orange supernatant were transferred into brown glass vials for analysis by High Performance Liquid Chromatography (HPLC).

HPLC. A reversed phase HPLC method was developed for the simultaneous determination of astaxanthin, zeaxanthin, canthaxanthin, β-carotene, and lycopene. The method was also able to separate the main cis-isomers of zeaxanthin. Chromatography was performed using an Agilent 1100 HPLC system equipped with a thermostatted autosampler and a diode array detector. The method parameters were as follows:

| | |
|---|---|
| Column | YMC Carotenoid C30 column, particle size 5 micron 250* 4.6 mm I.D., steel (YMC, Part No. CT99S052546WT) |
| Guard column | Pelliguard LC-18 cartridge, 20 mm (SUPELCO, Part No. 59654) |
| Mobile phase | Methanol (MeOH)/Methyl tert-butyl ether (TBME) gradient |

| | % MeOH | % TBME |
|---|---|---|
| Start | 80 | 20 |
| 10 min. | 65 | 35 |
| 20 min. | 10 | 90 |

| | |
|---|---|
| Run time | 28 min. |
| Typical column pressure | 90 bar at start |
| Flow rate | 1.0 ml/min. |
| Detection | UV at 450 nm |
| Injection volume | 10 µl |
| Column temperature | 15° C. |

Reagents. Methanol and TBME were HPLC grade and were obtained from EM Science and J. T. Baker, respectively. DMSO (Omnisolve) was purchased from EM Science. THF (HPLC solvent) was from Burdick and Jackson.

Calculations. Quantitative analyses were performed with a two level calibration using external standards (provided by Hoffmann-La Roche, Basel, Switzerland). Calculations were based on peak areas.

Selectivity. The selectivity of the method were verified by injecting standard solutions of the relevant carotenoid reference compounds. The target compounds (all-trans-carotenoids) were completely separated and showed no interference. Some minor cis isomers may coelute, although these potentially interfering isomers are rare and need not be considered in routine analyses. The retention times of the compounds are listed in Table 1.

TABLE 1

HPLC retention times for carotenoids.

| Carotenoid | Retention time (min.) |
|---|---|
| Astaxanthin | 6.99 |
| Adonixanthin | 7.50 |
| 15-cis-Zeaxanthin | 7.80 |
| 13-cis-Zeaxanthin | 8.23 |
| all-trans-Zeaxanthin | 9.11 |
| Canthaxanthin | 9.95 |
| Cryptoxanthin | 13.45 |

TABLE 1-continued

HPLC retention times for carotenoids.

| Carotenoid | Retention time (min.) |
|---|---|
| β-Carotene | 17.40 |
| Lycopene | 21.75 |

Linearity. 25 Milligrams of all-trans-zeaxanthin were dissolved in 50 ml of DMSO/THF mixture (giving a final zeaxanthin concentration 500 µg/ml). A dilution series was prepared (final zeaxanthin concentrations of 250, 100, 50, 10, 5, 1, and 0.1 µg/ml) and analyzed by the HPLC method described above. A linear range was found from 0.1 µg/ml to 250 µg/ml. The correlation coefficient was 0.9998.

Limit of detection. The lower limit of detection for zeaxanthin by this method was determined to be 60 µg/l. A higher injection volume and optimization of the integration parameters made it possible to lower the detection limit to approximately 5 µg/l.

Reproducibility. The retention time for all-trans-zeaxanthin was very stable (relative standard deviation (RSD), 0.2%). The peak area reproducibility, based on ten repetitive analyses of the same culture sample, was determined to be 0.17% RSD for all trans-zeaxanthin and 1.0% for cryptoxanthin.

Preparation of Crude Extracts and Enzyme Assay Methods.

Preparation of crude extracts. Crude extracts of *Paracoccus* and *E. coli* were prepared by resuspending washed cell pellets in 1 ml of extraction buffer (buffer used depended on the enzyme being assayed—compositions are specified along with each enzyme assay procedure described below). Cell suspensions were placed in a 2-ml plastic vial and disrupted by agitation with glass beads using a Mini Bead Beater 8 (Biospec Products, Bartlesville, Okla., USA). Disruption was performed at 4° C. using a medium agitation setting. The disrupted preparations were centrifuged at 21,000×g for 20 minutes at 4° C. to sediment the cell debris, and the supernatants were used directly for enzyme assays.

Protein determinations. Protein concentrations in crude extracts were determined by the method of Bradford (Anal. Biochem. 72, 248-254, 1976) using the Bio-Rad Protein Assay Reagent (Bio-Rad, Hercules, Calif., USA). Bovine serum albumin was used as the reference protein for construction of standard curves.

Acetyl-CoA acetyltransferase assays. Crude extracts were prepared in 150 mM EPPS (N-[2-hydroxyethyl] piperizine-N'-[3-propanesulfonic acid]) buffer, pH 8.0. Assays were performed in the thiolysis direction according to the method described by Slater et al. (J. Bacteriol., 180, 1979-1987, 1998). This assay measures the disappearance of acetoacetyl-CoA spectrophotometrically at 304 nm. Reaction mixtures contained 150 mM EPPS buffer (pH 8.0), 50 mM $MgCl_2$, 100 µM CoA, 40 µM acetoacetyl-CoA and crude extract. Reactions were carried out at 30° C. and were initiated by addition of crude extract. The disappearance of acetoacetyl-CoA at 304 nm was monitored using a SpectraMAX Plus plate reader (Molecular Devices Corp., Sunnyvale, Calif., USA) and a quartz microtiter plate (any standard spectrophotometer can also be used). Activity (expressed as U/mg protein) was calculated using a standard curve constructed with acetoacetyl-CoA (1 unit of activity=1 µmol acetoacetyl-CoA consumed/min.). The lower limit of detection of Acetyl-CoA acetyltransferase activity was 0.006 U/mg.

HMG-CoA synthase assays. HMG-CoA synthase was assayed according to the method of Honda et al. (Hepatology 27, 154-159, 1998). In this assay, the formation of HMG-CoA from acetyl-CoA and acetoacetyl-CoA is measured directly by separating the reaction product and substrates by HPLC. Crude extracts were prepared in 50 mM Tris-HCl buffer (pH 8.0). Reaction mixtures (0.1 ml) contained 50 mM Tris-HCl buffer (pH 8.0), 0.1 mM EDTA, 20 mM $MgCl_2$, 0.1 mM acetoacetyl-CoA, 0.8 mM acetyl-CoA and crude extract. Reactions were pre-incubated for 2 minutes at 30° C. before adding the crude extract. After 5 minutes of reaction at 30° C., the reactions were stopped by adding 0.2 ml of 200 mM tetra-butyl ammonium phosphate (TBAP, dissolved in methanol-water (3:2, final pH was 5.5) and containing 0.2 mM propionyl-CoA as an internal recovery standard). The mixture was then centrifuged for 3 minutes at 21,000×g at 4° C. and subsequently kept on ice until analyzed by reversed phase ion-pair HPLC. HMG-CoA and propionyl-CoA were separated from acetyl-CoA and acetoacetyl-CoA using a Nova-Pak C18 column (3.9×150 mm, Waters Corporation, Milford, Mass., USA). The injection volume was 20 µl, the mobile phase was 50 mM TBAP dissolved in methanol-water (1:1, final pH was 5.5), and the flow rate was 1.0 ml/min. HMG-CoA and propionyl-CoA were detected by absorbance at 254 nm. HMG-CoA produced in the reaction was quantified by comparison with a standard curve created using authentic HMG-CoA. Activity is defined as U/mg protein. One unit of activity=1 nmol HMG-CoA produced/min. The lower limit of detection of HMG-CoA synthase was about 1 U/mg.

HMG-CoA reductase assays. Crude extracts were prepared in 25 mM potassium phosphate buffer (pH 7.2) containing 50 mM KCl, 1 mM EDTA and a protease inhibitor cocktail (Sigma Chemical Co., St. Louis, Mo., USA, catalog #P-2714). Assays were performed according to the method of Takahashi et al. (J. Bacteriol., 181, 1256-1263 (1999)). This assay measures the HMG-CoA dependent oxidation of NADPH spectrophotometrically at 340 nm. Reaction mixtures contained 25 mM potassium phosphate buffer (pH 7.2), 50 mM KCl, 1 mM EDTA, 5 mM dithiothreitol, 0.3 mM NADPH, 0.3 mM R,S-HMG-CoA and crude extract. Reactions were performed at 30° C. and were initiated by the addition of HMG-CoA. HMG-CoA-dependent oxidation of NADPH was monitored at 340 nm using a SpectraMAX Plus plate reader (Molecular Devices Corp., Sunnyvale, Calif., USA) and a quartz microtiter plate (any standard spectrophotometer may be used). Activity (expressed as U/mg protein) was calculated using a standard curve constructed with NADPH (1 unit of activity=1 µmol NADPH oxidized/min.). The lower limit of detection of HMG-CoA reductase activity was 0.03 U/mg.

Mevalonate kinase, phosphomevalonate kinase and mevalonate diphosphate decarboxylase assays. The preparation of substrates and the assay procedures for mevalonate kinase, phosphomevalonate kinase and mevalonate diphosphate decarboxylase have been described in detail by Popják (Methods Enzymol., 15, 393-425, 1969). For all assays, one unit of enzyme activity is defined as 1 µmol of product formed/minute. In addition to these spectrophotometric and radiochromatographic assays, alternate methods, for example using HPLC separation of reaction substrates and products, can be used. The lower limit of detection of mevalonate kinase, phosphomevalonate kinase and mevalonate diphosphate decarboxylase is typically about 0.001 U/mg protein.

IPP isomerase assays. Crude extracts were prepared in 50 mM Tris-HCl buffer (pH 7.5). Assays were performed using the method of Spurgeon et al. (Arch. Biochem. Biophys. 230, 445-454, 1984). This assay is based on the difference in acid-lability of IPP and DMAPP. Reaction mixtures (0.1 ml final volume) contained 50 mM Tris-HCl buffer (pH 7.5), 2 mM dithiothreitol, 5 mM $MgCl_2$, 20 µM [1-$^{14}$C]-IPP and crude extract. Reactions were carried out at 30° C. for 15 minutes and terminated by the addition of 0.3 ml of a mixture of concentrated HCl:methanol (4:1) and an additional incubation at 37° C. for 20 minutes. Hexane (0.9 ml) was added and the tubes were mixed (4 times for 10 seconds using a vortex mixer). After centrifugation (21,000×g, 5 minutes), 0.6 ml of the hexane layer was transferred to a scintillation vial, scintillation fluid was added, and the radioactivity counted. Activity is expressed as U/mg protein. One unit of activity=1 pmol [1-$^{14}$C]-IPP incorporated into acid labile products/min. The lower limit of detection of IPP isomerase activity was 1 U/mg.

FPP synthase assays. Crude extracts were prepared in 50 mM Tris-HCl buffer (pH 8.0). The FPP synthase assay procedure was similar to the IPP isomerase assay described above, being based on the difference in acid lability of IPP and FPP (Spurgeon et al., Arch. Biochem. Biophys. 230, 445-454, 1984). Reaction mixtures (0.1 ml final volume) contained 50 mM Tris-HCl buffer (pH 8.0), 2 mM dithiothreitol, 5 mM $MgCl_2$, 20 µM [1-$^{14}$C]-IPP, 25 µM GPP (geranyl pyrophosphate) and crude extract. Reactions were carried out at 30° C. for 15 minutes and terminated by the addition of 0.3 ml of a mixture of concentrated HCl:methanol (4:1) and an additional incubation at 37° C. for 20 minutes. Hexane (0.9 ml) was added and the tubes were mixed (4×, 10 seconds using a vortex mixer). After centrifugation (21,000×g, 5 minutes), 0.6 ml of the hexane layer was transferred to a scintillation vial, scintillation fluid was added, and the radioactivity counted. Units of enzyme activity, and the lower limit of detection, were the same as defined above for IPP isomerase. In cases where high IPP isomerase activity interferes with measurement of FPP synthase activity, crude extract may be preincubated for 5 minutes in the presence of 5 mM iodoacetamide to inhibit IPP isomerase activity.

GGPP synthase assays. Crude extracts were prepared in 50 mM Tris-HCl buffer (pH 8.0) containing 2 mM dithiothreitol. GGPP synthase was assayed according to the procedure of Kuzuguchi et al. (J. Biol. Chem., 274, 5888-5894, 1999). This assay is based on the same principle as described above for FPP synthase. Reaction mixtures (0.1 ml final volume) contained 50 mM Tris-HCl buffer (pH 8.0), 2 mM dithiothreitol, 5 mM $MgCl_2$, 20 µM [1-$^{14}$C]-IPP, 25 µM FPP and crude extract. All reaction conditions and subsequent treatment of samples for scintillation counting were identical to those described above for FPP synthase. Treatment of extract with iodoacetamide to inhibit IPP isomerase activity may also be used as above. Units of enzyme activity, and the lower limit of detection, were the same as defined above for IPP isomerase.

Acetoacetyl-CoA reductase assays. Crude extracts are prepared in 50 mM Tris-HCl buffer (pH 7.5) containing 50 mM KCl and 5 mM dithiothreitol. Acetoacetyl-CoA reductase was assayed according to the procedure of Chohan and Copeland (Appl. Environ. Microbiol., 64, 2859-2863, 1998). This assay measures the acetoacetyl-CoA-dependent oxidation of NADPH spectrophotometrically at 340 nm. Reaction mixtures (1 ml) contain 50 mM Tris-HCl buffer (pH 8.5), 15 mM $MgCl_2$, 250 µM NADPH, and 100 µM acetoacetyl-CoA. Reactions are performed at in a quartz cuvette at. 30° C. and are initiated by the addition of acetoacetyl-CoA. Activity (expressed as U/mg protein) was calculated using a standard curve constructed with NADPH (1 unit of activity=1 µmol NADPH oxidized/min). The lower limit of detection of acetoacetyl-CoA reductase activity is about 0.01 U/mg.

Example 2

Taxonomic Reclassification of *Flavobacterium* sp. as *Paracoccus*

This Example describes the taxonomic re-classification of the zeaxanthin-producing bacterium formerly designated *Flavobacterium* sp. strain R-1512 (ATCC 21588) as *Paracoccus* sp. strain R-1512 (ATCC 21588).

A comprehensive genomic and biochemical/physiological analysis was performed by the Belgian Coordinated Collections of Microorganisms/Laboratorium voor Microbiologie, Universiteit Gent (BCCM™/LMG), using state-of-the-art methods currently accepted as the scientific standards for bacterial classification. Besides *Paracoccus* sp. strain R-1512, several other bacteria belonging to the genus *Paracoccus* were included in the study (summarized in Table 2).

TABLE 2

Bacteria used in taxonomic study.

| Bacterium | Strain designation | Source or reference |
|---|---|---|
| *Paracoccus* sp. | R-1512 (ATCC 21588) | American Type Culture Collection (environmental isolate); Schocher and Wiss, U.S. Pat. No. 3,891,504 |
| *Paracoccus* sp. | R1534 | Hohmann et al., U.S. Pat. No. 6,087,152 (mutant derived from R-1512) |
| *Paracoccus* sp. | R114 | This work (mutant derived from R-1512) |
| *Paracoccus* sp. | R-1506 | This work (environmental isolate) |
| *Paracoccus* sp. | MBIC3024 | H. Kasai, Kamaishi Institute, Japan |
| *Paracoccus* sp. | MBIC3966 | H. Kasai, Kamaishi Institute, Japan |
| *Paracoccus* sp. | MBIC4017 | H. Kasai, Kamaishi Institute, Japan |
| *Paracoccus* sp. | MBIC4020 | H. Kasai, Kamaishi Institute, Japan |
| *Paracoccus marcusii* | DSM 11574$^T$ | Harker et al., Int. J. Syst. Bacteriol. 48, 543-548, 1998. |

TABLE 2-continued

Bacteria used in taxonomic study.

| Bacterium | Strain designation | Source or reference |
|---|---|---|
| *Paracoccus carotinifaciens* | E-396[T] | Tsubokura et at., Int. J. Syst. Bacteriol. 49, 277-282, 1999. |
| *Paracoccus solventivorans* | DSM 6637[T] | Siller et. al., Int. J. Syst. Bacteriol. 46, 1125-1130, 1996. |

Strains R1534 and R114 are mutants derived from strain R-1512 by classical mutagenesis and screening for improved zeaxanthin production. The primary screening was accomplished by selecting the highest color intensity producing colonies. A secondary screening was accomplished in liquid culture media by the HPLC methods according to Example 1. Strain R-1506 is an independent isolate obtained from the same initial screening of environmental microorganisms that provided strain R-1512. Strains MBIC3024, MBIC3966, MBIC4017 and MBIC4020 were identified as members of the genus *Paracoccus* by the nucleotide sequences of their 16S rDNA genes (DNA sequences were deposited in the public EMBL database, see Table 5). *Paracoccus marcusii* DSM 11574[T] and *Paracoccus carotinifaciens* E-396[T] are recently described type strains of carotenoid-producing bacteria (Harker et al. Int. J. Syst. Bacteriol., 48, 543-548, 1998; Tsubokura et al., Int. J. Syst. Bacteriol. 49, 277-282, 1999). *Paracoccus solventivorans* DSM 6637[T] was included as a "control" strain, being a member of the genus *Paracoccus* but distantly related to the other bacteria used.

Preliminary experiments resulted in the following conclusions. Each of the methods set forth herein has a well-recognized ability to define taxonomic relatedness or relative degree of similarity between organisms. The methods and their use for delineating bacterial taxa were described and compared in detail by Van Damme et al., Microbiological Reviews 60, 407-438 (1996) and Janssen et al., Microbiology 142, 1881-1893 (1996).

1. Fatty acid analysis of the cell membranes of strains R1534 and R114 showed that the two strains were highly similar and indicated a taxonomic relatedness of these strains to *Paracoccus denitrificans* and *Rhodobacter capsulatus*.
2. One-dimensional gel electrophoresis of cellular proteins showed a high similarity (i.e., a relatedness at the intra-species level) between R1534 and R114, but the profiles did not justify allocation of these strains to either *R. capsulatus* or *P. denitrificans*.
3. DNA:DNA hybridization between strain R1534 and *R. capsulatus* LMG2962[T] and *P. denitrificans* LMG4218[T] confirmed that strain R1534 is neither *R. capsulatus* nor *P. denitrificans*.
4. Sequencing of 16S rDNA genes from strains R1534 and R114 showed that these organisms belong to the genus *Paracoccus*, but that they represent a new species. The highest degree of sequence similarity was observed with the 16S rDNA gene of *Paracoccus* sp. strains MBIC3966, MBIC4020 and MBIC3024.
5. DNA fingerprinting of strains R1534 and R-1512 using Amplified Fragment Length Polymorphism (AFLP™) showed high overall similarity of the genomic DNA from the two strains, indicating an infraspecific relatedness (i.e. AFLP™ can differentiate between two members of the same species).

In the following sections, the results and conclusions of the present comprehensive taxonomic study of *Paracoccus* sp. strain R-1512 (and its mutant derivatives R1534 and R114) are set forth.

16S rDNA sequencing and phylogenetic study. The bacteria set forth in Table 2 were grown in LMG medium 185 ((TSA) BBL 11768 supplemented where necessary with 1.5% Difco Bacto agar). Genomic DNA was prepared according to the protocol of Niemann et al. (J. Appl. Microbiol. 82, 477-484, 1997). Genes coding for 16S rDNA were amplified from genomic DNA from strains R-1512, R1534, R114 and R-1506 by polymerase chain reaction (PCR) using the primers shown in Table 3.

TABLE 3

Primers used for PCR amplification of DNA coding for 16S rDNA in *Paracoccus* sp. strains R-1512, R1534, R114, and R-1506.

| Primer name[a] | Synonym | Sequence (5'→3') | Position[b] |
|---|---|---|---|
| 16F27 | PA | AGA GTT TGA TCC TGG CTC AG (SEQ ID NO:1) | 8-27 |
| 16F38 | ARI C/T | CTG GCT CAG GAC/T GAA CGC TG (SEQ ID NO:2) | 19-38 |
| 16R1522 | PH | AAG GAG GTG ATC CAG CCG CA (SEQ ID NO:3) | 1541-1522 |

[a]F, forward primer; R, reverse primer. Forward primer 16F27 was used for strains R1534 and R-1506, while forward primer 16F38 was used for strains R-1512 and R114. The reverse primer 16R1522 was used for all strains.
[b]Hybridization position referring to *E. coli* 16S rDNA gene sequence numbering.

The PCR-amplified DNAs were purified using the Qiaquick PCR Purification Kit (Qiagen GmbH, Hilden, Germany). Complete sequencing was performed using an Applied Biosystems, Inc. 377 DNA Sequencer and the protocols of the manufacturer (Perkin-Elmer, Applied Biosystems Division, Foster City, Calif., USA) using the "ABI PRISM™ Big Dye™ Terminator Cycle Sequencing Ready Reaction Kit (with AmpliTaq® DNA Polymerase, Fs)". The primers used for DNA sequencing are shown in Table 4.

TABLE 4

Primers used for sequencing PCR-amplified segments of genes coding for 16S rDNA in *Paracoccus* sp. strains R-1512, R1534, R114 and R-1506.

| Primer name[a] | Synonym | Sequence (5'→3') | Position[b] |
|---|---|---|---|
| 16F358 | *Gamma | CTC CTA CGG GAG GCA GCA GT (SEQ ID NO:4) | 339-358 |
| 16F536 | *PD | CAG CAG CCG CGG TAA TAC (SEQ ID NO:5) | 519-536 |
| 16F926 | *O | AAC TCA AAG GAA TTG ACG G (SEQ ID NO:6) | 908-926 |

TABLE 4-continued

Primers used for sequencing PCR-amplified
segments of genes coding for 16S rDNA in
Paracoccus sp. strains R-1512, R1534, R114
and R-1506.

| Primer name[a] | Synonym | Sequence (5'→3') | Position[b] |
|---|---|---|---|
| 16F1112 | *3 | AGT CCC GCA ACG AGC GCA AC (SEQ ID NO:7) | 1093–1112 |
| 16F1241 | *R | GCT ACA CAC GTG CTA CAA TG (SEQ ID NO:8) | 1222–1241 |
| 16R339 | Gamma | ACT GCT GCC TCC CGT AGG AG (SEQ ID NO:9) | 358–339 |
| 16R519 | PD | GTA TTA CCG CGG CTG CTG (SEQ ID NO:10) | 536–519 |
| 16R1093 | 3 | GTT GCG CTC GTT GCG GGA CT (SEQ ID NO:11) | 1112–1093 |

[a]F, forward primer; R, reverse primer.
[b]Hybridization position referring to E. coli 16S rDNA gene sequence numbering.

Five forward and three reverse primers were used to obtain a partial overlap of sequences, ensuring highly reliable assembled sequence data. Sequence assembly was performed using the program AutoAssembler (Perkin-Elmer, Applied Biosystems Division, Foster City, Calif., USA). Phylogenetic analysis was performed using the software package GeneCompar™ (v. 2.0, Applied Maths B. V. B. A., Kortrijk, Belgium) after including the consensus sequences (from strains R-1512, R1534, R114 and R-1506) in an alignment of small ribosomal subunit sequences collected from the international nucleotide sequence library EMBL. This alignment was pairwise calculated using an open gap penalty of 100% and a unit gap penalty of 0%. A similarity matrix was created by homology calculation with a gap penalty of 0% and after discarding unknown bases. A resulting tree was constructed using the neighbor-joining method.

Figure 3:
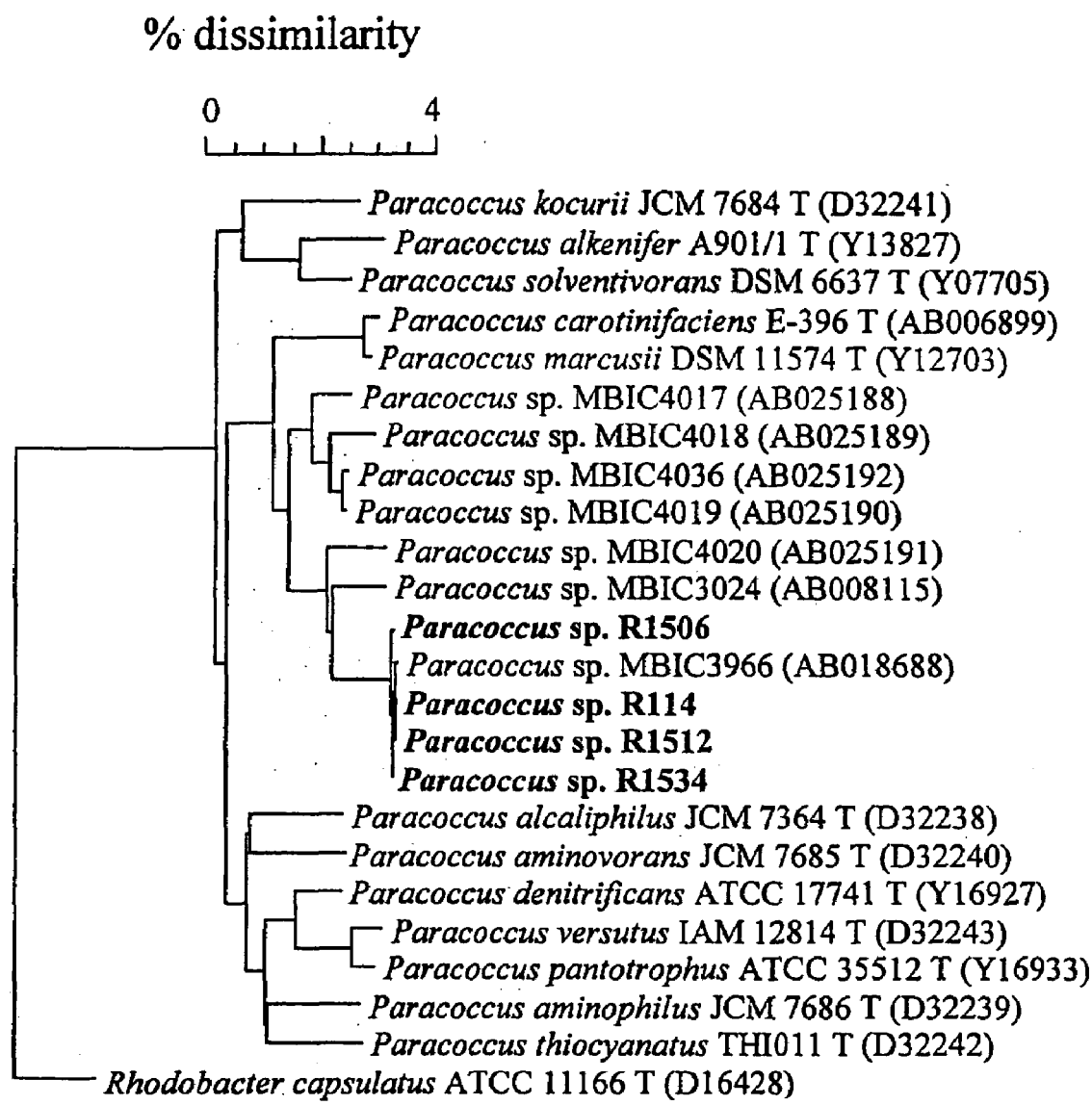
FIG. 3 shows a phylogenetic tree depicting the phylogenetic relatedness between *Paracoccus* sp. strains R-1512, R1534, R114, R-1506, MBIC3966, and other members of the genus *Paracoccus*.

FIG. 2 shows the nucleotide sequence of the 16s rDNA gene from Paracoccus sp. strain R-1512 (SEQ ID NO:12). The distance matrix, presented as the percentage of 16S rDNA sequence similarity, between strain R-1512 and its closest relatives, is shown in Table 5. The sequences from strains R-1512 and its mutant derivatives R1534 and R114 were identical. The sequence from R-1506 differed by only one nucleotide from the sequence from latter strains. This demonstrated strains R-1512 and R-1506 are phylogenetically highly related and likely belong to the same species (confirmed by DNA:DNA hybridization, see below). Comparison of the R-1512 and R-1506 sequences with those publicly available at the EMBL library located R-1512 and R-1506 in the genus Paracoccus. However, the sequence similarities observed with all currently taxonomically validly described Paracoccus species was <97%, the value generally accepted as the limit for a possible relatedness at the species level (Stackebrandt and Goebel, Int. J. Syst. Bacteriol., 44, 846-849, 1994). This demonstrated that strains R-1512 (and its mutant derivatives) and R-1506 belong to one or two new Paracoccus species. Sequence similarities of >97% (significant for a possible relationship at the species level), were observed between four unnamed Paracoccus strains and strains R-1512, R1534, R114 and R-1506, suggesting that one or more of the unnamed (MBIC) strains may relate at the species level to strains R-1512 and R-1506. Based on cluster analysis (phylogenetic tree, see FIG. 3), strains R-1512, R1534, R114, R-1506 and four unnamed Paracoccus strains (MBIC3024, MBIC3966, MBIC4017 and MBIC4020) were selected for DNA:DNA hybridization experiments to analyze species relatedness.

TABLE 5

Distance matrix, presented as the percentage of 16S rDNA sequence similarity, between Paracoccus sp. strain R-1512 and its closest relatives.

| Strain[a] | EMBL Accession number | % Similarity |
|---|---|---|
| R-1512 | — | 100 |
| R1534 | — | 100 |
| R114 | — | 100 |
| R-1506 | — | 99.9 |
| Paracoccus sp. MBIC3966 | AB018688 | 100 |
| Paracoccus sp. MBIC3024 | AB008115 | 98.2 |
| Paracoccus sp. MBIC4020 | AB025191 | 98.1 |
| Paracoccus sp. MBIC4036 | AB025192 | 97.0 |
| Paracoccus sp. MBIC4017 | AB025188 | 96.9 |
| Paracoccus sp. MBIC4019 | AB025190 | 96.8 |
| Paracoccus sp. MBIC4018 | AB025189 | 96.4 |
| Paracoccus marcusii DSM 11574[T] | Y12703 | 96.2 |
| Paracoccus carotinifaciens E-396[T] | AB006899 | 96.1 |
| Paracoccus solventivorans DSM 6637[T] | Y07705 | 95.4 |
| Paracoccus thiocyanaticus THIO11[T] | D32242 | 95.3 |
| Paracoccus aminophilus JCM 7686[T] | D32239 | 95.1 |
| Paracoccus alcaliphilus JCM 7364[T] | D32238 | 95.0 |
| Paracoccus pantotrophicus ATCC 35512[T] | Y16933 | 95.0 |
| Paracoccus denitrificans ATCC 17741[T] | Y16927 | 94.8 |
| Paracoccus versutus IAM 12814[T] | D32243 | 94.7 |
| Paracoccus kocurii JCM 7684[T] | D32241 | 94.6 |
| Paracoccus aminovorans JCM 7685[T] | D32240 | 94.4 |
| Paracoccus alkenifer A901/1[T] | Y13827 | 94.3 |
| Rhodobacter capsulatus ATCC 11166[T] | D16428 | 92.9 |

[a]Type strains are followed by a[T]

DNA:DNA hybridization and determination of G+C content. The bacteria set forth in Table 5 were grown in LMG medium 185. Genomic DNA was prepared according to the protocol of Wilson (In F. M. Ausabel, R. Brent, R. E. Kingston, D. D. Moore, J. G. Seidman, J. A. Smith and K. Struhl (ed.), Current Protocols in Molecular Biology, Greene Publishing and Wiley Interscience, New York, p. 2.4.1-2.4.5, 1987). The G+C content of the DNA's was determined by HPLC according to Mesbach et al. (Int. J. Syst. Bacteriol. 39, 159-167, 1989) as modified by Logan et al. (Int. J. Syst. Evol. Microbiol. 50, 1741-1753, 2000). Reported values are the mean of these measurements on the same DNA sample. DNA:DNA hybridizations were performed using the initial renaturation rate method as described by De Ley et al. (Eur. J. Biochem. 12, 133-142, 1970). The hybridization temperature was 81.5° C. For this method, an average deviation of +/−5.8% has been reported by Vauterin et al. (Int. J. Syst. Bacteriol. 45, 472-489, 1995). The G+C content of the bacterial DNA's and the results of the DNA hybridization experiments are summarized in Table 6.

TABLE 6

G + C content (mol %) of DNA from *Paracoccus* spp. strains and per cent DNA homology between the strains.

| Strain | % G + C | % DNA Homology | | | | | | |
|---|---|---|---|---|---|---|---|---|
| R-1512 | 67.6 | 100 | | | | | | |
| R1534 | 67.7 | 96 | 100 | | | | | |
| R114 | 67.5 | 100 | 97 | 100 | | | | |
| R-1506 | 67.5 | 94 | 90 | 88 | 100 | | | |
| MBIC3024 | 65.4 | 31 | nd[a] | nd | 31 | 100 | | |
| MBIC3966 | 66.9 | 93 | nd | nd | 88 | 32 | 100 | |
| MBIC4017 | 67.2 | 32 | nd | nd | 31 | 24 | 24 | 100 |
| MBIC4020 | 68.4 | 27 | nd | nd | 25 | 25 | 23 | 34 | 100 |

[a]not determined

Strains R-1512, R1534, R114, R-1506 and MBIC3966 showed a DNA homology of >70% (the generally accepted limit for species delineation (Wayne et al. Int. J. Syst. Bacteriol. 37, 463-464, 1987)), and therefore belong to the same species within the genus *Paracoccus*. The G+C content of these five strains varied from 66.9%-67.7%, thus remaining within 1%, characteristic for a well defined species. On the other hand, the low DNA homology between strains MBIC3024, MBIC4017 and MBIC4020 and strains R-1512, R1534, R114, R-1506 and MBIC3966 showed that MBIC3024, MBIC4017 and MBIC4020 each belong to a different genomic species within the genus *Paracoccus*.

DNA fingerprinting using AFLP™. AFLP™ is a PCR-based technique for whole genome DNA fingerprinting via the selective amnplification and selective visualization of restriction fragments (Vos et al. Nucleic Acids Research 23, 4407-4414, 1995; Janssen et al. Microbiology 142, 1881-1893, 1996). In this analysis, *Paracoccus* sp. strains R-1512, R1534, R114, R-1506, MBIC3966, and *Paracoccus marcusii* DSM 11574[T] were compared to evaluate infraspecies relatedness. These bacteria were grown in LMG medium 185. Genomic DNA from each of these bacteria was prepared according to the protocol of Wilson (In F. M. Ausabel, R. Brent, R. E. Kingston, D. D. Moore, J. G. Seidman, J. A. Smith and K. Struhl (ed.), Current Protocols in Molecular Biology, Greene Publishing and Wiley Interscience, New York, p. 2.4.1-2.4.5 (1987)). Purified DNA was digested by two restriction enzymes, a 4-base cutter and a 6-base cutter. In this way, a limited number of fragments with two different ends and of suitable size for efficient PCR were obtained. Adaptors (small double-stranded DNA molecules of 15-20 bp) containing one compatible end were ligated to the appropriate "sticky" end of the restriction fragments. Both adaptors are restriction halfsite-specific, and have different sequences. These adaptors serve as binding sites for PCR primers. Here, the restriction enzymes used were ApaI (a hexacutter, recognition sequence GGGCC/C) and TaqI (a tetracutter, recognition sequence T/GCA). The sequences of the adaptors ligated to the sticky ends generated by cleavage with the restriction enzymes are shown in Table 7 (SEQ ID Nos:13-22). PCR was used for selective amplification of the restriction fragments. The PCR primers specifically annealed with the adaptor ends of the restriction fragments. Because the primers contain, at their 3' end, one so-called "selective base" that extends beyond the restriction site into the fragment, only those restriction fragments that have the appropriate complementary sequence adjacent to the restriction site were amplified. The sequences of the six PCR primer combinations used are also shown in Table 7.

TABLE 7

Adaptors and PCR primers used for AFLP™ analysis.

| | Sequence |
|---|---|
| Adaptors corresponding to restriction enzyme ApaI | |
| Adaptor 93A03 | 5'-TCGTAGACTGCGTACAGGCC-3' (SEQ ID NO:13) |
| Adaptor 93A04 | 3'-CATCTGACGCATGT-5' (SEQ ID NO:14) |
| Adaptors corresponding to restriction enzyme TaqI | |
| Adaptor 94A01 | 5'-GACGATGAGTCCTGAC-3' (SEQ ID NO:15) |
| Adaptor 94A02 | 3'-TACTCAGGACTGGC-5' (SEQ ID NO:16) |
| Primer combination 1 (PC A) | |
| A01 | 5'GACTGCGTACAGGCCCA3' (SEQ ID NO:17) |
| T01 | 5'CGATGAGTCCTGACCGA3' (SEQ ID NO:18) |
| Primer combination 2 (PC B) | |
| A01 | 5'GACTGCGTACAGGCCCA3' (SEQ ID NO:17) |
| T02 | 5'CGATGAGTCCTGACCGAC3' (SEQ ID NO:19) |
| Primer combination 3 (PC D) | |
| A02 | 5'GACTGCGTACAGGCCCC3' (SEQ ID NO:20) |
| T01 | 5'CGATGAGTCCTGACCGAA3' (SEQ ID NO:18) |
| Primer combination 4 (PC I) | |
| A03 | 5'GACTGCGTACAGGCCCG3' (SEQ ID NO:21) |
| T03 | 5'CGATGAGTCCTGACCGAG3' (SEQ ID NO:22) |
| Primer combination 5 (PC G) | |
| A03 | 5'GACTGCGTACAGGCCCG3' (SEQ ID NO:21) |
| T01 | 5'CGATGAGTCCTGACCGAA3' (SEQ ID NO:18) |
| Primer combination 6 (PC H) | |
| A03 | 5'GACTGCGTACAGGCCCG3' (SEQ ID NO:21) |
| T02 | 5'CGATGAGTCCTGACCGAC3' (SEQ ID NO:19) |

Figure 4:
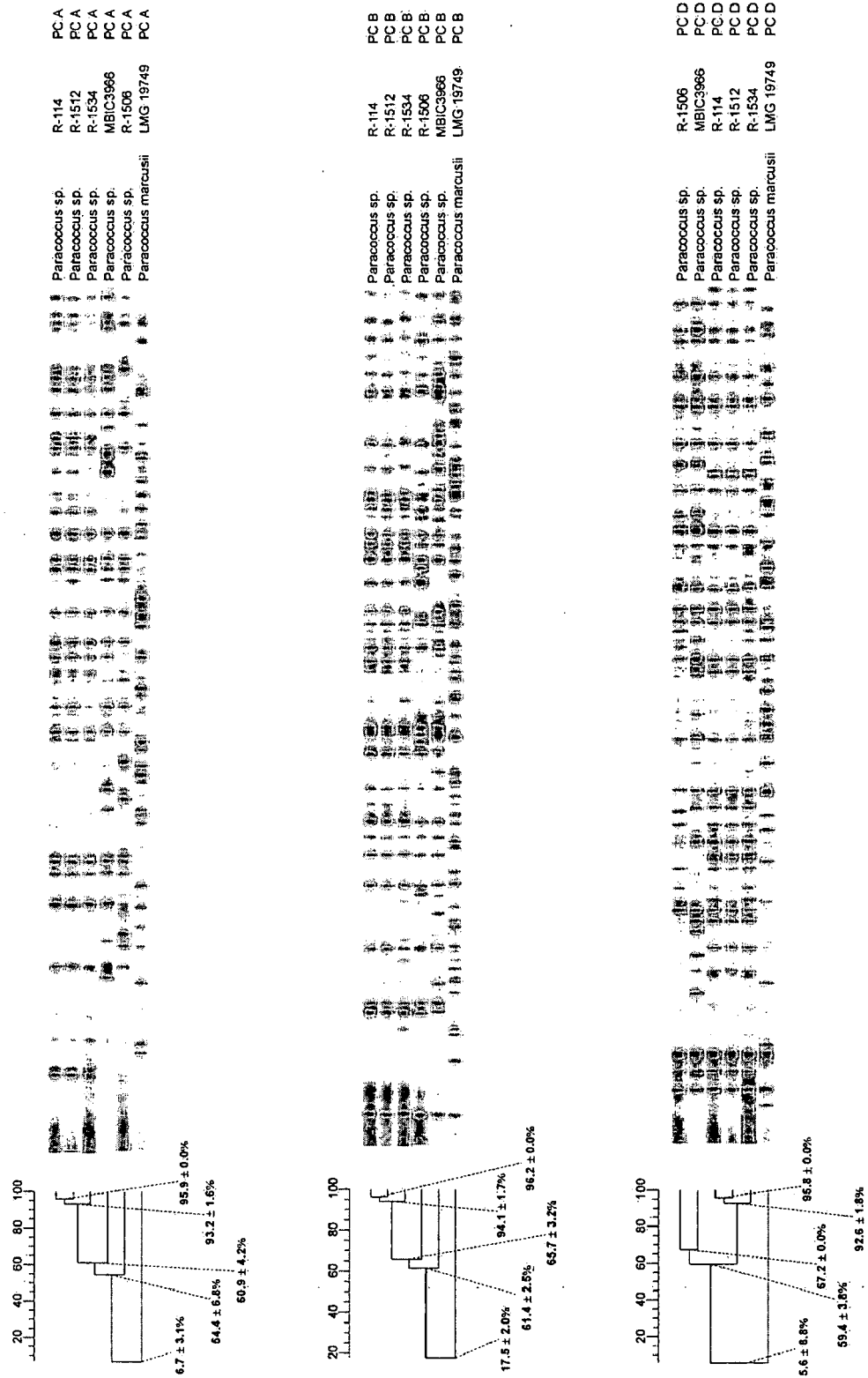
FIG. 4 shows an AFLP™ analysis of *Paracoccus* sp. strains R-1512, RI 534, R114, R-1506, MBIC3966, and *Paracoccus marcusii* DSM 11574$^T$ using primer combinations A, B and D. Numbers are the % similarities at each branchpoint on the dendrogram.
Figure 5:
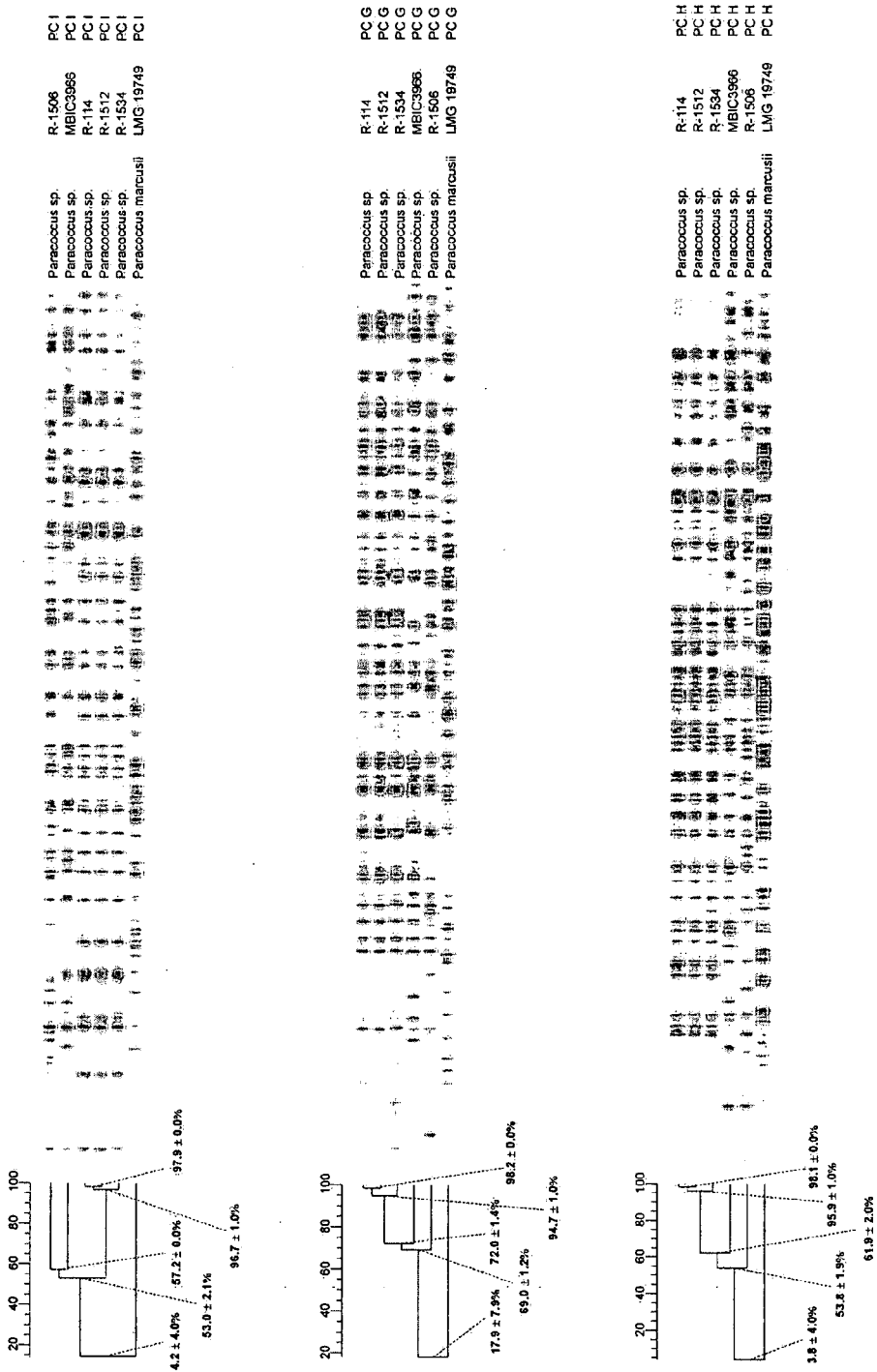
FIG. 5 shows an AFLP™ analysis of *Paracoccus* sp strains R-1512, R1534, R114, R-1506, MBIC3966, and *Paracoccus marcusii* DSM 11574$^T$ using primer combinations I, G and H. Numbers are the % similarities at each branchpoint on the dendrogram.

Following amplification, the PCR products were separated according to their length on a high resolution polyacrylamide gel using a DNA sequencer (ABI 377). Fragments that contained an adaptor specific for the restriction halfsite created by the 6-bp cutter were visualized by autoradiography due to the 5'-end labeling of the corresponding primer with $^{32}$P. The electrophoretic patterns were scanned and numerically analyzed with GelCompar™ 4.2 software (Applied Maths, B. V. B. A.; Kortrijk, Belgium) and clustered using the Pearson curve matching coefficient and unweighted pair group averages linking (clustering methods were reviewed by Sneath and Sokal, In: Numerical Taxonomy. Freeman & Son, San Francisco (1973)). The results are shown in FIGS. 4 and 5.

In all six primer combinations (PC A-H, Table 7), the DNA fingerprints of *Paracoccus* sp. strains R-1512, R1534 and R114 were highly similar if not identical. In cases where minor differences were observed, reproducibility was not evaluated. The high similarity or identity among the three strains was expected as strains R1534 and R114 were derived from strain R-1512. With all primer combinations, strains R-1512, R1534 and R114 were clearly discriminated from strains R-1506 and MBIC3966, the latter two strains equally belonging to the new *Paracoccus* species. However, the fingerprints provide no clear indication that strains R-1512, R1534 and R114 are more related to either R-1506 or MBIC3966. Under the conditions used, the five strains of the new species cluster at an average level of about 58% similarity (this value is the mean of the six values of the branching points of the new species in the six AFLP™ experiments (six primer combinations)), and the cluster can clearly be discriminated from the profile of *Paracoccus marcusii* DSM 11574$^T$, the type strain of a phylogenetically related carotenoid-producing *Paracoccus* species. The mean similarity value of the six branching points for *Paracoccus marcusii* DSM 11574$^T$ and the new species was about 11%.

Fatty acid analysis. The fatty acid composition of the cell membranes of *Paracoccus* sp. strains R-1512, R1534, R114, R-1506, MBIC3966 were compared to the type strains *Paracoccus marcusii* DSM 11574$^T$, *Paracoccus carotinifaciens* E-396$^T$ and *Paracoccus solventivorans* DSM 6637$^T$. The bacteria were grown for 24 hours at 28° C. in LMG medium 185. The fatty acid compositions were determined by gas chromatography using the commercial system MIDI (Microbial Identification System, Inc., DE, USA). Extraction and analysis of fatty acids was performed according to the recommendations of the MIDI system. Table 8 summarizes the results for all strains tested. For the five strains of the new *Paracoccus* species (R-1512, R1534, R114, R-1506, MBIC3966), the mean profile was calculated. All eight organisms showed a comparable fatty acid composition of their cell membranes, with 18:1 w7c as the major compound. Only minor differences in fatty acid composition were observed between the new *Paracoccus* species and the three type strains.

Utilization of carbon sources for growth. For testing the aerobic utilization of carbon sources, BIOLOG-SF-N Microplate microtiter plates (Biolog Inc., Hayward, Calif., USA) containing 95 substrates were used with the exception that the substrate in well E6 was D,L-lactic acid methyl ester instead of the usual sodium salt of D,L-lactic acid. Cells from each of the strains identified in Table 9 were grown for 24 hours at 28° C. in LMG medium 12 (Marine Agar, Difco 0979). A cell suspension with a density equivalent to 0.5 McFarland units was prepared in sterile distilled water. From this suspension, 18 drops were transferred into 21 ml of AUX medium (API 20NE, bioMérieux, France) and mixed gently. 0.1 Milliliters of the suspension was transferred to each well of the BIOLOG MicroPlates, and the plates were incubated at 30° C. Wells were visually checked for growth after 48 hours and after 6 days. Also, at 6 days the visual scoring was confirmed by reading the microtiter plates using the BIOLOG plate reader.

The results of the BIOLOG analysis are shown in Table 9. Growth (positive reaction) was determined as increased turbidity compared to the reference well without substrate. A distinction was made between good growth (+), weak growth (±) and no growth (−). Results in parentheses are those obtained after 6 days if different from the results obtained after 48 hours. A question mark indicates an unclear result at 6 days. Of the 95 carbon sources tested, 12 could be used, and 47 could not be used, for growth by all five strains comprising the new *Paracoccus* species (R-1512, R1534, R114, R-1506 and MBIC3966). These five strains gave variable growth responses to the remaining 36 substrates. The new *Paracoccus* species could be distinguished from the two other carotenoid-producing bacteria (*Paracoccus marcusii* DSM 11574$^T$ and *Paracoccus carotinifaciens* E-396$^T$) by their inability to use seven carbon sources (adonitol, i-erythritol, gentiobiose, β-methylglucoside, D-sorbitol, xylitol and quinic acid). Two carbon sources that were utilized by all five members of the new *Paracoccus* species (L-asparagine and L-aspartic acid) were not used for growth by *Paracoccus marcusii* DSM 11574$^T$.

TABLE 8

Fatty acid composition of cell membranes of *Paracoccus* sp. strains R-1512, R1534, R114, R-1506, MBIC3966 and three type strains of other *Paracoccus* species.

| | Mean % for: *Paracoccus* sp. strains | % for: | | |
|---|---|---|---|---|
| Name | R-1512, R1534, R114, R-1506 and MBIC3966 | *Paracoccus marcusii* DSM 11574$^T$ | *Paracoccus carotinifaciens* E-396$^T$ | *Paracoccus solventivorans* DSM 6637$^T$ |
| 10:0 3OH | 4.9 ± 1.1 | 6.2 | 3.4 | 3.6 |
| Unnamed 11.799 | 3.6 ± 0.5 | 4.9 | 2.8 | 3.0 |
| Unnamed 15.275 | 1.5 ± 0.3 | 2.9 | 1.1 | ND$^a$ |
| 16:0 | 0.3 ± 0.2 | ND | 0.3 | 0.7 |
| 17:1 w8c | ND | ND | 0.6 | 0.8 |
| 17:0 | 0.1 ± 0.1 | ND | 0.3 | 1.3 |
| 18:1 w7c | 80.5 ± 1.8 | 80.3 | 84.0 | 79.0 |
| 18:0 | 3.6 ± 0.4 | 2.6 | 5.2 | 6.6 |
| 18:0 3OH | 0.6 ± 0.4 | ND | ND | ND |

TABLE 8-continued

Fatty acid composition of cell membranes of *Paracoccus* sp. strains R-1512, R1534, R114, R-1506, MBIC3966 and three type strains of other *Paracoccus* species.

| Name | Mean % for: *Paracoccus* sp. strains R-1512, R1534, R114, R-1506 and MBIC3966 | % for: *Paracoccus marcusii* DSM 11574$^T$ | *Paracoccus carotinifaciens* E-396$^T$ | *Paracoccus solventivorans* DSM 6637$^T$ |
|---|---|---|---|---|
| 19:0 | ND | ND | ND | 0.7 |
| 20:1 w7c | 0.8 ± 0.2 | ND | 0.2 | 2.0 |
| Summed feature 2 | 2.7 ± 0.4 | 3.0 | 2.1 | 2.6 |
| Summed feature 3 | 0.7 ± 0.5 | ND | 0.2 | ND |
| TOTAL | 99.3 | 99.9 | 100.2 | 100.3 |

$^a$ND, not detected

Biochemical tests. Selected biochemical features were tested using the API 20NE strip (bioMérieux, France). Cells from each of the bacterial strains identified in Table 10 were grown for 24 hours at 28° C. on LMG medium 12. Cell suspensions were prepared and strips inoculated according to the instructions of the manufacturer. Strips were incubated at 28° C. and results determined after 24 and 48 hours. The results are summarized in Table 10. Of the nine features tested, only one (urease activity) gave a variable response among the five strains of the new *Paracoccus* species. These nine tests did not differentiate between the new *Paracoccus* species and *Paracoccus marcusii* DSM 11574$^T$ and *Paracoccus carotinifaciens* E-396$^T$.

TABLE 9

Utilization of carbon sources for growth by *Paracoccus* spp. strains.

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574$^T$ | *P. carotinifaciens* E-396$^T$ | *P. solventivorans* DSM 6637$^T$ |
|---|---|---|---|---|---|---|---|---|
| α-Cyclodextrin | − | − | − | − | − | − | − | − |
| Dextrin | − | − | − | − | − | − | − | −(±) |
| Glycogen | − | − | − | − | − | − | − | − |
| Tween 40 | − | − | − | − | − | − | −(?) | − |
| Tween 80 | − | − | − | − | − | − | − | − |
| N-Acetyl-D-galactosamine | − | − | − | − | − | − | − | − |
| N-Acetyl-D-glucosamine | − | − | − | − | − | − | − | −(?) |
| Adonitol | − | − | − | − | − | + | + | − |
| L-Arabinose | − | − | − | − | − | + | − | + |
| D-Arabitol | + | + | + | + | ±(+) | + | + | − |
| Cellobiose | ±(+) | ±(+) | −(?) | −(+) | −(±) | + | + | −(+) |
| i-Erythritol | − | − | − | − | − | + | + | − |
| D-Fructose | + | + | + | + | − | + | + | + |
| L-Fucose | − | − | − | − | − | − | + | − |
| D-Galactose | + | + | + | ±(+) | ±(+) | + | + | −(±) |
| Gentiobiose | − | − | − | − | − | + | + | −(±) |
| α-D-Glucose | + | + | + | ±(+) | −(+) | + | ±(+) | + |
| m-Inositol | + | + | + | −(+) | −(+) | + | −(±) | − |
| α-Lactose | + | ±(+) | −(+) | −(+) | −(+) | + | + | ±(+) |
| Lactulose | −(±) | −(+) | −(+) | −(±) | − | + | + | −(+) |
| Maltose | + | + | −(+) | −(+) | −(±) | + | + | −(+) |
| D-Mannitol | + | + | + | + | −(+) | + | + | −(±) |
| D-Mannose | + | + | + | + | −(±) | + | + | −(+) |
| D-Melibiose | + | + | + | −(+) | −(+) | + | + | −(?) |
| β-Methylglucoside | − | − | − | − | − | + | + | + |
| D-Psicose | −(+) | ±(+) | ±(+) | − | −(+) | − | ± | − |
| D-Raffinose | − | − | − | − | − | −(+) | + | − |
| L-Rhamnose | − | − | − | − | − | − | − | −(?) |
| D-Sorbitol | − | − | − | − | − | + | + | − |
| Sucrose | + | + | ±(+) | −(+) | − | + | + | + |
| D-Trehalose | + | + | −(+) | −(+) | −(+) | + | + | + |
| Turanose | −(+) | −(+) | − | − | − | + | + | + |
| Xylitol | − | − | − | − | − | + | + | − |
| Methylpyruvate | ± | − | ± | −(?) | ± | − | + | −(±) |
| Mono-methylsuccinate | ±(+) | ± | −(±) | −(+) | −(±) | −(+) | + | − |
| Acetic acid | − | − | ± | − | − | − | − | + |

TABLE 9-continued

Utilization of carbon sources for growth by *Paracoccus* spp. strains.

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574[T] | *P. carotinifaciens* E-396[T] | *P. solventivorans* DSM 6637[T] |
|---|---|---|---|---|---|---|---|---|
| Cis-aconitic acid | − | ± | ± | − | − | ± | − | − |
| Citric acid | − | ± | ± | − | − | ± | − | − |
| Formic acid | − | − | − | − | − | − | − | − |
| D-Galactonic acid lactone | −(±) | −(±) | −(±) | − | − | − | −(±) | −(?) |
| D-Galacturonic acid | − | − | − | − | − | −(+) | −(±) | − |
| D-Gluconic acid | + | + | + | −(±) | −(±) | + | + | + |
| D-Glucosaminic acid | − | − | − | − | − | − | − | − |
| D-Glucuronic acid | ± | + | + | −(±) | − | ±(+) | − | − |
| α-Hydroxybutyric acid | −(±) | − | −(±) | − | −(+) | − | − | − |
| β-Hydroxybutyric acid | + | + | + | −(±) | ± | −(+) | + | + |
| γ-Hydroxybutyric acid | − | − | − | − | − | − | − | − |
| p-Hydroxyphenylacetic acid | − | − | − | − | − | − | − | −(+) |
| Itaconic acid | − | − | − | − | − | − | − | − |
| α-Ketobutyric acid | − | − | − | − | − | − | − | −(±) |
| α-Ketoglutaric acid | − | − | − | −(±) | −(?) | −(±) | −(+) | −(±) |
| α-Ketovaleric acid | − | − | − | − | − | − | − | − |
| D,L-Lactic acid methyl ester | − | − | − | − | − | − | − | − |
| Malonic acid | − | − | − | − | − | − | − | − |
| Propionic acid | − | ± | ± | − | − | ± | + | + |
| Quinic acid | − | − | − | − | − | + | + | − |
| D-Saccharic acid | −(+) | ± | − | −(±) | − | − | − | − |
| Sebacic acid | −(+) | −(+) | −(+) | −(+) | −(±) | − | −(+) | − |
| Succinic acid | − | − | − | − | − | −(+) | ± | −(?) |
| Bromosuccinic acid | − | − | − | − | − | ± | − | − |
| Succinamic acid | − | − | − | − | − | −(+) | −(+) | − |
| Glucuronamide | − | − | − | − | −(±) | − | − | − |
| Alaninamide | − | − | − | − | − | −(+) | + | − |
| D-Alanine | − | − | −(+) | − | − | − | − | − |
| L-Alanine | + | + | + | + | − | −(+) | + | + |
| L-Alanyl-glycine | −(+) | − | −(+) | − | − | − | −(+) | −(?) |
| L-Asparagine | + | + | ±(+) | + | ±(+) | − | + | − |
| L-Aspartic acid | + | + | ±(+) | −(+) | −(+) | − | + | − |
| L-Glutamic acid | + | + | + | + | ±(+) | −(+) | + | −(+) |
| Glycyl-L-aspartic acid | − | − | − | −(±) | − | − | − | − |
| Glycyl-L-glutamic acid | −(?) | − | − | −(?) | − | − | −(±) | − |
| L-Histidine | − | − | − | − | − | −(?) | − | + |
| Hydroxy-L-proline | − | − | − | − | − | − | − | + |
| L-Leucine | −(±) | −(+) | −(+) | −(+) | − | −(+) | −(?) | −(+) |
| L-Ornithine | − | −(+) | ±(+) | −(±) | − | − | −(+) | − |
| L-Phenylalanine | − | − | − | − | − | − | − | − |
| L-Proline | + | + | + | + | − | −(+) | + | + |
| L-Pyroglutamic acid | + | + | + | + | ±(+) | −(+) | + | − |
| D-Serine | − | − | − | − | − | − | − | − |
| L-Serine | ± | ±(+) | −(+) | −(±) | −(+) | −(+) | −(+) | + |
| L-Threonine | − | − | − | − | − | −(+) | − | − |
| D,L-Carnitine | − | − | − | − | − | − | − | − |
| γ-Aminobutyric acid | − | − | − | − | −(+) | − | −(+) | −(+) |
| Urocanic acid | − | − | − | − | − | − | − | −(+) |
| Inosine | − | −(±) | − | − | − | −(±) | −(+) | −(+) |
| Uridine | − | − | − | − | − | −(±) | −(+) | − |
| Thymidine | − | − | − | − | − | −(±) | −(±) | − |
| Phenylethylamine | − | − | − | − | − | − | − | − |
| Putresceine | − | − | − | − | − | − | − | − |
| 2-Aminoethanol | − | − | − | − | − | − | − | − |

TABLE 9-continued

Utilization of carbon sources for growth by *Paracoccus* spp. strains.

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574[T] | *P. carotinifaciens* E-396[T] | *P. solventivorans* DSM 6637[T] |
|---|---|---|---|---|---|---|---|---|
| 2,3-Butanediol | − | − | − | − | − | − | − | − |
| Glycerol | + | + | + | −(+) | − | + | + | − |
| D,L-α-Glycerolphosphate | − | − | − | − | −(±) | − | − | − |
| Glucose-1-phosphate | − | − | − | − | − | − | −(±) | − |
| Glucose-6-phosphate | − | − | − | − | − | − | − | − |

TABLE 10

Biochemical features of *Paracoccus* spp. strains.

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574[T] | *P. carotinifaciens* E-396[T] | *P. solventivorans* DSM 6637[T] |
|---|---|---|---|---|---|---|---|---|
| Reduction nitrate to nitrite | − | − | − | − | − | − | − | + |
| Reduction nitrate to nitrogen | − | − | − | − | − | − | − | + |
| Indole from tryptophan | − | − | − | − | − | − | − | − |
| Fermentation of glucose | − | − | − | − | − | − | − | − |
| Arginine hydrolase | − | − | − | − | − | − | − | − |
| Urease | Slow + 5 days | − | − | Slow + 5 days | + | − | − | − |
| Esculine hydrolysis (β-glucosidase) | weak | Slow + 5 days | Slow + 5 days | + | + | + | + | + |
| Gelatine hydrolysis (protease) | − | − | − | − | − | − | − | − |
| β-Galactosidase | + | + | + | + | + | + | + | − |

Physiological tests. Several physiological and morphological tests were performed on the five strains of the new *Paracoccus* species, along with *Paracoccus marcusii* DSM 11574[T], *Paracoccus carotinifaciens* E-396[T] and *Paracoccus solventivorans* DSM 6637[T]. The methods used for each test were as follows.

Temperature range for growth. Cells were grown for 24 hours at 28° C. on LMG medium 12. A cell suspension with a density of between 1-2 McFarland units was prepared in sterile distilled water. From this suspension, 3 drops were transferred onto the agar surface of LMG medium 12. One drop was diluted by streaking, the other 2 drops were left undisturbed. The plates were incubated under aerobic conditions at 10° C., 25° C., 30° C., 33° C., 37° C. and 40° C., and checked for growth after 24 hours, 48 hours and 5 days. Growth was determined as visual growth (confluent in the drops and as colonies in the streaks with diluted inoculum) compared to the growth at 30° C. (i.e., the "control"). Scoring was done (vs. the control plate) as follows; better growth (++), good (equivalent to the control) growth (+), weaker growth (±), poor growth (±), and no growth (−). Results in parentheses are those observed in the streaks if different from the confluent growth in the undisturbed drops.

Salt tolerance. Cells were grown for 24 hours at 28° C. on LMG medium 12. A cell suspension with a density of between 1-2 McFarland units was prepared in sterile distilled water. From this suspension, 3 drops were transferred onto the agar surface of LMG medium 12 supplemented with NaCl to reach final concentrations of 3%, 6% and 8%. One drop was diluted by streaking, the other 2 drops were left undisturbed. The plates were incubated under aerobic conditions at 28° C. and checked for growth after 24 hours, 48 hours and 5 days. Growth was determined as visual growth (confluent in the drops and as colonies in the streaks with diluted inoculum) compared to the growth without added NaCl (control). Scoring was done (vs. the control plate) as follows; better growth (++), good (equivalent to the control) growth (+), weaker growth (±), poor growth (±), and no growth (−). Results in parentheses are those observed in the streaks if different from the confluent growth in the undisturbed drops.

pH Range for growth. Cells were grown for 24 hours at 28° C. in LMG medium 12. A cell suspension with a density of between 1-2 McFarland units was prepared in sterile distilled water. From this suspension, 3 drops were transferred into tubes containing 10 ml liquid LMG medium 12 with modified pH, giving final pH values after autoclaving of pH 6.1, pH 6.3, pH 7.0, pH 7.7, pH 8.1 and pH 9.1. The liquid cultures were incubated aerobically (with shaking) at 28° C. Growth was checked at 24 hours, 48 hours, 3 days and 6 days. Growth was determined as increased turbidity (measured as % transmission using the BIOLOG turbidimeter) compared to growth at pH 7.0 (control). Scoring was done (vs. the control) as follows; better growth (++), good (equivalent to the control) growth (+), weaker growth (±), poor growth (±), and no growth (−).

Starch hydrolysis. Cells were grown for 24 hours at 28° C. on LMG medium 12 plates. A loopful of cells was taken from the plate and transferred as one streak onto the agar surface of LMG medium 12 supplemented with 0.2% soluble starch. Plates were then incubated under aerobic conditions at 28° C. When the strains had developed good growth (after 48 hours), the plate was flooded with lugol solution (0.5% $I_2$ and 1% KI in distilled water). Hydrolysis was determined as a clear zone alongside the growth (in contrast to the blue color of the agar where starch was not hydrolyzed).

Denitrification. Cells were grown for 24 hours at 28° C. on LMG medium 12 plates. A loopful of cells was taken from the plate and stabbed into tubes containing semi-solid (0.1% agar) LMG medium 12 supplemented with 1% $KNO_3$. The plates were incubated at 28° C. for 5 days. Denitrification ($N_2$ from nitrate) was determined as gas formation alongside the stab.

Growth under anaerobiosis without electron acceptor added. Cells were grown for 24 hours at 28° C. on LMG medium 12 plates. A loopful of cells was taken from the plate and streaked onto the agar surface of LMG medium 12. The agar plates were incubated under anaerobic conditions (ca. 10% $CO_2$+ca. 90% $N_2$) at 30° C. Plates were checked for growth after 24 hours and after 5 days. Growth was determined visually and compared to the aerobic (control) condition., Scoring was done (vs. the control) as follows; better growth (++), good (equivalent to the control) growth (+), weaker growth (±), poor growth (±), and no growth (−).

Growth under anaerobic conditions with glucose added (fermentation). Cells were grown for 24 hours at 28° C. on LMG medium 12 plates. A loopful of cells was taken from the plate and stabbed into tubes containing the basal agar medium of Hugh and Leifson (J. Bacteriol. 66, 24-26, 1953). Paraffin oil was added to the top of the medium, and the tubes were incubated at 30° C. Tubes were checked for growth and acid formation after 48 hours and after 5 days. Growth was determined visually. Scoring was done as follows; good growth (+), poor growth (±), and no growth (−).

Growth under anaerobic conditions with $KNO_3$ as electron acceptor. Cells were grown for 24 hours at 28° C. on LMG medium 12 plates. A loopful of cells was taken from the plate and streaked onto the agar surface of LMG medium 12 supplemented with 0.1% $KNO_3$. The plates were incubated under anaerobic conditions (ca. 10% $CO_2$+ca. 90% $N_2$) at 30° C., and checked for growth after 3 days. Growth was determined as visual growth compared to the aerobic (control) condition. Scoring was done (vs. the control) as follows; better growth (++), good (equivalent to the control) growth (+), weaker growth (±), poor growth (±), and no growth (−).

Catalase and oxidase reactions. Cells were grown for 24 hours at 28° C. on LMG medium 12 plates. A positive result for catalase activity was the production of gas bubbles after suspending a colony in one drop of 10% $H_2O_2$. A positive result for oxidase activity was the development of a purple-red color after rubbing a colony on filter paper soaked with 1% tetramethylparaphenylene.

Colony pigmentation. Cells were grown for 5 days at 28° C. on LMG medium 12. Color of colonies was observed visually.

Cell morphology and motility. Cells were grown for 24 hours at 28° C. on LMG medium 12. Cell suspensions were made in sterile saline. Cell morphology and motility were observed microscopically using an Olympus light microscope equipped with phase contrast optics (magnification 1000×).

The results of the physiological and morphological tests are summarized in Table 11. The five strains of the new *Paracoccus* species responded essentially identically in all physiological and morphological tests performed. The tests that gave identical responses for all five strains of the new *Paracoccus* species and that allowed discrimination of these organisms from *Paracoccus marcusii* DSM 11574$^T$ and/or *Paracoccus carotinifaciens* E-396$^T$ were: growth at 40° C., growth with 8% NaCl, growth at pH 9.1, and colony pigmentation.

Zeaxanthin production in strains R-1512, R1534, R114 and R-1506 strains. Strains R-1512, R1534, R114, and R-1506 were grown in ME medium, which contains (per liter distilled water): 5 g glucose, 10 g yeast extract, 10 g tryptone, 30 g NaCl and 5 g $MgSO_4.7H_2O$. The pH of the medium was adjusted to 7.2 with 5N NaOH before sterilizing by autoclaving. All cultures (25-ml volume in 250-ml baffled Erlenmeyer flasks with plastic caps) were grown at 28° C. with shaking at 200 rpm. Seed cultures were inoculated from frozen glycerolized stocks and grown overnight. Aliquots were transferred to the experimental flasks to achieve an initial optical density at 660 nm ($OD_{660}$) of 0.16. Cultures were then grown at 28° C. with shaking at 200 rpm. Growth was monitored throughout the cultivation and at 6, 10 (or 15 for strain R114), and 24 hours, an aliquot of the culture was removed for analysis of carotenoids by the method described in Example 1.

Figure 6:
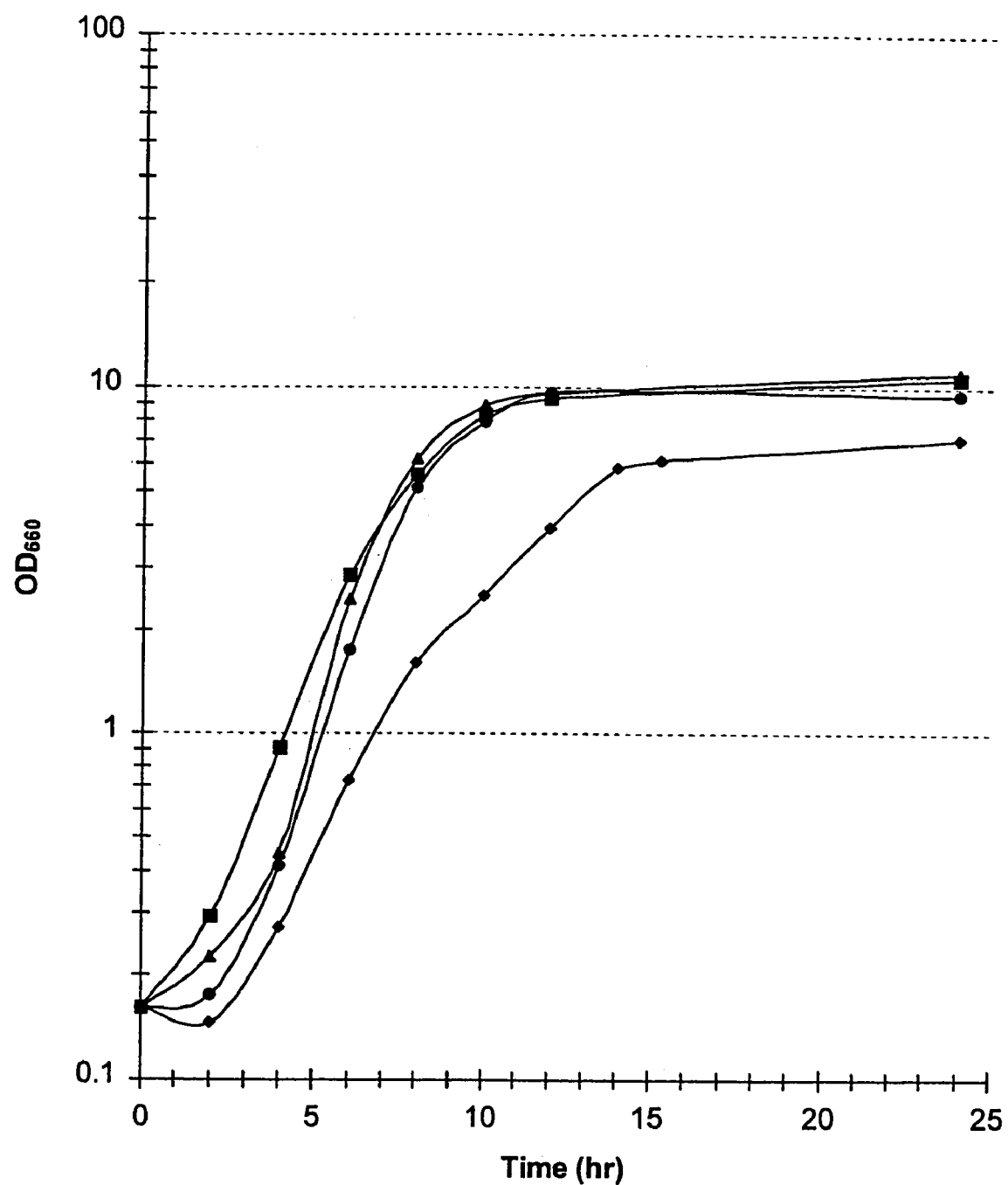
FIG. 6 shows a graph of the growth of *Paracoccus* sp. strains R-1512 (triangles), R1534 (squares), R114 (diamonds) and R-1506 (circles) in ME medium.

A representative growth profile of the four strains is shown in FIG. 6. The doubling times of strains R-1512, R1534 and R-1506 under these conditions were 0.85 hours, 1.15 hours and 1.05 hours, respectively. Strain R114 reproducibly exhibited a biphasic growth profile; in the representative experiment shown in FIG. 6 the doubling time of strain R114 in the initial phase was 1.4 hours while the doubling time in the second phase was 3.2 hours.

Table 12 shows the zeaxanthin production and Specific Formation (zeaxanthin production normalized to $OD_{660}$) by the *Paracoccus* sp. strains in ME medium. The data are averages of four independent experiments, and within each experiment each strain was tested in duplicate flasks. The improved zeaxanthin production in the classically-derived mutant strains R1534 and R114 compared to the parental strain R-1512 is clearly shown. Zeaxanthin production by strain R-1506 was approximately the same as strain R-1512. No other carotenoids were detected in any of the cultures.

TABLE 11

Physiological characteristics of *Paracoccus* spp. strains

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574[T] | *P. carotinifaciens* E-396[T] | *P. solventivorans* DSM 6637[T] |
|---|---|---|---|---|---|---|---|---|
| Growth at 10° C. | | | | | | | | |
| After 24 h | − | − | − | − | − | − | − | − |
| After 5 days | ±(±) | ±(±) | ±(−) | ±(±) | ±(−) | ±(±) | ±(±) | ±(±) |
| Growth at 25° C. | | | | | | | | |
| After 24 h | + | + | + | + | +(±) | +(±) | +(±) | +(−) |
| After 5 days | + | + | + | + | + | + | + | + |
| Growth at 30° C. | | | | | | | | |
| After 24 h | + | + | + | + | + | + | + | + |
| After 5 days | + | + | + | + | + | + | + | + |
| Growth at 33° C. | | | | | | | | |
| After 24 h | + | + | + | + | + | + | + | + |
| After 5 days | + | + | + | + | + | + | + | + |
| Growth at 37° C. | | | | | | | | |
| After 24 h | + | + | +(±) | + | + | ±(−) | ±(−) | + |
| After 5 days | + | + | + | + | + | ±(−) | ±(±) | + |
| Growth at 40° C. | | | | | | | | |
| After 24 h | + | +(±) | +(−) | +(±) | ±(−) | − | − | +(*) |
| After 5 days | + | +(±) | +(−) | + | +(−) | − | − | +(*) |
| Growth with 3% NaCl | | | | | | | | |
| After 24 h | + | + | + | + | + | + | + | ± |
| After 5 days | + | + | + | + | + | + | + | + |
| Growth with 6% NaCl | | | | | | | | |
| After 24 h | +(±) | ±(±) | ±(±) | + | ±(±) | ±(−) | ±(−) | − |
| After 5 days | + | + | + | + | +(*) | +(±) | +(±) | − |
| Growth with 8% NaCl | | | | | | | | |
| After 24 h | +(±) | ±(±) | ±(−) | +(±) | ±(±) | − | − | − |
| After 5 days | + | + | + | + | +(*) | ±(−) | ±(−) | − |
| Growth at pH 6.1 | | | | | | | | |
| After 24 h | + | + | + | + | − | − | − | − |
| After 6 days | + | + | + | + | + | + | + | + |
| Growth at pH 6.3 | | | | | | | | |
| After 24 h | + | + | + | + | + | ± | + | ± |
| After 6 days | + | + | + | + | + | + | + | + |
| Growth at pH 7.0 | | | | | | | | |
| After 24 h | + | + | + | + | + | + | + | + |
| After 6 days | + | + | + | + | + | + | + | + |
| Growth at pH 7.7 | | | | | | | | |
| After 24 h | + | + | + | + | + | ± | ± | ± |
| After 6 days | + | + | + | + | + | + | + | + |
| Growth at pH 8.1 | | | | | | | | |
| After 24 h | + | + | + | + | + | − | − | ± |
| After 6 days | + | + | + | + | + | + | + | + |
| Growth at pH 9.1 | | | | | | | | |
| After 24 h | ± | + | − | − | + | − | − | − |
| After 6 days | + | + | + | + | + | − | + | + |
| Starch hydrolysis | − | − | − | − | − | − | − | − |
| Denitrification | − | − | − | − | − | − | − | + |
| Growth in anaerobiosis without electron acceptor added | − | − | − | − | − | − | − | − |
| Growth in anaerobiosis with glucose added (fermentation) | − | − | − | − | − | − | − | ± |
| Growth in anaerobiosis with KNO₃ added | − | − | − | − | − | − | − | − |

TABLE 11-continued

Physiological characteristics of *Paracoccus* spp. strains

| | *Paracoccus* sp. strain R-1512 | *Paracoccus* sp. strain R1534 | *Paracoccus* sp. strain R114 | *Paracoccus* sp. strain R-1506 | *Paracoccus* sp. strain MBIC3966 | *P. marcusii* DSM 11574$^T$ | *P. carotinifaciens* E-396$^T$ | *P. solventivorans* DSM 6637$^T$ |
|---|---|---|---|---|---|---|---|---|
| Catalase reaction | + | + | + | + | + | + | + | + |
| Oxidase reaction | + | + | + | + | + | + | + | + |
| Gram stain | − | − | − | − | − | − | − | − |
| Motility | − | − | − | − | − | − | − | − |
| Colony pigmentation | yellow-orange | yellow-orange | yellow-orange | yellow-orange | yellow-orange | orange-pink | orange-pink | pale yellow |
| Cell morphology | short rod to coccoid | short rod to coccoid | short rod to coccoid | coccoid | short rod to coccoid | short rod | short rod | short rod |
| Cell dimensions (μm) | 0.8 × 1.2 | 0.8 × 1.2 | 0.8 × 1.2 | 0.9 × 1.1 | 0.8 × 1.2 to 1.5 | 0.8 × 1.5 to 2.0 | 0.9 × 2.0 to 2.5 | 0.8 × 1.5 to 2.0 |

TABLE 12

Zeaxanthin production by *Paracoccus* sp. strains R-1512, R1534, R114 and R-1506.

| Strain | Time (hours) | Zeaxanthin (mg/l) Average | Zeaxanthin (mg/l) Standard Deviation | Specific Formation (mg zeaxanthin/OD$_{660}$) Average | Specific Formation (mg zeaxanthin/OD$_{660}$) Standard Deviation |
|---|---|---|---|---|---|
| R-1512 | 6 | 0.23 | 0.10 | 0.10 | 0.04 |
| | 10 | 2.05 | 0.70 | 0.25 | 0.08 |
| | 24 | 3.78 | 0.59 | 0.38 | 0.06 |
| R1534 | 6 | 0.75 | 0.10 | 0.26 | 0.02 |
| | 10 | 3.45 | 0.57 | 0.43 | 0.07 |
| | 24 | 9.13 | 0.97 | 0.95 | 0.06 |
| R114 | 6 | 0.65 | 0.17 | 0.86 | 0.24 |
| | 15 | 7.53 | 1.12 | 1.13 | 0.21 |
| | 24 | 19.7 | 1.82 | 2.68 | 0.20 |
| R-1506 | 6 | 0.13 | 0.06 | 0.07 | 0.01 |
| | 10 | 1.35 | 0.31 | 0.19 | 0.04 |
| | 24 | 3.55 | 0.68 | 0.38 | 0.07 |

Example 3

IPP Biosynthesis via the Mevalonate Pathway in the Zeaxanthin-Producing *Paracoccus* sp. Strain R114

In order to determine the biosynthetic origin (i.e., the mevalonate or DXP pathway) of isoprenoid precursors in *Paracoccus* sp. strain R114, a "retrobiosynthesis" approach (Eisenreich, W. and Bacher, A. In: J. K. Setiow, (ed.) Genetic Engineering, Principles and Methods, Kluwer Academic/Plenum Publishers, New York, Vol. 22, p. 121-153, 2000) was taken. This predictive approach for data analysis permits the unequivocal assessment of glucose catabolism from the analysis of a single down-stream natural product. In the present work, this involved growth of the bacterium in media containing various binary mixtures of unlabeled glucose and specific $^{13}$C-labeled glucoses, followed by purification of the zeaxanthin produced and analysis of the labeling patterns by NMR spectroscopy. Details of the methods used and the experimental results are given below.

Growth of *Paracoccus* sp. strain R114 for $^{13}$C labeling experiments. Unlabelled D-glucose monohydrate was purchased from Fluka (Milwaukee, Wis., USA). [U-$^{13}$C$_6$]-D-Glucose was purchased from Isotec (Miamisburg, Ohio, USA), while [1-$^{13}$C$_1$] D-glucose, [2-$^{13}$C$_1$] D-glucose and [6-$^{13}$C$_1$] D-glucose were from Cambridge Isotope Laboratories (Andover, Mass., USA). Yeast extract and peptone (from casein, pancreatically digested) were purchased from EM Science (Gibbstown, N.J., USA). All other salts and solvents were analytical grade and were purchased from standard chemicals suppliers.

All cultures were initiated from frozen cell suspensions (cell density of 12 OD$_{660}$ units, 25% glycerol, stored at −70° C.). One ml of thawed cell suspension was used to inoculate pre-cultures (500-ml baffled shake flasks) containing 100 ml of 362F/2medium having the following composition: 30 g/l D-glucose, 10 g/l yeast extract, 10 g/l peptone, 5 g/l NaCl, 2.5 g/l MgSO$_4$7H$_2$O, 0.75 g/l (NH$_4$)$_2$HPO$_4$, 0.625 g/l K$_2$HPO$_4$, 0.2 g/l (NH$_4$)$_2$Fe(SO$_4$)$_2$.6H$_2$O, 187.5 mg/l CaCl$_2$.2H$_2$O, 15 mg/l ZnSO$_4$.7H$_2$O, 12.5 mg/l FeCl$_3$.6H$_2$O, 5 mg/l MnSO$_4$.H$_2$O, 0.5 mg/l NiSO$_4$.6H$_2$O, 15 mg/l Na-EDTA and 9.375 μl/l HCl (37% stock solution). The initial pH of the medium was 7.2.

The pre-culture was incubated at 28° C. with shaking at 200 rpm for 24 h, after which time the OD$_{660}$ was about 22 absorbance units. The main cultures were grown in Bioflo 3000 bioreactors (New Brunswick Scientific, Edison, N.J., USA) containing 362F/2 medium containing the following composition: 30 g/l total D-glucose (see below for ratios of $^{13}$C-labeled:unlabeled glucose), 20 g/l yeast extract, 10 g/l peptone, 10 g/l NaCl, 5 g/l MgSO$_4$.7H$_2$0, 1.5 g/l (NH$_4$)$_2$HPO$_4$, 1.25 g/l K$_2$HPO$_4$, 0.4 g/l (NH$_4$)$_2$Fe(SO$_4$)$_2$.6H$_2$O, 375 mg/l CaCl$_2$.2H$_O$, 30 mg/l ZnSO$_4$.7H$_2$O, 25 mg/l FeCl$_3$.6H$_2$O, 10 mg/l MnSO$_4$.H$_2$O, 1 mg/l NiSO$_4$.6H$_2$O, 30 mg/l Na-EDTA and 18.75 μl/l HCl (37% stock solution). The amounts of each $^{13}$C-labeled glucose used (expressed as a percentage of the total 30 g/l glucose in the medium) in four separate experiments were: Condition 1, 4% [U-$^{13}$C$_6$] D-glucose; Condition 2, 50% [1-$^{13}$C$_1$] D-glucose; Condition 3, 25% [2-$^{13}$C$_1$] D-glucose+ 1% [U-$^{13}$C$_6$] D-glucose; Condition 4, 25% [6-$^{13}$C$_1$] D-glucose+1% [U-$^{13}$C$_6$] D-glucose. A control with only unlabeled glucose was also included. For Conditions 1 and 2 (and the unlabeled control), the culture volume was 2 l, while the culture volume for Conditions 3 and 4 was 1 l. The bioreactors were inoculated with pre-culture (20 ml/l initial volume) and cultivation proceeded for 22-24 hours, at which time no glucose was left in the medium. Cultivation conditions were: 28° C., pH 7.2 (controlled with 25% H$_3$PO$_4$ and 28% NH$_4$OH), dissolved oxygen controlled (in a cascade with agitation) at a minimum of 40%, agitation rate and aeration rate 300 rpm (minimum) and 1 vvm, respectively.

Purification of zeaxanthin. At the end of the cultivations, the cultures were cooled down to 15° C. Five hundred ml of absolute ethanol was added per liter of culture and stirring was continued at 100 rpm for 20 min. The treated culture was centrifuged for 20 min. at 5000×g, and the supernatant was discarded. The wet pellet was then extracted with 5 volumes of THF for 20 min. with stirring. The extracted mixture was centrifuged, the supernatant saved and the resulting pellet extracted a second time with 1 volume THF under the same conditions and again centrifuged. The supernatants (extracts) were combined and concentrated to 50 ml by rotary evaporation. Five milliliters of hexane were added to the concentrated THF solution. After mixing, the system formed an emulsion that could be separated by centrifugation. The aqueous phase was collected, diluted with an equal volume of saturated NaCl solution and re-extracted with dichloromethane. The dichloromethane phase was collected and combined with the THF/hexane phase. The mixture of organic extracts was concentrated again in a rotary evaporator to remove dichloromethane. The solution was then applied to a silica gel column and eluted with a mixture of n-hexane and ether (1:1). A small light yellow band eluted first and was discarded. The main zeaxanthin product eluted in a broad band that moved slowly in the column. About 2 liters of solvent was needed to elute the main band completely. The eluate was collected in a round-bottomed flask and the solvent was removed by rotary evaporation at 40° C. The residue was dissolved in a small amount of dichloroethane at 40° C. and the solution was then allowed to cool slowly. Hexane was added to the mixture drop-wise until a turbidity was observed. The crystallization was complete within 48 hours at 4° C. The crystals were collected on a paper filter, washed with cold methanol and dried under vacuum.

Figure 7:
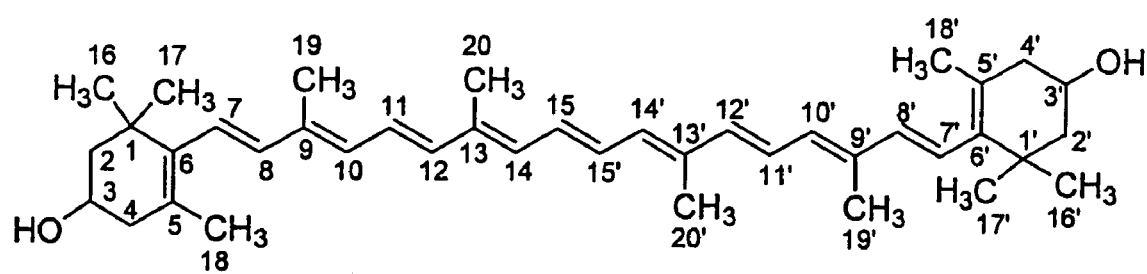
FIG. 7 shows the structure of zeaxanthin with the numbering of carbon atoms used herein.

NMR studies. Zeaxanthin was analyzed by NMR spectroscopy. For reference, the chemical structure of zeaxanthin, including numbering of carbon atoms, is shown in FIG. 7. $^1$H-NMR and $^{13}$C-NMR spectra were recorded at 500.13 MHz and 125.6 MHz, respectively, with a Bruker DRX 500 spectrometer. Acquisition and processing parameters for one-dimensional experiments and two-dimensional INADEQUATE experiments were according to standard Bruker software (XWINNMR). The solvent was deuterated chloroform. The chemical shifts were referenced to solvent signals.

$^{13}$C NMR spectra of the isotope labeled zeaxanthin samples and of the zeaxanthin sample at natural $^{13}$C abundance were recorded under the same experimental conditions. Integrals were determined for every $^{13}$C NMR signal, and the signal integral for each respective carbon atom in the labeled compound was referenced to that of the natural abundance material, thus affording relative $^{13}$C abundances for each position in the labeled molecular species. The relative abundances were then converted into absolute abundances from $^{13}$C coupling satellites in the $^1$H NMR signal of H-18 at 1.71 ppm. In the $^{13}$C NMR spectrum of the multiply-labeled zeaxanthin sample each satellite was integrated separately. The integral of each respective satellite pair was then referenced to the total signal integral of a given carbon atom. Zeaxanthin comprises a total of eight isoprenoid moieties (2 DMAPP units and 6 IPP units, refer to FIG. 1B); only 20 $^{13}$C NMR signals are observed due to chemical shift degeneracy.

Figure 8:
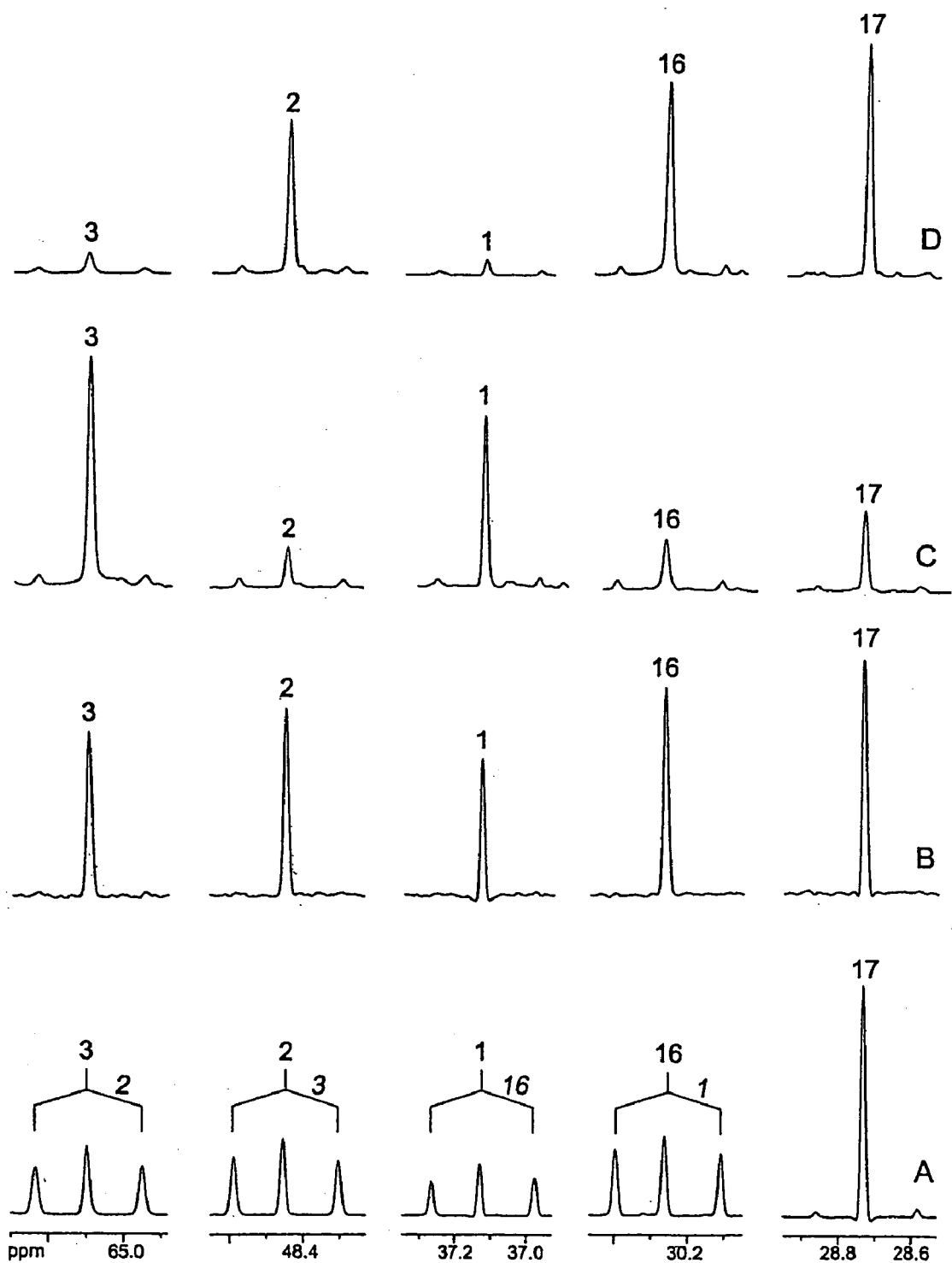
FIG. 8 shows the $^{13}C$ NMR signals of purified $^{13}C$-labeled zeaxanthin produced by *Paracoccus* sp. strain R114 grown in the presence of: (A), [U-$^{13}C_6$] glucose; (B), [1-$^{13}C_1$] glucose; (C), [2-13C$_1$] glucose; and (D), [6-$^{13}C_1$] glucose.
Figure 9:
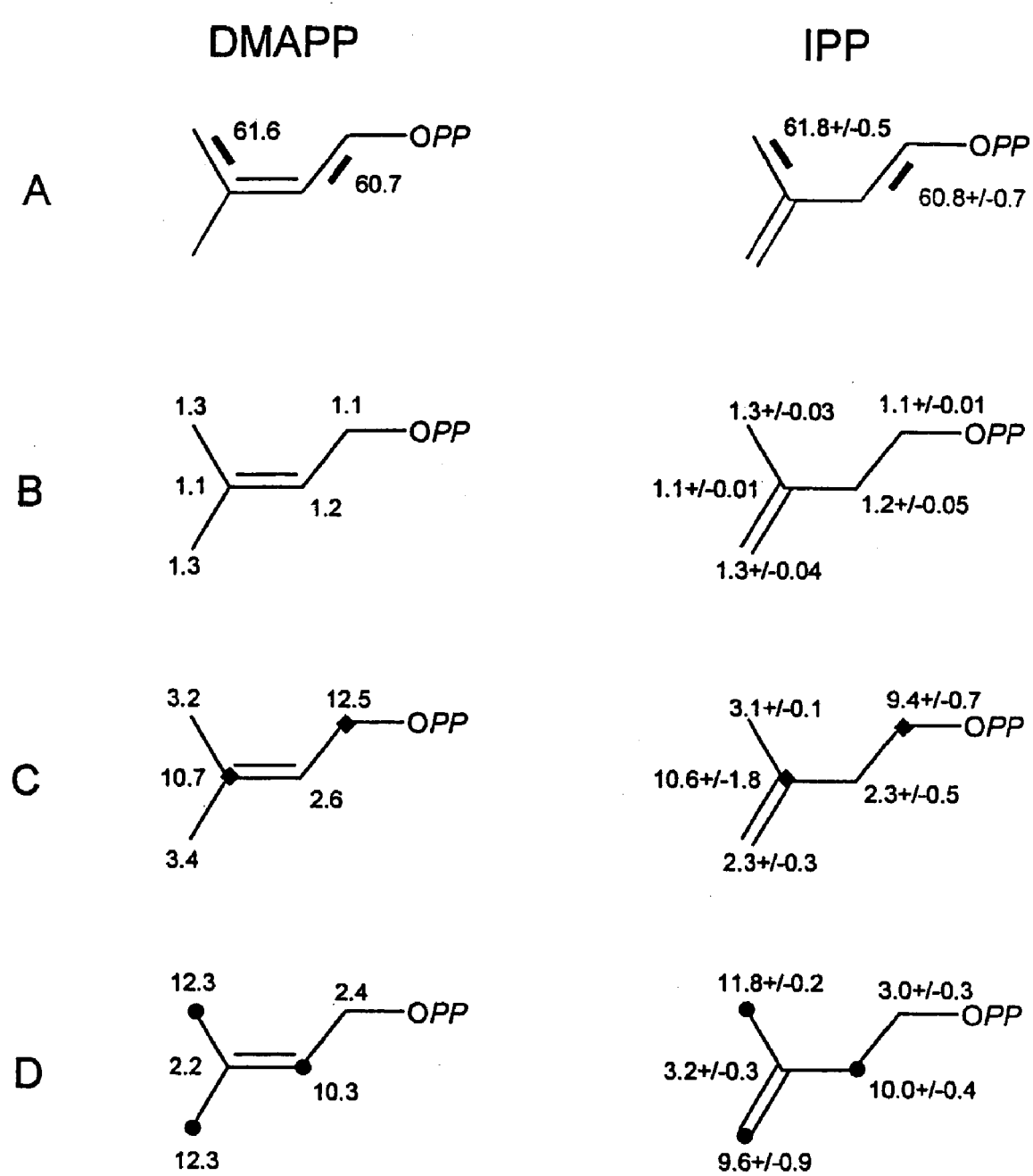
FIG. 9 depicts the reconstructed labeling patterns of isoprenoid precursor units (DMAPP and IPP, refer to FIG. 1B) of zeaxanthin. The four sets of results correlate to growth of *Paracoccus* sp. strain R114 in the presence of (A), [U-$^{13}C_6$] glucose; (B), [1-$^{13}C_1$] glucose; (C), [2-$^{13}C_1$] glucose; and (D), [6-$^{13}C_1$] glucose. Symbols ♦ and ● indicate carbon atoms enriched from [2-$^{13}C_1$] glucose and [6-$^{13}C_1$]

In the experiment with the mixture of [U-$^{13}$C$_6$] glucose and unlabeled glucose (1:7.5; w/w), all carbon atoms of zeaxanthin were labeled and showed satellites due to $^{13}$C$^{13}$C couplings (Table 13). FIG. 8 shows the signals representing the zeaxanthin atoms derived from the DMAPP starter unit. The signals of 4 carbon atoms shown in FIG. 8 have intense satellites due to $^{13}$C$^{13}$C couplings (61.2±0.6% in the global NMR signal intensity of a given atom, Table 13, FIG. 9). The signal accounting for the methyl atoms C-17/C-17' displayed only weak $^{13}$C-coupled satellites at a relative intensity of 6%. The central signals represent material derived from unlabeled glucose. The signals showed no evidence of long-range coupling. Carbon connectivity was easily gleaned from $^{13}$C$^{13}$C coupling constants (Table 13) and from two-dimensional INADEQUATE experiments.

Three of the carbon atoms in FIG. 8 acquired label from [6-$^{13}$C$_1$] glucose. The other two carbons were labeled from [2-$^{13}$C_] glucose. No significant amounts of label were contributed to zeaxanthin by [1-$^{13}$C$_1$] glucose.

The $^{13}$C abundance for all non-isochronous carbon atoms was determined by comparison with spectra of unlabeled zeaxanthin and by evaluation of the $^1$H$^{13}$C coupling satellites in $^1$H NMR spectra (Table 13). The fraction of jointly transferred carbon atom pairs in the experiment with [U-$^{13}$C$_6$] glucose was determined by integration of the coupling satellites.

The labeling patterns of the IPP building block (FIG. 9) can be reconstructed accurately as shown by the standard deviations found for the reconstructed IPP precursor. The re-constructed labeling patterns of DMAPP and IPP were identical within the experimental limits.

TABLE 13

NMR results for $^{13}$C labeled zeaxanthin produced by *Paracoccus* sp. strain R114 supplied with $^{13}$C labeled glucoses.

| | δ | | $^{13}$C-labeled glucose precursor | | | |
| --- | --- | --- | --- | --- | --- | --- |
| | | | [1-$^{13}$C]- | [2-$^{13}$C]- | [6-$^{13}$C]- | [U-$^{13}$C$_6$]glucose |
| Position | $^{13}$C, ppm | $J_{cc}$, Hz | % $^{13}$C | % $^{13}$C | % $^{13}$C | % $^{13}$C | % $^{13}$C$^{13}$C |
| 1, 1' | 37.13 | 36.0 (16, 16') | 1.10 | 10.71 | 2.22 | 3.47 | 61.2 |
| 2, 2' | 48.46 | 35.8 (3, 3') | 1.20 | 2.58 | 10.27 | 3.65 | 61.1 |
| 3, 3' | 65.10 | 35.8 (2, 2') | 1.12 | 12.47 | 2.38 | 3.64 | 60.4 |
| 4, 4' | 42.57 | 37.1 | 1.27 | 2.59 | 10.63 | 3.89 | 8.4 |
| 5, 5' | 126.17 | 44.2 (18, 18') | 1.14 | 12.45 | 3.19 | 3.68 | 61.1 |
| 6, 6' | 137.77 | 56.4 (7, 7') | 1.30 | 2.15 | 9.98 | 3.60 | 60.4 |
| 7, 7' | 125.59 | 56.2 (6, 6') | 1.12 | 10.11 | 2.82 | 4.09 | 61.4 |
| 8, 8' | 138.50 | 71.6, 55.7 | 1.28 | 2.24 | 9.95 | 3.92 | 4.3, 5.0 |
| 9, 9' | 135.69 | 43.1 (19, 19') | 1.12 | 9.53 | 2.95 | 3.84 | 61.7 |
| 10, 10' | 131.31 | 59.7 (11, 11') | 1.21 | 3.18 | 9.61 | 3.80 | 61.1 |

TABLE 13-continued

NMR results for $^{13}$C labeled zeaxanthin produced by *Paracoccus* sp. strain R114 supplied with $^{13}$C labeled glucoses.

| | | | $^{13}$C-labeled glucose precursor | | | | |
|---|---|---|---|---|---|---|---|
| | δ | | [1-$^{13}$C]- | [2-$^{13}$C]- | [6-$^{13}$C]- | [U-$^{13}$C$_6$]glucose | |
| Position | $^{13}$C, ppm | J$_{cc}$, Hz | % $^{13}$C | % $^{13}$C | % $^{13}$C | % $^{13}$C | % $^{13}$C$^{13}$C |
| 11, 11' | 124.93 | 59.7 (10, 10') | 1.10 | 8.79 | 2.70 | 4.02 | 61.0 |
| 12, 12' | 137.57 | 70.5 | 1.20 | 2.01 | 8.80 | 3.59 | 5.1 |
| 13, 13' | 136.48 | 43.1 (20, 20') | 1.12 | 9.86 | 3.59 | 3.93 | 61.4 |
| 14, 14' | 132.60 | 60.4 (15, 15') | 1.21 | 2.83 | 10.51 | 3.77 | 59.5 |
| 15, 15' | 130.08 | 60.4 (14, 14') | 1.12 | 9.18 | 3.33 | 4.02 | 61.2 |
| 16, 16' | 30.26 | 36.3 (1, 1') | 1.27 | 3.19 | 12.31 | 3.91 | 62.0 |
| 17, 17' | 28.73 | 34.9 (1, 1') | 1.30 | 3.43 | 12.31 | 3.88 | 6.0 |
| 18, 18' | 21.62 | 44.2 (5, 5') | 1.27 | 3.01 | 11.66 | 3.70 | 62.0 |
| 19, 19' | 12.82 | 43.1 (9, 9') | 1.29 | 3.12 | 11.64 | 3.86 | 62.3 |
| 20, 20' | 12.75 | 42.9 (13, 13') | 1.33 | 3.21 | 11.99 | 3.75 | 62.1 |

The experimental labeling patterns determined above can be compared with various predictions, taking into account not only the mevalonate pathway vs. the DXP pathway for isoprenoid biosynthesis, but also different pathways of glucose metabolism. Eubacteria typically utilize glucose primarily via the glycolytic pathway or via the Entner-Doudoroff pathway. Glycolysis generates two triose phosphate molecules from glucose. FIG. 10 (Scheme A) shows that the C-1 and C-6 of glucose are both diverted to the 3-position of the triose phosphates produced during glycolysis. On the other hand, in the Entner-Doudoroff pathway, glucose is converted to a mixture of glyceraldehyde 3-phosphate and pyruvate. The C-1 of glucose is exclusively diverted to C-1 of pyruvate, and the C-6 of glucose is exclusively diverted to C-3 of glyceraldehyde 3-phosphate (Scheme B in FIG. 10).

Intermediates and products of the glycolytic and Entner-Doudoroff pathways serve as starting material for both isoprenoid biosynthetic pathways. With regard to the mevalonate pathway, pyruvate as well as triose phosphate can be converted to the precursor acetyl-CoA. Glucose catabolism via the glycolytic pathway diverts label from C-1 as well as C-6 of glucose to the methyl group of acetyl-CoA (FIG. 10, Scheme A). Glucose catabolism via the Entner-Doudoroff pathway results in loss of C-1 from glucose during the transformation of pyruvate to acetyl-CoA (FIG. 10, Scheme B).

Schemes A and B in FIG. 11 show the predicted labeling patterns for IPP produced from acetyl-CoA through the mevalonate pathway. Schemes A and B further assume glucose metabolism via glycolysis and the Entner-Doudoroff pathways, respectively. Schemes C and D assume IPP production via the DXP pathway and further assume glucose metabolism via. glycolysis (C) or the Entner-Doudoroff pathways (D). FIG. 12, Schemes A-D, shows the predicted labeling patterns for zeaxanthin produced from IPP formed via the corresponding schemes A-D in FIG. 11, and further shows (Scheme E) the actual observed labeling patterns of zeaxanthin purified from *Paracoccus* sp. strain R114 grown in the presence of the glucoses labeled in different positions.

The experimentally observed enrichment and $^{13}$C$^{13}$C coupling patterns of the zeaxanthin produced by *Paracoccus* sp. strain R114 were in perfect agreement with the labeling pattern required for zeaxanthin biosynthesis by the combination of the Entner-Doudoroff pathway and the mevalonate pathway. If both the glycolytic and Entner-Doudoroff pathways had been simultaneously operative under the experimental conditions used, at least some label from [1-$^{13}$C$_1$] glucose should have been contributed to the zeaxanthin. Furthermore, the mevalonate pathway can at best contribute blocks of two carbon atoms to terpenoids, while in the DXP pathway three carbon units can be delivered to isoprenoids via triose phosphate precursors. Although such three-carbon blocks become separated by the rearrangement involved in the DXP pathway, blocks of three labeled carbon atoms can still be recognized via long-range coupling. Corresponding $^{13}$C-$^{13}$C long-range couplings have been observed in the biosynthesis of the carotenoid lutein from [2,3,4,5-$^{13}$C$_4$] 1-deoxy-D-xylulose by cultured plant cells (*Cantharantus roseus*) (Arigoni et al., Proc. Nat. Acad. Sci. 94, 10600-10605, 1997). No such long-range coupling was observed in the present experiments with zeaxanthin produced by *Paracoccus* sp. strain R114.

It should be noted that while the results presented here confirm isoprenoid production in *Paracoccus* sp. strain R114 via the mevalonate pathway, and indicate that, under the growth conditions used, there, was little or no glucose metabolism via glycolysis, they do not rule out the possibility of some metabolism of glucose via the pentose phosphate pathway in addition to the Entner-Doudoroff pathway. Quantitative determination of glucose metabolism via the latter two pathways could be obtained by analysis of labeling patterns of pyruvate-derived amino acids (as was done for *Paracoccus denitrificans* (Dunstan et al., Biomedical and Environ. Mass Spectrometry, 19:369-381 (1990))0.

Example 4

Cloning and Sequencing of the Genes Encoding IPP Isomerase and the Enzymes of the Mevalonate Pathway from *Paracoccus* sp. Strain R114

Culture conditions. *Paracoccus* sp. strain R114 was grown at 28° C. in F-medium (10 g/l tryptone, 10 g/l yeast extract, 30 g/l NaCl, 10 g/l D-glucose, 5 g/l MgSO$_4$.7H$_2$O, pH 7.0)or in the pre-culture medium described in Example 3 above. Liquid cultures were grown in a rotary shaker at 200 rpm.

Isolation of genomic DNA. A 600-ml culture of *Paracoccus* sp. strain R114 was centrifuged for 10 minutes at 10,000×g at 4° C. and the pellet was washed once with 200 ml lysis buffer (0.1M NaCl, 50 mM EDTA, 10 mM Tris- HCl, pH 7.5) and once with 100 ml lysis buffer. The final pellet was resuspended in 20 ml lysis buffer containing 50 mg lysozyme and 1 mg RNase A (DNase free). After incubation for 15 minutes at 37° C., 1.5 ml of 20% sodium N-lauroyl-sarcosinate and 2.25 mg of proteinase K were added. After incubation at 50° C. for 30-60 minutes, the lysate was extracted with one volume of buffer-saturated phenol, pH 7.5-7.8 (LifeTechnologies, Rockville, Md., USA) by gentle but thorough mixing. The emulsion was centrifuged for 20 minutes at 30,000×g and the aqueous phase was re-extracted with phenol. The phases were separated as before and the aqueous phase was extracted twice with one volume phenol:chloroform (1:1). At this step centrifugation for 20 minutes at 3,200×g in a swinging bucket rotor was sufficient to obtain satisfactory phase separation. After a final extraction with one volume of chloroform, 0.1 volume 3M sodium-acetate (pH 5.2) was added and the solution was overlaid with 2 volumes ice-cold ethanol. The precipitated DNA was spooled with a glass-rod, soaked in 70% ethanol for 5 minutes, rinsed with chloroform and then air dried for 5-10 minutes. The DNA was resuspended overnight in 5 ml TE (10 mM Tris-HCl, pH 7.5, 1 mM EDTA). Since the solution was yellow due to traces of zeaxanthin, the organic extractions and the spooling were repeated as above to obtain a clear preparation.

Isolation of λ-DNA: The Qiagen® Lambda Kit (Qiagen, Hilden, Germany) was used following the manufacturer's instructions.

Polymerase chain reaction (PCR): Oligonucleotides were purchased from LifeTechnologies (Rockville, Md., USA). PCR was performed in a GeneAmp® PCR system 9700 (PE Applied Biosystems, Foster City, Calif., USA) using the GC-rich PCR system (Roche Molecular Biochemicals, Mannheim, Germany) according to the manufacturers instructions. Typically, the $MgCl_2$ concentration used was 1.5 mM and the resolution solution was added to 1M final concentration.

DNA Labeling and detection: The PCR DIG Probe Synthesis Kit and the DIG Luminescent Detection Kit were used for DNA labeling and detection, respectively (both obtained from Roche Molecular Biochemicals, Mannheim, Germany)

DNA sequencing: Sequencing reactions were performed using the BigDye® DNA sequencing kit (PE Applied Biosystems, Foster City, Calif., USA) according to the manufacturers instructions. Sequencing reactions were purified on DyeEx™ spin columns (Qiagen, Hilden, Germany) and fragment separation and detection was done with an ABI Prism™ 310 Genetic Analyzer (PE Applied Biosystems, Foster City, Calif., USA).

λ-library: A custom made library with partially Sau3AI digested Paracoccus sp. strain R114 DNA in lambda FIX® II was purchased from Stratagene (La Jolla, Calif., USA).

Cloning, sequencing and characterization of the mevalonate pathway gene cluster from Paracoccus sp. strain R114. One of the enzymes of the mevalonate pathway, mevalonate diphosphate decarboxylase, contains highly conserved regions spanning several amino acids. Three such regions were chosen from an alignment of all available eubacterial mevalonate diphosphate decarboxylases and oligonucleotides were designed using the preferred codon usage found in the carotenoid gene cluster of Paracoccus sp. strain R1534 (Table 14).

The oligonucleotides designed from two homology regions are shown in Table 15. To reduce the degree of degeneracy, sets of oligonucleotides were designed from each peptide. For instance, oligonucleotides mvd-103a-d differ only in the third nucleotide from the 3' end, each accounting for one possible codon for glycine (GGA, although rarely used, was included because of the close proximity to the 3' end). Alternate amino acids were accounted for by designing oligonucleotides to both residues, e.g. oligonucleotides mvd-101a and mvd-101b are specific for leucine or isoleucine, respectively, in the second position of peptide 1 (Table 15). PCR with oligonucleotides mvd-101 and mvd-104 or mvd-106, using Paracoccus sp. strain 114 DNA as template, gave a product of the expected size. The PCR product was cloned in the vector pCR®2.1-TOPO (Invitrogen, Carlsbad, Calif., USA) and sequenced (hatched box in FIG. 13). The cloned fragment was used as a probe for a Southern analysis of Paracoccus sp. strain R114 DNA and was found to hybridize to a BamHI-SalI fragment of about 950 bp (data not shown). Paracoccus sp. strain R114 DNA was cut with BamHI and SalI and the fragments were separated by agarose gel electrophoresis. The region around 950 bp was isolated and cloned in the vector pUC19. This partial library was then screened using the mvd-PCR fragment as a probe and the insert of a positive clone (box C in FIG. 13) was sequenced. In parallel, a λ-library prepared from Paracoccus sp. strain R114 DNA was screened using the mvd-PCR fragment as a probe. DNA was isolated from two positive λ-clones and cut with BamHI and SalI or EcoRI and SalI. A number of the restriction fragments were isolated and cloned in the vector pUC19. Several of the fragments contained sequences homologous to genes encoding proteins of the mevalonate pathway (boxes A, B, D, L, M in FIG. 13). The clones connecting these individual sequences (FIG. 13, boxes 26-1, 22-1, 14-1, 4-3, 49-1 and mvd11-3) were obtained by PCR with primers derived from the sequences of the cloned restriction fragments using the DNA of the λ-clones as template. The assembled sequence from all fragments (SEQ ID NO:42, 44, 46, 48, 50, and 52)[1] and the sequences of the encoded proteins are shown in FIG. 14 (SEQ ID Nos:43, 45, 47, 49, 51, and 53).

[1]Due to a limitation of the PatentIn Program, operons with overlapping genes cannot be shown as a single sequence. Thus, for each gene in the mevalonate operon shown in FIG. 14, the entire nucleotide sequence of the operon is repeated for each gene. Accordingly, SEQ ID Nos:42, 44, 46, 48, 50, and 52 are identical. For purposes of the present invention, we use SEQ ID NO:42 to refer to the nucleotide sequence of the mevalonate operon.

The arrangement of the mevalonate pathway genes in the Paracoccus sp. strain R114 is unique when compared to known mevalonate gene clusters of other bacteria (FIG. 15). Besides Paracoccus sp. strain R114, only Borrelia burgdorferi and Streptomyces sp. strain CL190 (Takagi et al., J. Bacteriol. 182, 4153-4157, 2000) have all mevalonate genes in a single operon (Wilding et al., J. Bacteriol. 182, 4319-4327, 2000). In Streptococcus pyrogenes all mevalonate genes are clustered in a single locus but they are grouped in two operons. All other species have two loci with the two kinases and the mevalonate diphosphate decarboxylase grouped in one operon and the HMG-CoA synthase and the HMG-CoA reductase on a second locus, either forming an operon (in Streptococcus pneumoniae) or as separate transcription units. All species except the members of Staphylococcus have an additional gene linked with the mevalonate cluster, which was recently identified as an IPP isomerase (idi gene in Streptomyces sp. strain CL190) (Kaneda et al., Proc. Nat. Acad. Sci. 98, 932-937, 2001). The two Enterococcus species

TABLE 14

Codon usage in *Paracoccus* sp. strain R1534 carotenoid (crt) genes

| Amino acid | Codon | Number used | % Used |
|---|---|---|---|
| A—Ala | GCT | 3 | 1.4 |
| | GCC | 96 | 46.2 |
| | GCA | 15 | 7.2 |
| | GCG | 94 | 45.2 |
| C—Cys | TGT | 0 | 0.0 |
| | TGC | 15 | 100.0 |
| D—Asp | GAT | 46 | 38.0 |
| | GAC | 75 | 62.0 |
| E—Glu | GAA | 17 | 25.4 |
| | GAG | 50 | 74.6 |
| F—Phe | TTT | 3 | 5.6 |
| | TTC | 51 | 94.4 |
| G—Gly | GGT | 16 | 10.8 |
| | GGC | 87 | 58.8 |
| | GGA | 5 | 3.4 |
| | GGG | 40 | 27.0 |
| H—His | CAT | 30 | 56.6 |
| | CAC | 23 | 43.4 |
| I—Ile | ATT | 5 | 6.4 |
| | ATC | 72 | 92.3 |
| | ATA | 1 | 1.3 |
| K—Lys | AAA | 4 | 14.3 |
| | AAG | 24 | 85.7 |
| L—Leu | TTA | 0 | 0.0 |
| | TTG | 5 | 2.9 |
| | CTT | 15 | 8.7 |
| | CTC | 11 | 6.4 |
| | CTA | 1 | 0.6 |
| | CTG | 140 | 81.4 |
| M—Met | ATG | 49 | 100.0 |
| N—Asn | AAT | 4 | 20.0 |
| | AAC | 16 | 80.0 |

TABLE 14-continued

Codon usage in *Paracoccus* sp. strain R1534 carotenoid (crt) genes

| Amino acid | Codon | Number used | % Used |
|---|---|---|---|
| P—Pro | CCT | 2 | 2.3 |
| | CCC | 41 | 47.7 |
| | CCA | 3 | 3.5 |
| | CCG | 40 | 46.5 |
| Q—Gln | CAA | 6 | 11.3 |
| | CAG | 47 | 88.7 |
| R—Arg | CGT | 11 | 7.3 |
| | CGC | 103 | 68.2 |
| | CGA | 2 | 1.3 |
| | CGG | 26 | 17.2 |
| | AGA | 2 | 1.3 |
| | AGG | 7 | 4.6 |
| S—Ser | TCT | 1 | 1.1 |
| | TCC | 17 | 19.5 |
| | TCA | 0 | 0.0 |
| | TCG | 39 | 44.8 |
| | AGT | 2 | 2.3 |
| | AGC | 28 | 32.2 |
| T—Thr | ACT | 2 | 2.7 |
| | ACC | 36 | 48.9 |
| | ACA | 4 | 5.3 |
| | ACG | 33 | 44.0 |
| V—Val | GTT | 6 | 5.7 |
| | GTC | 61 | 57.5 |
| | GTA | 1 | 0.9 |
| | GTG | 38 | 35.8 |
| W—Trp | TGG | 27 | 100.0 |
| Y—Tyr | TAT | 28 | 62.2 |
| | TAC | 17 | 37.8 |

TABLE 15

Oligonucleotides designed from two conserved bacterial Mvd peptides.

| | |
|---|---|
| Peptide 1 | AlaLeuIleLysTyrTrpGlyLys (SEQ ID NO:23) Ile[2] |
| Nucleotide sequence[1] | CCSCTGATCAARTAYTGGGGBAARATC (SEQ ID NO:24) |
| Oligonucleotide mvd-101a (5'-3') | GCSCTGATCAARTAYTGGGG (SEQ ID NO:25) |
| Oligonucleotide mvd-101b (5'-3') | GCSATCATCAARTAYTGGGG (SEQ ID NO:26) |
| Oligonucleotide mvd-103a (5'-3') | ATCAARTAYTGGGGTAA (SEQ ID NO:27) |
| Oligonucleotide mvd-103b (5'-3') | ATCAARTAYTGGGGCAA (SEQ ID NO:28) |
| Oligonucleotide mvd-103c (5'-3') | ATCAARTAYTGGGGGAA (SEQ ID NO:29) |
| Oligonucleotide mvd-103d (5'-3') | ATCAARTAYTGGGGAAA (SEQ ID NO:30) |
| Peptide 2 | ThrMetAspAlaGlyProAsnVal (SEQ ID NO:31) Gln[2] |
| Nucleotide sequence[1] (5'-3') | ACSATGGAYGCSGGBCCSAAYGTS CAR (SEQ ID NO:32) |
| Complement (3'-5') | TGSTACCTRCGSCCVGGSTTRCAS GTY (SEQ ID NO:33) |
| Oligonucleotide mvd-104a (3'-5') | TGGTACCTACGSCCVGG (SEQ ID NO:34) |
| Oligonucleotide mvd-104b (3'-5') | TGGTACCTGCGSCCVGG (SEQ ID NO:35) |
| Oligonucleotide mvd-104c (3'-5') | TGCTACCTACGSCCVGG (SEQ ID NO:36) |
| Oligonucleotide mvd-104d (3'-5') | TGCTACCTGCGSCCVGG (SEQ ID NO:37) |
| Oligonucleotide mvd-106a (3'-5') | TACCTACGSCCVGGSTTRCA (SEQ ID NO:38) |
| Oligonucleotide mvd-106b | TACCTGCGSCCVGGSTTRCA (SEQ ID NO:39) |

TABLE 15-continued

Oligonucleotides designed from two conserved bacterial
Mvd peptides.

(3'-5')
Oligonucleotide mvd-106c TACCTACGSCCVGGSGTYCA (SEQ ID NO:40)
(3'-5')
Oligonucleotide mvd-106d TACCTGCGSCCVGGSGTYCA (SEQ ID NO:41)
(3'-5')

[1]using the preferred codons of *Paracoccus* sp. strain R1534, see table 1
[2]alternate amino acid present in some enzyme S=C or G; R=A or G; Y=C or T; B=C or G or T; V=A or C or G and *Staphylococcus haemolyticus* have an acetyl-CoA acetyltransferase gene linked with the HMG-CoA reductase gene. In the *Enterococcus* species the latter two genes are fused.

The genes of the mevalonate operon from *Paracoccus* sp. strain R114 were identified by homology of the gene products to proteins in general databases. An alignment of the HMG-CoA reductase from *Paracoccus* sp. strains R114 (SEQ ID NO:43) and from three *Streptomyces* species (SEQ ID Nos:54-56) is shown in FIG. 16. There are two classes of HMG-CoA reductases (Bochar et al., Mol. Genet. Metab. 66, 122-127, 1999; Boucher et al., Mol. Microbiol. 37, 703-716, 2000). Eubacterial HMG-CoA reductases are generally of class II, whereas class I enzymes are found in eukaryotes and archaea. The *Streptomyces* and the *Paracoccus* HMG-CoA reductases together with the enzyme from *Vibrio cholerae* are the only eubacterial HMG-CoA reductases of class I known so far.

An alignment of the IPP isomerase (idi) from *Paracoccus* sp. strain R114 (SEQ ID NO:45) with the best matches found in the EMBL database is shown in FIG. 17 (SEQ ID NOs:57-73). The first nine sequences are from eubacteria and the next eight sequences are from archaea. Interestingly, one eukaryotic species, the protozoan parasite *Leishmania major* (SEQ ID NO:73), also has a protein that is highly homologous. This is unexpected because other eukaryotes have a different idi, designated type 1 (Kaneda et al. Proc. Nat. Acad. Sci. 98, 932-937, 2001). A conserved hypothetical protein from *Bacillus subtilis*, YpgA, also has substantial homology but is considerably smaller than the type 2 idi's listed in FIG. 17. An alignment of bacterial HMG-CoA synthases is shown in FIG. 18 (SEQ ID NOs:47 and 74-84) and an alignment of bacterial mevalonate diphosphate decarboxylases is presented in FIG. 19 (SEQ ID NO:53 and 85-94). Two proteins from *Myxococcus xanthus*, Tac and Taf (database accession numbers q9xb06 and q9xb03, respectively) and a protein from *B. subtilis*, PksG, a putative polyketide biosynthesis protein (database accession number p40830), have substantial homology to the *Paracoccus* sp. strain R114 HMG-CoA synthase. The homology between the *Paracoccus* sp. strain R114 HMG-CoA synthase and the Tac and Taf proteins of the *M. xanthus* is greater than the homology between the HMG-CoA synthases from *Paracoccus* sp. strain R114 and eukaryotes. The bacterial HMG-CoA synthases and the bacterial mevalonate diphosphate decarboxylases share substantial homology with their eukaryotic orthologs. Archaeal HMG-CoA synthases form a more distantly related group of enzymes (Wilding et al., J. Bacteriol. 182, 4319-4327, 2000) and no mevalonate diphosphate decarboxylase orthologs are found in archaea (Smit, A. and Mushegian, A., Genome Res, 10, 1468-1484, 2000).

Alignments of the mevalonate kinase (Mvk) (SEQ ID NO:49) and the phosphomevalonate kinase (Pink) (SEQ ID NO:51) from *Paracoccus* sp. strain R114 to the orthologous proteins from other bacteria (SEQ ID NOs:95-104 (Mvk) and 105-114 (Pmk)) are shown in FIGS. 20 and 21, respectively. There is much less homology among the bacterial kinases than among the bacterial orthologs of the other enzymes of the mevalonate pathway. The mevalonate kinase from *Paracoccus* sp. strain R114 (SEQ ID NO:49) has a 37 amino acid insert in the amino-terminal region, which is lacking in other mevalonate kinases. Together with the bacterial Mvk's some archaeal enzymes, e.g. from *Archaeoglobus fulgidus*, *Methanobacterium thermoautotrophicum* and *Pyrococcus abyssi*, are among the best homologues to the Mvk from *Paracoccus* sp. strain R114. The homology among bacterial phosphomevalonate kinases is even weaker than the homology among the bacterial mevalonate kinases. The proteins with the best homologies to the Pmk from *Paracoccus* sp. strain R114 (SEQ ID NO:51) are Mvk's from archaea, e.g. *Aeropyrum pernix*, *Pyrococcus horikoshii*, *M. thermoautotrophicum*, *P. abyssi* and *A. fulgidus*. Since no Pmk's are found in archaea (Smit, A. and Mushegian, A., Genome Res, 10, 1468-1484, 2000), this suggests that the same kinase might perform both phosphorylations.

Example 5

Over-expression of the Mevalonate Pathway Genes and the idi Gene from *Paracoccus* sp. Strain R114 in *E. coli*

Cloning and expression of the mevalonate operon in *E. coli*. A λ clone, designated clone 16, from the *Paracoccus* sp. strain R114 λ library (see Example 4) was used as a template for PCR amplification of the entire mevalonate operon. Primers Mevop-2020 and Mevop-9027 (Table 16) were used for PCR.

TABLE 16

Primers used for amplification of mevalonate operon from *Paracoccus* sp. strain R114.

| Primer | Sequence (5'→3') |
| --- | --- |
| Mevop-2020 | GGGCAAGCTTGTCCACGGCACGACCAAGCA (SEQ ID NO:115) |
| Mevop-9027 | CGTAATCCGCGGCCGCGTTTCCAGCGCGTC (SEQ ID NO:116) |

The resulting PCR product was cloned in TOPO-XL (Invitrogen, Carlsbad, Calif., USA), resulting in plasmid TOPO-XL-mev-op16. The insert carrying the mevalonate operon was excised with HindIII and SacI and cloned in the HindIII-SacI cut vector pBBR1MCS2 (Kovach et al., Gene 166, 175-176, 1995), resulting in plasmid pBBR-K-mev-op16. Plasmid pBBR-K-mev-op16 was used to transform electroporation-competent *E. coli* strain TG1 (Stratagene, La Jolla, Calif.; Sambrook et al., In: Nolan, C. (ed.), Molecular Cloning: A Laboratory Manual (Second Edition), p. A.12, 1989). Two representative positive transformants (*E. coli* TG1/pBBR-K-mev-op16-1 and *E. coli* TG1/pBBR-K-mev-op16-2) were grown in Luria Broth (LB, GibcoBRL, Life Technologies) containing 50 mg/l kanamycin and tested for HMG-CoA reductase activity (encoded by the *Paracoccus* sp. strain R114 mvaA gene) using the methods described in Example 1. The results are shown in Table 17. *E. coli* does not possess a gene coding for the enzyme HMG-CoA reductase, hence the lack of detectable activity. The crude extracts of both representative transformants of *E. coli* TG1/pBBR-K-mev-op16 had easily measurable HMG-CoA reductase activity, demonstrating the heterologous expression of the cloned mvaA gene.

TABLE 17

HMG-CoA reductase activity in crude extracts of *E. coli* TG1 cells carrying the cloned mevalonate gene cluster from *Paracoccus* sp. strain R114.

| Strain | HMG-CoA reductase activity (U/mg) |
|---|---|
| *E. coli* TG1 | Not detected[a] |
| *E. coli* TG1/pBBR-K-mev-op16-1 | 0.25 |
| *E. coli* TG1/pBBR-K-mev-op16-2 | 0.78 |

[a]Less than 0.03 U/mg

Cloning and expression of the idi gene and the individual mevalonate pathway genes from *Paracoccus* sp. strain R114 in *E. coli*. The coding regions of the mevalonate operon genes from *Paracoccus* sp. strain R114 were amplified by PCR using the primers shown in Table 18. The primers were designed such that the ATG start codons constituted the second half of an NdeI site (cleavage recognition site CATATG), and BamHI sites (GGATCC) were introduced immediately after the stop codons. All PCR products were cloned in the pCR®2.1-TOPO vector. The names of the resulting vectors are listed in Table 19. Except for the mevalonate kinase gene, all genes contained restriction sites for BamHI, NdeI or EcoRI, which had to be eliminated in order to facilitate later cloning steps. The sites were eliminated by introducing silent mutations using the QuikChange™ site-directed mutagenesis kit (Stratagene, La Jolla, Calif., USA) and the oligonucleotides shown in Table 20. The mutagenized coding regions were excised from the TOPO-plasmids with BamHI and NdeI and ligated with the BamHI-NdeI cleaved expression vectors pDS-His and pDS. These expression vectors were derived from pDSNdeHis, which is described in Example 2 of European Patent Application EP 821063 (1999). The plasmid pDS-His was constructed from pDSNdeHis by deleting a 857 bp NheI and XbaI fragment carrying a silent chloramphenicol acetyl-transferase gene. The plasmid pDS was constructed from pDS-His by replacing a small EcoRI-BamHI fragment with the annealed primers S/D-1 (5' AATTAAAG-GAGGGTTTCATATGAATTCG) (SEQ ID NO:117) and S/D-2 (5' GATCCGAATTCATATGAAACCCTCCTTT) (SEQ ID NO:118).

TABLE 18

Oligonucleotides for the cloning of the mevalonate operon genes.

| | | Forward primer | | Reverse primer | |
|---|---|---|---|---|---|
| Gene | Name | Sequence (5'-3') | Name | Sequence (5'-3') |
| mvaA | MvaA-Nde | AAGGCCTCATATGAT TCCCATACCCCGGT (SEQ ID NO:119) | MvaA-Bam | CGGGATCCTCATCG CTCCATCTCCATGT (SEQ ID NO:120) |
| idi | Idi-Nde | AAGGCCTCATATGAC CGACAGCAAGGATCA (SEQ ID NO:121) | Idi-Bam | CGGGATCCTCATTG ACGGATAAGCGAGG (SEQ ID NO:122) |
| hsc | Hcs-Nde | AAGGCCTCATATGAA AGTGCCTAAGATGA (SEQ ID NO:123) | Hcs-Bam | CGGGATCCTCAGGC CTGCCGGTCGACAT (SEQ ID NO:124) |
| mvk | Mvk-Nde[1] | AAGGCCTCATATGAG CACCGGCAGGCCTGA AGCA (SEQ ID NO:125) | Mvk-Bam[2] | CGGGATCCTCATCC CTGCCCCGGCAGCG GTT (SEQ ID NO:126) |
| pmk | Pmk-Nde | AAGGCCTCATATGGA TCAGGTCATCCGCGC (SEQ ID NO:127) | Pmk-Bam | CGGGATCCTCAGTC ATCGAAAACAAGTC (SEQ ID NO:128) |
| mvd | Mvd-Nde | AAGGCCTCATATGAC TGATGCCGTCCGCGA (SEQ ID NO:129) | Mvd-Bam | CGGGATCCTCAACG CCCCTCGAACGGCG (SEQ ID NO:130) |

[1]The second codon TCA was changed to AGC (silent mutation - both codons encode serine).
[2]The last codon GGC was changed to GGA (silent mutation - both codons encode glycine).

TABLE 19

Names of expression plasmids and construction intermediates.

| Gene | PCR fragments in pCR ® 2.1-TOPO | After first mutagenesis | After 2nd mutagenesis | Genes in pDS | Genes in pDS-His |
|---|---|---|---|---|---|
| mvaA | TOPO-mvaA-BB | TOPO-mvaA-B | TOPO-mvaA | pDS-mvaA | pDS-His-mvaA |
| idi | TOPO-ORFX-B | TOPO-idi | n/a | pDS-idi | pDS-His-idi |
| hsc | TOPO-hcs-EN | TOPO-hcs-N | TOPO-hcs | pDS-hcs | pDS-His-hcs |
| mvk | TOPO-mvk | n/a | n/a | pDS-mvk | pDS-His-mvk |
| pmk | TOPO-pmk-B | TOPO-pmk | n/a | Nd | pDS-His-pmk |
| mvd | TOPO-mvd-B | TOPO-mvd | n/a | pDS-mvd | pDS-His-mvd | n/a: not applicable;
nd: not done

TABLE 20

Oligonucleotides for site-directed mutagenesis.

| Gene/ Site | Forward primer | | Reverse primer | |
|---|---|---|---|---|
| | Name | Sequence (5'-3') | Name | Sequence (5'-3') |
| mvaA/ BamHI-1 | Mva-B1up | CCGGCATTCGGG CGGCATCCAGGT CTCGCTG (SEQ ID NO:131) | Mva-B1down | CAGCGAGACCTG GATGCCGCCCGA ATGCCGG (SEQ ID NO:132) |
| mvaA/ BamHI-2 | Mva-B2up | CGTGCAGGGCTG GATTCTGTCGGA ATACCCG (SEQ ID NO:133) | Mva-B2down | CGGGTATTCCGA CAGAATCCAGCC CTGCACG (SEQ ID NO:134) |
| idi/ BamHI | Idi-Bup2 | GGGCTGCGCGCC GGCATCCGGCAT TTCGACG (SEQ ID NO:135) | Idi-Bdown2 | CGTCGAAATGCC GGATGCCGGCGC GCAGCCC (SEQ ID NO:136) |
| hcs/ EcoRI | Hcs-Eup | GGGTGCGACGG GCGAGTTCTTCG ATGCGCGG (SEQ ID NO:137) | Hcs-Edown | CCGCGCATCGAA GAACTCGCCCGT CGCACCC (SEQ ID NO:138) |
| hcs/ NdeI | Hcs-Nup-c | CACGCCCGTCAC ATACGACGAATA CGTTGCC (SEQ ID NO:139) | Hcs-Ndown-c | GGCAACGTATTC GTCGTATGTGAC GGGCGTG (SEQ ID NO:140) |
| pmk/ BamHI | Pmk-Bup | GAGGCTCGGGCT TGGCTCCTCGGC GGCGGTG (SEQ ID NO:141) | Pmk-Bdown | CACCGCCGCCGA GGAGCCAAGCC CGAGCCTC (SEQ ID NO:142) |
| mvd/ BamHI | Mvd-Bup | CGGCACGCTGCT GGACCCGGGCG ACGCCTTC (SEQ ID NO:143) | Mvd-Bdown | GAAGGCGTCGCC CGGGTCCAGCAG CGTGCCG (SEQ ID NO:144) |

*E. coli* strain M15 (Villarejo, M. R. and Zabin, I. J. Bacteriol. 120, 466-474, 1974) carrying the lacI (lac repressor)-containing plasmid pREP4 (EMBL/GenBank accession number A25856) was transformed with the ligation mixtures and recombinant cells were selected for by growth on LB-Agar plates supplemented with 100 mg/L ampicillin and 25 mg/L kanamycin. Positive clones containing the correct mevalonate operon gene insert were verified by PCR.

For expression of the inserted genes, each of the *E. coli* strains were grown overnight at 37° C. in LB medium containing 25 mg/L kanamycin and 100 mg/L ampicillin. The next day, 25 ml of fresh medium was inoculated with 0.5 ml of the overnight cultures and the new cultures were grown at 37° C. When the $OD_{600}$ of the cultures reached 0.4, expression of the cloned genes was induced by addition of isopropyl-β-D-thiogalactopyranoside (IPTG) to a final concentration of 1 mM, and the incubation of the cultures (with shaking) was continued for four hours, after which the cells were collected by centrifugation.

Crude extract preparation, HMG-CoA reductase assays, and IPP isomerase assays were performed as described in Example 1. Tables 21 and 22 show the HMG-CoA reductase and IPP isomerase activities, respectively, in the recombinant *E. coli* strains. Upon IPTG induction, strains M15/pDS-mvaA and M15/pDS-idi contained high levels of the HMG-CoA reductase and IPP isomerase activity, respectively. This illustrates the ability to over-express the mevalonate pathway genes (and overproduce their cognate gene products in an active form) from *Paracoccus* sp. strain R114 in *E. coli*.

TABLE 21

Induction of HMG-CoA reductase activity in *E. coli* strains over-expressing the cloned mvaA gene from *Paracoccus* sp. strain R114.

| Strain/plasmid | IPTG Induction | HMG-CoA reductase activity (U/mg) |
|---|---|---|
| M15/pDS-mvaA | − | 8.34 |
| M15/pDS-mvaA | + | 90.0 |
| M15/pDS-His-mvaA | − | 1.74 |
| M15/pDS-His-mvaA | + | 2.95 |
| M15/pDS-mvd[a] | − | 0.05 |

[a]M15/pDS-mvd was included as a negative control

TABLE 22

Induction of IPP isomerase activity in *E. coli* strains over-expressing the cloned idi gene from *Paracoccus* sp. strain R114.

| Strain/plasmid | IPTG Induction | IPP isomerase activity (U/mg) |
|---|---|---|
| M15/pDS-idi | − | Not detected[b] |
| M15/pDS-idi | + | 22.0 |
| M15/pDS-His-idi | − | Not detected |
| M15/pDS-His-idi | + | Not detected |
| M15/pDS-mvd[a] | − | Not detected |

[a]M15/pDS-mvd was included as a negative control
[b]<1 U/mg

FIGS. 22 and 23 show the results of sodium dodecylsulfate-polyacrylamide gel electrophoresis (SDS-PAGE) analysis of the crude extracts used for the enzyme assays summarized in Tables 21 and 22, respectively. For strains E. coli M15/pDS-mvaA and E. coli M15/pDS-His-mvaA, the presence or absence of a highly expressed protein of the expected molecular mass (36.3 kD) correlated with the HMG-CoA reductase activity measured in the extracts (Table 21). The absence of the His-tagged protein could be explained by reduced expression at the level of transcription or translation by instability of the mRNA or the protein. The crude extracts of E. coli M15/pDS-idi and E. coli M15/pDS-His-idi both showed highly expressed proteins of the expected molecular masses of 37.3 kD and 39.0 kD, respectively. However, only the extract from E. coli M15/pDs-idi had increased IPP isomerase activity (Table 22), indicating that the histidine-tagged form of the enzyme was not functional under these conditions.

FIGS. 24-27 show the results of SDS-PAGE analysis of crude extracts of E. coli strains over-expressing the other four genes of the Paracoccus sp. strain R114 mevalonate operon (hcs, pmk, mvk, and mvd, refer to Table 19). In all four cases, high expression of the native form of the enzyme was not detected upon IPTG induction, although some expression cannot be ruled out. On the other hand, high expression was observed with the His-tagged form of all four proteins (FIGS. 24-27).

Example 6

Improved Zeaxanthin Production in Paracoccus sp. strain R114 by Over-Expression of the crtE Gene Construction of pBBR-K-Zea4. pBBR-K-Zea4-up and pBBR-K-Zea4-down and effects of these plasmids on zeaxanthin production in Paracoccus sp. strain R114. The carotenoid (crt) gene cluster of Paracoccus sp. strain R1534 was excised from plasmid pZea-4 (Pasamontes et al., Gene 185, 35-41, 1997) as an 8.3 kb BamHI—EcoRI fragment. This fragment containing the crt gene cluster was ligated into the BamHI and EcoRI-cut vector pBBR1MCS-2 (GenBank accession #U23751) resulting in pBBR-K-Zea4 (FIG. 28). Plasmid pBBR-K-Zea4 was introduced into Paracoccus sp. strain R114 by conjugation to test for improved zeaxanthin production. The control strain R114 and two independent isolates of strain R114/pBBR-K-Zea4 were tested for zeaxanthin production in shake flask cultures (using medium 362F/2, see Example 11). The data in Table 23 show that both recombinant strains carrying plasmid pBBR-K-Zea4 produced significantly higher levels of zeaxanthin than R114, and had higher specific rates of production (mg zeaxanthin/$OD_{660}$). This suggested that one or more of the genes within the cloned insert in pBBR-K-Zea4 encoded an enzyme(s) that was limiting for zeaxanthin production in Paracoccus sp. strain R114.

TABLE 23

Zeaxanthin production by strains R114 and R114/pBBR-K-Zea4.

| Strain | 24 Hours | | 48 Hours | | 72 Hours | |
|---|---|---|---|---|---|---|
| | $ZXN^a$ (mg/l) | Spec. Form.[b] | ZXN (mg/l) | Spec. Form. | ZXN (mg/l) | Spec. Form. |
| R114 | 54.5 | 2.2 | 81.7 | 4.1 | 78.1 | 4.5 |
| R114/pBBR-K-Zea4 (clone 4) | 41.0 | 3.0 | 100.7 | 5.2 | 97.6 | 6.2 |
| R114/pBBR-K-Zea4 (clone 5) | 41.1 | 3.1 | 110.5 | 5.7 | 102.1 | 6.5 |

[a]Zeaxanthin
[b]Specific Formation (mg ZXN/1/$OD_{660}$)

To localize the positive effect, two plasmid derivatives were created that contained subcloned regions of the cloned insert present in pBBR-K-Zea4 (refer to FIG. 28). The "upstream" region of the pBBR-K-Zea4 insert, comprising ORF 5 and the genes atoB and crtE, (Pasamontes et al., Gene 185, 35-41, 1997) is flanked by unique sites for the restriction enzymes XbaI and AvrII. Plasmid pBBR-K-Zea4-down was constructed by digesting pBBR-K-Zea4 with these two enzymes and deleting the "upstream" region. Analogously, plasmid pBBR-K-Zea4-up was constructed by deletion of the "downstream" region within the cloned insert in pBBR-K-Zea4, using the restriction enzymes EcoRV and StuI. The two new plasmids were transferred to Paracoccus sp. strain R114 by conjugation. Zeaxanthin production was compared (shake flask cultures, same conditions as described above) in strains R114 (host control), R114/pBBR-K (empty vector control), R114/pBBR-K-Zea4-down and R114/pBBR-K-Zea4-up (Table 24). The data clearly showed that the positive effect on zeaxanthin production was a result of the presence in multiple copies of the cloned segment containing ORF5, atoB and crtE, i.e., the insert present in plasmid pBBR-K-Zea4-up. In further work (not shown), a series of deletion plasmids was constructed from pBBR-K-Zea4-up. By introducing each of these plasmids into strain R114 and testing for zeaxanthin production, it was determined that it was over-expression of the crtE gene that was providing the improved zeaxanthin production in strains R114/pBBR-K-Zea4 and pBBR-K-Zea4-up. This result is consistent with the activity of GGPP synthase (encoded by crtE, refer to FIG. 1B) being limiting for zeaxanthin production in Paracoccus sp. strain R114. Using the methods described in Example 1, crude extract of strain R114/pBBR-K-Zea4-up was found to have 2.6-fold higher GGPP synthase activity than R114 (data not shown). To prove this directly, a new plasmid allowing over-expression of only the crtE gene was constructed as described in the following two sections.

TABLE 24

Zeaxanthin production by strains carrying deletion derivatives of plasmid pBBR-K-Zea4.

| Strain | 24 Hours | | 48 Hours | | 72 Hours | |
|---|---|---|---|---|---|---|
| | $ZXN^a$ (mg/l) | Spec. Form.[b] | ZXN (mg/l) | Spec. Form. | ZXN (mg/l) | Spec. Form. |
| R114 | 35.0 | 1.2 | 75.7 | 4.1 | 73.9 | 4.4 |
| R114/pBBR-K | 32.0 | 1.5 | 59.3 | 3.1 | 63.3 | 3.9 |
| R114/pBBR-K-Zea4-up | 51.5 | 2.2 | 98.8 | 5.5 | 85.5 | 5.7 |
| R114/pBBR-K-Zea4-down | 41.6 | 1.8 | 63.4 | 3.3 | 66.4 | 3.9 |

[a]Zeaxanthin
[b]Specific Formation (mg ZXN/1/$OD_{660}$)

Construction of the expression vectors pBBR-K-PcrtE and pBBR-tK-PcrtE. The vector pBBR1MCS-2 was cut with BstXI and Bsu36I and the larger fragment was ligated with the annealed oligonucleotides MCS-2 up (5' TCA-GAATTCGGTACCATATGAAGCTTGGATCCGGGG 3') (SEQ ID NO:145) and MCS-2 down (5' GGATCCAAGCT-TCATATGGTACCGAATTC 3') (SEQ ID NO:146), resulting in vector pBBR-K-Nde. The 270 bp region upstream of the crtE gene in the carotenoid gene cluster from *Paracoccus* sp. strain R114, which contains the putative crtE promoter (PcrtE) including the ribosome binding site and the crtE start codon (Pasamontes et al., Gene 185, 35-41, 1997) was amplified from *Paracoccus* sp. strain R114 DNA by PCR with primers crtE-up (5' GGAATTCGCTGCT-GAACGCGATGGCG 3') (SEQ ID NO:147) and crtE-down (5' GGGGTACCATATGTGCCTTCGTTGCGTCAGTC 3') (SEQ ID NO:148). The PCR product was cut with EcoRI and NdeI and inserted into the EcoRI-NdeI cut backbone of pBBR-K-Nde, yielding plasmid pBBR-K-PcrtE. An NdeI site, which contains the ATG start codon of crtE, was included in primer crtE-down. Hence, any introduced coding region with the start codon embedded in a NdeI site should be expressed using the ribosomal binding site of crtE. The plasmid pBBR-K-PcrtE was cut with BamHI and the annealed oligonucleotides pha-t-up (5' GATCCGGCGTGT-GCGCAATTTAATTGCGCACACGCCCCCT-GCGTTTAAAC 3') (SEQ ID NO:149) and pha-t-down (5' GATCGTTTAAACGCAGGGGGCGTGTGCG-CAATTAAATTGCGCACACGCCG 3') (SEQ ID NO:150) were inserted. The insertion was verified by sequencing, and the version of the plasmid having the oligos inserted in the orientation that reconstitutes the BamHI site closer to the PcrtE promoter was named pBBR-tK-PcrtE. The inserted sequence carries the putative transcriptional terminator found between the *Paracoccus* sp. strain R114 phaA and phaB genes (see Example 10) and should, therefore, ensure proper termination of the transcripts initiated from the PcrtE promoter.

Construction of plasmid pBBR-K-PcrtE-crtE-3. To construct a multi-copy plasmid for increased expression of the crtE gene in the *Paracoccus* sp. strain R114 host, the crtE gene was amplified from plasmid p59-2 (Pasamontes et al., Gene 185, 35-41, 1997) by PCR using the primers crtE-Nde (5' AAGGCCTCATATGACGCCCAAGCAGCAATT 3') (SEQ ID NO:151) and crtE-Bam (5' CGGGATCCTAG-GCGCTGCGGCGGATG 3') (SEQ ID NO:152). The amplified fragment was cloned in the pCR®2.1-TOPO vector, resulting in plasmid TOPO-crtE. The NdeI-BamHI fragment from TOPO-crtE was subcloned in NdeI-BamHI-digested plasmid pBBR-K-PcrtE, yielding pBBR-K-PcrtE-crtE. Finally, pBBR-K-PcrtE-crtE-3 was constructed by replacing the smaller BglII fragment from pBBR-K-PcrtE-crtE with the smaller BglII fragment from pBBR-K-Zea4-up. Plasmid pBBR-K-PcrtE-crtE-3 was transferred to *Paracoccus* sp. strain R114 by electroporation. Using the methods described in Example 1, GGPP synthase activity in crude extracts was found to be 2.9-fold higher in strain R114/pBBR-K-PcrtE-crtE-3 than in strain R114 (data not shown). This degree of elevated activity was similar to that observed in R114/pBBR-K-Zea4-up. Table 25 shows the zeaxanthin production by strain R114/pBBR-K-PcrtE-crtE-3 was essentially identical to strain R114/pBBR-K-Zea4-up.

TABLE 25

Comparison of zeaxanthin production by strains R114/pBBR-K-PcrtE-crtE-3 and R114/pBBR-K-Zea4-up.

| Strain | 24 Hours | | 48 Hours | | 72 Hours | |
|---|---|---|---|---|---|---|
| | ZXN[a] (mg/l) | Spec. Form.[b] | ZXN (mg/l) | Spec. Form. | ZXN (mg/l) | Spec. Form. |
| R114 | 49.0 | 1.6 | 83.9 | 3.3 | 97.8 | 4.3 |
| R114/pBBR-K | 42.6 | 1.8 | 73.7 | 3.8 | 88.8 | 4.9 |
| R114/pBBR-K-PcrtE-crtE-3 | 64.6 | 2.9 | 127.0 | 5.8 | 165.6 | 8.5 |
| R114/pBBR-K-Zea4-up | 64.7 | 2.9 | 118.0 | 5.9 | 158.0 | 10.1 |

[a]Zeaxanthin
[b]Specific Formation (mg ZXN/1/OD$_{660}$)

Example 7

Expression of Individual Genes of the *Paracoccus* sp. strain R114 Mevalonate Operon in the Native Host, *Paracoccus* sp. strain R114

Expression of individual cloned genes of the *Paracoccus* sp. strain R114 mevalonate operon in the *Paracoccus* sp. strain R114 host. The mutagenized coding regions of the mevalonate operon genes in TOPO-plasmids (see Example 5) were excised with BamHI and NdeI and ligated with the BamHI-NdeI cleaved vector pBBR-tK-PcrtE (see Example 6). The resulting plasmids pBBR-tK-PcrtE-mvaA, pBBR-tK-PcrtE-idi, pBBR-tK-PcrtE-hcs, pBBR-tK-PcrtE-mvk, pBBR-tK-PcrtE-pmk and pBBR-tK-PcrtE-mvd were introduced into *Paracoccus* sp. strain R114 by electroporation. Transformants were selected on agar medium containing 50 mg/l kanamycin and verified by PCR.

To illustrate that the plasmid-borne mevalonate pathway genes can be expressed in the native host *Paracoccus* sp. strain R114, HMG-CoA reductase activity was compared in crude extracts of strains R114/pBBR-K (control) and R114/pBBR-tK-PcrtE-mvaA (methods used are set forth in Example 1). The specific activities of HMG-CoA reductase in strains R114/pBBR-K and R114/pBBR-tK-PcrtE-mvaA were 2.37 U/mg and 6.0 U/mg, respectively. Thus the presence of the mvaA gene on a multicopy plasmid (and expressed from the PcrtE promoter) resulted in a 2.5-fold increase in HMG-CoA reductase activity relative to the basal (i.e., chromosomally encoded) activity of R114 carrying the empty vector pBBR-K.

Example 8

Construction of "Mini-Operons" for Simultaneous Over-Expression the Cloned Genes of the Mevalonate Pathway with the *Paracoccus* sp. Strain R114 crtE Gene Plasmid constructions. As was shown in Example 6, introduction of plasmid pBBR-K-PcrtE-crtE-3 into *Paracoccus* sp. strain R114 resulted in increased production of zeaxanthin, indicating that GGPP synthase activity was rate limiting for zeaxanthin biosynthesis in strain R114. Example 7 further showed that genes coding for the enzymes of the mevalonate pathway could be over-expressed in the native host *Paracoccus* sp. strain R114, and resulted in increased activity of the encoded enzyme. However, none of the recombinant strains of *Paracoccus* sp. strain R114 that carried plasmids containing each individual gene of the mevalonate operon showed increased zeaxanthin production compared to strain R114 (data not shown). It is possible that the benefit of over-expression of the genes of the mevalonate operon in *Paracoccus* sp. strain R114 could be masked by the downstream "bottleneck" in the zeaxanthin pathway (GGPP synthase). Creation of plasmids that allow simultaneous over-expression of each mevalonate pathway gene (or perhaps combinations of these genes) together with crtE could relieve all rate limitations in the overall zeaxanthin biosynthetic pathway, thereby improving zeaxanthin production. The next section describes the construction of "mini-operons" designed to allow co-over-expression of crtE and each of the genes coding for the five enzymes of the mevalonate pathway.

The crtE, mvaA, idi and mvk genes were excised from the respective TOPO-plasmids (described in Examples 5 and 6) with BamHI and NdeI and ligated with BamHI-NdeI-cleaved vector pOCV-1 (described in Example 12). The crtE gene does not have an adenine as the last nucleotide of the coding region, and in addition, has a TAG rather than a TGA stop codon and an unsuitable distance between the stop codon and the BamHI site. Therefore, the end of crtE does not meet the requirements of the operon construction vectors (refer to Example 12) and crtE must be the last gene in any operon constructed with pOCV-1-crtE. To meet the requirement for an adenine as the first nucleotide of the second codon and the last nucleotide of the last codon, mutations had to be introduced in three genes of the mevalonate operon. The second codon of pmk, GAT, encoding Asp, was changed into AAT, encoding Asn. The last codon of mvd ends with a T and the last codons of pmk and hcs end with C. Changing these nucleotides to A results in silent mutations except for pmk where the last amino acid is changed from Asp to Glu. Oligonucleotides were designed to introduce the necessary changes by PCR. The sequences of the oligonucleotides and the templates used for those PCR reactions are shown in Table 26. All PCR products were cloned in the pCR®2.1-TOPO vector, resulting in plasmids TOPO-mvd$^{OCV}$, TOPO-pmk$^{OCV}$ and TOPO-hcs$^{OCV}$. The inserts were excised with NdeI and BamHI and ligated with the NdeI-BamHI cut backbone of pOCV-2 (see Example 12). The final cloning steps to assemble each of the "mini-operons" were analogous, and are illustrated by the representative scheme for construction of pBBR-K-PcrtE-mvaA-crtE-3 (FIG. 29).

TABLE 26

Oligonucleotides and templates used for PCR in the construction of plasmids TOPO-mvd$^{OCV}$, TOPO-pmk$^{OCV}$ and TOPO-hcs$^{OCV}$.

| Gene | Forward primer Name | Forward primer Sequence (5'-3') | Reverse primer Name | Reverse primer Sequence (5'-3') | Template |
|---|---|---|---|---|---|
| Hcs | Hcs-Nde | AAGGCCTCATA TGAAAGTGCCT AAGATGA (SEQ ID NO:123) | Hcs-mut3 | CCGGATCCTCA TGCCTGCCGGT CGACATAG (SEQ ID NO:153) | pBBR-tK-PcrtE-hcs |
| Pmk | Pmk-mut5 | GAAGGCACATA TGAATCAGGTC ATCCGCGC (SEQ ID NO:154) | Pink-mut3 | GCCGGATCCTC ATTCATCGAAA ACAAGTCC (SEQ ID NO:155) | pBBR-tK-PcrtE-pmk |
| Mvd | Myd-Nde | AAGGCCTCATA TGACTGATGCC GTCCGCGA (SEQ ID NO:129) | Mvd-mut3 | ACGCCGGATCC TCATCGCCCCT CGAACGGC (SEQ ID NO:156) | pBBR-tK-PcrtE-mvd |

Example 9

Cloning and Sequencing of the ispA Gene Encoding FPP Synthase from *Paracoccus* sp. Strain R114

Because FPP synthase lies in the central pathway for zeaxanthin biosynthesis in *Paracoccus* sp. strain R114 (see FIG. 1B), increasing the activity of this enzyme by increasing the dosage of the ispA gene has the potential to improve zeaxanthin production. For this reason, the ispA gene from *Paracoccus* sp. strain R114 was cloned and sequenced as follows. The amino acid sequences of six bacterial FPP synthases were obtained from public databases. These sequences have several highly conserved regions. Two such regions, and the oligonucleotides used for PCR, are shown in Table 27. PCR with oligonucleotides GTT-1 and GTT-2, using *Paracoccus* sp. strain R114 DNA as template, gave a product of the expected size. The PCR product was cloned in the vector pCR®2.1-TOPO and sequenced. The cloned fragment was used as a probe for a Southern analysis of *Paracoccus* sp. strain R114 DNA and was found to hybridize to a BamHI-NcoI fragment of about 1.9 kb (data not shown). *Paracoccus* sp. strain R114 DNA was cut with BamHI and NcoI and the fragments were separated by agarose gel electrophoresis. The region between 1.5 and 2.1 kb was isolated and cloned in the BamHI and NcoI sites of a cloning vector. This partial library was then screened using the ispA-PCR fragment as a probe, and two positive clones were isolated. Sequencing confirmed that the plasmids of both clones contained the ispA gene. Upstream of ispA (SEQ ID NO:159) is the gene for the small subunit of exonuclease VII, XseB (SEQ ID NO:158), and downstream is the dxs gene (SEQ ID NO:160) encoding the 1-deoxyxylulose-5-phosphate synthase. This is the same gene arrangement as found in *E. coli*. The sequence of the NcoI-BamHI fragment is shown in FIG. 30 (SEQ ID NO:157).

Using the same general cloning strategy described in Examples 5-7, a new plasmid, pBBR-tK-PcrtE-ispA-2 was constructed to allow for over-expression of the ispA gene in the native host *Paracoccus* sp. strain R114. The plasmid was introduced into strain R114 by electroporation, and transformants were confirmed by PCR. Three representative transformants and a control strain (R114/pBBR-K) were grown in 362F/2 medium (Example 11), crude extracts were prepared and assayed for activity of the ispA gene product, FPP synthase according to the methods described in Example 1. The basal (chromosomally-encoded) FPP synthase specific activity in R114/pBBR-K was 62.6 U/mg. The FPP synthase activity in the three transformants was 108.3 U/mg (73% increase), 98.5 U/mg (57% increase) and 83.8 U/mg (34% increase), demonstrating the over-expression of the ispA gene and overproduction of its product, FPP synthase, in an active form in *Paracoccus* sp. strain R114.

TABLE 27

Oligonucleotides designed from two conserved bacterial IspA peptides.

Peptide 1

| | |
|---|---|
| *Bradyrhizobium japonicum* | Val His Asp Asp Leu Pro (SEQ ID NO:161) |
| *Rhizobium* sp. strain NGR234 | Val His Asp Asp Leu Pro (SEQ ID NO:162) |
| *Bacillus stearothermophilus* | Ile His Asp Asp Leu Pro (SEQ ID NO:163) |
| *Bacillus subtilis* | Ile His Asp Asp Leu Pro (SEQ ID NO:164) |
| *Escherichia coli* | Ile His Asp Asp Leu Pro (SEQ ID NO:165) |
| *Haemophilus influenzae* | Ile His Asp Asp Leu Pro (SEQ ID NO:166) |
| Oligonucleotide GTT-1 (5'-3') | tc cay gay gay ctg cc (SEQ ID NO:167) |

Peptide 2

| | |
|---|---|
| *Bradyrhizobium japonicum* | Asp Asp Ile Leu Asp (SEQ ID NO:168) |
| *Rhizobium* sp. strain NGR234 | Asp Asp Ile Leu Asp (SEQ ID NO:169) |
| *Bacillus stearothermophilus* | Asp Asp Ile Leu Asp (SEQ ID NO:170) |
| *Bacillus subtilis* | Asp Asp Ile Leu Asp (SEQ ID NO:171) |
| *Escherichia coli* | Asp Asp Ile Leu Asp (SEQ ID NO:172) |
| *Haemophilus influenzae* | Asp Asp Ile Leu Asp (SEQ ID NO:173) |
| Reverse complement of Oligonucleotide GTT-2 (5'-3') | gay gay atc ctg gay (SEQ ID NO:174) |

Y = C or T

Example 10

Cloning and Sequencing of the Genes Coding for Acetyl-CoA Acetyltransferase from *Paracoccus* sp. Strain R114

The first committed step in IPP biosynthesis is the condensation of acetyl-CoA and acetoacetyl-CoA to hydroxymethylglutaryl-CoA (HMG-CoA) by HMG-CoA synthase. The substrate acetoacetyl-CoA is formed by the enzyme acetyl-CoA acetyltransferase (also known as acetoacetyl-CoA thiolase or β-ketothiolase) by condensation of two molecules of acetyl-CoA FIG. 1A). Because this reaction links central metabolism (at acetyl-CoA) to isoprenoid biosynthesis via the mevalonate pathway, increasing the activity of acetyl-CoA acetyltransferase by gene amplification has the potential to increase carbon flow to carotenoids and other isoprenoids in vivo. In *Paracoccus* sp. strain R114, there are at least two genes, atoB and phaA, that encode acetyl-CoA acetyltransferases. The end of the atoB gene is 165 nucleotides upstream of the start of crtE in *Paracoccus* sp. strains R1534 (Hohmann et al., U.S. Pat. No. 6,087,152 (2000)) and R114 (this work). The nucleotide sequence of the atoB gene (SEQ ID NO:175), and the corresponding amino acid sequence of the encoded acetyl-CoA acetyltransferase (SEQ ID NO:176), from *Paracoccus* sp. strain R1534 is shown in FIG. 31.

Using the same general strategy as described in Example 5, the atoB gene was cloned in plasmids pDS and pDS-His. The new plasmids, pDS-atoB and pDS-His-atoB were introduced into *E. coli* strain M15. The resulting strains M15/pDS-atoB and M15/pDS-His-atoB were grown with and without IPTG induction (as described in Example 5), and crude extracts were prepared for acetyl-CoA acetyltransferase assays (methods used were described in Example 1) and SDS-PAGE analysis. The acetyl-CoA acetyltransferase specific activities in extracts of M15/pDS-atoB and M15/pDS-His-atoB (with IPTG induction) were 0.2 U/mg and 13.52 U/mg, respectively. The basal activity measured in *E. coli* without the plasmids was 0.006 U/mg. FIG. 32 shows the overproduction of the cloned acetyl-CoA acetyltransferase upon IPTG induction. The degree of overproduction was much higher in M15/pDS-His-atoB, consistent with the measured acetyl-CoA acetyltransferase activity in the (induced) extracts of the two strains.

Acetoacetyl-CoA is also the substrate for the first committed step in poly-hydroxyalkanoate (PHA) biosynthesis. In many bacteria the genes involved in PHA biosynthesis are grouped in operons (Madison and Huisman, Microbiol. Mol. Biol. Rev., 63, 21-53, 1999). In *Paracoccus denitrificans* the phaA and phaB genes, encoding the acetyl-CoA acetyltransferase and acetoacetyl-CoA reductase, respectively, are clustered in an operon (Yabutani et al., FEMS Microbiol. Lett., 133, 85-90, 1995) whereas phaC, the gene encoding the last enzyme in the pathway, poly(3-hydroxyalkanoate) synthase, is not part of this operon (Ueda et al., J. Bacteriol. 178, 774-779, 1995). PCR fragments containing parts of phaA from *Paracoccus* sp. strain R1534 and phaC from *Paracoccus* sp. strain R114 were obtained using primers based on the *P. denitrificans* phaA and phaC gene sequences. The PCR fragments were then used as probes to screen a *Paracoccus* sp. strain R114 λ-library (see Example 4). Several λ-clones hybridizing with the phaA or the phaC probes were isolated, and the presence of the phaA or phaC genes in the inserts was verified by sequence analysis. Three phaA λ-clones were further analyzed by subcloning and sequencing, whereby the phaB was found downstream of phaA. Therefore, as is the case in *P. denitrificans*, the phaA and phaB genes are clustered whereas the phaC gene is located elsewhere in the genome. The nucleotide sequence of the phaAB cluster (SEQ ID NO:177) and the deduced amino acid sequences (SEQ ID NOs:178 and 179) are shown in FIG. 33. The clustering of genes involved in PHA biosynthesis in operons suggests that at least phaA and phaB are expressed together when the cell produces poly(3-hydroxyalkanoates). On the other hand, a putative transcriptional stop signal is found between the phaA and phaB genes from *Paracoccus* sp. strain R114 (FIG. 33), which is absent in the *P. denitrificans* phaAB operon (Yabutani et al., FEMS Microbiol. Lett., 133, 85-90, 1995). Thus, the expression of the two genes might not be coupled in *Paracoccus* sp. strain R114.

Using the same general strategy as described in Example 5, the phaA gene was cloned in plasmid pDS-His. The new plasmid, pDS-His-phaA, was introduced into *E. coli* strain M15. The resulting strain M15/pDS-His-phaA was grown with and without IPTG induction (as described in Example 5) and crude extracts were prepared for SDS-PAGE analysis. FIG. 34 shows the overproduction of the cloned His-tagged *Paracoccus* sp. strain R114 PhaA (acetyl-CoA acetyltransferase) upon IPTG induction in the *E. coli* M15 host.

The potential benefit of amplifying the atoB or phaA genes, encoding acetyl-Co acetyltransferase, on zeaxanthin production is mentioned above. In addition, it may be beneficial for zeaxanthin production to decrease or-eliminate the activity of actoacetyl-CoA reductase (the phaB gene product) to avoid diversion of some of the acetoacetyl-CoA formed in vivo to the PHA pathway. Mutants of *Paracoccus* sp. strain R114 lacking activity of phaB could be obtained by gene replacement techniques (specifically replacing the wild-type phaB gene in the chromosome with an inactive form of the gene) or by classical mutagenesis and screening.

Example 11

Model for the Industrial Production of Lycopene Using Mutants Derived from *Paracoccus* sp. Strain R114

Lycopene is a red carotenoid that is an intermediate in the biosynthesis of zeaxanthin in the new *Paracoccus* species represented by strain R-1512 and its mutant derivatives R1534 and R114. As lycopene itself has significant commercial potential, it was of interest to test the potential of the new *Paracoccus* species to produce lycopene by industrial fermentation. To obtain mutants blocked in zeaxanthin biosynthesis that accumulated lycopene, *Paracoccus* sp. strain R114 was subjected to mutagenesis with ultraviolet (UV) light followed by screening for red colonies. The UV mutagenesis was performed as follows. An overnight culture of strain R114 was grown in ME medium (see Example 2). The overnight culture was subcultured into fresh ME medium (initial $OD_{610}$=0.1) and incubated at 28° C. for 3 hours. Aliquots of this culture were centrifuged and the pellet washed with 20 mM potassium phosphate buffer (pH 7.2). After a second centrifugation, the pellet was resuspended to a final $OD_{610}$ of 0.1. Ten milliliter aliquots of the cell suspension were placed in a sterile 100-ml glass beaker. The thin layer of cell suspension was irradiated with UV light at a flux of 1450 µW/cm² for a pre-determined optimal length of time. The cell suspension was mixed during the irradiation by means of a paper clip in the beaker and a magnetic stirrer. The mutagenized cell suspensions (and the umnutagenized controls) were plated on 362/F2 agar medium (Table 28). Triplicate viable plate counts (in dim room light) were done on suspensions before and after mutagenesis. Plates were incubated for 4-5 days at 28° C., and the colonies were scored. Several red colonies (putative lycopene producers) were identified and purified by re-streaking. One mutant, designated UV7-1, was further evaluated for lycopene production.

Table 29 shows the zeaxanthin production and lycopene production by the control strain R114 and its mutant derivative UV7-1. Strain R114 produced only zeaxanthin. Mutant UV7-1 produced mostly lycopene, but also produced a residual amount of zeaxanthin, suggesting that the mutational block in UV7-1 (presumably in the crtY gene, refer to FIG. 1B) is not complete. These results show that it is possible to derive lycopene producing strains from *Paracoccus* sp. strain R114.

TABLE 28

| Recipe and preparation for medium 362F/2 | |
| --- | --- |
| Component | Amount |
| Glucose monohydrate | 33 g |
| Yeast extract | 10 g |
| Tryptone | 10 g |
| NaCl | 5 g |
| $MgSO_4 \cdot 7H_2O$ | 2.5 g |
| Agar (for solid medium) | 20 g |
| Distilled water | To 932 ml | adjust pH to 7.4
sterilize by filtration (liquid medium) or autoclaving (solid medium)
Add 2.5 ml each of microelements solution, NKP solution and CaFe solution

| Microelements solution | Amount per liter distilled water |
| --- | --- |
| $(NH_4)_2Fe(SO4)_2 \cdot 6H_2O$ | 80 g |
| $ZnSO_4 \cdot 7H_2O$ | 6 g |
| $MnSO_4 \cdot H_2O$ | 2 g |
| $NiSO_4 \cdot 6H_2O$ | 0.2 g |
| EDTA | 6 g | sterilize by filtration

| NKP solution | Amount per liter distilled water |
| --- | --- |
| $K_2HPO_4$ | 250 g |
| $(NH_4)_2HPO_4$ | 300 g | sterilize by filtration

| CaFe solution | Amount per liter distilled water |
| --- | --- |
| $CaCl_2 \cdot 2H_2O$ | 75 g |
| $FeCl_3 \cdot 6H_2O$ | 5 g |
| Concentrated HCl | 3.75 ml | sterilize by filtration

TABLE 29

Zeaxanthin and lycopene production by *Paracoccus* sp. strain R114 and its red mutant derivative UV7-1.

| | Zeaxanthin (mg/l) | Lycopene (mg/l) |
| --- | --- | --- |
| 24 hours | | |
| R114 | 36.65 | 0 |
| UV7-1 | 3.85 | 20.85 |
| 48 hours | | |
| R114 | 72.95 | 0 |
| UV7-1 | 5.75 | 85.95 |

TABLE 29-continued

Zeaxanthin and lycopene production by *Paracoccus* sp.
strain R114 and its red mutant derivative UV7-1.

|  | Zeaxanthin (mg/l) | Lycopene (mg/l) |
|---|---|---|
| 72 hours |  |  |
| R114 | 83.9 | 0 |
| UV7-1 | 5.85 | 124.55 |

Example 12

Model for the Industrial Production of Astaxanthin by Fermentation using Strains Derived from *Paracoccus* sp. Strain R114

Astaxanthin is a commercially important carotenoid used primarily in the aquaculture industry. Pasamontes and Tsygankov (European Patent Application 872,554 (1998)) showed that astaxanthin production could be achieved in *E. coli* by introducing plasmids containing combinations of the cloned carotenoid (crt) genes from *Paracoccus* sp. strain R1534 and *Paracoccus carotinifaciens* E-396$^T$. Together, the cloned crt genes (crtEBIYZ (see FIG. 1B) and crtW (β-carotene β-4 oxygenase) encoded a total biosynthetic pathway from FPP through zeaxanthin (see FIG. 1B) to astaxanthin. The sequences of the *P. carotinifaciens* E-396 crtW, *Paracoccus* sp. R1534 crtZ, and *Paracoccus* sp. R1534 crtE genes and encoded polypeptides are set forth in (SEQ ID NOs:180 and 181 (crtW); 182 and 184 (crtZ); and 184 and 185 (crtE)) However, it was not shown that astaxanthin production could be achieved in the *Paracoccus* sp. strain R114 host family. To demonstrate the utility of recombinant strains derived from strain R114 for astaxanthin production, the cloned crtW gene (SEQ ID NO:180) was introduced into strain R114 as follows.

TABLE 30

PCR primers used for the work described in Example 12.

| Primer name | Sequence |
|---|---|
| CrtW-Nde | 5' AAGGCCTCATATGAGCGCACATGCCCTGCC 3' (SEQ ID NO:186) |
| CrtW-Bam | 5' CGGGATCCTCATGCGGTGTCCCCCTTGG 3' (SEQ ID NO:187) |
| CrtZ-Nde | 5' AAGGCCTCATATGAGCACTTGGGCCGCAAT 3' (SEQ ID NO:188) |
| CrtZ-Bam | 5' AGGATCCTCATGTATTGCGATCCGCCCCTT 3' (SEQ ID NO:189) |

The crtW gene was amplified by PCR from the cloned crt cluster of *Paracoccus carotinifaciens* strain E-396$^T$ (Tsubokura et al., Int. J. Syst. Bacteriol., 49, 277-282, 1999; Pasamontes and Tsygankov, European Patent Application 872,554, 1998) using the primers crtW-Nde and crtW-Bam (Table 30). The primers were designed such that the ATG start codon constitutes the second half of an NdeI site (cleavage recognition site CATATG), and a BamHI site (GGATCC) was introduced immediately after the stop codon. The PCR product was cloned in the pCR®2.1-TOPO vector, resulting in plasmid TOPO-crtW. The crtW gene was excised with NdeI and BamHI and subcloned in the NdeI-BamHI cut vector pBBR-K-PcrtE (described in Example 6) to create plasmid pBBR-K-PcrtE-crtW.

Plasmid pBBR-K-PcrtE-crtW was transferred to *Paracoccus* sp. strain R114 using a standard bacterial conjugation procedure (*E. coli* strain S 17 (Priefer et al., J. Bacteriol. 163, 324-330 (1985)) was the donor organism). Transconjugants were selected on medium 362F/2 agar (Table 28) containing 50 mg/l kanamycin and purified by restreaking on the same medium. The presence of plasmid pBBR-K-PcrtE-crtW in the strain was confirmed by PCR. Carotenoid production by strains R114 (host control), R114/pBBR-K (empty vector control) and R114/pBBR-K-PcrtE-crtW was measured in shake flask cultures as described in Examples 1 and 2, except that liquid 362F/2 medium was used instead of ME medium. These results are shown in Table 31. The control strains R114 and R114/pBBR-K produced only zeaxanthin. In strain R114/pBBR-K-PcrtE-crtW, the zeaxanthin was completely consumed by the plasmid-encoded β-carotene β-4 oxygenase. However, although astaxanthin was produced, two other ketocarotenoids, adonixanthin and canthaxanthin, accumulated at higher levels. This indicated an imbalance in vivo of the β-carotene hydroxylase (encoded by the chromosomal crtZ gene in strain R114) and the cloned β-carotene β-4 oxygenase (CrtW).

To test this hypothesis, two new plasmids were created that contained the crtZ and crtW genes together in mini-operons. The order of the genes was made different in the two constructs (i.e., crtZ-crtW and crtW-crtZ) to try and create different ratios of expression of the crtZ and crtW genes. The construction of the new plasmids required the assembly of a special set of cloning vectors as follows. A series of operon construction vectors (based on the vector pCR®2.1-TOPO) was designed to facilitate the assembly of genes (in this case, crtZ and crtW) into operons. The genes of interest must have an ATG start codon, embedded in an NdeI site

TABLE 31

Astaxanthin production in *Paracoccus* sp. strain R114 containing plasmids expressing the crtW gene alone and in combination with the crtZ gene.

| Strain | ZXN | ADN | CXN | AXN | Total | Sp. Form.$^a$ |
|---|---|---|---|---|---|---|
| 24 hours |  |  |  |  |  |  |
| R114 | 46.5 | 0 | 0 | 0 | 46.5 | 2.1 |
| R114/pBBR-K | 38.8 | 0 | 0 | 0 | 41.4 | 2.2 |
| R114/pBBR-K-PcrtE-crtW | 0 | 13.0 | 21.8 | 2.3 | 37.5 | 2.1 |
| R114/pBBR-K-PcrtE-crtWZ | 0 | 14.9 | 29.5 | 1.3 | 45.6 | 2.1 |
| R114/pBBR-K-PcrtE-crtZW | 0 | 18.0 | 20.4 | 7.3 | 45.65 | 2.1 |
| 48 hours |  |  |  |  |  |  |
| R114 | 72.6 | 0 | 0 | 0 | 74.4 | 2.8 |
| R114/pBBR-K | 70.1 | 0 | 0 | 0 | 70.1 | 3.1 |
| R114/pBBR-K-PcrtE-crtW | 0 | 26.7 | 22.0 | 26.9 | 75.5 | 3.9 |
| R114/pBBR-K-PcrtE-crtWZ | 0 | 30.9 | 27.2 | 34.8 | 92.9 | 4.0 |
| R114/pBBR-K-PcrtE-crtZW | 0 | 15.7 | 11.2 | 58.3 | 85.1 | 4.1 |
| 72 hours |  |  |  |  |  |  |
| R114 | 82.5 | 0 | 0 | 0 | 82.5 | 5.3 |
| R114/pBBR-K | 82.9 | 0 | 0 | 0 | 82.9 | 5.1 |
| R114/pBBR-K-PcrtE-crtW | 0 | 19.7 | 17.0 | 46.8 | 83.5 | 5.2 |

TABLE 31-continued

Astaxanthin production in Paracoccus sp. strain R114 containing plasmids expressing the crtW gene alone and in combination with the crtZ gene.

| Strain | ZXN | ADN | CXN | AXN | Total | Sp. Form.[a] |
|---|---|---|---|---|---|---|
| R114/pBBR-K-PcrtE - crtWZ | 0 | 28.7 | 26.4 | 43.8 | 98.8 | 6.1 |
| R114/pBBR-K-PcrtE - crtZW | 0 | 18.3 | 14.4 | 66.3 | 98.9 | 5.9 |

[a]ZXN, zeaxanthin; AND, adonixanthin; CXN, canthaxanthin; AXN, astaxanthin.
[b]Specific Formation, expressed as mg/l total carotenoid/$OD_{660}$.

Furthermore, the first nucleotide after the start codon and the last nucleotide before the stop codon must be adenine and the gene must lack sites for at least one of the enzymes BsgI, BseMII, BseRI and GsuI. Four operon construction vectors were constructed, differing in the arrangements of their polylinker sequences (SEQ ID NOs: 190-197) (FIG. 35). The genes to be assembled in operons are first inserted individually between the NdeI and the BamHI sites of the appropriate operon construction vectors. The resulting plasmid with the upstream gene of the envisioned operon is then cut with one of the two enzymes at the end of the polylinker and with an enzyme, which has a unique site within the vector backbone. The plasmid containing the downstream gene of the envisioned operon is cut with one of the first two enzymes of the polylinker and with the same enzyme (with a unique site in the vector backbone) used for the first plasmid (containing the desired upstream gene). The fragments carrying the genes are isolated and ligated, resulting in a pOCV plasmid with both genes between the NdeI and the BamHI sites. More genes can be added in an analogous fashion. The assembled genes overlap such that the first two nucleotides, TG, of the TGA stop codon of the upstream gene coincide the last two nucleotides of the ATG start codon of the downstream gene. The same overlap is found between all genes in the carotenoid (crt) operon (crtZYIB) in Paracoccus sp. strain R1534 (Pasamontes et al., Gene 185, 35-41, 1997).

The pOCV backbone is derived from pCR®2.1-TOPO. The BseMII site in the region necessary for replication, upstream of the ColE1 origin, was eliminated by site directed mutagenesis changing the site from CTCAG into CACAG. The remaining three BseMII sites and one GsuI site were eliminated by removing a 0.8 kb DdeI-Asp700 fragment. The remaining vector was blunt-end ligated after fill-in of the DdeI recessed end. The polylinkers (FIG. 35) were inserted between the BamHI and XbaI sites by means of annealed oligonucleotides with the appropriate 5' overhangs.

Plasmid pBBR-K-PcrtE-crtZW, was constructed using the operon construction vector pOCV-2 as follows. The crtZ gene was amplified by PCR from Paracoccus sp. strain R114 using the primers crtZ-Nde and crtZ-Bam (Table 30). The primers were designed such that the ATG start codon constitutes the second half of a NdeI site (cleavage recognition site CATATG) and a BamHI site (GGATCC) was introduced immediately after the stop codon. The PCR product was cloned in the pCR®2.1-TOPO vector, resulting in plasmid TOPO-crtZ. To assemble the two genes in a mini-operon, both genes, crtZ and crtW were excised with NdeI and BamHI from the plasmids TOPO-crtZ and TOPO-crtW and subcloned in the NdeI-BamHI cut vector pOCV-2, creating plasmids pOCV-2-crtZ and pOCV-2-crtW. Plasmid pOCV-2-crtZ was cut with BseMII and PstI (there is a unique PstI site in the kanamycin resistance gene) and the 2.4 kb fragment (containing crtZ) was ligated with the crtw-containing 1876 bp BseRI-PstI fragment from pOCV-2-crtW. The resulting plasmid, pOCV-2-crtZW, was cut with NdeI and BamHI and the crtZW fragment was ligated with the NdeI-BamHI backbone of pBBR-K-PcrtE to yield pBBR-K-PcrtE-crtZW. Plasmid pBBR-K-PcrtE-crtWZ, was constructed in an analogous fashion.

The data in Table 31 show that the ratio of adonixanthin, canthaxanthin and astaxanthin did not change appreciably in strain R114/pBBR-K-PcrtE-crtWZ compared to strain pBBR-K-PcrtE-crtW. However, in strain pBBR-K-PcrtE-crtZW, the production of the ketocarotenoids was shifted in favor of astaxanthin. This result indicates that the level of expression is dependent on the position of the gene within the mini-operon, and suggests that increasing the in vivo level of β-carotene hydroxylase activity creates a balance between the activities of this enzyme and β-carotene β-4 oxygenase that is more favorable for full conversion of zeaxanthin to astaxanthin.

The results described in this Example also show that it is possible, through appropriate genetic engineering, to produce not only astaxanthin, but also other ketocarotenoids of commercial interest in Paracoccus sp. strain R114 or its relatives. For example, expression of a gene coding for β-carotene β-4 oxygenase in a crtZ mutant of strain R114 (lacking β-carotene hydroxylase activity) would provide for production of exclusively ketocarotenoids, e.g., echinenone or canthaxanthin, without co-production of hydroxylated carotenoids. Taken together, the results presented in this Example and Example 11 show the broad utility of Paracoccus sp. strain R114 and its relatives to produce industrially important carotenoids.

Example 13

Accumulation of Mevalonate in Cultures of Paracoccus sp. Strain R114 Overexpressing Genes of the Mevalonate Pathway This Example shows that overexpression of the genes of the mevalonate pathway in Paracoccus sp. strain R114 leads to increased carbon flow through the mevalonate pathway. The construction of plasmid pBBR-K-mev-op16-2 was described in Example 5. Plasmid pBBR-K-mev-op-up-4 was constructed as follows. A DNA fragment containing most of the mvaA gene and the entire idi and hcs genes (see FIG. 13) was obtained on a 3.1 kb SmaI-SalI fragment following partial digestion of a λ-clone containing the Paracoccus sp. strain R114 mevalonate operon (see Example 4). This fragment was subcloned in pUC19, yielding the plasmid pUC19mev-op-up'. To facilitate subcloning, the KpnI-HindIII fragment of pUC19mev-op-up' containing the mevalonate genes was recloned in the vector pBluescriptKS+, resulting in plasmid pBluKSp-mev-op-up'. A 1.7 kb SalI fragment from pUC19mev-op-up' was then cloned in the SalI site of plasmid 2ES2-1, which is a pUC19-derived plasmid containing the cloned SalI-EcoRI fragment M from Paracoccus sp. strain R114 (see Example 4 and FIG. 13). This resulted in plasmid pUC19mev-op-up-2. Plasmid pUC-mev-op-up-3 was then obtained by combining the BbsI-BsaI fragment from pUC19mev-op-up-2 carrying the beginning of the mevalonate operon with the BbsI-BsaI fragment from pBluKSp-mev-op-up' containing idi and hcs. Separately, a unique MluI site was introduced between the NsiI and KpnI sites of the vector pBBR1MCS-2 (refer to Example 5) by inserting an annealed primer containing an MluI restriction site. The resulting new cloning vector pBBR-K-Mlu was cut with MluI and KpnI and the MluI-KpnI fragment from pUCmev-op-up-3, containing the first three genes of the mevalonate operon, was inserted, yielding plasmid pBBR-K-mev-op-up-3.

Plasmid pBBR-K-mev-op-up-4 was then constructed by insertion of the SmaI fragment from plasmid 16SB3, which contains most of the mvk gene and the 5' end of pmk (plasmid 16SB3 is a pUC 19-derived plasmid containing the *Paracoccus* sp. strain R114 SalI-BamHI fragment A; refer to Example 4 and FIG. 13). The insert of plasmid pBBR-K-mev-op-up-4 contains the putative mevalonate operon promoter region, the first four genes of the mevalonate operon, and the 5' end of pmk.

Plasmids pBBR-K-mev-op16-2 and pBBR-K-mev-op-up-4 were each introduced into *Paracoccus* sp. strain R114 by electroporation. Production of zeaxanthin and mevalonate by the new strains were compared to the control strain R114. The strains were grown in baffled shake flasks in liquid medium 362F/2 (see Example 11) for 72 hours. For strains R114/pBBR-K-mev-op16-2 and R114/pBBR-K-mev-op-up-4, kanamycin (50 mg/l) was also added to the cultures. The cultivation temperature was 28° C. and shaking was at 200 rpm. Zeaxanthin was measured by the method set forth in Example 1.

Mevalonate in culture supernatants was measured as follows. A 0.6 ml sample of the culture was centrifuged for 4 minutes at 13,000×g. Four hundred microliters of the supernatant were added to 400 microliters of methanol and mixed by vortexing for 1 minute. The mixture was centrifuged again for 4 minutes at 13,000×g. The resulting supernatant was then analyzed directly by gas chromatography (GC) using the method of Lindemann et al. (J. Pharm. Biomed. Anal. 9, 311-316, 1991) with minor modification as follows. The GC was a Hewlett-Packard 6890plus instrument (Hewlett-Packard, Avondale, Pa., USA) equipped with a cool-on-column injector and a flame ionization detector. One microliter of sample prepared as described above was injected onto a fused silica capillary column (15 m length× 0.32mm ID) coated with a 0.52 micron film of crosslinked modified polyethylene glycol (HP-FFAP, Agilent Technologies, USA). Helium was used as the carrier gas at an inlet pressure of 0.6 bar. The temperature of the programmable injector was ramped from 82° C. to 250° C. at a rate of 30° C./minute. The column temperature profile was 80° C. for 0.5 minutes, followed by a linear temperature gradient at 15° C./min to 250° C. and finally held at 250° C. for 5 minutes. The detector temperature was maintained at 320° C.

In the first experiment, zeaxanthin and mevalonate production were measured in strains R114 and R114/pBBR-K-mev-op16-2 (Table 32). Both strains produced similar amounts of zeaxanthin, but strain R114/pBBR-K-mev-op16-2 produced a four-fold higher level of mevalonate. These results show that overexpression of the genes of the mevalonate pathway in *Paracoccus* sp. strain R114 results in increased carbon flow through the mevalonate pathway. The accumulation of mevalonate was expected because strain R114/PBBR-K-mev-op16-2 does not have an overexpressed crtE gene, and the crtE gene product (GGPP synthase) is known to be a limiting step in zeaxanthin production in *Paracoccus* sp. strain R114 (see Examples 6 and 8). Cells having a limiting amount of GGPP synthase, upon overproduction of the enzymes of the mevalonate pathway, would be expected to accumulate FPP (refer to FIG. 1B), and it is well known that FPP is a potent inhibitor of mevalonate kinase (Dorsey and Porter, J. Biol. Chem., 243, 4667-4670, 1968; Gray and Kekwick, Biochimica et Biophysica Acta, 279, 290-296, 1972; Hinson et al. J. Lipids Res. 38, 2216-2223, 1997). Therefore, accumulation of FPP resulting from overexpression of the genes of the mevalonate pathway would cause inhibition of mevalonate kinase, which in turn is manifested as mevalonate accumulation in the culture.

TABLE 32

Zeaxanthin and mevalonate production in strains R114 and R114/pBBR-K-mev-op16-2.

| Strain/plasmid | Mevalonate (mg/l) | Zeaxanthin (mg/l) |
| --- | --- | --- |
| R114 | 50.5 | 70.0 |
| R114/pBBR-K-mev-op16-2 | 208.2 | 65.2 |

In a second experiment, using the assays described previously zeaxanthin and mevalonate production were measured in strain R114 and two independent isolates of R114/pBBR-K-mev-op-up-4 (Table 33). These results again show that overexpression of the genes of the mevalonate pathway increased carbon flow through the mevalonate pathway.

TABLE 33

Zeaxanthin and mevalonate production in strains R114 and R114/pBBR-K-mev-op-up-4.

| Strain/plasmid | Mevalonate (mg/l) | Zeaxanthin (mg/l) |
| --- | --- | --- |
| R114 | 45 | 67.5 |
| R114/pBBR-K-mev-op-up-4 (Isolate 1) | 133.2 | 53.7 |
| R114/pBBR-K-mev-op-up-4 (Isolate 2) | 163.7 | 47.6 |

Deposit of Biological Materials

The following biological material was deposited under the terms of the Budapest Treaty with the American Type Culture Collection (ATCC) at 10801 University Blvd., Manassas, Va. 20110-2201, USA, and were assigned the following accession numbers:

| Strain | Accession No. | Date of Deposit |
| --- | --- | --- |
| *Paracoccus* sp. R114 | PTA-3335 | Apr. 24, 2001 |
| *Paracoccus* sp. R1534 | PTA-3336 | Apr. 24, 2001 |
| *Paracoccus* sp. R-1506 | PTA-3431 | Jun. 5, 2001 |

All patents, patent applications, and publications cited above are incorporated herein by reference in their entirety as if recited in full herein.

The invention being thus described, it will be obvious that the same may be varied in many ways. Such variations are not to be regarded as a departure from the spirit and scope of the invention and all such modifications are intended to be included within the scope of the following claims.

What is claimed is:

1. An isolated polypeptide comprising an amino acid sequence selected from the group consisting of: SEQ ID NO: 47; an amino acid sequence of a fragment of SEQ ID NO: 47 having hydroxymethylglutaryl-CoA synthase (HMG-CoA synthase) activity; an amino acid sequence of a polypeptide having HMG-CoA synthase activity, which is encoded by a polynucleotide that hybridizes to the nucleic acid sequence of SEQ ID NO: 46 under the following conditions: hybridization in 40% formamide, 1M NaCl, 1% sodium dodecyl sulfate (SDS) at 37° C., followed by at least one wash in 0.2×SSC at 60° C. for 20 minutes; and an amino acid sequence of a polypeptide having HMG-CoA synthase activity, which is at least 95% identical to SEQ ID NO: 47.

2. An isolated polypeptide of claim 1 having the amino acid sequence of SEQ ID NO: 47.

3. An isolated polypeptide according to claim 2 comprising amino acids corresponding to positions 269-298 of SEQ ID NO: 47.

4. An isolated polypeptide of claim 2 consisting of the amino acid sequence of SEQ ID NO: 47.

5. An isolated polypeptide of claim 1 comprising an amino acid sequence of a polypeptide having HMG-CoA synthase activity, which is encoded by a polynucleotide that hybridizes to the nucleic acid sequence of SEQ ID NO: 46 under the following conditions: hybridization in 40% formamide, 1M NaCl. 1% SDS at 37° C., followed by at least one wash in 0.2×SSC at 60° C. for 20 minutes.

6. An isolated pofypeptide of claim 5 consisting of an amino acid sequence of a polypeptide having HMG-CoA synthase activity, which is encoded by a potynucleotide that hybridizes to the nucleic acid sequence of SEQ ID NO: 46 under the following conditions: hybridization in 40% formamide, 1M NaCl, 1% SDS at 37° C., followed by at least one wash in 0.2×SSC at 60° C. for 20 minutes.

7. An isolated polypeptide of claim 1 comprising an amino acid sequence of a polypeptide having HMG-CoA synthase activity, which is at least 95% identical to SEQ ID NO: 47.

8. An isolated polypeptlde of claim 7 consisting of an amino acid sequence of a polypeptide having HMG-CoA synthase activity, which is at least 95% identical to SEQ ID NO: 47.

9. An isolated polypeptide comprising an amino acid sequence of a fragment of SEQ ID NO: 47, which polypeptide has HMG-CoA synthase activity.

10. An isolated polypeptide of claim 9 consisting of an amino acid sequence of a fragment of SEQ ID NO: 47, which polypeptide lias HMG-CoA synthase activity.

* * * * *